(12) United States Patent
Kick et al.

(10) Patent No.: US 9,834,542 B2
(45) Date of Patent: Dec. 5, 2017

(54) LXR MODULATORS

(71) Applicants: BRISTOL-MYERS SQUIBB COMPANY, Princeton, NJ (US); Exelixis Patent Company LLC, South San Francisco, CA (US)

(72) Inventors: Ellen K. Kick, Pennington, NJ (US); Mandar Bodas, Bangalore (IN); Raju Mohan, Encinitas, CA (US); Meriah Valente, Pennington, NJ (US); Nicholas Wurtz, Pennington, NJ (US); Sharanabasappa Patil, Karnataka (IN)

(73) Assignees: Bristo-Myers Squibb Company, Princeton, NJ (US); Exelixis Patent Company LLC, South San Francisco, CA (US)

( * ) Notice: Subject to any disclaimer, the term of this patent is extended or adjusted under 35 U.S.C. 154(b) by 0 days.

(21) Appl. No.: 14/774,844

(22) PCT Filed: Mar. 14, 2014

(86) PCT No.: PCT/US2014/028274
§ 371 (c)(1),
(2) Date: Sep. 11, 2015

(87) PCT Pub. No.: WO2014/144037
PCT Pub. Date: Sep. 18, 2014

(65) Prior Publication Data
US 2016/0304499 A1  Oct. 20, 2016

Related U.S. Application Data

(60) Provisional application No. 61/786,974, filed on Mar. 15, 2013.

(51) Int. Cl.
| | |
|---|---|
| *A61K 31/497* | (2006.01) |
| *A61K 31/4178* | (2006.01) |
| *A61K 31/4192* | (2006.01) |
| *A61K 31/4439* | (2006.01) |
| *A61K 31/422* | (2006.01) |
| *C07D 403/10* | (2006.01) |
| *C07D 401/14* | (2006.01) |
| *C07D 405/14* | (2006.01) |
| *C07D 413/14* | (2006.01) |
| *C07D 233/64* | (2006.01) |
| *C07D 413/10* | (2006.01) |
| *C07D 403/14* | (2006.01) |

(52) U.S. Cl.
CPC ......... *C07D 403/10* (2013.01); *C07D 233/64* (2013.01); *C07D 401/14* (2013.01); *C07D 403/14* (2013.01); *C07D 405/14* (2013.01); *C07D 413/10* (2013.01); *C07D 413/14* (2013.01)

(58) Field of Classification Search
None
See application file for complete search history.

(56) References Cited

U.S. PATENT DOCUMENTS

| 5,017,607 A | 5/1991 | Chiesi |
|---|---|---|
| 5,138,069 A | 8/1992 | Carini et al. |
| 5,506,219 A | 4/1996 | Robl |
| 5,854,265 A | 12/1998 | Anthony |
| 5,859,035 A | 1/1999 | Anthony et al. |
| 5,874,452 A | 2/1999 | Anthony |
| 6,300,356 B1 | 10/2001 | Segal et al. |
| 7,482,366 B2 | 1/2009 | Bayne et al. |
| 7,998,986 B2 | 8/2011 | Bayne et al. |
| 7,998,995 B2 | 8/2011 | Boren et al. |
| 8,569,352 B2 | 10/2013 | Busch et al. |
| 8,618,154 B2 | 12/2013 | Busch et al. |
| 8,703,805 B2 | 4/2014 | Busch et al. |
| 9,000,022 B2 | 4/2015 | Busch et al. |
| 2007/0093470 A1 | 4/2007 | Chao et al. |
| 2012/0071534 A1 | 3/2012 | Busch et al. |
| 2014/0163081 A1 | 6/2014 | Busch et al. |
| 2015/0299136 A1 | 10/2015 | Busch et al. |
| 2016/0280661 A1 | 9/2016 | Busch |
| 2016/0289222 A1 | 10/2016 | Kick et al. |

FOREIGN PATENT DOCUMENTS

| CN | 102648184 A | 8/2012 |
|---|---|---|
| WO | 9736881 A1 | 10/1997 |
| WO | 9736897 A1 | 10/1997 |
| WO | 0200651 A2 | 1/2002 |
| WO | 2012135082 A1 | 10/2012 |

*Primary Examiner* — Samantha Shterengarts
(74) *Attorney, Agent, or Firm* — Fox Rothschild LLP

(57) ABSTRACT

The present invention provides compounds of Formula I: and pharmaceutically acceptable salts or solvates thereof, as modulators of liver X receptors (LXR), compositions comprising any of such novel compounds, methods of using these compounds or compositions as medicaments for prevention or treatment of diseases or disorders related to liver X receptor (LXR), as well as methods of preparing these LXR modulators and using them in the manufacture of medicaments.

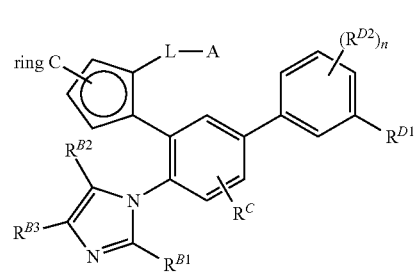

19 Claims, No Drawings

LXR MODULATORS

CROSS-REFERENCE TO RELATED APPLICATIONS

This application is a U.S. National Phase of International Application No. PCT/US2014/028274, filed Mar. 14, 2014, which claims priority of U.S. Provisional Application No. 61/786,974 filed Mar. 15, 2013, the contents of which are incorporated herein by reference in their entirety.

FIELD OF THE INVENTION

This invention relates to compounds that modulate the activity of liver X receptors (LXRs). The invention also provides pharmaceutical compositions comprising the compounds of the invention and methods of using those compositions, for example, for the treatment and/or prophylaxis of coronary heart disease, atherosclerosis, heart failure, and related cardiovascular diseases. In particular, pyrazole isomers and derivatives are provided for modulating the activity of LXRs.

BACKGROUND OF THE INVENTION

Blood cholesterol is a major risk factor for coronary heart disease (CHD) due to the central role that cholesterol metabolism plays in the disease. Circulating low density lipoprotein (LDL) is modified through oxidation in vascular tissue. Macrophages in the subendothelial space take up these cholesterol-rich particles and accumulate large quantities of cholesteryl esters and pro-inflammatory lipids, thereby becoming foam cells. This sets up a chronic inflammatory process in the arterial wall involving macrophages, other inflammatory cells, cytokines, and smooth muscle cells, followed by disruption of the arterial endothelial surface, vessel narrowing, and ultimately thrombosis and vessel occlusion resulting in myocardial infarction (MI). Lowering circulating LDL decreases the uptake of oxidized LDL by macrophages, thereby limiting this pathological process. Statins decrease risk for CHD by lowering LDL. In addition to cholesterol delivery mechanisms mediated by LDL, there is a cholesterol removal process termed reverse cholesterol transport (RCT) in which excess cholesterol in peripheral tissues is trafficked back to the liver where it is secreted via the bile into the intestine, and excreted in feces (Cuchel, M., Rader, D. J. (2006). Circulation 113(21): 2548-2555). The transfer of cholesterol to the liver takes place, in part, on high density lipoprotein (HDL) and this key role in RCT is one of the main reasons why HDL cholesterol (HDL-C) is often the lipid risk factor most closely correlated with CHD in epidemiologic studies. i.e. HDL-C has a strong inverse correlation with disease risk (Gordon, D. J. et al., (1989). Circulation 79(1):8-15; Duffy D. & Rader D. J. (2009). Nat Rev Cardiol 6 (7):455-63.). In addition, HDL has anti-oxidant activity that inhibits the generation of pro-inflammatory oxidized LDL.

The removal of cholesterol from atherosclerotic lesions is thought to attenuate the disease process and, thus, stimulating RCT is likely to be a beneficial therapeutic modality. This is a major rationale for developing LXR agonists for the treatment of atherosclerosis. LXRs (α and β isoforms) are master regulators of cellular and whole-body RCT controlling the transcription of genes involved in all major phases of movement of peripheral cellular cholesterol to the liver and out of the body.

LXRs are able to sense excess intracellular cholesterol by binding to and being transactivated by specific oxysterol cholesterol metabolites. Upon activation, LXRs induce the expression of a variety of cholesterol efflux transporters, apolipoproteins, and lipoprotein modification pathways in multiple tissues that facilitate the removal of excess cellular and whole-body cholesterol (Fiévet C, Staels B. (2009). Biochem Pharmacol. 77(8): 1316-27). It is anticipated that such an integrated stimulus of foam cell macrophage cholesterol efflux, trafficking in the circulation, uptake and metabolism in the liver, and excretion in feces will have a robust anti-atherosclerosis effect.

Two important target genes that are induced by LXR agonists in a variety of tissues, including foam cell macrophages, are the ABC transporters ABCA1 and ABCG1. These are lipid efflux transporters that pump cholesterol out of the cell onto HDL acceptors, generating HDL-C. They play a critical role in helping macrophage foam cells efflux excess sterol (Jessup, W., I. C. Gelissen, et al. (2006). Curr Opin Lipidol 17(3): 247-57). LXR agonists also induce apolipoprotein E in macrophages (Laffitte, B. A., J. J. Repa, et al. (2001). Proc Natl Acad Sci USA. 98(2): 507-12.), which also helps to promote cholesterol efflux from these cells. HDL-C can be taken up directly by the liver or the cholesterol can be first transferred to LDL via the cholesteryl ester transfer protein (CETP) and be delivered to the liver through the LDL receptor. LXRs also induce CETP expression in liver and adipose tissue (Luo, Y. and A. R. Tall (2000). J Clin Invest. 105(4): 513-20.), which could facilitate RCT flux via the LDL pathway. Excess hepatic cholesterol can be converted to bile acids or secreted directly into the bile for subsequent excretion. The liver secretion and intestinal excretion steps are also stimulated by LXR agonists through the induction of two additional ABC transporters, ABCG5 and ABCG8 (Repa, J. J., K. E. Berge, et al. (2002). J Biol Chem. 277(21): 18793-800.). These transporters pump cholesterol out of the hepatocyte into bile and also limit absorption of cholesterol by transporting enterocyte cholesterol into the lumen of the gut.

LXRs also inhibit the NF-κB-dependent induction in macrophages of a variety of inflammatory genes such as iNOS, COX-2 and IL-6 among others (Joseph, S. B., A. Castrillo, et al. (2003). Nat Med. 9(2): 213-9.), and LXR agonists inhibit inflammatory processes in vitro and in vivo. Recent studies also suggest that synthetic LXR agonists could affect acquired immunity by limiting T-cell proliferative responses to activating signals (Bensinger, S. J., M. N. Bradley, et al. (2008). Cell 134(1), 97-111.). These effects on innate and acquired immunity are additional potential anti-atherosclerotic mechanisms of LXR agonists.

LXRs also have favorable effects on glucose homeostasis. Treatment of diabetic mouse models with LXR agonists results in the inhibition of hepatic PGC-1, PEPCK, and glucose-6 phosphatase (G6Pase) and the stimulation of hepatic glucokinase, resulting in marked inhibition of hepatic glucose output (HGO) (Laffitte, B. A., L. C. Chao, et al. (2003). Proc Natl Acad Sci USA. 100(9): 5419-24.). In addition, GLUT4 expression in adipose tissue is upregulated by LXR agonism, thereby increasing peripheral glucose disposal. Consistent with this, LXR agonist treatment of cultured adipocytes increased glucose uptake. Finally, LXR agonism appears to downregulate glucocorticoid action in liver. LXR agonists inhibit hepatic 11β-HSD1 expression (Stulnig, T. M., U. Oppermann, et al. (2002). Diabetes. 51(8): 2426-33.), an enzyme that converts inactive cortisone to active corticosterone, thus likely lowering liver glucocorticoid. This downregulation of hepatic glucocorticoid activity is likely the mechanism for LXR regulation of PEPCK, G-6-Pase, and glucokinase. Thus, by both inhibiting hepatic glucose output and stimulating peripheral glucose disposal, LXR treatment markedly lowers plasma glucose in diabetic rodent models.

Recently LXRs have also been shown to be important regulators of prostate cancer cell survival. Disruption of lipid rafts in response to LXR-dependent cholesterol efflux (Dufour J. et al. (2012). *Curr Opin Pharmacol.* 2012 Jul. 19). Lowering membrane cholesterol results in a suppression of the AKT survival pathway and consequently apoptosis. Thus, stimulating the LXR-AKT pathway may be beneficial for prostate cancer. Similarly, LXR activation has been suggested to have utility in treating a variety of other cancers including those of the breast (Vedin, L-L. et al., (2009) *Carcinogenesis.* 30 (4): 575-79) and pancreas (Rasheed et al., (2012) *Cancer Research.* 72 (8), Supplement 1, Abstract 3494).

LXR agonists have also been suggested to be useful for the prevention and treatment of photo and chronological skin aging, through their positive effects on keratinocyte and fibroblast gene expression (Chang, K. C. et al., (2008) *Mol Endocrinol.* 22(11): 2407-19).

In addition to the positive effects on cholesterol metabolism, LXRs stimulate fatty acid and triglyceride (TG) synthesis in the liver, primarily through inducing the transcription factor SREBP-1c. Consequently, most LXR agonists cause at least some degree of undesirable accumulation of lipids within hepatocytes and elevated plasma TG and LDL (Groot, P. H., et al. (2005). *J Lipid Res.* 46(10): 2182-91), a property primarily attributed to LXRα specific activity (Peet, D. J., et al. (1998). *Cell.* 93(5): 693-704; Lund, E. G., et al. (2006). *Biochem Pharmacol.* 71(4): 453-63). This is the major mechanism-based adverse effect of the target class and is most pronounced in full pan agonists. Strategies to minimize the undesirable lipid effects include identifying LXRβ selective compounds that are also partial agonists. Partial agonists can display tissue-specific activation or repression of nuclear receptors (Albers, M., et al. (2006). *J Biol Chem.* 281(8): 4920-30), as was demonstrated for the anti-estrogen tamoxifen, which functions as an antagonist of estrogen signaling in breast tissue and an agonist in the uterus (Delmas, P. D., et al. (1997). *N Engl J Med* 337(23): 1641-1647). Characterization of LXR isoform-specific null mice indicates that LXRα is the predominant mediator of LXR activity in the liver Peet, D. J., et al. (1998). *Cell.* 93(5): 693-704; Lund, E. G., et al. (2006). *Biochem Pharmacol.* 71(4): 453-63). In macrophages, however, LXRβ alone is sufficient to mediate the effects of LXR ligands on target gene expression. Therefore, compounds with limited LXRα activity should have anti-atherogenic activity while limiting unwanted hepatic effects.

Liver X Receptors

LXRs are adopted orphan members of the nuclear receptor superfamily. There are two LXR isoforms, LXRα and LXRβ, and both heterodimerize with the Retinoid X Receptor (RXR) (Song, C., et al. (1994). *Proc Natl Acad Sci USA.* 91(23): 10809-13; Apfel, R., et al. (1994). *Mol Cell Biol.* 14(10): 7025-35; Willy, P. J., et al. (1995). *Genes Dev.* 9(9): 1033-45.). Both LXRs, when complexed with RXR, bind to distinct regions of DNA called LXR response elements (LXREs) present in the promoters of LXR target genes. The LXR response elements take the form of two degenerate hexad direct repeat sequences, the consensus being AGGTCA, separated by 4 nucleotides, collectively termed a DR4 repeat (Willy, P. J. and D. J. Mangelsdorf (1997). *Genes Dev.* 11(3): 289-98). LXR$_\alpha$ is found predominantly in the liver, with lower levels found in kidney, intestine, spleen and adrenal tissue (see, e.g., Willy, et al. (1995) *Gene Dev.* 9(9):1033-1045). LXR$_\beta$ is ubiquitous in mammals and was found in nearly all tissues examined.

SUMMARY OF THE INVENTION

The present disclosure provides novel compounds, including individual isomers, stereoisomers or mixture of isomers, tautomers, solvates, isotopes or a pharmaceutically acceptable salt thereof, which are useful as modulators of the activity of liver X receptors (LXRs).

In one embodiment, the present invention is directed to compounds of formula (I):

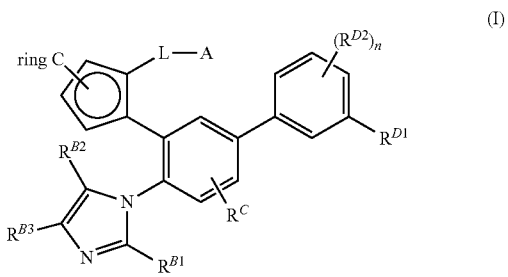

or an isomer, solvate, or a pharmaceutically acceptable salt thereof, wherein

L is a bond, —[C(R$^1$)$_2$]$_m$—, -cyclopropyl-, or —CO—;

m is 1 or 2;

n is 0, 1, 2, 3, or 4;

R$^1$ is independently selected from H, C$_{1-3}$alkyl, —OH, or halo;

A is phenyl, cyclohexyl, a 5 or 6 membered heterocyclyl, or a 5 or 6 membered heteroaryl, wherein the phenyl is optionally fused to a 5 or 6 membered heterocyclyl or 5 or 6 membered heteroaryl, wherein A is optionally substituted with 1, 2, or 3 R$^4$ groups, wherein each R$^4$ is independently R$^{41}$, —C$_1$-C$_6$alkyl-R$^{41}$, C$_1$-C$_6$alkyl, C$_1$-C$_6$ haloalkyl, C$_2$-C$_6$alkenyl, C$_2$-C$_6$alkynyl, C$_3$-C$_8$cycloalkyl, or heterocyclyl, wherein the cycloalkyl or heterocyclyl are each optionally substituted with 1, 2, 3, or 4 groups that are independently R$^{41}$, C$_1$-C$_6$alkyl, or —C$_1$-C$_6$alkyl-R$^{41}$, wherein each R$^{41}$ is independently halogen, cyano, nitro, —OR, —NR$_2$, —SR, —C(O)R, or —C(O)OR;

alternatively, 2R$^4$ on adjacent carbons can join to form a —O—CH$_2$—O—, —O—CH$_2$—CH$_2$—, —O—CH$_2$—CH$_2$—O—, or —O—CF$_2$—O—, —CH$_2$—CH$_2$—CH$_2$—;

ring C is a 5 membered heterocyclic ring selected from triazolyl, imidazolyl, pyrrazolyl, oxazolyl; wherein when ring C is pyrrazolyl, imidazolyl, or oxazolyl, then ring C is optionally substituted with C$_{1-4}$alkyl, C$_{2-3}$alkenyl, C$_{1-3}$haloalkyl, C$_{3-6}$cycloalkyl, CF$_3$, C$_{1-4}$alkyl-OH, C$_{1-4}$alkyl-O—C$_{1-3}$alkyl, C$_{1-3}$alkyl-NR$_2$; C$_{1-3}$alkyl-CO$_2$H, C$_{1-3}$alkyl-NHSO$_2$—C$_{1-3}$alkyl, —NH—C$_{1-3}$alkyl-OR, C$_{1-3}$alkyl-pyrrolidinyl;

R$^{B1}$ is hydrogen, C$_{1-3}$alkyl, halo, or C$_{1-3}$haloalkyl;

R$^{B2}$ is hydrogen, C$_{1-3}$alkyl, halo, or C$_{1-3}$haloalkyl

R$^{B3}$ is hydrogen, C$_{1-4}$alkyl, halo, CN, C$_{1-4}$haloalkyl, —C(O)—C$_{1-3}$alkyl, —CO—NH$_2$, —CO—NR$_2$, or —C$_{1-3}$ alkyl-OH, each $R^{D1}$ and $R^{D2}$ are independently $R^{D3}$, $C_1$-$C_6$alkyl, —$C_1$-$C_6$alkyl-$R^{D3}$, $C_1$-$C_6$haloalkyl, $C_2$-$C_6$alkenyl, $C_2$-$C_6$alkynyl, $C_3$-$C_8$cycloalkyl, or heterocyclyl, wherein the cycloalkyl and heterocyclyl are each optionally substituted with 1, 2, 3, or 4 groups that are independently $R^{D3}$, $C_1$-$C_6$alkyl, $C_3$-$C_6$cycloalkyl, or —$C_1$-$C_6$alkyl-$R^{D3}$, wherein
  each $R^{D3}$ is independently halogen, cyano, —OR, —$NR_2$, —SR, —C(O)R, —C(O)OR, —C(O)$NR_2$, —S(O)R, —S(O)$_2$R, —S(O)R, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)$_2$R, —N(R)S(O)$_2$OR, —N(R)S(O)$_2NR_2$, or —S(O)$_2$N(R)C(O)$NR_2$; and
$R^C$ is hydrogen, halogen, cyano, or $C_1$-$C_3$alkyl;
each R group is independently hydrogen, $C_1$-$C_6$alkyl, —$C_1$-$C_6$alkyl-$R^2$, $C_1$-$C_6$haloalkyl, —$C_1$-$C_6$haloalkyl-$R^2$, $C_2$-$C_6$alkenyl, $C_2$-$C_6$alkynyl, or $C_3$-$C_8$cycloalkyl, wherein
  each $R^2$ is independently cyano, —$OR^3$, —$N(R^3)_2$, —$N(R^3)S(O)_2R^3$, —$N(R^3)S(O)_2OR^3$, or —$N(R^3)S(O)_2N(R^3)_2$, wherein each $R^3$ is independently hydrogen, $C_1$-$C_6$alkyl, or $C_1$-$C_6$haloalkyl.

In another embodiment, the present invention is directed to compounds of the formula:

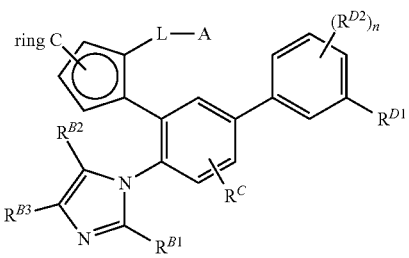

or a pharmaceutically acceptable salt thereof, wherein
L is a bond, —[C($R^1$)$_2$]$_m$—, -cyclopropyl-, or —CO—;
m is 1 or 2;
$R^1$ is independently selected from H, $C_{1-3}$alkyl, —OH, or halo;
A is phenyl, cyclohexyl, benzofuranyl, 2,3-dihydro-1H-indenyl, pyridyl, pyrazinyl, pyrimidinyl, dihydrobenzofuranyl, pyridin-2(1H)-one, imidazo[1,2-a]pyridinyl, or piperidinyl, wherein A is optionally substituted with 1, 2, or 3 $R^4$ groups; wherein
  each $R^4$ is independently halo, CN, $C_1$-$C_6$alkyl, $C_1$-$C_6$haloalkyl, —O—R, $NR_2$, —O—$C_1$-$C_6$alkyl, —O—$C_1$-$C_6$alkyl-$C_{3-6}$cycloalkyl, —S—R, —CO—R, —C(O)O—R, —$C_1$-$C_6$alkyl-CO—$NR_2$, pyrrolidinone, or pyrrolidinyl;
  alternatively, 2$R^4$ on adjacent carbons can join to form a —O—$CH_2$—O—, —O—$CH_2$—$CH_2$—, —O—$CH_2$—$CH_2$—O—, or —O—$CF_2$—O—;
ring C is a 5 membered heterocyclic ring selected from triazolyl, imidazolyl, pyrrazolyl, oxazolyl; wherein when ring C is pyrrazolyl, imidazolyl, or oxazolyl, then ring C is optionally substituted with $C_{1-4}$alkyl, $C_{2-3}$alkenyl, $C_{1-3}$haloalkyl, $C_{3-6}$cycloalkyl, —$CF_3$, —$C_{1-4}$alkyl-OH, —$C_{1-4}$alkyl-O—$C_{1-3}$alkyl, —$C_{1-3}$alkyl-$NR_2$; —$C_{1-3}$alkyl-$CO_2H$, —$C_{1-3}$alkyl-$NHSO_2$—$C_{1-3}$alkyl, —NH—$C_{1-3}$alkyl-OR, or —$C_{1-3}$alkyl-pyrrolidinyl;
$R^{B1}$ is hydrogen, $C_{1-3}$alkyl, halo, or $C_{1-3}$haloalkyl;
$R^{B2}$ is hydrogen, methyl or halo;
$R^{B3}$ is hydrogen, $C_{1-4}$alkyl, halo, CN, $C_{1-4}$haloalkyl, cyclopropyl, —CO—$NH_2$, —CO—$NR_2$, or —$C_{1-3}$alkyl-OH,
$R^C$ is hydrogen, halogen, or cyano;
n is 0, 1, 2, 3, or 4; and
$R^{D1}$ is —$SO_2$—$C_{1-6}$alkyl, —$SO_2$—$C_{1-6}$haloalkyl, —$SO_2$—$C_{3-6}$cycloalkyl, —$SO_2$—$C_{1-6}$alkyl-OH, —$SO_2$—$C_{1-6}$alkyl-O—$C_{1-6}$alkyl, —C(Me)$_2$-COOH, C(Me)$_2$-CONR$_2$, -cyclopropyl-CONR$_2$, —$SO_2NR_2$, —$SO_2NR$—$C_{1-6}$alkyl-OH, —$SO_2$-pyrrolidinyl, or —CONR$_2$
$R^{D2}$ is independently $C_{1-6}$ haloalkyl, —$C_{1-6}$ alkyl-OH, halo, —$C_{1-6}$ alkyl-O—$C_{1-6}$ alkyl, —$C_{1-6}$alkyl-NHSO$_2$—$C_{1-6}$alkyl, $C_{1-6}$ haloalkyl, or —O—$C_{1-6}$alkyl-O—$C_{1-6}$haloalkyl,
each R group is independently hydrogen, $C_1$-$C_6$alkyl, —$C_1$-$C_6$alkyl-$R^2$, $C_1$-$C_6$haloalkyl, —$C_1$-$C_6$haloalkyl-$R^2$, $C_2$-$C_6$alkenyl, $C_2$-$C_6$alkynyl, $C_3$-$C_6$cycloalkyl;
each $R^2$ is independently —$OR^3$, wherein each $R^3$ is independently hydrogen, $C_1$-$C_6$alkyl, or $C_1$-$C_6$haloalkyl.

In another embodiment, the present invention provides a compound of formula (I)

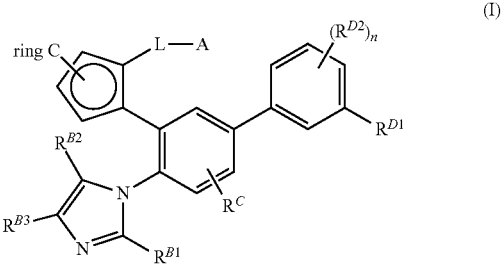

(I)

or a pharmaceutically acceptable salt or solvate, wherein:
L is a bond, —[C($R^1$)$_2$]$_m$—, -cyclopropyl-, or —CO—;
m is 1 or 2;
n is 0, 1, 2, 3, or 4;
$R^1$ is independently selected from H, $C_{1-3}$alkyl, $C_{1-3}$haloalkyl, —OH, and halo;
A is phenyl, cyclohexyl, a 5 or 6 membered heterocycle, or a 5 or 6 membered heteroaryl, wherein the phenyl is optionally fused to a 5 or 6 membered heterocycle or 5 or 6 membered heteroaryl, wherein A is optionally substituted with 1, 2, or 3 $R^4$ groups, wherein
  each $R^4$ is independently $R^{A1}$, —$C_1$-$C_6$alkyl-$R^{A1}$, $C_1$-$C_6$alkyl, $C_1$-$C_6$ haloalkyl, $C_2$-$C_6$alkenyl, $C_2$-$C_6$alkynyl, $C_3$-$C_8$cycloalkyl, or heterocyclyl, wherein the cycloalkyl or heterocyclyl are each optionally substituted with 1, 2, 3, or 4 groups that are independently $R^{A1}$, $C_1$-$C_6$alkyl, or —$C_1$-$C_6$alkyl-$R^{A1}$, wherein
  each $R^{A1}$ is independently halogen, cyano, nitro, —OR, —$NR_2$, —SR, —C(O)R, or —C(O)OR;
alternatively, 2$R^4$ on adjacent carbons can join to form a —O—$CH_2$—O—, —O—$CH_2$—$CH_2$—, —O—$CH_2$—$CH_2$—O—, —$CH_2$—$CH_2$—$CH_2$—, or —O—$CF_2$—O—;
ring C is a 5 membered heterocyclic ring selected from triazolyl, imidazolyl, pyrrazolyl, and oxazolyl; wherein when ring C is pyrrazolyl, imidazolyl, or oxazolyl, then ring C is optionally substituted with $C_{1-4}$alkyl, $C_{2-3}$alkenyl, $C_{1-3}$haloalkyl, $C_{3-6}$cycloalkyl, —$CF_3$, —$C_{1-4}$alkyl-OH, —$C_{1-4}$alkyl-O—$C_{1-3}$alkyl, —$C_{1-3}$alkyl- NR$_2$, —C$_{1-3}$alkyl-CO$_2$H, —C$_{1-3}$alkyl-NHSO$_2$—C$_{1-3}$alkyl, —NH—C$_{1-3}$alkyl-OR, or —C$_{1-3}$alkyl-pyrrolidinyl;

R$^{B1}$ is hydrogen, C$_{1-3}$alkyl, halo, or C$_{1-3}$haloalkyl;

R$^{B2}$ is hydrogen or halo;

R$^{B3}$ is hydrogen, C$_{1-3}$alkyl, halo, CN, C$_{1-3}$haloalkyl, —C(O)—C$_{1-3}$alkyl, —CO—NH$_2$, —CO—N(R)$_2$, or —C$_{1-3}$alkyl-OH, R$^{D1}$ and R$^{D2}$ are each independently R$^{D3}$, C$_1$-C$_6$alkyl, —C$_1$-C$_6$alkyl-R$^{D3}$, C$_1$-C$_6$haloalkyl, C$_2$-C$_6$alkenyl, C$_2$-C$_6$alkynyl, or C$_3$-C$_8$cycloalkyl, or heterocyclyl, wherein the cycloalkyl or heterocyclyl are each optionally substituted with 1, 2, 3, or 4 groups that are independently R$^{D3}$, C$_1$-C$_6$alkyl, C$_3$-C$_6$cycloalkyl, or —C$_1$-C$_6$alkyl-R$^{D3}$, wherein each R$^{D3}$ is independently halogen, cyano, —OR, —NR$_2$, —SR, —C(O)R, —C(O)OR, —C(O)NR$_2$, —S(O)R, —S(O)$_2$R, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)$_2$R, —N(R)S(O)$_2$OR, —N(R)S(O)$_2$NR$_2$, or —S(O)$_2$N(R)C(O)NR$_2$;

R$^C$ is hydrogen, halogen, C$_1$-C$_6$alkyl, cyano, or nitro; and each R group is independently hydrogen, C$_1$-C$_6$alkyl, —C$_1$-C$_6$alkyl-R$^2$, C$_1$-C$_6$haloalkyl, —C$_1$-C$_6$haloalkyl-R$^2$, C$_2$-C$_6$alkenyl, C$_2$-C$_6$alkynyl, C$_3$-C$_8$cycloalkyl, or —C$_1$-C$_6$alkyl-C$_3$-C$_8$cycloalkyl, wherein each R$^2$ is independently cyano, —OR$^3$, —N(R$^3$)$_2$, —N(R$^3$)S(O)$_2$R$^3$, —N(R$^3$)S(O)$_2$OR$^3$, or —N(R$^3$)S(O)$_2$N(R$^3$)$_2$, wherein each R$^3$ is independently hydrogen, C$_1$-C$_6$alkyl, or C$_1$-C$_6$haloalkyl.

In another embodiment, the present invention is directed to compounds of formula (I)

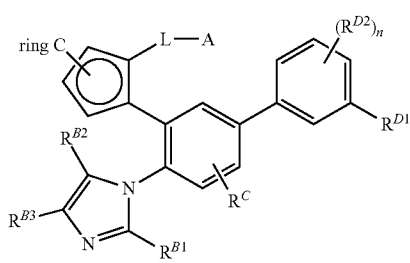

(I)

or a pharmaceutically acceptable salt or solvate thereof, wherein:

L is a bond, —[C(R$^1$)$_2$]$_m$—, -cyclopropyl-, or —CO—;

m is 1 or 2;

R$^1$ is independently selected from H, C$_{1-3}$alkyl, C$_{1-3}$haloalkyl, —OH, and halo;

A is phenyl, cyclohexyl, naphthalenyl, benzofuranyl, 2,3-dihydro-1H-indenyl, 1H-indolyl, pyridyl, pyrazinyl, pyrimidinyl, dihydrobenzofuranyl, pyridin-2(1H)-one, imidazo[1,2-a]pyridinyl, or piperidinyl, wherein A is optionally substituted with 1, 2, or 3 R$^A$ groups; wherein each R$^A$ is independently halo, CN, C$_{1-6}$alkyl, C$_1$-C$_6$haloalkyl, —O—R, —NR$_2$, —O—C$_{1-6}$alkyl, —O—C$_{1-6}$alkyl-C$_{3-6}$cycloalkyl, —S—R, —CO—R, —C(O)O—R, —C$_1$-C$_6$alkyl-CO—NR$_2$, pyrrolidinone, or pyrrolidinyl;

alternatively, 2R$^A$ on adjacent carbons can join to form a —O—CH$_2$—O—, —O—CH$_2$—CH$_2$—, —O—CH$_2$—CH$_2$—O—, or —O—CF$_2$—O—;

ring C is a 5 membered heterocyclic ring selected from triazolyl, imidazolyl, pyrrazolyl, and oxazolyl; wherein when ring C is pyrrazolyl, imidazolyl, or oxazolyl, then ring C is optionally substituted with C$_{1-4}$alkyl, C$_{2-3}$alkenyl, C$_{1-3}$haloalkyl, C$_{3-6}$cycloalkyl, —CF$_3$, —C$_{1-4}$alkyl-OH, —C$_{1-4}$alkyl-O—C$_{1-3}$alkyl, —C$_{1-3}$alkyl-NR$_2$; —C$_{1-3}$alkyl-CO$_2$H, —C$_{1-3}$alkyl-NHSO$_2$—C$_{1-3}$alkyl, —NH—C$_{1-3}$alkyl-OR, or —C$_{1-3}$alkyl-pyrrolidinyl;

R$^{B1}$ is hydrogen, C$_{1-3}$alkyl, halo, or C$_{1-3}$haloalkyl;

R$^{B2}$ is hydrogen or halo;

R$^{B3}$ is hydrogen, C$_{1-3}$alkyl, halo, CN, C$_{1-4}$haloalkyl, cyclopropyl, —CO—NH$_2$, —CO—NR$_2$, or —C$_{1-3}$alkyl-OH, R$^C$ is hydrogen, halogen, or cyano;

n is 0, 1, 2, 3, or 4; and

R$^{D1}$ is —SO$_2$—C$_{1-6}$alkyl, —SO$_2$—C$_{1-6}$haloalkyl, —SO$_2$—C$_{3-6}$cycloalkyl, —SO$_2$—C$_{1-6}$alkyl-OH, —SO$_2$—C$_{1-6}$ alkyl-O—C$_{1-6}$alkyl, —C(Me)$_2$-COOH, —C(Me)$_2$-CONR$_2$, -cyclopropyl-CONR$_2$, —SO$_2$NR$_2$, —SO$_2$NR—C$_{1-6}$alkyl-OH, —SO$_2$-pyrrolidinyl, —CONR$_2$ R$^{D2}$ is independently —C$_{1-6}$haloalkyl-C$_{1-6}$alkyl-OH, halo, —C$_{1-6}$ alkyl-O—C$_{1-6}$ alkyl, —C$_{1-6}$alkyl-NHSO$_2$—C$_{1-6}$alkyl, C$_{1-6}$ haloalkyl, or —O—C$_{1-6}$ alkyl-O—C$_{1-6}$haloalkyl, each R group is independently hydrogen, C$_1$-C$_6$alkyl, —C$_1$-C$_6$alkyl-R$^2$, C$_1$-C$_6$haloalkyl, —C$_1$-C$_6$haloalkyl-R$^2$, C$_2$-C$_6$alkenyl, C$_2$-C$_6$alkynyl, or C$_3$-C$_8$cycloalkyl; and each R$^2$ is independently —OR$^3$, wherein each R$^3$ is independently hydrogen, C$_1$-C$_6$alkyl, or C$_1$-C$_6$haloalkyl.

The present invention also provides processes and intermediates for making the compounds of the present invention.

Another aspect of this invention is directed to a composition comprising a compound of the invention together with a pharmaceutically acceptable carrier, diluent, or excipient. When water is a carrier or diluent, the composition optionally further comprises another pharmaceutically acceptable carrier or diluent and/or a pharmaceutically acceptable excipient. Within this aspect are such compositions for pharmaceutical use.

Another aspect of this invention is directed to methods of treating, inhibiting, or ameliorating the symptoms of a disease or disorder that is modulated or otherwise affected by LXR activity or in which LXR activity is implicated, comprising administering to a subject in need thereof a therapeutically effective amount of a compound of the present invention or an individual isomer or mixture of isomers or a pharmaceutically acceptable salt thereof.

Another aspect of this invention is directed to methods of modulating cholesterol metabolism to a subject in need thereof, comprising administering an effective cholesterol metabolism-modulating amount of a compound of the present invention or an individual isomer or mixture of isomers or a pharmaceutically acceptable salt thereof.

Another aspect of this invention is directed to methods of preventing or treating atherosclerosis in a subject in need thereof, comprising administering an effective cholesterol metabolism-modulating amount of a compound of the present invention or an individual isomer or mixture of isomers or a pharmaceutically acceptable salt thereof.

Another aspect of this invention is directed to methods of modulating LXR activity to a subject in need thereof, comprising contacting the nuclear receptor with a compound of the present invention or an individual isomer or mixture of isomers or a pharmaceutically acceptable salt thereof.

Another aspect of this invention is directed to methods of increasing cholesterol efflux from cells of a subject in need thereof, comprising administering an effective cholesterol efflux-increasing amount of a compound of the present invention or an individual isomer or mixture of isomers or a pharmaceutically acceptable salt thereof.

Another aspect of this invention is directed to methods of increasing the expression of ATP-Binding Cassette A1 (ABCA1) and ATP-Binding Cassette G1 (ABCG1) in the cells of a subject in need thereof, comprising administering an effective ABCA1 and ABCG1 expression-increasing amount of a compound of the present invention or an individual isomer or mixture of isomers or a pharmaceutically acceptable salt thereof.

Another aspect of this invention is directed to methods of treating, inhibiting, or ameliorating one or more symptoms of a disease or disorder which is affected by cholesterol, comprising administering to a subject in need thereof a therapeutically effective amount of a compound of the present invention or an individual isomer or mixture of isomers or a pharmaceutically acceptable salt thereof.

Another aspect of this invention is directed to pharmaceutical compositions comprising a compound of the present invention or an individual isomer or mixture of isomers or a pharmaceutically acceptable salt thereof and at least one pharmaceutically acceptable carrier or excipient.

Another aspect of this invention is directed to regulation of reverse cholesterol transport and inflammatory signaling pathways that are implicated in human disease pathology including atherosclerosis and associated diseases such as myocardial infarction, peripheral arterial disease, and ischemic stroke in a subject in need thereof, comprising administering an effective reverse cholesterol transport and inflammatory signaling pathways regulating amount of a compound of the present invention or an individual isomer or mixture of isomers or a pharmaceutically acceptable salt thereof.

Another aspect of this invention is directed to treatment of the metabolic syndrome which comprises a constellation of disorders of metabolism including obesity, hypertension, insulin resistance, and diabetes including treatment of diseases resulting from compromised metabolism and immunity including atherosclerosis and diabetes as well as autoimmune disorders and diseases in a subject in need thereof, comprising administering a therapeutically effective amount of a compound of the present invention or an individual isomer or mixture of isomers or a pharmaceutically acceptable salt thereof.

Another aspect of this invention is directed to treatment of atherosclerosis, insulin resistance, osteoarthritis, stroke, hyperglycemia, dyslipidemia, psoriasis, aged and UV skin wrinkling, diabetes, cancer, Alzheimer's disease, inflammation, immunological disorders, lipid disorders, obesity, diabetic kidney disease, conditions characterized by a perturbed epidermal barrier function, conditions of disturbed differentiation or excess proliferation of the epidermis or mucous membrane, or cardiovascular disorders in a subject in need thereof, comprising administering a therapeutically effective amount of a compound of the present invention or an individual isomer or mixture of isomers or a pharmaceutically acceptable salt thereof.

Another aspect of this invention is directed to treatment of atherosclerosis, comprising administering a therapeutically effective amount of a compound of the present invention or an individual isomer or mixture of isomers or a pharmaceutically acceptable salt thereof.

The compounds of the invention may be useful in therapy.

The compounds of the invention may be used for the manufacture of a medicament for the treatment and/or prophylaxis of diseases or disorders associated with modulation of LXR activity.

The compounds of the invention can be used alone, in combination with other compounds of the present invention, or in combination with one or more, preferably one to two other agent(s).

Other features and advantages of the invention will be apparent from the following detailed description and claims.

DETAILED DESCRIPTION OF THE INVENTION

In one embodiment, the present invention is directed to compounds of formula (I)

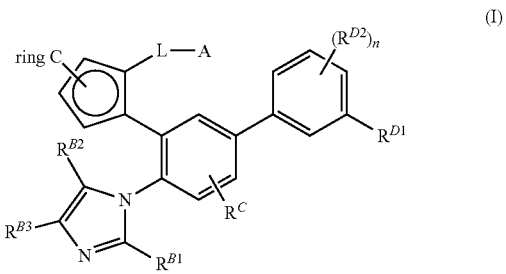

or an isomer, solvate, or a pharmaceutically acceptable salt thereof, wherein:

L is a bond, —[C(R$^1$)$_2$]$_m$—, -cyclopropyl-, or —CO—;

m is 1 or 2;

n is 0, 1, 2, 3, or 4;

R$^1$ is independently selected from H, C$_{1-3}$alkyl, —OH, and halo;

A is phenyl, cyclohexyl, a 5 or 6 membered heterocyclyl, or a 5 or 6 membered heteroaryl, wherein the phenyl is optionally fused to a 5 or 6 membered heterocyclyl or 5 or 6 membered heteroaryl, wherein A is optionally substituted with 1, 2, or 3 R$^A$ groups, wherein each R$^A$ is independently R$^{A1}$, —C$_1$-C$_6$alkyl-R$^{A1}$, C$_1$-C$_6$alkyl, C$_1$-C$_6$ haloalkyl, C$_2$-C$_6$alkenyl, C$_2$-C$_6$alkynyl, C$_3$-C$_8$cycloalkyl, or heterocyclyl, wherein the cycloalkyl or heterocyclyl are each optionally substituted with 1, 2, 3, or 4 groups that are independently R$^{A1}$, C$_1$-C$_6$alkyl, or —C$_1$-C$_6$alkyl-R$^{A1}$, wherein each R$^{A1}$ is independently halogen, cyano, nitro, —OR, —NR$_2$, —SR, —C(O)R, or —C(O)OR;

alternatively, 2R$^A$ on adjacent carbons can join to form a —O—CH$_2$—O—, —O—CH$_2$—CH$_2$—, —O—CH$_2$—CH$_2$—O—, —CH$_2$—CH$_2$—CH$_2$—, or —O—CF$_2$—O—;

ring C is a 5 membered heterocyclic ring selected from triazolyl, imidazolyl, pyrrazolyl, and oxazolyl; wherein when ring C is pyrrazolyl, imidazolyl, or oxazolyl, then ring C is optionally substituted with C$_{1-4}$alkyl, C$_{2-3}$alkenyl, C$_{1-3}$haloalkyl, C$_{3-6}$cycloalkyl, —CF$_3$, —C$_{1-4}$alkyl-OH, —C$_{1-4}$alkyl-O—C$_{1-3}$alkyl, —C$_{1-3}$alkyl-NR$_2$, —C$_{1-3}$alkyl-CO$_2$H, —C$_{1-3}$alkyl-NHSO$_2$—C$_{1-3}$alkyl, —NH—C$_{1-3}$alkyl-OR, or —C$_{1-3}$alkyl-pyrrolidinyl;

R$^{B1}$ is hydrogen, C$_{1-3}$alkyl, halo, or C$_{1-3}$haloalkyl;

R$^{B2}$ is hydrogen or halo;

$R^{B3}$ is hydrogen, $C_{1-3}$alkyl, halo, CN, $C_{1-3}$haloalkyl, —C(O)—$C_{1-3}$alkyl, —CO—$NH_2$, —CO—$N(R)_2$, or —$C_{1-3}$alkyl-OH, $R^{D1}$ and $R^{D2}$ are each independently $R^{D3}$, $C_1$-$C_6$alkyl, —$C_1$-$C_6$alkyl-$R^{D3}$, $C_1$-$C_6$haloalkyl, $C_2$-$C_6$alkenyl, $C_2$-$C_6$alkynyl, $C_3$-$C_8$cycloalkyl, or heterocyclyl, wherein the cycloalkyl or heterocyclyl are each optionally substituted with 1, 2, 3, or 4 groups that are independently $R^{D3}$, $C_1$-$C_6$alkyl, $C_3$-$C_6$cycloalkyl, or —$C_1$-$C_6$alkyl-$R^{D3}$, wherein each $R^{D3}$ is independently halogen, cyano, —OR, —$NR_2$, —SR, —C(O)R, —C(O)OR, —C(O)$NR_2$, —S(O)R, —S(O)$_2$R, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)$_2$R, —N(R)S(O)$_2$OR, —N(R)S(O)$_2NR_2$, or —S(O)$_2$N(R)C(O)$NR_2$; and $R^C$ is hydrogen, halogen, $C_1$-$C_6$alkyl, cyano, or nitro;

each R group is independently hydrogen, $C_1$-$C_6$alkyl, —$C_1$-$C_6$alkyl-$R^2$, $C_1$-$C_6$haloalkyl, —$C_1$-$C_6$haloalkyl-$R^2$, $C_2$-$C_6$alkenyl, $C_2$-$C_6$alkynyl, $C_3$-$C_8$cycloalkyl, or —$C_1$-$C_6$alkyl-$C_3$-$C_8$cycloalkyl, wherein each $R^2$ is independently cyano, —$OR^3$, —$N(R^3)_2$, —$N(R^3)S(O)_2R^3$, —$N(R^3)S(O)_2OR^3$, or —$N(R^3)S(O)_2 N(R^3)_2$, wherein each $R^3$ is independently hydrogen, $C_1$-$C_6$alkyl, or $C_1$-$C_6$haloalkyl.

In another embodiment, the present invention is directed to compounds of formula (I)

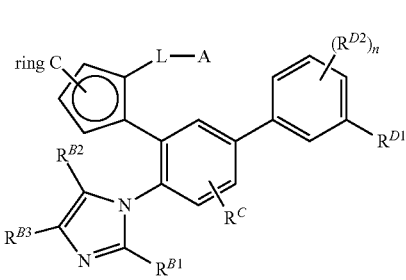

(I)

or an isomer, solvate, or a pharmaceutically acceptable salt thereof, wherein:

L is a bond, —[C($R^1$)$_2$]$_m$—, -cyclopropyl-, or —CO—; m is 1 or 2;

$R^1$ is independently selected from H, $C_{1-3}$alkyl, —OH, and halo;

A is phenyl, cyclohexyl, naphthalenyl, benzofuranyl, 2,3-dihydro-1H-indenyl, 1H-indolyl, pyridyl, pyrazinyl, pyrimidinyl, dihydrobenzofuranyl, pyridin-2(1H)-one, imidazo[1,2-a]pyridinyl, or piperidinyl, wherein A is optionally substituted with 1, 2, or 3 $R^A$ groups; wherein each $R^A$ is independently halo, CN, $C_{1-6}$alkyl, $C_1$-$C_6$haloalkyl, —O—R, —$NR_2$, —O—$C_{1-6}$alkyl, —O—$C_{1-6}$alkyl-$C_{3-6}$cycloalkyl, —S—R, —CO—R, —C(O)O—R, —$C_1$-$C_6$alkyl-CO—$NR_2$, pyrrolidinone, or pyrrolidinyl;

alternatively, 2$R^A$ on adjacent carbons can join to form a —O—$CH_2$—O—, —O—$CH_2$—$CH_2$—, —O—$CH_2$—$CH_2$—O—, or —O—$CF_2$—O—;

ring C is a 5 membered heterocyclic ring selected from triazolyl, imidazolyl, pyrrazolyl, and oxazolyl; wherein when ring C is pyrrazolyl, imidazolyl, or oxazolyl, then ring C is optionally substituted with $C_{1-4}$alkyl, $C_{2-3}$alkenyl, $C_{1-3}$haloalkyl, $C_{3-6}$cycloalkyl, —$CF_3$, —$C_{1-4}$alkyl-OH, —$C_{1-4}$alkyl-O—$C_{1-3}$alkyl, —$C_{1-3}$alkyl-$NR_2$; —$C_{1-3}$alkyl-$CO_2H$, —$C_{1-3}$alkyl-$NHSO_2$—$C_{1-3}$alkyl, —NH—$C_{1-3}$alkyl-OR, or —$C_{1-3}$alkyl-pyrrolidinyl;

$R^{B1}$ is hydrogen, $C_{1-3}$alkyl, halo, or $C_{1-3}$haloalkyl;

$R^{B2}$ is hydrogen or halo;

$R^{B3}$ is hydrogen, $C_{1-3}$alkyl, halo, CN, $C_{1-4}$haloalkyl, cyclopropyl, —CO—$NH_2$, —CO—$NR_2$, or —$C_{1-3}$alkyl-OH, $R^C$ is hydrogen, halogen, or cyano;

n is 0, 1, 2, 3, or 4; and $R^{D1}$ is —$SO_2$—$C_{1-6}$alkyl, —$SO_2$—$C_{1-6}$haloalkyl, —$SO_2$—$C_{3-6}$cycloalkyl, —$SO_2$—$C_{1-6}$alkyl-OH, —$SO_2$—$C_{1-6}$ alkyl-O—$C_{1-6}$alkyl, —C(Me)$_2$-COOH, —C(Me)$_2$-$CONR_2$, -cyclopropyl-$CONR_2$, —$SO_2NR_2$, —$SO_2NR$—$C_{1-6}$alkyl-OH, —$SO_2$-pyrrolidinyl, —$CONR_2$ $R^{D2}$ is independently —$C_{1-6}$haloalkyl-$C_{1-6}$alkyl-OH, halo, —$C_{1-6}$ alkyl-O—$C_{1-6}$ alkyl, —$C_{1-6}$alkyl-$NHSO_2$—$C_{1-6}$alkyl, $C_{1-6}$ haloalkyl, or —O—$C_{1-6}$ alkyl-O—$C_{1-6}$haloalkyl, each R group is independently hydrogen, $C_1$-$C_6$alkyl, —$C_1$-$C_6$alkyl-$R^2$, $C_1$-$C_6$haloalkyl, —$C_1$-$C_6$haloalkyl-$R^2$, $C_2$-$C_6$alkenyl, $C_2$-$C_6$alkynyl, or $C_3$-$C_8$cycloalkyl;

each $R^2$ is independently —$OR^3$, wherein each $R^3$ is independently hydrogen, $C_1$-$C_6$alkyl, or $C_1$-$C_6$haloalkyl.

In one embodiment, the present invention is directed to compounds of formula (I)

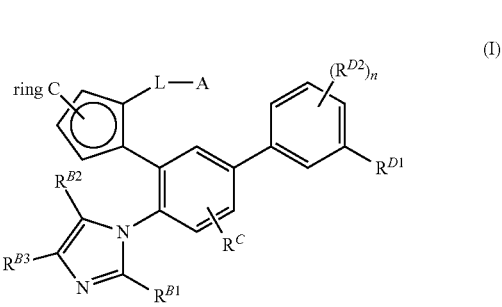

(I)

or an isomer, solvate, or a pharmaceutically acceptable salt thereof.

In one aspect, the present invention comprises compound of formula (I), wherein $R^{B1}$ is H, alkyl, or haloalkyl;

$R^{B2}$ is H, alkyl, or halo; and $R^C$ is hydrogen or halo.

In another aspect, the present invention comprises compound of formula (I), wherein L is a bond; and A is phenyl, pyridyl or pyrimidinyl.

In another aspect, the present invention comprises compound of formula (I), wherein L is a bond; and A is phenyl, pyridyl or pyrimidinyl, wherein A is optionally substituted with 1, 2, or 3 $R^A$ groups.

In another aspect, the present invention comprises compound of formula (I), wherein ring C is a 5 membered heterocyclic ring selected from triazolyl, imidazolyl, pyrrazolyl, and oxazolyl; wherein when ring C is oxazolyl, then ring C is optionally substituted with $C_{1-4}$alkyl, $C_{2-3}$alkenyl, $C_{1-3}$haloalkyl, $C_{3-6}$cycloalkyl, $CF_3$, $C_{1-4}$alkyl-OH, $C_{1-4}$ alkyl-O—$C_{1-3}$alkyl, $C_{1-3}$alkyl-NR$^2$; $C_{1-3}$alkyl-CO$_2$H, $C_{1-3}$ alkyl-NHSO$_2$—$C_{1-3}$alkyl, —NH—$C_{1-3}$alkyl-OR, $C_{1-3}$alkyl-pyrrolidinyl.

In another aspect, the present invention comprises compound of formula (I), wherein R$^{D1}$ is —SO$_2$-alkyl, SO$_2$NR$_2$, —C(Me)$_2$-CONH$_2$, or

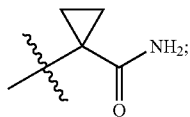

and

R$^{D2}$ is —$C_{1-6}$alkyl-OH, or halo.

In another aspect, the present invention comprises compound of formula (I), wherein ring C is a 5 membered heterocyclic ring selected from triazolyl, imidazolyl, pyrrazolyl, oxazolyl; wherein when ring C is oxazolyl, then ring C is optionally substituted with $C_{1-4}$alkyl, CF$_3$, cyclopropyl, $C_{1-3}$alkyl-N(CH$_3$)$_2$; $C_{1-4}$alkyl-OH, $C_{1-4}$alkyl-O—$C_{1-3}$alkyl.

In another aspect, the present invention comprises compound of formula (I), wherein ring C is a 5 membered heterocyclic ring selected from triazolyl, imidazolyl, pyrrazolyl, oxazolyl; wherein when ring C is oxazolyl, then ring C is optionally substituted with CH$_3$, CF$_3$, cyclopropyl.

In another aspect, the present invention comprises compound of formula (I), wherein R$^{D1}$ is —SO$_2$—CH$_3$, or SO$_2$NR$_2$.

In another aspect, the present invention comprises compound of formula (I), wherein R$^{D1}$ is —SO$_2$—CH$_3$.

In another aspect, the present invention comprises compound of formula (I), wherein the compound is of formula Ia, Ib, Ic, Id, Ie, or If (Ia)
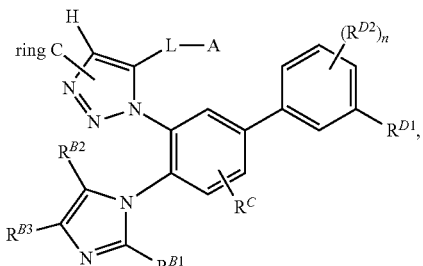

(Ib)
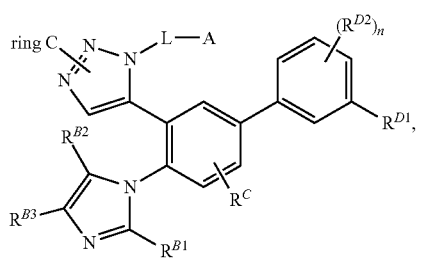

(Ic)
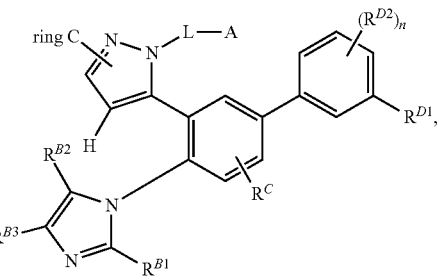

(Id)
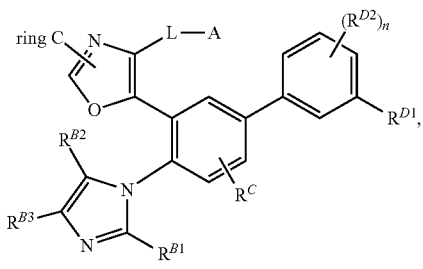

(Ie)
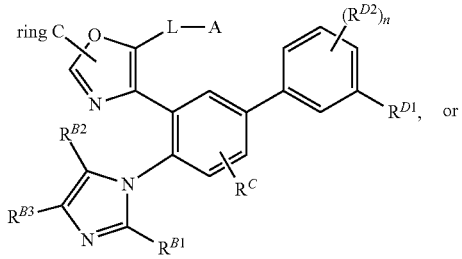

(If)
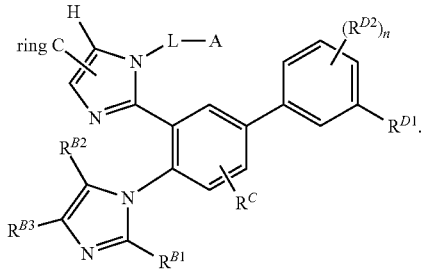

In another aspect, the present invention comprises compound of formula (I), wherein the compound is of formula Ia (Ia)
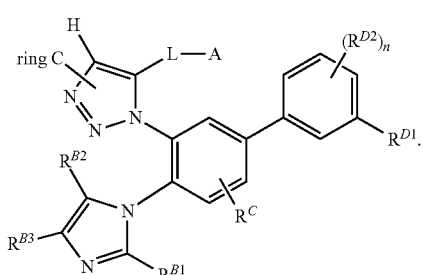

In another aspect, the present invention comprises compound of formula (I), wherein the compound is of formula Id

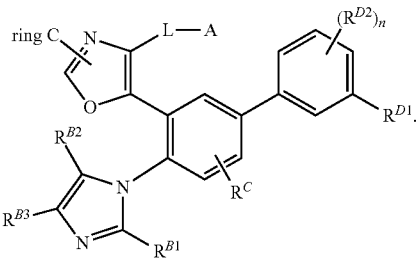

(Id)

In another aspect, the present invention comprises compound of formula (I), wherein the compound is of formula Ie

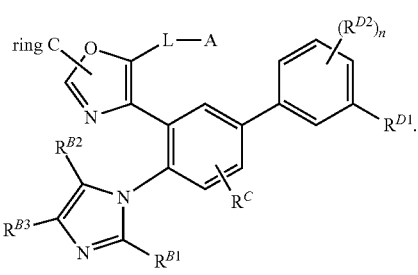

(Ie)

In another aspect, the present invention comprises compound of formula (I), wherein L is a bond.

In another aspect, the present invention comprises compound of formula (I), wherein A is phenyl, pyridyl or pyrimidinyl.

In another aspect, the present invention comprises compound of formula (I), wherein A is phenyl, pyridyl or pyrimidinyl, wherein A is optionally substituted with 1, 2, or 3 $R^A$ groups.

In another aspect, the present invention comprises compound of formula (I), wherein A is phenyl.

In another aspect, the present invention comprises compound of formula (I), wherein A is phenyl, wherein A is optionally substituted with 1, 2, or 3 $R^A$ groups.

In another aspect, the present invention comprises compound of formula (I), wherein each $R^A$ is independently $R^{A1}$, —$C_1$-$C_6$alkyl-$R^{A1}$, $C_1$-$C_6$alkyl, $C_1$-$C_6$ haloalkyl, $C_2$-$C_6$alkenyl, $C_2$-$C_6$alkynyl, $C_3$-$C_8$cycloalkyl, or 5 or 6 membered heterocyclyl, wherein the cycloalkyl or heterocyclyl are each optionally substituted with 1, 2, 3, or 4 groups that are independently $R^{A1}$, $C_1$-$C_6$alkyl, or —$C_1$-$C_6$alkyl-$R^{A1}$, wherein each $R^{A1}$ is independently halogen, cyano, nitro, —OR, —$NR_2$, —SR, —C(O)R, or —C(O)OR;

In another aspect, the present invention comprises compound of formula (I), wherein A is a phenyl and $R^A$ is O—$CF_2$—O—, —O—$CF_3$, or halo.

In another aspect, the present invention comprises compound of formula (I), wherein A is phenyl—4-$R^A$ In another aspect, the present invention comprises compound of formula (I), wherein A is pyridyl and $R^A$ is —$OCH_3$, halo.

In another aspect, the present invention comprises compound of formula (I), wherein ring C is a 5 membered heterocyclic ring selected from triazolyl, imidazolyl, pyrazolyl, oxazolyl; wherein when ring C is oxazolyl, then ring C is optionally substituted with $C_{1-4}$alkyl, $C_{2-3}$alkenyl, $C_{1-3}$haloalkyl, $C_{3-6}$cycloalkyl, $CF_3$, $C_{1-4}$alkyl-OH, $C_{1-4}$alkyl-O—$C_{1-3}$alkyl, $C_{1-3}$alkyl-$NR^2$; $C_{1-3}$alkyl-$CO_2H$, $C_{1-3}$alkyl-$NHSO_2$—$C_{1-3}$alkyl, —NH—$C_{1-3}$alkyl-OR, or $C_{1-3}$alkyl-pyrrolidinyl.

In another aspect, the present invention comprises compound of formula (I), wherein ring C is a 5 membered heterocyclic ring selected from triazolyl, imidazolyl, pyrazolyl, oxazolyl; wherein when ring C is oxazolyl, then ring C is optionally substituted with $C_{1-4}$alkyl, $CF_3$, cyclopropyl, $C_{1-3}$alkyl-$N(CH_3)_2$; $C_{1-4}$alkyl-OH, or $C_{1-4}$alkyl-O—$C_{1-3}$alkyl.

In another aspect, the present invention comprises compound of formula (I), wherein ring C is a 5 membered heterocyclic ring selected from triazolyl, imidazolyl, pyrazolyl, oxazolyl; wherein when ring C is oxazolyl, then ring C is optionally substituted with $CH_3$, $CF_3$, or cyclopropyl.

In another aspect, the present invention comprises compound of formula (I), wherein $R^C$ is hydrogen or halo.

In another aspect, the present invention comprises compound of formula (I), wherein $R^C$ is hydrogen.

In another aspect, the present invention comprises compound of formula (I), wherein $R^{B2}$ is H, alkyl, or halo.

In another aspect, the present invention comprises compound of formula (I), wherein $R^{B1}$ is H, alkyl, or haloalkyl.

In another aspect, the present invention comprises compound of formula (I), wherein $R^{D1}$ is —$SO_2$-alkyl, —$SO_2NR_2$, —$C(Me)_2$-$CONH_2$, or

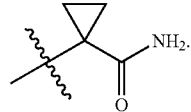 [SMILES: *C1(C(N)=O)CC1]

In another aspect, the present invention comprises compound of formula (I), wherein $R^{D1}$ is —$SO_2$—$CH_3$ or —$SO_2NR_2$.

In another aspect, the present invention comprises compound of formula (I), wherein $R^{D1}$ is —$SO_2$—$CH_3$.

In another aspect, the present invention comprises compound of formula (I), wherein $R^{D2}$ is —$C_{1-6}$ alkyl-OH or halo.

In another aspect, the present invention comprises compound of formula (I), wherein each R group is independently hydrogen, $C_1$-$C_6$alkyl, —$C_1$-$C_6$alkyl-$R^2$, $C_1$-$C_6$haloalkyl, —$C_1$-$C_6$haloalkyl-$R^2$, $C_2$-$C_6$alkenyl, $C_2$-$C_6$alkynyl, or $C_3$-$C_8$cycloalkyl, wherein each $R^2$ is independently cyano, —$OR^3$, —$N(R^3)_2$, —$N(R^3)S(O)_2R^3$, —$N(R^3)S(O)_2OR^3$, or —$N(R^3)S(O)_2N(R^3)_2$, or $C_{3-6}$cycloalkyl, wherein each $R^3$ is independently hydrogen, $C_1$-$C_6$alkyl, or $C_1$-$C_6$haloalkyl.

In another aspect, the present invention comprises compound of formula (I), wherein $R^1$ is independently selected from H, $C_{1-3}$alkyl, $C_{1-3}$haloalkyl, —OH, or halo.

In another aspect, the present invention comprises compound of formula (I), wherein each $R^{A1}$ is independently halogen, cyano, nitro, —OR, —$NR_2$, —SR, —C(O)R, —C(O)$NR^2$, or —C(O)OR.

In another embodiment, the present invention provides a compound of formula (I)

(I)

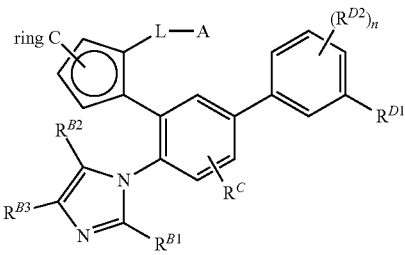

or a pharmaceutically acceptable salt or solvate, wherein:
L is a bond, —[C(R$^1$)$_2$]$_m$—, -cyclopropyl-, or —CO—;
m is 1 or 2;
n is 0, 1, 2, 3, or 4;
R$^1$ is independently selected from H, C$_{1-3}$alkyl, C$_{1-3}$haloalkyl, —OH, and halo;
A is phenyl, cyclohexyl, a 5 or 6 membered heterocycle, or a 5 or 6 membered heteroaryl, wherein the phenyl is optionally fused to a 5 or 6 membered heterocycle or 5 or 6 membered heteroaryl, wherein A is optionally substituted with 1, 2, or 3 R$^A$ groups, wherein
  each R$^A$ is independently R$^{A1}$, —C$_1$-C$_6$alkyl-R$^{A1}$, C$_1$-C$_6$alkyl, C$_1$-C$_6$ haloalkyl, C$_2$-C$_6$alkenyl, C$_2$-C$_6$alkynyl, C$_3$-C$_8$cycloalkyl, or heterocyclyl, wherein the cycloalkyl or heterocyclyl are each optionally substituted with 1, 2, 3, or 4 groups that are independently R$^{A1}$, C$_1$-C$_6$alkyl, or —C$_1$-C$_6$alkyl-R$^{A1}$, wherein
  each R$^{A1}$ is independently halogen, cyano, nitro, —OR, —NR$_2$, —SR, —C(O)R, or —C(O)OR;
  alternatively, 2R$^A$ on adjacent carbons can join to form a —O—CH$_2$—O—, —O—CH$_2$—CH$_2$—, —O—CH$_2$—CH$_2$—O—, —CH$_2$—CH$_2$—CH$_2$—, or —O—CF$_2$—O—;
ring C is a 5 membered heterocyclic ring selected from triazolyl, imidazolyl, pyrrazolyl, and oxazolyl; wherein when ring C is pyrrazolyl, imidazolyl, or oxazolyl, then ring C is optionally substituted with C$_{1-4}$alkyl, C$_{2-3}$alkenyl, C$_{1-3}$haloalkyl, C$_{3-6}$cycloalkyl, —CF$_3$, —C$_{1-4}$alkyl-OH, —C$_{1-4}$alkyl-O—C$_{1-3}$alkyl, —C$_{1-3}$alkyl-NR$_2$, —C$_{1-3}$alkyl-CO$_2$H, —C$_{1-3}$alkyl-NHSO$_2$—C$_{1-3}$alkyl, —NH—C$_{1-3}$alkyl-OR, or —C$_{1-3}$alkyl-pyrrolidinyl;
R$^{B1}$ is hydrogen, C$_{1-3}$alkyl, halo, or C$_{1-3}$haloalkyl;
R$^{B2}$ is hydrogen or halo;
R$^{B3}$ is hydrogen, C$_{1-3}$alkyl, halo, CN, C$_{1-3}$haloalkyl, —C(O)—C$_{1-3}$alkyl, —CO—NH$_2$, —CO—N(R)$_2$, or —C$_{1-3}$alkyl-OH,
R$^{D1}$ and R$^{D2}$ are each independently R$^{D3}$, C$_1$-C$_6$alkyl, —C$_1$-C$_6$alkyl-R$^{D3}$, C$_1$-C$_6$haloalkyl, C$_2$-C$_6$alkenyl, C$_2$-C$_6$alkynyl, or C$_3$-C$_8$cycloalkyl, or heterocyclyl, wherein the cycloalkyl or heterocyclyl are each optionally substituted with 1, 2, 3, or 4 groups that are independently R$^{D3}$, C$_1$-C$_6$alkyl, C$_3$-C$_6$cycloalkyl, or —C$_1$-C$_6$alkyl-R$^{D3}$, wherein
each R$^{D3}$ is independently halogen, cyano, —OR, —NR$_2$, —SR, —C(O)R, —C(O)OR, —C(O)NR$_2$, —S(O)R, —S(O)$_2$R, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)$_2$R, —N(R)S(O)$_2$OR, —N(R)S(O)$_2$NR$_2$, or —S(O)$_2$N(R)C(O)NR$_2$;
R$^C$ is hydrogen, halogen, C$_1$-C$_6$alkyl, cyano, or nitro; and
each R group is independently hydrogen, C$_1$-C$_6$alkyl, —C$_1$-C$_6$alkyl-R$^2$, C$_1$-C$_6$haloalkyl, —C$_1$-C$_6$haloalkyl-R$^2$, C$_2$-C$_6$alkenyl, C$_2$-C$_6$alkynyl, C$_3$-C$_8$cycloalkyl, or —C$_1$-C$_6$alkyl-C$_3$-C$_8$cycloalkyl, wherein each R$^2$ is independently cyano, —OR$^3$, —N(R$^3$)$_2$, —N(R$^3$)S(O)$_2$R$^3$, —N(R$^3$)S(O)$_2$OR$^3$, or —N(R$^3$)S(O)$_2$ N(R$^3$)$_2$, wherein each R$^3$ is independently hydrogen, C$_1$-C$_6$alkyl, or C$_1$-C$_6$haloalkyl.

In another embodiment, the present invention is directed to compounds of formula (I)

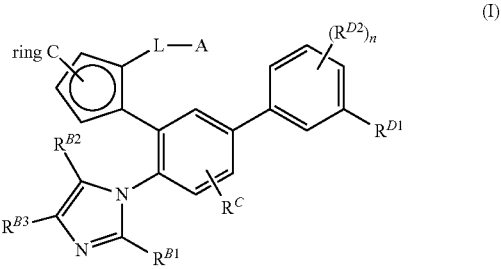

(I)

or a pharmaceutically acceptable salt or solvate thereof, wherein:
L is a bond, —[C(R$^1$)$_2$]$_m$—, -cyclopropyl-, or —CO—;
m is 1 or 2;
R$^1$ is independently selected from H, C$_{1-3}$alkyl, C$_{1-3}$haloalkyl, —OH, and halo;
A is phenyl, cyclohexyl, naphthalenyl, benzofuranyl, 2,3-dihydro-1H-indenyl, 1H-indolyl, pyridyl, pyrazinyl, pyrimidinyl, dihydrobenzofuranyl, pyridin-2(1H)-one, imidazo[1,2-a]pyridinyl, or piperidinyl, wherein A is optionally substituted with 1, 2, or 3 R$^A$ groups; wherein
  each R$^A$ is independently halo, CN, C$_{1-6}$alkyl, C$_1$-C$_6$haloalkyl, —O—R, —NR$_2$, —O—C$_{1-6}$alkyl, —O—C$_{1-6}$alkyl-C$_{3-6}$cycloalkyl, —S—R, —CO—R, —C(O)O—R, —C$_1$-C$_6$alkyl-CO—NR$_2$, pyrrolidinone, or pyrrolidinyl;
alternatively, 2R$^A$ on adjacent carbons can join to form a —O—CH$_2$—O—, —O—CH$_2$—CH$_2$—, —O—CH$_2$—CH$_2$—O—, or —O—CF$_2$—O—;
ring C is a 5 membered heterocyclic ring selected from triazolyl, imidazolyl, pyrrazolyl, and oxazolyl; wherein when ring C is pyrrazolyl, imidazolyl, or oxazolyl, then ring C is optionally substituted with C$_{1-4}$alkyl, C$_{2-3}$alkenyl, C$_{1-3}$haloalkyl, C$_{3-6}$cycloalkyl, —CF$_3$, —C$_{1-4}$alkyl-OH, —C$_{1-4}$alkyl-O—C$_{1-3}$alkyl, —C$_{1-3}$alkyl-NR$_2$; —C$_{1-3}$alkyl-CO$_2$H, —C$_{1-3}$alkyl-NHSO$_2$—C$_{1-3}$alkyl, —NH—C$_{1-3}$alkyl-OR, or —C$_{1-3}$alkyl-pyrrolidinyl;
R$^{B1}$ is hydrogen, C$_{1-3}$alkyl, halo, or C$_{1-3}$haloalkyl;
R$^{B2}$ is hydrogen or halo;
R$^{B3}$ is hydrogen, C$_{1-3}$alkyl, halo, CN, C$_{1-4}$haloalkyl, cyclopropyl, —CO—NH$_2$, —CO—NR$_2$, or —C$_{1-3}$alkyl-OH,
R$^C$ is hydrogen, halogen, or cyano;
n is 0, 1, 2, 3, or 4; and
R$^{D1}$ is —SO$_2$—C$_{1-6}$alkyl, —SO$_2$—C$_{1-6}$haloalkyl, —SO$_2$—C$_{3-6}$cycloalkyl, —SO$_2$—C$_{1-6}$alkyl-OH, —SO$_2$—C$_{1-6}$ alkyl-O—C$_{1-6}$alkyl, —C(Me)$_2$—COOH, —C(Me)$_2$—CONR$_2$, -cyclopropyl-CONR$_2$, —SO$_2$NR$_2$, —SO$_2$NR—C$_{1-6}$alkyl-OH, —SO$_2$-pyrrolidinyl, —CONR$_2$
R$^{D2}$ is independently —C$_{1-6}$haloalkyl-C$_{1-6}$alkyl-OH, halo, —C$_{1-6}$ alkyl-O—C$_{1-6}$ alkyl, —C$_{1-6}$alkyl-NHSO$_2$—C$_{1-6}$alkyl, C$_{1-6}$ haloalkyl, or —O—C$_{1-6}$ alkyl-O—C$_{1-6}$haloalkyl, each R group is independently hydrogen, $C_1$-$C_6$alkyl, —$C_1$-$C_6$alkyl-$R^2$, $C_1$-$C_6$haloalkyl, —$C_1$-$C_6$haloalkyl-$R^2$, $C_2$-$C_6$alkenyl, $C_2$-$C_6$alkynyl, or $C_3$-$C_8$cycloalkyl; and each $R^2$ is independently —$OR^3$, wherein each $R^3$ is independently hydrogen, $C_1$-$C_6$alkyl, or $C_1$-$C_6$haloalkyl.

In another embodiment, the present invention comprises compounds of formula (I), or a pharmaceutically acceptable salt or solvate thereof, wherein ring C is a 5 membered heterocyclic ring selected from triazolyl, imidazolyl, pyrrazolyl, and oxazolyl; wherein when ring C is pyrrazolyl, imidazolyl, or oxazolyl, then ring C is optionally substituted with $C_{1-4}$alkyl, $C_{2-3}$alkenyl, $C_{1-3}$haloalkyl, $C_{3-6}$cycloalkyl, $CF_3$, $C_{1-4}$alkyl-OH, $C_{1-4}$alkyl-O—$C_{1-3}$alkyl, $C_{1-3}$alkyl-$NR^2$; $C_{1-3}$alkyl-$CO_2H$, $C_{1-3}$alkyl-$NHSO_2$—$C_{1-3}$alkyl, —NH—$C_{1-3}$alkyl-OR, $C_{1-3}$alkyl-pyrrolidinyl.

In another embodiment, the present invention comprises compounds of formula (I), or a pharmaceutically acceptable salt or solvate thereof, wherein ring C is a 5 membered heterocyclic ring selected from triazolyl, imidazolyl, pyrrazolyl, oxazolyl; wherein when ring C is pyrrazolyl, imidazolyl, or oxazolyl, then ring C is optionally substituted with $C_{1-4}$alkyl, $CF_3$, cyclopropyl, $C_{1-3}$alkyl-$N(CH_3)_2$; $C_{1-4}$alkyl-OH, $C_{1-4}$alkyl-O—$C_{1-3}$alkyl.

In another embodiment, the present invention comprises compounds of formula (I), or a pharmaceutically acceptable salt or solvate thereof, wherein ring C is a 5 membered heterocyclic ring selected from triazolyl, imidazolyl, pyrrazolyl, oxazolyl; wherein when ring C is pyrrazolyl, imidazolyl, or oxazolyl, then ring C is optionally substituted with $CH_3$, $CF_3$, cyclopropyl.

In another embodiment, the present invention comprises compounds of formula (I), or a pharmaceutically acceptable salt or solvate thereof, wherein ring C is a 5 membered heterocyclic ring selected from triazolyl, imidazolyl, pyrrazolyl, oxazolyl; wherein when ring C is pyrrazolyl, imidazolyl, or oxazolyl, then ring C is optionally substituted with $C_{1-4}$alkyl, $C_{2-3}$alkenyl, $C_{1-3}$haloalkyl, $C_{3-6}$cycloalkyl, $CF_3$, $C_{1-4}$alkyl-OH, $C_{1-4}$alkyl-O—$C_{1-3}$alkyl, $C_{1-3}$alkyl-$NR^2$; $C_{1-3}$alkyl-$CO_2H$, $C_{1-3}$alkyl-$NHSO_2$—$C_{1-3}$alkyl, —NH—$C_{1-3}$alkyl-OR, or $C_{1-3}$alkyl-pyrrolidinyl.

In another embodiment, the present invention comprises compounds of formula (I), or a pharmaceutically acceptable salt or solvate thereof, wherein ring C is a 5 membered heterocyclic ring selected from triazolyl, imidazolyl, pyrrazolyl, oxazolyl; wherein when ring C is pyrrazolyl, imidazolyl, or oxazolyl, then ring C is optionally substituted with $C_{1-4}$alkyl, $CF_3$, cyclopropyl, $C_{1-3}$alkyl-$N(CH_3)_2$; $C_{1-4}$alkyl-OH, or $C_{1-4}$alkyl-O—$C_{1-3}$alkyl.

In another embodiment, the present invention comprises compounds of formula (I), or a pharmaceutically acceptable salt or solvate thereof, wherein ring C is a 5 membered heterocyclic ring selected from triazolyl, imidazolyl, pyrrazolyl, oxazolyl; wherein when ring C is pyrrazolyl, imidazolyl, or oxazolyl, then ring C is optionally substituted with $CH_3$, $CF_3$, or cyclopropyl.

The various compounds described herein, or their pharmaceutically acceptable salts, may contain one or more asymmetric centers and may thus give rise to isomers, such as enantiomers, diastereomers, and other stereoisomeric forms. Such forms may be defined, in terms of absolute stereochemistry, as (R)- or (S)-, or as (D)- or (L)- for amino acids. The present invention is meant to include all such possible individual stereoisomers and mixtures thereof, including their racemic and optically pure enantiomeric or diastereomeric forms. The compounds are normally prepared as racemates and can conveniently be used as such, or optically active (+) and (−), (R)- and (S)-, or (D)- and (L)-isomers or corresponding diastereomers may be prepared using chiral synthons or chiral reagents, or they may be resolved from racemic mixtures using conventional techniques, such as chiral chromatography or reverse phase HPLC. When the compounds described herein contain olefinic double bonds or other centers of geometric asymmetry, and unless specified otherwise, it is intended that the compounds include both E and Z geometric isomers.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2H$ or D and $^3H$ or T, carbon such as $^{11}C$, $^{13}C$, and $^{14}C$, chlorine, such as $^{36}Cl$, fluorine such as $^{18}F$, iodine, such as $^{123}I$ and $^{125}I$, nitrogen, such as $^{13}N$ and $^{15}N$, oxygen, such as $^{15}O$, $^{17}O$, and $^{18}O$, phosphorus, such as $^{32}P$, and sulfur, such as $^{35}S$. Certain isotopically-labeled compounds of the invention, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, $^2H$ or D, may afford certain therapeutic advantages resulting from greater metabolic stability, for example, increase in vivo half-life or reduced dosage requirements, and hence may be preferred in some circumstances. Substitution with positron emitting isotopes, such as $^{11}C$, $^{18}F$, $^{15}O$, and $^{13}N$, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The present invention may be embodied in other specific forms without parting from the spirit or essential attributes thereof. This invention encompasses all combinations of aspects and/or embodiments of the invention noted herein. It is understood that any and all aspects or embodiments of the present invention may be taken in conjunction with any other aspect or embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Definitions

The following terms and expressions used herein have the indicated meanings.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)OC$_1$-C$_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms, or 1 to 8 carbon atoms, 1 to 6 carbon atoms, 1 to 4 carbon atoms, or 1 to 3 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CH(CH$_3$)—, —CH$_2$CH (CH$_2$CH$_3$)CH$_2$—.

The term "alkyloxycarbonyl" as used herein means an —C(O)OR$^0$ group, where R$^0$ is an alkyl group as defined herein.

The term "alkylcarbonyloxy" as used herein means an —OC(O)R$^0$ group, where R$^0$ is an alkyl group as defined herein.

The term "alkylthio" as used herein, means an —SR$^0$ group, where R$^0$ is an alkyl group as defined herein.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino" as used herein, means a —NH$_2$ group.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3 (4H)-on-7-yl, 2H-benzo[b][1,4]oxazin3 (4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2 (3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo [d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "arylalkyl" and "-alkylaryl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "carboxy" as used herein, means a —CO$_2$H group.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1] nonane, and bicyclo[4.2.1]nonane. Fused bicyclic cycloalkyl ring systems contain a monocyclic cycloalkyl ring fused to a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

"Cycloalkenyl" as used herein refers to a monocyclic or a bicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

"Nuclear receptor" refers to a receptor that activates or represses transcription of one or more genes in the nucleus (but can also have second messenger signaling actions), typically in conjunction with other transcription factors. The nuclear receptor is activated by the natural cognate ligand for the receptor. Nuclear receptors are ordinarily found in the cytoplasm or nucleus, rather than being membrane-bound. A nuclear receptor is a member of a superfamily of regulatory proteins that are receptors for various endogenous small molecules, e.g., steroids, retinoids, vitamin D and thyroid hormones. These proteins bind to cis-acting elements in the promoters of their target genes and modulate gene expression in response to a ligand therefore. Nuclear receptors may be classified based on their DNA binding properties. For example, the glucocorticoid, estrogen, androgen, progestin and mineralocorticoid receptors bind as homodimers to hormone response elements (HREs) organized as inverted repeats. Another example are receptors, including those activated by retinoic acid, thyroid hormone, vitamin D$_3$, fatty acids/peroxisome proliferators and ecdysone, that bind to HREs as heterodimers with a common partner, the retinoid X receptor (RXR). Among the latter receptors is LXR.

"Liver X receptor" or "LXR" refers to a nuclear receptor implicated in cholesterol biosynthesis. As used herein, the term LXR refers to both LXR$_\alpha$ and LXR$_\beta$, two forms of the protein found in mammals. Liver X receptor-α or LXR$_\alpha$ refers to the receptor described in U.S. Pat. Nos. 5,571,696, 5,696,233 and 5,710,004, and Willy et al. (1995) Gene Dev. 9(9): 1033-1045. Liver X receptor-β or LXR$_\beta$ refers to the receptor described in Peet et al. (1998) Curr. Opin. Genet. Dev. 8(5):571-575; Song et al. (1995) Ann. N.Y. Acad. Sci. 761:38-49; Alberti et al. (2000) Gene 243(1-2):93-103; and references cited therein; and in U.S. Pat. Nos. 5,571,696, 5,696,233 and 5,710,004.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

Compounds described herein may form salts or solvates which are also within the scope of this invention. Reference to a compound described herein is understood to include reference to salts thereof, unless otherwise indicated. The term "salt(s)", as employed herein, denotes acidic and/or basic salts formed with inorganic and/or organic acids and bases. In addition, when a compound described herein contains both a basic moiety and an acidic moiety, zwitterions ("inner salts") may be formed and are included within the term "salt(s)" as used herein. In one embodiment, the salts are pharmaceutically acceptable (i.e., non-toxic, physiologically acceptable), although other salts are also useful, e.g., in isolation or purification steps which may be employed during preparation. Salts of the compounds described herein may be formed, for example, by reacting a compound with an amount of acid or base, such as an equivalent amount, in a medium such as one in which the salt precipitates or in an aqueous medium followed by lyophilization.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. In one aspect, inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. In another aspect, organic bases are isopropylamine, diethylamine, ethanolamine, trimethylamine, dicyclohexylamine, choline and caffeine.

"Acid addition salts" and "base addition salts" which are not pharmaceutically acceptable may be useful in the preparation and/or purification of the compounds.

The present invention is intended to cover the compounds in their neutral state, salts of those compounds, or mixtures of the compounds in their neutral state with one or more salt forms, or mixtures of salt forms.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Modulating" or "modulate" refers to the treating, prevention, suppression, enhancement or induction of a function, condition or disorder. For example, it is believed that the compounds of the present invention can modulate atherosclerosis by stimulating the removal of cholesterol from atherosclerotic lesions in a human.

"Treating" or "treatment" as used herein covers the treatment, propylaxis treatment, and/or reducing the risk of a disease or disorder described herein, in a subject, such as a human, and includes:

i. inhibiting a disease or disorder, i.e., arresting its development; or ii. relieving a disease or disorder, i.e., causing regression of the disorder.

"Subject" refers to a warm blooded animal such as a mammal, such as a human, or a human child, which is afflicted with, or has the potential to be afflicted with one or more diseases and disorders described herein.

"Atherosclerosis" refers to a process whereby atherosclerotic plaques form within the inner lining of the artery wall leading to atherosclerotic cardiovascular diseases. Atherosclerotic cardiovascular diseases can be recognized and understood by physicians practicing in the relevant fields of medicine, and include without limitation, restenosis, coronary heart disease (also known as coronary artery disease or ischemic heart disease), cerebrovascular disease including ischemic stroke, multi-infarct dementia, and peripheral vessel disease, including intermittent claudication, and erectile dysfunction.

"Dyslipidemia" refers to abnormal levels of lipoproteins in blood plasma including both depressed and/or elevated levels of lipoproteins (e.g., elevated levels of Low Density Lipoprotein, (LDL), Very Low Density Lipoprotein (VLDL) and depressed levels of High Density Lipoprotein (HDL).

"$EC_{50}$" refers to a dosage, concentration or amount of a particular test compound that elicits a dose-dependent response at 50% of maximal expression of a particular response that is induced, provoked or potentiated by the particular test compound.

"Cholesterol" refers to a steroid alcohol that is an essential component of cell membranes and myelin sheaths and, as used herein, incorporates its common usage. Cholesterol also serves as a precursor for steroid hormones and bile acids.

"Triglyceride(s)" or "TGs" refers to three fatty acid molecules esterified to a glycerol molecule and serve to store fatty acids which are used by muscle cells for energy production or are taken up and stored in adipose tissue.

"$IC_{50}$" refers to an amount, concentration or dosage of a particular test compound that achieves a 50% inhibition of a maximal response, such as modulation of nuclear receptor, including the $LXR_\alpha$ or $LXR_\beta$ activity, in an assay that measures such response.

"LXR" or "LXRs" refers to both $LXR_\alpha$ and $LXR_\beta$.

"$LXR_\alpha$" (LXR alpha) refers to all mammalian forms of such receptor including, for example, alternative splice isoforms and naturally occurring isoforms. Representative $LXR_\alpha$ species include, without limitation the rat (Genbank Accession NM_031627), mouse (Genbank Accession BC012646), and human (GenBank Accession No. U22662) forms of the receptor.

"$LXR_\beta$" (LXR beta) refers to all mammalian forms of such receptor including, for example, alternative splice isoforms and naturally occurring isoforms. Representative $LXR_\beta$ species include, without limitation the rat (GenBank Accession NM_031626), mouse (Genbank Accession NM_009473), and human (GenBank Accession No. U07132) forms of the receptor.

"Obese" and "obesity" refer to a Body Mass Index (BMI) greater than 27.8 $kg/m^2$ for men and 27.3 $kg/m^2$ for women (BMI equals weight $(kg)/(height)^2(m^2)$).

"Stable compound" and "stable structure" are meant to indicate a compound that is sufficiently robust to survive isolation to a useful degree of purity from a reaction mixture, and formulation into an efficacious therapeutic agent. The present invention is intended to cover stable compounds.

Utility

The compounds of the invention exhibit valuable pharmacological properties and are particularly useful as LXR agonists, antagonists, inverse agonists, partial agonists and antagonists, or are selective to $LXR_\alpha$ or to $LXR_\beta$. The compounds of the invention are useful for the treatment of diseases or disorders described herein, such as those associated with, or having symptoms arising from the complications of, altered cholesterol transport, reverse cholesterol transport, fatty acid metabolism, cholesterol absorption, cholesterol re-absorption, cholesterol secretion, cholesterol excretion, or cholesterol metabolism.

These diseases include, for example, atherosclerosis, atherosclerotic cardiovascular diseases, (see, e.g., International Patent Application Publication Nos. WO 00/57915 and WO 00/37077), dyslipidemia, hyperglycemia, insulin resistance, diabetes, obesity, syndrome X (US Patent Application Publication No. 20030073614, International Patent Application Publication No. WO 01/82917), excess lipid deposition in peripheral tissues such as skin (xanthomas) (see, e.g., U.S. Pat. Nos. 6,184,215 and 6,187,814), stroke, peripheral occlusive disease, memory loss (*Brain Research* (1997), Vol. 752, pp. 189-196), optic nerve and retinal pathologies (i.e., macular degeneration, retintis pigmentosa), repair of traumatic damage to the central or peripheral nervous system (*Trends in Neurosciences* (1994), Vol. 17, pp. 525-530), prevention of the degenerative process due to aging (*American Journal of Pathology* (1997), Vol. 151, pp. 1371-1377), or Alzheimer's disease (see, e.g., International Patent Application Publication No. WO 00/17334; *Trends in Neurosciences* (1994), Vol. 17, pp. 525-530), prevention of degenerative neuropathies occurring in diseases such as diabetic neuropathies (see, e.g., International Patent Application Publication No. WO 01/82917), multiple sclerosis (*Annals of Clinical Biochem.* (1996), Vol. 33, No. 2, pp. 148-150), and autoimmune diseases (*J. Lipid Res.* (1998), Vol. 39, pp. 1740-1743).

Also provided, are methods of increasing the expression of ATP-Binding Cassette (ABCA1), (see, e.g., International Patent Application Publication No. WO 00/78972) thereby increasing reverse cholesterol transport in mammalian cells using the claimed compounds and compositions.

Accordingly in another aspect, the invention also includes methods to remove cholesterol from tissue deposits such as atherosclerotic plaques or xanthomas in a subject with atherosclerosis or atherosclerotic cardiovascular disease manifest by clinical signs of such disease, wherein the methods comprise administering to the subject a therapeutically effective amount of a compound or composition of the present invention. Additionally, the instant invention also provides a method for preventing or reducing the risk of a first or subsequent occurrence of an atherosclerotic cardiovascular disease event including ischemic heart disease, ischemic stroke, multi-infarct dementia, and intermittent claudication comprising the administration of a prophylactically effective amount of a compound or composition of the present invention to a subject at risk for such an event.

The compounds of the present invention can also be used in methods for decreasing hyperglycemia and insulin resistance, i.e., in methods for treating diabetes (International Patent Application Publication No. WO 01/82917), and in methods of treatment, prevention, or amelioration of disorders related to, or arising as complications of diabetes, hyperglycemia or insulin resistance including the cluster of disease states, conditions or disorders that make up "Syndrome X" (See US Patent Application 20030073614) comprising the administration of a therapeutically effective amount of a compound or composition of the present invention to a subject in need of such treatment. Additionally, the instant invention also provides a method for preventing or reducing the risk of developing hyperglycemia, insulin resistance, diabetes or syndrome X in a subject, comprising the administration of a prophylactically effective amount of a compound or composition of the present invention to a subject at risk for such an event.

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996). Uncontrolled hyperglycemia is associated with increased and premature mortality due to an increased risk for macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: type 1 diabetes (formerly referred to as insulin-dependent diabetes or IDEM); and type 2 diabetes (formerly referred to as noninsulin dependent diabetes or NIDDM). Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequate control of glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese subjects and lipid oxidation is increased.

Premature development of atherosclerosis and an increased rate of cardiovascular and peripheral vascular diseases are characteristic features of subjects with diabetes. Hyperlipidemia is an important precipitating factor for these diseases. Hyperlipidemia is a disorder generally characterized by an abnormal increase in serum lipids, e.g., cholesterol and triglyceride, in the bloodstream and is an important risk factor in developing atherosclerosis and heart disease. For a review of disorders of lipid metabolism, see, e.g., Wilson, J. et al., (ed.), Disorders of Lipid Metabolism, Chapter 23, Textbook of Endocrinology, 9th Edition, (W. B. Sanders Company, Philadelphia, Pa. U.S.A. 1998).

Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. Ann. Chim. Med. (1927), Vol. 5, pp. 1061-1079). Epidemiological studies since then have confirmed the association and have shown a several-fold increase in coronary deaths among diabetic subjects when compared with non-diabetic subjects (see, e.g., Garcia, M. J. et al., Diabetes (1974), Vol. 23, pp. 105-11 (1974); and Laakso, M. and Lehto, S., Diabetes Reviews (1997), Vol. 5, No. 4, pp. 294-315). Several lipoprotein abnormalities have been described among diabetic subjects (Howard B., et al., Arteriosclerosis (1978), Vol. 30, pp. 153-162).

Further provided by this invention are methods of using the compounds of the invention to treat obesity, as well as the complications of obesity. Obesity is linked to a variety of medical disorders including diabetes and hyperlipidemia. Obesity is also a known risk factor for the development of type 2 diabetes (See, e.g., Barrett-Conner, E., Epidemol. Rev. (1989), Vol. 11, pp. 172-181; and Knowler, et al., Am. J Clin. Nutr. (1991), Vol. 53, pp. 1543-1551).

Administration and Formulation

A compound of the invention can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumor, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

A compound of the invention can be administered in any acceptable solid, semi-solid, liquid or gaseous dosage form. Acceptable dosage forms include, but are not limited to, aerosols, capsules, creams, emulsions, gases, gels, grains, liniments, lotions, ointments, pastes, powders, solutions, suspensions, syrups and tablets. Acceptable delivery systems include, but are not limited to, biodegradable implants (e.g., poly(DL-lactide), lactide/glycolide copolymers and lactide/caprolactone copolymers), capsules, douches, enemas, inhalers, intrauterine devices, nebulizers, patches, pumps and suppositories.

A dosage form of the invention may be comprised solely of a compound of the invention or the compound of the invention may be formulated along with conventional excipients, pharmaceutical carriers, adjuvants, and/or other medicinal or pharmaceutical agents. Acceptable excipients include, but are not limited to, (a) antiadherents, such as croscarmellose sodium, crosprovidone, sodium starch glycolate, microcrystalline cellulose, starch and talc; (b) binders, such as cellulose, gelatin, hydroxypropyl cellulose, lactose, maltitol, polyethylene glycol, polyvinyl pyrrolidone, sorbitol, starch, sugar, sucrose and xylitol; (c) coatings, such as cellulose, shellac, zein and enteric agents; (d) disintegrants, such as cellulose, crosslinked polyvinyl pyrrolidone, sodium carboxymethyl cellulose, methylcellulose, microcrystalline cellulose, sodium starch glycolate and starch; (e) filling agents, such as calcium carbonate, cellulose, dibasic calcium phosphate, glucose, lactose, mannitol, sorbitol and sucrose; (f) flavoring agents; (g) coloring agents; (h) glidants, such as calcium stearate, colloidal silicon dioxide, glyceryl behenate, glyceryl monostearate, glyceryl palmitostearate, hydrogenated vegetable oil, magnesium stearate, magnesium trisilicate, mineral oil, polyethylene glycols, silicon dioxide, starch, stearate, stearic acid, talc, sodium stearyl fumarate, sodium benzoate and zinc; (i) lubricants, such as calcium stearate, hydrogenated vegetable oils, magnesium stearate, mineral oil, polyethylene glycol, sodium stearyl fumarate, stearin, stearic acid and talc; and (j) preservatives, such as chlorobutanol, citric acid, cysteine, methionine, methyl paraben, phenol, propyl paraben, retinyl palmitate, selenium, sodium citrate, sorbic acid, vitamin A, vitamin C and vitamin E. Capsules may contain any of the afore listed excipients, and may additionally contain a semi-solid or liquid carrier, such as a polyethylene glycol or vegetable-based oils. Pharmaceutical carriers include soluble polymers, microparticles made of insoluble or biodegradable natural and synthetic polymers, microcapsules or microspheres, lipoproteins, liposomes and micelles.

The pharmaceutical composition may be in the form of a liquid, e.g., an elixir, syrup, solution, emulsion, suspension, or other like forms or may be presented as a dry product for reconstitution with water or other suitable vehicle before use. Liquid preparations may contain conventional additives such as (a) liquid diluents, such as water, saline, Ringer's solution, fixed oils such as synthetic mono or diglycerides, or polyethylene glycols, glycerin, propylene glycol or other solvents; (b) surfactants, suspending agents, or emulsifying agents, such as polyoxyethylene sorbitan fatty acid esters, saturated polyglycolized glycerides, monoglycerides, fatty acid esters, block copolymers of ethylene oxide and propylene oxide, polyoxyl stearates, ethoxylated castor oils, and ethoxylated hydroxystearic acids; (c) buffers, such as acetates, citrates or phosphates; (d) chelating agents, such as ethylenediaminetetraacetic acid; (e) antibacterial agents, such as benzyl alcohol or methyl paraben; (f) antioxidants, such as ascorbic acid or sodium bisulfite; (g) isotonic agents, sodium chloride or dextrose; as well as sweetening and flavoring agents, dyes and preservatives.

A pharmaceutical composition of the invention will contain a therapeutically effective amount of a compound of the invention, as an individual stereoisomer or mixture of stereoisomers, or a pharmaceutically acceptable salt thereof, with the remainder of the pharmaceutical composition comprised of one or more pharmaceutically acceptable excipients. Generally, for oral administration, a compound of the invention, as an individual stereoisomer or mixture of stereoisomers, or a pharmaceutically acceptable salt thereof will comprise from 1% to 99% by weight of a pharmaceutically acceptable composition, with the remainder of the composition comprised of one or more pharmaceutically acceptable excipients. Typically, a compound of the invention, as an individual stereoisomer or mixture of stereoisomers, or a pharmaceutically acceptable salt thereof will comprise from 5% to 75% by weight of a pharmaceutically acceptable composition, with the remainder of the composition comprised of one or more pharmaceutically acceptable excipients. For parenteral administration, a compound of the invention, as an individual stereoisomer or mixture of stereoisomers, or a pharmaceutically acceptable salt thereof will comprise from 0.01% to 1% by weight of a pharmaceutically acceptable composition. Methods for preparing the dosage forms of the invention are known, or will be apparent, to those skilled in this art; for example, see Remington's Pharmaceutical Sciences, 18th Ed., (Mack Publishing Company, Easton, Pa., 1990).

A therapeutically effective amount of a compound of the invention will vary depending upon a sundry of factors including the activity, metabolic stability, rate of excretion and duration of action of the compound, the age, weight, general health, sex, diet and species of the subject, the mode and time of administration of the compound, the presence of adjuvants or additional therapeutically active ingredients in a composition, and the severity of the disease for which the therapeutic effect is sought.

The compounds of the invention can be administered to human subjects at dosage levels in the range of about 0.1 to about 10,000 mg per day. A normal human adult having a body weight of about 70 kilograms can be administered a dosage in the range of from about 0.15 µg to about 150 mg per kilogram of body weight per day. Typically, a normal adult human will be administered from about 0.1 mg to about 25 mg, or 0.5 mg to about 10 mg per kilogram of body weight per day. The compounds of the invention may be administered in one or more unit dose forms. The unit doses may be administered one to four times a day, or two times a day, or once a day. In an alternate method of describing an effective dose, an oral unit dose is one that is necessary to achieve a blood serum level of about 0.05 to 20 µg/ml or about 1 to 20 µg/ml in a subject. The optimum dose of a compound of the invention for a particular subject can be determined by one of ordinary skill in the art.

Compounds of the invention, or an individual isomer or mixture of isomers or a pharmaceutically acceptable salt thereof, may also be administered simultaneously with, prior to, or after administration of one or more of the therapeutic agents described below. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and an HMG-CoA reductase inhibitor can be administered to the subject together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In one embodiment, the compounds of the invention are used in combination with one or more of the following therapeutic agents in treating atherosclerosis: antihyperlipidemic agents, plasma HDL-raising agents, antihypercholesterolemic agents, cholesterol biosynthesis inhibitors (such as HMG CoA reductase inhibitors, such as lovastatin, simvastatin, pravastatin, fluvastatin, atorvastatin and rivastatin), acyl-coenzyme A:cholesterol acytransferase (ACAT) inhibitors, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In another embodiment, the compounds of the invention are used in combination with one or more of the following therapeutic agents in treating cholesterol biosynthesis inhibitor, particularly an HMG-CoA reductase inhibitor. The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art. For instance, suitable assays are described or disclosed in U.S. Pat. No. 4,231,938 and WO 84/02131. Examples of suitable HMG-CoA reductase inhibitors include, but are not limited to, lovastatin (MEVACOR®; see, U.S. Pat. No. 4,231,938); simvastatin (ZOCOR®; see, U.S. Pat. No. 4,444,784); pravastatin sodium (PRAVACHOL®; see, U.S. Pat. No. 4,346,227); fluvastatin sodium (LESCOL®; see, U.S. Pat. No. 5,354,772); atorvastatin calcium (LIPITOR®; see, U.S. Pat. No. 5,273,995) and rivastatin (also known as cerivastatin; see, U.S. Pat. No. 5,177,080). The structural formulae of these and additional HMG-CoA reductase inhibitors that can be used in combination with the compounds of the invention are described at page 87 of M. Yalpani, "Cholesterol Lowering Drugs," *Chemistry & Industry*, pp. 85-89 (5 Feb. 1996). In presently preferred embodiments, the HMG-CoA reductase inhibitor is selected from lovastatin and simvastatin.

In an additional embodiment, the compounds of the invention are used in combination with one or more of the following therapeutic agents in treating with one or more additional active diabetes agents depending on the desired target therapy (see, e.g., Turner, N. et al., *Prog. Drug Res.* (1998), Vol. 51, pp. 33-94; Haffner, S., Diabetes Care (1998), Vol. 21, pp. 160-178; and DeFronzo, R. et al. (eds.), *Diabetes Reviews* (1997), Vol. 5, No. 4). A number of studies have investigated the benefits of combination therapies with oral agents (see, e.g., Mahler, R., *J. Clin. Endocrinol. Metab.* (1999), Vol. 84, pp. 1165-71; United Kingdom Prospective Diabetes Study Group: UKPDS 28, *Diabetes Care* (1998), Vol. 21, pp. 87-92; Bardin, C. W. (ed.), *Current Therapy In Endocrinology And Metabolism,* 6th Edition (Mosby—Year Book, Inc., St. Louis, Mo. 1997); Chiasson, J. et al., *Ann. Intern. Med.* (1994), Vol. 121, pp. 928-935; Coniff, R. et al., *Clin. Ther.* (1997), Vol. 19, pp. 16-26; Coniff, R. et al., *Am. J. Med.* (1995), Vol. 98, pp. 443-451; Iwamoto, Y. et al., *Diabet. Med.* (1996), Vol. 13, pp. 365-370; Kwiterovich, P., *Am. J. Cardiol* (1998), Vol. 82 (12A), pp. 3U-17U). These studies indicate that diabetes and hyperlipidemia modulation can be further improved by the addition of a second agent to the therapeutic regimen.

In a further embodiment, the compounds of the invention are used in combination with one or more of the following therapeutic agents in treating in treating diabetes: sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-SO4); antiglucocorticoids; TNFα inhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as the therapeutic agents discussed above for treating atherosclerosis.

In yet another embodiment, the compounds of the invention are used in combination with one or more of the following therapeutic agents in treating obesity or obesity-related disorders. Such agents, include, but are not limited to, phenylpropanolamine, phentermine, diethylpropion, mazindol, fenfluramine, dexfenfluramine, phentiramine, $β_3$ adrenoceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

Example A Scintillation Proximity Assay (SPA)

The SPA assay measures the radioactive signal generated by the binding of $^3$H-24,25-epoxycholesterol to LXR$_α$-RXR$_α$ or LXR$_β$-RXR$_α$ heterodimers The basis of the assay is the use of SPA beads containing a scintillant, such that when binding to the receptor brings the labeled ligand into proximity with the bead, the energy from the label stimulates the scintillant to emit light. The light is measured using a standard microplate scintillation reader. The ability of a ligand to bind to a receptor can be measured by assessing the degree to which the compound can compete off a radiolabelled ligand with known affinity for the receptor.

Required Materials:

1. Label: 24(S),25-[26,27-(3H)]-epoxy-cholesterol (Perkin Elmer)

2. LXR$_α$ lysate: Baculovirus expressed LXR$_α$/RXR heterodimer both with a 6-HIS tag produced as a crude lysate 3. LXR$_β$ lysate: Baculovirus expressed LXR$_β$/RXR heterodimer both with a 6-HIS tag produced as a crude lysate 4. SPA beads: YSi copper His-tag SPA beads (Perkin Elmer)

5. Plates: Optiplate, Opaque, 384-well plate (Perkin Elmer)

6. Protein lysate dilution buffer: (20 mM Tris-HCl pH 7.9, 500 mM NaCl, 5 mM Imidazole).

7. 2×SPA Buffer: (40 mM $K_2HPO_4$/$KH_2PO_4$ pH7.3, 100 mM NaCl, 0.05% Tween 20, 20% Glycerol, 4 mM EDTA)

8. 2×SPA Buffer w/o EDTA: (40 mM $K_2HPO_4$/$KH_2PO_4$ pH7.3, 100 mM NaCl, 0.05% Tween 20, 20% Glycerol)

Stock Solutions
0.5 M K$_2$HPO$_4$/KH$_2$PO$_4$ pH 7.3
0.6 0.5 M EDTA pH 8.0
5 M NaCl
6 10% Tween-20
Glycerol Preparation of Protein Lysates Baculovirus expression plasmids for human RXR α□□□ (accession No NM_002957), LXR$_\alpha$ (accession No U22662), and LXR$_\beta$ (accession No U07132) were made by cloning the appropriate full-length cDNAs into the pBacPakhis2 vector (Clontech, Calif.) following standard procedures. Insertion of the cDNAs into the pBAcPakhis2 vector polylinker created an in frame fusion to the cDNA to an N-terminal poly-His tag present in pBacPakhis1. Correct cloning was confirmed by restriction mapping, and/or sequencing.

Cell lysates were prepared by infecting healthy, Sf9 insect cells at a density of approximately 2.0×10$^6$/ml at 27° C., in a total volume of 1 L per 3 L sized shake flasks, cultured under standard conditions. To prepare the LXR$_\alpha$ lysate, insect cells were co-infected with the recombinant viruses containing LXR$_\alpha$ and RXR$_\alpha$ in a ratio of 2:1. To prepare the LXR$_\beta$ lysate, insect cells were co-infected with the recombinant viruses containing LXR$_\beta$ and RXR$_\alpha$ in a ratio of 2:1. In both cases cells were incubated for 68 hours at 27° C. with constant shaking prior to harvesting.

After incubation, cells were harvested by centrifugation and pelleted. Cell pellets were resuspended in 40 ml of freshly prepared ice-cold extraction buffer (20 mM Tris pH 8.0, 10 mM Imidazole, 400 mM NaCl, 10% glycerol, 0.1 mM DTT and EDTA free protease inhibitor tablet (Sigma Catalog No:S8830)), per 1 L culture.

Cells were homogenized slowly on ice using a Dounce homogenizer to achieve 80-90% cell lysis. The homogenate was centrifuged in a pre-chilled rotor (Ti50 or Ti70, or equivalent) at 45,000 rpm for 40 minutes at 4° C. Aliquots of the supernatant were frozen on dry ice and stored frozen at −80° C. until quantification and quality control.

Preparation of Screening Reagents

[$^3$H] 24,25 Epoxycholesterol (EC) solution: For a single 384-well plate, 52.26 µL of [$^3$H] EC (specific activity 76 Ci/mmol, concentration 1 mCi/mL) was added to 4.5 mL of 2×SPA buffer to provide for a final concentration of 76.25 nM. For each additional 384-well plate, an additional 52.27 L of [$^3$H] EC was added to 4.5 mL of additional 2×SPA buffer. The final concentration of [$^3$H] EC in the well was 25 nM.

LXR$_\alpha$ lysate (prepared as above) was diluted with protein lysate dilution buffer. 9000 µL of diluted LXR$_\alpha$ lysate was prepared per 384-well plate and 9000 µL of diluted LXR$_\alpha$ lysate was prepared for each additional 384-well plate.

LXR$_\beta$ lysate (prepared as above) was diluted with protein lysate dilution buffer. 9000 µL of diluted LXR$_\beta$ lysate was prepared per 384-well plate and 9000 µL of diluted LXRβ lysate was prepared for each additional 384-well plate.

SPA bead solution: 4.5 mL of 2×SPA buffer w/o EDTA, 3.6 mL of H$_2$O, and 0.9 mL of Ysi His-tag SPA beads (vortex well before taking) were mixed together to prepare 10% SPA bead solution for a 384-well plate involving LXR$_\alpha$ lysate. 4.5 mL of 2×SPA buffer w/o EDTA, 2.7 mL of H$_2$O, and 1.8 mL of Ysi His-tag SPA beads (vortex well before taking) were mixed together to prepare 20% SPA bead solution for a 384-well plate involving LXR$_\beta$ lysate.

Procedure:

Appropriate dilutions of each compound were prepared in a 384-well plate and pipetted into the appropriate wells of two 384 well plate at 1 µL per well.

20 µL of [$^3$H] EC was added to each well of both 384 well plates.

20 µl of diluted LXR$_\alpha$ lysate was added to each well of the first 384 well plate.

20 µL of diluted LXR$_\beta$ lysate was added to each well of the second 384 well plate.

20 µL of 10% SPA bead solution was added to each well of first 384 well plate. 20 µL of 20% SPA bead solution was added to each well of second 384 well plate The plates were covered with clear sealer, placed on a shaker (300 RPM) for 10 minutes then incubated at ambient temperature for 10 minutes and then spinned at 1000 RPM for 10 minutes at ambient temperature.

The Plates were analyzed using a luminescent plate reader (MicroBeta, Wallac) using the program projectAD 3H_384CPM. The setting for n projectAD 3H_384CPM was:

Counting Mode: CPM;
Sample Type: Top-read;
Count time: 1 minute.

Assays for LXR$_\alpha$ and LXR$_\beta$ were performed in the identical manner. The determined Ki represents the average of at least three independent dose response experiments. The binding affinity for each compound may be determined by non-linear regression analysis using the one site competition formula to determine the IC$_{50}$ where:

$$Y = \text{Bottom} + (\text{Top} - \text{Bottom})/(1+10^{X-\log IC50}).$$

The Ki is than calculated using the Cheng and Prusoff equation where:

$$Ki = IC_{50}/(1+[\text{Concentration of Ligand}]/Kd \text{ of Ligand}).$$

For this assay, typically the Concentration of Ligand=25 nM and the Kd of EC for the receptor is 200 nM as determined by saturation binding.

The compounds of the invention demonstrated the ability to bind to LXR$_\beta$ and/or LXR$_\alpha$, when tested in this assay.

Example B Co-Transfection Assay

To measure the ability of compounds to activate or inhibit the transcriptional activity of LXR in a cell based assay, the co-transfection assay was used. It has been shown that LXR functions as a heterodimer with RXR. For the co-transfection assay, expression plasmids for LXRα and LXRβ are introduced separately via transient transfection into mammalian cells along with a luciferase reporter plasmid that contains one copy of a DNA sequence that is bound by LXR-RXR heterodimers (LXRE; Willy, P. et. al. 1995). LXRs heterodimerize with the endogenous RXR. Treatment of transfected cells with an LXR agonist increases the transcriptional activity of LXR, which is measured by an increase in luciferase activity. Similarly, LXR antagonist activity can be measured by determining the ability of a compound to competitively inhibit the activity of a LXR agonist.

Required Materials

CV-1 African Green Monkey Kidney Cells

Co-transfection expression plasmids, comprising full-length LXR$_\alpha$ (pCMX-h LXR$_\alpha$□ or LXR$_\beta$ (pCMX-hLXR$_\beta$), reporter plasmid (LXREx1-Tk-Luciferase), and control (pCMX-Galactosidase expression vector) (Willey et al. Genes & Development 9 1033-1045 (1995)).

Transfection reagent such as FuGENE6 (Roche) or Transit 2020 (Mirus Bio)

1× cell lysis buffer:
22.4 mM Tricine pH 8.0
0.56 mM EGTA pH 8.0
5.6 mM $MgSO_4$
0.6% Triton X-100
5.6% glycerol
10× luciferase substrate solution:
10 mM HEPES pH 6.5
2.75 mM D-Luciferin
0.75 mM Coenzyme-A
3.7 mM ATP
96 mM DTT Preparation of Screening Reagents CV-1 cells were prepared 24 hours prior to the experiment by plating them into T-175 flasks or 500 $cm^2$ dishes in order to achieve 70-80% confluency on the day of the transfection. The number of cells to be transfected was determined by the number of plates to be screened. Each well of a 384 well plate requires $1.5 \times 10^4$ cells. DNA Transfection Reagent was prepared by mixing the required plasmid DNAs with a cationic lipid transfection reagent Transit 2020 (Mirus Bio) for CV1 by following the instructions provided with the reagents. Optimal DNA amounts were determined empirically per cell line and size of vessel to be transfected. For each T175 $cm^2$ flask a total of 59 ug for CV1 of DNA, 133 uL Transit2020 and 4.5 mL DMEM for CV1 was mixed and added. Cells were then incubated at least 5 hours at 37° C. to prepare screening cells.

Luciferase assay reagent (*Steady-Glo Luciferase Assay System by Promega, CAT#E2550) was prepared by combining before use:
1 part of 10× Luciferase substrate solution
9 parts of 1× cell lysis buffer.

Procedure

Assay plates were prepared by dispensing 5 µL of compound per well of a 384 well plate to achieve final compound concentration of 10 µM and no more than 0.5% DMSO. Media was removed from the screening cells, the cells trypsinized, harvested cells by centrifugation, counted, and plated at a density of approximately $1.5 \times 10^4$ cells in the 384 well assay plate prepared above in a volume of about 95 uL. Assay plates containing both compounds and screening cells (100 µL in total volume) were incubated for 20 hours at 37° C.

After incubation with compounds, media was removed from the cells and luciferase assay reagent (50 µL/well) added. After ~2 minutes at ambient temperature, the assay plates were read on a luminometer (PE Biosystems Northstar reader with on-board injectors, or Envision(Perkin Elmer) or equivalent).

The LXR/LXRE co-transfection assay can be used to establish the $EC_{50}/IC_{50}$ values for potency and percent activity or inhibition for efficacy. Efficacy defines the activity of a compound relative to a high control 1-(2,4-difluorobenzyl)-2-oxo-6-(4-phenoxyphenyl)-4-(trifluoromethyl)-1,2-dihydropyridine-3-carbonitrileor a low control (DMSO/vehicle). The dose response curves are generated from a 11 point curve with concentrations differing by ½ LOG units. Each point represents the average of 2 wells of data from duplicate 384 well plate.

The data from this assay is fitted to the following equation, from which the $EC_{50}$ value may be solved:

$$Y = Bottom + (Top - Bottom)/(1 + 10^{((logEC50-X)*HillSlope)}).$$

The $EC_{50}/IC_{50}$ is therefore defined as the concentration at which an agonist or antagonist elicits a response that is halfway between the Top (maximum) and Bottom (baseline) values. The $EC_{50}/IC_{50}$ values represented are the averages of at least 2 and normally 3 independent experiments. The determination of the relative efficacy or % control for an agonist is by comparison to the maximum response achieved by 1-(2,4-difluorobenzyl)-2-oxo-6-(4-phenoxyphenyl)-4-(trifluoromethyl)-1,2-dihydropyridine-3-carbonitrile that is measured individually in each dose response experiment.

Table 1 lists LXRβ $EC_{50}$ values and % efficacy measurements for Example B Cotransfection Assay for the following Examples

| Example | LXRβ EC50 (µM) | % Efficacy |
|---|---|---|
| 1 | 0.040 | 116 |
| 2 | 0.680 | 80 |
| 3 | 1.950 | 74 |
| 4 | 0.559 | 89 |
| 5 | 0.258 | 91 |
| 6 | 0.848 | 93 |
| 7 | 0.408 | 55 |
| 8 | 0.143 | 91 |
| 9 | 0.066 | 75 |
| 10 | 0.541 | 62 |
| 11 | 0.332 | 79 |
| 12 | 0.133 | 62 |
| 13 | 0.957 | 74 |
| 18 | 0.283 | 62 |
| 19 | 1.070 | 80 |
| 20 | 0.130 | 93 |
| 21 | 0.502 | 65 |
| 22 | 0.113 | 99 |
| 23 | 0.507 | 101 |
| 24 | 0.512 | 90 |
| 25 | 0.529 | 116 |
| 26 | 0.541 | 93 |
| 27 | 0.561 | 83 |
| 28 | 0.589 | 117 |
| 29 | 0.605 | 65 |
| 30 | 0.605 | 85 |
| 31 | 0.606 | 90 |
| 32 | 0.633 | 84 |
| 33 | 0.649 | 103 |
| 34 | 0.661 | 94 |
| 35 | 0.663 | 68 |
| 36 | 0.724 | 60 |
| 37 | 0.758 | 96 |
| 39 | 0.860 | 92 |
| 40 | 0.954 | 87 |
| 41 | 1.047 | 74 |
| 42 | 1.064 | 43 |
| 43 | 1.143 | 85 |
| 44 | 1.267 | 95 |
| 45 | 1.840 | 53 |
| 46 | 2.311 | 62 |
| 47 | 2.541 | 64 |
| 48 | 0.158 | 89 |
| 49 | 0.164 | 105 |
| 50 | 0.171 | 88 |
| 51 | 0.158 | 107 |
| 52 | 0.172 | 82 |
| 53 | 0.175 | 90 |
| 54 | 0.148 | 84 |
| 55 | 0.180 | 110 |
| 56 | 0.133 | 101 |
| 57 | 0.215 | 82 |
| 58 | 0.217 | 78 |
| 59 | 0.218 | 95 |
| 60 | 0.245 | 121 |
| 61 | 0.265 | 87 |
| 62 | 0.276 | 91 |
| 63 | 0.281 | 68 |
| 64 | 0.289 | 86 |
| 65 | 0.297 | 80 |
| 66 | 0.306 | 98 |
| 67 | 0.127 | 81 |
| 68 | 0.307 | 80 |
| 69 | 0.341 | 113 |
| 70 | 0.361 | 40 |

| Example | LXRβ EC50 (μM) | % Efficacy |
|---|---|---|
| 71 | 0.400 | 105 |
| 72 | 0.473 | 80 |
| 73 | 0.476 | 99 |
| 74 | 0.488 | 72 |
| 75 | 0.127 | 97 |
| 76 | 0.500 | 69 |
| 77 | 3.332 | 63 |
| 78 | 0.102 | 94 |
| 79 | 0.227 | 71 |
| 80 | 2.688 | 81 |
| 81 | 0.085 | 99 |
| 82 | 0.260 | 89 |
| 83 | 1.159 | 69 |
| 84 | 0.852 | 96 |
| 85 | 0.118 | 123 |
| 86 | 0.583 | 77 |
| 87 | 0.662 | 89 |
| 88 | 0.306 | 111 |
| 89 | 0.316 | 83 |
| 90 | 0.176 | 105 |
| 91 | 0.484 | 109 |
| 92 | 0.502 | 93 |
| 93 | 2.147 | 40 |
| 94 | 2.337 | 71 |
| 95 | 2.847 | 139 |
| 98 | 1.031 | 91 |
| 99 | 1.010 | 86 |
| 100 | 1.114 | 97 |
| 101 | 0.782 | 73 |
| 102 | 1.941 | 57 |
| 103 | 1.244 | 52 |
| 105 | 0.227 | 70 |
| 106 | 0.281 | 48 |
| 107 | 0.201 | 83 |
| 108 | 0.149 | 62 |
| 109 | 0.111 | 53 |
| 110 | 0.103 | 77 |
| 111 | 0.930 | 92 |
| 112 | 0.973 | 53 |
| 113 | 0.524 | 72 |
| 114 | 0.940 | 98 |
| 115 | 0.920 | 79 |
| 116 | 0.982 | 59 |
| 117 | 1.024 | 76 |
| 118 | 1.044 | 61 |
| 119 | 0.820 | 85 |
| 120 | 0.795 | 91 |
| 121 | 0.651 | 100 |
| 122 | 0.643 | 64 |
| 123 | 1.105 | 36 |
| 124 | 1.161 | 64 |
| 125 | 0.355 | 83 |
| 126 | 0.270 | 93 |
| 127 | 0.776 | 55 |
| 129 | 1.499 | 65 |
| 130 | 0.896 | 68 |
| 131 | 0.821 | 77 |
| 132 | 0.431 | 61 |
| 133 | 0.256 | 71 |
| 134 | 0.166 | 68 |
| 135 | 0.886 | 70 |
| 136 | 0.764 | 69 |
| 137 | 1.094 | 63 |
| 138 | 1.292 | 99 |
| 139 | 1.495 | 71 |
| 140 | 0.383 | 64 |
| 141 | 0.619 | 106 |
| 142 | 0.205 | 63 |
| 143 | 0.942 | 98 |
| 144 | 0.110 | 98 |
| 145 | 0.233 | 110 |
| 146 | 0.251 | 112 |
| 147 | 0.413 | 76 |
| 148 | 0.447 | 42 |
| 149 | 0.444 | 75 |
| 150 | 1.291 | 56 |
| 151 | 0.214 | 148 |
| 152 | 1.226 | 49 |
| 154 | 0.527 | 91 |
| 155 | 0.701 | 93 |
| 156 | 1.638 | 93 |
| 157 | 1.132 | 104 |
| 158 | 1.411 | 88 |
| 159 | 0.783 | 97 |
| 162 | 0.977 | 65 |
| 163 | 1.602 | 61 |
| 164 | 0.203 | 59 |
| 165 | 0.643 | 66 |
| 166 | 1.647 | 78 |
| 167 | 0.779 | 107 |
| 168 | 0.945 | 81 |
| 169 | 0.570 | 93 |
| 170 | 3.332 | 92 |
| 171 | 3.090 | 60 |
| 172 | 1.033 | 159 |
| 173 | 0.264 | 148 |
| 174 | 0.467 | 88 |
| 175 | 0.315 | 79 |
| 176 | 0.792 | 68 |
| 177 | 0.894 | 78 |
| 178 | 0.638 | 89 |
| 179 | 0.620 | 105 |
| 180 | 0.606 | 48 |
| 181 | 0.502 | 70 |
| 182 | 0.494 | 78 |
| 183 | 1.485 | 74 |
| 184 | 0.337 | 86 |
| 185 | 0.297 | 77 |
| 186 | 0.168 | 81 |
| 187 | 0.518 | 92 |
| 188 | 1.745 | 89 |
| 189 | 1.792 | 95 |
| 190 | 0.208 | 119 |
| 191 | 0.452 | 102 |
| 192 | 0.598 | 42 |
| 193 | 0.598 | 62 |
| 195 | 0.574 | 83 |
| 196 | 0.241 | 68 |
| 197 | 0.252 | 76 |
| 198 | 0.092 | 87 |
| 199 | 0.384 | 66 |
| 200 | 0.074 | 83 |
| 201 | 0.127 | 81 |
| 202 | 0.106 | 77 |
| 203 | 0.127 | 71 |
| 204 | 0.110 | 97 |
| 205 | 0.111 | 85 |
| 206 | 0.088 | 95 |
| 207 | 0.176 | 76 |
| 208 | 1.269 | 77 |
| 209 | 0.214 | 80 |
| 210 | 0.394 | 78 |
| 211 | 0.127 | 99 |
| 212 | 0.430 | 101 |
| 213 | 0.094 | 89 |
| 214 | 0.210 | 87 |
| 215 | 0.334 | 86 |
| 216 | 0.286 | 91 |
| 219 | 1.521 | 44 |
| 220 | 0.782 | 102 |
| 221 | 0.111 | 69 |
| 222 | 1.850 | 43 |
| 223 | 1.768 | 63 |
| 224 | 0.411 | 57 |
| 225 | 1.105 | 91 |
| 226 | 0.677 | 92 |
| 227 | 0.865 | 118 |
| 228 | 2.555 | 67 |
| 229 | 0.949 | 72 |
| 230 | 2.051 | 24 |
| 231 | 1.685 | 37 |
| 232 | 1.972 | 74 |
| 233 | 1.335 | 92 |
| 234 | 1.200 | 75 |

| Example | LXRβ EC50 (μM) | % Efficacy |
|---|---|---|
| 235 | 2.267 | 85 |
| 236 | 0.198 | 89 |
| 237 | 0.192 | 98 |
| 238 | 0.489 | 90 |
| 240 | 0.142 | 129 |
| 241 | 0.405 | 111 |
| 242 | 0.201 | 105 |
| 243 | 0.238 | 107 |
| 244 | 0.223 | 110 |
| 245 | 0.216 | 102 |
| 246 | 0.475 | 91 |
| 247 | 0.315 | 99 |
| 248 | 0.185 | 88 |
| 286 | 0.152 | 84 |
| 287 | 0.026 | 80 |
| 288 | 0.074 | 81 |
| 289 | 0.122 | 75 |
| 290 | 0.030 | 43 |
| 291 | 0.047 | 69 |
| 292 | 0.065 | 70 |
| 293 | 0.114 | 97 |
| 294 | 0.057 | 87 |
| 295 | 0.040 | 80 |
| 296 | 0.572 | 75 |
| 297 | 0.351 | 75 |
| 298 | 0.317 | 71 |
| 299 | 0.017 | 77 |
| 300 | 0.012 | 61 |
| 301 | 0.049 | 91 |
| 302 | 0.025 | 81 |
| 303 | 0.021 | 68 |
| 304 | 0.028 | 100 |
| 354 | 0.425 | 77 |
| 355 | 0.105 | 98 |
| 356 | 0.599 | 79 |
| 357 | 0.106 | 98 |
| 358 | 0.116 | 87 |
| 359 | 0.138 | 91 |
| 360 | 0.170 | 93 |
| 361 | 0.183 | 89 |
| 362 | 0.691 | 75 |
| 363 | 0.288 | 58 |
| 364 | 0.410 | 55 |
| 365 | 0.307 | 81 |
| 366 | 0.077 | 89 |
| 367 | 0.175 | 78 |
| 368 | 0.465 | 77 |
| 369 | 1.139 | 29 |
| 370 | 1.037 | 26 |
| 371 | 0.248 | 45 |
| 372 | 0.838 | 33 |
| 373 | 0.040 | 97 |
| 374 | 0.050 | 72 |
| 375 | 0.103 | 84 |
| 376 | 0.064 | 84 |
| 377 | 0.048 | 77 |
| 378 | 0.049 | 24 |
| 379 | 0.825 | 21 |
| 380 | 0.053 | 91 |
| 381 | 0.018 | 81 |
| 382 | 0.057 | 62 |
| 383 | 0.023 | 67 |
| 384 | 0.012 | 72 |
| 385 | 0.015 | 79 |
| 386 | 0.073 | 64 |
| 387 | 0.019 | 73 |
| 388 | 1.379 | 32 |
| 389 | 0.239 | 39 |
| 390 | 2.085 | 62 |
| 391 | 0.207 | 51 |
| 392 | 0.187 | 53 |
| 393 | 0.064 | 56 |
| 394 | 0.615 | 60 |
| 395 | 1.234 | 61 |
| 396 | 0.034 | 71 |
| 397 | 0.025 | 63 |
| 398 | 0.055 | 79 |
| 399 | 0.028 | 76 |
| 400 | 1.163 | 55 |
| 401 | 0.272 | 60 |
| 402 | 0.043 | 88 |
| 404 | 0.159 | 69 |
| 405 | 0.068 | 59 |
| 406 | 0.181 | 68 |
| 407 | 0.118 | 70 |
| 408 | 0.332 | 55 |
| 409 | 0.130 | 45 |
| 410 | 0.204 | 49 |
| 411 | 0.255 | 60 |
| 412 | 0.518 | 72 |
| 413 | 0.426 | 63 |
| 414 | 0.657 | 70 |
| 415 | 1.496 | 86 |
| 416 | 0.030 | 76 |
| 417 | 0.043 | 56 |
| 418 | 0.740 | 73 |
| 419 | 0.145 | 66 |
| 420 | 0.082 | 86 |
| 421 | 0.218 | 76 |
| 422 | 0.110 | 74 |
| 423 | 0.061 | 74 |
| 424 | 0.046 | 59 |
| 425 | 0.203 | 71 |
| 426 | 0.118 | 92 |
| 427 | 0.143 | 63 |
| 428 | 3.087 | 50 |
| 429 | 0.074 | 83 |
| 430 | 0.225 | 88 |
| 431 | 0.358 | 85 |
| 432 | 0.045 | 83 |
| 433 | 0.030 | 76 |
| 434 | 0.462 | 65 |
| 435 | 0.069 | 87 |
| 436 | 0.076 | 77 |
| 437 | 0.034 | 76 |
| 438 | 1.383 | 65 |
| 439 | 0.410 | 80 |
| 440 | 0.214 | 75 |
| 441 | 1.312 | 38 |
| 442 | 0.729 | 58 |
| 443 | 0.234 | 75 |
| 444 | 0.125 | 74 |
| 445 | 0.036 | 69 |
| 446 | 0.836 | 51 |
| 447 | 0.269 | 64 |
| 448 | 0.096 | 58 |
| 449 | 0.183 | 57 |
| 450 | 0.045 | 49 |
| 451 | 0.126 | 61 |
| 452 | 0.083 | 55 |
| 453 | 0.071 | 43 |
| 454 | 0.037 | 38 |
| 455 | 0.192 | 43 |
| 456 | 0.057 | 45 |
| 457 | 0.058 | 76 |
| 458 | 0.398 | 62 |
| 459 | 0.174 | 77 |
| 460 | 0.550 | 64 |
| 461 | 0.127 | 61 |
| 462 | 0.233 | 73 |
| 463 | 0.155 | 73 |
| 464 | 4.680 | 42 |
| 465 | 0.240 | 45 |
| 466 | 0.198 | 84 |
| 467 | 0.066 | 65 |
| 468 | 0.442 | 47 |
| 469 | 0.089 | 70 |
| 470 | 0.109 | 56 |
| 471 | 0.201 | 45 |
| 472 | 0.199 | 50 |
| 473 | 0.280 | 50 |
| 474 | 0.119 | 53 |
| 475 | 0.069 | 56 |
| 476 | 0.726 | 39 |

-continued

| Example | LXRβ EC50 (μM) | % Efficacy |
|---|---|---|
| 477 | 0.271 | 66 |
| 478 | 0.032 | 89 |
| 479 | 0.030 | 81 |
| 480 | 0.063 | 74 |
| 481 | 0.054 | 66 |
| 482 | 0.040 | 71 |
| 483 | 0.040 | 66 |
| 484 | 0.048 | 57 |
| 485 | 0.032 | 55 |
| 486 | 0.109 | 89 |
| 487 | 0.815 | 59 |
| 488 | 0.017 | 66 |
| 489 | 1.082 | 35 |
| 490 | 0.076 | 54 |
| 491 | 0.063 | 71 |
| 492 | 0.034 | 64 |
| 493 | 0.040 | 95 |
| 494 | 0.047 | 90 |
| 495 | 0.071 | 108 |
| 496 | 0.048 | 116 |
| 497 | 0.088 | 124 |
| 498 | 0.087 | 76 |
| 499 | 0.050 | 74 |
| 500 | 0.085 | 96 |
| 501 | 1.619 | 38 |
| 502 | 1.251 | 37 |
| 503 | 0.045 | 71 |
| 504 | 0.091 | 77 |
| 505 | 0.144 | 87 |
| 506 | 0.349 | 77 |
| 507 | 0.035 | 62 |
| 508 | 0.082 | 68 |
| 509 | 0.058 | 70 |
| 510 | 0.061 | 76 |
| 511 | 0.115 | 79 |
| 512 | 0.136 | 71 |
| 513 | 0.137 | 64 |
| 514 | 3.002 | 77 |
| 515 | 1.210 | 19 |
| 516 | 0.270 | 41 |
| 517 | 0.146 | 47 |
| 518 | 0.107 | 49 |
| 519 | 0.140 | 100 |
| 520 | 0.022 | 86 |
| 521 | 0.021 | 71 |
| 522 | 0.042 | 86 |
| 523 | 0.067 | 102 |
| 524 | 0.514 | 66 |
| 525 | 0.650 | 67 |
| 526 | 1.774 | 74 |
| 527 | 0.107 | 54 |
| 528 | 0.133 | 20 |
| 529 | 0.054 | 101 |
| 530 | 0.739 | 71 |
| 531 | 0.422 | 74 |
| 532 | 0.016 | 89 |
| 533 | 0.233 | 73 |
| 534 | 0.197 | 55 |
| 535 | 0.617 | 62 |
| 536 | 0.280 | 82 |
| 537 | 0.661 | 100 |
| 538 | 0.205 | 79 |
| 539 | 0.206 | 81 |
| 540 | 0.028 | 106 |
| 541 | 0.025 | 90 |
| 542 | 0.082 | 89 |
| 543 | 0.067 | 48 |
| 544 | 0.035 | 41 |
| 545 | 0.038 | 32 |
| 546 | 0.119 | 51 |
| 547 | 0.474 | 39 |
| 548 | 0.084 | 43 |
| 549 | 0.483 | 87 |
| 550 | 0.625 | 85 |
| 551 | 0.522 | 79 |
| 552 | 0.913 | 82 |
| 553 | 0.156 | 60 |
| 554 | 0.226 | 31 |
| 555 | 0.018 | 96 |
| 556 | 0.013 | 100 |
| 557 | 0.014 | 82 |
| 558 | 0.010 | 82 |
| 559 | 0.034 | 76 |
| 560 | 0.016 | 75 |
| 561 | 0.013 | 71 |
| 562 | 0.034 | 77 |
| 563 | 0.013 | 70 |
| 564 | 0.164 | 57 |
| 565 | 0.354 | 30 |
| 566 | 0.227 | 94 |
| 567 | 0.111 | 93 |
| 568 | 0.552 | 68 |
| 569 | 0.214 | 90 |
| 570 | 0.199 | 93 |
| 571 | 0.157 | 49 |
| 572 | 0.095 | 46 |
| 573 | 0.127 | 50 |
| 574 | 0.233 | 63 |
| 600 | 0.020 | 101 |
| 601 | 0.030 | 74 |
| 602 | 0.025 | 87 |
| 603 | 0.040 | 91 |
| 604 | 0.054 | 86 |
| 605 | 0.091 | 89 |
| 606 | 0.052 | 79 |
| 607 | 0.046 | 92 |
| 608 | 0.090 | 100 |
| 609 | 0.036 | 91 |
| 610 | 0.257 | 94 |
| 611 | 0.554 | 62 |
| 612 | 0.517 | 64 |
| 613 | 1.156 | 62 |
| 614 | 0.047 | 103 |
| 615 | 0.031 | 96 |
| 616 | 0.045 | 96 |
| 617 | 0.037 | 84 |
| 618 | 0.783 | 66 |
| 619 | 0.051 | 112 |
| 620 | 0.202 | 94 |
| 621 | 0.790 | 81 |
| 622 | 0.410 | 85 |
| 623 | 0.203 | 80 |
| 624 | 0.042 | 112 |
| 625 | 0.073 | 117 |
| 626 | 0.057 | 62 |
| 627 | 0.269 | 93 |
| 628 | 0.412 | 82 |
| 629 | 0.303 | 31 |
| 630 | 0.103 | 30 |
| 631 | 0.216 | 43 |
| 632 | 0.034 | 41 |
| 633 | 0.161 | 66 |
| 634 | 0.249 | 68 |
| 635 | 0.229 | 58 |
| 636 | 0.702 | 41 |
| 637 | 0.579 | 40 |
| 638 | 0.143 | 79 |
| 639 | 0.129 | 81 |
| 640 | 0.218 | 61 |
| 641 | 0.721 | 59 |
| 642 | 1.146 | 32 |
| 643 | 0.341 | 84 |
| 644 | 0.408 | 37 |
| 645 | 0.144 | 32 |
| 646 | 0.572 | 44 |
| 647 | 0.350 | 49 |

General Methods

LCMS Method A: Column: PUROSPHER@Star RP-18 (4.0×55 mm), 3 μm

Mobile phase A: 20 mM NH$_4$OAc in 90% H$_2$O, 10% MeCN

Mobile phase B: 20 mM NH$_4$OAc in 10% H$_2$O, 90% MeCN

Flow: 2.5 mL/min

LCMS Method B: Column: ZORBOX SB C18 (4.6×50 mm), 5 μm (positive mode)
Mobile phase A: 10% MeOH; 90% H$_2$O; 0.1% TFA
Mobile phase B: 90% MeOH; 10% H$_2$O; 0.1% TFA
Flow: 5 mL/min
HPLC Method A: Column: SUNFIRE C18 (4.6×150 mm), 3.5 micron BBRC/LC/011
0.05% TFA in Water pH adjusted to 2.5 using diluted ammonia
Mobile phase A: Buffer:MeCN (95:5)
Mobile Phase B: MeCN:Buffer (95:5)
Flow: 1 mL/min

| Time | % B |
|------|-----|
| 0    | 10  |
| 12   | 100 |
| 15   | 100 |

Synthesis

The compounds of the present invention may be prepared in a number of methods well known to those skilled in the art, including, but not limited to those described below, or through modifications of these methods by applying standard techniques known to those skilled in the art of organic synthesis. The compounds were named using ChemBioDraw Ultra 12.0 (CambridgeSoft). The reagents and starting materials are commercially available, or readily synthesized by well-known techniques by one of ordinary skill in the arts. It is understood that in the following description, combinations of substituents and/or variables of the depicted formulae are permissible only if such contributions result in stable compounds. Unless otherwise indicated, all compounds associated with NMR and/or mass spectra data were prepared and the NMR and mass spectra measured.

ABBREVIATIONS

Ac: acetic (AcOH: acetic acid, EtOAc: ethyl acetate, KOAc: potassium acetate, Ac$_2$O: acetic anhydride, AcCl: acetyl chloride)
Accufluor®: 1-Fluoro-4-hydroxy-1,4-diazoniabicyclo[2,2,2]octanebis(tetrafluoroborate)
AIBN: azobisisobutyronitrile
aq: aqueous
CAN: ceric ammonium nitrate
Cp*Ru(COD)Cl: 1,5-cyclooctadiene(pentamethylcyclopentadienyl)ruthenium(II) chloride
DAST:
DCE: 1,2-dichloroethane
DCM: dichloromethane
Dess-Martin Periodinane (DMP): 1,1,1-Tris(acetyloxy)-1,1-dihydro-1,2-benziodoxol-3-(1H)-one
DMA: N,N-dimethylacetamide
DME: 1,2-dimethoxyethane
DMF: dimethylformamide
DMS: dimethyl sulfide
DMSO: dimethyl sulfoxide
dppf (e.g: PdCl$_2$(dppf)): 1,1'-bis(diphenylphosphino)ferrocene
EDCI: 1-ethyl-3-(3-dimethylaminopropyl) carbodiimide
EPO: eosinophil peroxidase
ESI: electrospray ionization
Et: ethyl (EtOH: ethanol, EtOAc: ethyl acetate, NaOEt: sodium ethoxide, Et$_3$N: triethylamine)
GCMS: gas chromatography-mass spectrometry
HOBt: 1-hydroxybenzotriazole
HPLC: high-performance liquid chromatography
hrs: hours
Hx: hexanes
IR: infrared spectroscopy
LCMS: liquid chromatography-mass spectrometry
LDA: lithium diisopropylamide
LHMDS: lithium hexamethyldisilazide
m-CPBA: meta-chloroperoxybenzoic acid
Me: methyl (MeOH: methanol, MeCN: acetonitrile, MeMgBr: methyl magnesium bromide, MeTHF: 2-methyltetrahydrofuran, NaOMe: sodium methoxide)
min: minutes
MPO: myeloperoxidase
MS: mass spectrometry
MW (or μwave): microwave
NBS: N-bromosuccinimide
NCS: N-chlorosuccinimide
NIS: N-iodosuccinimide
NFTh: 1-Fluoro-4-hydroxy-1,4-diazoniabicyclo[2,2,2]octanebis(tetrafluoroborate)
NMR: nuclear magnetic resonance
ppm: part per million
pTSA (or pTsOH): para-toluenesulfonic acid
PyBOP: benzotriazol-1-yl-oxytripyrrolidinophosphonium hexafluorophosphate
RAP: relative area percent
rt: room temperature
RT: retention time
TBABr: tetrabutylammonium bromide
TFA: trifluoroacetic acid
THF: tetrahydrofuran
TLC: thin layer chromatography
TMSCN: trimethylsilyl cyanide
TosMIC: Toluenesulfonylmethyl isocyanide Intermediates Within the embodiments of the invention, a variety of boronic acids and boronates are required for assembly of compounds. In one general method, arylbromides are transformed into the desired coupling partner such as boronate (I-1d) using a Pd-mediated reaction with bis-pinacolato-diboron. Numerous functionalities can be incorporated on I-1d by one skilled in the art. The general synthesis of phenyl sulfone analogs is shown below in Intermediate Scheme 1. Intermediates of the type I-1d can be prepared by treating an appropriately substituted 1-bromo-3-fluorobenzene (I-1a) with an appropriate base such as LHMDS followed by addition of a thiol reagent (RSNa) to afford I-1b. Oxidation to the sulfone can be achieved with mCPBA affording I-1c. Subsequent treatment of the bromide with palladium boronylation conditions such as PdCl$_2$(dppf), bis(pinacoloato) diboron and KOAc affords Intermediate I-1d. Modifications of this route known to one skilled in the art can be achieved to obtain various substituents at R$^{D2}$. For instance, reduction of a carboxylic acid with reagents such as BH$_3$ in THF provides a methylalcohol.

Intermediate Scheme 1.

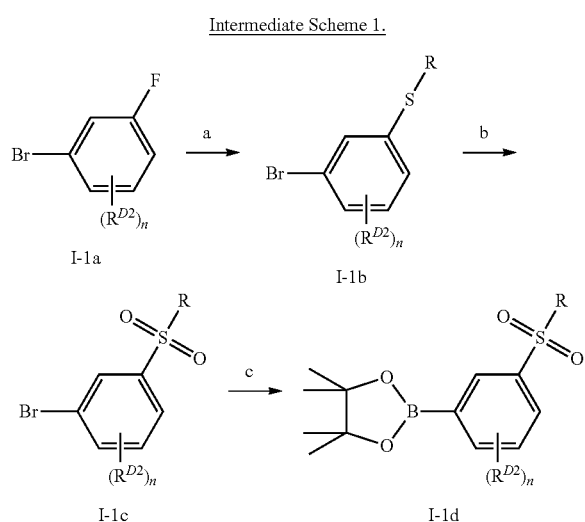

a) i. LHMDS, THF; ii. R₄SNa, reflux; b) mCPBA, CH₂Cl₂; c) PdCl₂(dppf), bis(pinocolato)diboron, KOAc, DMSO, 80° C.

Intermediate 1

(2-fluoro-6-(methylsulfonyl)-4-(4,4,5,5-tetramethyl-1,3,2-dioxaborolan-2-yl)phenyl)methanol

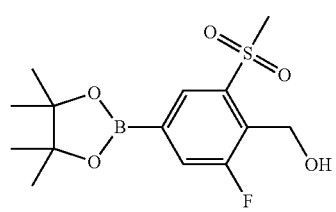 [SMILES: CC1(C)OB(c2cc(F)c(CO)c(S(C)(=O)=O)c2)OC1(C)C]

Intermediate 1a

Preparation of
4-bromo-2-fluoro-6-(methylthio)benzoic acid

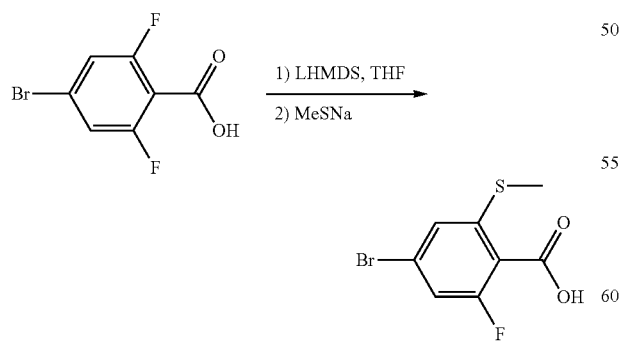

To a 500 mL round bottom flask attached with condenser was added 4-bromo-2,6-difluorobenzoic acid (16.0 g, 67.5 mmol) and anhydrous THF (110 mL). The reaction flask was cooled in an ice bath prior to dropwise addition of 1.0 M LHMDS (74.0 mL, 1.1 equiv). The reaction suspension was stirred at rt for 20 min prior to addition of sodium thiomethoxide (5.21 g, 74.2 mmol). The reaction solution was allowed to stir at reflux for 3 hr. The reaction was determined to be complete after quenching a reaction aliquot in dilute aq. HCl and running GCMS: found m/z=265, 267 parent ions. The cooled reaction mixture was quenched with H₂O and diluted with EtOAc (200 mL). The reaction mixture was transferred to a separatory funnel, and 1.0 N aq. HCl was added to give a pH=2-3 solution. The EtOAc layer was separated, washed with brine, dried over Na₂SO₄, and concentrated in vacuo to afford 14.6 g (81% yield) of the intermediate 6-fluoro-4-bromo-2-methylsulfanyl-benzoic acid as a waxy white solid. 1H NMR (400 MHz, CDCl₃) δ 7.18 (s, 1H), 7.12 (dd, J=8 Hz, 1H), 2.49 (s, 3H); GCMS m/z=265, 267 [M]+.

Alternatively, the intermediate 6-fluoro-4-bromo-2-methylsulfanyl-benzoic acid was prepared as follows:

To a 20 L flask was charged dimethyl formamide (14.5 L, 10.0 vol), followed by NaOH (294 g, 1.2 eq) and the reaction mass cooled to −15 to −10° C. 4-bromo-2,6-difluororbenzoic acid (1450 g, 1.0 equiv) was added over a period of 10-15 min at −15 to −10° C. and stirred for an additional 10-15 min. Sodium thiomethoxide (515 g, 1.2 equiv) was added over a period of 5-10 min at −10 to −5° C. On completion of the addition, the temperature of the reaction was raised to 25-28° C. over a period of 45 to 60 min and maintained at that temperature 1.5-2 h. The temperature of the reaction was then raised to 60-65° C. over a period of 30-60 min and maintained at 60-65° C. for 5 hrs until the reaction was deemed complete. The reaction mixture was then cooled to 20-25° C. and quenched with a cooled (5-10° C.) solution of 2N HCl (5.05 L of 12N HCl in 30.3 L water). Following the quench, EtOAc (14.5 L, 10 vol) was added and the mixture stirred for 10-15 min. The phases were separated and the aqueous layer was extracted with EtOAc (7.25 L, 5 vol). The two phases were separated and the combined organic layer was washed with a brine solution (725 g of NaCl in 3.63 L of water). The phases were separated and the organic layer was washed with water (7.25 L, 5 vol). The phases were separated and the organic layer was dried over sodium sulfate (1450 g). The organic layer was filtered to remove the sodium sulfate, which was then washed with EtOAc (2.90 L, 2 vol). The organic layer was concentrated under reduced pressure at 45-50° C./30-40 mm Hg to ~1 to 1.2 volumes and petroleum ether (7.25 L, 5 vol) was added at 40-45° C. over a period of 15-20 min. The solution was cooled to 20-25° C. over a period of 20-25 min. The solid was filtered and washed with petroleum ether (2.90 L, 2 vol) and the product dried under vacuum at 25-28° C., 0.4 to 0.7 mbar to afford 1410 g (87% yield, 99.4 Area %) of the intermediate 6-fluoro-4-bromo-2-methylsulfanyl-benzoic acid.

Intermediate 1b

Preparation of
(4-bromo-2-fluoro-6-(methylthio)phenyl)methanol

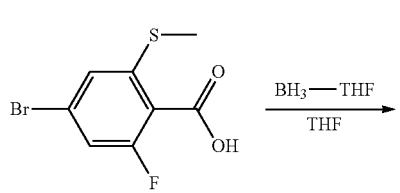

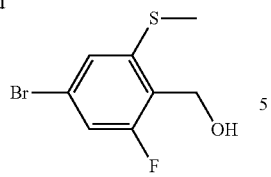

Into a N₂ purged 500 mL round bottom flask attached with condenser was added 6-fluoro-4-bromo-2-methylsulfanyl-benzoic acid (14.6 g, 55.0 mmol) and anhydrous THF (70.0 mL). The reaction solution was allowed to cool to 0° C. prior to dropwise addition of a 1.0 M BH₃-THF (83.0 mL, 1.5 equiv) solution in THF. The reaction solution was stirred at rt then at reflux for an additional 2 hr. The reaction solution was cooled prior to quenching with a 1:1 H₂O/THF solution. The reaction solution was transferred to a separatory funnel with EtOAc (100 mL) and an aqueous solution of K₂CO₃ was added. The EtOAc phase was separated, washed with brine, dried over Na₂SO₄, and concentrated in vacuo. The crude product was purified by chromatography through a 110 g SiO₂ column using a solvent gradient of 100% Hx to 55% EtOAc. The purified title product was obtained as a solid white wax (13.7 g, 99% yield). $^1$H NMR (400 MHz, CDCl₃) δ 7.13 (s, 1H), 7.06 (dd, J$_1$=8 Hz, J$_2$=2 Hz, 1H), 4.77 (s, 2H), 2.51 (s, 3H), 2.20-2.05 (br s, 1H); GCMS m/z=251, 253 [M]⁺.

Alternatively, the intermediate (4-bromo-2-fluoro-6-(methylthio)phenyl)methanol was prepared as follows:

To a 20 L flask was charged 4-bromo-2-fluoro-6-(methylthio)benzoic acid (1400 g, 1.0 eq) followed by THF (14 L, 10 vol) under nitrogen. To this solution was added borane-dimethyl sulfide complex (800 g, 1000 mL) at 25-28° C. over a period of 30-45 min. The reaction temperature was raised to 60-65° C. over a period of 30-45 min and the temperature maintained until HPLC showed <1% of 4-bromo-2-fluoro-6-(methylthio)benzoic acid (~3-4 hrs). On completion of the reaction the mixture was cooled to 10-15° C. over a period of 30-40 min. The reaction was then quenched with MeOH (2.1 L, 1.5 vol) over a period of 1 to 1½ hrs at 10-15° C. The reaction mass was then concentrated under vacuum at 40-50° C./0.4 to 0.7 mbar to 1 to 1.5 volumes. The resultant mixture was dissolved in DCM (8.4 L, 6 vol). The organic layer was washed with an ammonium chloride solution (560 g NH₄Cl in 2.8 L water, 2 vol). The phases were separated and the organic layer was washed with 10% NaHCO₃ solution (2.8 L, 2 vol), saturated brine solution (2.1 L, 1.5 vol) and water (4.2 L, 3 vol). The organic layer was separated and dried over sodium sulfate (700 g). The sodium sulfate was removed by filtration and washed with DCM (2.8 L, 2 vol). The organic layer was concentrated under vacuum at 40-45° C./0.4 to 0.7 mbar to 1 to 1.2 vol to afford the product which was dried under vacuum at 45-50° C./0.4 to 0.7 mbar. The title product was obtained in 90% yield (1200 g) with 90.1 Area %.

Intermediate 1c

Preparation of (4-bromo-2-fluoro-6-(methanesulfonyl)phenyl)-methanol

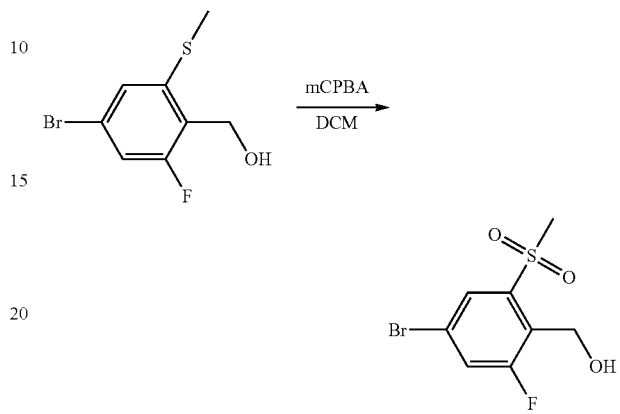

To a 500 mL flask was added (4-bromo-2-fluoro-6-(methylthio)phenyl)methanol (13.7 g, 54.6 mmol) and anhydrous DCM (125 mL). The solution was cooled to 0-3° C. in an ice bath prior to portion wise addition of 3-chloroperbenzoic acid (77% max., Aldrich) (18.8 g, 2 equiv). The reaction solution was then allowed to warm to rt where it remained for 18 hrs. The reaction was then concentrated in vacuo to remove DCM and the residue was washed into a separatory funnel with EtOAc and 1 M aq. NaOH. The EtOAc layer was separated, washed with 1 M aq NaOH, dried over Na₂SO₄, and concentrated in vacuo. The residue was purified by flash chromatography (Biotage, 65×200 mm SiO₂ column, gradient elution from 100% Hx to 90% EtOAc/Hx). Appropriate fractions were combined and concentrated in vacuo to afford the title compound as a colorless, semi-crystalline solid, yield: 8.10 g (52%). $^1$H NMR (400 MHz, DMSO-d₆) δ 7.98 (dd, J=8 Hz, 1H), 7.91 (s, 1H), 5.45 (t, J=8 Hz, 1H), 4.88 (dd, J$_1$=8 Hz, J$_2$=2 Hz, 2H), 3.42 (s, 3H); $^{19}$F NMR (400 MHz, DMSO-d₆) δ-111.8 ppm; GCMS m/z=283, 285 [M]⁺.

Intermediate 1

Preparation of (2-fluoro-6-(methylsulfonyl)-4-(4,4,5,5-tetramethyl-1,3,2-dioxaborolan-2-yl)phenyl)methanol

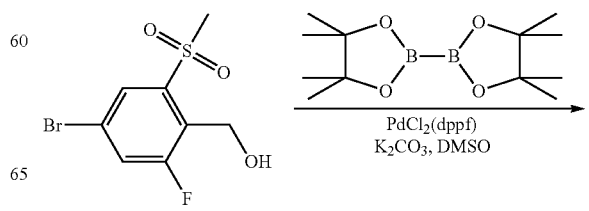

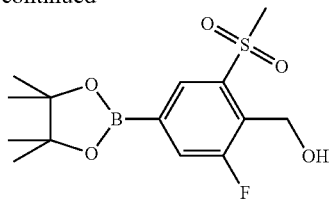

To a 100 mL round bottom flask, purged with dry $N_2$, was weighed (4-bromo-2-fluoro-6-(methanesulfonyl)phenyl)-methanol (1.98 g, 6.99 mmol), bis(pinacolato)diboron (2.13 g 1.2 equiv), dichloro[1,1'-bis(diphenylphosphino) ferrocene]palladium (II) DCM adduct (560 mg, 10 mol %), potassium carbonate (2.06 g, 3 equiv), and DMSO (25.0 mL). The resulting suspension was allowed to stir at 90° C. for 3 hrs. An aliquot of reaction solution was found to contain no more starting bromide as determined by LCMS analysis. The cooled reaction suspension was diluted with EtOAc (50 mL) and water (50 mL) and filtered through a Celite padded Buchner Funnel. The resulting filtrate was transferred to a separatory funnel, and the organic phase was separated. The aqueous phase was extracted with EtOAc, and the combined EtOAc phases were washed with brine, dried over $Na_2SO_4$, and concentrated in vacuo. The residue was purified by silica gel flash chromatography (Biotage SP-1, 40 g $SiO_2$ column, gradient elution from 100% Hx to 60% EtOAc/Hx) to afford a clear viscous oil. The product was isolated as an amorphous white powder by dissolving in DCM and reprecipitation resulted upon addition of Hx. The title compound was isolated as a solid white powder, yield: 1.90 g (82% yield). $^1$H NMR (400 MHz, $CDCl_3$) δ 8.28 (s, 1H), 7.79 (d, J=8 Hz, 1H), 5.03 (d, J=8 Hz, 2H), 3.23 (s, 3H) 3.05 (t, J=8 Hz, 1H), 1.35 (s, 6H); $^{19}$F NMR (400 MHz, $CDCl_3$) δ-116.3 ppm.

Alternatively, the intermediate (2-fluoro-6-(methylsulfonyl)-4-(4,4,5,5-tetramethyl-1,3,2-dioxaborolan-2-yl)phenyl)methanol was prepared as follows:

To a 500 mL jacketed reactor equipped with a stir bar, temperature probe, reflux condenser and a nitrogen inlet was charged methyl tetrahydrofuran (MeTHF) (75 mL, 5 volumes) followed by potassium acetate (5.2 g, 53 mmol, 1 equiv.) and (oxydi-2,1-phenylene)bis(diphenylphosphine) (320 mg; 600 μmoles, 0.011 equiv.) and bis(pinacolato) diboron (18 g, 69 mmol, 1.3 equiv.). The reaction flask was evacuated to less than 150 Torr, and then back filled with nitrogen. This degassing procedure was repeated 3 times. $Pd(OAc)_2$ (94 mg; 420 μmoles, 0.0075 equiv.) was charged to the reactor and the reaction flask was evacuated to less than 150 Torr, and then back filled with nitrogen and the sequence repeated 3 times. The resulting slurry was allowed to age at 20-25° C. for 15 min. Upon completion of the 15 min age, the slurry was heated to an internal temperature of 80° C. As the mixture in the reactor was heating to temperature, in a separate flask was charged (4-bromo-2-fluoro-6-(methanesulfonyl)phenyl)-methanol (15 g, 53 mmol, 1 equiv.) followed by MeTHF (75 mL, 5 volumes). The resulting solution was degassed by bubbling nitrogen subsurface for not less than 15 min. prior to use. Once the catalyst mixture had reached reflux, the degassed solution of (4-bromo-2-fluoro-6-(methanesulfonyl)phenyl)-methanol in MeTHF was added to the reaction in a single portion and allowed to react. The reaction typically takes ~20 hrs to complete after the addition of substrate. Upon completion (typically <0.75 RAP of starting material the reaction was cooled to 20-25° C. Once at rt the reaction was diluted with MeTHF (75 mL, 5 volumes) and washed with a 5 wt % NaCl solution (7.5 volumes, 110 mL) for at least 15 min. The phases were separated and the upper product rich MeTHF stream was filtered through Celite to remove insoluble palladium residues. The Celite cake was washed with MeTHF (75 mL, 5 volumes). The reaction was treated with functionalized silica (30 equiv) to remove palladium and color. The slurry was agitated for at least 60 min and then filtered to remove the silica. The used silica was washed with MeTHF (5 volumes, 75 mL). The combined organic phase was washed with water (5 volumes, 75 mL). The organic was distilled to 5 volumes (75 mL) under vacuum (60-70 Torr, bath temp of 30° C.). When the 75 mL landmark was reached the distillation was stopped and heptane (75 mL, 5 volumes) was added dropwise to the reaction solution. After ~35 mL of heptanes had been added the product began to crystallize from the solution. On completion of the addition the product was isolated by filtration and the wet cake washed with MeTHF-heptanes (1:9) solution (2×75 mL) and dried at 50° C. The title product was obtained a white solid, 14 g, (78% yield) with 99.6 Area %.

Intermediate 2

4,4,5,5-tetramethyl-2-(4-methyl-3-(methylsulfonyl)phenyl)-1,3,2-dioxaborolane

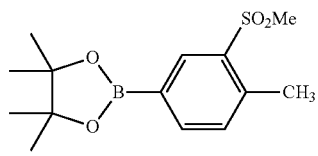

Intermediate 2 was prepared from 4-bromo-1-methyl-2-(methylsulfonyl)benzene in a similar procedure as Intermediate 1d. MS (ESI) 297.2 [M+H]+. $^1$H NMR (400 MHz, CHLOROFORM-d) δ ppm 8.46 (s, 1H), 7.92 (d, 1H, J=7.4 Hz), 7.35 (d, 1H, J=7.4 Hz), 3.08 (s, 3H), 2.74 (s, 3H), 1.31 (s, 12H).

Intermediate 3

N,N-dimethyl-3-(4,4,5,5-tetramethyl-1,3,2-dioxaborolan-2-yl)benzamide

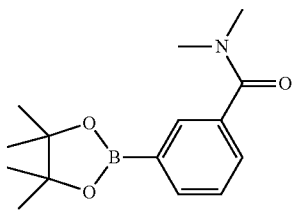 [SMILES: CN(C)C(=O)c1cccc(B2OC(C)(C)C(C)(C)O2)c1]

Intermediate 3a

Preparation of 3-bromo-N,N-dimethylbenzamide

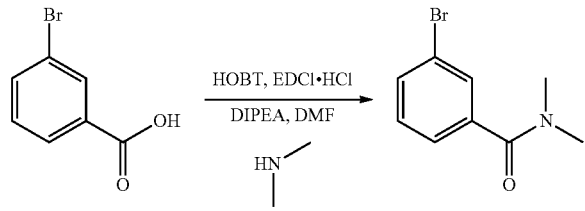

To a mixture of 3-bromobenzoic acid (2.7 g, 14 mmol), 1-hydroxybenzotriazole (3.6 g, 27 mmol), EDC (5.1 g, 27 mmol) and diisopropylethylamine (8.7 mL, 47 mmol) in DMF (50 mL) was added dimethylamine (1.2 g, 14 mL, 27 mmol) at 0° C. and the reaction mixture was stirred overnight at rt under a nitrogen atmosphere. The reaction mixture was diluted with water (40 mL) and extracted with EtOAc (2×50 mL). The combined organic extracts were washed with water, brine, dried over Na$_2$SO$_4$ and concentrated to give crude product. The crude was triturated with pet ether and filtered, and the solid was dried under vacuum to yield the title compound (2.9 g, 95% yield). MS (ESI) 229.1 [M+H]$^+$.

Intermediate 3 was prepared from Intermediate 3a in a similar procedure as Intermediate 1d. MS (ESI) 276.2 [M+H]$^+$.

Intermediate 4

1-(3-(4,4,5,5-tetramethyl-1,3,2-dioxaborolan-2-yl)phenyl)cyclopropanecarboxamide

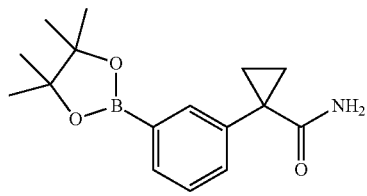 [SMILES: CC1(C)OB(c2cccc(C3(C(N)=O)CC3)c2)OC1(C)C]

Intermediate 4a

Preparation of 1-(3-bromophenyl)cyclopropanecarboxamide

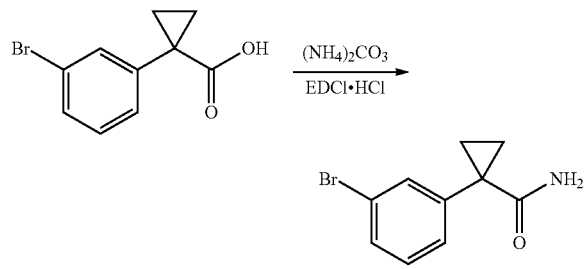

To a mixture of 1-(3-bromophenyl)cyclopropanecarboxylic acid (0.5 g, 2.074 mmol), 1-hydroxybenzotriazole (0.364 g, 2.70 mmol), EDC (0.517 g, 2.70 mmol) and triethylamine (0.867 mL, 6.22 mmol) in DMF (8 mL) was added ammonium carbonate (0.239 g, 2.489 mmol) at 0° C. The reaction mixture was stirred overnight at rt under a nitrogen atmosphere. The reaction mixture was diluted with water (40 mL) and extracted with EtOAc (2×50 mL). Combined organic extracts were washed with water, brine, dried over Na$_2$SO$_4$ and concentrated to give crude product. Crude material was triturated with pet ether and filtered. The solid was dried under vacuum to give 1-(3-bromophenyl)cyclopropanecarboxamide (0.4 g, 1.666 mmol, 80% yield) as a off white solid. MS (ESI) [M+H]$^+$: 241.0

Intermediate 4

Preparation of 1-(3-(4,4,5,5-tetramethyl-1,3,2-dioxaborolan-2-yl)phenyl)cyclopropanecarboxamide

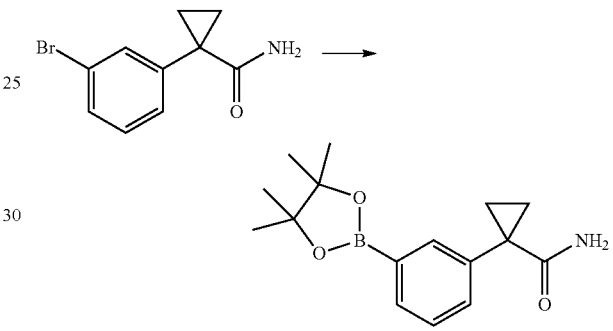

To a mixture of Intermediate 4a (200 mg, 0.833 mmol), bis(pinacolato)diboron (275 mg, 1.083 mmol) and potassium acetate (245 mg, 2.50 mmol) in dioxane (5 mL) was added dppf (23.09 mg, 0.042 mmol) and PdCl$_2$(dppf) (30.5 mg, 0.042 mmol). The reaction mixture was stirred at 85° C. for 12 h under nitrogen atmosphere. The reaction mixture was cooled to rt, diluted with water (30 mL) and extracted with EtOAc (2×25 mL). The combined organic extracts were washed with water, brine, dried over Na$_2$SO$_4$ and concentrated to give crude product. Crude solid was washed with 10% EtOAc in hexane (20 mL), filtered, and dried under vacuum to give 1-(3-(4,4,5,5-tetramethyl-1,3,2-dioxaborolan-2-yl)phenyl)cyclopropanecarboxamide (150 mg, 0.522 mmol, 62.7% yield) as a off white solid. MS (ESI) [M+H]$^+$: 288.1

Intermediate 5

2-(3-(cyclopropylsulfonyl)phenyl)-4,4,5,5-tetramethyl-1,3,2-dioxaborolane

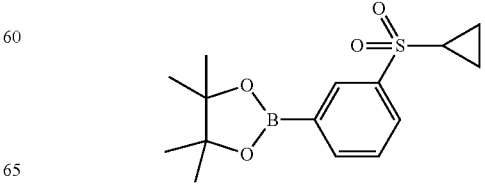

Intermediate 5a

Preparation of (3-bromophenyl)(cyclopropyl)sulfane

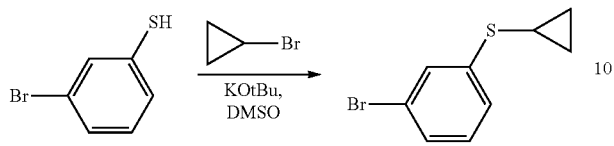

To a cooled (0° C.) solution of potassium tert butoxide (0.36 g, 2.9 mmol) in DMSO (12 mL) was added 3-bromothiophenol (0.50 g, 2.6 mmol) under a nitrogen atmosphere and the reaction mixture was stirred for 15 min. A solution of cyclopropylbromide (0.96 g, 7.8 mmol) in DMSO (1.0 mL) was added dropwise. The reaction mixture was allowed to warm to rt, and followed by heating to 80° C. for 48 hrs. The reaction mixture was cooled to rt and diluted with cold water (10 mL) and EtOAc (10 mL). The layers were separated and the aqueous layer was extracted EtOAc (20 mL×2). The combined organic extracts were washed with water, brine, dried over $Na_2SO_4$ and concentrated in vacuo to give the title compound (0.40 g, 66% yield). MS (ESI) 230.1 $[M+H]^+$.

Intermediate 5 was prepared from Intermediate 5a using procedures similar to Intermediate 1. MS (ESI) 309.1 $[M+H]^+$.

Intermediate 6

2-(3-((difluoromethyl)sulfonyl)phenyl)-4,4,5,5-tetramethyl-1,3,2-dioxaborolane

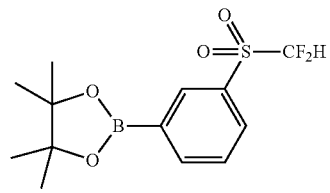 [SMILES: CC1(C)OB(c2cccc(S(=O)(=O)C(F)F)c2)OC1(C)C]

Intermediate 6a

Preparation of (3-bromophenyl)(difluoromethyl)sulfane

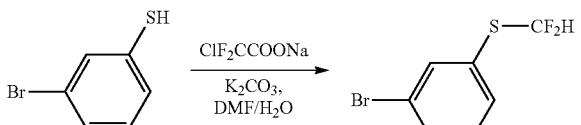

A solution of 3-bromothiophenol (0.50 g, 2.6 mmol), potassium carbonate (0.73 g, 5.3 mmol) and sodium chlorodifluoroacetate (0.81 g, 5.3 mmol) in DMF (4.5 mL) and water (0.50 mL) was heated to 130° C. for 1 hr. The reaction mixture was cooled to rt and diluted with diethyl ether (25 mL). The organic solution was washed with a citric acid solution, brine, dried over $Na_2SO_4$ and concentrated in vacuo to give the crude product. The crude product was purified by silica gel column chromatography using EtOAc: Hx (2:8) as an eluent to afford the title compound (0.60 g, 95% yield). MS (ESI) 239.8 $[M+H]^+$.

Intermediate 6 was prepared from Intermediate 6a using procedures similar to Intermediate 1. MS (ESI) 319.1 $[M+H]^+$.

Intermediate 7

(2-chloro-6-(methylsulfonyl)-4-(4,4,5,5-tetramethyl-1,3,2-dioxaborolan-2-yl)phenyl)methanol

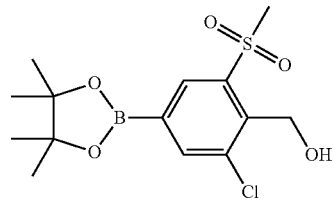 [SMILES: CC1(C)OB(c2cc(Cl)c(CO)c(S(C)(=O)=O)c2)OC1(C)C]

Intermediate 7 can be prepared by similar chemistry described above from commercially available 2-chloro-6-fluorobenzaldehyde; however iridium borylation using [Ir(OMe)(COD)]$_2$ can be used to install the boronate at the para position compared to the hydroxymethyl substituent.

Intermediate 8

2-methyl-2-(3-(4,4,5,5-tetramethyl-1,3,2-dioxaborolan-2-yl)phenyl)propanamide

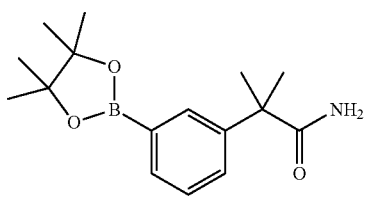 [SMILES: CC(C)(C(N)=O)c1cccc(B2OC(C)(C)C(C)(C)O2)c1]

Intermediate 8a

Preparation of 2-(3-bromophenyl)-2-methylpropanenitrile

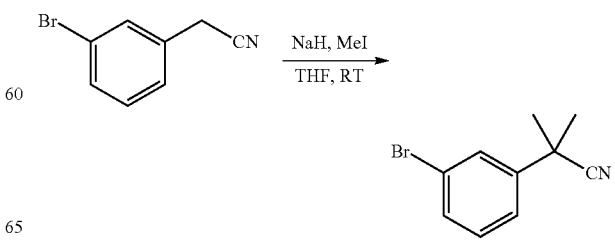

To a dried 1 L double neck round bottom flask fitted with a U tube (for nitrogen atmosphere) and septum was added 2-(3-bromophenyl)acetonitrile (25 g, 128 mmol). THF (350 mL) was added and the reaction solution was cooled to 0° C. Then NaH (18.36 g, 383 mmol) was added to the reaction mixture portion-wise (5 g each time). The reaction mixture was stirred at 0° C. for 2 h. MeI (39.9 mL, 638 mmol) was added at 0° C. dropwise through an addition funnel and the mixture was stirred for 0.5 h at 0° C. and then warmed to rt. After 3 h at rt the starting material was consumed completely based on TLC. The reaction mixture was quenched with ice cold water (400 mL) at −10° C. The aqueous was extracted with EtOAc (3×250 mL). The organic layers were washed with brine (1×200 mL), dried over Na$_2$SO$_4$, filtered and concentrated to get crude brown product. The material was purified by combiflash using 120 g silica column and eluting with up to 10% EtOAc in pet ether as eluent to get 2-(3-bromophenyl)-2-methylpropanenitrile (16.1 g, 71.8 mmol, 56.3% yield) as clear liquid.

$^1$H NMR (400 MHz, CHLOROFORM-d) δ ppm 7.60 (m, 1H) 7.44 (m, 2H) 7.24-7.29 (m, 1H) 1.72 (s, 6H).

Intermediate 8b

Preparation of 2-(3-bromophenyl)-2-methylpropanamide

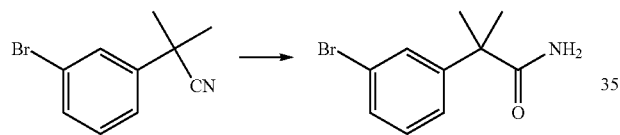

To 2-(3-bromophenyl)-2-methylpropanenitrile (870 mg, 3.88 mmol) was added H$_2$SO$_4$ (2.1 mL, 39.4 mmol) dropwise at rt and the reaction mixture was stirred at rt overnight. Ice cold water (15 mL) was added to the reaction mixture dropwise, and the mixture was stirred for 5 min. The reaction mixture was filtered, and washed with cold water until washings become neutral. The solids were also washed with pet.ether (3×20 mL), and dried under high vacuum to obtain 2-(3-bromophenyl)-2-methylpropanamide (500 mg, 2.065 mmol, 53.2% yield) as white amorphous solid. $^1$H NMR (400 MHz, DMSO-d$_6$) δ ppm 7.46-7.49 (m, 1H) 7.43 (dt, J=7.53, 1.51 Hz, 1H) 7.28-7.36 (m, 2H) 6.92-7.02 (m, 2H) 1.43 (s, 6H).

Intermediate 8

Preparation of 2-methyl-2-(3-(4,4,5,5-tetramethyl-1,3,2-dioxaborolan-2-yl)phenyl)propanamide

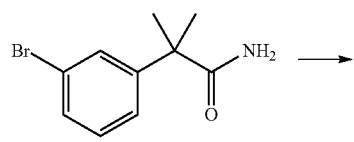

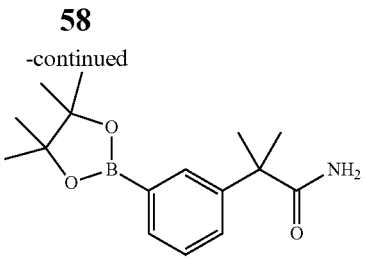

A suspension of 2-(3-bromophenyl)-2-methylpropanamide (5 g, 20.65 mmol), bis(pinacolato)diboron (6.29 g, 24.78 mmol) and potassium acetate (6.08 g, 62.0 mmol) in DME (95 mL) was purged with nitrogen for 20 minutes at rt, followed by addition of PdCl$_2$(dppf) (0.453 g, 0.620 mmol) and purging with nitrogen for 10 min. The reaction mixture was heated at 100° C. for 1 h, and the starting material was consumed by TLC. The reaction mixture was cooled to rt, filtered through a celite bed, and washed with EtOAc (3×50 mL). The filtrate was concentrated to afford brown gummy solid, which was purified by combiflash using 120 g silica column eluting with 60% of EtOAc in pet ether as eluent to get Intermediate 8 (2.2 g, 7.61 mmol, 36.8% yield) as white crystalline solid.

$^1$H NMR (400 MHz, DMSO-d$_6$) δ ppm 7.64 (s, 1H), 7.53 (dt, J=7.22, 1.04 Hz, 1H), 7.49 (ddd, J=7.84, 2.07, 1.38 Hz, 1H), 7.32-7.37 (m, 1H), 6.90 (d, J=17.32 Hz, 2H), 1.43 (s, 6H), 1.31 (s, 12H).

Intermediate 9

2,2-dimethyl-2,3-dihydrobenzofuran-5-carbaldehyde

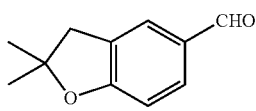

Intermediate 9a 4-bromo-2-(2-methylallyl)phenol

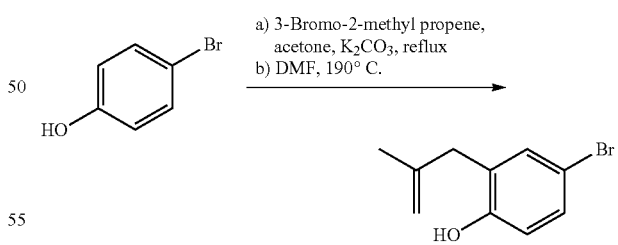

a) 3-Bromo-2-methyl propene, acetone, K$_2$CO$_3$, reflux
b) DMF, 190° C.

To a solution of 4-bromophenol (300 mg, 1.7 mmol) in acetone (7 mL) was added K$_2$CO$_3$ (1.2 g, 8.7 mmol) and 3-bromo-2-methylpropene (192 mL, 1.91 mmol). The reaction mixture was refluxed for overnight. The resulting mixture was cooled to ambient temperature and then diluted with CH$_2$Cl$_2$. The organic layer was washed with water and brine, dried over MgSO$_4$, and concentrated in vacuo to give 1-bromo-4-(2-methyl-allyloxy)benzene (392 mg), which was directly used for the next step. 1H NMR (CDCl$_3$, 300 MHz) δ ppm 7.36 (t, 1H, J=2.7 Hz), 7.33 (t, 1H, J=2.8 Hz), 6.80 (t, 1H, J=2.8 Hz), 6.77 (t, 1H, J=2.7 Hz), 5.06 (br s, 1H), 4.98 (br s, 1H), 4.38 (s, 2H), 1.80 (s, 3H).

A solution of 1-bromo-4-(2-methylallyloxy)benzene (260 mg, 1.1 mmol) in DMF (7 mL) was refluxed overnight. After cooling to ambient temperature and dilution with Et₂O, the organic layer was washed with water and brine, dried over MgSO₄, and concentrated in vacuo. The residue was purified by silica gel column chromatography (EtOAc/n-hexane=1:3) to afford 4-bromo-2-(2-methylallyl)phenol (221 mg, 87%). 1H NMR (CDCl₃, 300 MHz) δ ppm 7.08-7.18 (m, 2H), 6.63 (d, 1H, J=9.2 Hz), 5.79 (s, 1H), 4.82 (s, 1H), 4.72 (s, 1H), 3.23 (s, 2H), 1.64 (s, 3H).

Intermediate 9

2,2-dimethyl-2,3-dihydrobenzofuran-5-carbaldehyde

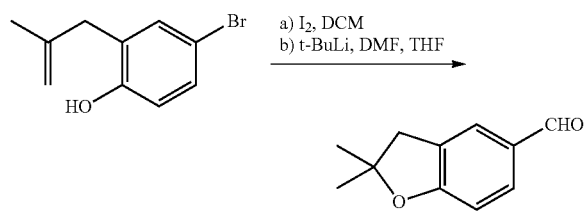

To a solution of phenol 9a (120 mg, 0.53 mmol) in DCM (5 mL) was added 12 (27 mg, 0.11 mmol). The reaction mixture was stirred at room temperature for 12 h, then quenched by addition of saturated aqueous Na₂S₂O₃ and diluted with CH₂Cl₂. The organic layer was washed with water and brine, dried over MgSO₄, and concentrated en vacuo. The residue was purified by silica gel column chromatography (EtOAc/n-hexane=1:3) to afford 5-bromo-2,2-dimethyl-2,3-dihydrobenzofuran (96 mg). 1H NMR (CDCl₃, 300 MHz) δ ppm 7.18-7.27 (m, 2H), 6.63 (d, 1H, J=8.4 Hz), 3.00 (s, 2H), 1.48 (s, 6H).

To a solution of 5-bromo-2,2-dimethyl-2,3-dihydrobenzofuran (170 mg, 0.75 mmol) in THF (4 mL) was added dropwise of t-BuLi (1.7 M in hexanes, 885 mL) at −78° C., then warmed to 0° C. To the reaction mixture was added DMF (64 mL, 0.83 mmol), then the reaction mixture was stirred at 0° C. for 30 min followed by dilution with Et₂O. The organic layer was washed with water and brine, dried over MgSO₄, and concentrated in vacuo. The residue was purified by silica gel column chromatography (EtOAc/n-hexane=1:3) to afford 2,2-dimethyl-2,3-dihydrobenzofuran-5-carbaldehyde (114 mg). 1H NMR (CDCl₃, 300 MHz) δ ppm 9.77 (s, 1H), 7.67 (s, 1H), 7.64 (d, 1H, J=8.3 Hz), 6.80 (d, 1H, J=8.3 Hz), 3.02 (s, 2H), 1.48 (s, 6H).

EXAMPLES

Preparation of Compounds of the Invention

Scheme 1

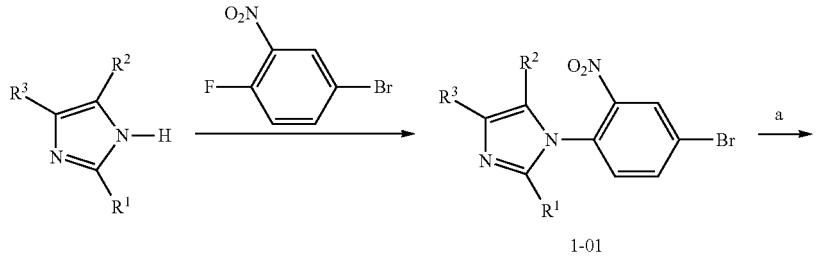

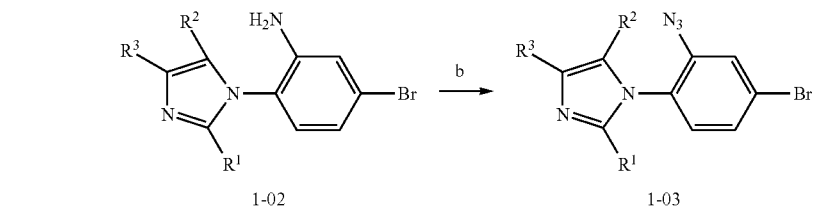

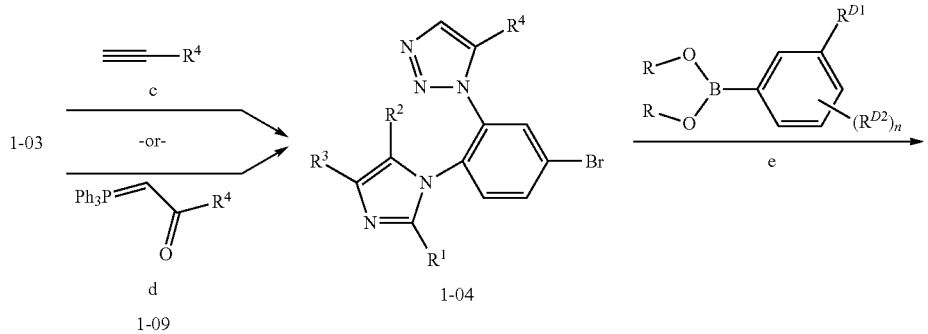

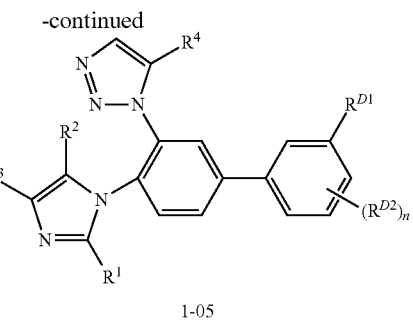

1-05

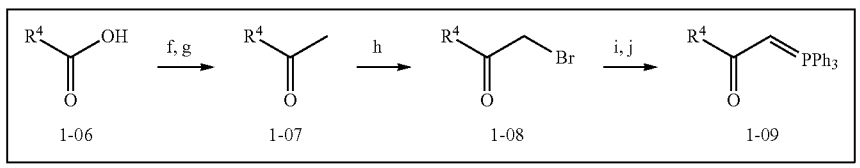

(a) SnCl₂·2 H₂O, EtOH, reflux; (b) NaNO₂; NaN₃, TFA/HCl, 0° C.-rt; (c) Cp*RuCl(cod), THF; (d) toluene, reflux; (e) K₂CO₃, PdCl₂(dppf), DME/H₂O, 80° C. (f) SOCl₂, CHCl₃; (g) TMS-diazomethane, ACN/THF; (h) Aq. HBr, HOAc; (i) PPh₃, toluene; (j) NaOH, H₂O/CHCl₃.

Particular embodiments of the invention comprise compounds exemplified by general structure 1-05 shown in Scheme 1. In general, structures of the type 1-05 are prepared by a process that commences with the preparation of intermediate (1-01) by a $S_NAr$ reaction of 2-methyl-4-trifluoromethyl imidazole with 4-bromo-1-fluoro-2-nitrobenzene (Scheme 1). The intermediate (1-01) can be transformed by SnCl₂·2H₂O-mediated reduction of the nitro group to provide the corresponding aniline (1-02). Subsequently, exposure of 1-02 to sodium nitrite at reduced temperature, followed by sodium azide and warming, provides an intermediate azide (1-03). Triazoles of type (1-04) are then obtained either by directly subjecting azide (1-03) to catalytic Cp*RuCl(cod) in the presence of an appropriate terminal alkyne (where A can be a substituted phenyl, heteroaryl, or alkyl group). Alternately, the azide (1-03) may be reacted with various triphenyl phosphorane reagents (1-09) to afford triazole (1-04). Finally, metal mediated cross-coupling reactions, such as Suzuki Coupling reactions with the aryl boronic acid or ester derivatives are utilized to append substituted aromatic rings to provide the fully elaborated compounds (1-05). Structures of the type (1-05) are also accessible when the sequence of steps delineated in Scheme 1 is modified.

The phosphoranes (1-09) can be prepared from a carboxylic acid (1-05), which is converted to the acid chloride, followed by one carbon homologation with TMS-diazomethane to the ketone 1-07. The ketone 1-07 can be brominated to afford the α-bromoketone (1-06). The bromide (1-06) is converted to the phosphorane (1-08) in two steps by reaction with triphenylphosphine followed by treatment with base such as NaOH in CH₃Cl.

Standard manipulations, readily apparent to one skilled in the art, of the R¹, R², and R³ substituent(s) can be accomplished, to access further functional group diversity about the corresponding imidazole ring. Transformations that can be carried out include but are not limited to fluorination, chlorination, amide preparation, carbonyl reduction.

Example 1

{4'-[5-chloro-2-methyl-4-(trifluoromethyl)-1H-imidazol-1-yl]-3-fluoro-5-(methylsulfonyl)-3'-(5-{4-[(trifluoromethyl)oxy]phenyl}-1H-1,2,3-triazol-1-yl)biphenyl-4-yl}methanol

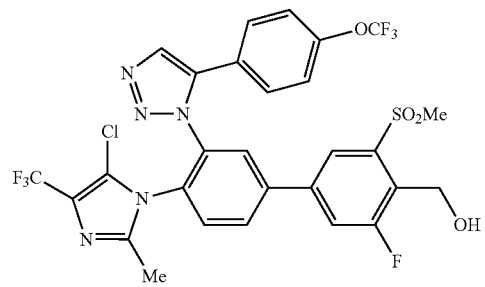 [SMILES: Cc1nc(C(F)(F)F)c(Cl)n1-c1ccc(-c2cc(F)c(CO)c(S(C)(=O)=O)c2)cc1-n1nncc1-c1ccc(OC(F)(F)F)cc1]

Example 1a

Preparation of 1-(4-bromo-2-nitrophenyl)-2-methyl-4-(trifluoromethyl)-1H-imidazole

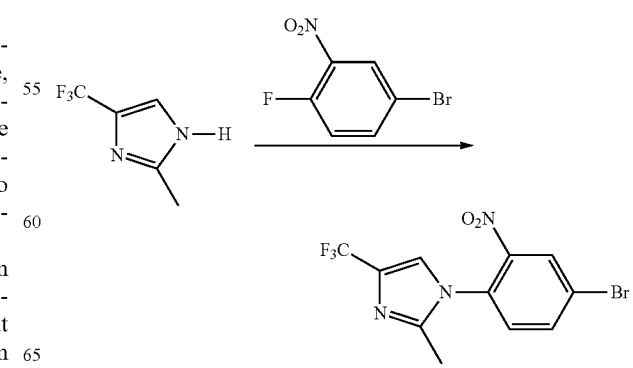

In a 500 mL round bottom flask, 2-methyl-4-(trifluoromethyl)-1H-imidazole (9.50 g, 63.3 mmol), 4-bromo-1-fluoro-2-nitrobenzene (13.9 g, 63.3 mmol) and K₂CO₃ (21.9 g, 158 mmol) were brought up in DMF (120 mL) and stirred at 85° C. for 14 hrs. The reaction was poured into water (100 mL) and extracted with diethyl ether (100 mL×3). The combined organic phase was concentrated in vacuo, re-precipitated with a Hx/EtOAc mixture, and was concentrated in vacuo to afford the title compound (16.3 g, 46.3 mmol, 73% yield). MS (ESI) 352.3 [M+H]$^+$.

Example 1b

Preparation of 5-bromo-2-(2-methyl-4-(trifluoromethyl)-1H-imidazol-1-yl)aniline

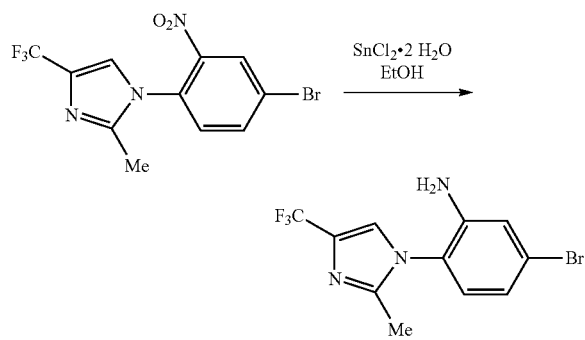

To a 1 L round bottom flask fitted with a condenser was added Example 1a (30.0 g, 85.7 mmol), tin(II) chloride dihydrate (96.7 g, 429 mmol), and EtOH (300 mL). The reaction was allowed to stir at reflux for 21 hr. The reaction was cooled to rt and quenched by the addition of NaOH (34.3 g, 857 mmol) dissolved in water. The reaction was then heated to reflux again, and another portion of NaOH (34.3 g, 857 mmol) was added. After refluxing for 1 h, the reaction was cooled to rt, and 200 mL of DCM was added to the vigorously stirring mixture. This mixture was then transferred to a separatory funnel and the DCM layer was separated. The aqueous layer was then extracted again with DCM (200 mL×2), and the DCM layers were combined and washed with water and brine. After drying over MgSO₄, the solvent was evaporated in vacuo to yield the intermediate 5-bromo-2-(methyl-4-(trifluoromethyl)-1H-imidazol-1-yl) aniline (26.6 g, 83.1 mmol).

Alternatively, Example 1b could be prepared as follows:

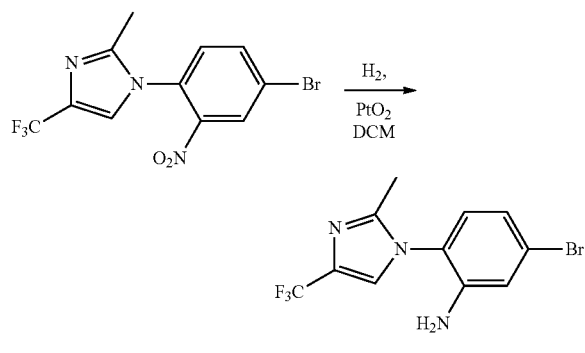

To an oven-dried N₂ purged Parr flask, was added Example 1a (16.3 g, 46.3 mmol) and anhydrous CH₂Cl₂ (90 mL), followed by PtO₂-hydrate (490 mg, 3 wt %). The flask was attached to a Parr Shaker Hydrogenator and evacuated/backfilled with 50 psi H₂ three times. The final H₂ pressure was set to 60 psi and the reaction mixture was shaken for 4.5 hrs. Most of the product precipitated out of solution as an off-white solid, which was filtered from solution to give the title compound (11.0 g, 34.1 mmol). The mother liquor was concentrated in vacuo and the remaining crude product was purified by chromatography thru a SiO₂ column using a mobile phase gradient of EtOAc and Hx to afford the title compound (14.7 g, 45.6 mmol, 99% yield). MS (ESI) 319, 321 [M+H]$^+$.

Example 1c

Preparation of 1-(2-azido-4-bromophenyl)-2-methyl-4-(trifluoromethyl)-1H-imidazole

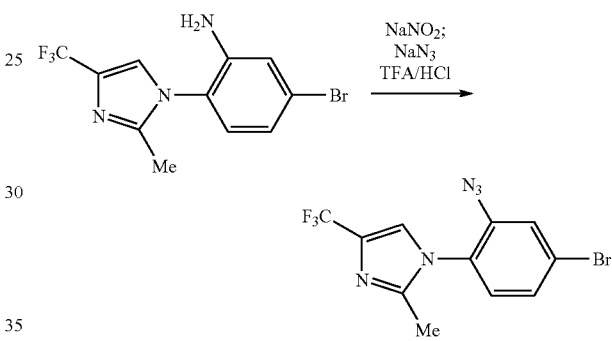

In a 40 mL vial, Example 1b (1.90 g, 5.94 mmol) was dissolved in TFA (10.0 mL) and concentrated HCl (1.00 mL), and cooled to 0° C. A solution of NaNO₂ (820 mg, 11.9 mmol) dissolved in minimal water was added to the vial dropwise. After the mixture had been allowed to stir at 0° C. for 30 min, a solution of NaN₃ (1.16 g, 17.8 mmol) dissolved in minimal water was added dropwise. Upon completion of the addition, the mixture was allowed to warm slowly to rt. After the mixture had stirred at rt for 1 h, it was carefully treated with saturated aqueous NaHCO₃ to neutralize the solution. The solution was extracted with EtOAc, and the extracts were washed with water and brine. The organics were then dried over MgSO₄ and concentrated in vacuo to yield the title compound (2.08 g, 6.01 mmol).

Example 1d

Preparation of 1-(2-azido-4-bromophenyl)-5-chloro-2-methyl-4-(trifluoromethyl)-1H-imidazole

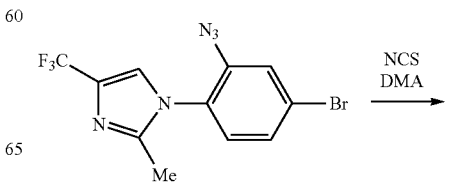

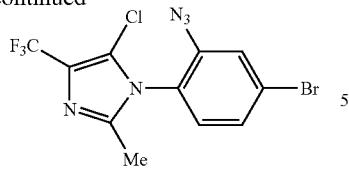

A 40 mL vial was charged with Example 1c (0.19 g, 0.55 mmol), DMA (5.0 mL), and NCS (0.15 g, 1.1 mmol) and heated to 80° C. for 24 h. The mixture was then cooled to rt, poured into 1 M KOH, and extracted with diethyl ether. The ether layer was then washed with 1 M KOH, water, and brine, dried over MgSO$_4$, and concentrated in vacuo. The residue was purified by flash column chromatography to yield the title compound (0.21 g, 0.55 mmol).

Example 1e

Preparation of 1-(5-bromo-2-(5-chloro-2-methyl-4-(trifluoromethyl)-1H-imidazol-1-yl)phenyl)-5-(4-(trifluoromethoxy)phenyl)-1H-1,2,3-triazole

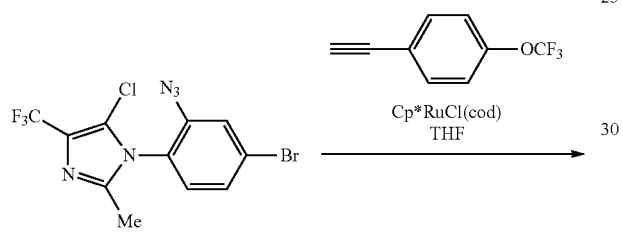

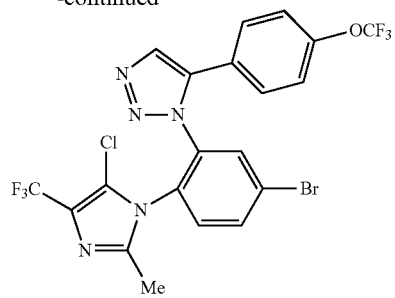

A 40 mL vial was charged with Example 1d (0.21 g, 0.55 mmol), dry THF (10 mL), and 4-(trifluoromethoxy)phenylacetylene (0.13 mL, 0.83 mmol), and then argon was bubbled through the reaction mixture for 15 min. Cp*RuCl (cod) (21 mg, 0.055 mmol) was then added to the reaction mixture and argon was bubbled through for an additional 5 min. The reaction mixture was allowed to stir for 3 days, then the solvent was evaporated and the residue purified by flash column chromatography to yield the title compound (0.18 g, 0.32 mmol).

Example 1f

Preparation of {4'-[5-chloro-2-methyl-4-(trifluoromethyl)-1H-imidazol-1-yl]-3-fluoro-5-(methylsulfonyl)-3'-(5-{4-[(trifluoromethyl)oxy]phenyl}-1H-1,2,3-triazol-1-yl)biphenyl-4-yl}methanol

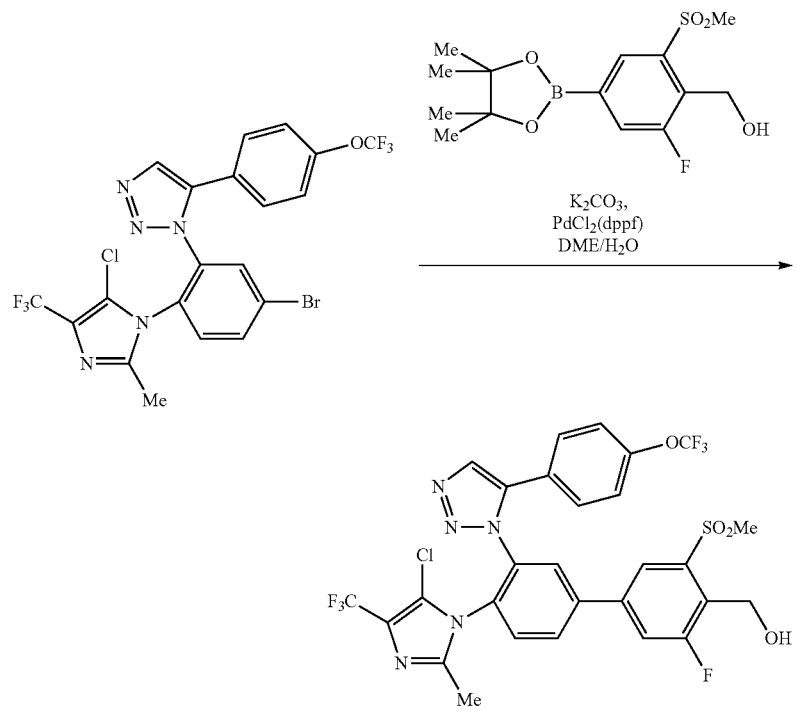

An 8 mL vial was charged with Example 1e (58 mg, 0.10 mmol), DME (2.0 mL) and water (0.20 mL). The solution was sparged with argon for 10 min prior to addition of Intermediate 1, (35 mg, 0.11 mmol), K$_2$CO$_3$ (42 mg, 0.31 mmol), and PdCl$_2$(dppf)-DCM adduct (4.0 mg, 5.0 μmol). The reaction mixture was allowed to stir at 60° C. for 20 h. The reaction was poured into brine and extracted with EtOAc. The organic phase was dried over Na$_2$SO$_4$ and concentrated in vacuo. The residue was purified by preparative HPLC to afford the title compound (42 mg, 0.060 mmol, 60% yield). MS (ESI) 690.3 [M+H]$^+$. $^1$H NMR (400 MHz, CDCl$_3$) δ ppm 8.22 (d, J=1.1 Hz, 1H), 8.14 (d, J=2.1 Hz, 1H), 7.98 (dd, J=8.3, 2.1 Hz, 1H), 7.76 (s, 1H), 7.72 (dd, J=9.7, 1.8 Hz, 1H), 7.50 (d, J=8.3 Hz, 1H), 7.21 (d, J=8.1 Hz, 2H), 7.11-7.03 (m, 2H), 5.13 (d, J=1.6 Hz, 2H), 4.88 (s, 1H), 3.33 (s, 3H), 1.84 (s, 3H).

Example 2

Preparation of 5-(4-chlorophenyl)-1-{4-[2-chloro-4-(trifluoromethyl)-1H-imidazol-1-yl]-3'-(methylsulfonyl)biphenyl-3-yl}-1H-1,2,3-triazole Example 2a

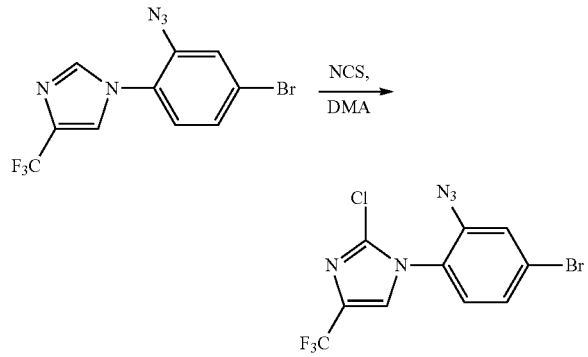

In a 50 mL round bottom flask, 1-(2-azido-4-bromophenyl)-4-(trifluoromethyl)-1H-imidazole (prepared using procedures described in Example 1) (0.22 g, 0.67 mmol), was dissolved in DMA (15 mL). NCS (88 mg, 0.67 mmol) was added and the reaction mixture was heated to 100° C. The reaction was followed by LCMS. After 1 hr a 1:1 ratio starting material to product was observed. An additional 180 mg of NCS was added and the mixture was heated for 1 h. This operation was repeated twice. The reaction mixture was poured into water and extracted in EtOAc. The organic phase was dried over Na$_2$SO$_4$, filtered, and concentrated in vacuo to afford the title product, which was used for subsequent chemistry without further purification, (250 mg, 0.67 mmol). MS (ESI) 365, 367 [M+H]$^+$.

Example 2 was prepared from Example 2a using similar procedures described in Example 1. MS (ES) 578 [M+H]$^+$. $^1$H NMR (400 MHz, CDCl$_3$) δ 8.29 (s, 1H), 8.20 (dd, J=5.1, 2.0 Hz, 1H), 8.08 (d, J=7.8 Hz, 1H), 8.06-7.93 (m, 2H), 7.85-7.74 (m, 2H), 7.63-7.50 (m, 1H), 7.34-7.27 (m, 2H), 6.88 (t, J=8.1 Hz, 2H), 6.79 (s, 1H), 3.16 (s, 3H).

Example 3

2-methyl-1-[3'-(methylsulfonyl)-3-(5-{4-[(trifluoromethyl)oxy]phenyl}-1H-1,2,3-triazol-1-yl)biphenyl-4-yl]-N-(2,2,2-trifluoroethyl)-1H-imidazole-4-carboxamide

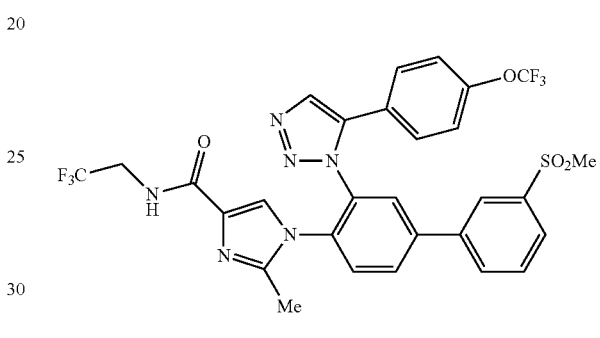

Example 3a

Preparation of methyl 1-(4-bromo-2-nitrophenyl)-2-methyl-1H-imidazole-4-carboxylate

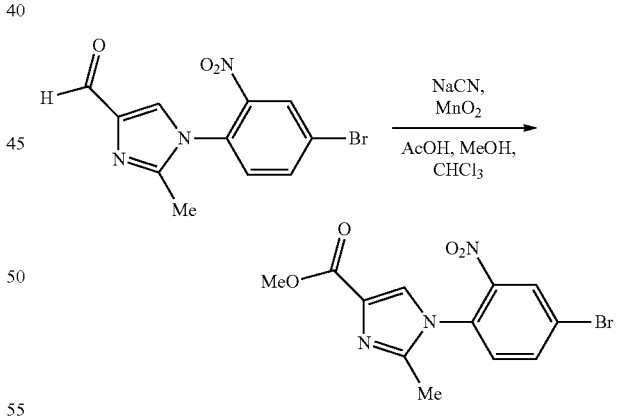

To a solution of 1-(4-bromo-2-nitrophenyl)-2-methyl-1H-imidazole-4-carbaldehyde (prepared from 2-methyl-1H-imidazole-4-carbaldehyde by a similar procedure described in Example 1a) (5.94 g, 19.2 mmol) in MeOH (100 mL) and AcOH (1.64 mL, 28.7 mmol) was added NaCN (4.69 g, 95.8 mmol), CHCl$_3$ (80.0 mL) and MnO$_2$ (33.3 g, 383 mmol). After stirring at rt for 3 h, the reaction mixture was filtered through a pad of Celite and concentrated in vacuo. After most of the volatiles were gone, the remaining solution was made basic with saturated aq NaHCO$_3$ and was extracted with DCM (×3). The combined organics were washed with brine, dried over MgSO₄ and concentrated in vacuo to yield the crude title compound (6.19 g, 20.0 mmol).

Example 3b

Preparation of 2-methyl-1-(3'-(methylsulfonyl)-3-(5-(4-(trifluoromethoxy)phenyl)-1H-1,2,3-triazol-1-yl) biphenyl-4-yl)-1H-imidazole-4-carboxylic acid

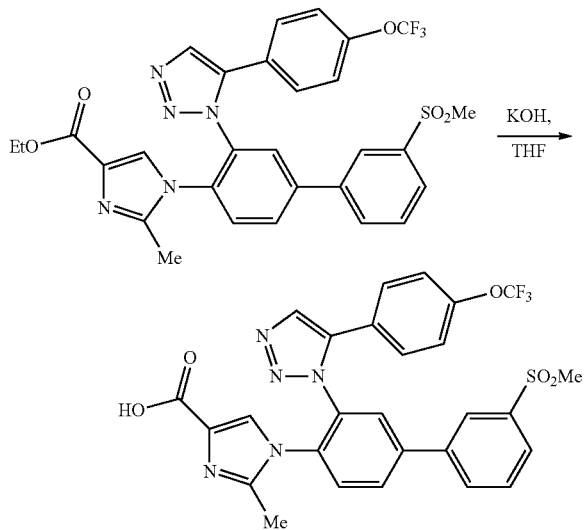

Ethyl 2-methyl-1-(3'-(methylsulfonyl)-3-(5-(4-(trifluoromethoxy)phenyl)-1H-1,2,3triazol-1-yl)biphenyl-4-yl)-1H-imidazole-4-carboxylate was prepared from Example 3a following the procedures described in Example 1b, 1e, and 1f.

A solution of ethyl 2-methyl-1-(3'-(methylsulfonyl)-3-(5-(4-(trifluoromethoxy)phenyl)-1H-1,2,3-triazol-1-yl)biphenyl-4-yl)-1H-imidazole-4-carboxylate (0.47 g, 0.77 mmol) and KOH (1 M, 2.0 mL) in THF (20 mL) was stirred at rt for 6 h. The reaction solution was acidified with HCl (1 M) and then extracted with EtOAc. The combined organic extracts were washed with H₂O, followed by brine, dried over MgSO₄ and concentrated in vacuo to yield the title compound (0.36 g, 0.62 mmol).

Example 3c

Preparation of 2-methyl-1-[3'-(methylsulfonyl)-3-(5-{4-[(trifluoromethyl)oxy]phenyl}-1H-1,2,3-triazol-1-yl) biphenyl-4-yl]-N-(2,2,2-trifluoroethyl)-1H-imidazole-4-carboxamide

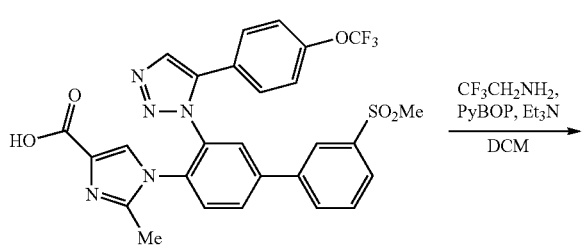

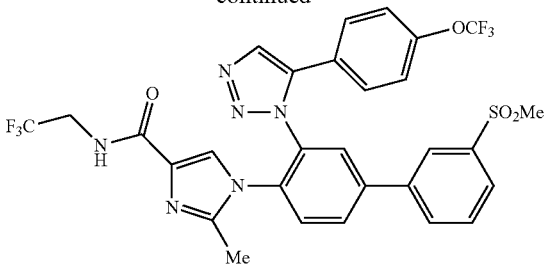

To a solution of Example 3b (63.0 mg, 0.11 mmol) in DCM (2.0 mL), was added 2,2,2-trifluoroethylamine (0.010 mL, 0.12 mmol), Et₃N (0.050 mL, 0.32 mmol), and PyBOP (62 mg, 0.12 mmol). After stirring for 16 h, the reaction mixture was diluted with EtOAc, and washed successively with 1 M HCl, H₂O, 1 M KOH, H₂O, and brine. The organic phase was dried over Na₂SO₄ and concentrated in vacuo. The resulting residue was purified by preparative HPLC to yield the title compound (40 mg, 0.060 mmol, 55% yield). MS (ESI) 665.3 [M+H]⁺. 1H NMR (400 MHz, CDCl₃) δ ppm 8.95-8.58 (m, 1H), 8.24 (s, 1H), 8.08-8.09 (m, 2H), 8.03. (d, J=8.2 Hz, 1H), 7.92 (d, J=7.4 Hz, 1H), 7.83. (s, 1H), 7.78 (dd, J=8.8, 6.7 Hz, 1H), 7.57 (s, 1H), 7.23 (s, 2H), 7.07 (d, J=7.0 Hz, 2H), 6.85 (s, 1H), 4.03 (dd, J=15.5, 9.0 Hz, 2H), 3.15 (s, 3H), 2.10 (s, 3H).

Example 4

5-[4-(fluoromethyl)phenyl]-1-{3'-(methylsulfonyl)-4-[2-methyl-4-(trifluoromethyl)-1H-imidazol-1-yl] biphenyl-3-yl}-1H-1,2,3-triazole

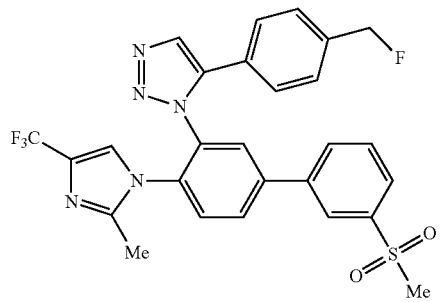 [SMILES: Cc1nc(C(F)(F)F)cn1-c1ccc(-c2cccc(S(C)(=O)=O)c2)cc1-n1nncc1-c1ccc(CF)cc1]

Example 4a

Preparation of methyl 4-(hydroxymethyl)benzoate

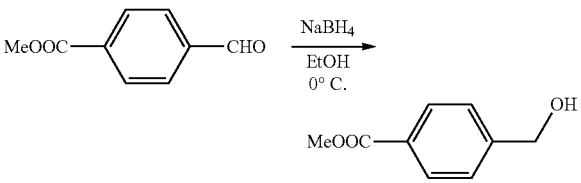

Into a three neck, 1 L round bottom flask fitted with a thermocouple probe was added methyl 4-formylbenzoate (16.6 g, 100 mmol) and EtOH (250 mL). The solution was cooled in an ice bath and NaBH₄ (1.17 g, 31.0 mmol) was added portionwise over 30 min keeping the internal temperature below 5° C. After stirring for 1 hr, the reaction was quenched by the addition of a small amount of acetone, followed by AcOH (10 mL). The reaction mixture was then allowed to warm to rt, and was stirred for 16 hrs. The quenched reaction mixture was diluted with H₂O and made basic by the careful addition of solid Na₂CO₃. The mixture was concentrated in vacuo to remove most of the EtOH. The resulting residue was diluted with EtOAc and additional H₂O. The layers were separated and the basic aqueous layer was further extracted with EtOAc (3×). The organic extracts were washed with brine, dried over Na₂SO₄, filtered, and concentrated in vacuo to afford the title compound as a white solid (16.5 g, 99.4 mmol, 99% yield). MS (ESI) 166 [M+H]⁺. ¹H NMR (400 MHz, CDCl₃) δ ppm 8.00 (d, J=8.3 Hz, 2H), 7.41 (d, J=8.5 Hz, 2H), 4.74 (s, 2H), 3.90 (s, 3H), 2.34 (s, 1H).

Example 4b

Preparation of methyl 4-(fluoromethyl)benzoate

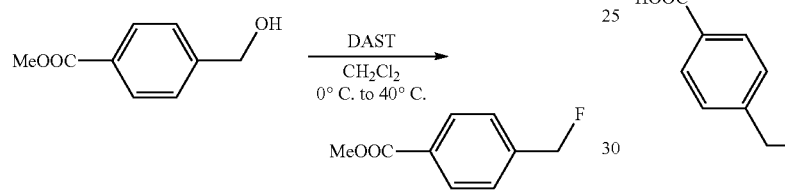

Into 1 L round bottom flask was added Example 4a (10.4 g, 62.6 mmol), and CH₂Cl₂ (250 mL). The resulting solution was cooled in an ice bath and DAST (12.5 mL, 95.4 mmol) was added dropwise. After stirring for several min at 0° C., the ice bath was removed and the reaction mixture was allowed to warm to rt. After 90 min at rt the reaction mixture was cooled in an ice bath and carefully quenched by the addition of NaHCO₃ solution with vigorous stirring. After warming to rt and sitting for 16 hrs, the layers were separated and the basic aqueous layer was further extracted with CH₂Cl₂ (3×). The combined organic extracts were dried over Na₂SO₄, filtered, and concentrated in vacuo to afford a dark brown oil. The crude product was purified by chromatography on a 300 g silica column, eluting with a gradient of 100% Hx to 100% EtOAc to afford the title compound as a brown oil (4.03 g, 24.0 mmol, 38% yield). MS (ESI) 168 [M+H]⁺. ¹H NMR (400 MHz, CDCl₃) δ ppm 8.07 (d, J=7.9 Hz, 2H), 7.43 (d, J=7.8 Hz, 2H), 5.45 (d, $J_{(H-F)}$=47.2 Hz, 2H), 3.93 (s, 3H).

Example 4c

Preparation of 4-(fluoromethyl)benzoic acid

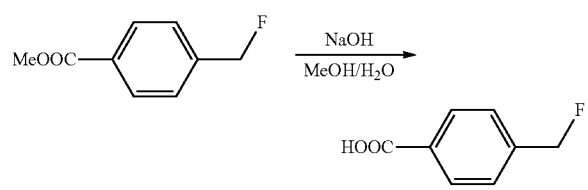

To a solution of Example 4b (4.0 g, 24 mmol) in MeOH (100 mL) was added 20% (w/v) NaOH in water (10 mL, 50 mmol). After stirring at rt for 16 hrs, the reaction was quenched by the addition of AcOH (2.0 mL), and concentrated in vacuo to afford an off-white paste. The paste was taken up in a minimal amount of MeOH, and 20% (w/v) NaOH was added to afford a brown solution. This brown solution was added slowly to a vigorously stirred solution of 20 mL of concentrated HCl in 200 mL of ice water. The resulting suspension was filtered, and the resulting solids were washed with cold water, dried on the filter and then dried under vacuum to afford the title compound as a beige powder (3.2 g, 21 mmol, 87% yield). ¹H NMR (400 MHz, DMSO) δ ppm 7.97 (d, J=7.6 Hz, 2H), 7.51 (d, J=7.0 Hz, 2H), 5.50 (d, $J_{(H-F)}$=47.2 Hz, 2H).

Example 4d

Preparation of 2-bromo-1-(4-(fluoromethyl)phenyl)ethanone

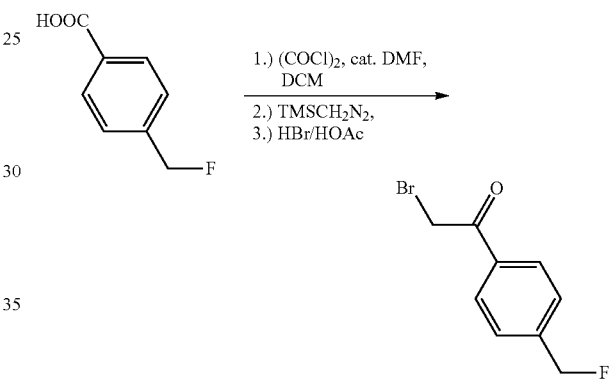

To a 250 mL round bottom flask was added Example 4c (3.2 g, 21 mmol), and CH₂Cl₂ (80 mL). The resulting solution was treated with oxalyl chloride (3.0 mL, 34 mmol) followed by a few drops of DMF. After stirring for 64 hrs at rt, the brown solution was concentrated in vacuo to afford the intermediate, 4-(fluoromethyl)benzoyl chloride as a brown oil. The crude intermediate was dissolved in a mixture of THF (30 mL) and MeCN (30 mL), and the resulting solution was cooled in an ice bath. The cold solution was stirred and treated dropwise with a solution of trimethylsilyl diazomethane (20 mL of a 2.0 M solution in diethyl ether, 40 mmol). After stirring for 1 hr at 0° C., the solution was concentrated in vacuo to afford a dark solid. This solid was taken up in AcOH (20 mL), cooled in an ice bath and treated dropwise with 48% aqueous HBr (vigorous gas evolution). After stirring 2 hrs at 0° C., the reaction mixture was carefully added to a stirred suspension of Na₂CO₃ in ice water (vigorous gas evolution). The basic mixture was diluted with EtOAc and transferred to a separatory funnel. The layers were separated and the basic aqueous layer was extracted with additional EtOAc (3×). The combined organic extracts were washed with brine, dried over Na₂SO₄, filtered and concentrated in vacuo to afford the title compound as a dark brown oil that was carried on to the next step without purification (5.1 g, 21 mmol). MS (ESI) 230, 232 [M+H]⁺. ¹H NMR (400 MHz, CDCl₃) δ ppm 8.01 (d, J=7.7 Hz, 2H), 7.49 (d, J=8.0 Hz, 2H), 5.47 (d, $J_{(H-F)}$=47.0 Hz, 2H), 4.45 (s, 2H).

Example 4e

Preparation of (2-(4-(fluoromethyl)phenyl)-2-oxoethyl)triphenylphosphonium bromide

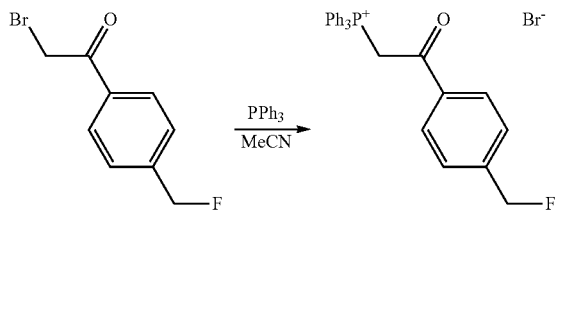

To a solution of Example 4d (5.1 g, 21 mol) in MeCN (30 mL) was added triphenylphosphine (5.4 g, 21 mmol) to afford a pale brown solution. After stirring at rt for 16 hrs the reaction mixture was concentrated in vacuo to afford the title compound as a dark syrup. This crude salt was carried on to the phosphorane formation without purification. MS (ESI): 413.1 [M+H]$^+$ (for phosphonium cation). $^1$H NMR (400 MHz, CDCl$_3$) δ ppm 7.97 (d, J=8.1 Hz, 2H), 7.77-7.61 (m, 9H), 7.54 (td, J=7.7, 3.4 Hz, 6H), 7.45 (d, J=7.9 Hz, 2H), 5.44 (d, J$_{(H-F)}$=47.2 Hz, 2H), 2.61 (s, 2H).

Example 4f

Preparation of 1-(4-(fluoromethyl)phenyl)-2-(triphenylphosphoranylidene)ethanone

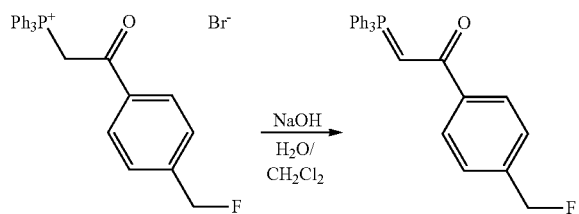

To a solution of Example 4e (3.6 g, 7.4 mmol) in CH$_2$Cl$_2$ (15 mL) was added 20% (w/v) aq NaOH solution. The resulting mixture was stirred vigorously at rt for 2 hrs, then the layers were allowed to separate and the basic aqueous was extracted with CH$_2$Cl$_2$ (3×). The combined organic extracts were dried over Na$_2$SO$_4$, filtered, and concentrated in vacuo to afford the title compound as a dark syrup. This crude phosphorane was used in the subsequent step without purification.

Example 4g

Preparation of 5-(4-(fluoromethyl)phenyl)-1-(4-(2-methyl-4-(trifluoromethyl)-1H-imidazol-1-yl)-3'-(methylsulfonyl) biphenyl-3-yl)-1H-1,2,3-triazole

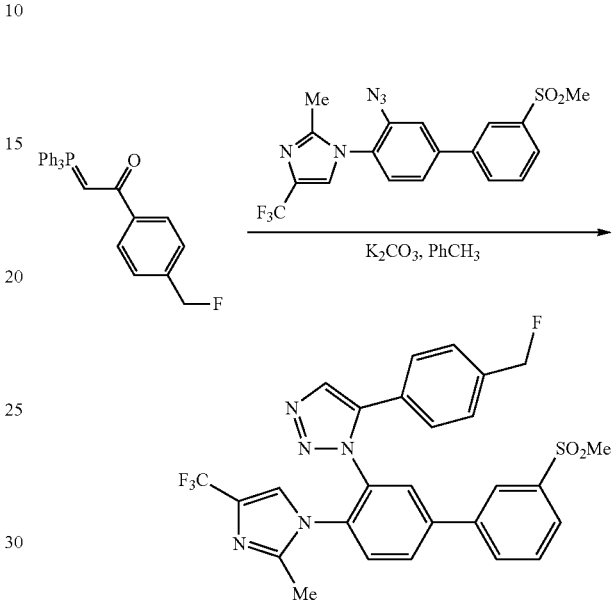

To a 5 mL microwave reaction vial was added 1-(3-azido-3'-(methylsulfonyl)biphenyl-4-yl)-2-methyl-4-(trifluoromethyl)-1H-imidazole (prepared by similar procedures described in Example 1) (75 mg, 0.18 mmol), Example 4f (380 mg, 0.93 mmol), K$_2$CO$_3$ (120 mg, 0.87 mmol), and toluene (2.0 mL). The resulting mixture was heated in the microwave reactor at 100° C. for 30 min. The reaction was incomplete and the reaction vial was heated an additional 1 hr at 120° C. in the microwave reactor. After cooling to rt, the reaction mixture was filtered and concentrated in vacuo to afford a brown solid. The crude product was purified by chromatography on a 25 g silica column eluting with a gradient of 100% Hx to 100% EtOAc to afford a partially purified product, which was further purified by preparative HPLC to afford the title compound as a clear colorless oil (17 mg, 0.031 mmol, 17% yield). MS (ESI) 556.1 [M+H]$^+$. $^1$H NMR (400 MHz, CDCl$_3$) δ ppm 8.31 (t, J=1.7 Hz, 1H), 8.24 (d, J=2.1 Hz, 1H), 8.10-8.02 (m, 2H), 7.96 (dd, J=8.3, 2.1 Hz, 1H), 7.83-7.76 (m, 2H), 7.43 (d, J=8.3 Hz, 1H), 7.33 (d, J=7.1 Hz, 2H), 6.96 (d, J=7.7 Hz, 2H), 6.23 (s, 1H), 5.37 (d, J$_{(H-F)}$=47.2 Hz, 2H), 3.16 (s, 3H), 1.66 (s, 3H).

Example 5

5-[4-(difluoromethyl)phenyl]-1-{3'-(methylsulfonyl)-4-[2-methyl-4-(trifluoromethyl)-1H-imidazol-1-yl]biphenyl-3-yl}-1H-1,2,3-triazole

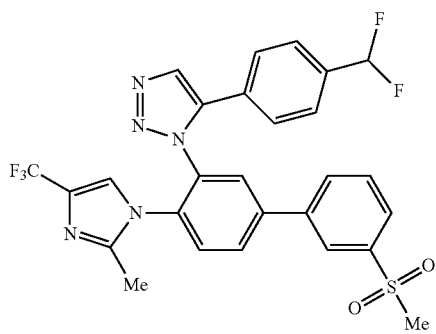 [SMILES: Cc1nc(C(F)(F)F)cn1-c1ccc(-c2cccc(S(C)(=O)=O)c2)cc1-n1nncc1-c1ccc(C(F)F)cc1]

Example 5a

Preparation of methyl 4-(difluoromethyl)benzoate

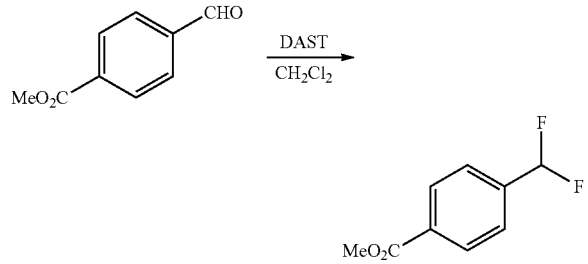

To a cooled (0° C.) solution of methyl 4-formylbenzoate (9.0 g, 55 mmol) in CH$_2$Cl$_2$ (250 mL) was added DAST (11 mL, 84 mmol) dropwise. After stirring for 2 hrs, the cooling bath was removed and the reaction mixture was allowed to warm to rt. After 6 hrs at rt, the reaction was incomplete as judged by GC/MS analysis. The reaction mixture was treated with additional DAST (4.4 mL, 33 mmol). After stirring for 16 hrs at rt, the reaction was quenched by pouring the mixture onto ice. The aqueous layer was made basic by careful addition of solid Na$_2$CO$_3$, with vigorous stirring. The layers were separated and the basic aqueous solution was further extracted with CH$_2$Cl$_2$ (3×) The combined organic extracts were dried over Na$_2$SO$_4$, filtered, and concentrated in vacuo to afford the title compound as a brown solid. The material was carried on to the next step without further purification. $^1$H NMR (400 MHz, CDCl$_3$) δ ppm 8.13 (d, J=8.0 Hz, 2H), 7.59 (d, J=8.2 Hz, 2H), 6.69 (t, J$_{(H-F)}$=56.1 Hz, 1H), 3.95 (s, 3H).

Example 5 was prepared from Example 5a by the procedures described in Example 4. MS (ESI): 574.1 [M+H]$^+$. $^1$H NMR (400 MHz, CDCl$_3$) δ 8.31 (t, J=1.7 Hz, 1H), 8.25 (d, J=2.1 Hz, 1H), 8.06 (m, 2H), 7.97 (dd, J=8.3, 2.1 Hz, 1H), 7.84-7.76 (m, 2H), 7.46 (m, 3H), 7.03 (d, J=8.1 Hz, 2H), 6.63 (t, J$_{(H-F)}$=56.0 Hz, 1H), 6.22 (s, 1H), 3.16 (s, 3H), 1.64 (s, 3H).

Example 6

1-(4-(4-(difluoromethyl)-2-methyl-1H-imidazol-1-yl)-3'-(methylsulfonyl)-[1,1'-biphenyl]-3-yl)-5-(4-(trifluoromethoxy)phenyl)-1H-1,2,3-triazole

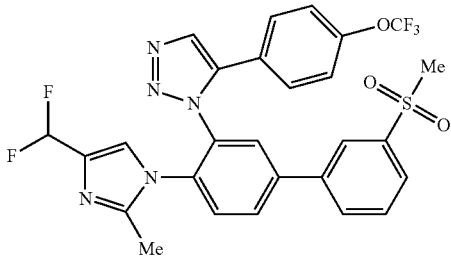 [SMILES: Cc1nc(C(F)F)cn1-c1ccc(-c2cccc(S(C)(=O)=O)c2)cc1-n1nncc1-c1ccc(OC(F)(F)F)cc1]

Example 6a

Preparation of 1-(4-bromo-2-nitrophenyl)-4-(difluoromethyl)-2-methyl-1H-imidazole

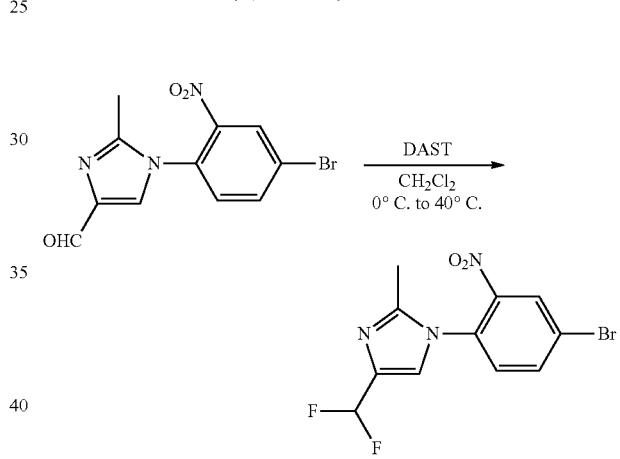

To a cooled (0° C.) solution of 1-(4-bromo-2-nitrophenyl)-2-methyl-1H-imidazole-4-carbaldehyde (prepared from 2-methyl-1H-imidazole-4-carbaldehyde by a similar procedure described in Example 1a) (7.2 g, 23 mmol) in CH$_2$Cl$_2$ (84 mL) was added DAST (6.0 mL, 46 mmol) dropwise. After 10 min the ice bath was removed and the reaction was allowed to warm to rt. After 20 hrs stirring at rt, GC/MS analysis showed unreacted aldehyde remaining. The reaction mixture was then heated to 40° C. for 2 hrs at which time there was still unreacted aldehyde present. An additional portion of DAST was added (2.0 mL, 15 mmol), and after 1 hr at 40° C., heating was discontinued. The cooled reaction was carefully quenched by the addition of EtOAc and saturated aq NaHCO$_3$. The resulting dark colored suspension was filtered to remove insolubles and the filtrate was transferred to a separatory funnel. The layers were separated and the aqueous was extracted with EtOAc (3×). The combined organic extracts were washed with brine, dried over Na$_2$SO$_4$, filtered and concentrated to afford a crude dark oil. The crude material was purified by flash chromatography on 160 g of silica eluting with a gradient from 100% CH$_2$Cl$_2$ to 50% MeCN/CH$_2$Cl$_2$ to afford the title compound as a dark solid (4.2 g, 13 mmol, 57% yield). MS (ESI) 331, 333 [M+H]$^+$. $^1$H NMR (400 MHz, CDCl$_3$) δ 8.26

(d, J=2.2 Hz, 1H), 7.92 (dd, J=8.4, 2.2 Hz, 1H), 7.34 (d, J=8.4 Hz, 1H), 7.13 (t, J=2.1 Hz, 1H), 6.67 (t, J$_{(H-F)}$=55.8 Hz, 1H), 2.23 (s, 3H).

Example 6b

Preparation of 5-bromo-2-(4-(difluoromethyl)-2-methyl-1H-imidazol-1-yl)aniline

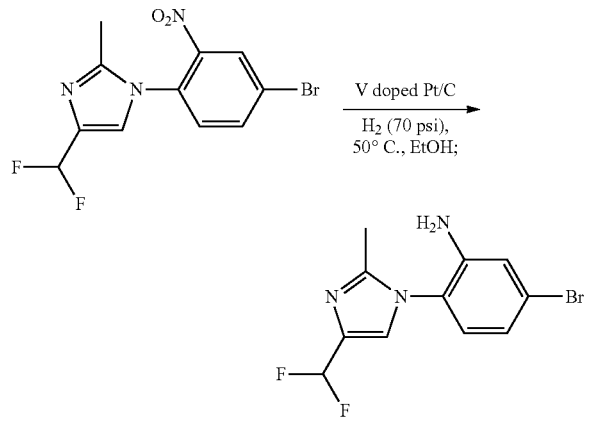

A glass Parr pressure bottle was charged with Example 6a (5.5 g, 17 mmol), EtOH (50 mL), and Degussa XBV/W hydrogenation catalyst (3% Pt/0.6% V on carbon) (890 mg, 16% by weight). The black suspension was shaken on the Parr shaker hydrogenator at 69 psi hydrogen pressure for 3 hrs. At this time the reaction was incomplete. The reaction bottle was then shaken at 70 psi. hydrogen pressure while heating to 50° C. After 16 hrs, the reaction was still incomplete, with intermediate hydroxylamine visible in the MS. The reaction was treated with an additional 600 mg of the hydrogenation catalyst, and was shaken under 70 psi of hydrogen pressure at 60° C. After an additional 20 hrs, the reaction was complete with no visible sign of the intermediate hydroxylamine present in the MS. The reaction suspension was cooled, and filtered through a pad of Celite. The pad was washed thoroughly with EtOH and the filtrate was concentrated in vacuo to afford the title compound as a yellow solid (5.0 g, 17 mmol, 99% yield). MS (ESI) 302, 304 [M+H]$^+$. $^1$H NMR (400 MHz, CDCl$_3$) δ 7.13 (t, J=2.1 Hz, 1H), 7.02 (d, J=1.8 Hz, 1H), 6.96-6.89 (m, 2H), 6.66 (t, J$_{(H-F)}$=55.8 Hz, 1H), 3.76 (s, 2H), 2.24 (s, 3H).

Example 6c

Preparation of 1-(5-bromo-2-(4-(difluoromethyl)-2-methyl-1H-imidazol-1-yl)phenyl)-5-(4-(trifluoromethoxy)phenyl)-1H-1,2,3-triazole

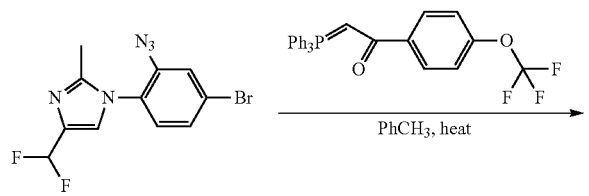

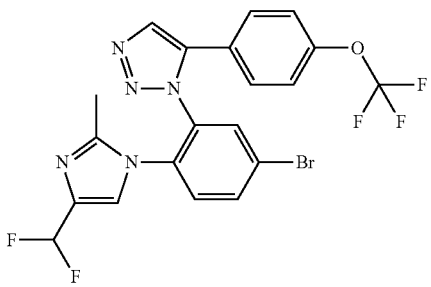

Into a 50 mL round bottom flask was placed 1-(2-azido-4-bromopheny(difluoromethyl)-2-methyl-1H-imidazole (prepared from Example 6b by a similar procedure described in Example 1c) (470 mg, 1.4 mmol), triphenylphosporayilydene-1-(4-(trifluoromethoxy)phenyl)ethanone (690 mg, 1.5 mmol) (prepared from 4-(trifluoromethoxy)benzoic acid by procedures similar to those described in Examples 4d, 4e and 4f) and toluene (12 mL). The golden solution was heated at reflux for 6 hrs and then allowed to stir at rt overnight. The reaction mixture was treated with a small amount of 4-bromobenzaldehyde and heated to reflux for 1 hr to consume the remaining triphenylphosporayilydene-1-(4-(trifluoromethoxy)phenyl)ethanone. The reaction mixture was concentrated in vacuo to afford a brown-orange oil. This crude material was purified by flash chromatography on 40 g of silica eluting with a gradient from 0-100% EtOAc/Hx to afford the title compound (660 mg, 1.3 mmol, 90% yield). MS (ESI) 514, 516 [M+H]$^+$. $^1$H NMR (400 MHz, CDCl$_3$) δ ppm 8.15 (d, J=2.2 Hz, 1H), 7.85 (dd, J=8.5, 2.2 Hz, 1H), 7.72 (s, 1H), 7.20 (m, 3H), 6.99-6.91 (m, 2H), 6.40 (t, J=55.4 Hz, 1H), 6.13 (s, 1H), 1.59 (s, 3H).

Example 6 was prepared from Example 6c and 3-(methylsulfonyl)phenylboronic acid using procedures similar to that described in Example 1f, except by heating the reaction via microwave at 120° C. for 20 min MS (ESI) 590.1 [M+H]$^+$. 1H NMR (400 MHz, CDCl$_3$) δ ppm 8.32 (s, 1H), 8.23 (d, J=2.0 Hz, 1H), 8.06 (m, 2H), 7.96 (dd, J=8.3, 2.1 Hz, 1H), 7.83-7.73 (m, 2H), 7.44 (d, J=8.3 Hz, 1H), 7.18 (d, J=8.4 Hz, 2H), 6.97 (d, J=8.7 Hz, 2H), 6.43 (t, J$_{(H-F)}$=55.5 Hz, 1H), 6.19 (s, 1H), 3.16 (s, 3H), 1.65 (s, 3H).

Scheme 2

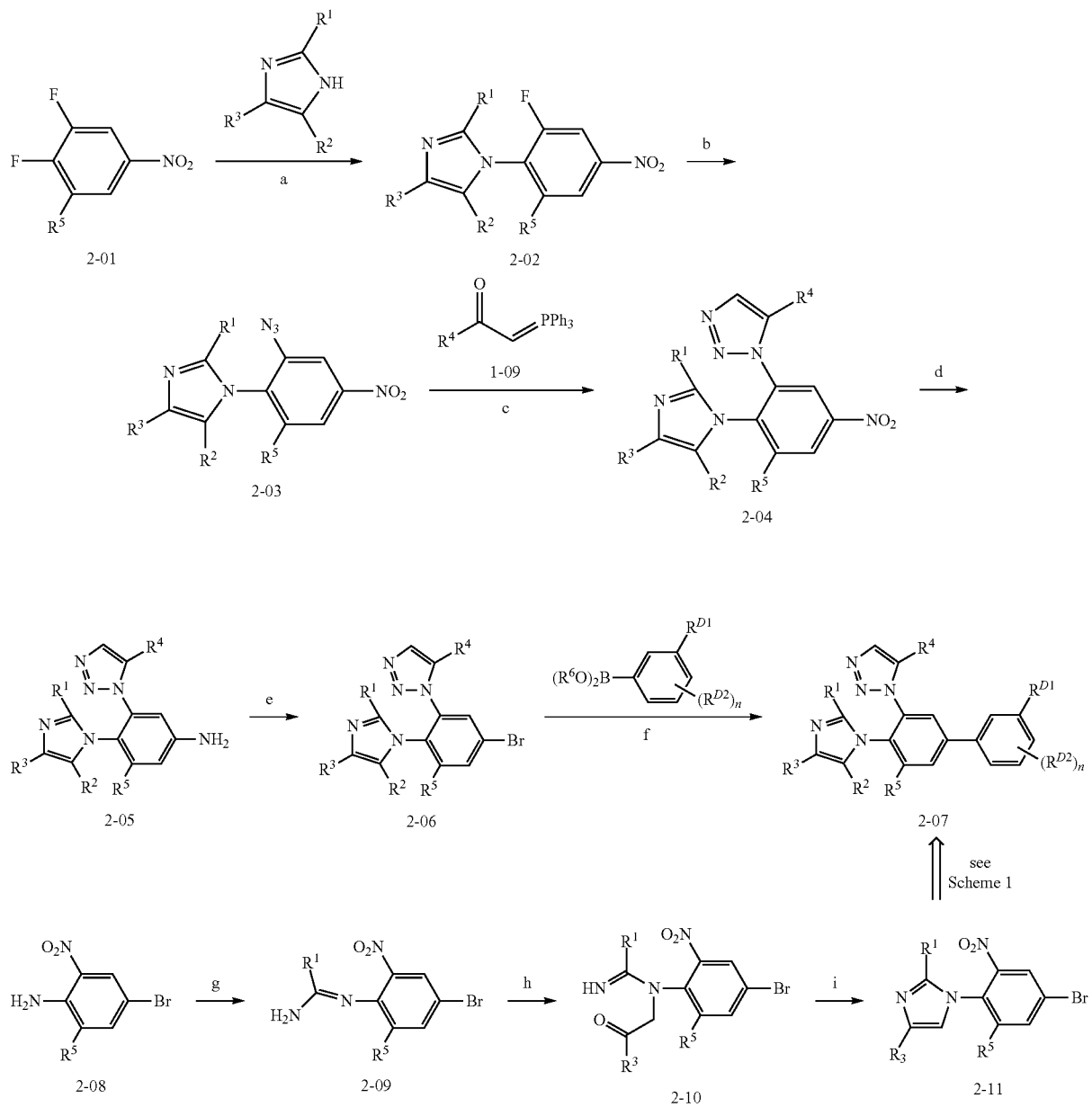

(a) Cs₂CO₃, DMF; (b) NaN₃, DMSO; (c) toluene, 80° C.; (d) SnCl₂•2 H₂O, EtOH; (e) tBuONO, CuBr₂, ACN; (f) PdCl₂dppf, K₂CO₃, DME, H₂O; (g) R¹CN, 4M HCl in dioxane, pTSA; (h) R³COCH₂Br, NaHCO₃, THF; (i) toluene, pTSA.

Additional compounds of the invention are exemplified by general structure (2-07) that contain various substituent groups represented by $R^5$ (Scheme 2). A substituted imidazole undergoes a $S_NAr$ reaction with the 2,3-difluoro-5-nitrobenzene derivative (2-01) in the presence of $Cs_2CO_3$ in DMF to give the nitrophenyl imidazole (2-02). The aryl fluoride (2-02) is converted to the azide (2-03) by reaction with $NaN_3$ in DMSO. The phosphorane derivative (1-09) reacts with the azide (2-03) to yield the triazole (2-04). The nitrophenyl (2-04) is reduced to the aniline (2-05) with $SnCl_2$-$2H_2O$ in EtOH. The aniline imidazole (2-05) is converted to the bromide (2-06) by reaction with t-BuONO and $CuBr_2$ in ACN. Suzuki coupling between the aryl bromide (2-06) with the aryl boronic acid or ester derivatives produces the final triazole product (2-07).

Alternatively, compounds that contain a substituent at $R^5$ on the structure such as 2-07 can be prepared from the aniline (2-08), which reacts with $R^1CN$ in the presence of HCl and pTSA to yield the amidine (2-09). The amidine (2-09) is alkylated with an α-bromoketone to provide 2-10. The ketoimine (2-10) cyclizes to form the imidazole (2-11) in the presence of catalytic pTSA. The nitrophenyl bromide (2-11) can then be converted to the final triazole product (2-07) through similar steps shown in Scheme 1 and described in Example 1.

Example 7

1-(5-chloro-3'-(methylsulfonyl)-4-(4-(trifluoromethyl)-1H-imidazol-1-yl)biphenyl-3-yl)-5-(4-chlorophenyl)-1H-1,2,3-triazole

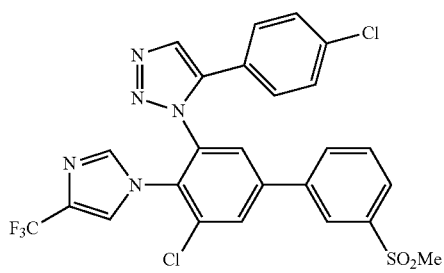 [SMILES: CS(=O)(=O)c1cccc(-c2cc(Cl)c(-n3cnc(C(F)(F)F)c3)c(-n3nncc3-c3ccc(Cl)cc3)c2)c1]

Example 7a

Preparation of 1-(2-chloro-6-fluoro-4-nitrophenyl)-4-(trifluoromethyl)-1H-imidazole 4-(Trifluoromethyl)-1H-imidazole (2.20 g, 27.1 mmol), 1-chloro-2,3-difluoro-5-nitrobenzene (5.00 g, 25.8 mmol) and Cs$_2$CO$_3$ (25.0 g, 77.4 mmol) were brought up in DMF (50.0 mL) and stirred at 70° C. for 2 hrs. The reaction mixture was poured into water (100 mL) and extracted with EtOAc (100 mL×3). The combined organics were dried over Na$_2$SO$_4$, filtered and concentrated in vacuo to give the crude product (7.80 g, 25.2 mmol, 98% yield). MS (ESI) 310 [M+H]$^+$.

Example 7b

Preparation of 1-(2-azido-6-chloro-4-nitrophenyl)-4-(trifluoromethyl)-1H-imidazole

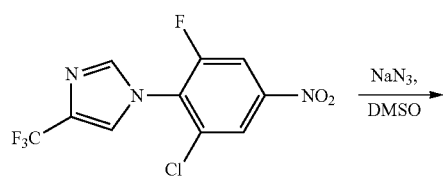

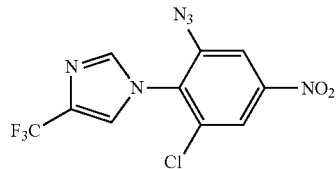

Example 7a (3.70 g, 11.9 mmol) and NaN$_3$ (850 mg, 13.1 mmol) were brought up in DMSO (50 mL) and stirred at 100° C. for 1 hr. The reaction mixture was poured into water (50 mL) and extracted with EtOAc (50 mL×2). The combined organics were dried over Na$_2$SO$_4$, filtered into a round bottom flask and concentrated in vacuo to give the title compound as crude brown oil (3.10 g, 9.32 mmol, 78% yield). MS (ESI) 333 [M+H]$^+$.

Example 7c

Preparation of 1-(3-chloro-5-nitro-2-(4-(trifluoromethyl)-1H-imidazol-1-yl)phenyl)-5-(4-chlorophenyl)-1H-1,2,3-triazole

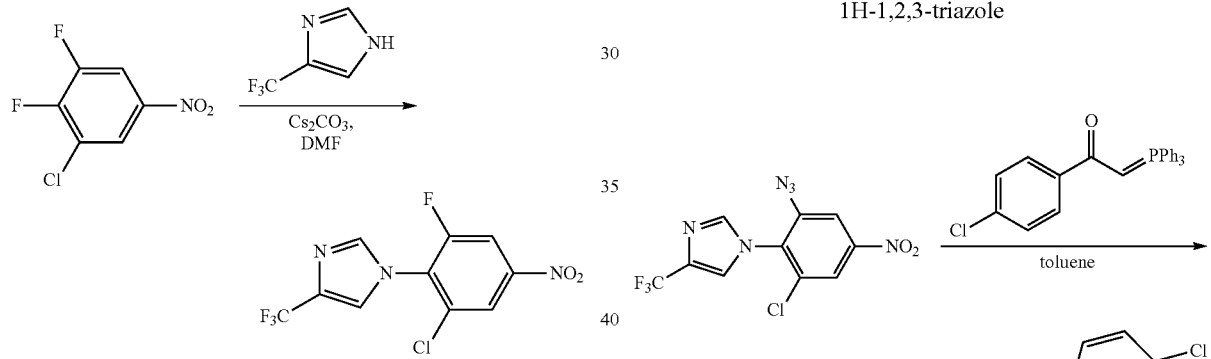

A solution of 1-(4-chlorophenyl)-2-(triphenylphosphoranylidene)ethanone (prepared from 4-chlorobenzoic acid by procedures similar to those described in Examples 4d, 4e and 4f) (2.00 g, 4.96 mmol) and Example 7b (1.50 g, 4.50 mmol) in anhydrous toluene (30 mL) was heated to a reflux for 1 hr. The solvent was removed from the reaction in vacuo and the crude residue was purified by chromatography thru a 25 g SiO$_2$ column using a mobile phase gradient of 20-80% EtOAc/Hx to afford the title compound (1.30 g, 2.77 mmol, 62% yield). MS (ESI) 470 [M+H]$^+$.

Example 7d

Preparation of 3-chloro-5-(5-(4-chlorophenyl)-1H-1,2,3-triazol-1-yl)-4-(4-(trifluoromethyl)-1H-imidazol-1-yl)aniline

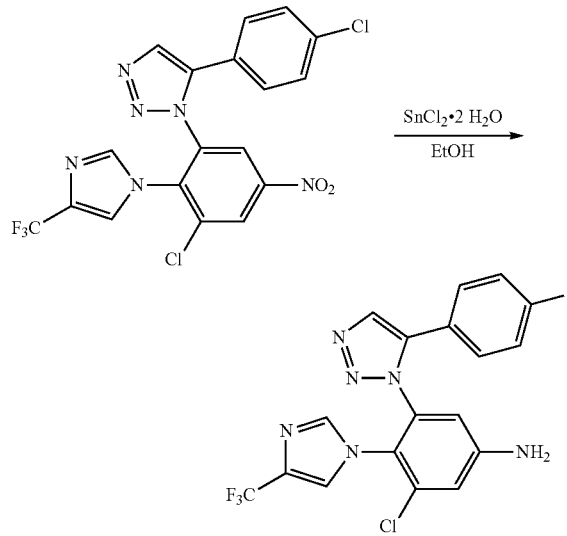

A solution of Example 7c (1.30 g, 2.77 mmol) and SnCl$_2$-2H$_2$O (2.50 g, 110 mmol) in EtOH (30 mL) was heated to 80° C. for 1 hr. To the solution was added NaOH (1M, 40 mL) and the reaction mixture was stirred at 80° C. for 10 min. The reaction mixture was filtered through celite and washed with CH$_2$Cl$_2$. The layers were separated and the aqueous layer was extracted with CH$_2$Cl$_2$. The combined organics were washed with water (50 mL×2), dried over Na$_2$SO$_4$, filtered and concentrated in vacuo to give the title compound as a pale orange solid (700 mg, 1.59 mmol, 58% yield). MS (ESI) 440 [M+H]$^+$.

Example 7e

Preparation of 1-(5-bromo-3-chloro-2-(4-(trifluoromethyl)-1H-imidazol-1-yl)phenyl)-5-(4-chlorophenyl)-1H-1,2,3-triazole

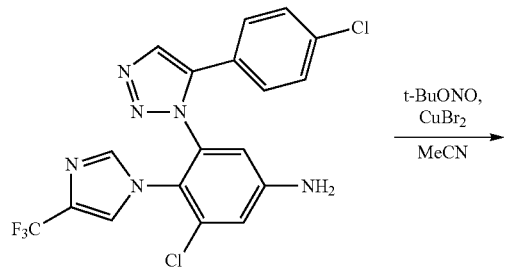

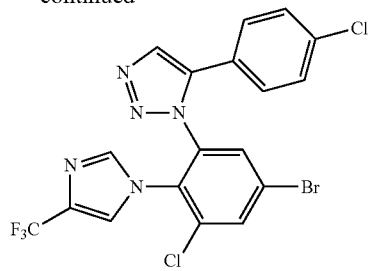

To a solution of CuBr$_2$ (430 mg, 1.92 mmol) and t-BuONO (320 μL, 2.70 mmol) in anhydrous MeCN (20 mL) at 0° C. was added Example 7d (700 mg, 1.60 mmol) and the mixture was allowed to stir at rt for 1 hr. The mixture was poured into ice cold 1M HCl (30 mL) and the layers were separated. The aqueous layer was extracted with DCM (40 mL). The combined organics were dried over Na$_2$SO$_4$, filtered and concentrated in vacuo to give the title compound (400 mg, 0.795 mmol, 50% yield). MS (ESI) 501, 503 [M+H]$^+$.

Example 7 was prepared from Example 7e and 3-(methylsulfonyl)phenylboronic acid using procedures similar to that described in Example 1f. MS (ESI) 579 [M+H]+. $^1$H NMR (400 MHz, CDCl$_3$) δ 8.28 (s, 1H), 8.17-8.04 (m, 3H), 8.01 (d, J=7.8 Hz, 1H), 7.81 (t, J=7.8 Hz, 1H), 7.76 (s, 1H), 7.34 (dd, J=8.7, 2.1 Hz, 2H), 6.87 (d, J=8.4 Hz, 2H), 6.86-6.75 (m, 1H), 6.52 (m, 1H), 3.15 (s, 3H). $^{19}$F NMR (376 MHz, CDCl$_3$) δ-63.24 (d, J=15.3 Hz, 3F).

Example 8

5-(2,4-dichlorophenyl)-1-{5-fluoro-3'-(methylsulfonyl)-4-[2-methyl-4-(trifluoromethyl)-1H-imidazol-1-yl]biphenyl-3-yl}-1H-1,2,3-triazole

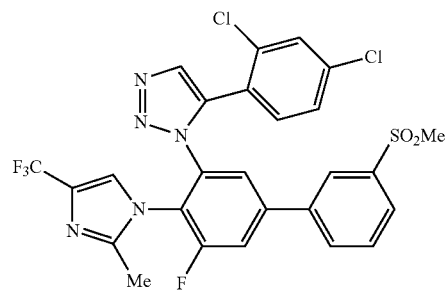 [SMILES: Cc1nc(C(F)(F)F)cn1-c1c(F)cc(-c2cccc(S(C)(=O)=O)c2)cc1-n1nncc1-c1ccc(Cl)cc1Cl]

Example 8a

Preparation of (Z)—N'-(4-bromo-2-fluoro-6-nitrophenyl)acetimidamide

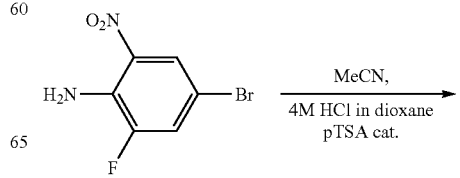

-continued

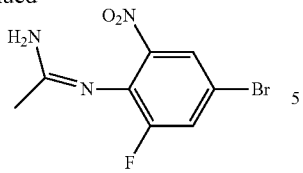

In a high pressure sealed flask, 4-bromo-2-fluoro-6-nitroaniline (10.0 g, 42.5 mmol) was brought up in 4M HCl in dioxane (50 mL) and pTSA (50.0 mg). The reaction solution was heated to 100° C. for 2 days. The solvent was removed in vacuo and the crude residue was purified by chromatography thru a 160 g SiO$_2$ column using the mobile phase 10% MeOH/1% NH$_2$OH in DCM to afford the title compound (11.0 g, 39.8 mmol, 94% yield). MS (ESI) 275, 277 [M+H]$^+$. $^1$H NMR (400 MHz, DMSO) δ ppm 7.98 (t, J=2.1 Hz, 1H), 7.76 (dd, J=10.8, 2.3 Hz, 1H), 7.46 (s, 2H), 2.51 (s, 3H).

Example 8b

Preparation of (Z)—N'-(4-bromo-2-fluoro-6-nitrophenyl)-N-(3,3,3-trifluoro-2-oxopropyl)acetimidamide

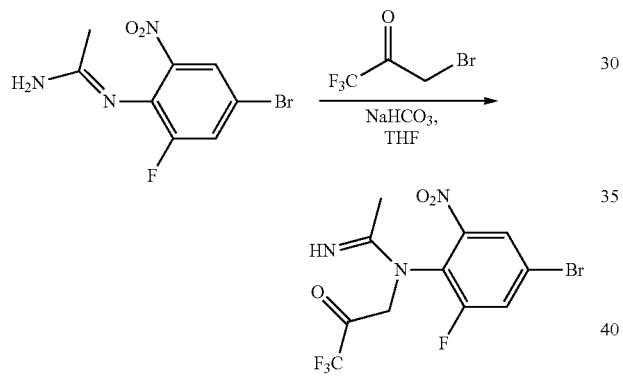

A solution of Example 8a (5.40 g, 19.6 mmol), NaHCO$_3$ (5.00 g, 58.8 mmol) and 3-bromo-1,1,1-trifluoropropan-2-one (4.10 mL, 39.2 mmol) in THF (50 mL) was heated to 80° C. for 40 min. The solvent was removed in vacuo and the crude residue was purified by chromatography thru a 80 g SiO$_2$ column using the mobile phase gradient of 30-100% EtOAc/Hx to afford the title compound (3.20 g, 8.29 mmol, 44% yield). MS (ESI) 385, 387 [M+H]$^+$.

Example 8c

Preparation of 1-(4-bromo-2-fluoro-6-nitrophenyl)-2-methyl-4-(trifluoromethyl)-1H-imidazole

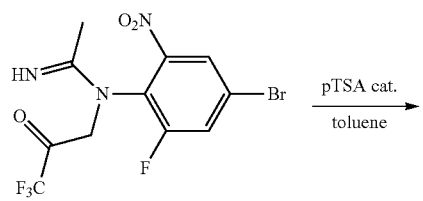

-continued

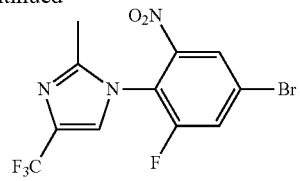

A solution of Example 8b (3.20 g, 8.29 mmol) and pTSA (50 mg) in toluene (30 mL) was heated to a reflux overnight. The solvent was removed from the reaction in vacuo and the crude residue was purified by chromatography thru a 50 g SiO$_2$ column using a mobile phase gradient of 10-30% EtOAc/Hx to afford the title compound (1.60 g, 4.35 mmol, 52% yield). MS (ESI) 367, 369 [M+H]$^+$.

Example 8 was prepared from Example 8c by procedures similar to those described in Example 1. MS (ESI) 610, 612 [M+H]$^+$. 1H NMR (400 MHz, CDCl$_3$) δ ppm 8.22 (s, 1H), 8.09 (d, J=7.8 Hz, 1H), 7.96 (m, 2H), 7.89-7.69 (m, 3H), 7.45 (d, J=1.8 Hz, 1H), 7.2 (m, 1H), 6.72 (d, J=8.3 Hz, 1H), 6.49 (s, 1H), 3.15 (s, 3H), 1.76 (s, 3H).

Example 9

(3-fluoro-3'-{5-[1-(4-methylphenyl)ethyl]-1H-1,2,3-triazol-1-yl}-5-(methylsulfonyl)-4'-[2-methyl-4-(trifluoromethyl)-1H-imidazol-1-yl]biphenyl-4-yl)methanol

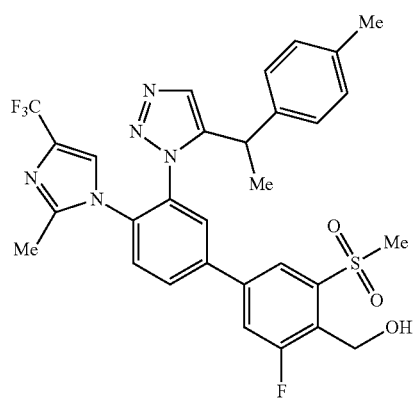

Example 9a

Preparation of 3-(p-tolyl)-1-(triphenylphosphoranylidene)butan-2-one

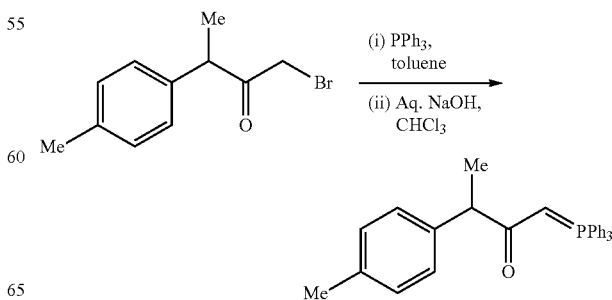

A solution of 1-bromo-3-p-tolylbutan-2-one (prepared from 2-p-tolylpropanoic acid using similar procedures described in Example 4d) (4.09 g, 17.0 mmol) and PPh₃ (4.45 g, 17.0 mmol) in anhydrous toluene (25 mL) was heated to 80° C. for 40 min. The solution was cooled to rt, and the resulting white precipitate was filtered from the solution to give the phoshonium salt. The crude phosphonium salt was brought up in CHCl₃ (20 mL) and aqueous NaOH (816 mg, 20.4 mmol, 10 mL), and the reaction mixture was stirred at rt for 2 hrs. The layers were separated and the organic layer was washed with water (25 mL), dried over Na₂SO₄, filtered into a round bottom flask and concentrated in vacuo to give the crude ylide (3.51 g, 8.31 mmol, 49% yield). MS (ESI) 423.3 [M+H]⁺.

Example 9b

Preparation of 1-(5-bromo-2-(2-methyl-4-(trifluoromethyl)-1H-imidazol-1-yl)phenyl)-5-(1-p-tolylethyl)-1H-1,2,3-triazole

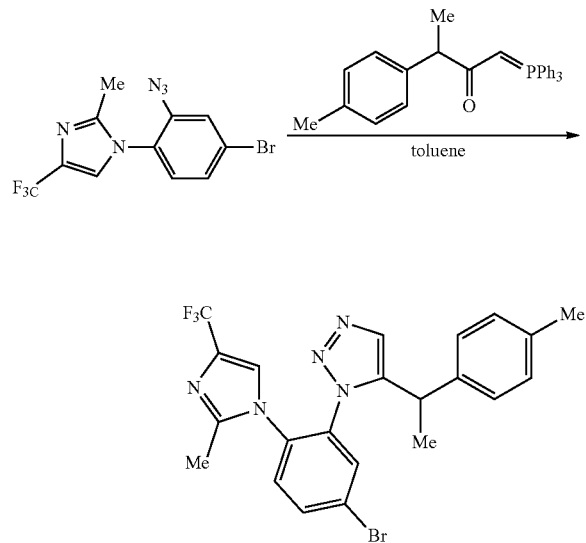

A solution of Example 9a (858 mg, 2.03 mmol) and Example 1c (700 mg, 2.03 mmol) in anhydrous toluene (20 mL) was heated to a reflux for 2.5 hrs. The solvent was removed from the reaction in vacuo and the crude residue was purified by chromatography thru a 25 g SiO₂ column using a mobile phase gradient of 0-55% EtOAc/Hx to afford the title compound (404 mg, 0.824 mmol, 41% yield). MS (ESI) 490.3 [M+H]⁺. Example 9 was prepared from Example 9b and Intermediate 1 using procedures similar to that described in Example 1f. MS (ESI) 614.2 [M+H]⁺.

Example 10

(4-chlorophenyl)(1-{3'-(methylsulfonyl)-4-[2-methyl-4-(trifluoromethyl)-1H-imidazol-1-yl]biphenyl-3-yl}-1H-1,2,3-triazol-5-yl)methanone

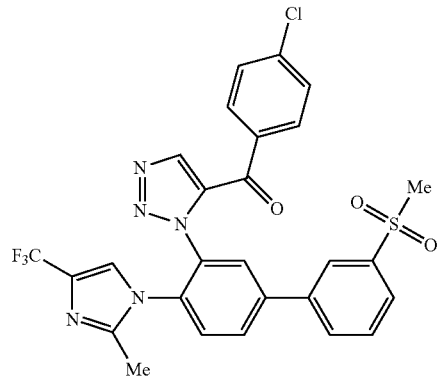 [SMILES: Cc1nc(C(F)(F)F)cn1-c1ccc(-c2cccc(S(C)(=O)=O)c2)cc1-n1nncc1C(=O)c1ccc(Cl)cc1]

Example 10a

Preparation of Phosphorane

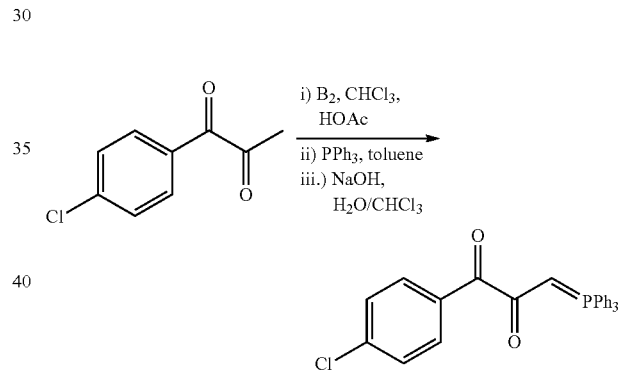

To a solution of 1-(4-chlorophenyl)propane-1,2-dione (4.63 g, 25.3 mmol) in CHCl₃ (25.0 mL) and HOAc (1.00 mL), was added Br₂ (1.30 mL, 25.3 mmol) in CHCl₃ (5.0 mL) dropwise. The reaction mixture was stirred at 55° C. for 1 hr, until the red Br₂ was consumed. The organic solution was washed with water (25 mL), dried over Na₂SO₄, filtered into a round bottom flask and concentrated in vacuo to give the crude 3-bromo-1-(4-chlorophenyl)propane-1,2-dione (5.31 g, 20.3 mmol, 80% yield). The crude dione (5.31 g, 20.3 mmol) was brought up in anhydrous toluene (40.0 mL) and to it was added PPh₃ (5.32 g, 20.3 mmol). The mixture was stirred at a reflux for 40 min. The solution was cooled in an ice bath, and the resulting solid black salt was filtered from the solution to give the phoshonium salt. MS (ESI) 443.4 [M+H]⁺ 465.3 [M+Na]⁺.

The crude phosphonium salt was brought up in CHCl₃ (25.0 mL) and aqueous NaOH (1.00 g, 25.0 mmol, 15.0 mL), and the reaction mixture was stirred at rt for 2 hrs. The layers were separated, the organic layer was washed with water (25 mL) and dried over Na₂SO₄, filtered into a round bottom flask and concentrated in vacuo to give the crude ylide (5.84 g, 13.2 mmol, 65% yield).

Example 10b

Preparation of (1-(5-bromo-2-(2-methyl-4-(trifluoromethyl)-1H-imidazol-1-yl)phenyl)-1H-1,2,3-triazol-5-yl) (4-chlorophenyl)methanone

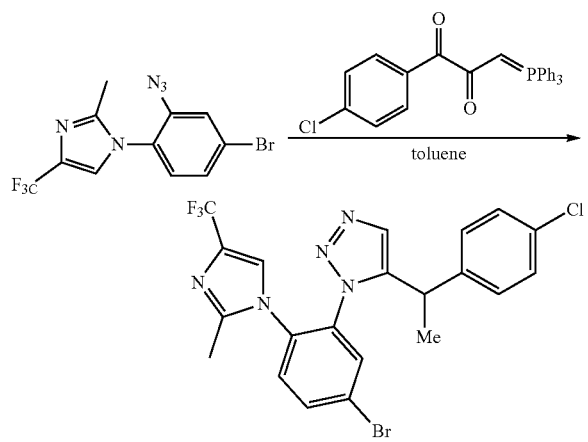

A solution of Example 10a (1.32 g, 2.98 mmol) and Example 1c (1.03 g, 2.98 mmol) in anhydrous toluene (30.0 mL) was heated to a reflux for 2.5 hrs. The solvent was removed from the reaction in vacuo and the crude residue was purified by chromatography thru a 40 g SiO$_2$ column using a mobile phase gradient of 0-50% EtOAc/Hx to afford the title compound (849 mg, 1.66 mmol, 56% yield). MS (ESI) 510.1 [M+H]$^+$.

Example 10c

Preparation of (4-chlorophenyl) (1-{3'-(methylsulfonyl)-4-[2-methyl-4-(trifluoromethyl)-1H-imidazol-1-yl]biphenyl-3-yl}-1H-1,2,3-triazol-5-yl)methanone

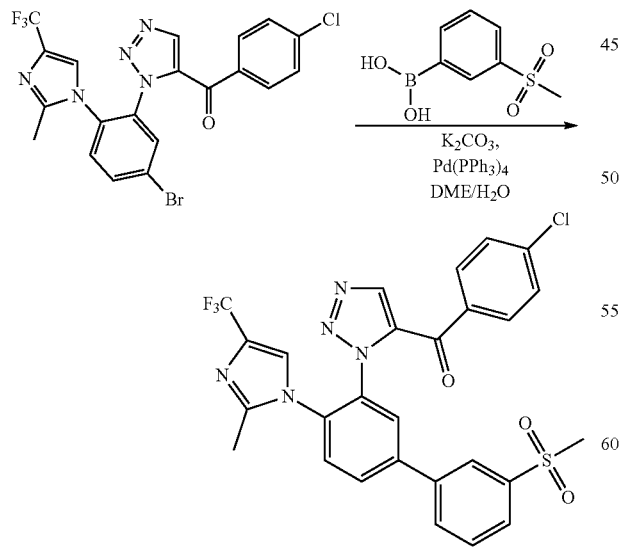

A solution of Example 10b (420 mg, 0.822 mmol), 3-(methylsulfonyl)phenylboronic acid (172 mg, 0.864 mmol), K$_2$CO$_3$ (341 mg, 2.47 mmol) and Pd(PPh$_3$)$_4$ (95.0 mg, 82.2 µmol) in DME (20.0 mL) and water (4.00 mL) was heated to 85° C. for 1 hr. The cooled reaction mixture was filtered through a celite pad, diluted with EtOAc (80 mL), washed with saturated aq NH$_4$Cl (50 mL), dried over Na$_2$SO$_4$, filtered into a round bottom flask and concentrated in vacuo. The crude material was purified by chromatography thru a 25 g SiO$_2$ column using a mobile phase gradient of 0-85% EtOAc/Hx to afford the title compound (390 mg, 0.666 mmol, 81% yield). MS (ESI) 586.2 [M+H]$^+$.

Example 11

1-(4-chlorophenyl)-2,2,2-trifluoro-1-(1-{3'-(methylsulfonyl)-4-[2-methyl-4-(trifluoromethyl)-1H-imidazol-1-yl]biphenyl-3-yl}-1H-1, 2,3-triazol-5-yl) ethanol

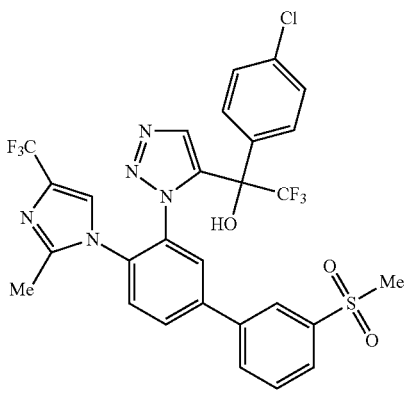 [SMILES: Cc1nc(C(F)(F)F)cn1-c1ccc(-c2cccc(S(C)(=O)=O)c2)cc1-n1nncc1C(O)(c1ccc(Cl)cc1)C(F)(F)F]

Example 11a

Preparation 1-(4-chlorophenyl)-2,2,2-trifluoro-1-(1-{3'-(methylsulfonyl)-4-[2-methyl-4-(trifluoromethyl)-1H-imidazol-1-yl]biphenyl-3-yl}-1H-1, 2,3-triazol-5-yl) ethanol

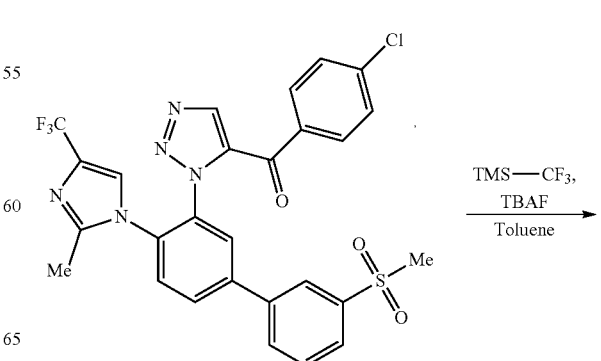

91
-continued

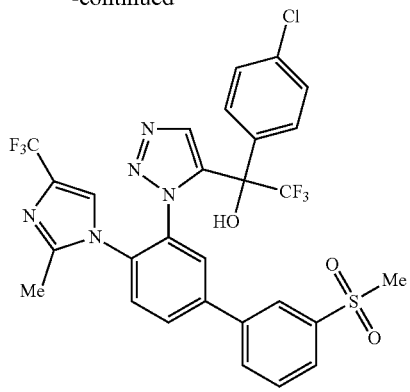

To a solution of Example 10 (133 mg, 0.227 mmol) in anhydrous toluene (5.0 mL) under a $N_2$ purged atmosphere was added TMS-$CF_3$ (97.0 mg, 0.681 mmol), followed by a 1.0 M TBAF-THF solution (0.227 mmol, 0.227 mL). The reaction mixture was stirred at 70° C. for 2 hrs. The reaction progress was monitored by LCMS and was found to have SM remaining. Another portion of TMS-$CF_3$ (97.0 mg, 0.681 mmol) and 1.0 M TBAF-THF solution (0.400 mmol, 0.400 mL) were added, and the reaction mixture was stirred at 70° C. for 18 hrs. The reaction solution was cooled to rt and diluted with EtOAc (20 mL), washed with saturated aq $NH_4Cl$ (20 mL), dried over $Na_2SO_4$, filtered into a round bottom flask and concentrated in vacuo. The crude material was purified by preparative HPLC with the following conditions: Column: Phenomenex Luna AXIA C18, 21.2×100 mm, 5-μm particles; Mobile Phase A: 10% MeCN—90% $H_2O$—0.1% TFA; Mobile Phase B: 90% MeCN— 10% $H_2O$— 0.1% TFA; Gradient: 30-100% B over 10 min, then a 4-minute hold at 100% B; Flow: 20 mL/min. The fractions containing the product were concentrated in vacuo to give the title compound (20.0 mg, 0.0305 mmol, 13% yield). MS (ESI) 656 [M+H]$^+$.

Example 12

Preparation of 5-[(4-chlorophenyl) (difluoro) methyl]-1-{3'-(methylsulfonyl)-4-[2-methyl-4-(trifluoromethyl)-1H-imidazol-1-yl]biphenyl-3-yl}-1H-1, 2,3-triazole

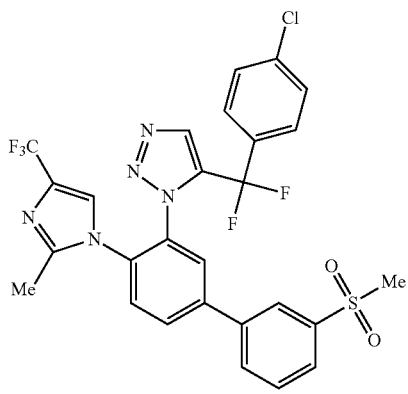 [SMILES: Cc1nc(C(F)(F)F)cn1-c1ccc(-c2cccc(S(C)(=O)=O)c2)cc1-n1nncc1C(F)(F)c1ccc(Cl)cc1]

Example 12a

Preparation of 5-[(4-chlorophenyl)(difluoro) methyl]-1-{3'-(methylsulfonyl)-4-[2-methyl-4-(trifluoromethyl)-1H-imidazol-1-yl]biphenyl-3-yl}-1H-1,2,3-triazole

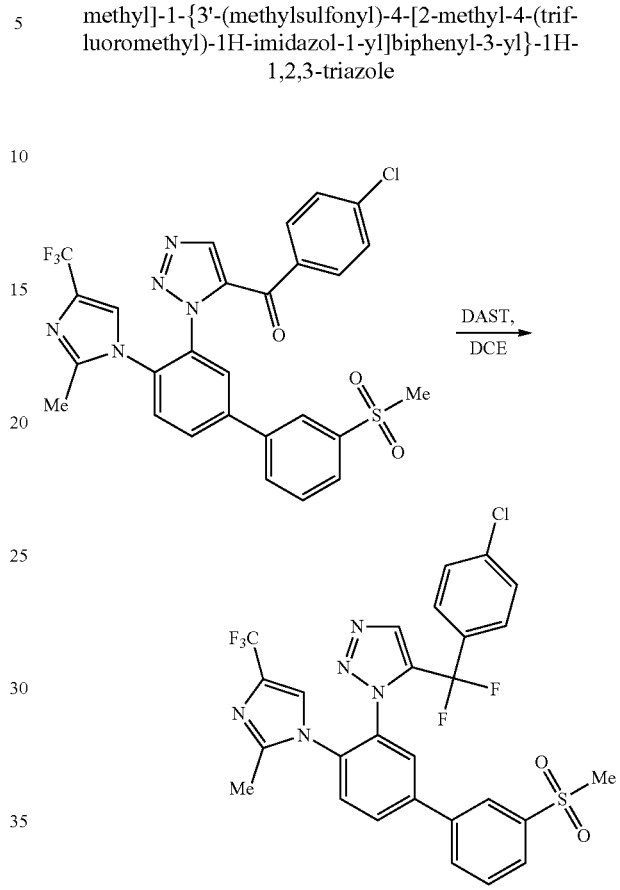

To a solution of Example 10 (201 mg, 0.343 mmol) in DCE (2.0 mL) under a $N_2$ purged atmosphere was added DAST (2.00 mL, 15.3 mmol) and the reaction mixture was stirred at 60° C. for 6 hrs. The reaction progress was monitored by LCMS and was found to have a 1:1 mixture of starting material: product remaining. Another portion of DAST (1.50 mL, 11.4 mmol) was added, and the reaction mixture was stirred at 75° C. for 16 hrs. The reaction solution was cooled to rt and diluted with DCM (50 mL), washed with saturated aq $NaHCO_3$ (30 mL), dried over $Na_2SO_4$, filtered into a round bottom flask and concentrated in vacuo. The crude material was purified by preparative HPLC with the following conditions: Column: Phenomenex Luna AXIA C18, 21.2×100 mm, 5-μm particles; Mobile Phase A: 10% MeCN—90% $H_2O$—0.1% TFA; Mobile Phase B: 90% MeCN—10% $H_2O$— 0.1% TFA; Gradient: 30-100% B over 17 min, then a 4-minute hold at 100% B; Flow: 35 mL/min. The fractions containing the product were concentrated in vacuo to give the title compound (79.0 mg, 38% yield). MS (ESI) 608.3 [M+H]+.

The following compounds were prepared in a manner similar to that described in the previous experimental procedures. If not commercially available, starting reagents can made using standard techniques that are readily apparent to one skilled in the art:

| Ex # | Structure | Name & Additional Characterization Data | Molecular Ion |
|---|---|---|---|
| 13 | 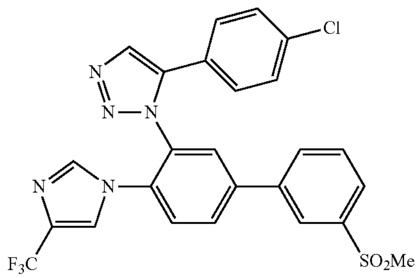 | 5-(4-chlorophenyl)-1-{3'-(methylsulfonyl)-4-[4-(trifluoromethyl)-1H-imidazol-1-yl]biphenyl-3-yl}-1H-1,2,3-triazole <br> $^1$H NMR (400 MHz, CDCl$_3$) δ 8.30 (s, 1H), 8.20 (d, J = 2.0 Hz, 1H), 8.13-7.91 (m, 3H), 7.85-7.75 (m, 2H), 7.50 (t, J = 8.6 Hz, 1H), 7.25 (d, J = 2.0 Hz, 1H), 6.85-6.71 (m, 3H), 6.54 (d, J = 1.1 Hz, 1H), 5.30 (s, 1H), 3.16 (s, 3H) | MS (ESI) 544.1 [M + H]$^+$. |
| 18 | 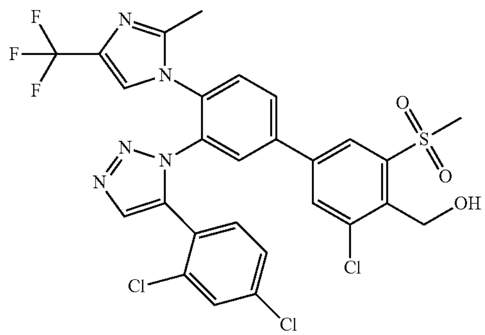 [SMILES: Cc1nc(C(F)(F)F)cn1-c1ccc(-c2cc(Cl)c(CO)c(S(C)(=O)=O)c2)cc1-n1nncc1-c1ccc(Cl)cc1Cl] | {3-chloro-3'-[5-(2,4-dichlorophenyl)-1H-1,2,3-triazol-1-yl]-5-(methylsulfonyl)-4'-[2-methyl-4-(trifluoromethyl)-1H-imidazol-1-yl]biphenyl-4-yl}methanol | MS (ESI) 658.5 [M + H]$^+$. |
| 19 | 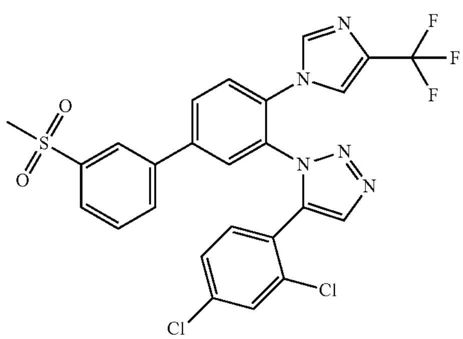 [SMILES: CS(=O)(=O)c1cccc(-c2ccc(-n3cnc(C(F)(F)F)c3)c(-n3nncc3-c3ccc(Cl)cc3Cl)c2)c1] | 5-(2,4-dichlorophenyl)-1-{3'-(methylsulfonyl)-4-[4-(trifluoromethyl)-1H-imidazol-1-yl]biphenyl-3-yl}-1H-1,2,3-triazole | MS (ESI) 578.3 [M + H]$^+$. |
| 20 | 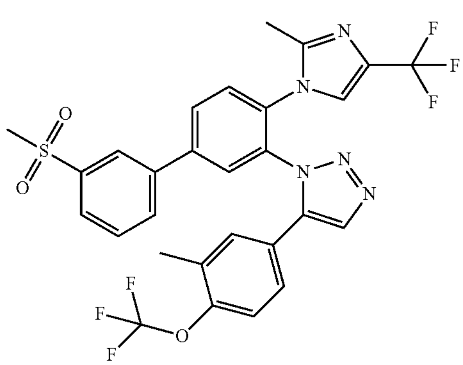 [SMILES: Cc1cc(-c2cnnn2-c2cc(-c3cccc(S(C)(=O)=O)c3)ccc2-n2cc(C(F)(F)F)nc2C)ccc1OC(F)(F)F] | 1-{3'-(methylsulfonyl)-4-[2-methyl-4-(trifluoromethyl)-1H-imidazol-1-yl]biphenyl-3-yl}-5-{3-methyl-4-[(trifluoromethyl)oxy]phenyl}-1H-1,2,3-triazole | MS (ESI) 622.2 [M + H]$^+$. |

| Ex # | Structure | Name & Additional Characterization Data | Molecular Ion |
|---|---|---|---|
| 21 | 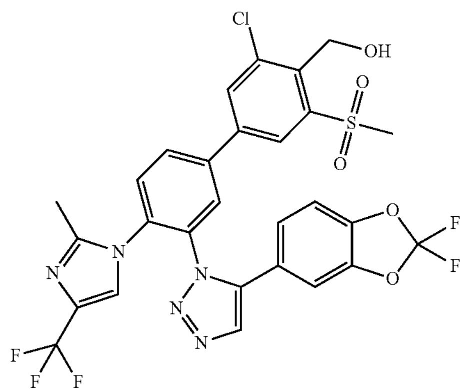 | {3-chloro-3'-[5-(2,2-difluoro-1,3-benzodioxol-5-yl)-1H-1,2,3-triazol-1-yl]-5-(methylsulfonyl)-4'-[2-methyl-4-(trifluoromethyl)-1H-imidazol-1-yl]biphenyl-4-yl}methanol | MS (ESI) 668.2 [M + H]+. |
| 22 | 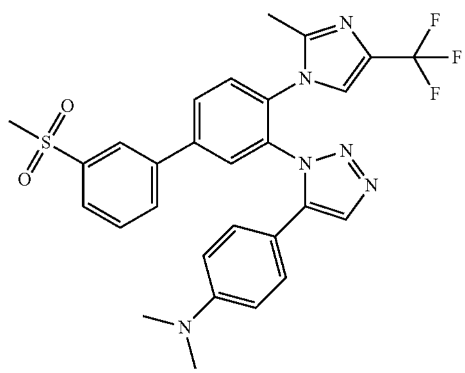 [SMILES: Cc1nc(C(F)(F)F)cn1-c1ccc(-c2cccc(S(C)(=O)=O)c2)cc1-n1nncc1-c1ccc(N(C)C)cc1] | N,N-dimethyl-4-(1-{3'-(methylsulfonyl)-4-[2-methyl-4-(trifluoromethyl)-1H-imidazol-1-yl]biphenyl-3-yl}-1H-1,2,3-triazol-5-yl)aniline | MS (ESI) 567.3 [M + H]+. |
| 23 | 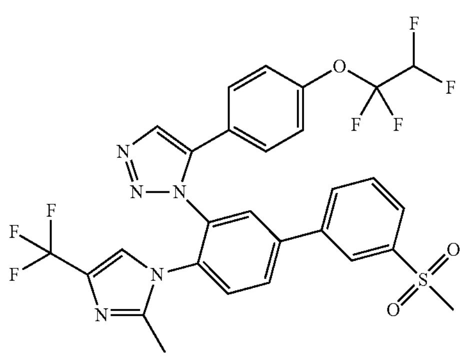 [SMILES: Cc1nc(C(F)(F)F)cn1-c1ccc(-c2cccc(S(C)(=O)=O)c2)cc1-n1nncc1-c1ccc(OC(F)(F)C(F)F)cc1] | 1-{3'-(methylsulfonyl)-4-[2-methyl-4-(trifluoromethyl)-1H-imidazol-1-yl]biphenyl-3-yl}-5-{4-[(1,1,2,2-tetrafluoroethyl)oxy]phenyl}-1H-1,2,3-triazole | MS (ESI) 640.3 [M + H]+. |
| 24 | 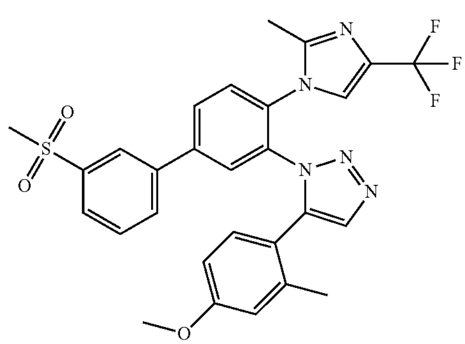 [SMILES: COc1ccc(-c2cnnn2-c2cc(-c3cccc(S(C)(=O)=O)c3)ccc2-n2cc(C(F)(F)F)nc2C)c(C)c1] | 5-[2-methyl-4-(methyloxy)phenyl]-1-{3'-(methylsulfonyl)-4-[2-methyl-4-(trifluoromethyl)-1H-imidazol-1-yl]biphenyl-3-yl}-1H-1,2,3-triazole | MS (ESI) 568.3 [M + H]+. |

| Ex # | Structure | Name & Additional Characterization Data | Molecular Ion |
|---|---|---|---|
| 25 | 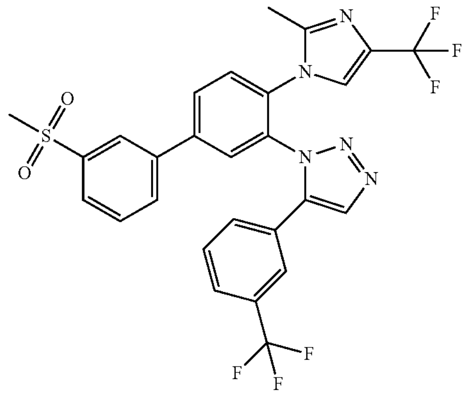 [SMILES: Cc1nc(C(F)(F)F)cn1-c1ccc(-c2cccc(S(C)(=O)=O)c2)cc1-n1nncc1-c1cccc(C(F)(F)F)c1] | 1-{3'-(methylsulfonyl)-4-[2-methyl-4-(trifluoromethyl)-1H-imidazol-1-yl]biphenyl-3-yl}-5-[3-(trifluoromethyl)phenyl]-1H-1,2,3-triazole | MS (ESI) 592.3 [M + H]+. |
| 26 | 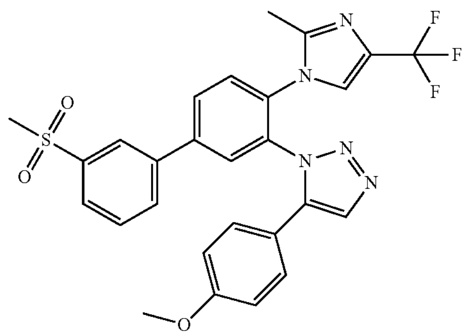 [SMILES: COc1ccc(-c2cnnn2-c2cc(-c3cccc(S(C)(=O)=O)c3)ccc2-n2cc(C(F)(F)F)nc2C)cc1] | 5-[4-(methyloxy)phenyl]-1-{3'-(methylsulfonyl)-4-[2-methyl-4-(trifluoromethyl)-1H-imidazol-1-yl]biphenyl-3-yl}-1H-1,2,3-triazole | MS (ESI) 554.3 [M + H]+. |
| 27 | 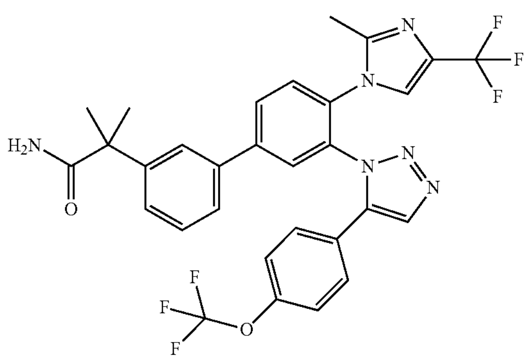 [SMILES: Cc1nc(C(F)(F)F)cn1-c1ccc(-c2cccc(C(C)(C)C(N)=O)c2)cc1-n1nncc1-c1ccc(OC(F)(F)F)cc1] | 2-methyl-2-{4'-[2-methyl-4-(trifluoromethyl)-1H-imidazol-1-yl]-3'-(5-{4-[(trifluoromethyl)oxy]phenyl}-1H-1,2,3-triazol-1-yl)biphenyl-3-yl}propanamide | MS (ESI) 615.0 [M + H]+. |
| 28 | 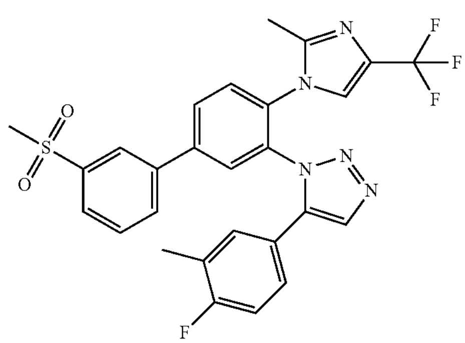 [SMILES: Cc1cc(-c2cnnn2-c2cc(-c3cccc(S(C)(=O)=O)c3)ccc2-n2cc(C(F)(F)F)nc2C)ccc1F] | 5-(4-fluoro-3-methylphenyl)-1-{3'-(methylsulfonyl)-4-[2-methyl-4-(trifluoromethyl)-1H-imidazol-1-yl]biphenyl-3-yl}-1H-1,2,3-triazole | MS (ESI) 556.3 [M + H]+. |

-continued

| Ex # | Structure | Name & Additional Characterization Data | Molecular Ion |
|---|---|---|---|
| 29 | 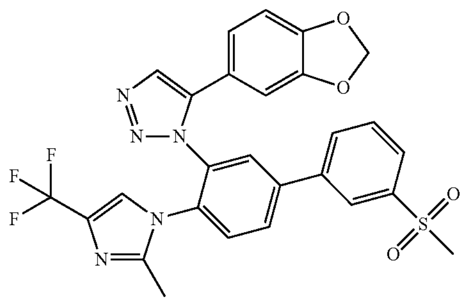 [SMILES: Cc1nc(C(F)(F)F)cn1-c1ccc(-c2cccc(S(C)(=O)=O)c2)cc1-n1nncc1-c1ccc2c(c1)OCO2] | 5-(1,3-benzodioxol-5-yl)-1-{3'-(methylsulfonyl)-4-[2-methyl-4-(trifluoromethyl)-1H-imidazol-1-yl]biphenyl-3-yl}-1H-1,2,3-triazole | MS (ESI) 568.2 [M + H]$^+$. |
| 30 | 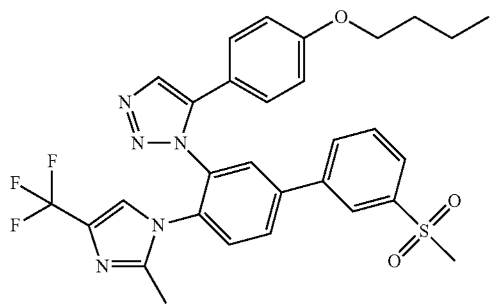 [SMILES: CCCCOc1ccc(-c2cnnn2-c2cc(-c3cccc(S(C)(=O)=O)c3)ccc2-n2cc(C(F)(F)F)nc2C)cc1] | 5-[4-(butyloxy)phenyl]-1-{3'-(methylsulfonyl)-4-[2-methyl-4-(trifluoromethyl)-1H-imidazol-1-yl]biphenyl-3-yl}-1H-1,2,3-triazole | MS (ESI) 596.3 [M + H]$^+$. |
| 31 | 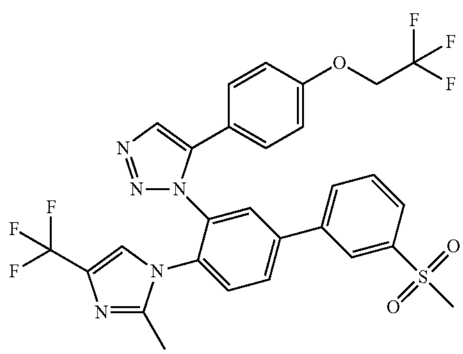 [SMILES: Cc1nc(C(F)(F)F)cn1-c1ccc(-c2cccc(S(C)(=O)=O)c2)cc1-n1nncc1-c1ccc(OCC(F)(F)F)cc1] | 1-{3'-(methylsulfonyl)-4-[2-methyl-4-(trifluoromethyl)-1H-imidazol-1-yl]biphenyl-3-yl}-5-{4-[(2,2,2-trifluoroethyl)oxy]phenyl}-1H-1,2,3-triazole | MS (ESI) 622.5 [M + H]$^+$. |
| 32 | 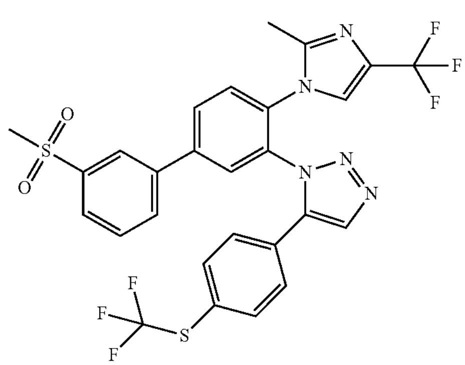 | 1-{3'-(methylsulfonyl)-4-[2-methyl-4-(trifluoromethyl)-1H-imidazol-1-yl]biphenyl-3-yl}-5-{4-[(trifluoromethyl)thio]phenyl}-1H-1,2,3-triazole | MS (ESI) 624.3 [M + H]$^+$ |

| Ex # | Structure | Name & Additional Characterization Data | Molecular Ion |
|---|---|---|---|
| 33 | 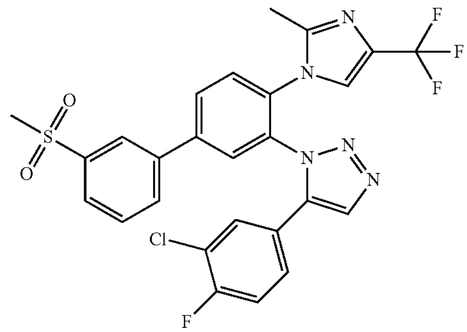 [SMILES: Cc1nc(C(F)(F)F)cn1-c1ccc(-c2cccc(S(C)(=O)=O)c2)cc1-n1nncc1-c1ccc(F)c(Cl)c1] | 5-(3-chloro-4-fluorophenyl)-1-{3'-(methylsulfonyl)-4-[2-methyl-4-(trifluoromethyl)-1H-imidazol-1-yl]biphenyl-3-yl}-1H-1,2,3-triazole | MS (ESI) 576.2 [M + H]$^+$. |
| 34 | 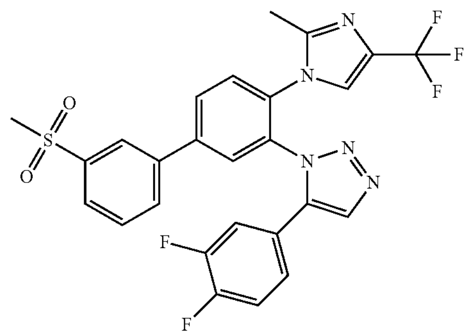 [SMILES: Cc1nc(C(F)(F)F)cn1-c1ccc(-c2cccc(S(C)(=O)=O)c2)cc1-n1nncc1-c1ccc(F)c(F)c1] | 5-(3,4-difluorophenyl)-1-{3'-(methylsulfonyl)-4-[2-methyl-4-(trifluoromethyl)-1H-imidazol-1-yl]biphenyl-3-yl}-1H-1,2,3-triazole | MS (ESI) 560.3 [M + H]$^+$. |
| 35 | 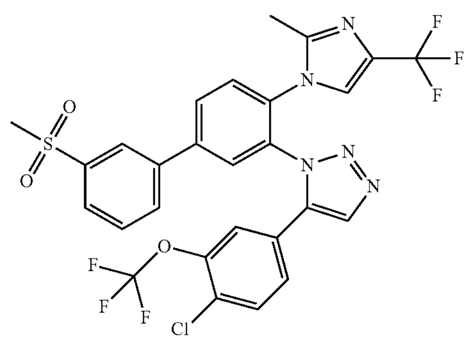 [SMILES: Cc1nc(C(F)(F)F)cn1-c1ccc(-c2cccc(S(C)(=O)=O)c2)cc1-n1nncc1-c1ccc(Cl)c(OC(F)(F)F)c1] | 5-{4-chloro-3-[(trifluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole | MS (ESI) 642.0 [M + H]$^+$. |
| 36 | 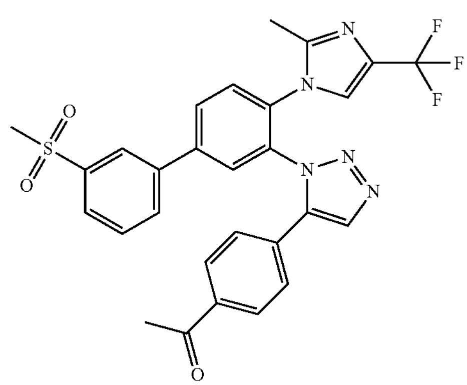 [SMILES: CC(=O)c1ccc(-c2cnnn2-c2cc(-c3cccc(S(C)(=O)=O)c3)ccc2-n2cc(C(F)(F)F)nc2C)cc1] | 1-[4-(1-{3'-(methylsulfonyl)-4-[2-methyl-4-(trifluoromethyl)-1H-imidazol-1-yl]biphenyl-3-yl}-1H-1,2,3-triazol-5-yl)phenyl]ethanone | MS (ESI) 566.3 [M + H]$^+$. |

| Ex # | Structure | Name & Additional Characterization Data | Molecular Ion |
|---|---|---|---|
| 37 | 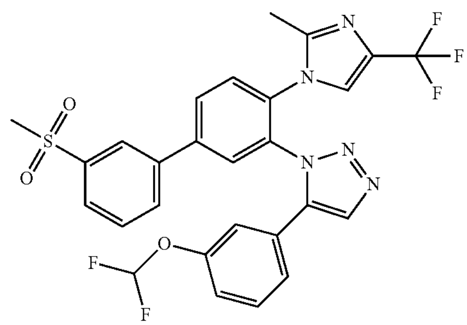 [SMILES: Cc1nc(C(F)(F)F)cn1-c1ccc(-c2cccc(S(C)(=O)=O)c2)cc1-n1nncc1-c1cccc(OC(F)F)c1] | 5-{3-[(difluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole | MS (ESI) 590.3 [M + H]+. |
| 39 | 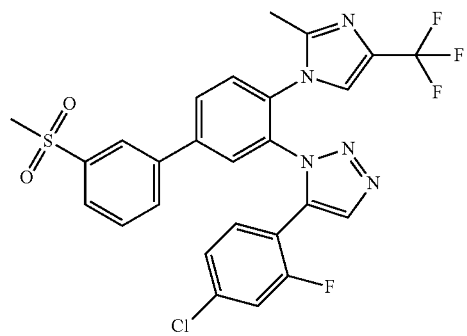 [SMILES: Cc1nc(C(F)(F)F)cn1-c1ccc(-c2cccc(S(C)(=O)=O)c2)cc1-n1nncc1-c1ccc(Cl)cc1F] | 5-(4-chloro-2-fluorophenyl)-1-{3'-(methylsulfonyl)-4-[2-methyl-4-(trifluoromethyl)-1H-imidazol-1-yl]biphenyl-3-yl}-1H-1,2,3-triazole | MS (ESI) 576.1 [M + H]+. |
| 40 | 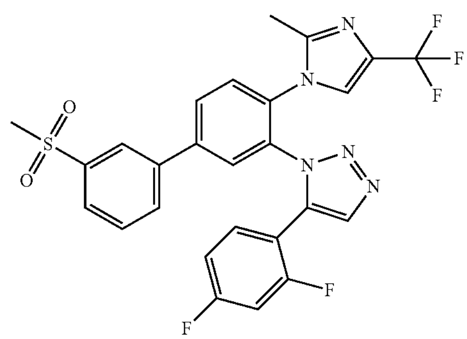 [SMILES: Cc1nc(C(F)(F)F)cn1-c1ccc(-c2cccc(S(C)(=O)=O)c2)cc1-n1nncc1-c1ccc(F)cc1F] | 5-(2,4-difluorophenyl)-1-{3'-(methylsulfonyl)-4-[2-methyl-4-(trifluoromethyl)-1H-imidazol-1-yl]biphenyl-3-yl}-1H-1,2,3-triazole | MS (ESI) 560.3 [M + H]+. |
| 41 | 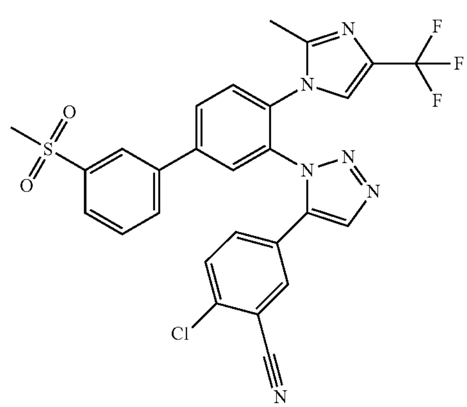 [SMILES: Cc1nc(C(F)(F)F)cn1-c1ccc(-c2cccc(S(C)(=O)=O)c2)cc1-n1nncc1-c1ccc(Cl)c(C#N)c1] | 2-chloro-5-(1-{3'-(methylsulfonyl)-4-[2-methyl-4-(trifluoromethyl)-1H-imidazol-1-yl]biphenyl-3-yl}-1H-1,2,3-triazol-5-yl)benzonitrile | MS (ESI) 583.3 [M + H]+. |

| Ex # | Structure | Name & Additional Characterization Data | Molecular Ion |
|---|---|---|---|
| 42 | 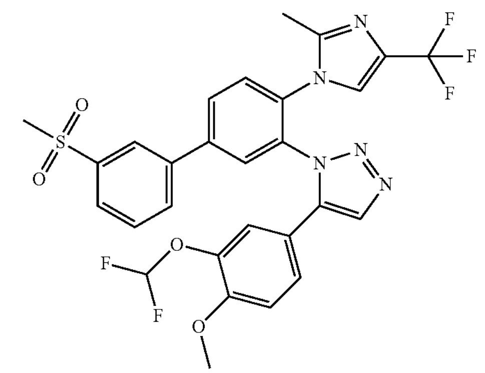 [SMILES: COc1ccc(-c2cnnn2-c2cc(-c3cccc(S(C)(=O)=O)c3)ccc2-n2cc(C(F)(F)F)nc2C)cc1OC(F)F] | 5-{3-[(difluoromethyl)oxy]-4-(methyloxy)phenyl}-1-{3'-(methylsulfonyl)-4-[2-methyl-4-(trifluoromethyl)-1H-imidazol-1-yl]biphenyl-3-yl}-1H-1,2,3-triazole | MS (ESI) 620.2 [M + H]⁺. |
| 43 | 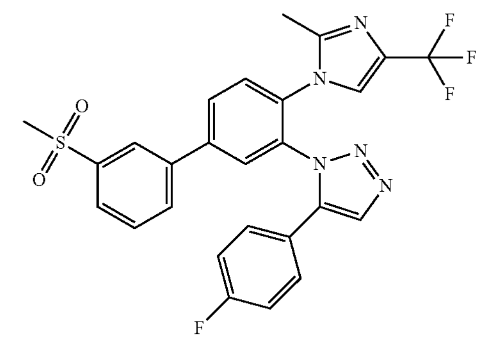 | 5-(4-fluorophenyl)-1-{3'-(methylsulfonyl)-4-[2-methyl-4-(trifluoromethyl)-1H-imidazol-1-yl]biphenyl-3-yl}-1H-1,2,3-triazole | MS (ESI) 542.0 [M + H]⁺. |
| 44 | 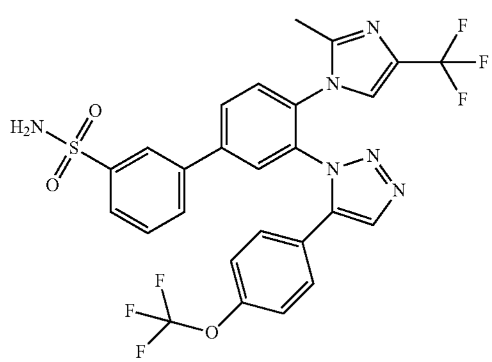 [SMILES: Cc1nc(C(F)(F)F)cn1-c1ccc(-c2cccc(S(N)(=O)=O)c2)cc1-n1nncc1-c1ccc(OC(F)(F)F)cc1] | 4'-[2-methyl-4-(trifluoromethyl)-1H-imidazol-1-yl]-3'-(5-{4-[(trifluoromethyl)oxy]phenyl}-1H-1,2,3-triazol-1-yl)biphenyl-3-sulfonamide | MS (ESI) 609.3 [M + H]⁺. |
| 45 | 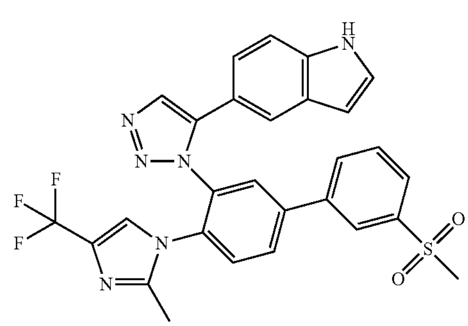 [SMILES: Cc1nc(C(F)(F)F)cn1-c1ccc(-c2cccc(S(C)(=O)=O)c2)cc1-n1nncc1-c1ccc2[nH]ccc2c1] | 5-(1-{3'-(methylsulfonyl)-4-[2-methyl-4-(trifluoromethyl)-1H-imidazol-1-yl]biphenyl-3-yl}-1H-1,2,3-triazol-5-yl)-1H-indole | MS (ESI) 563.3, 564.3 [M + H]⁺. |

| Ex # | Structure | Name & Additional Characterization Data | Molecular Ion |
|---|---|---|---|
| 46 | 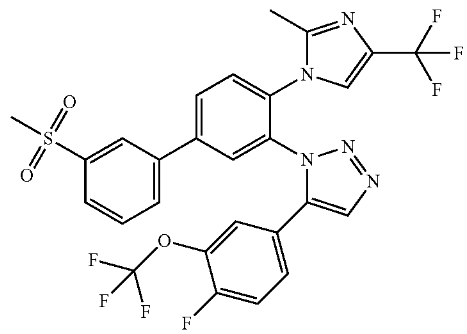 [SMILES: Cc1nc(C(F)(F)F)cn1-c1ccc(-c2cccc(S(C)(=O)=O)c2)cc1-n1nncc1-c1ccc(F)c(OC(F)(F)F)c1] | 5-{4-fluoro-3-[(trifluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole | MS (ESI) 626.2 [M + H]+. |
| 47 | 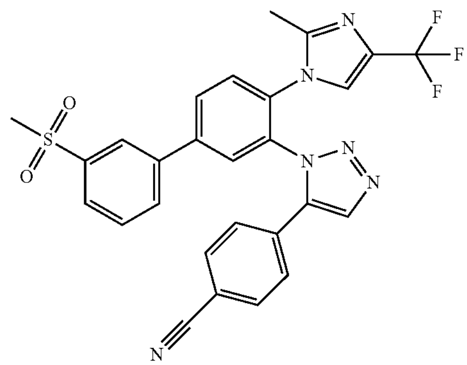 [SMILES: Cc1nc(C(F)(F)F)cn1-c1ccc(-c2cccc(S(C)(=O)=O)c2)cc1-n1nncc1-c1ccc(C#N)cc1] | 4-(1-{3'-(methylsulfonyl)-4-[2-methyl-4-(trifluoromethyl)-1H-imidazol-1-yl]biphenyl-3-yl}-1H-1,2,3-triazol-5-yl)benzonitrile | MS (ESI) 549.3 [M + H]+. |
| 48 | 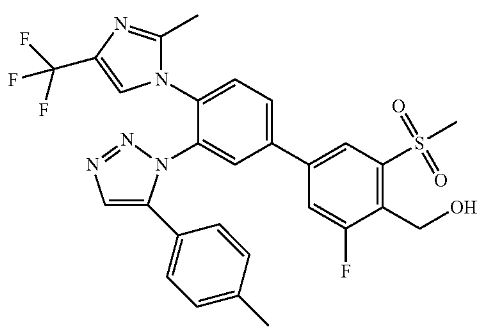 [SMILES: Cc1ccc(-c2cnnn2-c2cc(-c3cc(F)c(CO)c(S(C)(=O)=O)c3)ccc2-n2cc(C(F)(F)F)nc2C)cc1] | {3-fluoro-3'-[5-(4-methylphenyl)-1H-1,2,3-triazol-1-yl]-5-(methylsulfonyl)-4'-[2-methyl-4-(trifluoromethyl)-1H-imidazol-1-yl]biphenyl-4-yl}methanol | MS (ESI) 586.3 [M + H]+. |
| 49 | 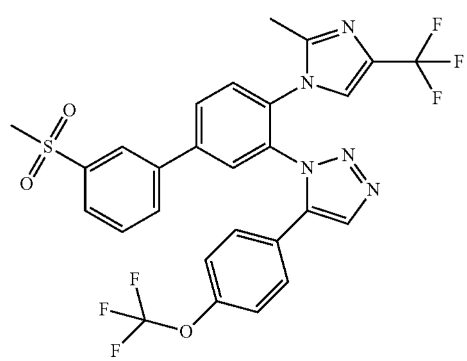 [SMILES: Cc1nc(C(F)(F)F)cn1-c1ccc(-c2cccc(S(C)(=O)=O)c2)cc1-n1nncc1-c1ccc(OC(F)(F)F)cc1] | 1-{3'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole | MS (ESI) 608.3 [M + H]+. |

-continued

| Ex # | Structure | Name & Additional Characterization Data | Molecular Ion |
|---|---|---|---|
| 50 | 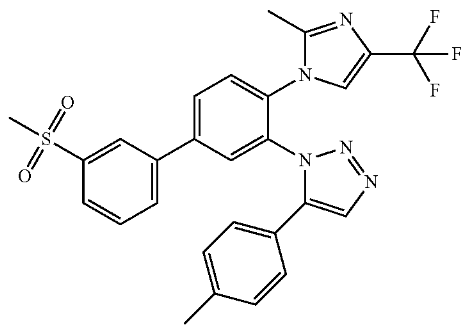 [SMILES: Cc1ccc(-c2cnnn2-c2cc(-c3cccc(S(C)(=O)=O)c3)ccc2-n2cc(C(F)(F)F)nc2C)cc1] | 5-(4-methylphenyl)-1-{3'-(methylsulfonyl)-4-[2-methyl-4-(trifluoromethyl)-1H-imidazol-1-yl]biphenyl-3-yl}-1H-1,2,3-triazole | MS (ESI) 538.3 [M + H]+. |
| 51 | 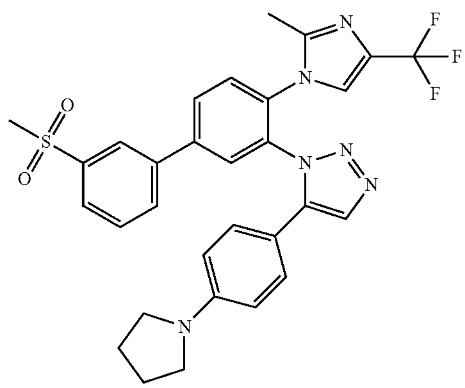 [SMILES: Cc1nc(C(F)(F)F)cn1-c1ccc(-c2cccc(S(C)(=O)=O)c2)cc1-n1nncc1-c1ccc(N2CCCC2)cc1] | 1-{3'-(methylsulfonyl)-4-[2-methyl-4-(trifluoromethyl)-1H-imidazol-1-yl]biphenyl-3-yl}-5-(4-pyrrolidin-1-ylphenyl)-1H-1,2,3-triazole | MS (ESI) 593.5 [M + H]+. |
| 52 | 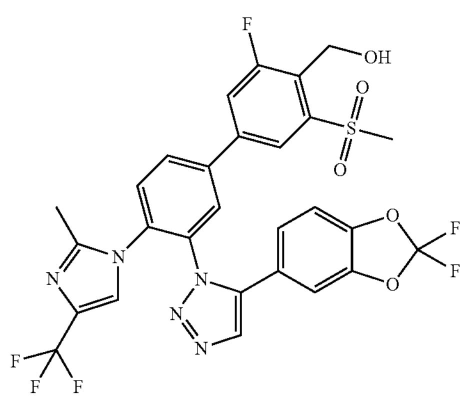 | {3'-[5-(2,2-difluoro-1,3-benzodioxol-5-yl)-1H-1,2,3-triazol-1-yl]-3-fluoro-5-(methylsulfonyl)-4'-[2-methyl-4-(trifluoromethyl)-1H-imidazol-1-yl]biphenyl-4-yl}methanol | MS (ESI) 652.2 [M + H]+. |
| 53 | 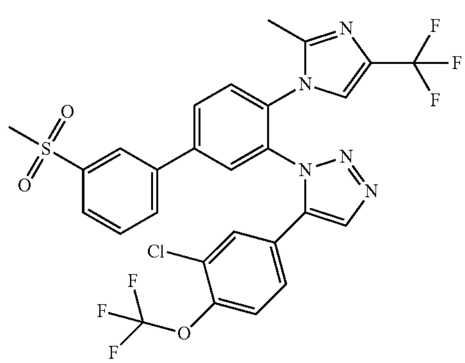 [SMILES: Cc1nc(C(F)(F)F)cn1-c1ccc(-c2cccc(S(C)(=O)=O)c2)cc1-n1nncc1-c1ccc(OC(F)(F)F)c(Cl)c1] | 5-{3-chloro-4-[(trifluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole | MS (ESI) 642.2 [M + H]+. |

| Ex # | Structure | Name & Additional Characterization Data | Molecular Ion |
|---|---|---|---|
| 54 | 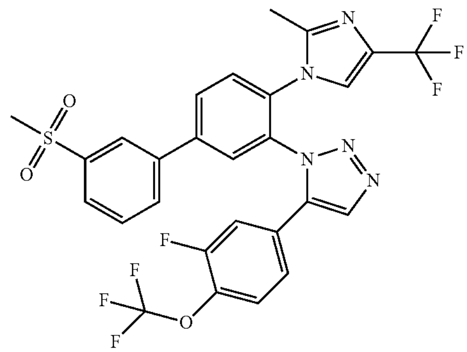 | 5-{3-fluoro-4-[(trifluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole | MS (ESI) 626.3 [M + H]+. |
| 55 | 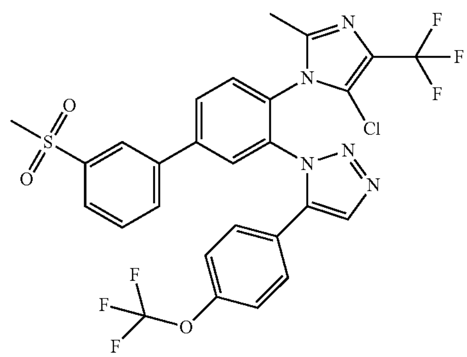 [SMILES: Cc1nc(C(F)(F)F)c(Cl)n1-c1ccc(-c2cccc(S(C)(=O)=O)c2)cc1-n1nncc1-c1ccc(OC(F)(F)F)cc1] | 1-{4-[5-chloro-2-methyl-4-(trifluoromethyl)-1H-imidazol-1-yl]-3'-(methylsulfonyl)biphenyl-3-yl}-5-{4-[(trifluoromethyl)oxy]phenyl}-1H-1,2,3-triazole | MS (ESI) 642.2 [M + H]+. |
| 56 | 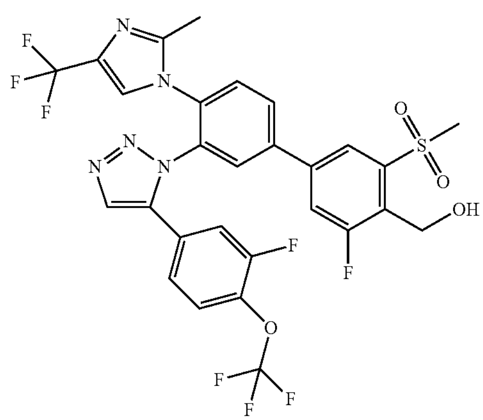 | {3-fluoro-3'-(5-{3-fluoro-4-[(trifluoromethyl)oxy]phenyl}-1H-1,2,3-triazol-1-yl)-5-(methylsulfonyl)-4'-[2-methyl-4-(trifluoromethyl)-1H-imidazol-1-yl]biphenyl-4-yl}methanol | MS (ESI) 674.5 [M + H]+. |
| 57 | 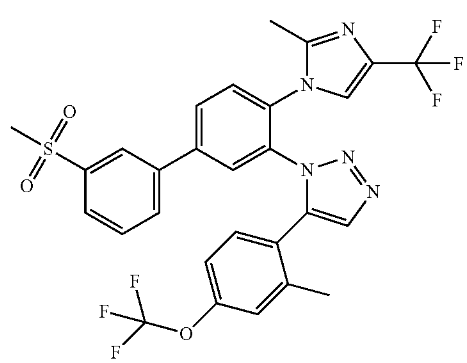 [SMILES: Cc1cc(OC(F)(F)F)ccc1-c1cnnn1-c1cc(-c2cccc(S(C)(=O)=O)c2)ccc1-n1cc(C(F)(F)F)nc1C] | 1-{3'-(methylsulfonyl)-4-[2-methyl-4-(trifluoromethyl)-1H-imidazol-1-yl]biphenyl-3-yl}-5-{2-methyl-4-[(trifluoromethyl)oxy]phenyl}-1H-1,2,3-triazole | MS (ESI) 622.2 [M + H]+. |

-continued

| Ex # | Structure | Name & Additional Characterization Data | Molecular Ion |
|---|---|---|---|
| 58 | 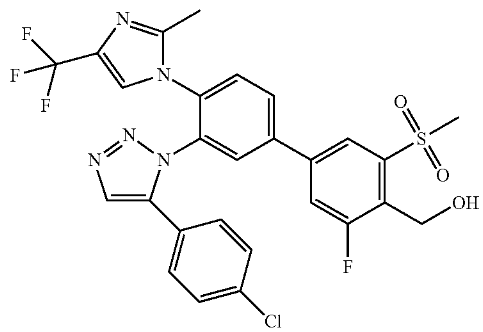 [SMILES: Cc1nc(C(F)(F)F)cn1-c1ccc(-c2cc(F)c(CO)c(S(C)(=O)=O)c2)cc1-n1nncc1-c1ccc(Cl)cc1] | {3'-[5-(4-chlorophenyl)-1H-1,2,3-triazol-1-yl]-3-fluoro-5-(methylsulfonyl)-4'-[2-methyl-4-(trifluoromethyl)-1H-imidazol-1-yl]biphenyl-4-yl}methanol | MS (ESI) 606.1 [M + H]+. |
| 59 | 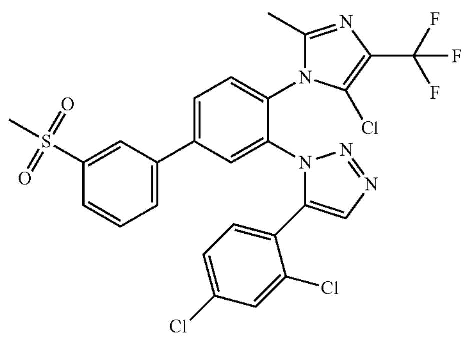 [SMILES: Cc1nc(C(F)(F)F)c(Cl)n1-c1ccc(-c2cccc(S(C)(=O)=O)c2)cc1-n1nncc1-c1ccc(Cl)cc1Cl] | 1-{4-[5-chloro-2-methyl-4-(trifluoromethyl)-1H-imidazol-1-yl]-3'-(methylsulfonyl)biphenyl-3-yl}-5-(2,4-dichlorophenyl)-1H-1,2,3-triazole | MS (ESI) 628.3 [M + H]+. |
| 60 | 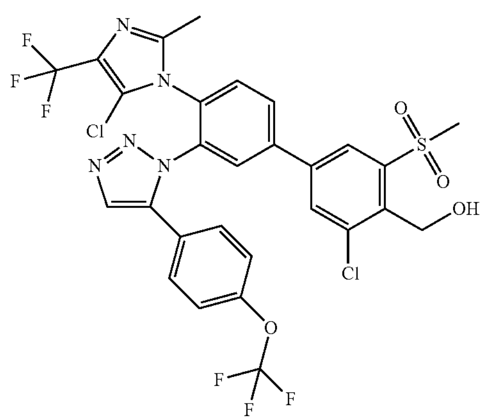 [SMILES: Cc1nc(C(F)(F)F)c(Cl)n1-c1ccc(-c2cc(Cl)c(CO)c(S(C)(=O)=O)c2)cc1-n1nncc1-c1ccc(OC(F)(F)F)cc1] | {3-chloro-4'-[5-chloro-2-methyl-4-(trifluoromethyl)-1H-imidazol-1-yl]-5-(methylsulfonyl)-3'-(5-{4-[(trifluoromethyl)oxy]phenyl}-1H-1,2,3-triazol-1-yl)biphenyl-4-yl}methanol | MS (ESI) 706.0 [M + H]+. |
| 61 | 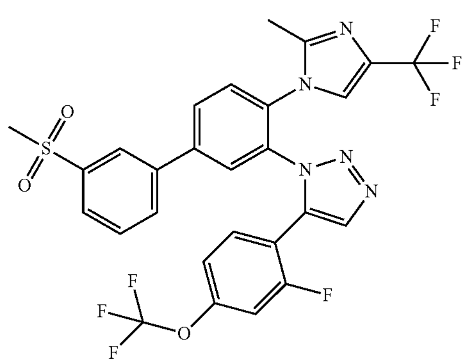 | 5-{2-fluoro-4-[(trifluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole | MS (ESI) 626.0 [M + H]+. |

-continued

| Ex # | Structure | Name & Additional Characterization Data | Molecular Ion |
|---|---|---|---|
| 62 | 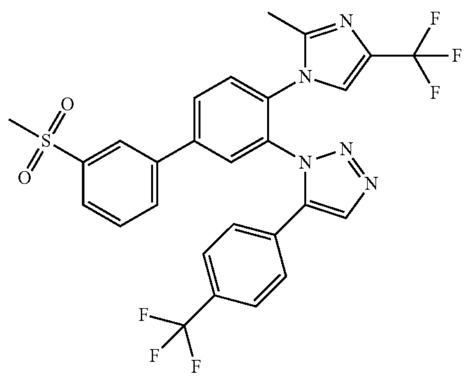 [SMILES: Cc1nc(C(F)(F)F)cn1-c1ccc(-c2cccc(S(C)(=O)=O)c2)cc1-n1nncc1-c1ccc(C(F)(F)F)cc1] | 1-{3'-(methylsulfonyl)-4-[2-methyl-4-(trifluoromethyl)-1H-imidazol-1-yl]biphenyl-3-yl}-5-[4-(trifluoromethyl)phenyl]-1H-1,2,3-triazole | MS (ESI) 592.3 [M + H]⁺. |
| 63 | 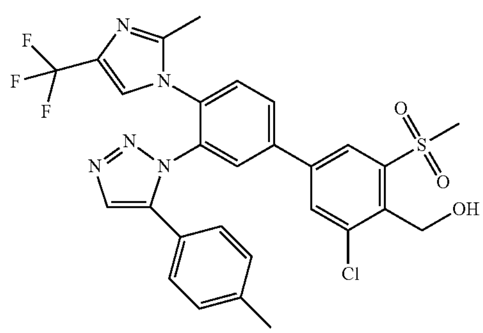 | {3-chloro-3'-[5-(4-methylphenyl)-1H-1,2,3-triazol-1-yl]-5-(methylsulfonyl)-4'-[2-methyl-4-(trifluoromethyl)-1H-imidazol-1-yl]biphenyl-4-yl}methanol | MS (ESI) 602.1 [M + H]⁺. |
| 64 | 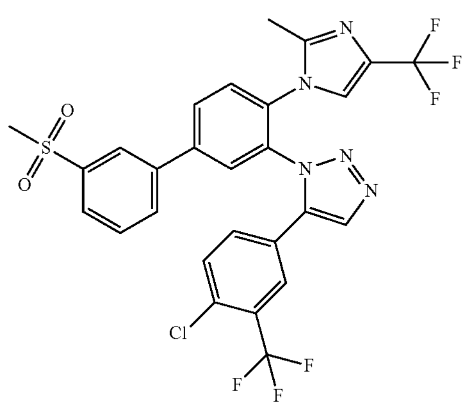 | 5-[4-chloro-3-(trifluoromethyl)phenyl]-1-{3'-(methylsulfonyl)-4-[2-methyl-4-(trifluoromethyl)-1H-imidazol-1-yl]biphenyl-3-yl}-1H-1,2,3-triazole | MS (ESI) 626.2 [M + H]⁺. |
| 65 | 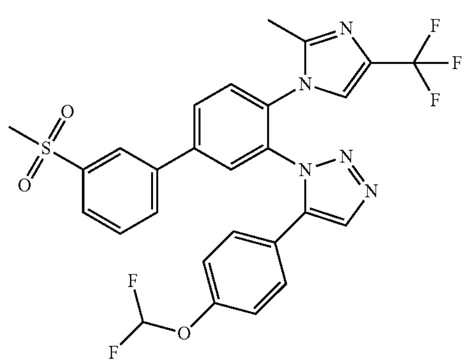 [SMILES: Cc1nc(C(F)(F)F)cn1-c1ccc(-c2cccc(S(C)(=O)=O)c2)cc1-n1nncc1-c1ccc(OC(F)F)cc1] | 5-{4-[(difluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole | MS (ESI) 590.3 [M + H]⁺. |

| Ex # | Structure | Name & Additional Characterization Data | Molecular Ion |
|---|---|---|---|
| 66 | 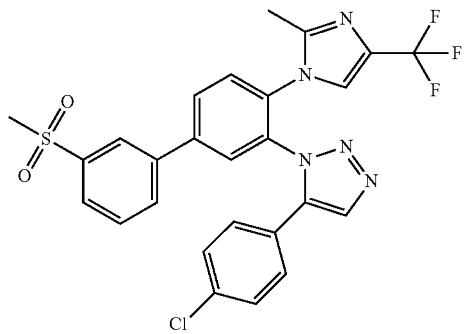 [SMILES: Cc1nc(C(F)(F)F)cn1-c1ccc(-c2cccc(S(C)(=O)=O)c2)cc1-n1nncc1-c1ccc(Cl)cc1] | 5-(4-chlorophenyl)-1-{3'-(methylsulfonyl)-4-[2-methyl-4-(trifluoromethyl)-1H-imidazol-1-yl]biphenyl-3-yl}-1H-1,2,3-triazole | MS (ESI) 558.3 [M + H]+. |
| 67 | 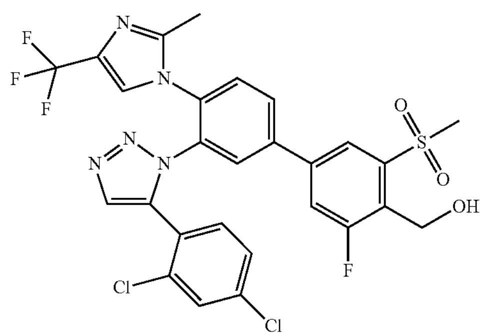 [SMILES: Cc1nc(C(F)(F)F)cn1-c1ccc(-c2cc(F)c(CO)c(S(C)(=O)=O)c2)cc1-n1nncc1-c1ccc(Cl)cc1Cl] | {3'-[5-(2,4-dichlorophenyl)-1H-1,2,3-triazol-1-yl]-3-fluoro-5-(methylsulfonyl)-4'-[2-methyl-4-(trifluoromcehyl)-1H-imidazol-1-yl]biphenyl-4-yl}methanol | MS (ESI) 640.3 [M + H]+. |
| 68 | 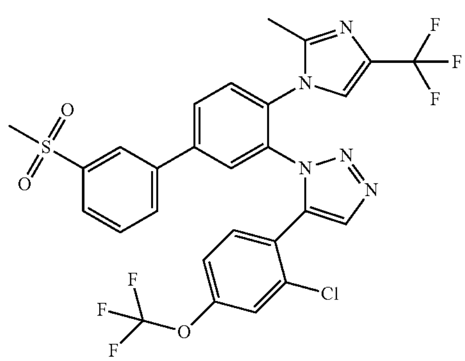 | 5-{2-chloro-4-[(trifluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole | MS (ESI) 642.2 [M + H]+. |
| 69 | 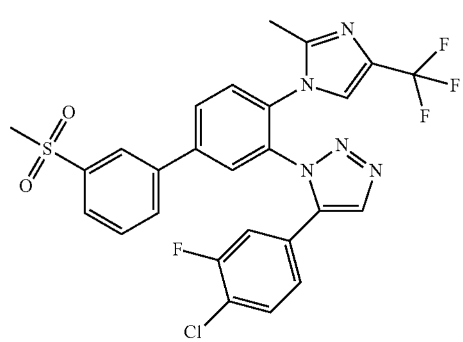 [SMILES: Cc1nc(C(F)(F)F)cn1-c1ccc(-c2cccc(S(C)(=O)=O)c2)cc1-n1nncc1-c1ccc(Cl)c(F)c1] | 5-(4-chloro-3-fluorophenyl)-1-{3'-(methylsulfonyl)-4-[2-methyl-4-(trifluoromethyl)-1H-imidazol-1-yl]biphenyl-3-yl}-1H-1,2,3-triazole | MS (ESI) 576.2 [M + H]+. |

| Ex # | Structure | Name & Additional Characterization Data | Molecular Ion |
|---|---|---|---|
| 70 | 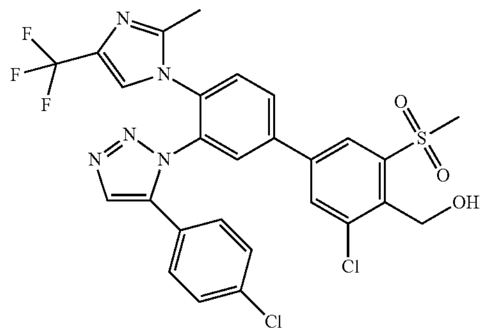 [SMILES: Cc1nc(C(F)(F)F)cn1-c1ccc(-c2cc(Cl)c(CO)c(S(C)(=O)=O)c2)cc1-n1nncc1-c1ccc(Cl)cc1] | {3-chloro-3'-[5-(4-chlorophenyl)-1H-1,2,3-triazol-1-yl]-5-(methylsulfony)-4'-[2-methyl-4-(trifluoromethyl)-1H-imidazol-1-yl]biphenyl-4-yl}methanol | MS (ESI) 622.1 [M + H]+. |
| 71 | 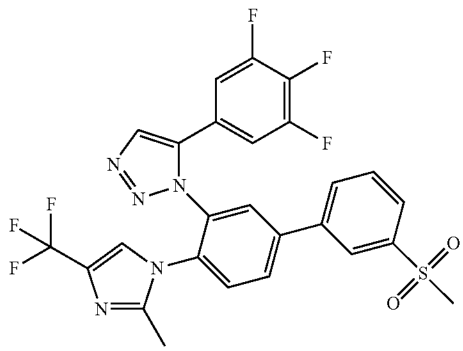 [SMILES: Cc1nc(C(F)(F)F)cn1-c1ccc(-c2cccc(S(C)(=O)=O)c2)cc1-n1nncc1-c1cc(F)c(F)c(F)c1] | 1-{3'-(methylsulfonyl)-4-[2-methyl-4-(trifluoromethyl)-1H-imidazol-1-yl]biphenyl-3-yl}-5-(3,4,5-trifluorophenyl)-1H-1,2,3-triazole | MS (ESI) 578.3 [M + H]+. |
| 72 | 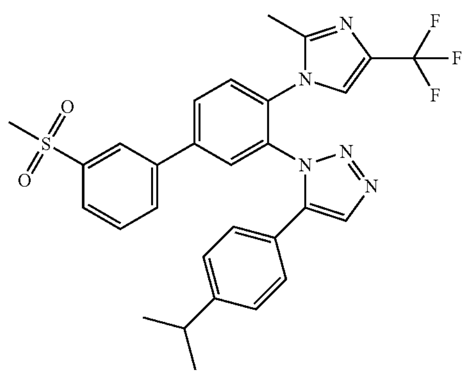 [SMILES: Cc1nc(C(F)(F)F)cn1-c1ccc(-c2cccc(S(C)(=O)=O)c2)cc1-n1nncc1-c1ccc(C(C)C)cc1] | 5-[4-(1-methylethyl)phenyl]-1-{3'-(methylsulfonyl)-4-[2-methyl-4-(trifluoromethyl)-1H-imidazol-1-yl]biphenyl-3-yl}-1H-1,2,3-triazole | MS (ESI) 566.2 [M + H]+. |
| 73 | 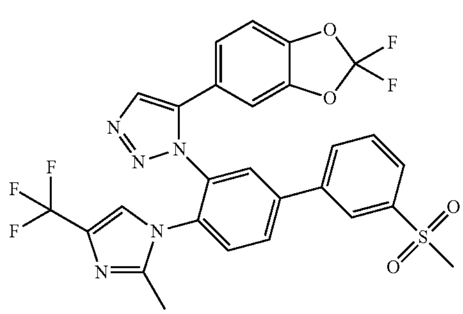 [SMILES: Cc1nc(C(F)(F)F)cn1-c1ccc(-c2cccc(S(C)(=O)=O)c2)cc1-n1nncc1-c1ccc2c(c1)OC(F)(F)O2] | 5-(2,2-difluoro-1,3-benzodioxol-5-yl)-1-{3'-(methylsulfonyl)-4-[2-methyl-4-(trifluoromethyl)-1H-imidazol-1-yl]biphenyl-3-yl}-1H-1,2,3-triazole | MS (ESI) 604.2 [M + H]+. |

| Ex # | Structure | Name & Additional Characterization Data | Molecular Ion |
|---|---|---|---|
| 74 | 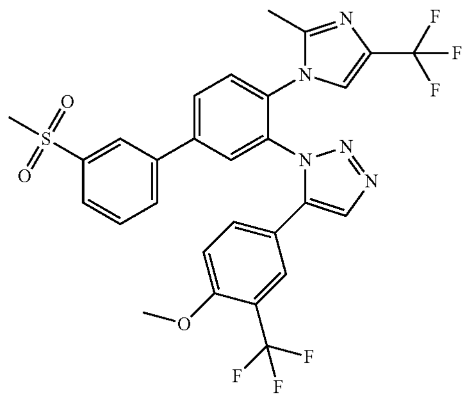 [SMILES: COc1ccc(-c2cnnn2-c2cc(-c3cccc(S(C)(=O)=O)c3)ccc2-n2cc(C(F)(F)F)nc2C)cc1C(F)(F)F] | 5-[4-(methyloxy)-3-(trifluoromethyl)phenyl]-1-{3'-(methylsulfonyl)-4-[2-methyl-4-(trifluoromethyl)-1H-imidazol-1-yl]biphenyl-3-yl}-1H-1,2,3-triazole | MS (ESI) 622.0 [M + H]+. |
| 75 | 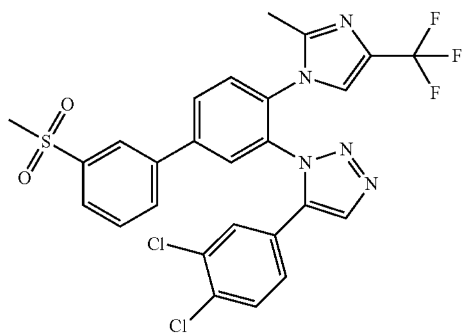 | 5-(3,4-dichlorophenyl)-1-{3'-(methylsulfonyl)-4-[2-methyl-4-(trifluoromethyl)-1H-imidazol-1-yl]biphenyl-3-yl}-1H-1,2,3-triazole | MS (ESI) 594.2 [M + H]+. |
| 76 | 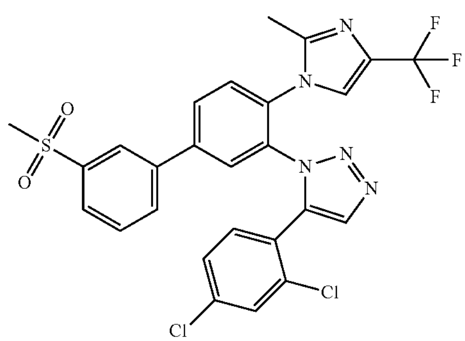 | 5-(2,4-dichlorophenyl)-1-{3'-(methylsulfonyl)-4-[2-methyl-4-(trifluoromethyl)-1H-imidazol-1-yl]biphenyl-3-yl}-1H-1,2,3-triazole | MS (ESI) 592.2 [M + H]+. |
| 77 | 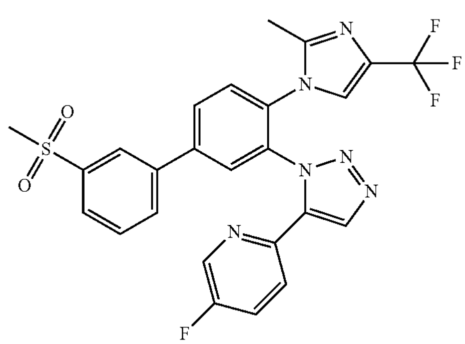 [SMILES: Cc1nc(C(F)(F)F)cn1-c1ccc(-c2cccc(S(C)(=O)=O)c2)cc1-n1nncc1-c1ccc(F)cn1] | 5-fluoro-2-(1-{3'-(methylsulfonyl)-4-[2-methyl-4-(trifluoromethyl)-1H-imidazol-1-yl]biphenyl-3-yl}-1H-1,2,3-triazol-5-yl)pyridine | MS (ESI) 543.1 [M + H]+. |

| Ex # | Structure | Name & Additional Characterization Data | Molecular Ion |
|---|---|---|---|
| 78 | 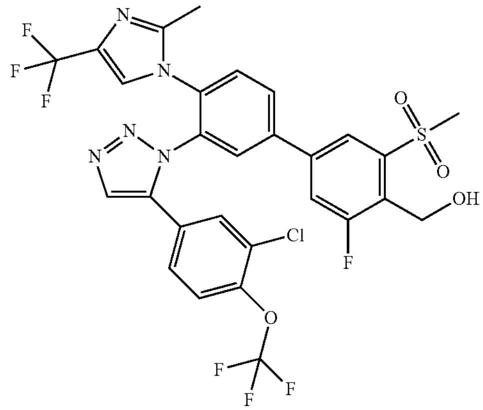 [SMILES: Cc1nc(C(F)(F)F)cn1-c1ccc(-c2cc(F)c(CO)c(S(C)(=O)=O)c2)cc1-n1nncc1-c1ccc(OC(F)(F)F)c(Cl)c1] | {3'-(5-{3-chloro-4-[(trifluoromethyl)oxy]phenyl}-1H-1,2,3-triazol-1-yl)-3-fluoro-5-(methylsulfonyl)-4'-[2-methyl-4-(trifluoromethyl)-1H-imidazol-1-yl]biphenyl-4-yl}methanol | MS (ESI) 690.3 [M + H]+. |
| 79 | 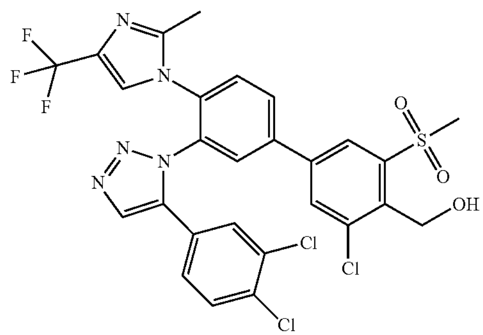 | {3-chloro-3'-[5-(3,4-dichlorophenyl)-1H-1,2,3-triazol-1-yl]-5-(methylsulfonyl)-4'-[2-methyl-4-(trifluoromethyl)-1H-imidazol-1-yl]biphenyl-4-yl}methanol | MS (ESI) 658.3 [M + H]+. |
| 80 | 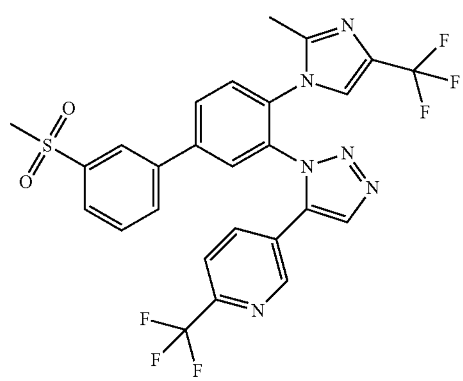 [SMILES: Cc1nc(C(F)(F)F)cn1-c1ccc(-c2cccc(S(C)(=O)=O)c2)cc1-n1nncc1-c1ccc(C(F)(F)F)nc1] | 5-(1-{3'-(methylsulfonyl)-4-[2-methyl-4-(trifluoromethyl)-1H-imidazol-1-yl]biphenyl-3-yl}-1H-1,2,3-triazol-5-yl)-2-(trifluoromethyl)pyridine | MS (ESI) 593.2 [M + H]+. |
| 81 | 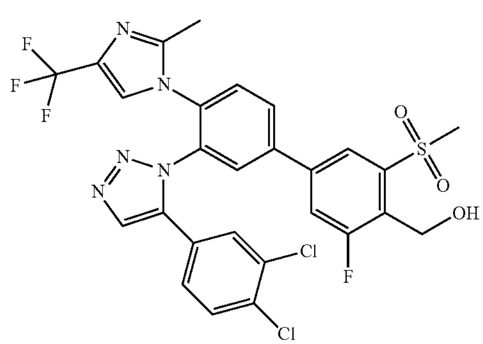 | {3'-[5-(3,4-dichlorophenyl)-1H-1,2,3-triazol-1-yl]-3-fluoro-5-(methylsulfonyl)-4'-[2-methyl-4-(trifluoromethyl)-1H-imidazol-1-yl]biphenyl-4-yl}methanol | MS (ESI) 640.2 [M + H]+. |

| Ex # | Structure | Name & Additional Characterization Data | Molecular Ion |
|---|---|---|---|
| 82 | 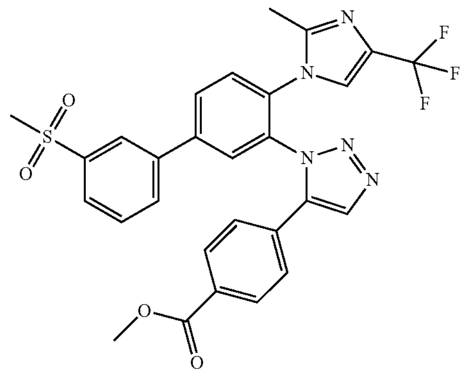 [SMILES: COC(=O)c1ccc(-c2cnnn2-c2cc(-c3cccc(S(C)(=O)=O)c3)ccc2-n2cc(C(F)(F)F)nc2C)cc1] | methyl 4-(1-{3'-(methylsulfonyl)-4-[2-methyl-4-(trifluoromethyl)-1H-imidazol-1-yl]biphenyl-3-yl}-1H-1,2,3-triazol-5-yl)benzoate | MS (ESI) 582.1 [M + H]+ |
| 83 | 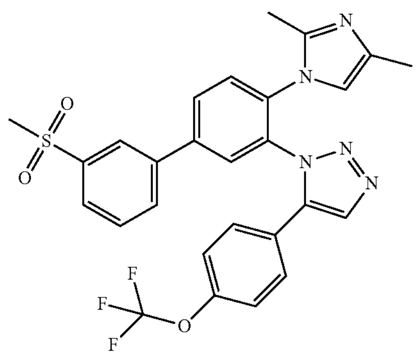 | 1-[4-(2,4-dimethyl-1H-imidazol-1-yl)-3'-(methylsulfonyl)biphenyl-3-yl]-5-{4-[(trifluoromethyl)oxy]phenyl}-1H-1,2,3-triazole | MS (ESI) 554.1 [M + H]+ |
| 84 | 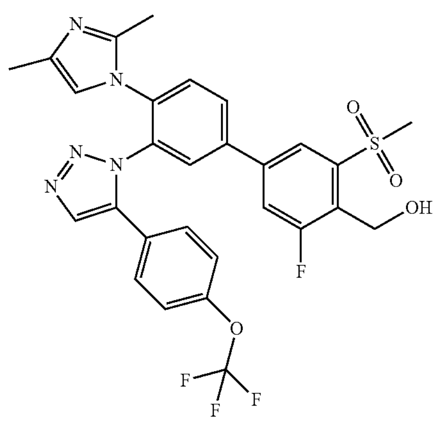 | [4'-(2,4-dimethyl-1H-imidazol-1-yl)-3-fluoro-5-(methylsulfonyl)-3'-(5-{4-[(trifluoromethyl)oxy]phenyl)-1H-1,2,3-triazol-1-yl)biphenyl-4-yl]methanol | MS (ESI) 602.1 [M + H]+ |
| 85 | 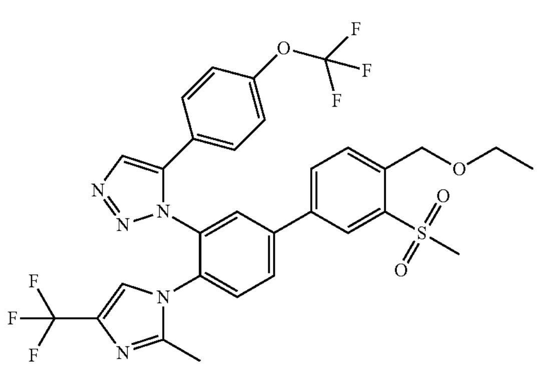 [SMILES: CCOCc1ccc(-c2ccc(-n3cc(C(F)(F)F)nc3C)c(-n3nncc3-c3ccc(OC(F)(F)F)cc3)c2)cc1S(C)(=O)=O] | 1-{4'-[(ethyloxy)methyl]-3'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole | MS (ESI) 666.2 [M + H]+ |

| Ex # | Structure | Name & Additional Characterization Data | Molecular Ion |
|---|---|---|---|
| 86 | 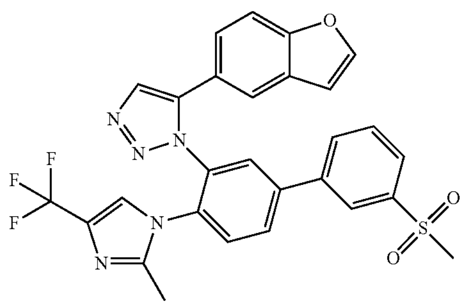 [SMILES: Cc1nc(C(F)(F)F)cn1-c1ccc(-c2cccc(S(C)(=O)=O)c2)cc1-n1nncc1-c1ccc2occc2c1] | 5-(1-benzofuran-5-yl)-1-{3'-(methylsulfonyl)-4-[2-methyl-4-(trifluoromethyl)-1H-imidazol-1-yl]biphenyl-3-yl}-1H-1,2,3-triazole | MS (ESI) 564.2 [M + H]+ |
| 87 | 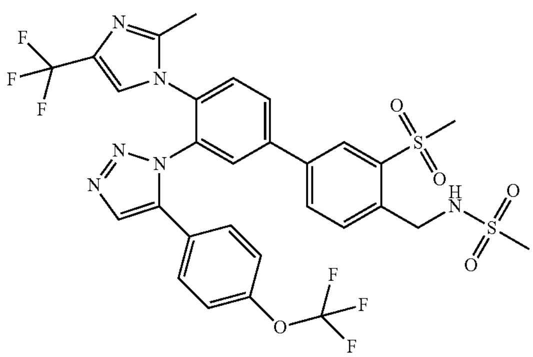 [SMILES: Cc1nc(C(F)(F)F)cn1-c1ccc(-c2ccc(CNS(C)(=O)=O)c(S(C)(=O)=O)c2)cc1-n1nncc1-c1ccc(OC(F)(F)F)cc1] | N-{[3-(methylsulfonyl)-4'-[2-methyl-4-(trifluoromethyl)-1H-imidazol-1-yl]-3'-(5-{4-[(trifluoromethyl)oxy]phenyl}-1H-1,2,3-triazol-1-yl)biphenyl-4-yl]methyl}methanesulfonamide | MS (ESI) 715.2 [M + H]+ |
| 88 | 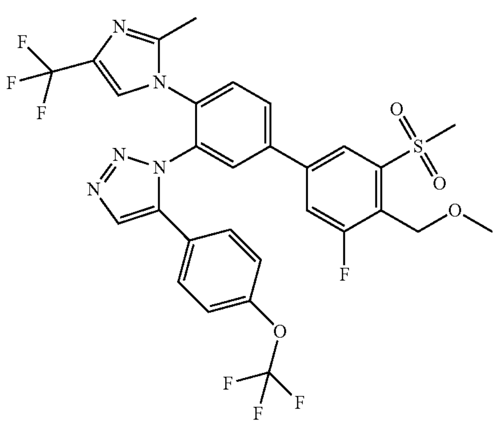 [SMILES: COCc1c(F)cc(-c2ccc(-n3cc(C(F)(F)F)nc3C)c(-n3nncc3-c3ccc(OC(F)(F)F)cc3)c2)cc1S(C)(=O)=O] | 1-{3'-fluoro-4'-[(methyloxy)methyl]-5'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole | MS (ESI) 670.1 [M + H]+. |
| 89 | 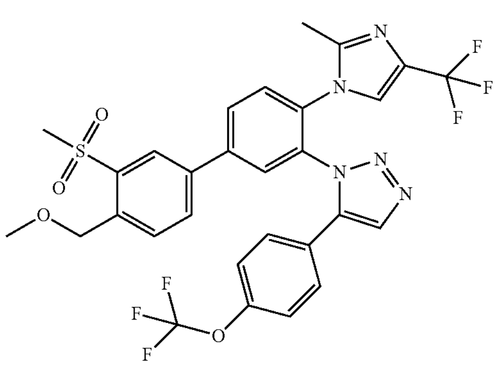 [SMILES: COCc1ccc(-c2ccc(-n3cc(C(F)(F)F)nc3C)c(-n3nncc3-c3ccc(OC(F)(F)F)cc3)c2)cc1S(C)(=O)=O] | 1-{4'-[(methyloxy)methyl]-3'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole | MS (ESI) 652.1 [M + H]+. |

| Ex # | Structure | Name & Additional Characterization Data | Molecular Ion |
|---|---|---|---|
| 90 | 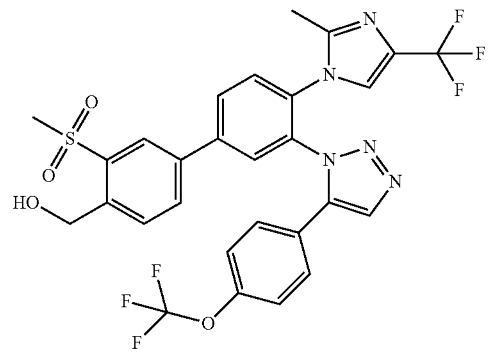 [SMILES: Cc1nc(C(F)(F)F)cn1-c1ccc(-c2ccc(CO)c(S(C)(=O)=O)c2)cc1-n1nncc1-c1ccc(OC(F)(F)F)cc1] | [3-(methylsulfonyl)-4'-[2-methyl-4-(trifluoromethyl)-1H-imidazol-1-yl]-3'-(5-{4-[(trifluoromethyl)oxy]phenyl}-1H-1,2,3-triazol-1-yl)biphenyl-4-yl]methanol | MS (ESI) 638.1 [M + H]⁺. |
| 91 | 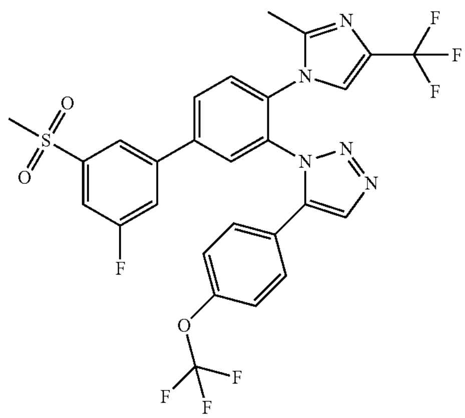 [SMILES: Cc1nc(C(F)(F)F)cn1-c1ccc(-c2cc(F)cc(S(C)(=O)=O)c2)cc1-n1nncc1-c1ccc(OC(F)(F)F)cc1] | 1-{3'-fluoro-5'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole | MS (ESI) 626.1 [M + H]⁺. |
| 92 | 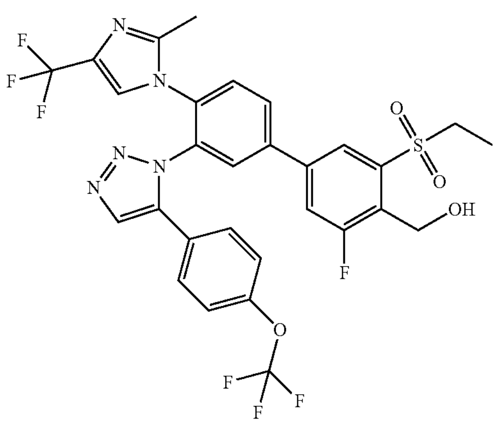 [SMILES: CCS(=O)(=O)c1cc(-c2ccc(-n3cc(C(F)(F)F)nc3C)c(-n3nncc3-c3ccc(OC(F)(F)F)cc3)c2)cc(F)c1CO] | [3-(ethylsulfonyl)-5-fluoro-4'-[2-methyl-4-(trifluoromethyl)-1H-imidazol-1-yl]-3'-(5-{4-[(trifluoromethyl)oxy]phenyl}-1H-1,2,3-triazol-1-yl)biphenyl-4-yl]methanol | MS (ESI) 670.1 [M + H]⁺. |
| 93 | 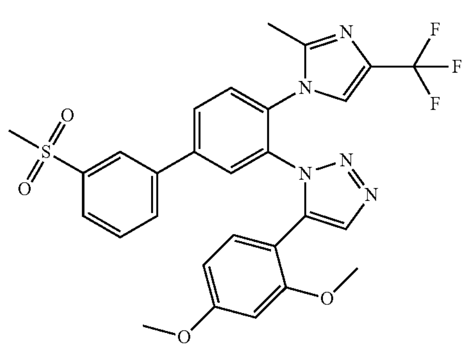 [SMILES: COc1ccc(-c2cnnn2-c2cc(-c3cccc(S(C)(=O)=O)c3)ccc2-n2cc(C(F)(F)F)nc2C)c(OC)c1] | 5-[2,4-bis(methyloxy)phenyl]-1-{3'-(methylsulfonyl)-4-[2-methyl-4-(trifluoromethyl)-1H-imidazol-1-yl]biphenyl-3-yl}-1H-1,2,3-triazole | MS (ESI) 584.2 [M + H]⁺. |

| Ex # | Structure | Name & Additional Characterization Data | Molecular Ion |
|---|---|---|---|
| 94 | 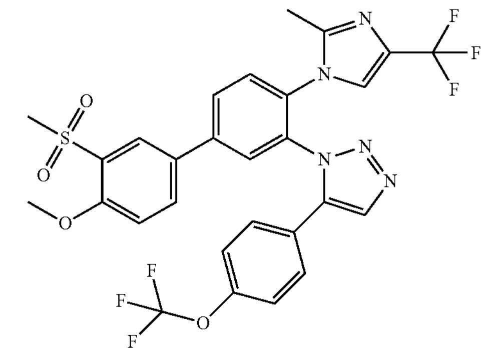 [SMILES: COc1ccc(-c2ccc(-n3cc(C(F)(F)F)nc3C)c(-n3nncc3-c3ccc(OC(F)(F)F)cc3)c2)cc1S(C)(=O)=O] | 1-{4'-(methyloxy)-3'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole | MS (ESI) 638.1 [M + H]⁺. |
| 95 | 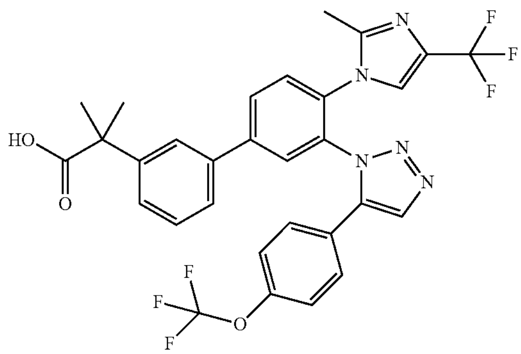 [SMILES: Cc1nc(C(F)(F)F)cn1-c1ccc(-c2cccc(C(C)(C)C(=O)O)c2)cc1-n1nncc1-c1ccc(OC(F)(F)F)cc1] | 2-methyl-2-{4'-[2-methyl-4-(trifluoromethyl)-1H-imidazol-1-yl]-3'-(5-{4-[(trifluoromethyl)oxy]phenyl}-1H-1,2,3-triazol-1-yl)biphenyl-3-yl}propanoic acid | MS (ESI) 616.2 [M + H]⁺. |
| 98 | 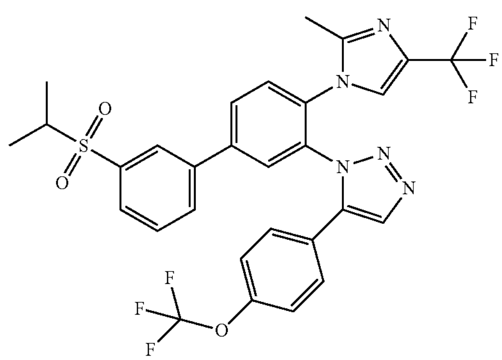 [SMILES: Cc1nc(C(F)(F)F)cn1-c1ccc(-c2cccc(S(=O)(=O)C(C)C)c2)cc1-n1nncc1-c1ccc(OC(F)(F)F)cc1] | 1-{3'-[(1-methylethyl)sulfonyl]-4-[2-methyl-4-(trifluoromethyl)-1H-imidazol-1-yl]biphenyl-3-yl}-5-{4-[(trifluoromethyl)oxy]phenyl}-1H-1,2,3-triazole | MS (ESI) 636.1 [M + H]⁺. |
| 99 | 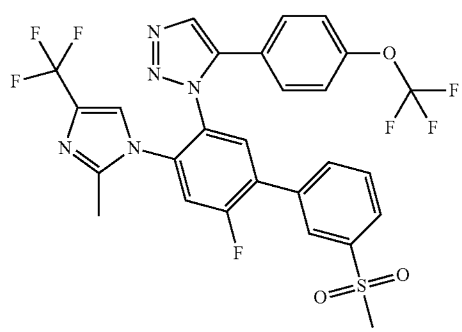 [SMILES: Cc1nc(C(F)(F)F)cn1-c1cc(F)c(-c2cccc(S(C)(=O)=O)c2)cc1-n1nncc1-c1ccc(OC(F)(F)F)cc1] | 1-{6-fluoro-3'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole | MS (ESI) 626.1 [M + H]⁺. |

-continued

| Ex # | Structure | Name & Additional Characterization Data | Molecular Ion |
|---|---|---|---|
| 100 | 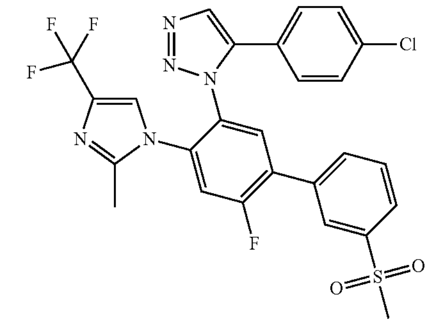 [SMILES: Cc1nc(C(F)(F)F)cn1-c1cc(F)c(-c2cccc(S(C)(=O)=O)c2)cc1-n1nncc1-c1ccc(Cl)cc1] | 5-(4-chlorophenyl)-1-{6-fluoro-3'-(methylsulfonyl)-4-[2-methyl-4-(trifluoromethyl)-1H-imidazol-1-yl]biphenyl-3-yl}-1H-1,2,3-triazole | MS (ESI) 576.1 [M + H]+. |
| 101 | 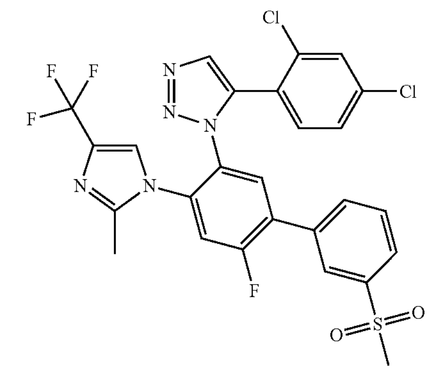 [SMILES: Cc1nc(C(F)(F)F)cn1-c1cc(F)c(-c2cccc(S(C)(=O)=O)c2)cc1-n1nncc1-c1ccc(Cl)cc1Cl] | 5-(2,4-dichlorophenyl)-1-{6-fluoro-3'-(methylsulfonyl)-4-[2-methyl-4-(trifluoromethyl)-1H-imidazol-1-yl]biphenyl-3-yl}-1H-1,2,3-triazole | MS (ESI) 610 [M + H]+. |
| 102 | 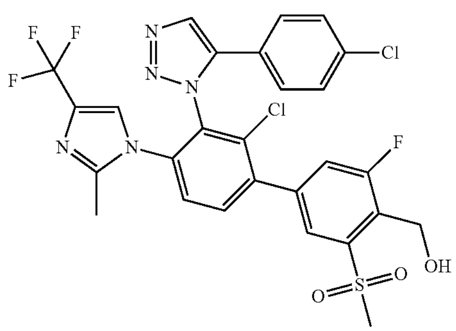 [SMILES: Cc1nc(C(F)(F)F)cn1-c1ccc(-c2cc(F)c(CO)c(S(C)(=O)=O)c2)c(Cl)c1-n1nncc1-c1ccc(Cl)cc1] | {2'-chloro-3'-[5-(4-chlorophenyl)-1H-1,2,3-triazol-1-yl]-3-fluoro-5-(methylsulfonyl)-4'-[2-methyl-4-(trifluoromethyl)-1H-imidazol-1-yl]biphenyl-4-yl}methanol | MS (ESI) 640.1 [M + H]+. |
| 103 | 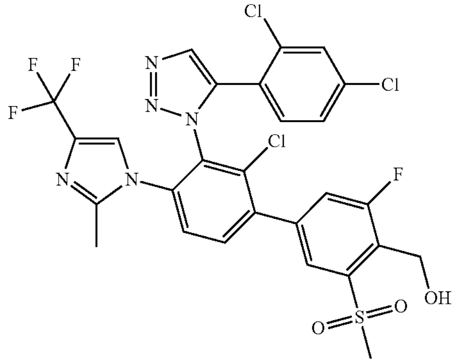 [SMILES: Cc1nc(C(F)(F)F)cn1-c1ccc(-c2cc(F)c(CO)c(S(C)(=O)=O)c2)c(Cl)c1-n1nncc1-c1ccc(Cl)cc1Cl] | {2'-chloro-3'-[5-(2,4-dichlorophenyl)-1H-1,2,3-triazol-1-yl]-3-fluoro-5-(methylsulfonyl)-4'-[2-methyl-4-(trifluoromethyl)-1H-imidazol-1-yl]biphenyl-4-yl}methanol | MS (ESI) 674 [M + H]+. |

| Ex # | Structure | Name & Additional Characterization Data | Molecular Ion |
|---|---|---|---|
| 105 | 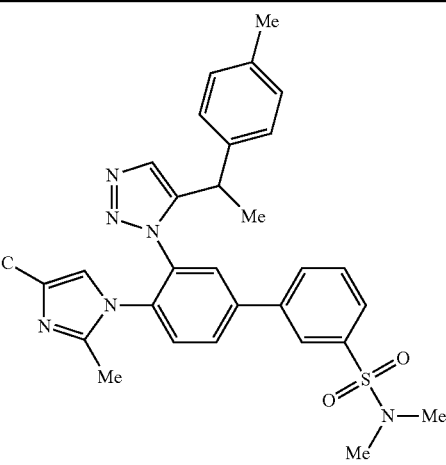 | N,N-dimethyl-3'-{5-[1-(4-methylphenyl)ethyl]-1H-1,2,3-triazol-1-yl}-4'-[2-methyl-4-(trifluoromethyl)-1H-imidazol-1-yl]biphenyl-3-sulfonamide | MS (ESI) 595.3 [M + H]+. |
| 106 | 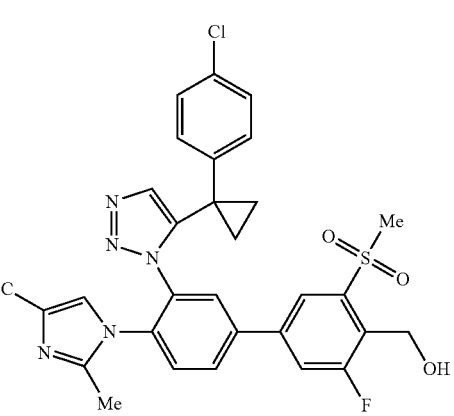 | (3'-{5-[1-(4-chlorophenyl)cyclopropyl]-1H-1,2,3-triazol-1-yl}-3-fluoro-5-(methylsulfonyl)-4'-[2-methyl-4-(trifluoromethyl)-1H-imidazol-1-yl]biphenyl-4-yl)methanol; | MS (ESI) 646.3 [M + H]+. |
| 107 | 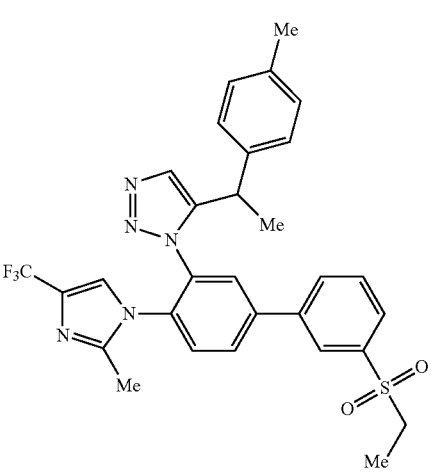 [SMILES: CCS(=O)(=O)c1cccc(-c2ccc(-n3cc(C(F)(F)F)nc3C)c(-n3nncc3C(C)c3ccc(C)cc3)c2)c1] | 1-{3'-(ethylsulfonyl)-4-[2-methyl-4-(trifluoromethyl)-1H-imidazol-1-yl]biphenyl-3-yl}-5-[1-(4-methylphenyl)ethyl]-1H-1,2,3-triazole | MS (ESI) 580.3 [M + H]+. |

| Ex # | Structure | Name & Additional Characterization Data | Molecular Ion |
|---|---|---|---|
| 108 | 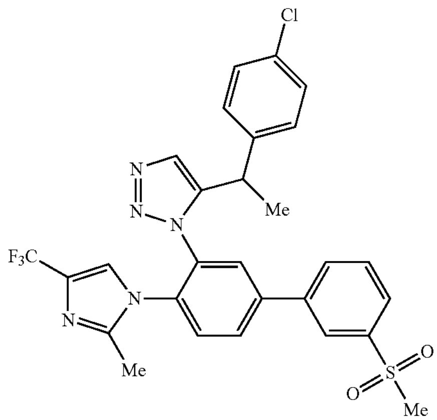 [SMILES: Cc1nc(C(F)(F)F)cn1-c1ccc(-c2cccc(S(C)(=O)=O)c2)cc1-n1nncc1C(C)c1ccc(Cl)cc1] | 5-[1-(4-chlorophenyl)ethyl]-1-{3'-(methylsulfonyl)-4-[2-methyl-4-(trifluoromethyl)-1H-imidazol-1-yl]biphenyl-3-yl}-1H-1,2,3-triazole | MS (ESI) 586.2 [M + H]+. |
| 109 | 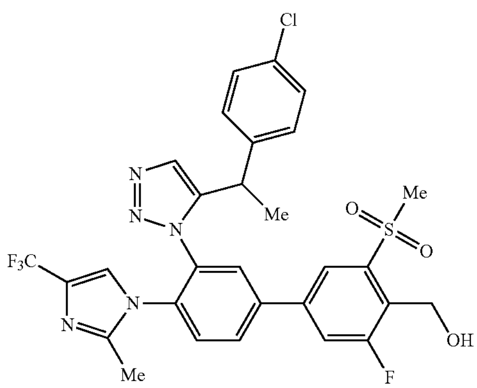 [SMILES: Cc1nc(C(F)(F)F)cn1-c1ccc(-c2cc(F)c(CO)c(S(C)(=O)=O)c2)cc1-n1nncc1C(C)c1ccc(Cl)cc1] | (3'-{5-[1-(4-chlorophenyl)ethyl]-1H-1,2,3-triazol-1-yl}-3-fluoro-5-(methylsulfonyl)-4'-[2-methyl-4-(trifluoromethyl)-1H-imidazol-1-yl]biphenyl-4-yl)methanol | MS (ESI) 634.1 [M + H]+. |
| 110 | 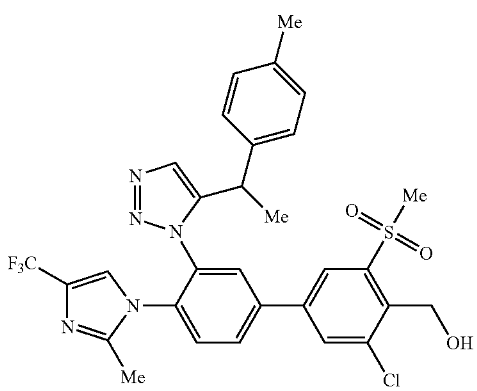 | (3-chloro-3'-{5-[1-(4-methylphenyl)ethyl]-1H-1,2,3-triazol-1-yl}-5-(methylsulfonyl)-4'-[2-methyl-4-(trifluoromethyl)-1H-imidazol-1-yl]biphenyl-4-yl)methanol | MS (ESI) 630.3 [M + H]+. |
| 111 | 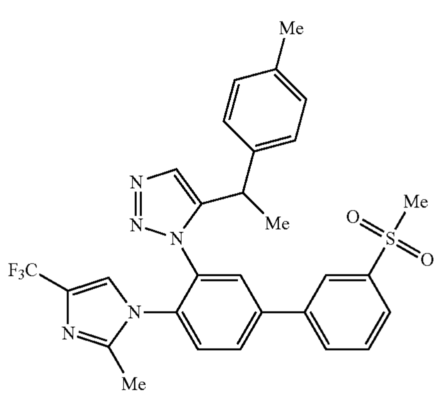 | 5-[1-(4-methylphenyl)ethyl]-1-{3'-(methylsulfonyl)-4-[2-methyl-4-(trifluoromethyl)-1H-imidazol-1-yl]biphenyl-3-yl}-1H-1,2,3-triazole | MS (ESI) 566.2 [M + H]+. |

| Ex # | Structure | Name & Additional Characterization Data | Molecular Ion |
|---|---|---|---|
| 112 | 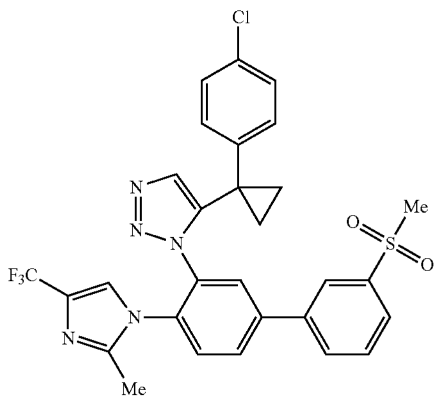 [SMILES: Cc1nc(C(F)(F)F)cn1-c1ccc(-c2cccc(S(C)(=O)=O)c2)cc1-n1nncc1C1(c2ccc(Cl)cc2)CC1] | 5-[1-(4-chlorophenyl)cyclopropyl]-1-{3'-(methylsulfonyl)-4-[2-methyl-4-(trifluoromethyl)-1H-imidazol-1-yl]biphenyl-3-yl}-1H-1,2,3-triazole | MS (ESI) 598.3 [M + H]+. |
| 113 | 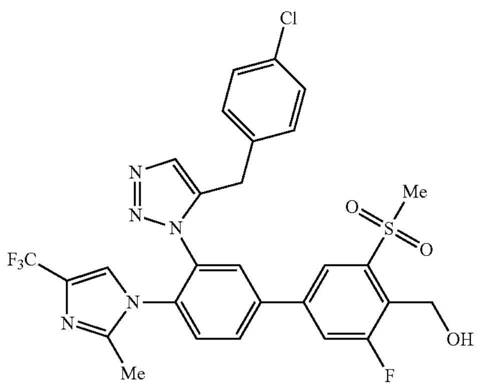 [SMILES: Cc1nc(C(F)(F)F)cn1-c1ccc(-c2cc(F)c(CO)c(S(C)(=O)=O)c2)cc1-n1nncc1Cc1ccc(Cl)cc1] | (3'-{5-[(chlorophenyl)methyl]-1H-1,2,3-triazol-1-yl}-3-fluoro-5-(methylsulfonyl)-4'-[2-methyl-4-(trifluoromethyl)-1H-imidazol-1-yl]biphenyl-4-yl)methanol | MS (ESI) 620.1 [M + H]+. |
| 114 | 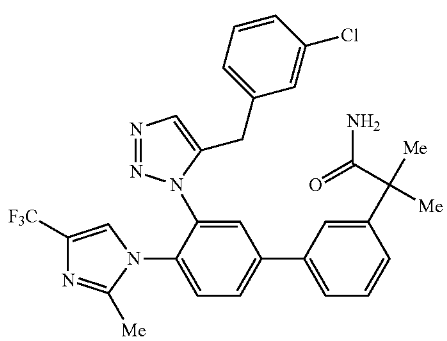 [SMILES: Cc1nc(C(F)(F)F)cn1-c1ccc(-c2cccc(C(C)(C)C(N)=O)c2)cc1-n1nncc1Cc1cccc(Cl)c1] | 2-(3'-{5-[(3-chlorophenyl)methyl]-1H-1,2,3-triazol-1-yl}-4'-[2-methyl-4-(trifluoromethyl)-1H-imidazol-1-yl]biphenyl-3-yl)-2-methylpropanamide | MS (ESI) 579.2 [M + H]+. |
| 115 | 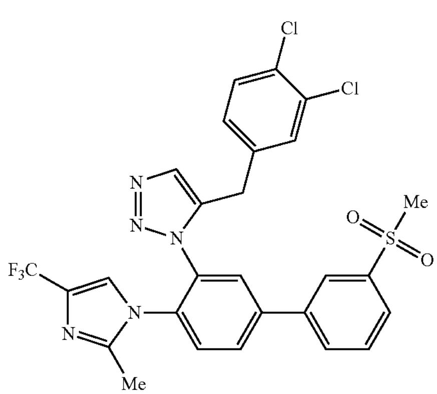 [SMILES: Cc1nc(C(F)(F)F)cn1-c1ccc(-c2cccc(S(C)(=O)=O)c2)cc1-n1nncc1Cc1ccc(Cl)c(Cl)c1] | 5-[(3,4-dichlorophenyl)methyl]-1-{3'-(methylsulfonyl)-4-[2-methyl-4-(trifluoromethyl)-1H-imidazol-1-yl]biphenyl-3-yl}-1H-1,2,3-triazole | MS (ESI) 606.1 [M + H]+. |

| Ex # | Structure | Name & Additional Characterization Data | Molecular Ion |
|---|---|---|---|
| 116 | 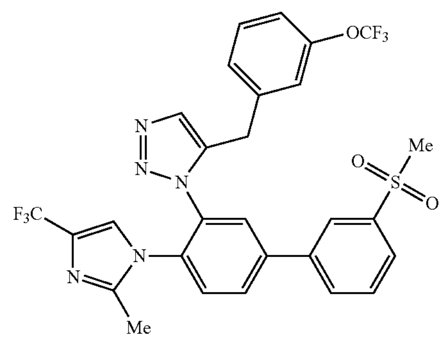 [SMILES: Cc1nc(C(F)(F)F)cn1-c1ccc(-c2cccc(S(C)(=O)=O)c2)cc1-n1nncc1Cc1cccc(OC(F)(F)F)c1] | 1-{3'-(methylsulfonyl)-4-[2-methyl-4-(trifluoromethyl)-1H-imidazol-1-yl]biphenyl-3-yl}-5-({3-[(trifluoromethyl)oxy]phenyl}methyl)-1H-1,2,3-triazole | MS (ESI) 622.1 [M + H]+. |
| 117 | 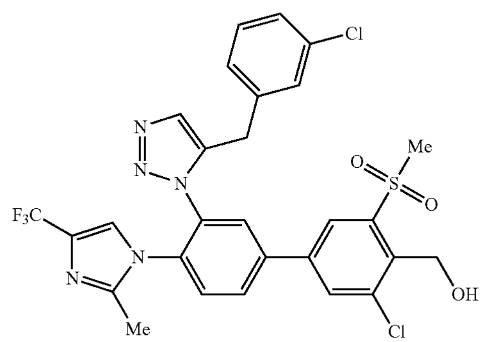 [SMILES: Cc1nc(C(F)(F)F)cn1-c1ccc(-c2cc(Cl)c(CO)c(S(C)(=O)=O)c2)cc1-n1nncc1Cc1cccc(Cl)c1] | (3-chloro-3'-{5-[(3-chlorophenyl)methyl]-1H-1,2,3-triazol-1-yl}-5-(methylsulfonyl)-4'-[2-methyl-4-(trifluoromethyl)-1H-imidazol-1-yl]biphenyl-4-yl)methanol | MS (ESI) 636.1 [M + H]+. |
| 118 | 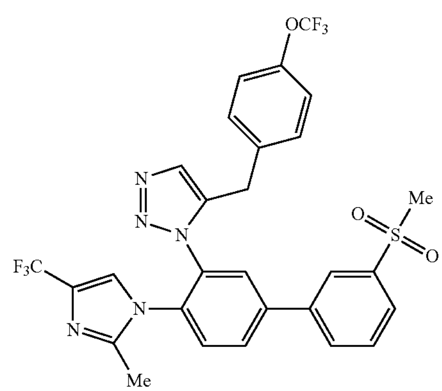 [SMILES: Cc1nc(C(F)(F)F)cn1-c1ccc(-c2cccc(S(C)(=O)=O)c2)cc1-n1nncc1Cc1ccc(OC(F)(F)F)cc1] | 1-{3'-(methylsulfonyl)-4-[2-methyl-4-(trifluoromethyl)-1H-imidazol-1-yl]biphenyl-3-yl}-5-({4-[(trifluoromethyl)oxy]phenyl}methyl)-1H-1,2,3-triazole | MS (ESI) 622.1 [M + H]+. |
| 119 | 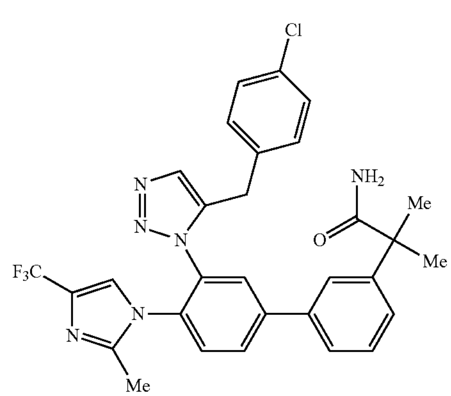 [SMILES: Cc1nc(C(F)(F)F)cn1-c1ccc(-c2cccc(C(C)(C)C(N)=O)c2)cc1-n1nncc1Cc1ccc(Cl)cc1] | 2-(3'-{5-[(4-chlorophenyl)methyl]-1H-1,2,3-triazol-1-yl}-4'-[2-methyl-4-(trifluoromethyl)-1H-imidazol-1-yl]biphenyl-3-yl)-2-methylpropanamide | MS (ESI) 579.2 [M + H]+. |

| Ex # | Structure | Name & Additional Characterization Data | Molecular Ion |
|---|---|---|---|
| 120 | 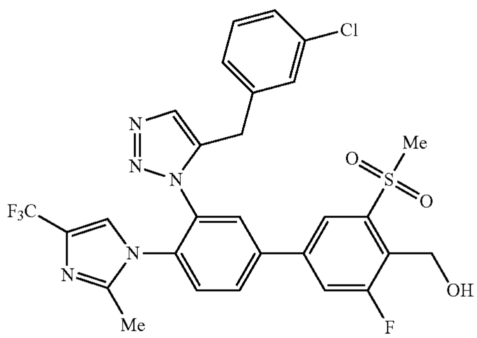 | (3'-{5-[(3-chlorophenyl)methyl]-1H-1,2,3-triazol-1-yl}-3-fluoro-5-(methylsulfonyl)-4'-[2-methyl-4-(trifluoromethyl)-1H-imidazol-1-yl]biphenyl-4-yl)methanol | MS (ESI) 620.1 [M + H]+. |
| 121 | 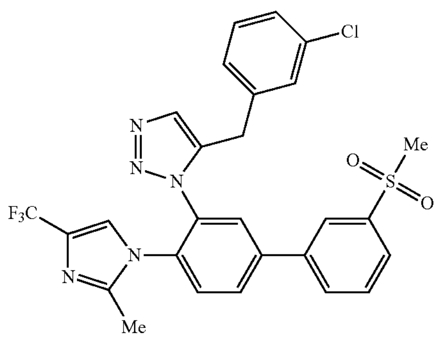 [SMILES: Cc1nc(C(F)(F)F)cn1-c1ccc(-c2cccc(S(C)(=O)=O)c2)cc1-n1nncc1Cc1cccc(Cl)c1] | 5-[(3-chlorophenyl)methyl]-1-{3'-(methylsulfonyl)-4-[2-methyl-4-(trifluoromethyl)-1H-imidazol-1-yl]biphenyl-3-yl}-1H-1,2,3-triazole | MS (ESI) 572.1 [M + H]+. |
| 122 | 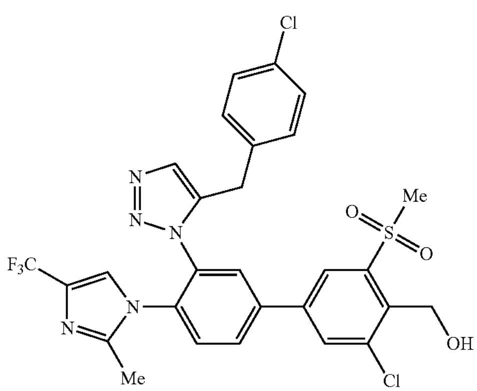 [SMILES: Cc1nc(C(F)(F)F)cn1-c1ccc(-c2cc(Cl)c(CO)c(S(C)(=O)=O)c2)cc1-n1nncc1Cc1ccc(Cl)cc1] | (3-chloro-3'-{5-[(4-chlorophenyl)methyl]-1H-1,2,3-triazol-1-yl}-5-(methylsulfonyl)-4'-[2-methyl-4-(trifluoromethyl)-1H-imidazol-1-yl]biphenyl-4-yl)methanol | MS (ESI) 636.1 [M + H]+. |
| 123 | 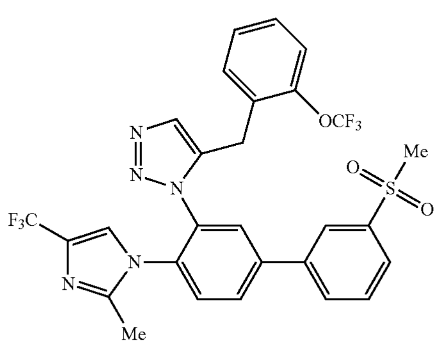 [SMILES: Cc1nc(C(F)(F)F)cn1-c1ccc(-c2cccc(S(C)(=O)=O)c2)cc1-n1nncc1Cc1ccccc1OC(F)(F)F] | 1-{3'-(methylsulfonyl)-4-[2-methyl-4-(trifluoromethyl)-1H-imidazol-1-yl]biphenyl-3-yl}-5-({2-[(trifluoromethyl)oxy]phenyl}methyl)-1H-1,2,3-triazole | MS (ESI) 622.1 [M + H]+. |

-continued

| Ex # | Structure | Name & Additional Characterization Data | Molecular Ion |
|---|---|---|---|
| 124 | 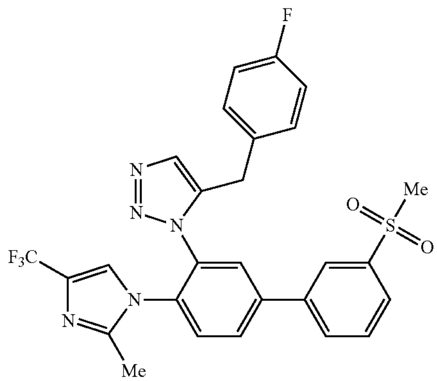 [SMILES: Cc1nc(C(F)(F)F)cn1-c1ccc(-c2cccc(S(C)(=O)=O)c2)cc1-n1nncc1Cc1ccc(F)cc1] | 5-[(4-fluorophenyl)methyl]-1-{3'-(methylsulfonyl)-4-[2-methyl-4-(trifluoromethyl)-1H-imidazol-1-yl]biphenyl-3-yl}-1H-1,2,3-triazole | MS (ESI) 556.1 [M + H]+. |
| 125 | 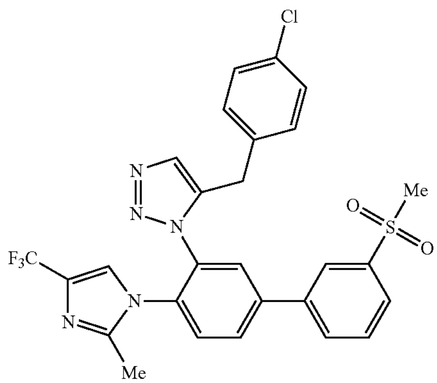 | 5-[(4-chlorophenyl)methyl]-1-{3'-(methylsulfonyl)-4-[2-methyl-4-(trifluoromethyl)-1H-imidazol-1-yl]biphenyl-3-yl}-1H-1,2,3-triazole | MS (ESI) 572.1 [M + H]+. |
| 126 | 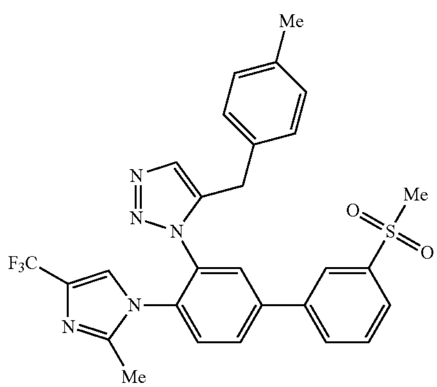 [SMILES: Cc1nc(C(F)(F)F)cn1-c1ccc(-c2cccc(S(C)(=O)=O)c2)cc1-n1nncc1Cc1ccc(Cl)cc1] | 5-[(4-methylphenyl)methyl]-1-{3'-(methylsulfonyl)-4-[2-methyl-4-(trifluoromethyl)-1H-imidazol-1-yl]biphenyl-3-yl}-1H-1,2,3-triazole | MS (ESI) 552.2 [M + H]+. |
| 127 | 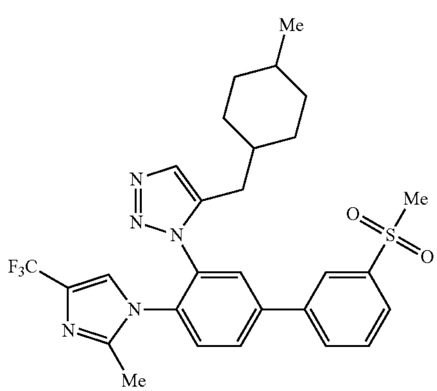 [SMILES: Cc1nc(C(F)(F)F)cn1-c1ccc(-c2cccc(S(C)(=O)=O)c2)cc1-n1nncc1CC1CCC(C)CC1] | 5-[(4-methylcyclohexyl)methyl]-1-{3'-(methylsulfonyl)-4-[2-methyl-4-(trifluoromethyl)-1H-imidazol-1-yl]biphenyl-3-yl}-1H-1,2,3-triazole | MS (ESI) 558.2 [M + H]+. |

| Ex # | Structure | Name & Additional Characterization Data | Molecular Ion |
|---|---|---|---|
| 129 | 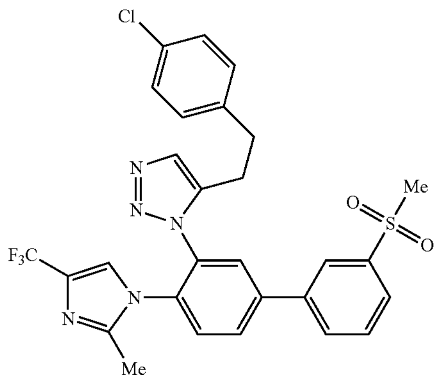 [SMILES: Cc1nc(C(F)(F)F)cn1-c1ccc(-c2cccc(S(C)(=O)=O)c2)cc1-n1nncc1CCc1ccc(Cl)cc1] | 5-[2-(4-chlorophenyl)ethyl]-1-{3'-(methylsulfonyl)-4-[2-methyl-4-(trifluoromethyl)-1H-imidazol-1-yl]biphenyl-3-yl}-1H-1,2,3-triazole | MS (ESI) 586.1 [M + H]+. |
| 130 | 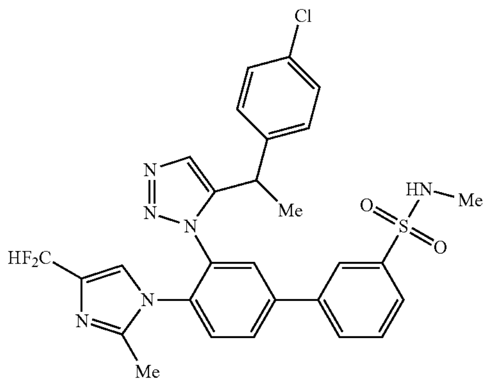 | 3'-{5-[1-(4-chlorophenyl)ethyl]-1H-1,2,3-triazol-1-yl}-4'-[4-(difluoromethyl)-2-methyl-1H-imidazol-1-yl]-N-methylbiphenyl-3-sulfonamide | MS (ESI) 583.1 [M + H]+. |
| 131 | 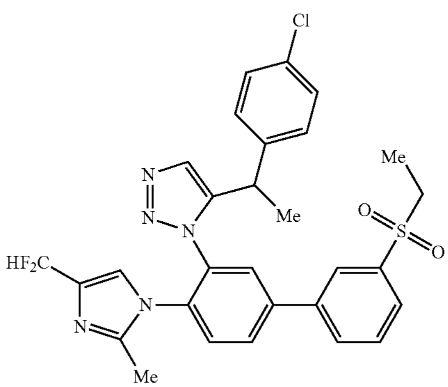 | 5-[1-(4-chlorophenyl)ethyl]-1-{4-[4-(difluoromethyl)-2-methyl-1H-imidazol-1-yl]-3'-(ethylsulfonyl)biphenyl-3-yl}-1H-1,2,3-triazole | MS (ESI) 582.1 [M + H]+. |
| 132 | 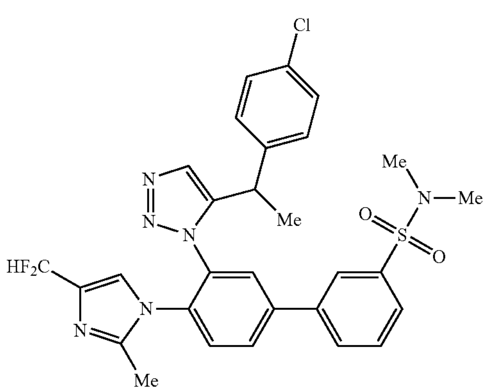 | 3'-{5-[1-(4-chlorophenyl)ethyl]-1H-1,2,3-triazol-1-yl}-4'-[4-(difluoromethyl)-2-methyl-1H-imidazol-1-yl]-N,N-dimethylbiphenyl-3-sulfonamide | MS (ESI) 597.2 [M + H]+. |

| Ex # | Structure | Name & Additional Characterization Data | Molecular Ion |
|---|---|---|---|
| 133 | 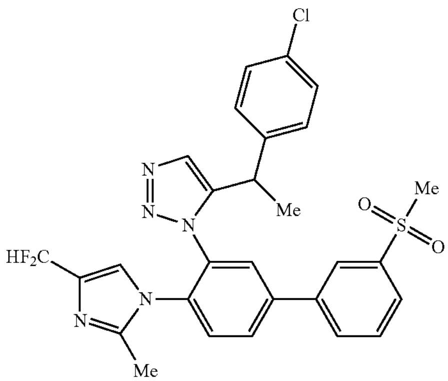 | 5-[1-(4-chlorophenyl)ethyl]-1-{4-[4-(difluoromethyl)-2-methyl-1H-imidazol-1-yl]-3'-(methylsulfonyl)biphenyl-3-yl}-1H-1,2,3-triazole | MS (ESI) 568.1 [M + H]+. |
| 134 | 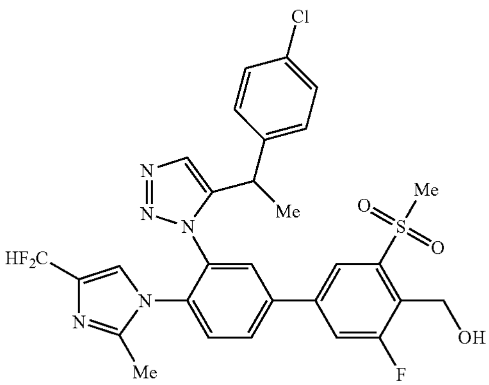 | [3'-{5-[1-(4-chlorophenyl)ethyl]-1H-1,2,3-triazol-1-yl}-4'-[4-(difluoromethyl)-2-methyl-1H-imidazol-1-yl]-3-fluoro-5-(methylsulfonyl)biphenyl-4-yl]methanol | MS (ESI) 616.1 [M + H]+. |
| 135 | 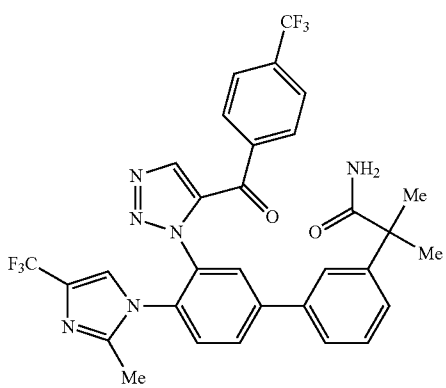 [SMILES: Cc1nc(C(F)(F)F)cn1-c1ccc(-c2cccc(C(C)(C)C(N)=O)c2)cc1-n1nncc1C(=O)c1ccc(C(F)(F)F)cc1] | 2-methyl-2-{4'-[2-methyl-4-(trifluoromethyl)-1H-imidazol-1-yl]-3'-(5-{[4-(trifluoromethyl)phenyl]carbonyl}-1H-1,2,3-triazol-1-yl)biphenyl-3-yl}propanamide | MS (ESI) 627.2 [M + H]+ |
| 136 | 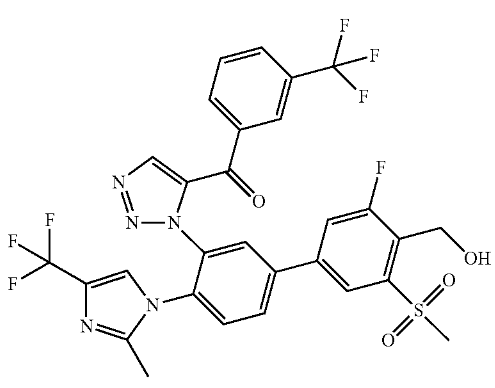 [SMILES: Cc1nc(C(F)(F)F)cn1-c1ccc(-c2cc(F)c(CO)c(S(C)(=O)=O)c2)cc1-n1nncc1C(=O)c1cccc(C(F)(F)F)c1] | (1-{3'-fluoro-4'-(hydroxymethyl)-5'-(methylsulfonyl)-4-[2-methyl-4-(trifluoromethyl)-1H-imidazol-1-yl]biphenyl-3-yl}-1H-1,2,3-triazol-5-yl)[3-(trifluoromethyl)phenyl]methanone | MS (ESI) 668.1 [M + H]+ |

| Ex # | Structure | Name & Additional Characterization Data | Molecular Ion |
|------|-----------|------------------------------------------|---------------|
| 137 | 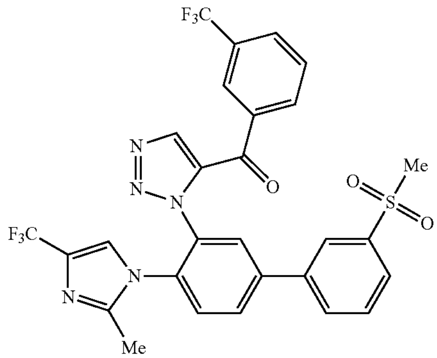 [SMILES: Cc1nc(C(F)(F)F)cn1-c1ccc(-c2cccc(S(C)(=O)=O)c2)cc1-n1nncc1C(=O)c1cccc(C(F)(F)F)c1] | (1-{3'-(methylsulfonyl)-4-[2-methyl-4-(trifluoromethyl)-1H-imidazol-1-yl]biphenyl-3-yl}-1H-1,2,3-triazol-5-yl)[3-(trifluoromethyl)phenyl]methanone | MS (ESI) 620.1 [M + H]+ |
| 138 | 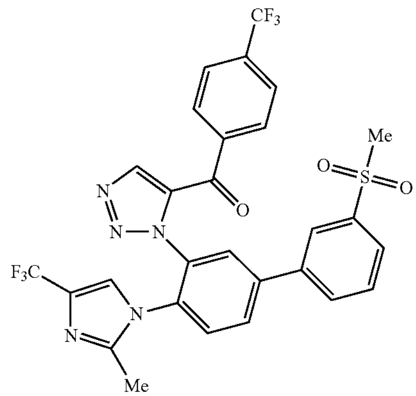 [SMILES: Cc1nc(C(F)(F)F)cn1-c1ccc(-c2cccc(S(C)(=O)=O)c2)cc1-n1nncc1C(=O)c1ccc(C(F)(F)F)cc1] | (1-{3'-(methylsulfonyl)-4-[2-methyl-4-(trifluoromethyl)-1H-imidazol-1-yl]biphenyl-3-yl}-1H-1,2,3-triazol-5-yl)[4-(trifluoromethyl)phenyl]methanone | MS (ESI) 620.3 [M + H]+ |
| 139 | 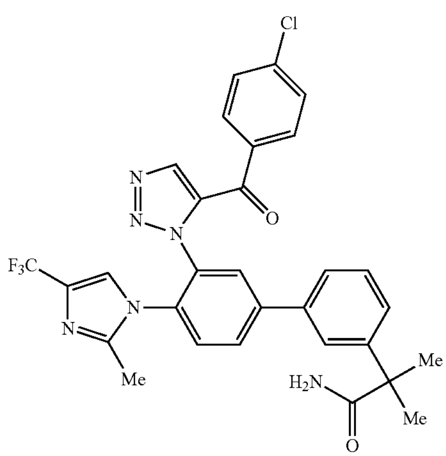 [SMILES: Cc1nc(C(F)(F)F)cn1-c1ccc(-c2cccc(C(C)(C)C(N)=O)c2)cc1-n1nncc1C(=O)c1ccc(Cl)cc1] | 2-(3'-{5-[(4-chlorophenyl)carbonyl]-1H-1,2,3-triazol-1-yl}-4'-[2-methyl-4-(trifluoromethyl)-1H-imidazol-1-yl]biphenyl-3-yl)-2-methylpropanamide | MS (ESI) 593.2 [M + H]+ |
| 140 | 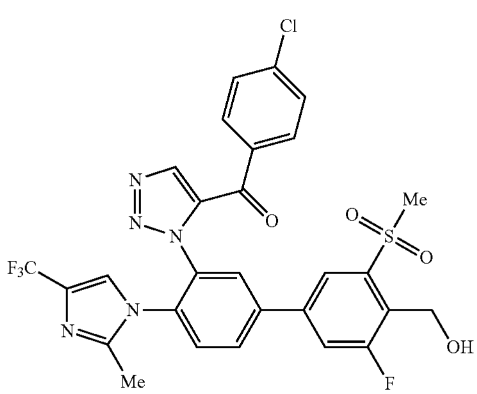 | (4-chlorophenyl)(1-{3'-fluoro-4'-(hydroxymethyl)-5'-(methylsulfonyl)-4-[2-methyl-4-(trifluoromethyl)-1H-imidazol-1-yl]biphenyl-3-yl}-1H-1,2,3-triazol-5-yl)methanone | MS (ESI) 634.1 [M + H]+ |

| Ex # | Structure | Name & Additional Characterization Data | Molecular Ion |
|---|---|---|---|
| 141 | 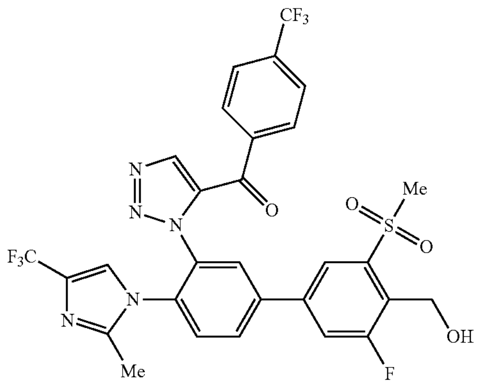 [SMILES: Cc1nc(C(F)(F)F)cn1-c1ccc(-c2cc(F)c(CO)c(S(C)(=O)=O)c2)cc1-n1nncc1C(=O)c1ccc(C(F)(F)F)cc1] | (1-{3'-fluoro-4'-(hydroxymethyl)-5'-(methylsulfonyl)-4-[2-methyl-4-(trifluoromethyl)-1H-imidazol-1-yl]biphenyl-3-yl}-1H-1,2,3-triazol-5-yl)[4-(trifluoromethyl)phenyl]methanone | MS (ESI) 668.1 [M + H]+ |
| 142 | 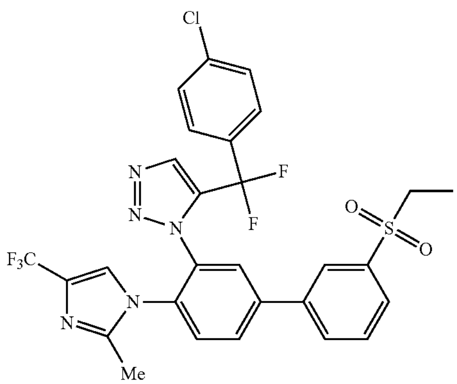 [SMILES: CCS(=O)(=O)c1cccc(-c2ccc(-n3cc(C(F)(F)F)nc3C)c(-n3nncc3C(F)(F)c3ccc(Cl)cc3)c2)c1] | 5-[(4-chlorophenyl)(difluoro)methyl]-1-{3'-(ethylsulfonyl)-4-[2-methyl-4-(trifluoromethyl)-1H-imidazol-1-yl]biphenyl-3-yl}-1H-1,2,3-triazole | MS (ESI) 622.1 [M + H]+. |
| 143 | 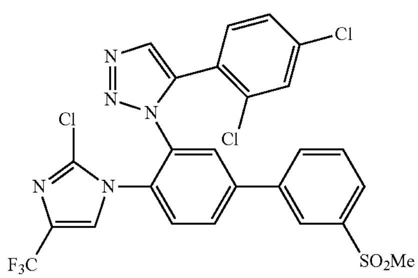 [SMILES: CS(=O)(=O)c1cccc(-c2ccc(-n3cc(C(F)(F)F)nc3Cl)c(-n3nncc3-c3ccc(Cl)cc3Cl)c2)c1] | 1-{4-[2-chloro-4-(trifluoromethyl)-1H-imidazol-1-yl]-3'-(methylsulfonyl)biphenyl-3-yl}-5-(2,4-dichlorophenyl)-1H-1,2,3-triazole | MS (ESI) 612 [M + H]+. |
| 144 | 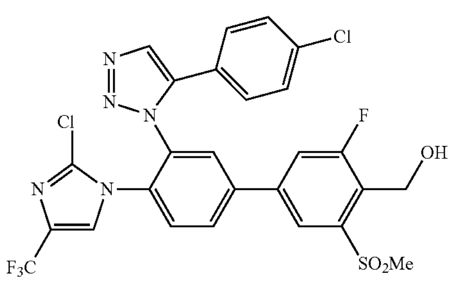 [SMILES: CS(=O)(=O)c1cc(-c2ccc(-n3cc(C(F)(F)F)nc3Cl)c(-n3nncc3-c3ccc(Cl)cc3)c2)cc(F)c1CO] | {3'-[5-(4-chlorophenyl)-1H-1,2,3-triazol-1-yl]-4'-[2-chloro-4-(trifluoromethyl)-1H-imidazol-1-yl]-3-fluoro-5-(methylsulfonyl)biphenyl-4-yl}methanol | MS (ESI) 626 [M + H]+. |

| Ex # | Structure | Name & Additional Characterization Data | Molecular Ion |
|---|---|---|---|
| 145 | 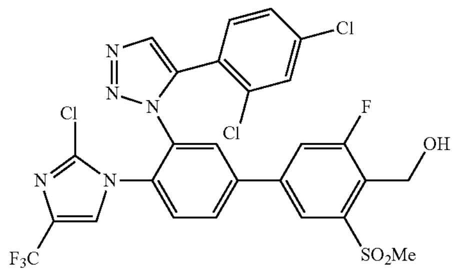 [SMILES: CS(=O)(=O)c1cc(-c2ccc(-n3cc(C(F)(F)F)nc3Cl)c(-n3nncc3-c3ccc(Cl)cc3Cl)c2)cc(F)c1CO] | {4'-[2-chloro-4-(trifluoromethyl)-1H-imidazol-1-yl]-3'-[5-(2,4-dichlorophenyl)-1H-1,2,3-triazol-1-yl]-3-fluoro-5-(methylsulfonyl)biphenyl-4-yl}methanol | MS (ESI) 660 [M + H]+. |
| 146 | 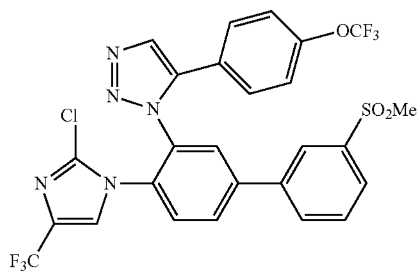 [SMILES: CS(=O)(=O)c1cccc(-c2ccc(-n3cc(C(F)(F)F)nc3Cl)c(-n3nncc3-c3ccc(OC(F)(F)F)cc3)c2)c1] | 1-{4-[2-chloro-4-(trifluoromethyl)-1H-imidazol-1-yl]-3'-(methylsulfonyl)biphenyl-3-yl}-5-{4-[(trifluoromethyl)oxy]phenyl}-1H-1,2,3-triazole | MS (ESI) 628.1 [M + H]+. |
| 147 | 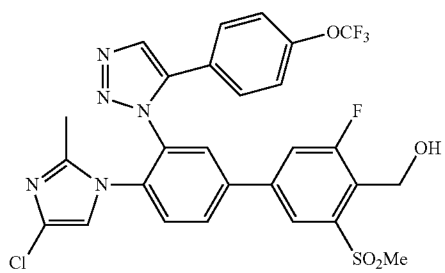 [SMILES: Cc1nc(Cl)cn1-c1ccc(-c2cc(F)c(CO)c(S(C)(=O)=O)c2)cc1-n1nncc1-c1ccc(OC(F)(F)F)cc1] | [4'-(4-chloro-2-methyl-1H-imidazol-1-yl)-3-fluoro-5-(methylsulfonyl)-3'-(5-{4-[(trifluoromethyl)oxy]phenyl}-1H-1,2,3-triazol-1-yl)biphenyl-4-yl]methanol | MS (ESI) 622.1 [M + H]+. |
| 148 | 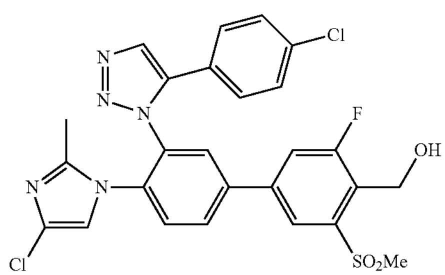 [SMILES: Cc1nc(Cl)cn1-c1ccc(-c2cc(F)c(CO)c(S(C)(=O)=O)c2)cc1-n1nncc1-c1ccc(Cl)cc1] | [4'-(4-chloro-2-methyl-1H-imidazol-1-yl)-3'-[5-(4-chlorophenyl)-1H-1,2,3-triazol-1-yl]-3-fluoro-5-(methylsulfonyl)biphenyl-4-yl]methanol | MS (ESI) 572.1 [M + H]+. |
| 149 | 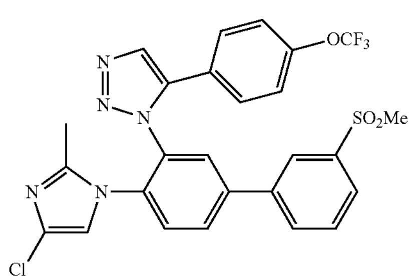 [SMILES: Cc1nc(Cl)cn1-c1ccc(-c2cccc(S(C)(=O)=O)c2)cc1-n1nncc1-c1ccc(OC(F)(F)F)cc1] | 1-[4-(4-chloro-2-methyl-1H-imidazol-1-yl)-3'-(methylsulfonyl)biphenyl-3-yl]-5-{4-[(trifluoromethyl)oxy]phenyl}-1H-1,2,3-triazole | MS (ESI) 574.1 [M + H]+. |

-continued

| Ex # | Structure | Name & Additional Characterization Data | Molecular Ion |
|---|---|---|---|
| 150 | 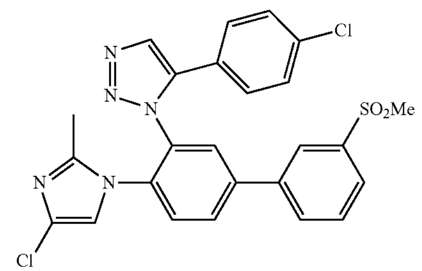 [SMILES: Cc1nc(Cl)cn1-c1ccc(-c2cccc(S(C)(=O)=O)c2)cc1-n1nncc1-c1ccc(Cl)cc1] | 1-[4-(4-chloro-2-methyl-1H-imidazol-1-yl)-3'-(methylsulfonyl)biphenyl-3-yl]-5-(4-chlorophenyl)-1H-1,2,3-triazole | MS (ESI) 524.1 [M + H]+. |
| 151 | 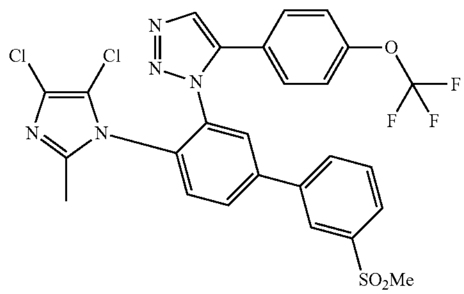 [SMILES: Cc1nc(Cl)c(Cl)n1-c1ccc(-c2cccc(S(C)(=O)=O)c2)cc1-n1nncc1-c1ccc(OC(F)(F)F)cc1] | 1-[4-(4,5-dichloro-2-methyl-1H-imidazol-1-yl)-3'-(methylsulfonyl)biphenyl-3-yl]-5-{4-[(trifluoromethyl)oxy]phenyl}-1H-1,2,3-triazole | MS (ESI) 608 [M + H]+. |
| 152 | 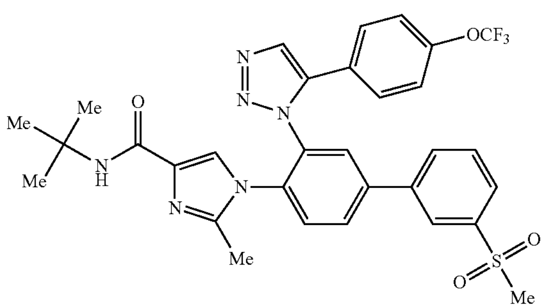 [SMILES: Cc1nc(C(=O)NC(C)(C)C)cn1-c1ccc(-c2cccc(S(C)(=O)=O)c2)cc1-n1nncc1-c1ccc(OC(F)(F)F)cc1] | N-(1,1-dimethylethyl)-2-methyl-1-[3'-(methylsulfonyl)-3-(5-{4-[(trifluoromethyl)oxy]phenyl}-1H-1,2,3-triazol-1-yl)biphenyl-4-yl]-1H-imidazole-4-carboxamide | MS (ESI) 639.3 [M + H]+. |
| 154 | 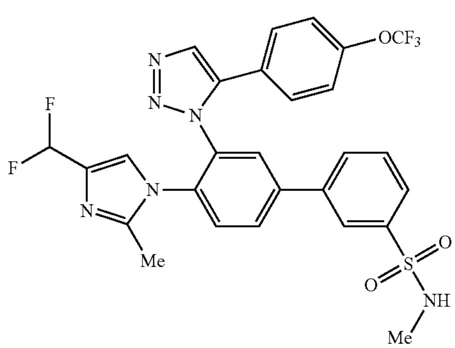 [SMILES: CNS(=O)(=O)c1cccc(-c2ccc(-n3cc(C(F)F)nc3C)c(-n3nncc3-c3ccc(OC(F)(F)F)cc3)c2)c1] | 4'-[4-(difluoromethyl)-2-methyl-1H-imidazol-1-yl]-N-methyl-3'-(5-{4-[(trifluoromethyl)oxy]phenyl}-1H-1,2,3-triazol-1-yl)biphenyl-3-sulfonamide | MS (ESI) 605.1 [M + H]+ |
| 155 | 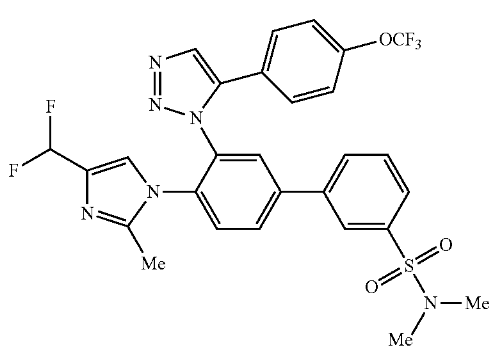 [SMILES: Cc1nc(C(F)F)cn1-c1ccc(-c2cccc(S(=O)(=O)N(C)C)c2)cc1-n1nncc1-c1ccc(OC(F)(F)F)cc1] | 4'-[4-(difluoromethyl)-2-methyl-1H-imidazol-1-yl]-N,N-dimethyl-3'-(5-{4-[(trifluoromethyl)oxy]phenyl}-1H-1,2,3-triazol-1-yl)biphenyl-3-sulfonamide | MS (ESI) 619.1 [M + H]+ |

-continued

| Ex # | Structure | Name & Additional Characterization Data | Molecular Ion |
|---|---|---|---|
| 156 | 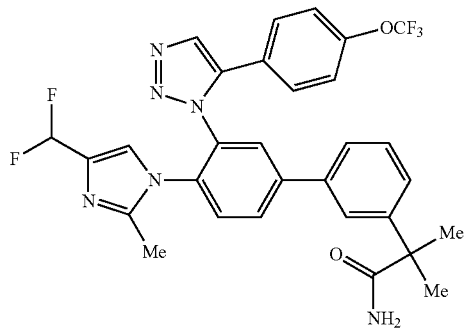 [SMILES: Cc1nc(C(F)F)cn1-c1ccc(-c2cccc(C(C)(C)C(N)=O)c2)cc1-n1nncc1-c1ccc(OC(F)(F)F)cc1] | 2-{4'-[4-(difluoromethyl)-2-methyl-1H-imidazol-1-yl]-3'-(5-{4-[(trifluoromethyl)oxy]phenyl}-1H-1,2,3-triazol-1-yl)biphenyl-3-yl}-2-methylpropanamide | MS (ESI) 597.2 [M + H]+ |
| 157 | 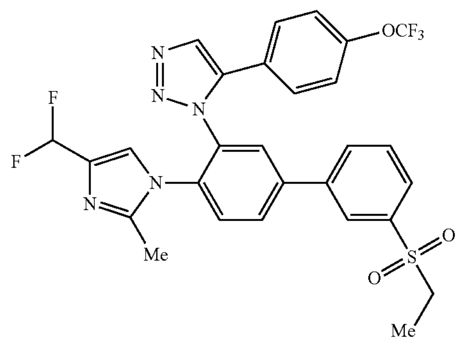 [SMILES: CCS(=O)(=O)c1cccc(-c2ccc(-n3cc(C(F)F)nc3C)c(-n3nncc3-c3ccc(OC(F)(F)F)cc3)c2)c1] | 1-{4-[4-(difluoromethyl)-2-methyl-1H-imidazol-1-yl]-3'-(ethylsulfonyl)biphenyl-3-yl}-5-{4-[(trifluoromethyl)oxy]phenyl}-1H-1,2,3-triazole | MS (ESI) 604.1 [M + H]+ |
| 158 | 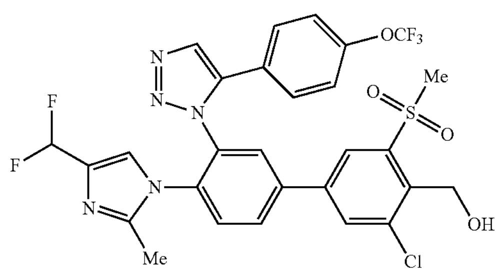 [SMILES: Cc1nc(C(F)F)cn1-c1ccc(-c2cc(Cl)c(CO)c(S(C)(=O)=O)c2)cc1-n1nncc1-c1ccc(OC(F)(F)F)cc1] | {3-chloro-4'-[4-(difluoromethyl)-2-methyl-1H-imidazol-1-yl]-5-(methylsulfonyl)-3'-(5-{4-[(trifluoromethyl)oxy]phenyl}-1H-1,2,3-triazol-1-yl)biphenyl-4-yl}methanol | MS (ESI) 654.1 [M + H]+ |
| 159 | 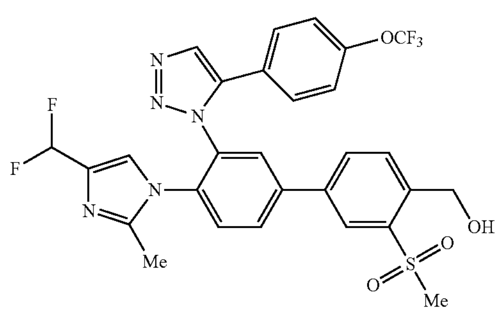 [SMILES: Cc1nc(C(F)F)cn1-c1ccc(-c2ccc(CO)c(S(C)(=O)=O)c2)cc1-n1nncc1-c1ccc(OC(F)(F)F)cc1] | {4'-[4-(difluoromethyl)-2-methyl-1H-imidazol-1-yl]-3-(methylsulfonyl)-3'-(5-{4-[(trifluoromethyl)oxy]phenyl}-1H-1,2,3-triazol-1-yl)biphenyl-4-yl}methanol | MS (ESI) 620.1 [M + H]+ |
| 162 | 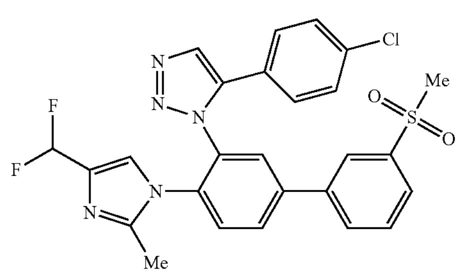 [SMILES: Cc1nc(C(F)F)cn1-c1ccc(-c2cccc(S(C)(=O)=O)c2)cc1-n1nncc1-c1ccc(Cl)cc1] | 5-(4-chlorophenyl)-1-{4-[4-(difluoromethyl)-2-methyl-1H-imidazol-1-yl]-3'-(methylsulfonyl)biphenyl-3-yl}-1H-1,2,3-triazole | MS (ESI) 540.1 [M + H]+ |

| Ex # | Structure | Name & Additional Characterization Data | Molecular Ion |
|---|---|---|---|
| 163 | 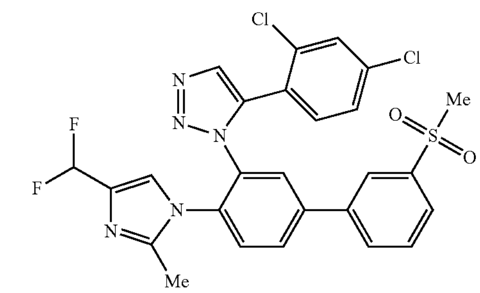 [SMILES: Cc1nc(C(F)F)cn1-c1ccc(-c2cccc(S(C)(=O)=O)c2)cc1-n1nncc1-c1ccc(Cl)cc1Cl] | 5-(2,4-dichlorophenyl)-1-{4-[4-(difluoromethyl)-2-methyl-1H-imidazol-1-yl]-3'-(methylsulfonyl)biphenyl-3-yl}-1H-1,2,3-triazole | MS (ESI) 574.1 [M + H]+ |
| 164 | 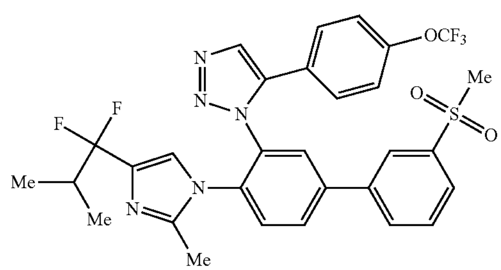 [SMILES: Cc1nc(C(F)(F)C(C)C)cn1-c1ccc(-c2cccc(S(C)(=O)=O)c2)cc1-n1nncc1-c1ccc(OC(F)(F)F)cc1] | 1-{4-[4-(1,1-difluoro-2-methylpropyl)-2-methyl-1H-imidazol-1-yl]-3'-(methylsulfonyl)biphenyl-3-yl}-5-{4-[(trifluoromethyl)oxy]phenyl}-1H-1,2,3-triazole | MS (ESI) 632.3 |
| 165 | 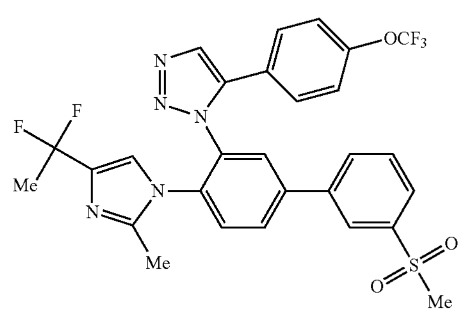 [SMILES: Cc1nc(C(C)(F)F)cn1-c1ccc(-c2cccc(S(C)(=O)=O)c2)cc1-n1nncc1-c1ccc(OC(F)(F)F)cc1] | 1-{4-[4-(1,1-difluoroethyl)-2-methyl-1H-imidazol-1-yl]-3'-(methylsulfonyl)biphenyl-3-yl}-5-{4-[(trifluoromethyl)oxy]phenyl}-1H-1,2,3-triazole | MS (ESI) 604.1 |
| 166 | 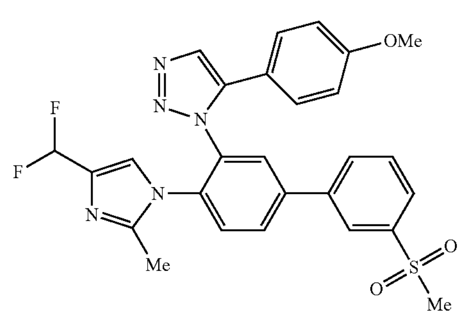 [SMILES: COc1ccc(-c2cnnn2-c2cc(-c3cccc(S(C)(=O)=O)c3)ccc2-n2cc(C(F)F)nc2C)cc1] | 1-{4-[4-(difluoromethyl)-2-methyl-1H-imidazol-1-yl]-3'-(methylsulfonyl)biphenyl-3-yl}-5-[4-(methyloxy)phenyl]-1H-1,2,3-triazole | MS (ESI) 536.1 [M + H]+ |
| 167 | 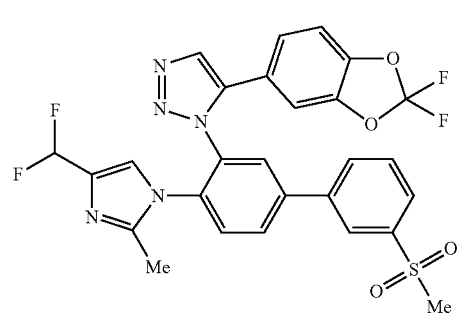 [SMILES: Cc1nc(C(F)F)cn1-c1ccc(-c2cccc(S(C)(=O)=O)c2)cc1-n1nncc1-c1ccc2c(c1)OC(F)(F)O2] | 5-(2,2-difluoro-1,3-benzodioxol-5-yl)-1-{4-[4-(difluoromethyl)-2-methyl-1H-imidazol-1-yl]-3'-(methylsulfonyl)biphenyl-3-yl}-1H-1,2,3-triazole | MS (ESI) 586.1 [M + H]+ |

| Ex # | Structure | Name & Additional Characterization Data | Molecular Ion |
|---|---|---|---|
| 168 | 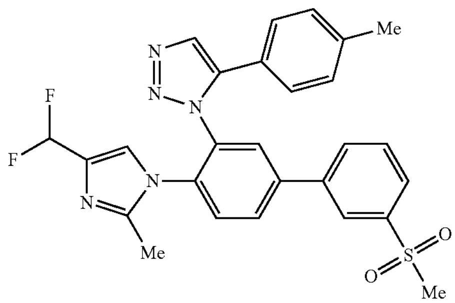 [SMILES: Cc1ccc(-c2cnnn2-c2cc(-c3cccc(S(C)(=O)=O)c3)ccc2-n2cc(C(F)F)nc2C)cc1] | 1-{4-[4-(difluoromethyl)-2-methyl-1H-imidazol-1-yl]-3'-(methylsulfonyl)biphenyl-3-yl}-5-(4-methylphenyl)-1H-1,2,3-triazole | MS (ESI) 520.2 [M + H]+ |
| 169 | 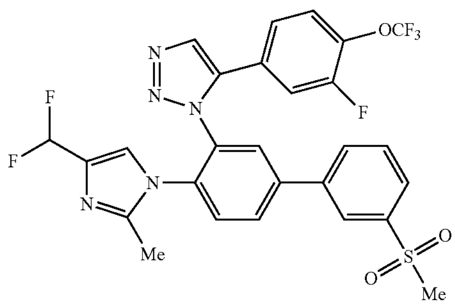 [SMILES: Cc1nc(C(F)F)cn1-c1ccc(-c2cccc(S(C)(=O)=O)c2)cc1-n1nncc1-c1ccc(OC(F)(F)F)c(F)c1] | 1-{4-[4-(difluoromethyl)-2-methyl-1H-imidazol-1-yl]-3'-(methylsulfonyl)biphenyl-3-yl}-5-{3-fluoro-4-[(trifluoromethyl)oxy]phenyl}-1H-1,2,3-triazole | MS (ESI) 608.1 [M + H]+ |
| 170 | 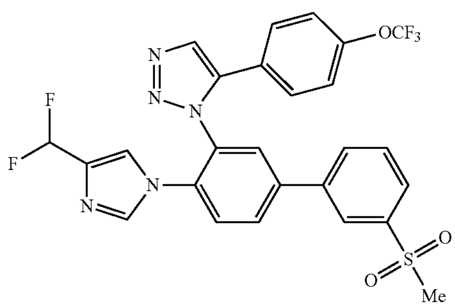 [SMILES: CS(=O)(=O)c1cccc(-c2ccc(-n3cnc(C(F)F)c3)c(-n3nncc3-c3ccc(OC(F)(F)F)cc3)c2)c1] | 1-{4-[4-(difluoromethyl)-1H-imidazol-1-yl]-3'-(methylsulfonyl)biphenyl-3-yl}-5-{4-[(trifluoromethyl)oxy]phenyl}-1H-1,2,3-triazole | MS (ESI) 576.1 [M + H]+ |
| 171 | 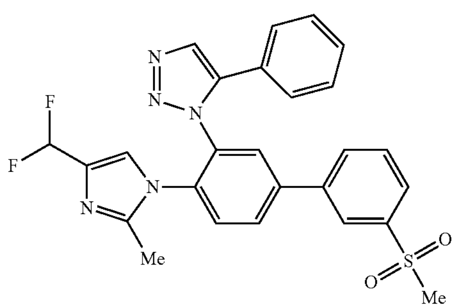 [SMILES: Cc1nc(C(F)F)cn1-c1ccc(-c2cccc(S(C)(=O)=O)c2)cc1-n1nncc1-c1ccccc1] | 1-{4-[4-(difluoromethyl)-2-methyl-1H-imidazol-1-yl]-3'-(methylsulfonyl)biphenyl-3-yl}-5-phenyl-1H-1,2,3-triazole | MS (ESI) 506.1 [M + H]+ |
| 172 | 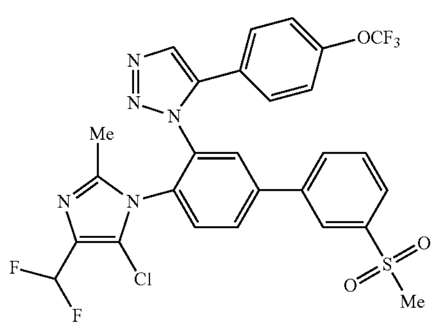 [SMILES: Cc1nc(C(F)F)c(Cl)n1-c1ccc(-c2cccc(S(C)(=O)=O)c2)cc1-n1nncc1-c1ccc(OC(F)(F)F)cc1] | 1-{4-[5-chloro-4-(difluoromethyl)-2-methyl-1H-imidazol-1-yl]-3'-(methylsulfonyl)biphenyl-3-yl}-5-{4-[(trifluoromethyl)oxy]phenyl}-1H-1,2,3-triazole | MS (ESI) 624.1 [M + H]+ |

-continued

| Ex # | Structure | Name & Additional Characterization Data | Molecular Ion |
|---|---|---|---|
| 173 | 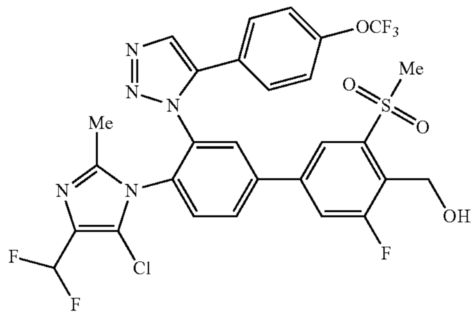 [SMILES: Cc1nc(C(F)F)c(Cl)n1-c1ccc(-c2cc(F)c(CO)c(S(C)(=O)=O)c2)cc1-n1nncc1-c1ccc(OC(F)(F)F)cc1] | {4'-[5-chloro-4-(difluoromethyl)-2-methyl-1H-imidazol-1-yl]-3-fluoro-5-(methylsulfonyl)-3'-(5-{4-[(trifluoromethyl)oxy]phenyl}-1H-1,2,3-triazol-1-yl)biphenyl-4-yl}methanol | MS (ESI) 672.1 [M + H]+ |
| 174 | 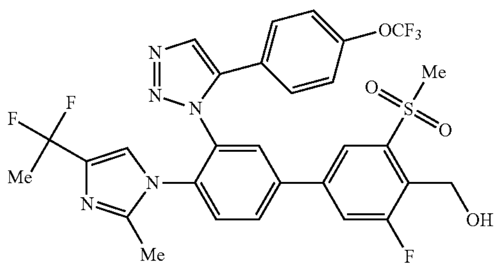 [SMILES: Cc1nc(C(C)(F)F)cn1-c1ccc(-c2cc(F)c(CO)c(S(C)(=O)=O)c2)cc1-n1nncc1-c1ccc(OC(F)(F)F)cc1] | {4'-[4-(1,1-difluoroethyl)-2-methyl-1H-imidazol-1-yl]-3-fluoro-5-(methylsulfonyl)-3'-(5-{4-[(trifluoromethyl)oxy]phenyl}-1H-1,2,3-triazol-1-yl)biphenyl-4-yl}methanol | MS (ESI) 652.1 [M + H]+ |
| 175 | 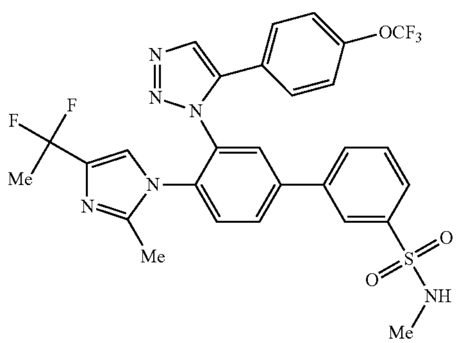 [SMILES: CNS(=O)(=O)c1cccc(-c2ccc(-n3cc(C(C)(F)F)nc3C)c(-n3nncc3-c3ccc(OC(F)(F)F)cc3)c2)c1] | 4'-[4-(1,1-difluoroethyl)-2-methyl-1H-imidazol-1-yl]-N-methyl-3'-(5-{4-[(trifluoromethyl)oxy]phenyl}-1H-1,2,3-triazol-1-yl)biphenyl-3-sulfonamide | MS (ESI) 619.1 [M + H]+ |
| 176 | 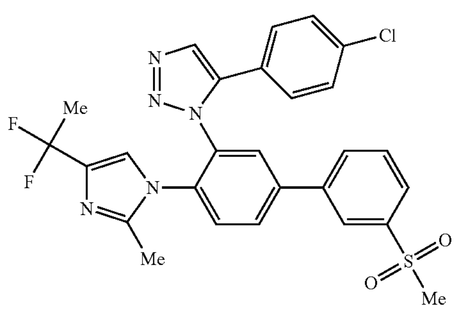 [SMILES: Cc1nc(C(C)(F)F)cn1-c1ccc(-c2cccc(S(C)(=O)=O)c2)cc1-n1nncc1-c1ccc(Cl)cc1] | 5-(4-chlorophenyl)-1-{4-[4-(1,1-difluoroethyl)-2-methyl-1H-imidazol-1-yl]-3'-(methylsulfonyl)biphenyl-3-yl}-1H-1,2,3-triazole | MS (ESI) 554.1 [M + H]+ |
| 177 | 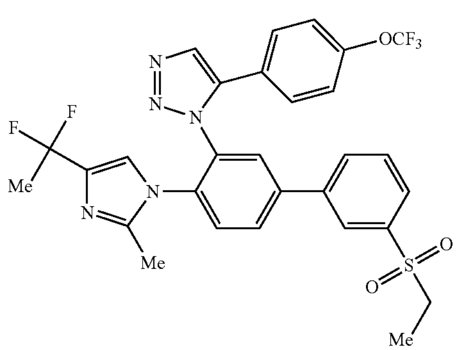 [SMILES: CCS(=O)(=O)c1cccc(-c2ccc(-n3cc(C(C)(F)F)nc3C)c(-n3nncc3-c3ccc(OC(F)(F)F)cc3)c2)c1] | 1-{4-[4-(1,1-difluoroethyl)-2-methyl-1H-imidazol-1-yl]-3'-(ethylsulfonyl)biphenyl-3-yl}-5-{4-[(trifluoromethyl)oxy]phenyl}-1H-1,2,3-triazole | MS (ESI) 618.2 [M + H]+ |

| Ex # | Structure | Name & Additional Characterization Data | Molecular Ion |
|---|---|---|---|
| 178 | 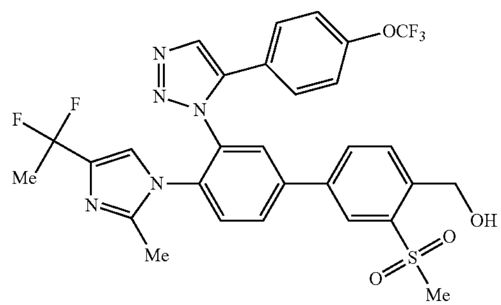 [SMILES: Cc1nc(C(C)(F)F)cn1-c1ccc(-c2ccc(CO)c(S(C)(=O)=O)c2)cc1-n1nncc1-c1ccc(OC(F)(F)F)cc1] | {4'-[4-(1,1-difluoroethyl)-2-methyl-1H-imidazol-1-yl]-3-(methylsulfonyl)-3'-(5-{4-[(trifluoromethyl)oxy]phenyl}-1H-1,2,3-triazol-1-yl)biphenyl-4-yl}methanol | MS (ESI) 634.1 [M + H]+ |
| 179 | 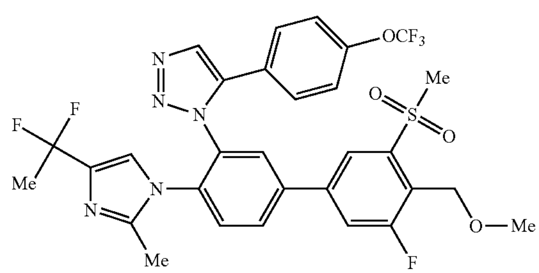 [SMILES: COCc1c(F)cc(-c2ccc(-n3cc(C(C)(F)F)nc3C)c(-n3nncc3-c3ccc(OC(F)(F)F)cc3)c2)cc1S(C)(=O)=O] | 1-{4-[4-(1,1-difluoroethyl)-2-methyl-1H-imidazol-1-yl]-3'-fluoro-4'-[(methyloxy)methyl]-5'-(methylsulfonyl)biphenyl-3-yl}-5-{4-[(trifluoromethyl)oxy]phenyl}-1H-1,2,3-triazole | MS (ESI) 666.2 [M + H]+ |
| 180 | 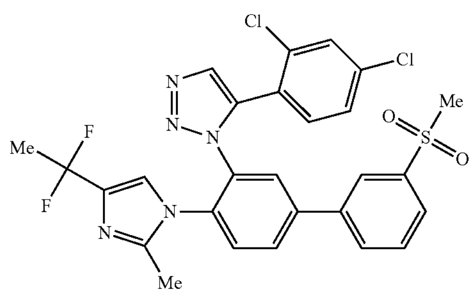 [SMILES: Cc1nc(C(C)(F)F)cn1-c1ccc(-c2cccc(S(C)(=O)=O)c2)cc1-n1nncc1-c1ccc(Cl)cc1Cl] | 5-(2,4-dichlorophenyl)-1-{4-[4-(1,1-difluoroethyl)-2-methyl-1H-imidazol-1-yl]-3'-(methylsulfonyl)biphenyl-3-yl}-1H-1,2,3-triazole | MS (ESI) 588.1 [M + H]+ |
| 181 | 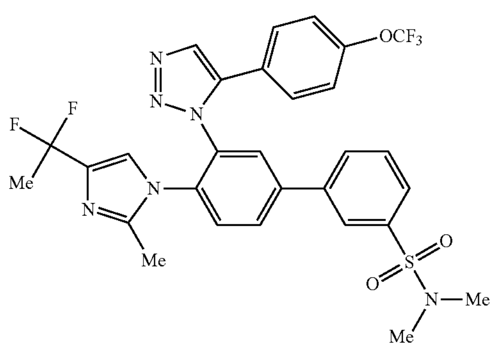 [SMILES: Cc1nc(C(C)(F)F)cn1-c1ccc(-c2cccc(S(=O)(=O)N(C)C)c2)cc1-n1nncc1-c1ccc(OC(F)(F)F)cc1] | 4'-[4-(1,1-difluoroethyl)-2-methyl-1H-imidazol-1-yl]-N,N-dimethyl-3'-(5-{4-[(trifluoromethyl)oxy]phenyl}-1H-1,2,3-triazol-1-yl)biphenyl-3-sulfonamide | MS (ESI) 633.2 [M + H]+ |
| 182 | 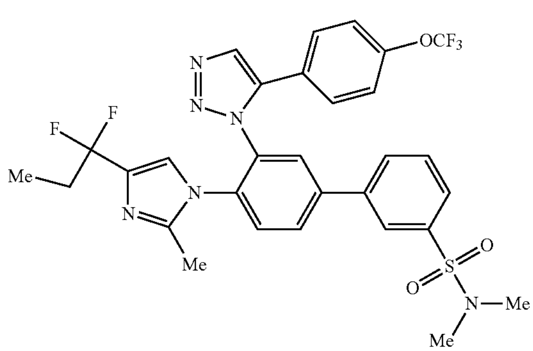 [SMILES: CCC(F)(F)c1cn(-c2ccc(-c3cccc(S(=O)(=O)N(C)C)c3)cc2-n2nncc2-c2ccc(OC(F)(F)F)cc2)c(C)n1] | 4'-[4-(1,1-difluoropropyl)-2-methyl-1H-imidazol-1-yl]-N,N-dimethyl-3'-(5-{4-[(trifluoromethyl)oxy]phenyl}-1H-1,2,3-triazol-1-yl)biphenyl-3-sulfonamide | MS (ESI) 647.2 [M + H]+ |

| Ex # | Structure | Name & Additional Characterization Data | Molecular Ion |
|---|---|---|---|
| 183 | 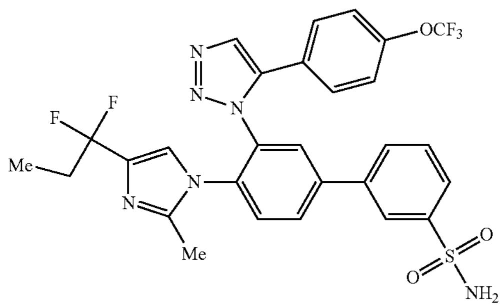 [SMILES: CCC(F)(F)c1cn(-c2ccc(-c3cccc(S(N)(=O)=O)c3)cc2-n2nncc2-c2ccc(OC(F)(F)F)cc2)c(C)n1] | 4'-[4-(1,1-difluoropropyl)-2-methyl-1H-imidazol-1-yl]-3'-(5-{4-[(trifluoromethyl)oxy]phenyl}-1H-1,2,3-triazol-1-yl)biphenyl-3-sulfonamide | MS (ESI) 619.1 [M + H]+ |
| 184 | 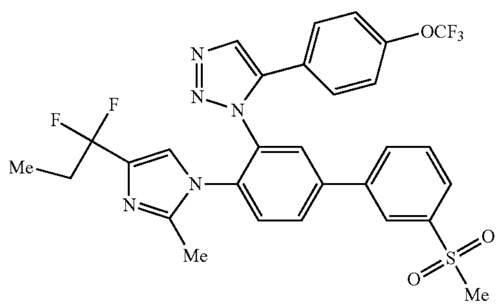 [SMILES: CCC(F)(F)c1cn(-c2ccc(-c3cccc(S(C)(=O)=O)c3)cc2-n2nncc2-c2ccc(OC(F)(F)F)cc2)c(C)n1] | 1-{4-[4-(1,1-difluoropropyl)-2-methyl-1H-imidazol-1-yl]-3'-(methylsulfonyl)biphenyl-3-yl}-5-{4-[(trifluoromethyl)oxy]phenyl}-1H-1,2,3-triazole | MS (ESI) 618.2 [M + H]+ |
| 185 | 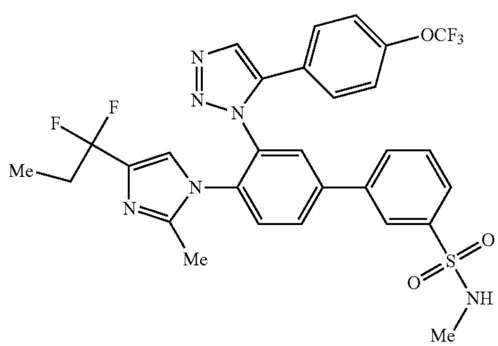 [SMILES: CCC(F)(F)c1cn(-c2ccc(-c3cccc(S(=O)(=O)NC)c3)cc2-n2nncc2-c2ccc(OC(F)(F)F)cc2)c(C)n1] | 4'-[4-(1,1-difluoropropyl)-2-methyl-1H-imidazol-1-yl]-N-methyl-3'-(5-{4-[(trifluoromethyl)oxy]phenyl}-1H-1,2,3-triazol-1-yl)biphenyl-3-sulfonamide | MS (ESI) 633.2 [M + H]+ |
| 186 | 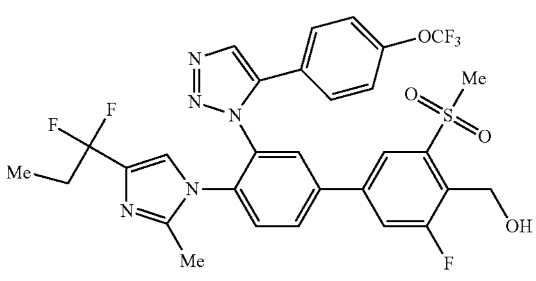 [SMILES: CCC(F)(F)c1cn(-c2ccc(-c3cc(F)c(CO)c(S(C)(=O)=O)c3)cc2-n2nncc2-c2ccc(OC(F)(F)F)cc2)c(C)n1] | {4'-[4-(1,1-difluoropropyl)-2-methyl-1H-imidazol-1-yl]-3-fluoro-5-(methylsulfonyl)-3'-(5-{4-[(trifluoromethyl)oxy]phenyl}-1H-1,2,3-txiazol-1-yl)biphenyl-4-yl}methanol | MS (ESI) 666.2 [M + H]+ |
| 187 | 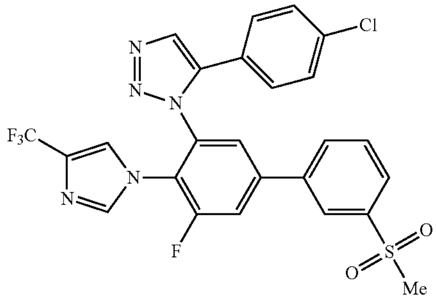 [SMILES: CS(=O)(=O)c1cccc(-c2cc(F)c(-n3cnc(C(F)(F)F)c3)c(-n3nncc3-c3ccc(Cl)cc3)c2)c1] | 5-(4-chlorophenyl)-1-{5-fluoro-3'-(methylsulfonyl)-4-[4-(trifluoromethyl)-1H-imidazol-1-yl]biphenyl-3-yl}-1H-1,2,3-triazole | MS (ESI) 562.1 [M + H]+. |

| Ex # | Structure | Name & Additional Characterization Data | Molecular Ion |
|---|---|---|---|
| 188 | 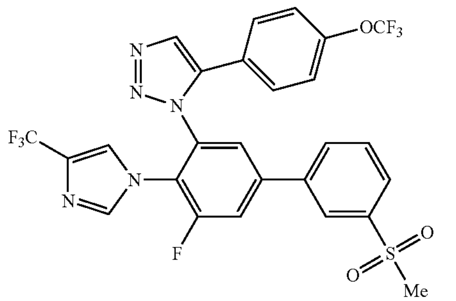 | 1-{5-fluoro-3'-(methylsulfonyl)-4-[4-(trifluoromethyl)-1H-imidazol-1-yl]biphenyl-3-yl}-5-{4-[(trifluoromethyl)oxy]phenyl}-1H-1,2,3-triazole | MS (ESI) 612.1 [M + H]+. |
| 189 | 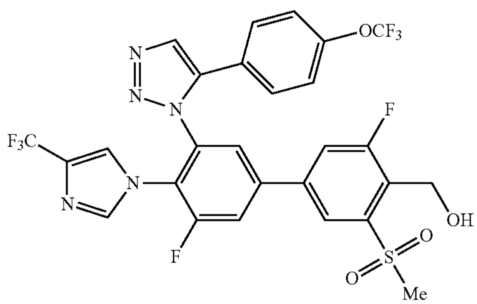 [SMILES: CS(=O)(=O)c1cc(-c2cc(F)c(-n3cnc(C(F)(F)F)c3)c(-n3nncc3-c3ccc(OC(F)(F)F)cc3)c2)cc(F)c1CO] | [3,3'-difluoro-5-(methylsulfonyl)-4'-[4-(trifluoromethyl)-1H-imidazol-1-yl]-5'-(5-{4-[(trifluoromethyl)oxy]phenyl}-1H-1,2,3-triazol-1-yl)biphenyl-4-yl]methanol | MS (ESI) 660.1 [M + H]+. |
| 190 | 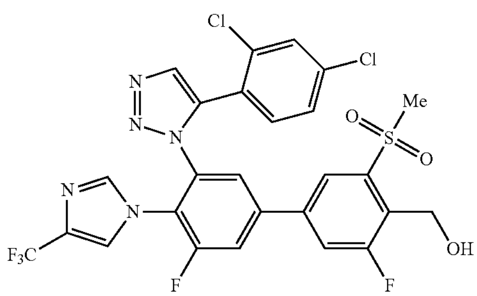 [SMILES: CS(=O)(=O)c1cc(-c2cc(F)c(-n3cnc(C(F)(F)F)c3)c(-n3nncc3-c3ccc(Cl)cc3Cl)c2)cc(F)c1CO] | {3'-[5-(2,4-dichlorophenyl)-1H-1,2,3-triazol-1-yl]-3,5'-difluoro-5-(methylsulfonyl)-4'-[4-(trifluoromethyl)-1H-imidazol-1-yl]biphenyl-4-yl}methanol | MS (ESI) 644 [M + H]+. |
| 191 | 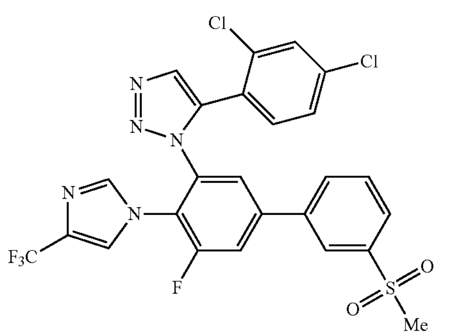 [SMILES: CS(=O)(=O)c1cccc(-c2cc(F)c(-n3cnc(C(F)(F)F)c3)c(-n3nncc3-c3ccc(Cl)cc3Cl)c2)c1] | 5-(2,4-dichlorophenyl)-1-{5-fluoro-3'-(methylsulfonyl)-4-[4-(trifluoromethyl)-1H-imidazol-1-yl]biphenyl-3-yl}-1H-1,2,3-triazole | MS (ESI) 596 [M + H]+. |
| 192 | 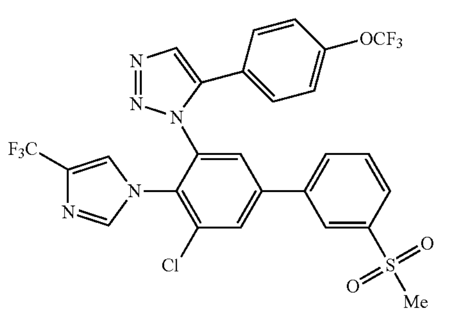 [SMILES: CS(=O)(=O)c1cccc(-c2cc(Cl)c(-n3cnc(C(F)(F)F)c3)c(-n3nncc3-c3ccc(OC(F)(F)F)cc3)c2)c1] | 1-{5-chloro-3'-(methylsulfonyl)-4-[4-(trifluoromethyl)-1H-imidazol-1-yl]biphenyl-3-yl}-5-{4-[(trifluoromethyl)oxy]phenyl}-1H-1,2,3-triazole | MS (ESI) 628.1 [M + H]+. |

| Ex # | Structure | Name & Additional Characterization Data | Molecular Ion |
|---|---|---|---|
| 193 | 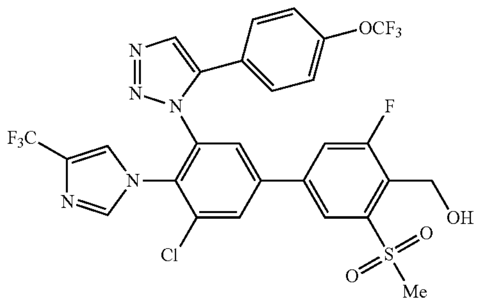 [SMILES: CS(=O)(=O)c1cc(-c2cc(Cl)c(-n3cnc(C(F)(F)F)c3)c(-n3nncc3-c3ccc(OC(F)(F)F)cc3)c2)cc(F)c1CO] | [3'-chloro-3-fluoro-5-(methylsulfonyl)-4'-[4-(trifluoromethyl)-1H-imidazol-1-yl]-5'-(5-{4-[(trifluoromethyl)oxy]phenyl}-1H-1,2,3-triazol-1-yl)biphenyl-4-yl]methanol | MS (ESI) 676.1 [M + H]+. |
| 195 | 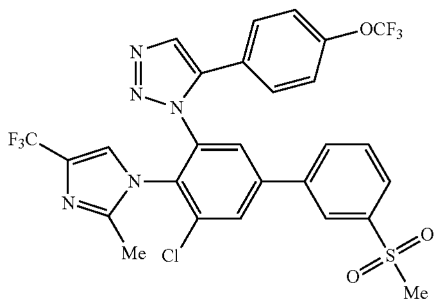 [SMILES: Cc1nc(C(F)(F)F)cn1-c1c(Cl)cc(-c2cccc(S(C)(=O)=O)c2)cc1-n1nncc1-c1ccc(OC(F)(F)F)cc1] | 1-{5-chloro-3'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole | MS (ESI) 642.1 [M + H]+ |
| 196 | 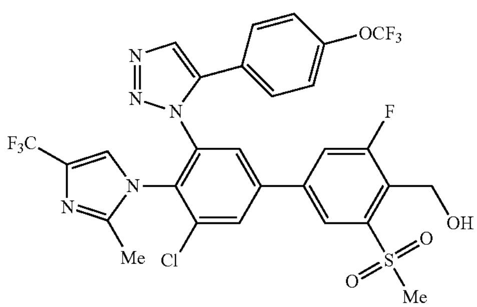 [SMILES: Cc1nc(C(F)(F)F)cn1-c1c(Cl)cc(-c2cc(F)c(CO)c(S(C)(=O)=O)c2)cc1-n1nncc1-c1ccc(OC(F)(F)F)cc1] | [3'-chloro-3-fluoro-5-(methylsulfonyl)-4'-[2-methyl-4-(trifluoromethyl)-1H-imidazol-1-yl]-5'-(5-{4-[(trifluoromethyl)oxy]phenyl}-1H-1,2,3-triazol-1-yl)biphenyl-4-yl]methanol | MS (ESI) 690.1 [M + H]+. |
| 197 | 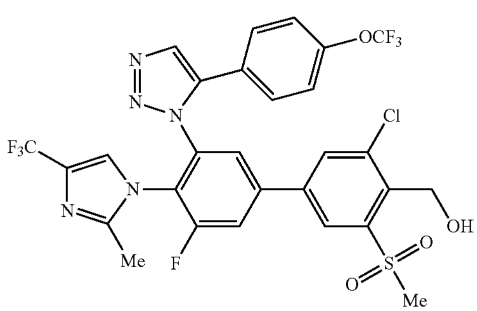 [SMILES: Cc1nc(C(F)(F)F)cn1-c1c(F)cc(-c2cc(Cl)c(CO)c(S(C)(=O)=O)c2)cc1-n1nncc1-c1ccc(OC(F)(F)F)cc1] | [3-chloro-3'-fluoro-5-(methylsulfonyl)-4'-[2-methyl-4-(trifluoromethyl)-1H-imidazol-1-yl]-5'-(5-{4-[(trifluoromethyl)oxy]phenyl}-1H-1,2,3-triazol-1-yl)biphenyl-4-yl]methanol | MS (ESI) 690.1 [M + H]+ |
| 198 | 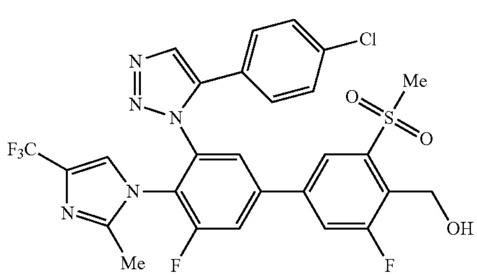 [SMILES: Cc1nc(C(F)(F)F)cn1-c1c(F)cc(-c2cc(F)c(CO)c(S(C)(=O)=O)c2)cc1-n1nncc1-c1ccc(Cl)cc1] | {3'-[5-(4-chlorophenyl)-1H-1,2,3-triazol-1-yl]-3,5'-difluoro-5-(methylsulfonyl)-4'-[2-methyl-4-(trifluoromethyl)-1H-imidazol-1-yl]biphenyl-4-yl}methanol | MS (ESI) 624.1 [M + H]+ |

| Ex # | Structure | Name & Additional Characterization Data | Molecular Ion |
|---|---|---|---|
| 199 | 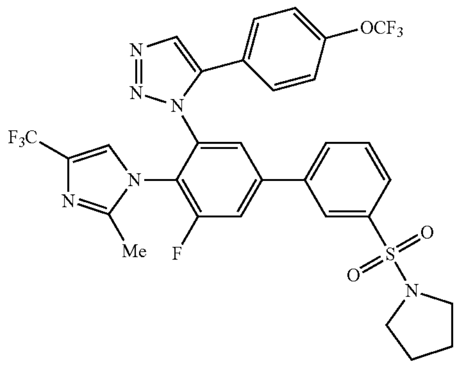 [SMILES: Cc1nc(C(F)(F)F)cn1-c1c(F)cc(-c2cccc(S(=O)(=O)N3CCCC3)c2)cc1-n1nncc1-c1ccc(OC(F)(F)F)cc1] | 1-{5-fluoro-4-[2-methyl-4-(trifluoromethyl)-1H-imidazol-1-yl]-3'-(pyrrolidin-1-ylsulfonyl)biphenyl-3-yl}-5-{4-[(trifluoromethyl)oxy]phenyl}-1H-1,2,3-triazole | MS (ESI) 681.1 [M + H]+ |
| 200 | 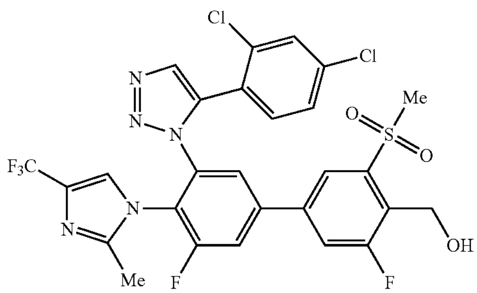 [SMILES: Cc1nc(C(F)(F)F)cn1-c1c(F)cc(-c2cc(F)c(CO)c(S(C)(=O)=O)c2)cc1-n1nncc1-c1ccc(Cl)cc1Cl] | {3'-[5-(2,4-dichlorophenyl)-1H-1,2,3-triazol-1-yl]-3,5'-difluoro-5-(methylsulfonyl)-4'-[2-methyl-4-(trifluoromethyl)-1H-imidazol-1-yl]biphenyl-4-yl}methanol | MS (ESI) 658 [M + H]+ |
| 201 | 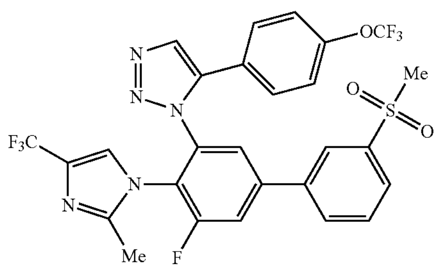 [SMILES: Cc1nc(C(F)(F)F)cn1-c1c(F)cc(-c2cccc(S(C)(=O)=O)c2)cc1-n1nncc1-c1ccc(OC(F)(F)F)cc1] | 1-{5-fluoro-3'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole | MS (ESI) 626.1 [M + H]+. |
| 202 | 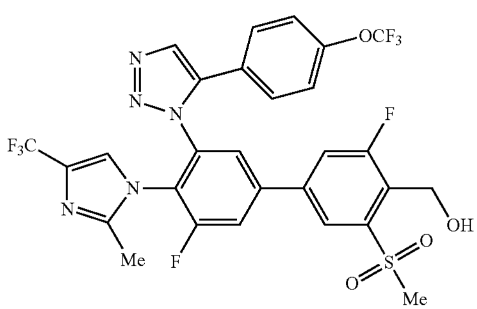 | [3,3'-difluoro-5-(methylsulfonyl)-4'-[2-methyl-4-(trifluoromethyl)-1H-imidazol-1-yl]-5'-(5-{4-[(trifluoromethyl)oxy]phenyl}-1H-1,2,3-triazol-1-yl)biphenyl-4-yl]methanol | MS (ESI) 674.1 [M + H]+. |
| 203 | 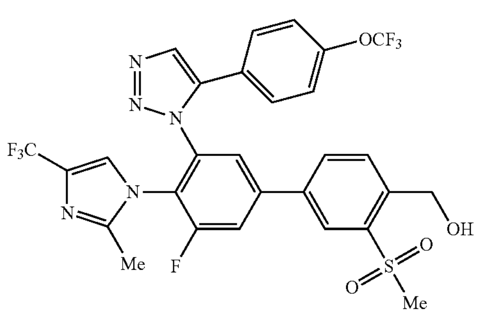 [SMILES: Cc1nc(C(F)(F)F)cn1-c1c(F)cc(-c2ccc(CO)c(S(C)(=O)=O)c2)cc1-n1nncc1-c1ccc(OC(F)(F)F)cc1] | [3'-fluoro-3-(methylsulfonyl)-4'-[2-methyl-4-(trifluoromethyl)-1H-imidazol-1-yl]-5'-(5-{4-[(trifluoromethyl)oxy]phenyl}-1H-1,2,3-triazol-1-yl)biphenyl-4-yl]methanol | MS (ESI) 656.1 [M + H]+ |

-continued

| Ex # | Structure | Name & Additional Characterization Data | Molecular Ion |
|---|---|---|---|
| 204 | 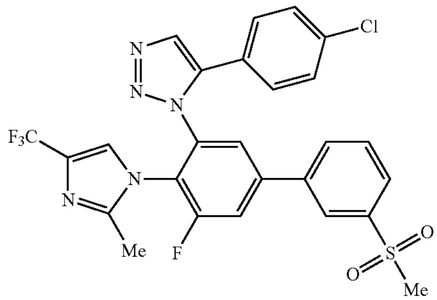 [SMILES: Cc1nc(C(F)(F)F)cn1-c1c(F)cc(-c2cccc(S(C)(=O)=O)c2)cc1-n1nncc1-c1ccc(Cl)cc1] | 5-(4-chlorophenyl)-1-{5-fluoro-3'-(methylsulfonyl)-4-[2-methyl-4-(trifluoromethyl)-1H-imidazol-1-yl]biphenyl-3-yl}-1H-1,2,3-triazole | MS (ESI) 576.1 [M + H]+ |
| 205 | 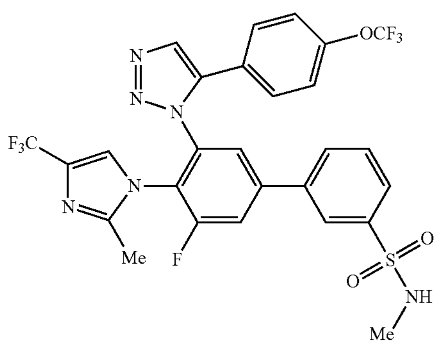 [SMILES: CNS(=O)(=O)c1cccc(-c2cc(F)c(-n3cc(C(F)(F)F)nc3C)c(-n3nncc3-c3ccc(OC(F)(F)F)cc3)c2)c1] | 3'-fluoro-N-methyl-4'-[2-methyl-4-(trifluoromethyl)-1H-imidazol-1-yl]-5'-(5-{4-[(trifluoromethyl)oxy]phenyl}-1H-1,2,3-triazol-1-yl)biphenyl-3-sulfonamide | MS (ESI) 641.1 [M + H]+. |
| 206 | 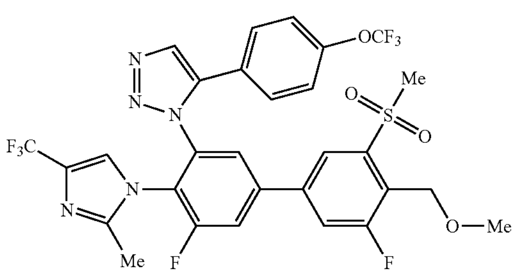 [SMILES: COCc1c(F)cc(-c2cc(F)c(-n3cc(C(F)(F)F)nc3C)c(-n3nncc3-c3ccc(OC(F)(F)F)cc3)c2)cc1S(C)(=O)=O] | 1-{3',5-difluoro-4'-[(methyloxy)methyl]-5'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole | MS (ESI) 688.1 [M + H]+. |
| 207 | 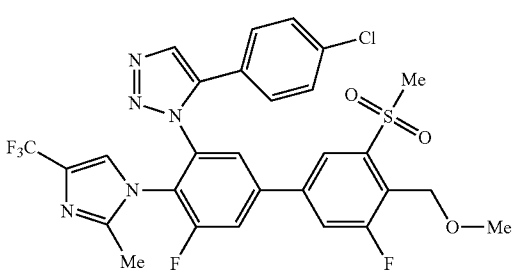 [SMILES: COCc1c(F)cc(-c2cc(F)c(-n3cc(C(F)(F)F)nc3C)c(-n3nncc3-c3ccc(Cl)cc3)c2)cc1S(C)(=O)=O] | 5-(4-chlorophenyl)-1-{3',5-difluoro-4'-[(methyloxy)methyl]-5'-(methylsulfonyl)-4-[2-methyl-4-(trifluoromethyl)-1H-imidazol-1-yl]biphenyl-3-yl}-1H-1,2,3-triazole | MS (ESI) 638.1 [M + H]+ |

| Ex # | Structure | Name & Additional Characterization Data | Molecular Ion |
|---|---|---|---|
| 208 | 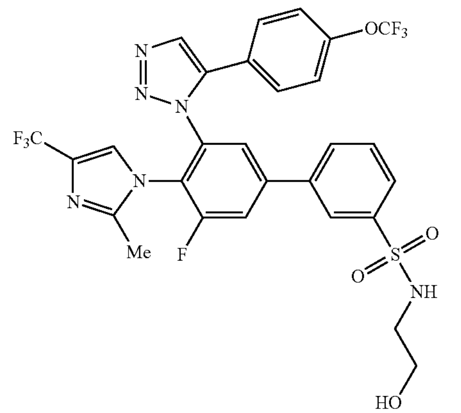 [SMILES: Cc1nc(C(F)(F)F)cn1-c1c(F)cc(-c2cccc(S(=O)(=O)NCCO)c2)cc1-n1nncc1-c1ccc(OC(F)(F)F)cc1] | 3'-fluoro-N-(2-hydroxyethyl)-4'-[2-methyl-4-(trifluoromethyl)-1H-imidazol-1-yl]-5'-(5-{4-[(trifluoromethyl)oxy]phenyl}-1H-1,2,3-triazol-1-yl)biphenyl-3-sulfonamide | MS (ESI) 671.1 [M + H]+. |
| 209 | 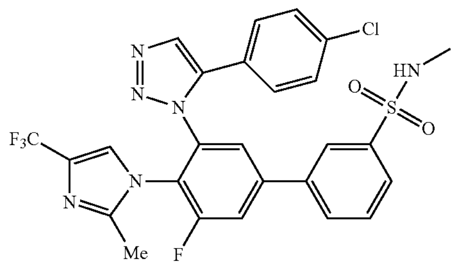 [SMILES: CNS(=O)(=O)c1cccc(-c2cc(F)c(-n3cc(C(F)(F)F)nc3C)c(-n3nncc3-c3ccc(Cl)cc3)c2)c1] | 3'-[5-(4-chlorophenyl)-1H-1,2,3-triazol-1-yl]-5'-fluoro-N-methyl-4'-[2-methyl-4-(trifluoromethyl)-1H-imidazol-1-yl]biphenyl-3-sulfonamide | MS (ESI) 591.1 [M + H]+. |
| 210 | 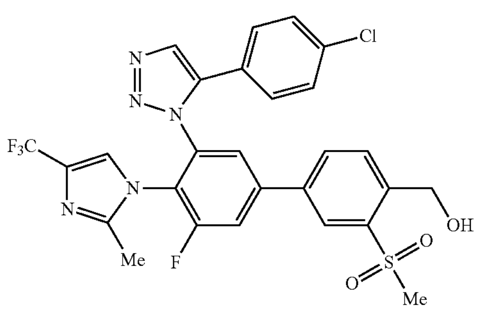 [SMILES: Cc1nc(C(F)(F)F)cn1-c1c(F)cc(-c2ccc(CO)c(S(C)(=O)=O)c2)cc1-n1nncc1-c1ccc(Cl)cc1] | {3'-[5-(4-chlorophenyl)-1H-1,2,3-triazol-1-yl]-5'-fluoro-3-(methylsulfonyl)-4'-[2-methyl-4-(trifluoromethyl)-1H-imidazol-1-yl]biphenyl-4-yl}methanol | MS (ESI) 606.1 [M + H]+. |
| 211 | 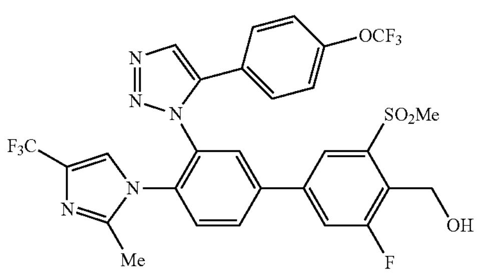 | (3-fluoro-4'-(2-methyl-4-(trifluoromethyl)-1H-imidazol-1-yl)-5-(methylsulfonyl)-3'-(5-(4-(trifluoromethoxy)phenyl)-1H-1,2,3-triazol-1-yl)-[1,1'-biphenyl]-4-yl)methanol | |
| 212 | 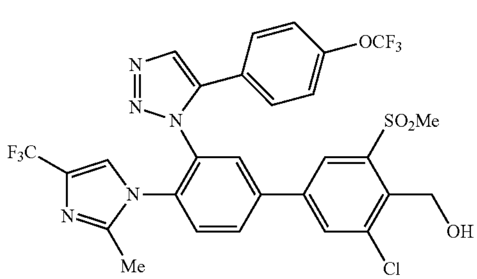 [SMILES: Cc1nc(C(F)(F)F)cn1-c1ccc(-c2cc(F)c(CO)c(S(C)(=O)=O)c2)cc1-n1nncc1-c1ccc(OC(F)(F)F)cc1] | (3-chloro-4'-(2-methyl-4-(trifluoromethyl)-1H-imidazol-1-yl)-5-(methylsulfonyl)-3'-(5-(4-(trifluoromethoxy)phenyl)-1H-1,2,3-triazol-1-yl)-[1,1'-biphenyl]-4-yl)methanol | |

| Ex # | Structure | Name & Additional Characterization Data | Molecular Ion |
|---|---|---|---|
| 213 | 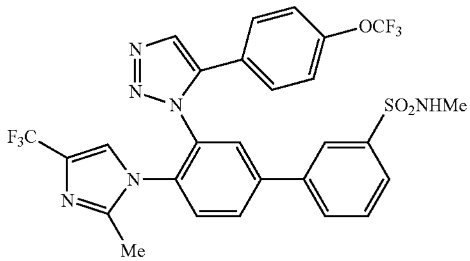 | N-methyl-4'-(2-methyl-4-(trifluoromethyl)-1H-imidazol-1-yl)-3'-(5-(4-(trifluoromethoxy)phenyl)-1H-1,2,3-triazol-1-yl)-[1,1'-biphenyl]-3-sulfonamide | |
| 214 | 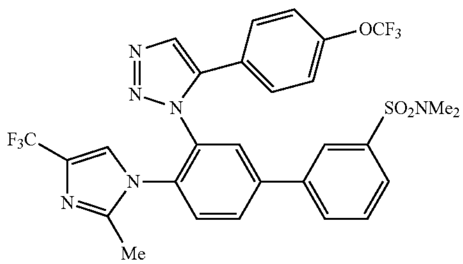 | N,N-dimethyl-4'-(2-methyl-4-(trifluoromethyl)-1H-imidazol-1-yl)-3'-(5-(4-(trifluoromethoxy)phenyl)-1H-1,2,3-triazol-1-yl)-[1,1'-biphenyl]-3-sulfonamide | |
| 215 | 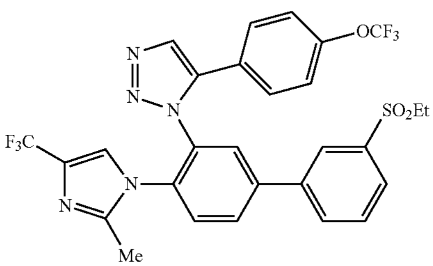 | 1-(3'-(ethylsulfonyl)-4-(2-methyl-4-(trifluoromethyl)-1H-imidazol-1-yl)-[1,1-biphenyl]-3-yl)-5-(4-(trifluoromethoxy)phenyl)-1H-1,2,3-triazole | |
| 216 | 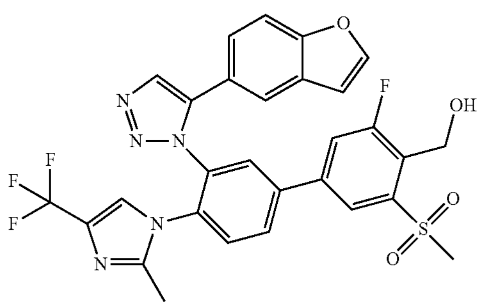 [SMILES: Cc1nc(C(F)(F)F)cn1-c1ccc(-c2cc(F)c(CO)c(S(C)(=O)=O)c2)cc1-n1nncc1-c1ccc2occc2c1] | (3'-(5-(benzofuran-5-yl)-1H-1,2,3-triazol-1-yl)-3-fluoro-4'-(2-methyl-4-(trifluoromethyl)-1H-imidazol-1-yl)-5-(methylsulfonyl)-[1,1'-biphenyl]-4-yl)methanol | |
| 219 | 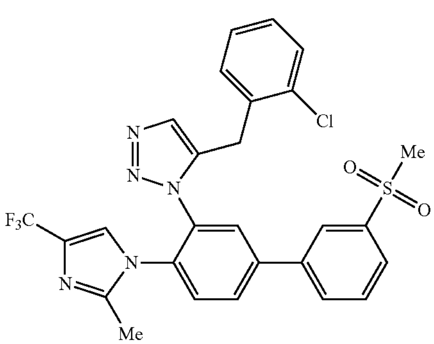 [SMILES: Cc1nc(C(F)(F)F)cn1-c1ccc(-c2cccc(S(C)(=O)=O)c2)cc1-n1nncc1Cc1ccccc1Cl] | 5-(2-chlorobenzyl)-1-(4-(2-methyl-4-(trifluoromethyl)-1H-imidazol-1-yl)-3'-(methylsulfonyl)-[1,1'-biphenyl]-3-yl)-1H-1,2,3-triazole | |

| Ex # | Structure | Name & Additional Characterization Data | Molecular Ion |
|---|---|---|---|
| 220 | 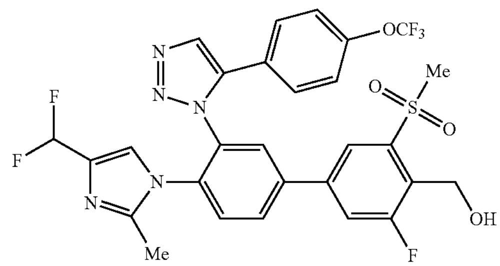 [SMILES: Cc1nc(C(F)F)cn1-c1ccc(-c2cc(F)c(CO)c(S(C)(=O)=O)c2)cc1-n1nncc1-c1ccc(OC(F)(F)F)cc1] | (4'-(4-(difluoromethyl)-2-methyl-1H-imidazol-1-yl)-3-fluoro-5-(methylsulfonyl)-3'-(5-(4-(trifluoromethoxy)phenyl)-1H-1,2,3-triazol-1-yl)-[1,1'-biphenyl]-4-yl)methanol | |
| 221 | 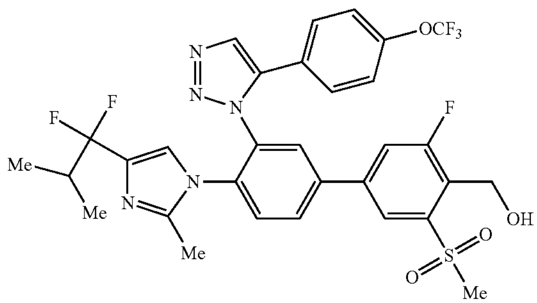 [SMILES: Cc1nc(C(F)(F)C(C)C)cn1-c1ccc(-c2cc(F)c(CO)c(S(C)(=O)=O)c2)cc1-n1nncc1-c1ccc(OC(F)(F)F)cc1] | (4'-(4-(1,1-difluoro-2-methylpropyl)-2-methyl-1H-imidazol-1-yl)-3-fluoro-5-(methylsulfonyl)-3'-(5-(4-(trifluoromethoxy)phenyl)-1H-1,2,3-triazol-1-yl)-[1,1'-biphenyl]-4-yl)methanol | |
| 222 | 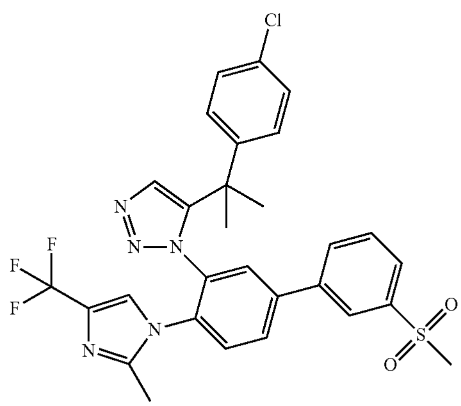 [SMILES: Cc1nc(C(F)(F)F)cn1-c1ccc(-c2cccc(S(C)(=O)=O)c2)cc1-n1nncc1C(C)(C)c1ccc(Cl)cc1] | 5-(2-(4-chlorophenyl)propan-2-yl)-1-(4-(2-methyl-4-(trifluoromethyl)-1H-imidazol-1-yl)-3'-(methylsulfonyl)-[1,1'-biphenyl]-3-yl)-1H-1,2,3-triazole | |
| 223 | 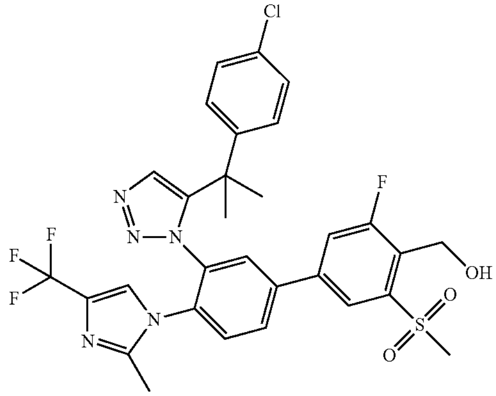 [SMILES: Cc1nc(C(F)(F)F)cn1-c1ccc(-c2cc(F)c(CO)c(S(C)(=O)=O)c2)cc1-n1nncc1C(C)(C)c1ccc(Cl)cc1] | (3'-(5-(2-(4-chlorophenyl)propan-2-yl)-1H-1,2,3-triazol-1-yl)-3-fluoro-4'-(2-methyl-4-(trifluoromethyl)-1H-imidazol-1-yl)-5-(methylsulfonyl)-[1,1'-biphenyl]-4-yl)methanol | |

| Ex # | Structure | Name & Additional Characterization Data | Molecular Ion |
|---|---|---|---|
| 224 | 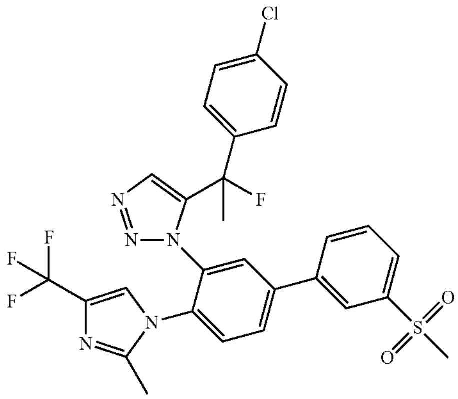 [SMILES: Cc1nc(C(F)(F)F)cn1-c1ccc(-c2cccc(S(C)(=O)=O)c2)cc1-n1nncc1C(C)(F)c1ccc(Cl)cc1] | 5-(1-(4-chlorophenyl)-1-fluoroethyl)-1-(4-(2-methyl-4-(trifluoromethyl)-1H-imidazol-1-yl)-3'-(methylsulfonyl)-[1,1'-biphenyl]-3-yl)-1H-1,2,3-triazole | |
| 225 | 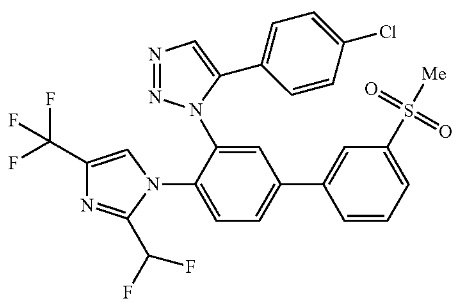 [SMILES: CS(=O)(=O)c1cccc(-c2ccc(-n3cc(C(F)(F)F)nc3C(F)F)c(-n3nncc3-c3ccc(Cl)cc3)c2)c1] | 5-(4-chlorophenyl)-1-(4-(2-(difluoromethyl)-4-(trifluoromethyl)-1H-imidazol-1-yl)-3'-(methylsulfonyl)-[1,1'-biphenyl]-3-yl)-1H-1,2,3-triazole | |
| 226 | 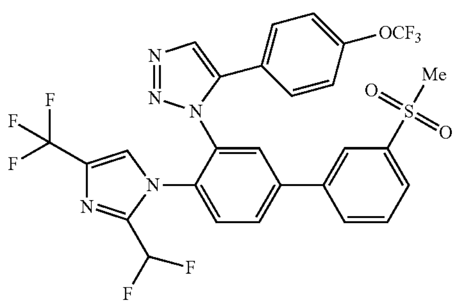 [SMILES: CS(=O)(=O)c1cccc(-c2ccc(-n3cc(C(F)(F)F)nc3C(F)F)c(-n3nncc3-c3ccc(OC(F)(F)F)cc3)c2)c1] | 1-(4-(2-(difluoromethyl)-4-(trifluoromethyl)-1H-imidazol-1-yl)-3'-(methylsulfonyl)-[1,1'-biphenyl]-3-yl)-5-(4-(trifluoromethoxy)phenyl)-1H-1,2,3-triazole | |
| 227 | 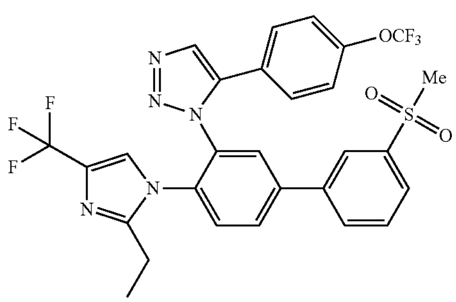 [SMILES: CCc1nc(C(F)(F)F)cn1-c1ccc(-c2cccc(S(C)(=O)=O)c2)cc1-n1nncc1-c1ccc(OC(F)(F)F)cc1] | 1-(4-(2-ethyl-4-(trifluoromethyl)-1H-imidazol-1-yl)-3'-(methylsulfonyl)-[1,1'-biphenyl]-3-yl)-5-(4-(trifluoromethoxy)phenyl)-1H-1,2,3-triazole | |
| 228 | 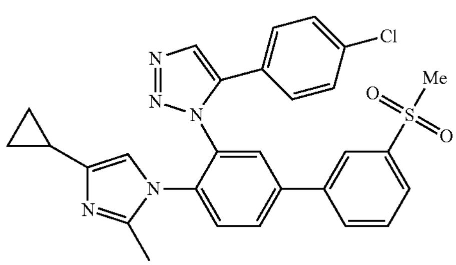 [SMILES: Cc1nc(C2CC2)cn1-c1ccc(-c2cccc(S(C)(=O)=O)c2)cc1-n1nncc1-c1ccc(Cl)cc1] | 5-(4-chlorophenyl)-1-(4-(4-cyclopropyl-2-methyl-1H-imidazol-1-yl)-3'-(methylsulfonyl)-[1,1'-biphenyl]-3-yl)-1H-1,2,3-triazole | |

| Ex # | Structure | Name & Additional Characterization Data | Molecular Ion |
|---|---|---|---|
| 229 | 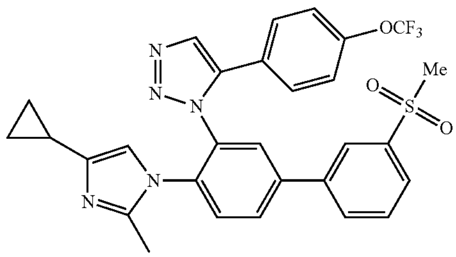 [SMILES: Cc1nc(C2CC2)cn1-c1ccc(-c2cccc(S(C)(=O)=O)c2)cc1-n1nncc1-c1ccc(OC(F)(F)F)cc1] | 1-(4-(4-cyclopropyl-2-methyl-1H-imidazol-1-yl)-3'-(methylsulfonyl)-[1,1'-biphenyl]-3-yl)-5-(4-(trifluoromethoxy)phenyl)-1H-1,2,3-triazole | |
| 230 | 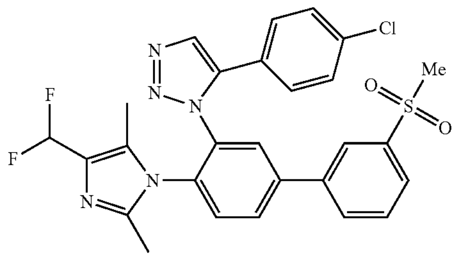 [SMILES: Cc1nc(C(F)F)c(C)n1-c1ccc(-c2cccc(S(C)(=O)=O)c2)cc1-n1nncc1-c1ccc(Cl)cc1] | 5-(4-chlorophenyl)-1-(4-(4-(difluoromethyl)-2,5-dimethyl-1H-imidazol-1-yl)-3'-(methylsulfonyl)-[1,1'-biphenyl]-3-yl)-1H-1,2,3-triazole | |
| 231 | 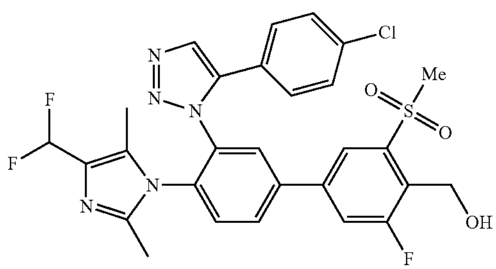 [SMILES: Cc1nc(C(F)F)c(C)n1-c1ccc(-c2cc(F)c(CO)c(S(C)(=O)=O)c2)cc1-n1nncc1-c1ccc(Cl)cc1] | (3'-(5-(4-chlorophenyl)-1H-1,2,3-triazol-1-yl)-4'-(4-(difluoromethyl)-2,5-dimethyl-1H-imidazol-1-yl)-3-fluoro-5-(methylsulfonyl)-[1,1'-biphenyl]-4-yl)methanol | |
| 232 | 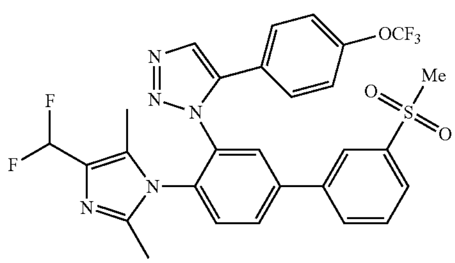 [SMILES: Cc1nc(C(F)F)c(C)n1-c1ccc(-c2cccc(S(C)(=O)=O)c2)cc1-n1nncc1-c1ccc(OC(F)(F)F)cc1] | 1-(4-(4-(difluoromethyl)-2,5-dimethyl-1H-imidazol-1-yl)-3'-(methylsulfonyl)-[1,1'-biphenyl]-3-yl)-5-(4-(trifluoromethoxy)phenyl)-1H-1,2,3-triazole | |
| 233 | 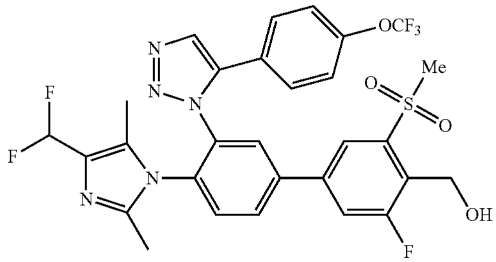 [SMILES: Cc1nc(C(F)F)c(C)n1-c1ccc(-c2cc(F)c(CO)c(S(C)(=O)=O)c2)cc1-n1nncc1-c1ccc(OC(F)(F)F)cc1] | (4'-(4-(difluoromethyl)-2,5-dimethyl-1H-imidazol-1-yl)-3-fluoro-5-(methylsulfonyl)-3'-(5-(4-(trifluoromethoxy)phenyl)-1H-1,2,3-triazol-1-yl)-[1,1'-biphenyl]-4-yl)methanol | |

| Ex # | Structure | Name & Additional Characterization Data | Molecular Ion |
|---|---|---|---|
| 234 | 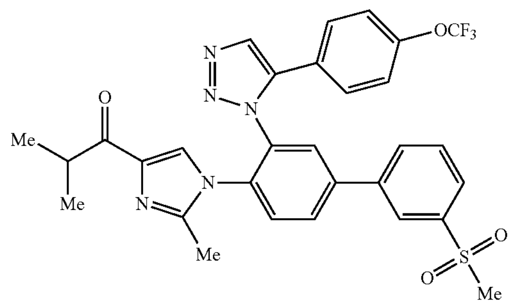 [SMILES: Cc1nc(C(=O)C(C)C)cn1-c1ccc(-c2cccc(S(C)(=O)=O)c2)cc1-n1nncc1-c1ccc(OC(F)(F)F)cc1] | 2-methyl-1-(2-methyl-1-(3'-(methylsulfonyl)-3-(5-(4-(trifluoromethoxy)phenyl)-1H-1,2,3-triazol-1-yl)-[1,1'-biphenyl]-4-yl)-1H-imidazol-4-yl)propan-1-one | |
| 235 | 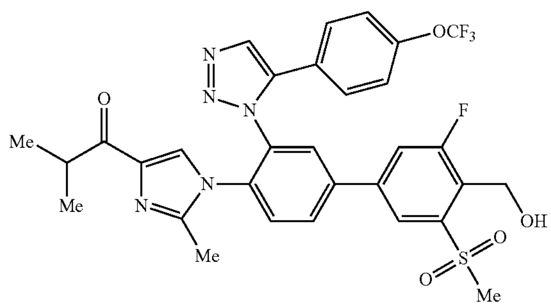 [SMILES: Cc1nc(C(=O)C(C)C)cn1-c1ccc(-c2cc(F)c(CO)c(S(C)(=O)=O)c2)cc1-n1nncc1-c1ccc(OC(F)(F)F)cc1] | 1-(1-(3'-fluoro-4'-(hydroxymethyl)-5'-(methylsulfonyl)-3-(5-(4-(trifluoromethoxy)phenyl)-1H-1,2,3-triazol-1-yl)-[1,1'-biphenyl]-4-yl)-2-methyl-1H-imidazol-4-yl)-2-methylpropan-1-one | |
| 236 | 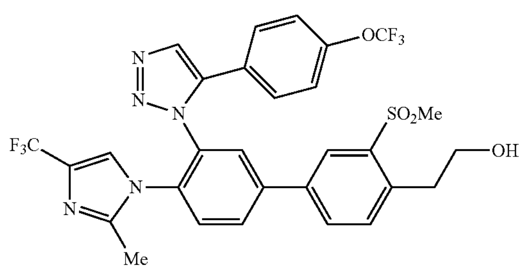 [SMILES: Cc1nc(C(F)(F)F)cn1-c1ccc(-c2ccc(CCO)c(S(C)(=O)=O)c2)cc1-n1nncc1-c1ccc(OC(F)(F)F)cc1] | 2-(4'-(2-methyl-4-(trifluoromethyl)-1H-imidazol-1-yl)-3-(methylsulfonyl)-3'-(5-(4-(trifluoromethoxy)phenyl)-1H-1,2,3-triazol-1-yl)-[1,1'-biphenyl]-4-yl)ethanol | |
| 237 | 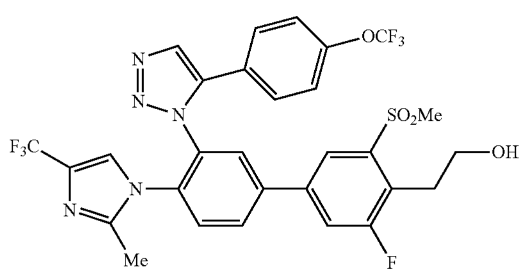 [SMILES: Cc1nc(C(F)(F)F)cn1-c1ccc(-c2cc(F)c(CCO)c(S(C)(=O)=O)c2)cc1-n1nncc1-c1ccc(OC(F)(F)F)cc1] | 2-(3-fluoro-4'-(2-methyl-4-(trifluoromethyl)-1H-imidazol-1-yl)-5-(methylsulfonyl)-3'-(5-(4-(trifluoromethoxy)phenyl)-1H-1,2,3-triazol-1-yl)-[1,1'-biphenyl]-4-yl)ethanol | |
| 238 | 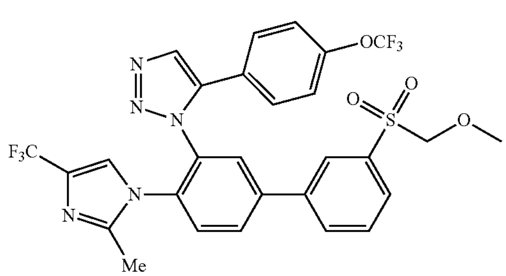 [SMILES: COCS(=O)(=O)c1cccc(-c2ccc(-n3cc(C(F)(F)F)nc3C)c(-n3nncc3-c3ccc(OC(F)(F)F)cc3)c2)c1] | 1-(3'-((methoxymethyl)sulfonyl)-4-(2-methyl-4-(trifluoromethyl)-1H-imidazol-1-yl)-[1,1'-biphenyl]-3-yl)-5-(4-(trifluoromethoxy)phenyl)-1H-1,2,3-triazole | |

Scheme 3

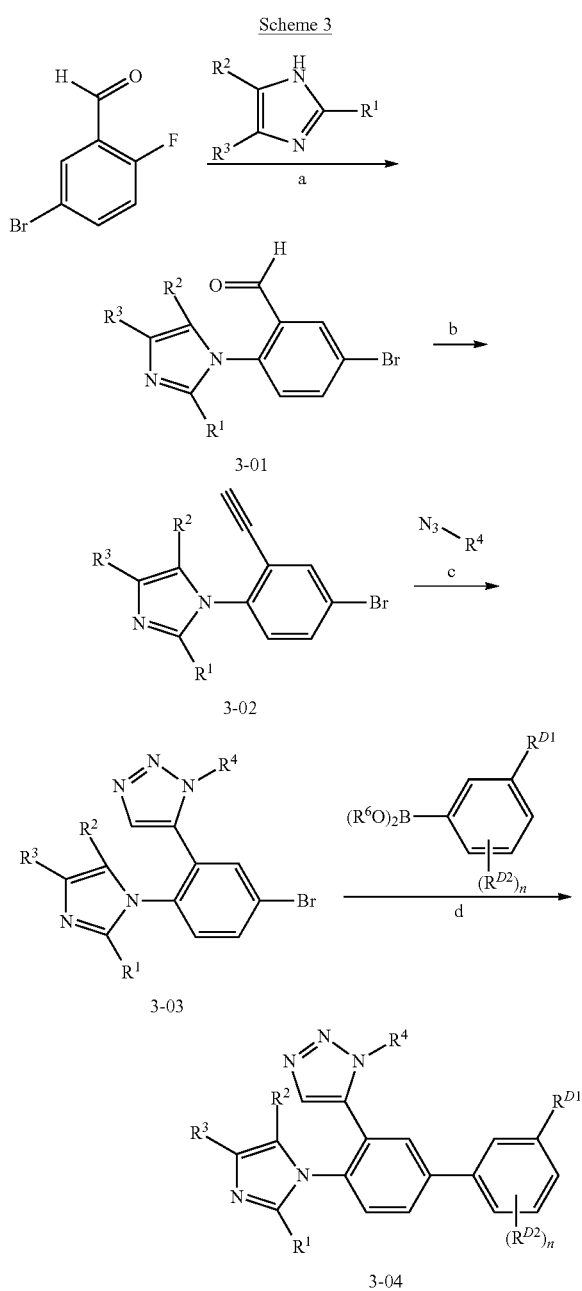

3-01

3-02

3-03

3-04

(a) K₂CO₃, DMF; (b) Bestmann-Ohira reagent, K₂CO₃, MeOH; (c) Cp*RuCl(cod), THF; (d) NCS, DMA, 65° C.; (e) K₂CO₃, PdCl₂(dppf), DME/H₂O, 80° C.

Particular embodiments of the invention comprise compounds exemplified by general structure 3-04 shown in Scheme 3. An appropriately substituted imidazole undergoes a S$_N$Ar reaction with 5-bromo-2-fluorobenzaldehyde in the presence of K₂CO₃ in DMF to give 3-01. The benzaldehyde 3-01 reacts with the Bestmann-Ohira reagent (dimethyl 1-diazo-2-oxopropylphosphonate in the presence of K₂CO₃ to give the alkyne (3-02). In a subsequent step, exposure of alkyne 3-02 to an appropriately substituted azide, under Cp*RuCl(cod) catalysis, provided the general triazole 3-03 in regioselective fashion. Compounds represented by the structure 3-04 are then obtained by subjecting 3-03 to a palladium-mediated coupling reaction.

Example 240

{4'-[5-chloro-2-methyl-4-(trifluoromethyl)-1H-imidazol-1-yl]-3'-[1-(4-chlorophenyl)-1H-1,2,3-triazol-5-yl]-3-fluoro-5-(methylsulfonyl)biphenyl-4-yl}methanol

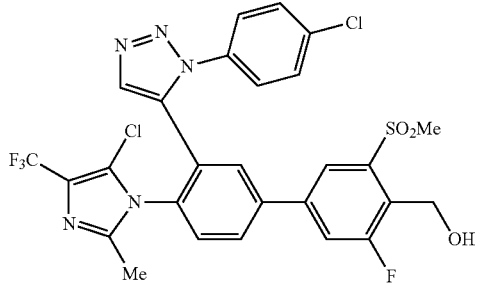 [SMILES: Cc1nc(C(F)(F)F)c(Cl)n1-c1ccc(-c2cc(F)c(CO)c(S(C)(=O)=O)c2)cc1-c1cnnn1-c1ccc(Cl)cc1]

Example 240a

Preparation of 1-(4-bromo-2-ethynylphenyl)-2-methyl-4-(trifluoromethyl)-1H-imidazole

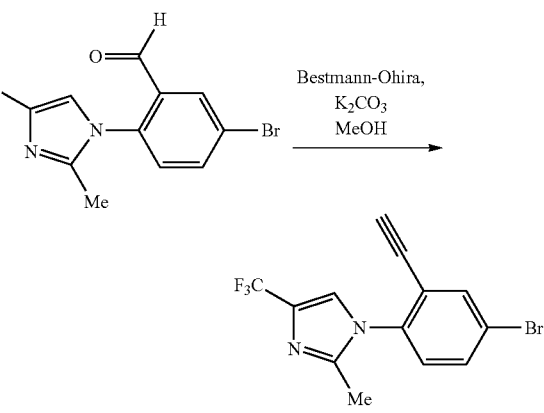

To a solution of 5-bromo-2-(2-methyl-4-(trifluoromethyl)-1H-imidazol-1-yl)benzaldehyde (prepared from 2-methyl-4-(trifluoromethyl)-1H-imidazole and 5-bromo-2-fluorobenzaldehyde by a similar procedure to Example 1a) (1.83 g, 5.49 mmol), and K₂CO₃ (1.52 g, 11.0 mmol) in MeOH (55 mL) was added dimethyl 1-diazo-2-oxopropylphosphonate (Bestmann-Ohira) (1.26 g, 6.58 mmol) dropwise, and the reaction mixture was allowed to stir for 18 h. The reaction mixture was poured into H₂O and extracted with diethyl ether. The combined organics were washed with H₂O and brine, dried over MgSO₄, and concentrated in vacuo. The residue was purified by flash column chromatography to yield the title compound (1.24 g, 3.77 mmol).

Example 240b

Preparation of 5-(5-bromo-2-(2-methyl-4-(trifluoromethyl)-1H-imidazol-1-yl)phenyl)-1-(4-chlorophenyl)-1H-1,2,3-triazole

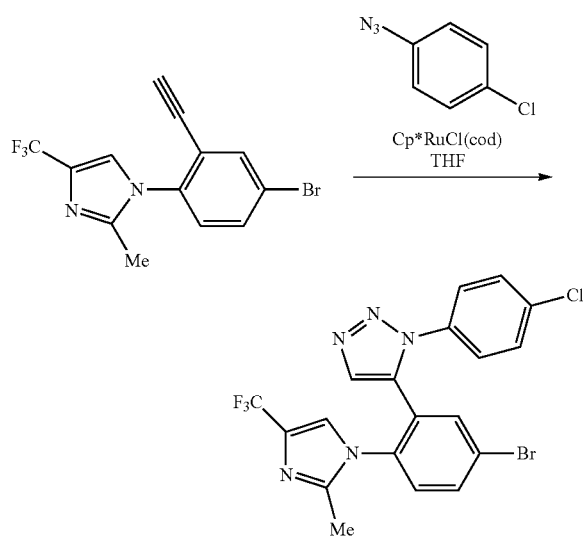

An 8 mL vial was charged with Example 240a (93.3 mg, 283 μmol), 1-azido-4-chlorobenzene (48.0 mg, 312 μmol), and dry THF (2.0 mL). Argon was bubbled through the reaction mixture for 15 min, Cp*RuCl(cod) (11.0 mg, 28.0 μmol) was added, and then argon was again bubbled through the reaction mixture for 5 min. After the reaction mixture was stirred for 19 hrs, the solvent was evaporated, and the residue was purified by flash column chromatography to yield the title compound (0.110 g, 228 μmol).

Example 240 was prepared from Example 240b using procedures similar to that described in Example 1d and 1f. MS (ESI) 640.3 [M+H]$^+$. 1H NMR (400 MHz, DMSO) δ 8.26-8.18 (m, 2H), 8.14 (d, J=1.6 Hz, 1H), 8.09 (dd, J=10.7, 1.8 Hz, 1H), 7.98 (s, 1H), 7.87 (d, J=8.2 Hz, 1H), 7.68-7.56 (m, 2H), 7.40-7.31 (m, 2H), 5.62 (s, 1H), 5.00 (s, 2H), 3.48 (s, 3H), 1.86 (s, 3H).

The following compounds were prepared in a manner similar to that described in the previous experimental procedures:

| Ex # | Structure | Name | Molecular Ion |
|---|---|---|---|
| 241 | 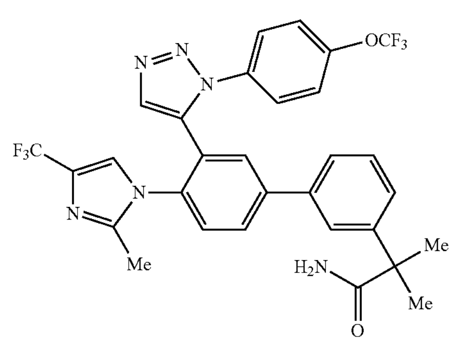 [SMILES: Cc1nc(C(F)(F)F)cn1-c1ccc(-c2cccc(C(C)(C)C(N)=O)c2)cc1-c1cnnn1-c1ccc(OC(F)(F)F)cc1] | 2-methyl-2-{4'-[2-methyl-4-(trifluoromethyl)-1H-imidazol-1-yl]-3'-(1-{4-[(trifluoromethyl)oxy]phenyl}-1H-1,2,3-triazol-5-yl)biphenyl-3-yl}propanamide | MS (ESI) 615.0 [M + H]$^+$. |
| 242 | 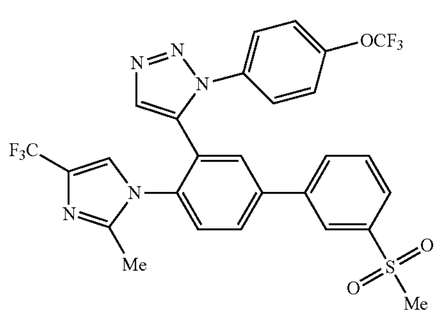 [SMILES: Cc1nc(C(F)(F)F)cn1-c1ccc(-c2cccc(S(C)(=O)=O)c2)cc1-c1cnnn1-c1ccc(OC(F)(F)F)cc1] | 5-{3'-(methylsulfonyl)-4-[2-methyl-4-(trifluoromethyl)-1H-imidazol-1-yl]biphenyl-3-yl}-1-{4-[(trifluoromethyl)oxy]phenyl}-1H-1,2,3-triazole | MS (ESI) 608.2 [M + H]$^+$. |

| Ex # | Structure | Name | Molecular Ion |
|---|---|---|---|
| 243 | 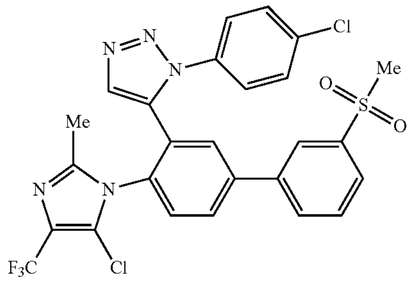 [SMILES: Cc1nc(C(F)(F)F)c(Cl)n1-c1ccc(-c2cccc(S(C)(=O)=O)c2)cc1-c1cnnn1-c1ccc(Cl)cc1] | 5-{4-[5-chloro-2-methyl-4-(trifluoromethyl)-1H-imidazol-1-yl]-3'-(methylsulfonyl)biphenyl-3-yl}-1-(4-chlorophenyl)-1H-1,2,3-triazole | MS (ESI) 592.3 [M + H]+. |
| 244 | 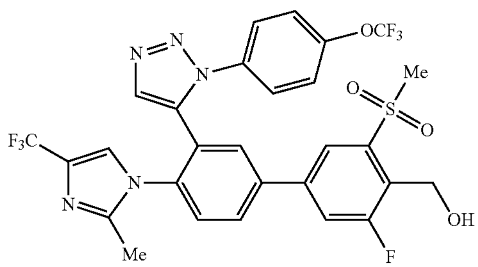 [SMILES: Cc1nc(C(F)(F)F)cn1-c1ccc(-c2cc(F)c(CO)c(S(C)(=O)=O)c2)cc1-c1cnnn1-c1ccc(OC(F)(F)F)cc1] | [3-fluoro-5-(methylsulfonyl)-4'-[2-methyl-4-(trifluoromethyl)-1H-imidazol-1-yl]-3'-(1-{4-[(trifluoromethyl)oxy]phenyl}-1H-1,2,3-triazol-5-yl)biphenyl-4-yl]methanol | MS (ESI) 656.3 [M + H]+. |
| 245 | 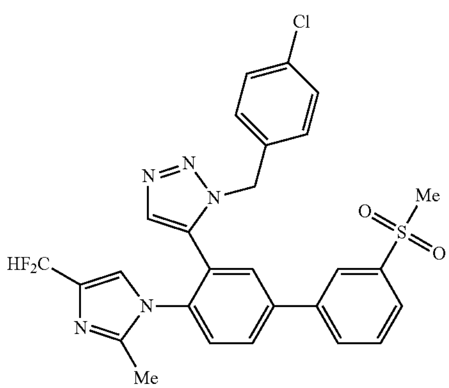 | 1-(4-chlorobenzyl)-5-(4-(4-(difluoromethyl)-2-methyl-1H-imidazol-1-yl)-3'-(methylsulfonyl)-[1,1'-biphenyl]-3-yl)-1H-1,2,3-triazole | |
| 246 | 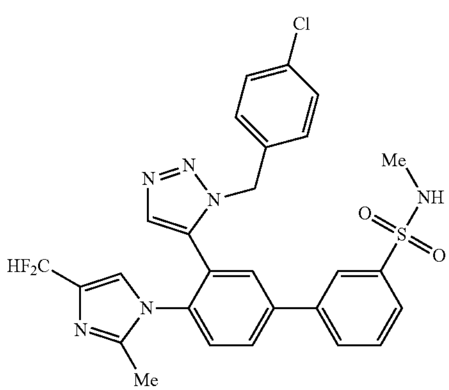 | 3'-(1-(4-chlorobenzyl)-1H-1,2,3-triazol-5-yl)-4'-(4-(difluoromethyl)-2-methyl-1H-imidazol-1-yl)-N-methyl-[1,1'-biphenyl]-3-sulfonamide | |

| Ex # | Structure | Name | Molecular Ion |
|---|---|---|---|
| 247 | 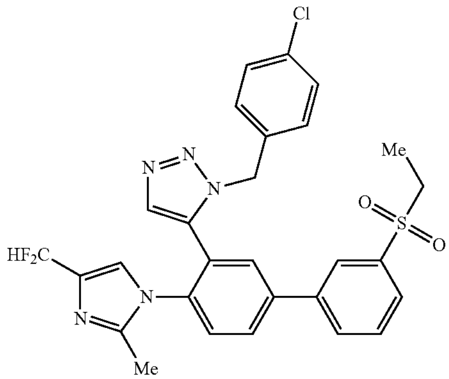 | 1-(4-chlorobenzyl)-5-(4-(4-(difluoromethyl)-2-methyl-1H-imidazol-1-yl)-3'-(ethylsulfonyl)-[1,1'-biphenyl]-3-yl)-1H-1,2,3-triazole | |
| 248 | 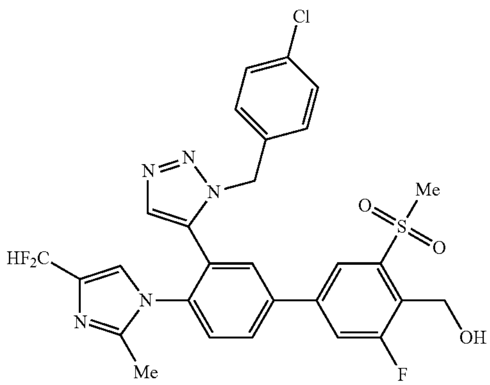 | (3'-(1-(4-chlorobenzyl)-1H-1,2,3-triazol-5-yl)-4'-(4-(difluoromethyl)-2-methyl-1H-imidazol-1-yl)-3-fluoro-5-(methylsulfonyl)-[1,1'-biphenyl]-4-yl)methanol | |
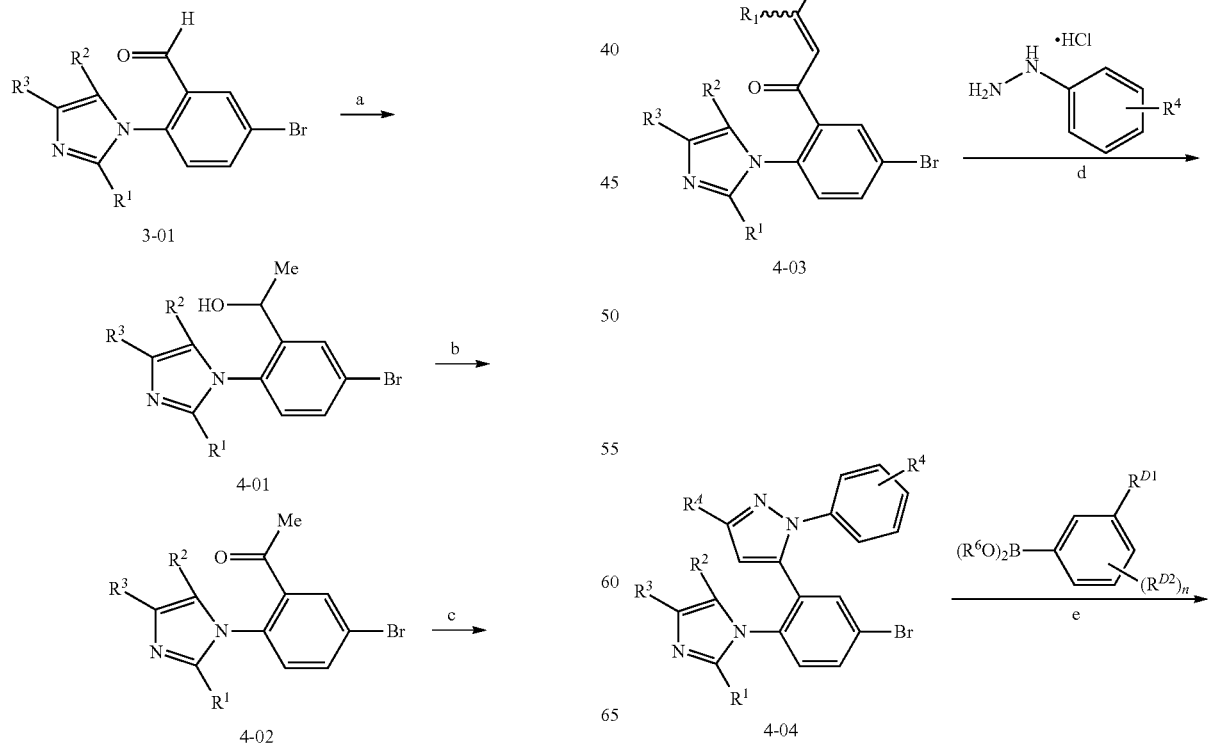
Scheme 4

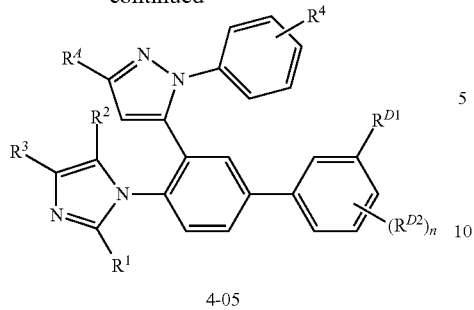

4-05

(a) MeMgBr, THF; (b) MnO$_2$, CHCl$_3$; (c) Me$_2$NC(OMe)$_2$R$_1$, DMA or DMF; (d) EtOH; (e) K$_2$CO$_3$, PdCl$_2$(dppf), DME/H$_2$O.

Compounds of the type (4-05) can be prepared by a process shown by the general route in Scheme 11. Aldehyde (3-01) is treated with methylmagnesium bromide, to provide the alcohol (4-01). Subsequently, exposure of this alcohol (4-01) to manganese (1V) oxide at reflux provides the ketone 4-02. Intermediate vinylogous amides of type 4-03 are then obtained by refluxing ketone 4-02 in either N,N-dimethylformamide or N,N-dimethylacetamide in the presence of the corresponding dimethyl acetal of the solvent employed. Cyclization of 4-03 is then accomplished in refluxing EtOH with an appropriate phenylhydrazine to afford 4-04. Suzuki coupling between the aryl bromide (4-04) with the aryl boronic acid or ester derivatives produces the final pyrazole product 4-05.

Example 286

1-(4-chlorophenyl)-5-{3'-(methylsulfonyl)-4-[2-methyl-4-(trifluoromethyl)-1H-imidazol-1-yl]biphenyl-3-yl}-1H-pyrazole

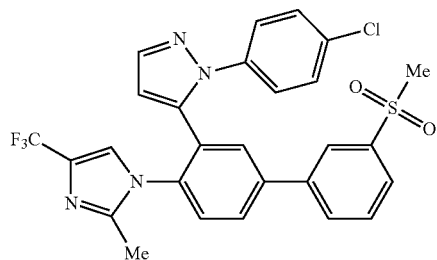 [SMILES: Cc1nc(C(F)(F)F)cn1-c1ccc(-c2cccc(S(C)(=O)=O)c2)cc1-c1ccnn1-c1ccc(Cl)cc1]

Example 286a

Preparation of 1-(5-bromo-2-(2-methyl-4-(trifluoromethyl)-1H-imidazol-1-yl)phenyl)ethanol

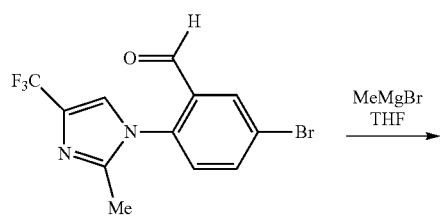

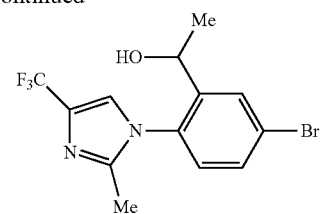

A 250 mL round bottom flask was charged with 5-bromo-2-(2-methyl-4-(trifluoromethyl)-1H-imidazol-1-yl)benzaldehyde (prepared from 2-methyl-4-(trifluoromethyl)-1H-imidazole and 5-bromo-2-fluorobenzaldehyde by a similar procedure to Example 1a) (2.64 g, 7.93 mmol) and THF (50 mL). The solution was cooled to 0° C., MeMgBr (3.96 mL, 11.89 mmol) was added slowly, and then the mixture was allowed to warm to rt. After 3 h the reaction was quenched with saturated aq NH$_4$Cl. The mixture was poured into H$_2$O and extracted with EtOAc (×2). The combined organics were washed with H$_2$O and brine, dried over MgSO$_4$ and concentrated in vacuo to yield the crude title compound (2.98 g, 8.54 mmol) that was used directly in the next step.

Example 286b

Preparation of 1-(5-bromo-2-(2-methyl-4-(trifluoromethyl)-1H-imidazol-1-yl)phenyl)ethanone

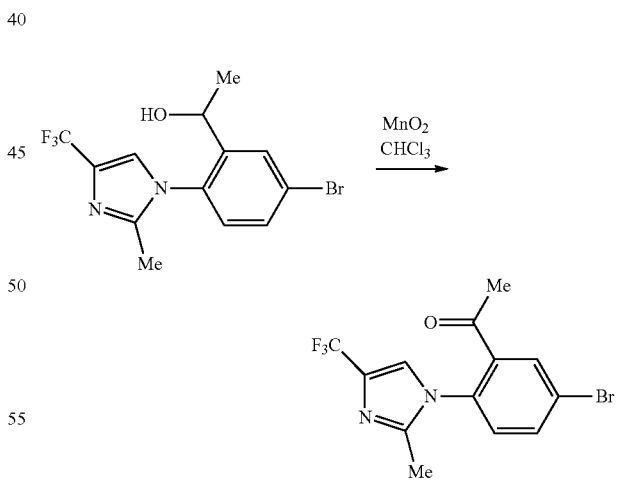

A 500 mL round bottom flask was charged with Example 286a (2.98 g, 8.54 mmol), CHCl$_3$ (100 mL), and MnO$_2$ (14.8 g, 171 mmol), and the mixture was heated to reflux for 17 h. The reaction mixture was filtered through a pad of Celite and the solvent was evaporated in vacuo to yield the crude title compound (2.60 g, 7.49 mmol).

Example 286c

Preparation of 1-(5-bromo-2-(2-methyl-4-(trifluoromethyl)-1H-imidazol-1-yl)phenyl)-3-(dimethylamino)prop-2-en-1-one

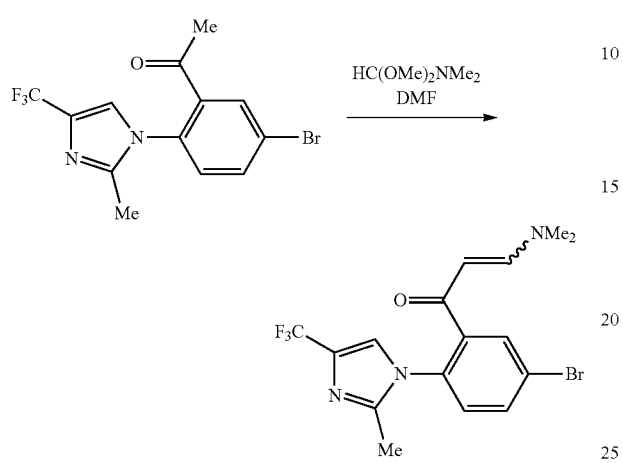

A 250 mL round bottom flask was charged with Example 286b (4.30 g, 12.4 mmol), DMF (50 mL), and N,N-dimethylformamide dimethyl acetal (2.47 mL, 18.6 mmol), and the mixture was heated to reflux for 20 h. The volatiles were evaporated in vacuo to yield the crude title compound (5.40 g, 13.4 mmol).

Example 286d

Preparation of 5-(5-bromo-2-(2-methyl-4-(trifluoromethyl)-1H-imidazol-1-yl)phenyl)-1-(4-chlorophenyl)-1H-pyrazole

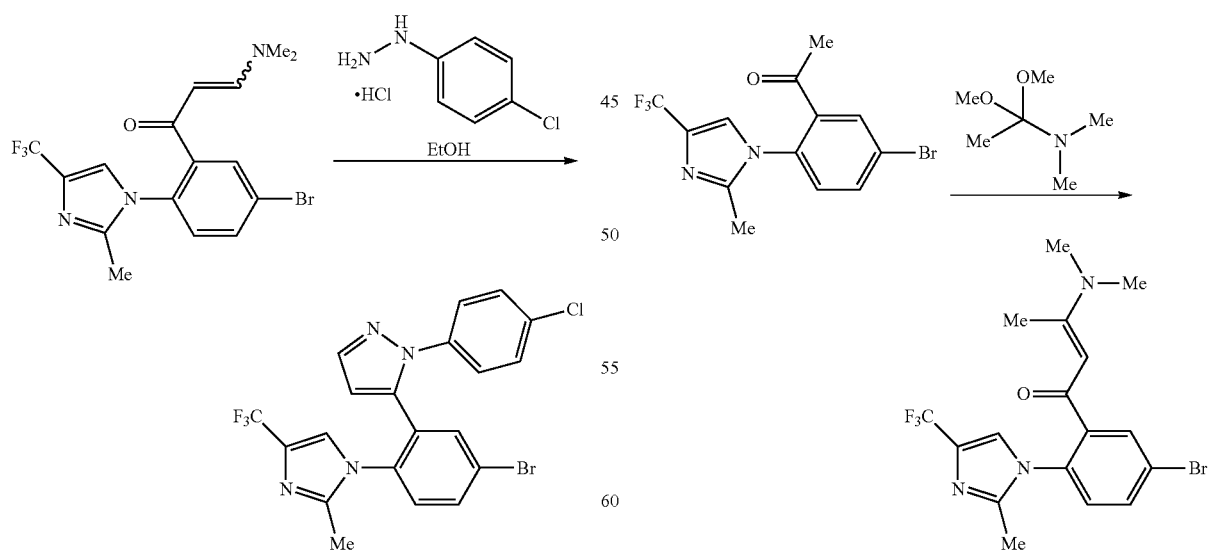

A 250 mL round bottom flask was charged with Example 286c (0.89 g, 2.2 mmol), EtOH (50 mL), and 4-chlorophenylhydrazine hydrochloride (0.59 g, 3.3 mmol), and the mixture was heated to reflux for 17 h. The volatiles were evaporated in vacuo, and the resulting residue was purified by column chromatography to yield the title compound (0.56 g, 1.2 mmol).

Example 286 was prepared from Example 286d and 3-methylsulfonylphenylboronic acid using procedures similar to that described in Example 1f. MS (ESI) 557.3, 559.3 [M+H]$^+$. $^1$H NMR (400 MHz, CDCl$_3$) δ 8.22 (s, 1H), 8.04 (d, J=7.7 Hz, 1H), 7.93 (m, 2H), 7.82 (s, 1H), 7.76 (m, 2H), 7.35 (s, 1H), 7.29 (m, 2H), 6.94 (d, J=8.6 Hz, 2H), 6.56 (s, 1H), 6.47 (s, 1H), 3.15 (s, 3H), 1.85 (s, 3H).

Example 287

Preparation of (3'-(1-(4-(difluoromethoxy)phenyl)-3-methyl-1H-pyrazol-5-yl)-3-fluoro-4'-(2-methyl-4-(trifluoromethyl)-1H-imidazol-1-yl)-5-(methylsulfonyl)biphenyl-4-yl)methanol

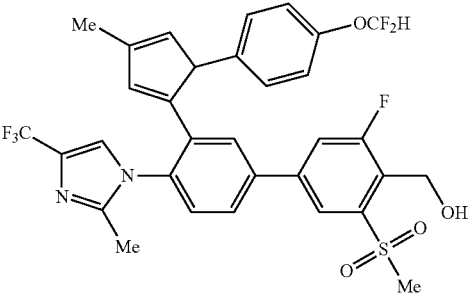

Example 287a

Preparation of (E)-1-(5-bromo-2-(2-methyl-4-(trifluoromethyl)-1H-imidazol-1-yl)phenyl)-3-(dimethylamino)but-2-en-1-one

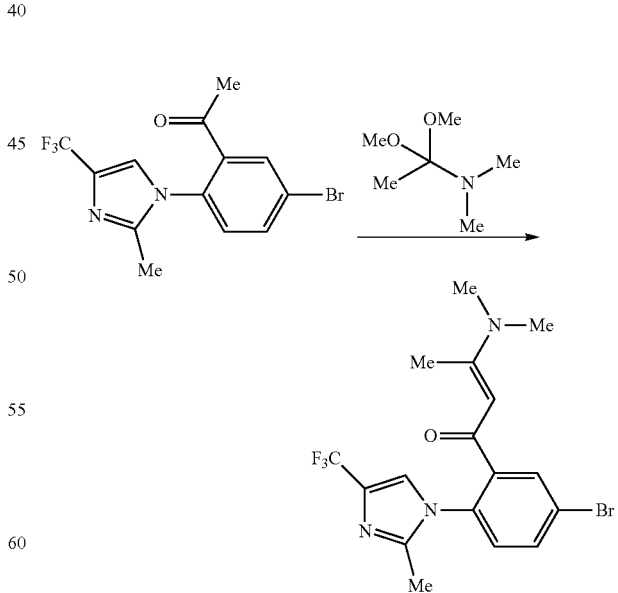

A solution of 5-bromo-2-(2-methyl-4-(trifluoromethyl)-1H-imidazol-1-yl)benzaldehyde (prepared from 2-methyl-4-(trifluoromethyl)-1H-imidazole and 5-bromo-2-fluorobenzaldehyde by a similar procedure to Example 1a) (500 mg, 1.4 mmol) and 1,1-dimethoxy-N,N-dimethylethanamine (320 μL, 2.2 mmol) in DMF (4 mL) was heated at 110° C. for 16 h. Additional 1,1-dimethoxy-N,N-dimethylethanamine (320 μL, 2.2 mmol) was added and the solution was continued heating for 3 h. Diethyl ether was added and the organic layer was washed with water and brine, and dried over Na₂SO₄. The volatiles were evaporated in vacuo to yield the crude title compound (460 mg, 1.1 mmol, 80% yield).

Example 287b

Preparation of 5-(5-bromo-2-(2-methyl-4-(trifluoromethyl)-1H-imidazol-1-yl)phenyl)-1-(4-(difluoromethoxy)phenyl)-3-methyl-1H-pyrazole

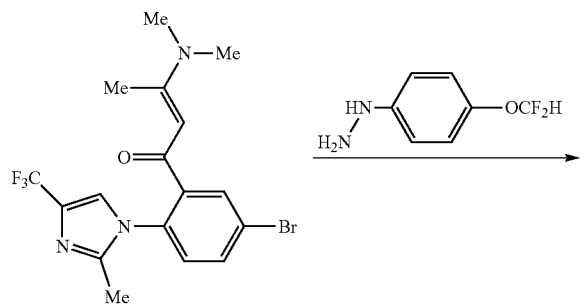

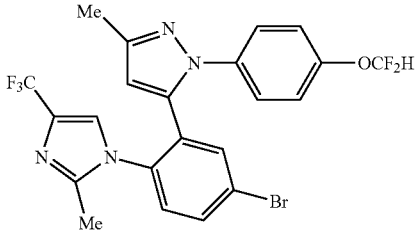

Example 287a (460 mg, 1.1 mmol) and (4-(difluoromethoxy)phenyl)hydrazine hydrochloride (260 mg, 1.2 mmol) were brought up in solution with EtOH (3.5 mL) and heated by microwave to 80° C. for 1 h. The volatiles were evaporated in vacuo and the residue was purified via column chromatography (eluent: 30% EtOAc/Hx) to afford the title compound (150 mg, 0.28 mmol, 26% yield).

Example 287 was prepared from Example 287b and Intermediate 1 using procedures similar to that described in Example 1f. MS (ESI) 651.2 [M+H].

The following compounds were prepared in a manner similar to that described in experimental procedure above:

| Ex # | Structure | Name Additional Characterization | Molecular Ion |
|---|---|---|---|
| 288 | 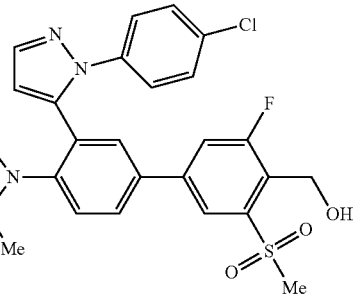 | {3'-[1-(4-chlorophenyl)-1H-pyrazol-5-yl]-3-fluoro-5-(methylsulfonyl)-4'-[2-methyl-4-(trifluoromethyl)-1H-imidazol-1-yl]biphenyl-4-yl}methanol | MS (ESI) 605.5 [M + H]⁺ |
| 289 | 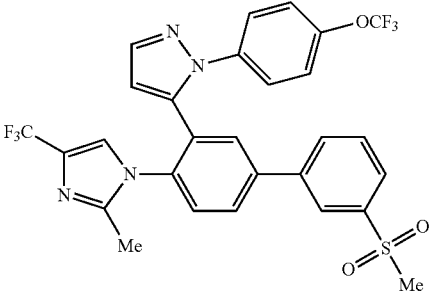 [SMILES: Cc1nc(C(F)(F)F)cn1-c1ccc(-c2cccc(S(C)(=O)=O)c2)cc1-c1ccnn1-c1ccc(OC(F)(F)F)cc1] | 5-{3'-(methylsulfonyl)-4-[2-methyl-4-(trifluoromethyl)-1H-imidazol-1-yl]biphenyl-3-yl}-1-{4-[(trifluoromethyl)oxy]phenyl}-1H-pyrazole | MS (ESI) 607.5 [M + H]⁺ |

| Ex # | Structure | Name Additional Characterization | Molecular Ion |
|---|---|---|---|
| 290 | 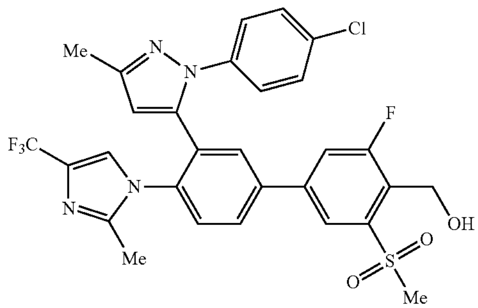 [SMILES: Cc1cc(-c2cc(-c3cc(F)c(CO)c(S(C)(=O)=O)c3)ccc2-n2cc(C(F)(F)F)nc2C)n(-c2ccc(Cl)cc2)n1] | {3'-[1-(4-chlorophenyl)-3-methyl-1H-pyrazol-5-yl]-3-fluoro-5-(methylsulfonyl)-4'-[2-methyl-4-(trifluoromethyl)-1H-imidazol-1-yl]biphenyl-4-yl}methanol | MS (ESI) 619.5 [M + H]+ |
| 291 | 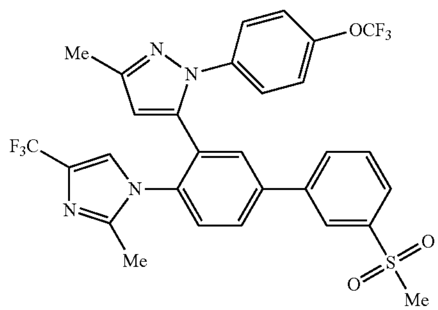 [SMILES: Cc1cc(-c2cc(-c3cccc(S(C)(=O)=O)c3)ccc2-n2cc(C(F)(F)F)nc2C)n(-c2ccc(OC(F)(F)F)cc2)n1] | 3-methyl-5-{3'-(methylsulfonyl)-4-[2-methyl-4-(trifluoromethyl)-1H-imidazol-1-yl]biphenyl-3-yl}-1-{4-[(trifluoromethyl)oxy]phenyl}-1H-pyrazole | MS (ESI) 621.5 [M + H]+ |
| 292 | 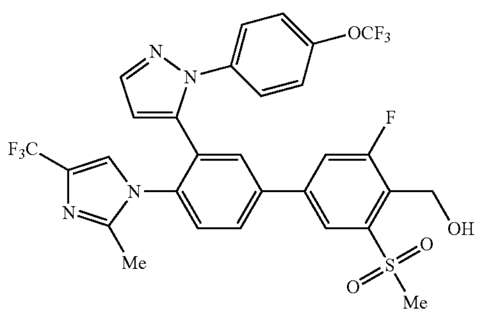 [SMILES: Cc1nc(C(F)(F)F)cn1-c1ccc(-c2cc(F)c(CO)c(S(C)(=O)=O)c2)cc1-c1ccnn1-c1ccc(OC(F)(F)F)cc1] | [3-fluoro-5-(methylsulfonyl)-4'-[2-methyl-4-(trifluoromethyl)-1H-imidazol-1-yl]-3'-(1-{4-[(trifluoromethyl)oxy]phenyl}-1H-pyrazol-5-yl)biphenyl-4-yl]methanol | MS (ESI) 655.5 [M + H]+ |
| 293 | 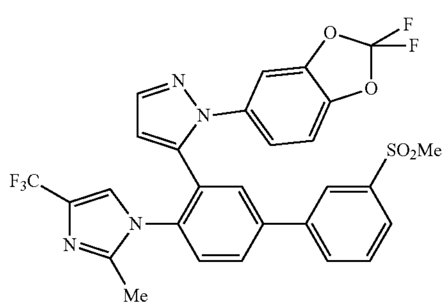 [SMILES: Cc1nc(C(F)(F)F)cn1-c1ccc(-c2cccc(S(C)(=O)=O)c2)cc1-c1ccnn1-c1ccc2c(c1)OC(F)(F)O2] | 1-(2,2-difluorobenzo[d][1,3]dioxol-5-yl)-5-(4-(2-methyl-4-(trifluoromethyl)-1H-imidazol-1-yl)-3'-(methylsulfonyl)biphenyl-3-yl)-1H-pyrazole | MS (ESI) 603.2 [M + H]+ |
| 294 | 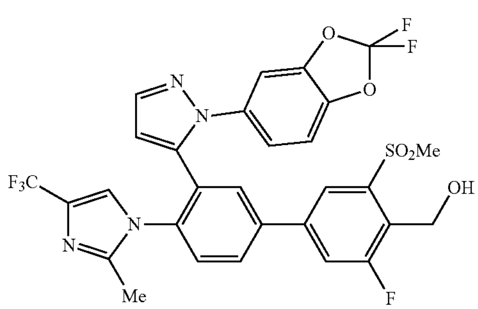 [SMILES: Cc1nc(C(F)(F)F)cn1-c1ccc(-c2cc(F)c(CO)c(S(C)(=O)=O)c2)cc1-c1ccnn1-c1ccc2c(c1)OC(F)(F)O2] | (3'-(1-(2,2-difluorobenzo[d][1,3]dioxol-5-yl)-1H-pyrazol-5-yl)-3-fluoro-4'-(2-methyl-4-(trifluoromethyl)-1H-imidazol-1-yl)-5-(methylsulfonyl)biphenyl-4-yl)methanol | MS (ESI) 651.2 [M + H]+ |

| Ex # | Structure | Name Additional Characterization | Molecular Ion |
|---|---|---|---|
| 295 | 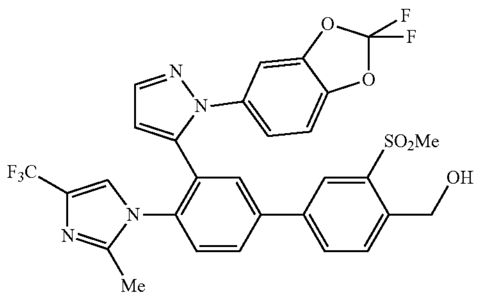 [SMILES: Cc1nc(C(F)(F)F)cn1-c1ccc(-c2ccc(CO)c(S(C)(=O)=O)c2)cc1-c1ccnn1-c1ccc2c(c1)OC(F)(F)O2] | (3'-(1-(2,2-difluorobenzo[d][1,3]dioxol-5-yl)-1H-pyrazol-5-yl)-4'-(2-methyl-4-(trifluoromethyl)-1H-imidazol-1-yl)-3-(methylsulfonyl)biphenyl-4-yl)methanol | MS (ESI) 633.2 [M + H]+ |
| 296 | 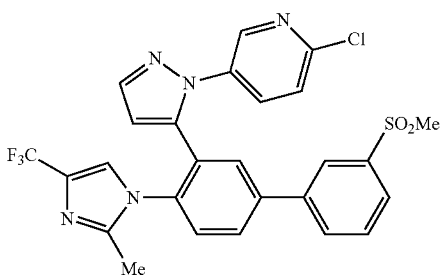 [SMILES: Cc1nc(C(F)(F)F)cn1-c1ccc(-c2cccc(S(C)(=O)=O)c2)cc1-c1ccnn1-c1ccc(Cl)nc1] | 2-chloro-5-(5-(4-(2-methyl-4-(trifluoromethyl)-1H-imidazol-1-yl)-3'-(methylsulfonyl)biphenyl-3-yl)-1H-pyrazol-1-yl)pyridine | MS (ESI) 558.2 [M + H]+ |
| 297 | 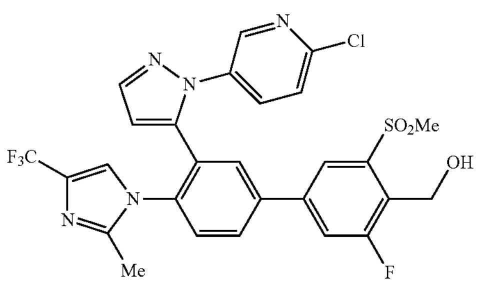 [SMILES: Cc1nc(C(F)(F)F)cn1-c1ccc(-c2cc(F)c(CO)c(S(C)(=O)=O)c2)cc1-c1ccnn1-c1ccc(Cl)nc1] | (3'-(1-(6-chloropyridin-3-yl)-1H-pyrazol-5-yl)-3-fluoro-4'-(2-methyl-4-(trifluoromethyl)-1H-imidazol-1-yl)-5-(methylsulfonyl)biphenyl-4-yl)methanol 1H NMR (400 MHz, CDCl$_3$) δ ppm 8.16 (s, 1 H), 7.93 (d, J = 2.01 Hz, 1 H), 7.80-7.88 (m, 3 H), 7.68 (dd, J = 9.79, 1.76 Hz, 1 H), 7.54 (dd, J = 8.53, 2.76 Hz, 1 H), 7.35-7.41 (m, 2 H), 6.63 (d, J = 1.76 Hz, 1 H), 6.51 (d, J = 1.25 Hz, 1 H), 5.10-5.15 (m, 2 H), 3.29-3.34 (m, 3 H), 2.90 (t, J = 6.90 Hz, 1 H), 1.85 (s, 3 H) | MS (ESI) 606.1 [M + H]+ |
| 298 | 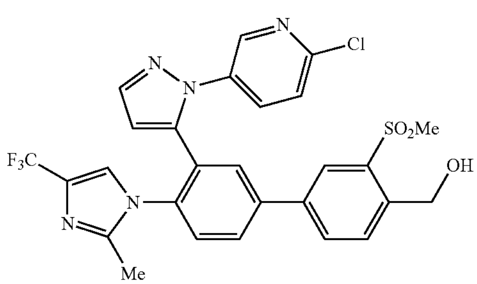 [SMILES: Cc1nc(C(F)(F)F)cn1-c1ccc(-c2ccc(CO)c(S(C)(=O)=O)c2)cc1-c1ccnn1-c1ccc(Cl)nc1] | (3'-(1-(6-chloropyridin-3-yl)-1H-pyrazol-5-yl)-4'-(2-methyl-4-(trifluoromethyl)-1H-imidazol-1-yl)-3-(methylsulfonyl)biphenyl-4-yl)methanol 1H NMR (400 MHz, CHLOROFORM-d) δ ppm 8.31 (d, J = 2.01 Hz, 1 H), 7.87-7.95 (m, 3 H), 7.75-7.86 (m, 3 H), 7.54 (dd, J = 8.66, 2.89 Hz, 1 H), 7.37 m, 2 H), 6.63 (d, J = 1.76 Hz, 1 H), 6.51 (d, J = 1.25 Hz, 1 H), 5.07 (s, 2 H), 3.26 (s, 3 H), 2.96 (t, J = 6.65 Hz, 1 H), 1.85 (s, 3 H) | MS (ESI) 588.2 [M + H]+ |
| 299 | 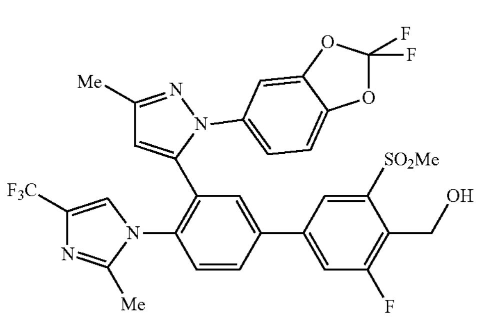 [SMILES: Cc1cc(-c2cc(-c3cc(F)c(CO)c(S(C)(=O)=O)c3)ccc2-n2cc(C(F)(F)F)nc2C)n(-c2ccc3c(c2)OC(F)(F)O3)n1] | (3'-(1-(2,2-difluorobenzo[d][1,3]dioxol-5-yl)-3-methyl-1H-pyrazol-5-yl)-3-fluoro-4'-(2-methyl-4-(trifluoromethyl)-1H-imidazol-1-yl)-5-(methylsulfonyl)biphenyl-4-yl)methanol 1H NMR (400 MHz, METHANOL-d4) δ ppm 8.22 (s, 1 H), 8.10 (d, J = 2 Hz, 1 H), 8.01 (dd, J = 8.66, 2.89 Hz, 1 H), 7.98 (m, 2 H), 7.57 (d, J = 8.4 Hz, 1H), 7.14 (d, J = 4.1 Hz, 1H), 6.95 (dd, J = 13.66, 2.89 Hz, 1 H), 6.77 (dd, J = 8.84, 2.41 Hz, 1 H), 6.54 (s, 1 H), 5.15 (s, 2 H), 3.41 (s, 3 H), 2.36 (s, 3 H), 1.87 (s, 3 H) | MS (ESI) 665.1 [M + H]+ |

| Ex # | Structure | Name Additional Characterization | Molecular Ion |
|---|---|---|---|
| 300 | 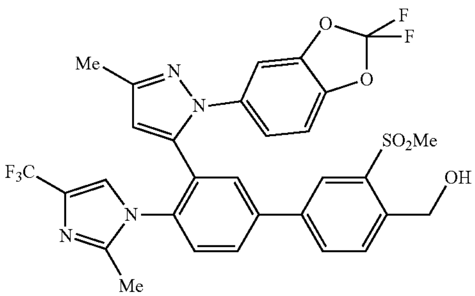 [SMILES: Cc1cc(-c2cc(-c3ccc(CO)c(S(C)(=O)=O)c3)ccc2-n2cc(C(F)(F)F)nc2C)n(-c2ccc3c(c2)OC(F)(F)O3)n1] | (3'-(1-(2,2-difluorobenzo[d][1,3]dioxol-5-yl)-3-methyl-1H-pyrazol-5-yl)-4'-(2-methyl-4-(trifluoromethyl)-1H-imidazol-1-yl)-3-(methylsulfonyl)biphenyl-4-yl)methanol | MS (ESI) 647.2 [M + H]+ |
| 301 | 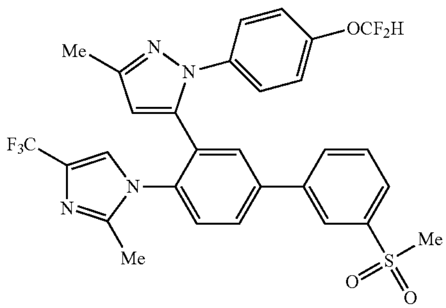 | 1-(4-(difluoromethoxy)phenyl)-3-methyl-5-(4-(2-methyl-4-(trifluoromethyl)-1H-imidazol-1-yl)-3'-(methylsulfonyl)biphenyl-3-yl)-1H-pyrazole | MS (ESI) 603.1 [M + H]+ |
| 302 | 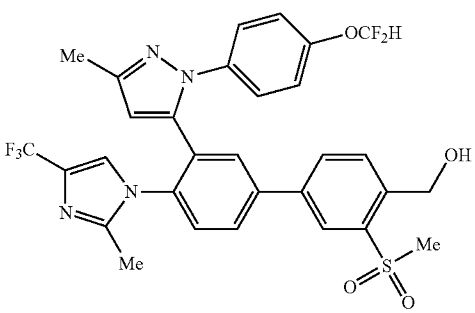 | (3'-(1-(4-(difluoromethoxy)phenyl)-3-methyl-1H-pyrazol-5-yl)-4'-(2-methyl-4-(trifluoromethyl)-1H-imidazol-1-yl)-3-(methylsulfonyl)-[1,1'-biphenyl]-4-yl)methanol | |
| 303 | 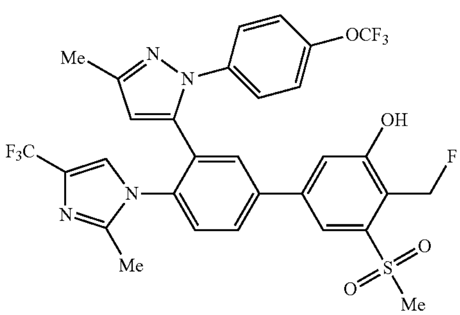 [SMILES: Cc1cc(-c2cc(-c3cc(O)c(CF)c(S(C)(=O)=O)c3)ccc2-n2cc(C(F)(F)F)nc2C)n(-c2ccc(OC(F)(F)F)cc2)n1] | 4-(fluoromethyl)-3'-(3-methyl-1-(4-(trifluoromethoxy)phenyl)-1H-pyrazol-5-yl)-4'-(2-methyl-4-(trifluoromethyl)-1H-imidazol-1-yl)-5-(methylsulfonyl)-[1,1'-biphenyl]-3-ol | MS (ESI) 669.4 [M + H]+ |
| 304 | 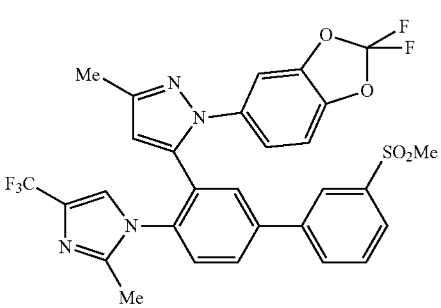 [SMILES: Cc1cc(-c2cc(-c3cccc(S(C)(=O)=O)c3)ccc2-n2cc(C(F)(F)F)nc2C)n(-c2ccc3c(c2)OC(F)(F)O3)n1] | 1-(2,2-difluorobenzo[d][1,3]dioxol-5-yl)-3-methyl-5-(4-(2-methyl-4-(trifluoromethyl)-1H-imidazol-1-yl)-3'-(methylsulfonyl)-[1,1'-biphenyl]-3-yl)-1H-pyrazole | MS (ESI) 617.2 [M + H]+ |

Scheme 5

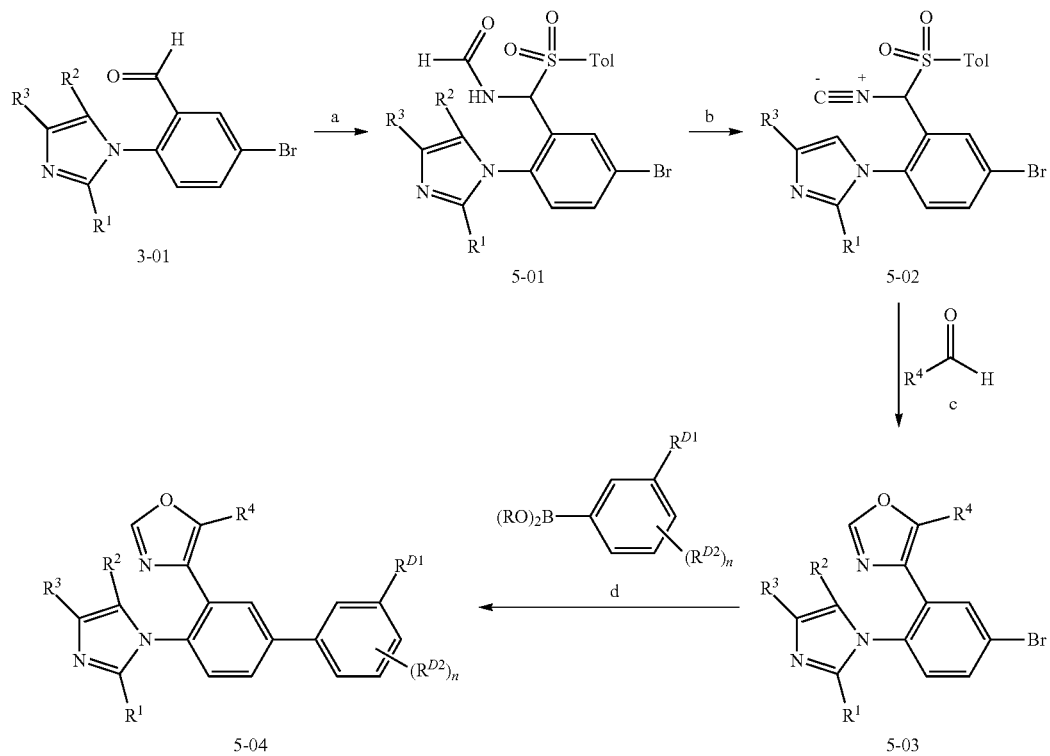

(a) HCONH₂, TMSCl; TolSO₂H, PhMe/MeCN, 50° C.; (b) POCl₃, Et₃N, THF, 0° C.; (c) K₂CO₃, MeOH/DME, reflux; (d) K₂CO₃, PdCl₂(dppf), DME/H₂O, 80° C.

Particular embodiments of the invention comprise compounds exemplified by general structure (5-04) shown in Scheme 5. In general, compounds represented by structure (5-04) are prepared by first reacting a benzaldehyde 3-01 with formamide and chlorotrimethylsilane, followed by 4-methylbenzenesulfinic acid to give the formamide 5-01. The resulting intermediate (5-01) is then reacted with phosphoryl chloride and triethylamine to provide 5-02. Reaction of this isocyanate with an appropriately substituted benzaldehyde in the presence of K₂CO₃ provides the oxazole (5-03). Compounds represented by the structure 5-04 are obtained by subjecting 5-03 to a palladium-mediated coupling reaction as described in Scheme 1.

Example 354

5-(4-chlorophenyl)-4-{3'-(methylsulfonyl)-4-[2-methyl-4-(trifluoromethyl)-1H-imidazol-1-yl]biphenyl-3-yl}-1,3-oxazole

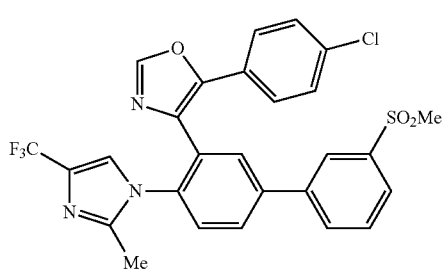 [SMILES: Cc1nc(C(F)(F)F)cn1-c1ccc(-c2cccc(S(C)(=O)=O)c2)cc1-c1ncoc1-c1ccc(Cl)cc1]

Example 354a

Preparation of N-((5-bromo-2-(2-methyl-4-(trifluoromethyl)-1H-imidazol-1-yl)phenyl)(tosyl)methyl)formamide

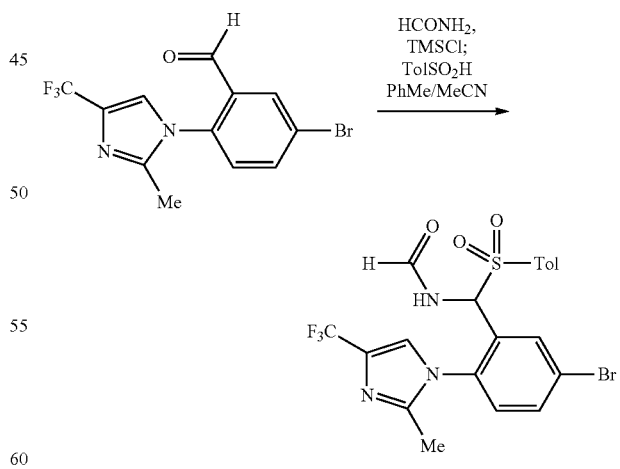

A 100 mL round-bottomed flask was purged with argon, then charged with dry MeCN (10 mL) and dry toluene (10 mL), followed by 5-bromo-2-(2-methyl-4-(trifluoromethyl)-1H-imidazol-1-yl)benzaldehyde (5.16 g, 15.5 mmol), formamide (1.54 mL, 38.7 mmol), and chlorotrimethylsilane (2.18 mL, 17.0 mmol). The reaction mixture was heated to 50° C. for 3 h, then 4-methylbenzenesulfinic acid (3.63 g, 23.2 mmol) was added and the mixture was allowed to stir at 50° C. for 16 h. The mixture was cooled to rt, diluted with EtOAc, and washed with H₂O and brine. The organic phase was dried over MgSO₄ and concentrated in vacuo to afford the crude title compound (8.89 g, 17.2 mmol) that was used directly in the next step.

Example 354b

Preparation of 1-(4-bromo-2-(isocyano(tosyl)methyl)phenyl)-2-methyl-4-(trifluoromethyl)-1H-imidazole

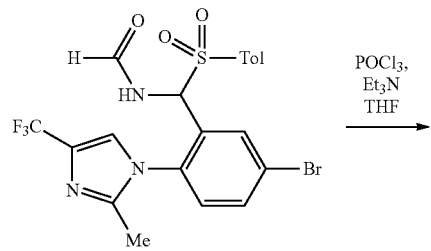

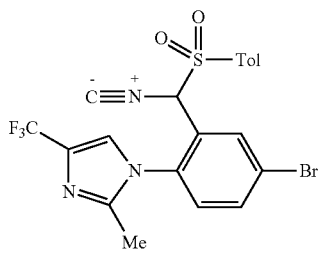

A 250 mL round-bottomed flask was purged with argon and charged with crude Example 354a (8.89 g, 17.2 mmol) and dry THF (100 mL). Phosphoryl chloride (3.15 mL, 34.4 mmol) was added and the reaction mixture was cooled to 0° C. Triethylamine (14.4 mL, 103 mmol) was then added slowly over 45 min, and the reaction vessel was held at 0° C. with stirring for an additional 45 min. EtOAc (30.0 mL) and water (30.0 mL) were added to the mixture, and vigorously stirred for 5 min. The aqueous layer was removed and the organics were washed with H₂O (×2), saturated aqueous NaHCO₃, and brine. After drying over MgSO₄, the solvent was removed in vacuo to yield crude title compound (7.92 g, 15.9 mmol) that was used directly in the next step.

Example 354c

Preparation of 4-(5-bromo-2-(2-methyl-4-(trifluoromethyl)-1H-imidazol-1-yl)phenyl)-5-(4-chlorophenyl)oxazole

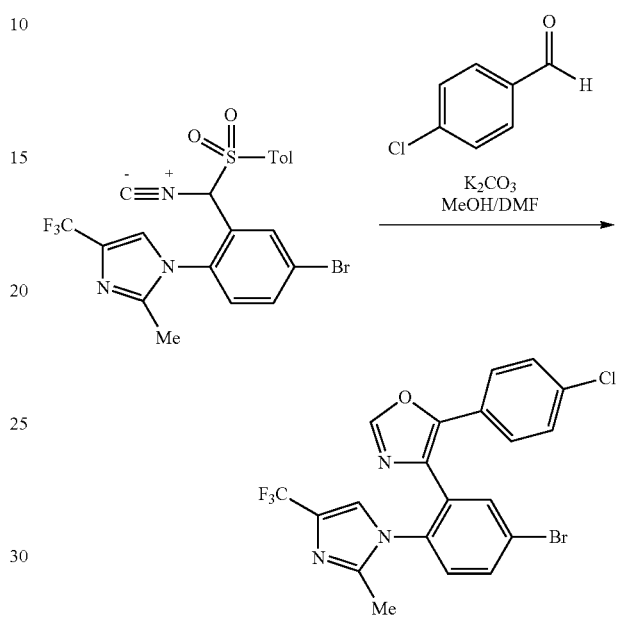

An 100 mL round-bottomed flask was charged with crude Example 354b (2.25 g, 4.52 mmol), 4-chlorobenzaldehyde (530 mg, 3.76 mmol), K₂CO₃ (1.25 g, 9.03 mmol), MeOH (30 mL), and DME (10 mL). The reaction mixture was heated at reflux for 20 h. The solvent was then evaporated in vacuo, and the residue was diluted with EtOAc, washed with H₂O and brine. After drying over MgSO₄, the solvent was evaporated in vacuo, and the resulting residue was purified by flash column chromatography to yield the title compound (260 mg, 0.540 mmol).

Example 354 was prepared from Example 354c and 3-(methylsulfonyl)-phenylboronic acid using procedures similar to that described in Example 1f. MS (ESI) 558.3 [M+H]+. ¹H NMR (400 MHz, CDCl₃) δ 8.22 (s, 1H), 8.03-7.92 (m, 4H), 7.83 (s, 1H), 7.72 (t, J=7.9 Hz, 1H), 7.47-7.42 (m, 1H), 7.32 (d, J=8.7 Hz, 2H), 7.22 (d, J=8.5 Hz, 2H), 6.80 (s, 1H), 3.12 (s, 3H), 2.06 (s, 3H).

Scheme 6

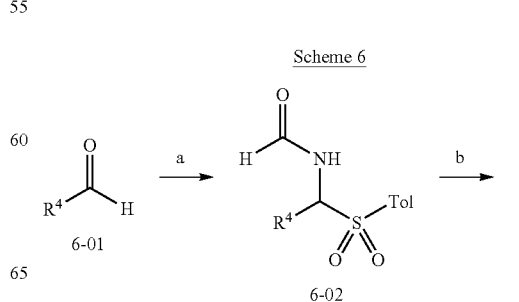

215
-continued

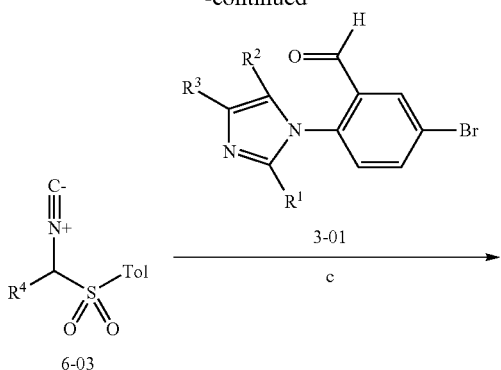

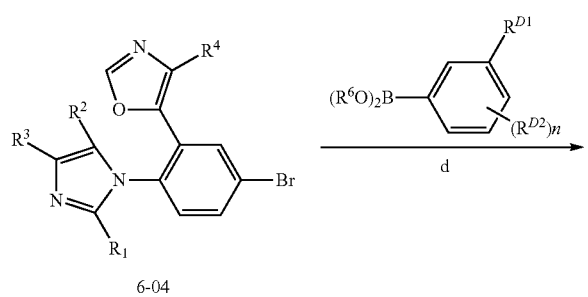

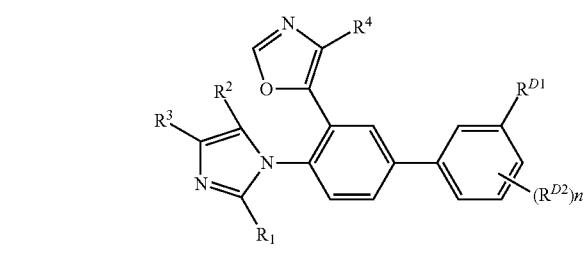

(a) HCONH₂, TMSCl; TolSO₂H, PhMe/ACN; (b) POCl₃, Et₃N, THF; (c) K₂CO₃, MeOH/DME, reflux; (d) K₂CO₃, PdCl₂(dppf), DME/H₂O, 80° C.

Additional embodiments of the invention comprise compounds exemplified by general structure (6-05) as shown in Scheme 6. In general, compounds represented by structure (6-05) are prepared by first reacting an appropriately substituted aldehyde 6-01 with formamide and chlorotrimethylsilane, followed by 4-methylbenzenesulfinic acid (TolSO₂H) to give (6-02). The resulting intermediate 6-02 is reacted with POCl₃ and Et₃N to provide 6-03. Reaction of this isocyanate (6-03) with the imidazolobenzaldehyde (3-01) in the presence of K₂CO₃ provides the oxazole (6-04). Compounds represented by the structure (6-05) are obtained by subjecting (6-04) to a palladium-mediated coupling reaction.

216

Example 355

{3'-[4-(4-chlorophenyl)-1,3-oxazol-5-yl]-3-fluoro-5-(methylsulfonyl)-4'-[2-methyl-4-(trifluoromethyl)-1H-imidazol-1-yl]biphenyl-4-yl}methanol

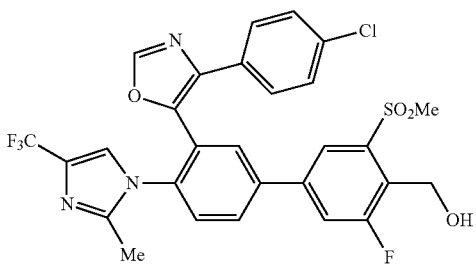 [SMILES: Cc1nc(C(F)(F)F)cn1-c1ccc(-c2cc(F)c(CO)c(S(C)(=O)=O)c2)cc1-c1ocnc1-c1ccc(Cl)cc1]

Example 355a

Preparation of N-((4-chlorophenyl)(tosyl)methyl)formamide

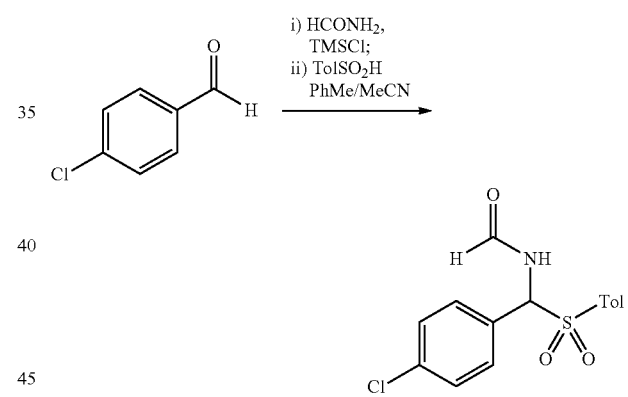

A 500 mL round-bottomed flask was purged with argon, charged with dry ACN (55 mL) and dry toluene (55 mL), followed by 4-chlorobenzaldehyde (14.8 g, 106 mmol), formamide (10.5 mL, 264 mmol), and chlorotrimethylsilane (14.7 mL, 116 mmol). The mixture was heated to 50° C. for 3 h, then 4-methylbenzenesulfinic acid (24.7 g, 158 mmol) was added and the reaction mixture was stirred at 50° C. for 16 h. The reaction mixture was cooled to rt, tert-butyl methyl ether (55 mL) was added, and the reaction mixture was stirred for 5 min. Water (275 mL) was added, and the mixture was cooled to 0° C. for 1 h. The precipitate was collected by filtration, washed with a small amount of tert-butyl methyl ether (35 mL), and dried in a vacuum oven to yield the title compound (25.3 g, 78.1 mmol).

Example 355b

Preparation of 1-chloro-4-(isocyano(tosyl)methyl)benzene

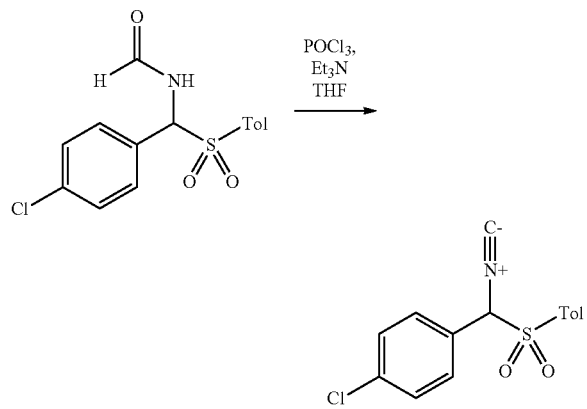

A 1 L round-bottomed flask was purged with argon and charged with Example 355a (25.3 g, 78.1 mmol) and dry THF (200 mL). POCl₃ (14.3 mL, 156 mmol) was added and the reaction mixture was cooled to 0° C. Triethylamine (65.3 mL, 469 mmol) was added slowly over 45 min, and the reaction mixture was held at 0° C. with stirring for an additional 45 min. Ethyl acetate (140 mL) and water (140 mL) were added to the mixture and stirred vigorously for 5 min. The aqueous layer was removed and the organics were washed with H$_2$O (2×140 mL), saturated aqueous NaHCO$_3$ (140 mL), and brine (70 mL). After drying over MgSO$_4$, the solvent was removed in vacuo to yield the crude title product that was used directly in the next step.

Example 355c

Preparation of 5-(5-bromo-2-(2-methyl-4-(trifluoromethyl)-1H-imidazol-1-yl)phenyl)-4-(4-chlorophenyl)oxazole

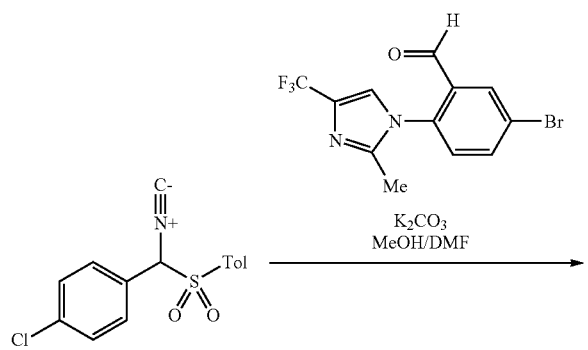

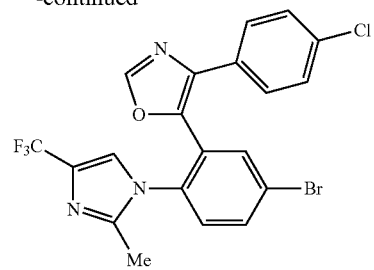

A 250 mL round-bottomed flask was charged with crude Example 355b (4.32 g, 14.1 mmol), 5-bromo-2-(2-methyl-4-(trifluoromethyl)-1H-imidazol-1-yl)benzaldehyde (prepared from 2-methyl-4-(trifluoromethyl)-1H-imidazole and 5-bromo-2-fluorobenzaldehyde by a similar procedure to Example 1a) (3.92 g, 11.8 mmol), K$_2$CO$_3$ (3.90 g, 28.2 mmol), MeOH (100 mL), and DME (30 mL). The mixture was heated at reflux for 2 h. The solvent was then evaporated in vacuo, and the residue was diluted with EtOAc, then washed with H$_2$O and brine. After drying over MgSO$_4$, the solvent was evaporated in vacuo, and the resulting residue was purified by flash column chromatography to yield the title compound (3.71 g, 7.69 mmol).

Example 355 was prepared from Example 355c and Intermediate 1 using procedures similar to that described in Example 1f. MS (ESI) 606.5 [M+H]⁺. ¹H NMR (400 MHz, MeOD) δ 8.38 (d, J=0.9 Hz, 1H), 8.24 (s, 1H), 8.20 (d, J=2.0 Hz, 1H), 8.09 (dd, J=8.3, 2.1 Hz, 1H), 7.94 (d, J=10.4 Hz, 1H), 7.71 (d, J=8.3 Hz, 1H), 7.37 (m, 4H), 7.25 (s, 1H), 5.16 (s, 2H), 3.42 (s, 3H), 2.03 (s, 3H).

Example 356

(4'-(4-(1,1-difluoroethyl)-2-methyl-1H-imidazol-1-yl)-3-fluoro-5-(methylsulfonyl)-3'-(4-(4-(trifluoromethoxy)phenyl)oxazol-5-yl)biphenyl-4-yl)methanol

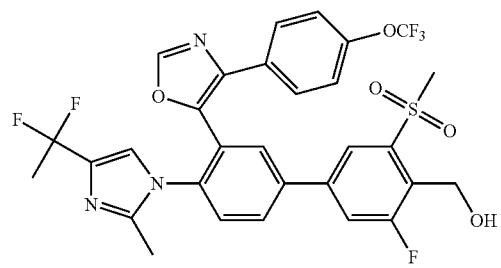 [SMILES: Cc1nc(C(C)(F)F)cn1-c1ccc(-c2cc(F)c(CO)c(S(C)(=O)=O)c2)cc1-c1ocnc1-c1ccc(OC(F)(F)F)cc1]

Example 356a

Preparation of 2-methyl-1H-imidazole-4-carbonitrile

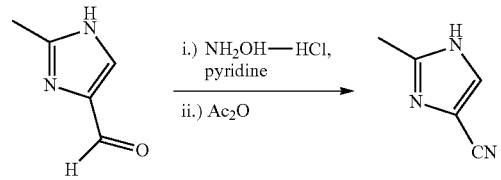

In a dry N₂ purged three-neck round bottom flask, 2-methyl-1H-imidazole-4-carbaldehyde (20.0 g, 182 mmol) and hydroxylamine hydrochloride (15.2 g, 218 mmol) were brought up in pyridine (150 mL) and stirred for 2 hrs at rt. The reaction mixture was brought to a reflux at 80° C., and acetic anhydride (34.3 mL, 363 mmol) was added dropwise over 30 min. The reaction mixture was allowed to cool to rt and was quenched with 10% NaOH (400 mL). The solution was diluted with EtOAc (300 mL) and the layers were separated. The aqueous layer was extracted with EtOAc (300 mL×2). The combined organics were washed with aq. NaCl (200 mL), dried over Na₂SO₄, filtered into a flask and concentrated in vacuo. The product was dissolved in toluene (200 mL×2) and re-concentrated in vacuo to give the title compound as a light tan solid, (19.5 g, 182 mmol, 100% yield). MS (ESI) 108 [M+H]⁺. ¹H NMR (400 MHz, DMSO) δ 7.82 (d, J=5.0 Hz, 1H), 2.30 (d, J=23.8 Hz, 3H).

Example 356b

Preparation of 1-(2-methyl-1H-imidazol-4-yl)ethanone

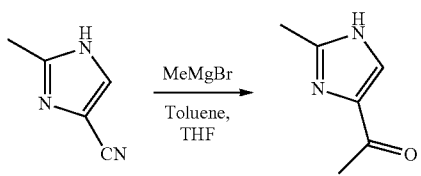

In a dry N₂ purged three-neck round bottom flask, MeMgBr in diethyl ether (153 mL, 458 mmol) was cooled to −10° C. A solution of 2-methyl-1H-imidazole-4-carbonitrile (15.3 g, 143 mmol) in toluene (300 mL) and THF (300 mL) was added dropwise via an addition funnel. The reaction solution was allowed to warm to rt and was stirred for 6 hrs. The reaction mixture was cooled to 0° C. quenched with 10% aq. H₂SO₄ (300 mL), then brought to pH=1, so the solids dissolved into solution. The organic layer was evaporated and then stirred in 1M HCl overnight. The reaction solution was neutralized to pH=7 with 2M NaOH. The water was evaporated and the crude material was purified by chromatography thru a 300 g SiO₂ column using a mobile phase gradient of 20% MeOH/CH₂Cl₂ with 0.1% NH₄OH to afford the title compound as yellow solid (17.0 g, 137 mmol, 96% yield). MS (ESI) 125 [M+H]⁺.

Example 356c

Preparation of 2-(4-acetyl-2-methyl-1H-imidazol-1-yl)-5-bromobenzonitrile

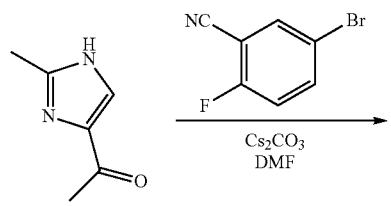

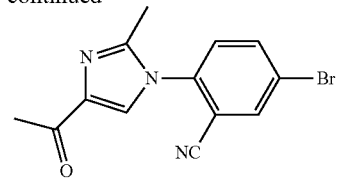

1-(2-methyl-1H-imidazol-4-yl)ethanone (8.00 g, 64.4 mmol), 5-bromo-2-fluorobenzonitrile (12.9 g, 64.5 mmol) and Cs₂CO₃ (63.0 g, 193 mmol) were brought up in DMF (40 mL) and stirred at 70° C. for 2 h. The reaction mixture was cooled to rt, and water (300 mL) was added to precipitate the product from solution. The solids were filtered and washed with water, followed by isopropyl ether. The solids were dried overnight to afford the title compound as a grey solid (8.20 g, 27.0 mmol, 42% yield). MS (ESI) 304, 306 [M+H]⁺.

Example 356d

Preparation of 5-bromo-2-(2-methyl-4-(2-methyl-, 3-dithiolan-2-yl)-1H-imidazol-1-yl)benzonitrile

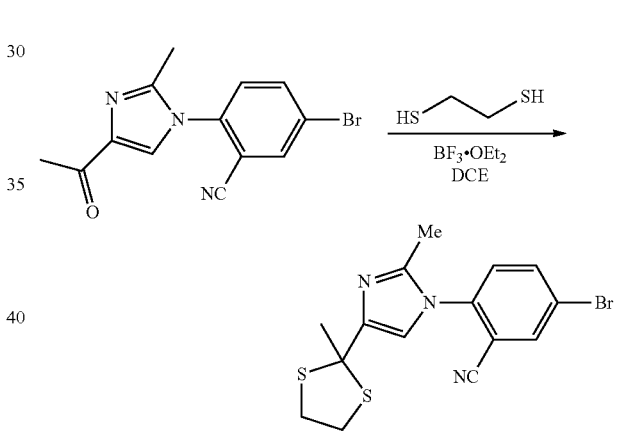

In a dry round bottom flask, 2-(4-acetyl-2-methyl-1H-imidazol-1-yl)-5-bromobenzonitrile (8.20 g, 27.0 mmol) and ethane-1,2-dithiol (3.40 mL, 40.4 mmol) were brought up in anhydrous DCE (100 mL). To the mixture was added BF₃·OEt₂ (8.20 mL, 64.7 mmol) dropwise and the mixture was heated to 67° C. for 4 h. The reaction mixture was poured into ice-cold saturated aq NaHCO₃ (100 mL) and then diluted with CH₂Cl₂ (100 mL). The layers were separated, and the aqueous layer was extracted with CH₂Cl₂ (50 mL×3). The combined organics were dried over Na₂SO₄, filtered into a round bottom flask and concentrated in vacuo to give the crude product. The crude material was purified by chromatography thru a 100 g SiO₂ column using a mobile phase gradient of 20% to 100% EtOAc/Hx to afford the title compound as pale orange/brown crystals (7.70 g, 20.3 mmol, 75% yield). MS (ESI) 379, 381 [M+H]⁺.

Example 356e

Preparation of 5-bromo-2-(4-(1,1-difluoroethyl)-2-methyl-1H-imidazol-1-yl)benzonitrile

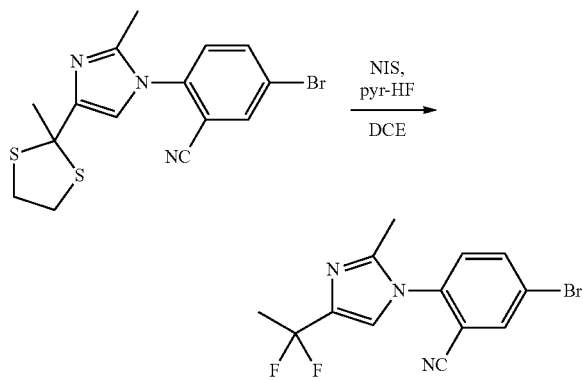

NIS (2.5 g, 11 mmol) was suspended in DCE (20 mL) and cooled to −78° C. followed by dropwise addition of HF-Pyridine (15.6 g, 158 mmol). The reaction mixture was further allowed to stir at −78° C. for 30 min. The Example 356d (550 mg, 1.4 mmol) was dissolved in DCE (5.0 mL) and added to the reaction mixture dropwise. The reaction solution was stirred at −78° C. for 15 min before it was quenched with saturated aq NaHCO$_3$ (25 mL) and saturated aq Na$_2$S$_2$O$_3$ (20 mL). The solution was extracted with DCM (40 mL×2). The combined organics were dried over Na$_2$SO$_4$, filtered into a round bottom flask and concentrated in vacuo to give the crude product. The crude material was purified by chromatography thru a 25 g SiO$_2$ column using a mobile phase gradient of 30% to 80% EtOAc/Hx to afford the title compound as a pale orange solid (360 mg, 1.1 mmol, 79% yield). MS (ESI) 326, 328 [M+H]$^+$.

Example 356f

Preparation of 5-bromo-2-(4-(1,1-difluoroethyl)-2-methyl-1H-imidazol-1-yl)benzaldehyde

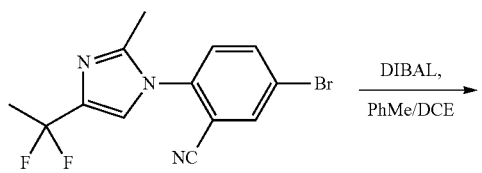

Example 356e (4.46 g, 13.7 mmol) was dissolved in anhydrous DCE (20 mL) and toluene (20 mL) and cooled to −60° C. DIBAL-H (20.5 mL, 20.5 mmol) in toluene was added dropwise, and the reaction mixture was maintained at −60° C. for one hr. The reaction solution was quenched with 1 M HCl (40 mL), and then heated to 80° C. for 30 min. After cooling to rt, the reaction solution was extracted with CH$_2$Cl$_2$ (50 mL×2). The combined organics were dried over Na$_2$SO$_4$, filtered into a round bottom flask and concentrated in vacuo to give the crude product. The crude material was purified by chromatography thru 80 g SiO$_2$ column using a mobile phase gradient of 30% to 100% EtOAc/Hx to afford the title compound as a yellow solid (2.40 g, 7.29 mmol, 53% yield). MS (ESI) 329, 331 [M+H]$^+$.

Example 356 was prepared from Example 356f using procedures similar to that described in Example 355 and Example 1f. MS (ESI) 652.1 [M+H]$^+$. 1H NMR (400 MHz, CDCl$_3$) δ 8.14 (s, 1H), 7.92 (m, 2H), 7.88-7.79 (m, 1H), 7.61 (d, J=9.8 Hz, 1H), 7.56-7.40 (m, 3H), 7.19 (m, 2H), 6.68 (t, J=7.4 Hz, 1H), 5.10 (d, J=6.6 Hz, 2H), 3.29 (s, 3H), 2.88 (t, J=6.6 Hz, 1H), 2.03 (s, 3H), 1.87 (t, J=18.2 Hz, 3H).

The following compounds were prepared in a manner similar to that described in the preceeding Examples:

| Ex # | Structure | Name | Molecular Ion |
|---|---|---|---|
| 357 | 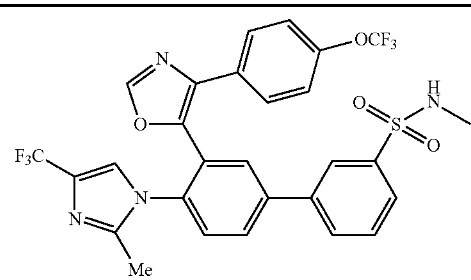 | N-methyl-4'-[2-methyl-4-(trifluoromethyl)-1H-imidazol-1-yl]-3'-(4-{4-[(trifluoromethyl)oxy]phenyl}-1,3-oxazol-5-yl)biphenyl-3-sulfonamide | MS (ESI) 623.5 [M + H]$^+$ |

-continued

| Ex # | Structure | Name | Molecular Ion |
|---|---|---|---|
| 358 | 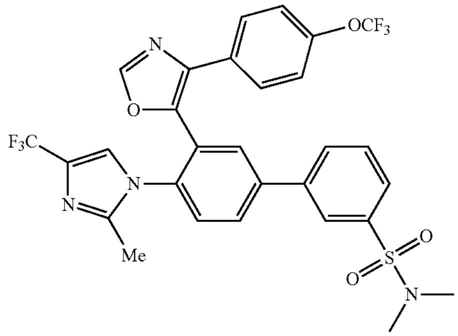 [SMILES: Cc1nc(C(F)(F)F)cn1-c1ccc(-c2cccc(S(=O)(=O)N(C)C)c2)cc1-c1ocnc1-c1ccc(OC(F)(F)F)cc1] | N,N-dimethyl-4'-[2-methyl-4-(trifluoromethyl)-1H-imidazol-1-yl]-3'-(4-{4-[(trifluoromethyl)oxy]phenyl}-1,3-oxazol-5-yl)biphenyl-3-sulfonamide | MS (ESI) 637.3 [M + H]+. |
| 359 | 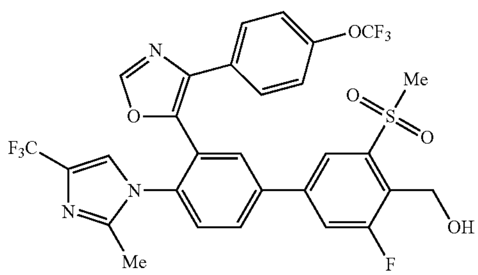 [SMILES: Cc1nc(C(F)(F)F)cn1-c1ccc(-c2cc(F)c(CO)c(S(C)(=O)=O)c2)cc1-c1ocnc1-c1ccc(OC(F)(F)F)cc1] | [3-fluoro-5-(methylsulfonyl)-4'-[2-methyl-4-(trifluoromethyl)-1H-imidazol-1-yl]-3'-(4-{4-[(trifluoromethyl)oxy]phenyl}-1,3-oxazol-5-yl)biphenyl-4-yl]methanol | MS (ESI) 656.3 [M + H]+. |
| 360 | 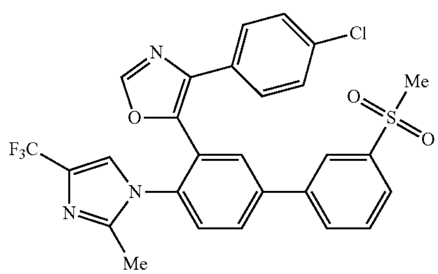 [SMILES: Cc1nc(C(F)(F)F)cn1-c1ccc(-c2cccc(S(C)(=O)=O)c2)cc1-c1ocnc1-c1ccc(Cl)cc1] | 4-(4-chlorophenyl)-5-{3'-(methylsulfonyl)-4-[2-methyl-4-(trifluoromethyl)-1H-imidazol-1-yl]biphenyl-3-yl}-1,3-oxazole | MS (ESI) 558.3 [M + H]+. |
| 361 | 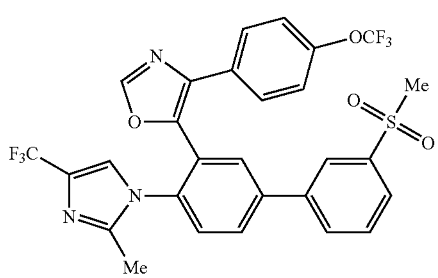 [SMILES: Cc1nc(C(F)(F)F)cn1-c1ccc(-c2cccc(S(C)(=O)=O)c2)cc1-c1ocnc1-c1ccc(OC(F)(F)F)cc1] | 5-{3'-(methylsulfonyl)-4-[2-methyl-4-(trifluoromethyl)-1H-imidazol-1-yl]biphenyl-3-yl}-4-{4-[(trifluoromethyl)oxy]phenyl}-1,3-oxazole | MS (ESI) 608.3 [M + H]+. |
| 362 | 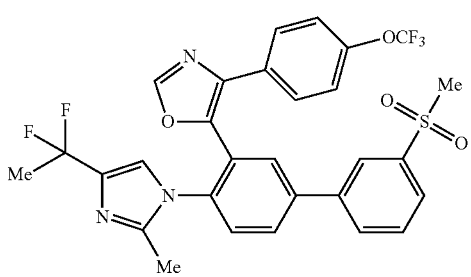 [SMILES: Cc1nc(C(C)(F)F)cn1-c1ccc(-c2cccc(S(C)(=O)=O)c2)cc1-c1ocnc1-c1ccc(OC(F)(F)F)cc1] | 5-{4-[4-(1,1-difluoroethyl)-2-methyl-1H-imidazol-1-yl]-3'-(methylsulfonyl)biphenyl-3-yl}-4-{4-[(trifluoromethyl)oxy]phenyl}-1,3-oxazole | MS (ESI) 604.1 [M + H]+ |

-continued

| Ex # | Structure | Name | Molecular Ion |
|---|---|---|---|
| 363 | 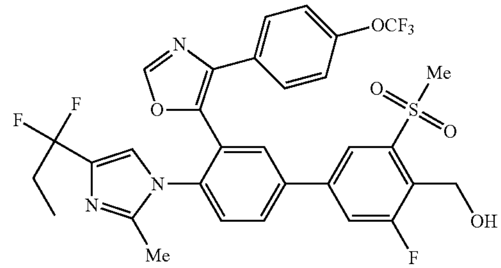 [SMILES: CCC(F)(F)c1cn(-c2ccc(-c3cc(F)c(CO)c(S(C)(=O)=O)c3)cc2-c2ocnc2-c2ccc(OC(F)(F)F)cc2)c(C)n1] | {4'-[4-(1,1-difluoropropyl)-2-methyl-1H-imidazol-1-yl]-3-fluoro-5-(methylsulfonyl)-3'-(4-{4-[(trifluoromethyl)oxy]phenyl}-1,3-oxazol-5-yl)biphenyl-4-yl}methanol | MS (ESI) 666.1 [M + H]+ |
| 364 | 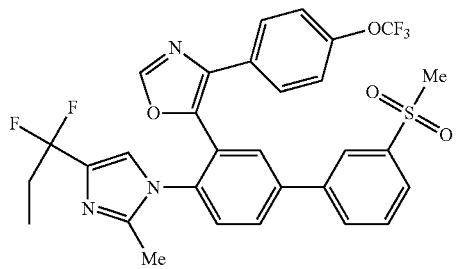 [SMILES: CCC(F)(F)c1cn(-c2ccc(-c3cccc(S(C)(=O)=O)c3)cc2-c2ocnc2-c2ccc(OC(F)(F)F)cc2)c(C)n1] | 5-{4-[4-(1,1-difluoropropyl)-2-methyl-1H-imidazol-1-yl]-3'-(methylsulfonyl)biphenyl-3-yl}-4-{4-[(trifluoromethyl)oxy]phenyl}-1,3-oxazole | MS (ESI) 618.1 [M + H]+ |
| 365 | 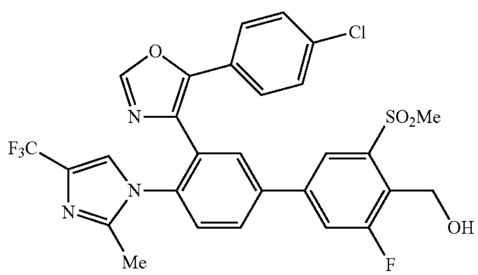 [SMILES: Cc1nc(C(F)(F)F)cn1-c1ccc(-c2cc(F)c(CO)c(S(C)(=O)=O)c2)cc1-c1ncoc1-c1ccc(Cl)cc1] | {3'-[5-(4-chlorophenyl)-1,3-oxazol-4-yl]-3-fluoro-5-(methylsulfonyl)-4'-[2-methyl-4-(trifluoromethyl)-1H-imidazol-1-yl]biphenyl-4-yl}methanol | MS (ESI) 606.5 [M + H]+ |

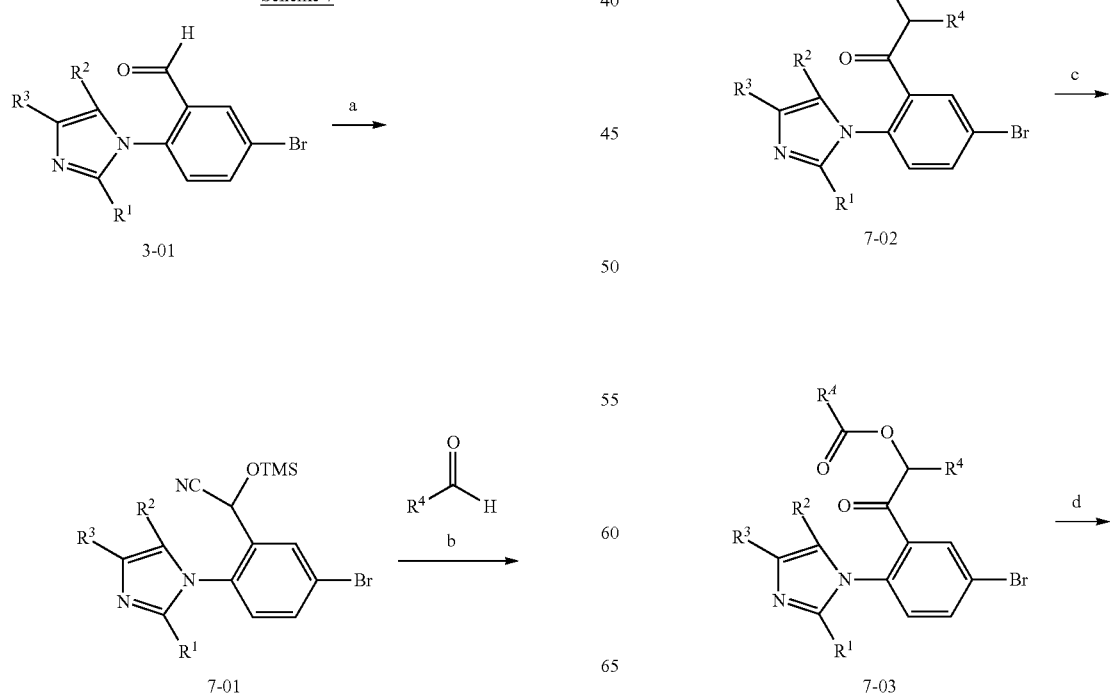

Scheme 7

227

-continued

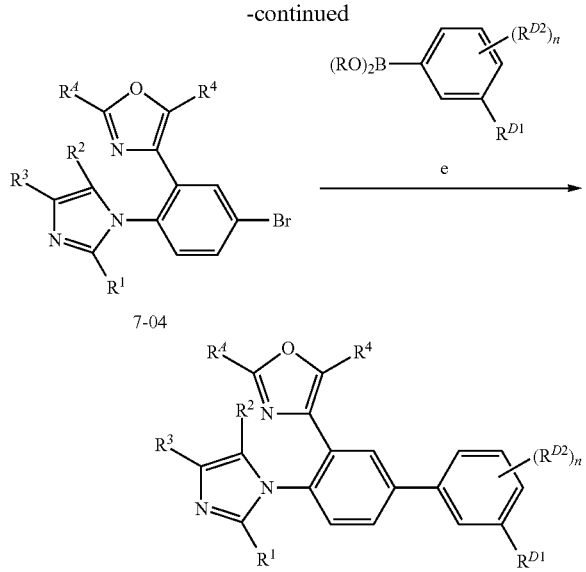

7-04

7-05

(a) TMSCN, ZnI₂, DCM; (b) LHMDS, THF, -78° C.-rt; (c) (R₂CO)₂O or R₂COCl, DMAP, DCM; (d) NH₄OAc, AcOH, reflux; (e) K₂CO₃, PdCl₂(dppf), DME/H₂O, 80° C.

Selected compounds of the invention, represented by structure (7-05), are prepared by first reacting the substituted imidazolobenzaldehyde (see 3-01) with trimethylsilyl cyanide in the presence of catalytic zinc iodide to afford the TMS-cyanohydrin (7-01). The intermediate 7-01 is deprotonated with lithium bis(trimethylsilyl)amide and subsequently reacted with an appropriate substituted aldehyde to provide benzoin (7-02). Reaction of 7-02 with an appropriately substituted anhydride or acid chloride reagent in the presence of catalytic 4-(dimethylamino)pyridine provides the acylated material (7-03), and cyclization is accomplished with ammonium acetate in acetic acid to afford oxazole 7-04. The final compounds represented by 7-05 are obtained by subjecting (7-04) to a palladium-mediated coupling reaction as known to own skilled in the art. Additional functional group transformations can be carried out during the synthesis as known to one skilled in the art to afford compounds of the invention.

Example 366

2-methyl-4-{3'-(methylsulfonyl)-4-[2-methyl-4-(trifluoromethyl)-1H-imidazol-1-yl]biphenyl-3-yl}-5-{4-[(trifluoromethyl)oxy]phenyl}-1,3-oxazole

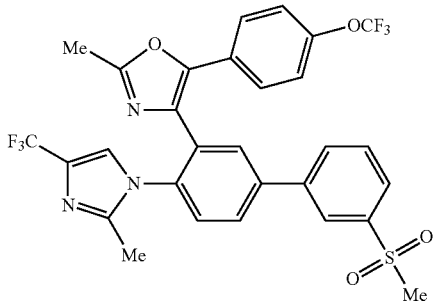 [SMILES: Cc1nc(-c2cc(-c3cccc(S(C)(=O)=O)c3)ccc2-n2cc(C(F)(F)F)nc2C)c(-c2ccc(OC(F)(F)F)cc2)o1]

228

Example 366a

Preparation of 2-(5-bromo-2-(2-methyl-4-(trifluoromethyl)-1H-imidazol-1-yl)phenyl)-2-(trimethylsilyloxy)acetonitrile

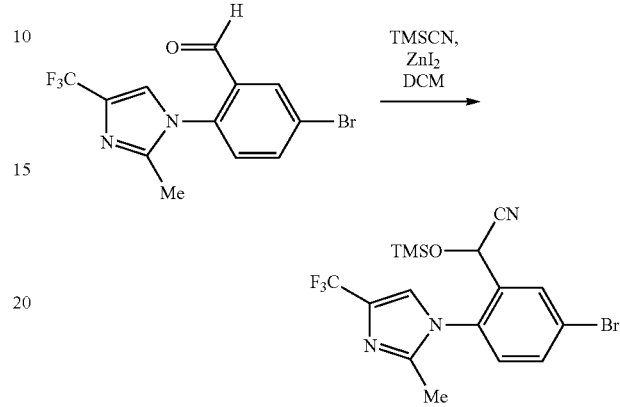

To a solution of 5-bromo-2-(2-methyl-4-(trifluoromethyl)-1H-imidazol-1-yl)benzaldehyde (1.29 g, 3.88 mmol) in DCM (10 mL) was added trimethylsilyl cyanide (0.540 mL, 4.07 mmol), and the reaction flask was cooled to 0° C. Zinc iodide (62.0 mg, 194 µmol) was added portionwise to the reaction solution, and the reaction mixture was allowed to warm to rt and stir for 17 h. The mixture was poured into brine, extracted with EtOAc, dried over MgSO₄, and concentrated in vacuo to yield the title compound (1.68 g, 3.89 mmol), which was carried forward without subsequent purification.

Example 366b

Preparation of 1-(5-bromo-2-(2-methyl-4-(trifluoromethyl)-1H-imidazol-1-yl)phenyl)-2-hydroxy-2-(4-(trifluoromethoxy)phenyl)ethanone

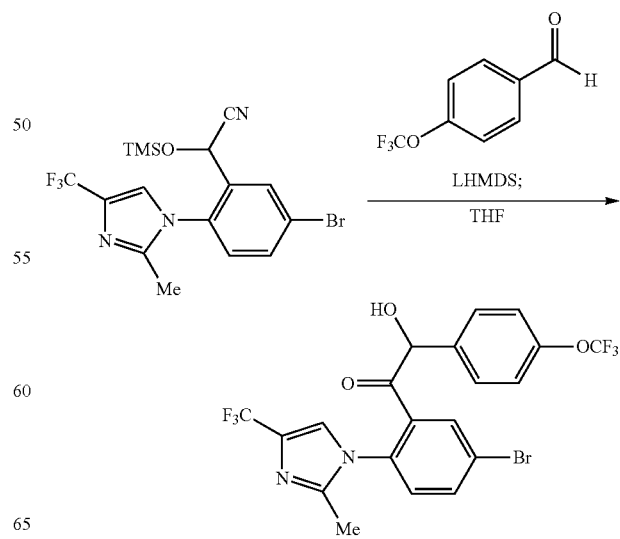

A 100 mL round-bottomed flask was purged with argon and charged with Example 366a (1.68 g, 3.89 mmol) and THF (20.0 mL) and cooled to −78° C. Lithium bis(trimethylsilyl)amide (4.86 mL, 4.86 mmol) was added slowly, and the reaction mixture was allowed to stir at −78° C. for 1 h. 4-(Trifluoromethoxy)benzaldehyde (0.580 mL, 4.08 mmol) was added dropwise, and the reaction mixture was subsequently allowed to warm to rt. After 1 h of stirring at rt, 1M HCl (5.0 mL) was added, and the mixture was allowed to stir for one hr. The reaction mixture was then extracted with EtOAc, washed with H$_2$O and brine, dried over MgSO$_4$, and concentrated in vacuo to yield the crude title compound that was taken on directly to the next step.

Example 366c

Preparation of 2-(5-bromo-2-(2-methyl-4-(trifluoromethyl)-1H-imidazol-1-yl)phenyl)-2-oxo-1-(4-(trifluoromethoxy)phenyl)ethyl acetate

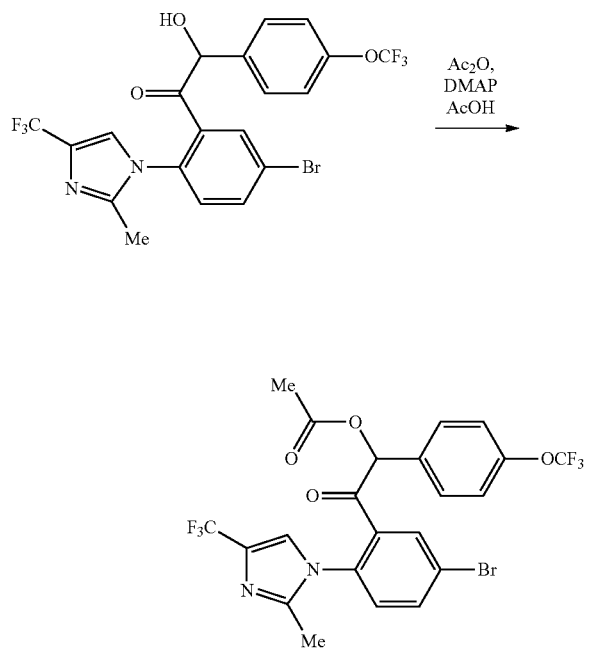

A 100 mL round-bottomed flask was charged with Example 366b (2.31 g, 4.42 mmol), DCM (20.0 mL), acetic anhydride (1.25 mL, 13.3 mmol), and 4-(dimethylamino)pyridine (5.0 mg). After stirring for 15 h, the mixture was poured into brine, extracted with EtOAc, and then washed with brine. The organics were dried over MgSO$_4$, concentrated in vacuo, and the resulting residue was purified by flash column chromatography to yield the title compound (490 mg, 0.870 mmol).

Example 366d

Preparation of 4-(5-bromo-2-(2-methyl-4-(trifluoromethyl)-1H-imidazol-1-yl)phenyl)-2-methyl-5-(4-(trifluoromethoxy)phenyl)oxazole

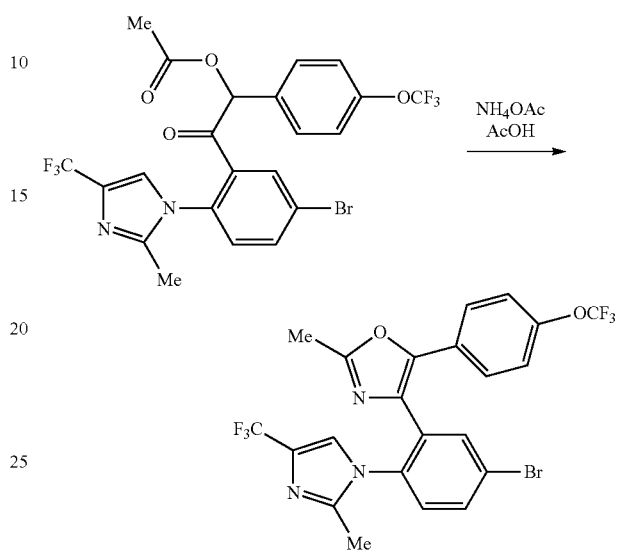

A 100 mL round-bottomed flask was charged with Example 366c (0.49 g, 0.87 mmol), ammonium acetate (0.67 g, 8.7 mmol), and acetic acid (30 mL). The mixture was heated to reflux for 30 h. The mixture was treated with KOH, extracted with EtOAc, and then washed with 1 M KOH, H$_2$O, and brine. The organics were then dried over MgSO$_4$ and concentrated in vacuo. The resulting residue was purified by flash column chromatography to yield the title compound (0.16 g, 290 μmol).

Example 366 was prepared from Example 366d and 3-methylsulfonylphenylboronic acid using procedures similar to that described in Example 1f. MS (ESI) 622.5 [M+H]$^+$. 1H NMR (400 MHz, CDCl$_3$) δ 8.18 (s, 1H), 8.02 (d, J=7.6 Hz, 1H), 7.93 (s, 1H), 7.82 (m, 2H), 7.71 (t, J=7.8 Hz, 1H), 7.52 (s, 1H), 7.44 (d, J=8.7 Hz, 2H), 7.19 (d, J=8.2 Hz, 2H), 6.92 (s, 1H), 3.12 (s, 3H), 2.47 (s, 3H), 2.17 (s, 3H).

Example 3675

(4-(difluoromethoxy)-3,5-difluorophenyl)-2-methyl-4-(4-(2-methyl-4-(trifluoromethyl)-1H-imidazol-1-yl)-3'-(methylsulfonyl)-[, 1'-biphenyl]-3-yl)oxazole

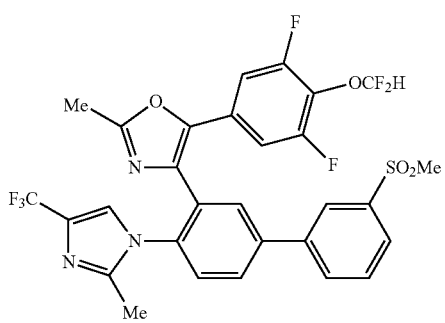

Example 367a

Preparation of 2-(5-bromo-2-(2-methyl-4-(trifluoromethyl)-1H-imidazol-1-yl)phenyl)-2-(trimethylsilyloxy)acetonitrile

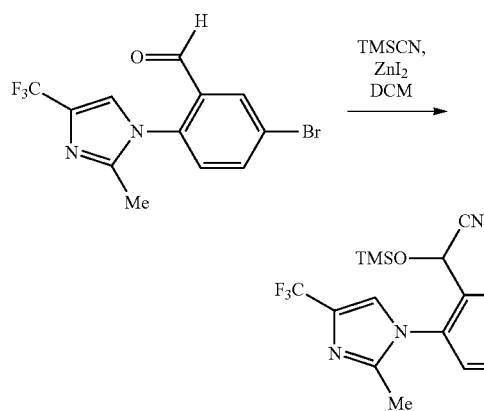

To a solution of 5-bromo-2-(2-methyl-4-(trifluoromethyl)-1H-imidazol-1-yl)benzaldehyde (1.29 g, 3.88 mmol) in DCM (10 mL) was added trimethylsilyl cyanide (0.540 mL, 4.07 mmol), and the reaction flask was cooled to 0° C. Zinc iodide (62.0 mg, 194 µmol) was added portionwise to the reaction solution, and then the reaction mixture was allowed to warm to rt and stir for 17 h. The mixture was poured into brine, extracted with EtOAc, dried over MgSO$_4$, and concentrated in vacuo to yield the title compound (1.68 g, 3.89 mmol), which was carried forward without subsequent purification.

Example 367b 1-(5-bromo-2-(2-methyl-4-(trifluoromethyl)-1H-imidazol-1-yl)phenyl)-2-(4-(difluoromethoxy)-3,5-difluorophenyl)-2-hydroxyethanone

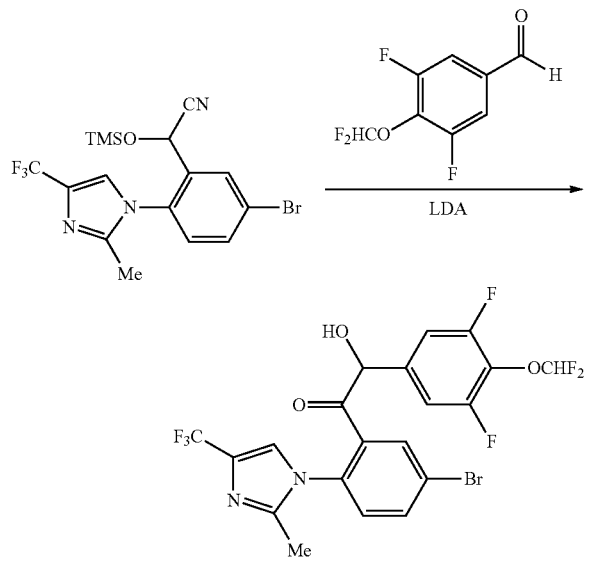

A 100 mL round-bottomed flask was purged with argon and charged with Example 367a (1.50 g, 3.47 mmol) and THF (30 mL) and cooled to −78° C. Lithium bis(trimethylsilyl)amide (3.47 mL, 6.94 mmol) was added slowly, and the reaction mixture was allowed to stir at −78° C. for 1 h. 4-(difluoromethoxy)-3,5-difluorobenzaldehyde (0.722 g, 3.47 mmol) in THF (5 mL) was added dropwise, and the reaction mixture was subsequently allowed to warm to rt. After 1 h of stirring at rt, 1M HCl (5.0 mL) was added, and the mixture was allowed to stir for one hr. The reaction mixture was then extracted with EtOAc, washed with H$_2$O and brine, dried over MgSO$_4$, and concentrated in vacuo to yield the crude title compound that was taken on directly to the next step. MS (ESI) 540.60 [M+H]$^+$

Example 367c 2-(5-bromo-2-(2-methyl-4-(trifluoromethyl)-1H-imidazol-1-yl)phenyl)-1-(4-(difluoromethoxy)-3,5-difluorophenyl)-2-oxoethylacetate

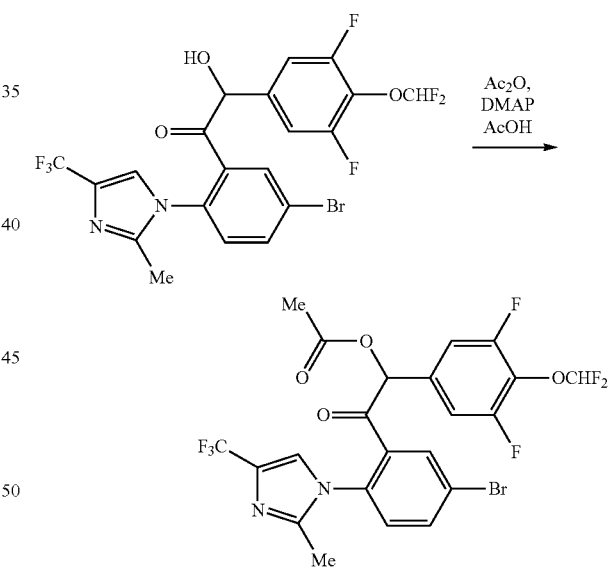

A 100 mL round-bottomed flask was charged with Example 367b (1.90 g, 3.51 mmol), DCM (30 mL), acetic anhydride (0.397 mL, 4.21 mmol), and triethyl amine (1.4 mL, 10 mmol). After stirring for 6 h, the mixture was poured into brine, extracted with EtOAc, and then washed with brine. The organics were dried over MgSO$_4$, concentrated in vacuo, and the resulting residue was purified by flash column chromatography to yield the title compound (2.1 g, 3.6 mmol). MS (ESI) 582.80 [M+H]$^+$

Example 367d 4-(5-bromo-2-(2-methyl-4-(trifluoromethyl)-1H-imidazol-1-yl)phenyl)-5-(4-(difluoromethoxy)-3,5-difluorophenyl)-2-methyloxazole

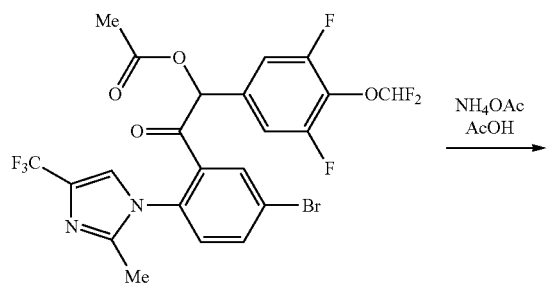

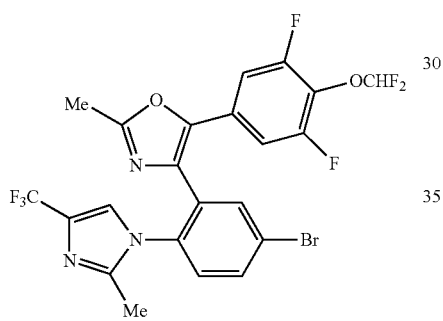

A 100 mL round-bottomed flask was charged with Example 367c (2.1 g, 3.6 mmol), ammonium acetate (0.278 g, 3.60 mmol), and acetic acid (25 mL). The mixture was heated to reflux for 6 h. Acetic acid was removed under reduced pressure. The mixture was extracted with DCM, and then washed with NaHCO₃, H₂O, and brine. The organics were dried over MgSO₄ and concentrated in vacuo. The resulting residue was purified by flash column chromatography to yield the title compound (0.30 g, 0.53 mmol). MS (ESI) 566.0 [M+H]⁺

Example 367 was prepared from Example 367d and 3-methylsulfonylphenylboronic acid using procedures similar to that described in Example 1f. MS (ESI) 640.0 [M+H]⁺.
¹H NMR (400 MHz, CHLOROFORM-d) δ ppm 8.17 (t, 1H, J=1.63 Hz), 8.03 (m, 1H), 7.94 (d, 1H, J=2.00 Hz), 7.85-7.91 (m, 2H), 7.71-7.77 (m, 1H), 7.55 (d, 1H, J=8.25 Hz), 7.06-7.13 (m, 2H), 7.01 (d, 1H, J=1.25 Hz), 6.43-6.81 (m, 1H), 3.12 (s, 3H), 2.45 (s, 3H), 2.16 (s, 3H)

Example 368

2,2-difluoro-5-(2-methyl-4-(4-(2-methyl-4-(trifluoromethyl)-1H-imidazol-1-yl)-3'-(methylsulfonyl)biphenyl-3-yl)oxazol-5-yl)-2,3-dihydrobenzofuran-3-ol

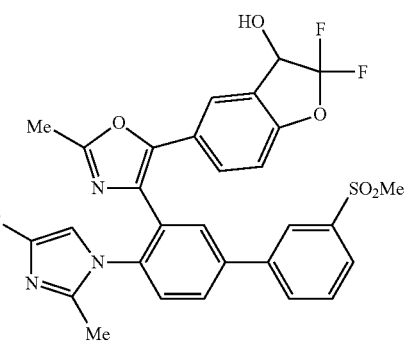

Example 368a

Preparation of methyl 3-oxo-2,3-dihydrobenzofuran-5-carboxylate

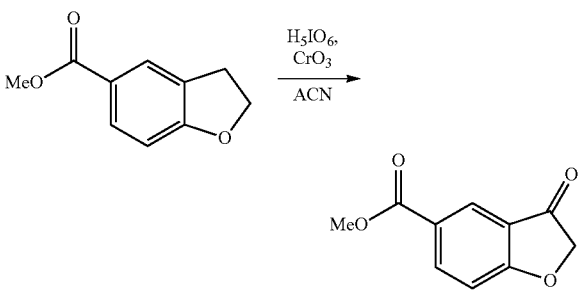

To a solution of periodic acid (12.8 g, 56.1 mmol) in MeCN (120 mL) was added chromium trioxide (3.37 g, 33.7 mmol) and methyl 2,3-dihydrobenzofuran-5-carboxylate (4.00 g, 22.5 mmol). A precipitate was formed immediately with the exothermic reaction, and the mixture was stirred vigorously for 3 hrs at rt. The reaction mixture was filtered through a celite bed and washed with EtOAc (40 mL×3). The filtrate was concentrated in vacuo and the residue was partitioned between water (80 mL) and DCM (80 mL). The layers were separated and the aqueous layer was extracted with DCM (80 mL×3). The combined organic layers were washed with a saturated solution of NaHSO₃ (50 mL×2), followed by a brine solution (50 mL), and then dried over Na₂SO₄, filtered and concentrated in vacuo to afford the crude product. The crude product was purified by column chromatography using a 40 g silica column and eluting with 40% EtOAc in petroleum ether to yield the title compound as a yellow solid (1.40 g, 7.29 mmol, 33% yield). GC MS (ESI) 192 [M+H]+.

Example 368b

Preparation of methyl 2-fluoro-3-oxo-2,3-dihydrobenzofuran-5-carboxylate

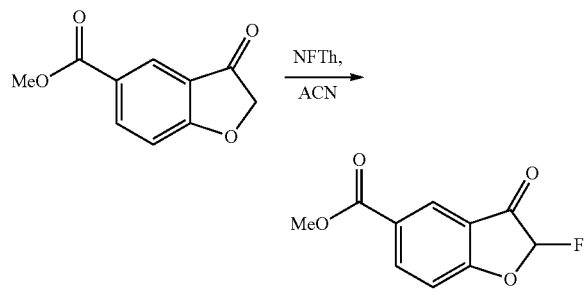

To a solution of Example 368a (200 mg, 1.04 mmol) in MeCN (25.0 mL) was added 1-Fluoro-4-hydroxy-1,4-diazoniabicyclo[2,2,2]octanebis(tetrafluoroborate) (908 mg, 2.60 mmol) and the reaction solution was heated to reflux for 3 hrs at 78° C. The MeCN was removed in vacuo and the residue was brought up in solution with DCM (25 mL) and stirred for 5 min. The mixture was filtered through a celite bed and washed with DCM (20 mL×3). The filtrate was washed with water (25 mL×2), followed by a brine solution (25 mL), and then dried over Na₂SO₄, filtered and concentrated in vacuo to give a yellow gummy solid as crude product. The crude product was purified by column chromatography using a 12 g silica column and eluting with 40% EtOAc in petroleum ether to yield the title compound as a colorless oil (148 mg, 0.704 mmol, 68% yield). GC MS (ESI) 210 [M+H]+.

Example 368c

Preparation of methyl 2,2-difluoro-3-oxo-2,3-dihydrobenzofuran-5-carboxylate

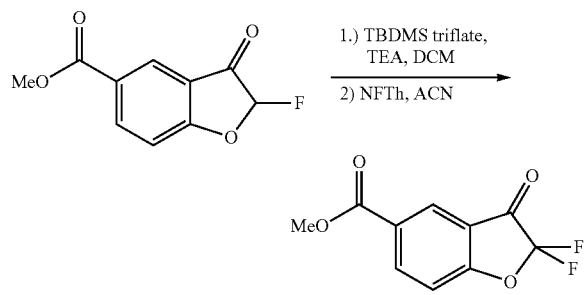

To a cold (0° C.) solution of Example 368b (1.10 g, 5.23 mmol) and TEA (4.38 mL, 31.4 mmol) in DCM (40.0 mL) was added tert-butyldimethylsilyl trifluoromethanesulfonate (2.77 g, 10.5 mmol) dropwise. The reaction mixture was stirred for 20 min at 0° C. and then warmed to rt and stirred overnight. The reaction mixture was diluted with DCM (80 mL), washed sequentially with saturated aqueous NaHCO₃ (70 mL×2), 1N HCl (50 mL×2), saturated aqueous NaHCO₃ (70 mL), and brine (50 mL). The organic solution was dried over Na₂SO₄, filtered and concentrated in vacuo to give a brown gummy solid as the crude intermediate. The intermediate residue was dissolved in MeCN (60.0 mL) and 1-Fluoro-4-hydroxy-1,4-diazoniabicyclo[2,2,2]octanebis(tetrafluoroborate) (4.56 g, 13.1 mmol) was added and the solution was stirred at rt for 3 hrs The MeCN was removed in vacuo, and the resulting residue was brought up into a solution with DCM (30 mL) and stirred for 15 min. The solution was filtered through a celite bed and washed with DCM (35 mL×2). The filtrate was washed with water (50 mL×3), followed by brine (50 mL). The combined organics were dried over Na₂SO₄, filtered and concentrated in vacuo to give the crude product as a brown gummy solid. The crude was purified by column chromatography using a 24 g silica column and eluting with 30% EtOAc in petroleum ether to yield the title compound as a colorless thick oil (750 mg, 3.29 mmol, 63% yield). GC MS (ESI) 228 [M+H]+.

Example 368d

Preparation of methyl 2,2-difluoro-3-hydroxy-2,3-dihydrobenzofuran-5-carboxylate

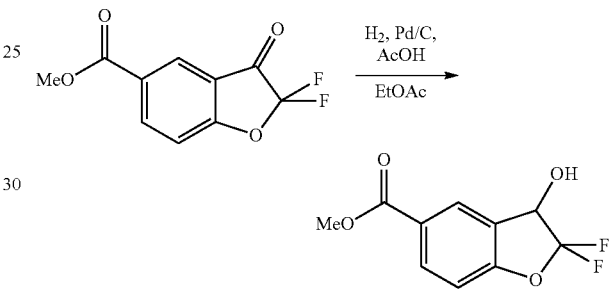

To a solution of Example 368c (500 mg, 2.19 mmol) in EtOAc (30.0 mL) and AcOH (3.00 mL, 52.4 mmol) was added Pd/C (150 mg, 0.141 mmol). The flask was evacuated and backfilled with 55 psi H₂ three times. The final H₂ pressure was set to 55 psi. The reaction mixture was stirred at 60° C. for 18 hrs. The inorganic solid was removed by filtration and washed with EtOAc. The filtrate was washed with water (75 mL×2), followed by saturated aqueous NaHCO₃ (30 mL×2) and brine (50 mL), dried over Na₂SO₄, filtered and concentrated in vacuo to give the title product as a yellow solid (460 mg, 2.00 mmol, 91% yield). GC MS (ESI) 230 [M+H]+.

Example 368e

Preparation of 2,2-difluoro-5-(hydroxymethyl)-2,3-dihydrobenzofuran-3-ol

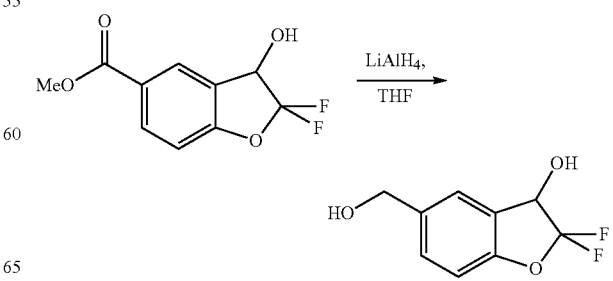

To the solution of Example 368d (460 mg, 2.0 mmol) in THF (25 mL) was added lithium aluminum hydride (2.0 mL, 4.0 mmol) at 0° C. The reaction mixture was stirred at 0° C. for 20 min, and then at rt for 2 hrs. The reaction was quenched with a saturated solution of sodium potassium tartarate (30 mL) and then extracted with EtOAc (50 mL×3). The combined organics were washed with a brine solution (50 mL), and then dried over Na$_2$SO$_4$, filtered and concentrated in vacuo to give the title product as an off-white solid (360 mg, 1.8 mmol, 89% yield). GC MS (ESI) 202 [M+H]+.

Example 368f

Preparation of 2,2-difluoro-3-hydroxy-2,3-dihydrobenzofuran-5-carbaldehyde

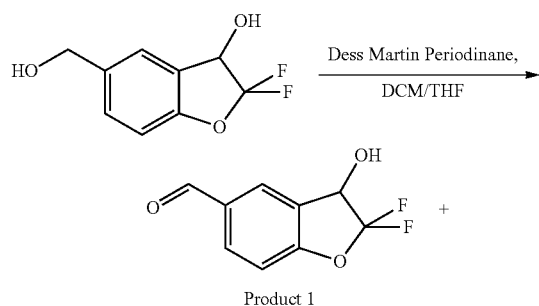

To the solution of Example 368e (360 mg, 1.8 mmol) in DCM (20 mL) and THF (5.0 mL) was added Dess-Martin Periodinane (1.1 g, 2.7 mmol) at 0° C. The reaction mixture was stirred at 0° C. for 10 min and at rt for two hrs. The mixture was filtered through a celite bed and washed with DCM (20 mL×3). The filtrate was washed with saturated aqueous NaHCO$_3$ (50 mL×2), followed by water (50 mL) and brine (50 mL), and then dried over Na$_2$SO$_4$, filtered and concentrated in vacuo to give a light brown crude product. The crude product was purified by column chromatography using a 40 g silica column and eluting with 0-30% gradient of EtOAc in petroleum ether to yield the Product 1 and 2. The major product was the title compound (Product 1, Example 368f) and was collected as an off-white solid (260 mg, 1.3 mmol, 73% yield). GC MS 200 [M+H]+. The minor product (Product 2) was collected as a yellow gummy solid (65 mg, 0.33 mmol, 18% yield). GC MS (ESI) 198 [M+H]+.

Example 368 was prepared from Example 368f and 366a using procedures similar to that described in Example 366 and 367. MS (ESI) 632.2 [M+H]+. 1H NMR (400 MHz, CDCl$_3$-d) δ ppm 7.97-8.03 (m, 2H), 7.88-7.92 (m, 2H), 7.77 (d, 1H, J=6.00 Hz), 7.72 (dd, 1H, J=10.4, 6.4 Hz), 7.52 (t, 1H, J=7.6 Hz), 7.51-7.53 (m, 1H), 7.32-7.38 (m, 1H), 6.99-7.02 (m, 1H), 6.92 (d, 1H, J=8.40 Hz), 5.22 (dd, 1H, J=10.00, 3.6 Hz), 3.10 (s, 3H), 2.44 (s, 3H), 2.07 (s, 3H).

Example 369

(1-(3-(5-(2,2-difluorobenzo[d][1,3]dioxol-5-yl)-2-methyloxazol-4-yl)-3'-(methylsulfonyl)biphenyl-4-yl)-2-methyl-1H-imidazol-4-yl)methanol

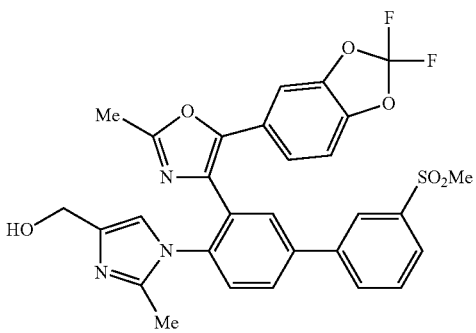 [SMILES: Cc1nc(-c2cc(-c3cccc(S(C)(=O)=O)c3)ccc2-n2cc(CO)nc2C)c(-c2ccc3c(c2)OC(F)(F)O3)o1]

Example 369a

Preparation of 2-methyl-1H-imidazole-4-carboxylic acid

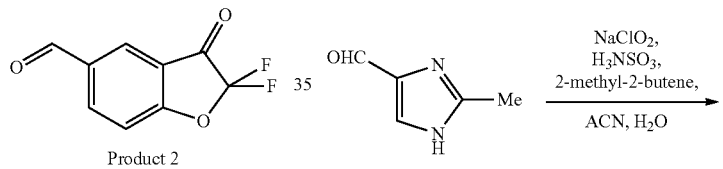

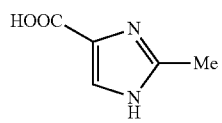

To a solution of 2-methyl-1H-imidazole-4-carbaldehyde (10 g, 91 mmol) in ACN (60 mL) at 0° C., was added sulphamic acid (11 g, 120 mmol), and the reaction solution was stirred for 5 min before 2-methyl-2-butene (13 mL, 120 mmol) was added. A solution of sodium chlorite (11 g, 120 mmol) in water was added dropwise to mixture, and the solution was stirred for 4 hrs at rt. The MeCN was removed in vacuo, and the reaction mixture was quenched with 1.5N HCl and extracted with EtOAc (250 mL×3). The combined organics were washed with brine (200 mL), dried over Na$_2$SO$_4$, filtered and concentrated in vacuo to give the title product (9.0 g, 71 mmol, 79% yield). $^1$H NMR (300 MHz, DMSO-d$_6$) δ ppm 11.94 (brs, 1H) 9.61 (s, 1H), 7.88 (s, 1H), 1.91 (s, 3H).

Example 369b

Preparation of ethyl 2-methyl-1H-imidazole-4-carboxylate

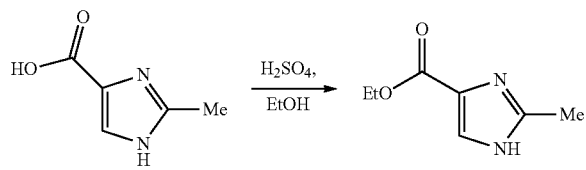 [SMILES: "EtOH" ; Cc1nc(C(=O)O)c[nH]1 ; CCOC(=O)c1c[nH]c(C)n1]

To a solution of Example 369a (9.0 g, 71 mmol) in EtOH (80 mL) was added sulfuric acid (7.6 mL, 140 mmol) dropwise, and the reaction solution was stirred at 60° C. overnight. EtOH was removed in vacuo, and the remaining mixture was quenched with 10% NaOH, and extracted with EtOAc (250 mL×3). The combined organics were washed with brine (200 mL), dried over $Na_2SO_4$, filtered and concentrated in vacuo to give the title product (5.0 g, 32 mmol, 45% yield). MS (ESI) 155.1 [M+H]+

Example 369c

Preparation of (1-(4-bromo-2-(5-(2,2-difluorobenzo[d][1,3]dioxol-5-yl)-2-methyloxazol-4-yl)phenyl)-2-methyl-1H-imidazol-4-yl)methanol

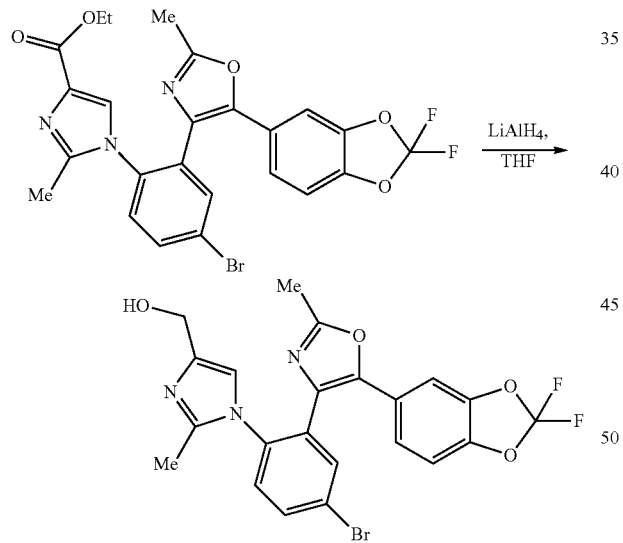

Ethyl 1-(4-bromo-2-(5-(2,2-difluorobenzo[d][1,3]dioxol-5-yl)-2-methyloxazol-4-yl)phenyl)-2-methyl-1H-imidazole-4-carboxylate was prepared from Example 369b using procedures similar to those described in Examples 366 and 367.

To a solution of ethyl 1-(4-bromo-2-(5-(2,2-difluorobenzo[d][1,3]dioxol-5-yl)-2-methyloxazol-4-yl)phenyl)-2-methyl-1H-imidazole-4-carboxylate (0.20 g, 0.37 mmol) in THF (10 mL) at 0° C. was added a solution of $LiAlH_4$ (0.18 mL, 0.37 mmol) in THF under a $N_2$ atmosphere. The reaction solution was stirred for 1 hr, and then quenched with 15 mL of saturated aqueous $NH_4Cl$ and extracted with EtOAc (20 mL×3). The combined organics were washed with brine (50 mL), and then dried over $Na_2SO_4$, filtered and concentrated in vacuo to give the title product as an off-white solid (0.15 g, 30 mmol, 81% yield). MS (ESI) 504.0 [M+H]+.

Example 369 was prepared from Example 369c and 3-methylsulfonylphenylboronic acid using procedures similar to that described in Example 1f. MS (ESI) 580.2 [M+H]+ $^1$H NMR (400 MHz, $CDCl_3$) δ ppm 8.17 (s, 1H), 8.01 (d, J=8.00 Hz, 1H), 7.84-7.90 (m, 2H) 7.78-7.82 (m, 1H), 7.71 (d, 1H, J=15.26 Hz), 7.45-7.53 (m, 1H), 7.10-7.15 (m, 2H), 6.99 (s, 1H) 4.41-4.45 (m, 2H), 3.11 (s, 3H), 2.46 (s, 3H), 2.10 (s, 3H).

Example 370

2-(1-(3-(5-(2,2-difluorobenzo[d][1,3]dioxol-5-yl)-2-methyloxazol-4-yl)-3'-fluoro-4'-(hydroxymethyl)-5'-(methylsulfonyl)biphenyl-4-yl)-2-methyl-1H-imidazol-4-yl)propan-2-ol

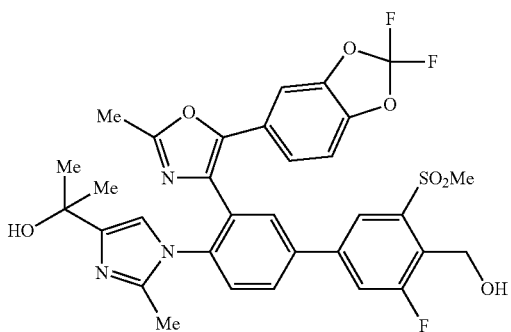 [SMILES: Cc1nc(-c2cc(-c3cc(F)c(CO)c(S(C)(=O)=O)c3)ccc2-n2cc(C(C)(C)O)nc2C)c(-c2ccc3c(c2)OC(F)(F)O3)o1]

Example 370a

Preparation of 2-(1-(4-bromo-2-(5-(2,2-difluorobenzo[d][1,3]dioxol-5-yl)-2-methyloxazol-4-yl)phenyl)-2-methyl-1H-imidazol-4-yl)propan-2-ol

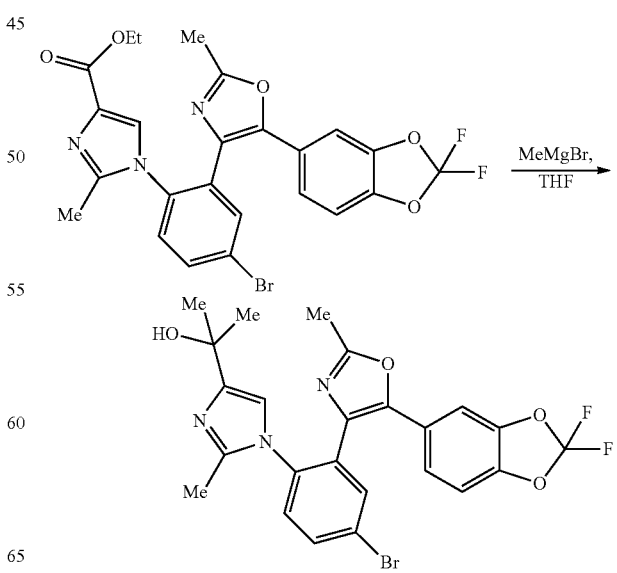

Ethyl 1-(4-bromo-2-(5-(2,2-difluorobenzo[d][1,3]dioxol-5-yl)-2-methyloxazol-4-yl)phenyl)-2-methyl-1H-imidazole-4-carboxylate was prepared from Example 369b using procedures similar to those described in Examples 366 and 367.

To a solution of ethyl 1-(4-bromo-2-(5-(2,2-difluorobenzo[d][1,3]dioxol-5-yl)-2-methyloxazol-4-yl)phenyl)-2-methyl-1H-imidazole-4-carboxylate (0.20 g, 0.37 mmol) in THF (10 mL) at 0° C. was added a solution of MeMgBr (0.37 mL, 1.1 mmol) in THF under a nitrogen atmosphere. The reaction solution was stirred overnight at rt, quenched with 20 mL of saturated aqueous NH₄Cl and then extracted with EtOAc (20 mL×3). The combined organics were washed with brine (50 mL), and then dried over Na₂SO₄, filtered and concentrated in vacuo to give the crude product. The crude product was purified by column chromatography to yield the title product (0.15 g, 28 mmol, 77% yield). MS (ESI) 532.0 [M+H]+.

Example 370 was prepared from Example 370a and Intermediate 1 using procedures similar to that described in Example 1f. MS (ESI) 656.2 [M+H]+ $^1$H NMR (400 MHz, CDCl₃-d) δ ppm 8.11 (s, 1H), 7.86 (d, J=2.00 Hz, 1H) 7.78 (dd, 1H, J=8.25, 2.25 Hz), 7.62 (dd, 1H, J=10.01, 1.75 Hz), 7.48-7.52 (m, 1H), 7.11-7.17 (m, 2H), 6.97-7.00 (m, 1H), 6.42 (s, 1H), 5.10 (s, 2H), 3.29 (s, 3H), 2.46 (s, 3H), 2.04 (s, 3H), 1.44 (s, 6H).

Example 371

1-(3-(5-(2,2-difluorobenzo[d][1,3]dioxol-5-yl)-2-methyloxazol-4-yl)-3'-(methylsulfonyl)biphenyl-4-yl)-2-methyl-1H-imidazole-4-carbonitrile

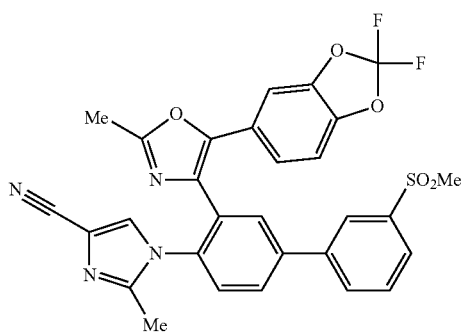 [SMILES: Cc1nc(-c2cc(-c3cccc(S(C)(=O)=O)c3)ccc2-n2cc(C#N)nc2C)c(-c2ccc3c(c2)OC(F)(F)O3)o1]

Example 371a

Preparation of 1-(4-bromo-2-(5-(2,2-difluorobenzo[d][1,3]dioxol-5-yl)-2-methyloxazol-4-yl)phenyl)-2-methyl-1H-imidazole-4-carboxylic aid

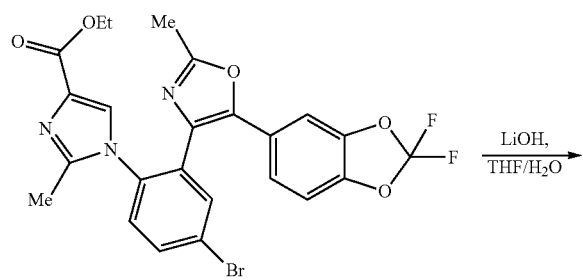

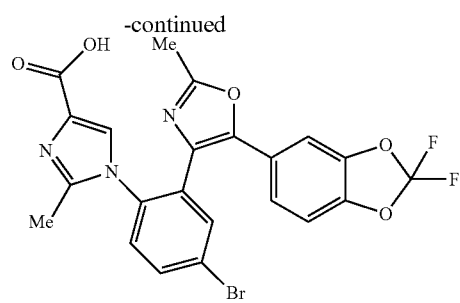

To a solution of ethyl 1-(4-bromo-2-(5-(2,2-difluorobenzo[d][1,3]dioxol-5-yl)-2-methyloxazol-4-yl)phenyl)-2-methyl-1H-imidazole-4-carboxylate (1.0 g, 1.8 mmol, Example 369) in water (5 mL) and THF (10 mL) was added LiOH (0.44 g, 18 mmol) and the reaction mixture was stirred overnight at rt. The reaction solution was diluted with water (20 mL) and then extracted with EtOAc (25 mL×3). The combined organics were washed with a brine solution (50 mL), and then dried over Na₂SO₄, filtered and concentrated in vacuo to yield the title product (0.90 g, 1.7 mmol, 95% yield). MS (ESI) 518.1 [M+H]+.

Example 371b

Preparation of 1-(4-bromo-2-(5-(2,2-difluorobenzo[d][1,3]dioxol-5-yl)-2-methyloxazol-4-yl)phenyl)-2-methyl-1H-imidazole-4-carboxamide

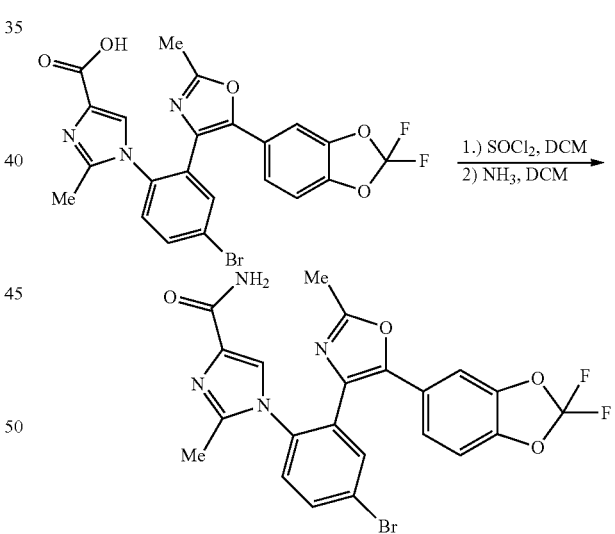

To a solution of Example 371a (0.50 g, 0.97 mmol) in DCM (15 mL) at 0° C. was added SOCl₂ (0.35 mL, 4.8 mmol) dropwise, and the reaction solution was heated to a reflux for 2 hrs. The intermediate acid chloride was concentrated in vacuo, and then brought up in a solution with ammonia (0.020 mL, 0.93 mmol) in DCM (15 mL) and stirred at rt overnight. The solution was concentrated in vacuo to give the crude product. The crude product was purified by column chromatography to yield the title compound (0.19 g, 0.37 mmol, 38% yield). MS (ESI) 519.1 [M+H]+.

Example 371c

Preparation of 1-(4-bromo-2-(5-(2,2-difluorobenzo[d][1,3]dioxol-5-yl)-2-methyloxazol-4-yl)phenyl)-2-methyl-1H-imidazole-4-carbonitrile

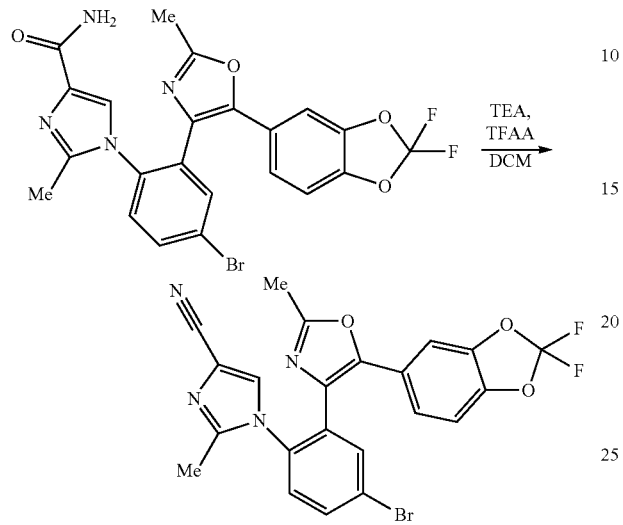

To a solution of Example 371b (0.10 g, 0.19 mmol) in DCM (10 mL) at 0° C. was added TEA (0.16 mL, 1.2 mmol) and TFAA (0.27 mL, 1.9 mmol). The reaction solution was stirred overnight at rt. The solution was diluted with ice cold water (15 mL) and then extracted with DCM (20 mL×3). The combined organics were washed with a brine solution (50 mL), and then dried over $Na_2SO_4$, filtered and concentrated in vacuo to yield the title product (90 mg, 0.18 mmol, 93% yield). MS (ESI) 499.2 [M+H]+.

Example 371 was prepared from Example 371c and 3-methylsulfonylphenylboronic acid using procedures similar to that described in Example 1f. MS (ESI) 575.2 [M+H]+. $^1$H NMR (400 MHz, $CDCl_3$-d) δ ppm 8.14 (t, J=1.63 Hz, 1H) 8.00-8.04 (m, 1H), 7.91 (s, 1H), 7.82-7.87 (m, 2H), 7.69-7.75 (m, 1H), 7.49 (d, J=8.25 Hz, 1H), 7.17-7.21 (m, 2H), 7.14 (d, J=1.50 Hz, 1H), 7.05 (d, J=8.25 Hz, 1H), 3.11 (s, 3H), 2.46 (s, 3H), 2.13 (s, 3H).

Example 372

1-(1-(3-(5-(2,2-difluorobenzo[d][1,3]dioxol-5-yl)-2-methyloxazol-4-yl)-3'-(methylsulfonyl)-[1,1'-biphenyl]-4-yl)-2-methyl-1H-imidazol-4-yl) ethanol

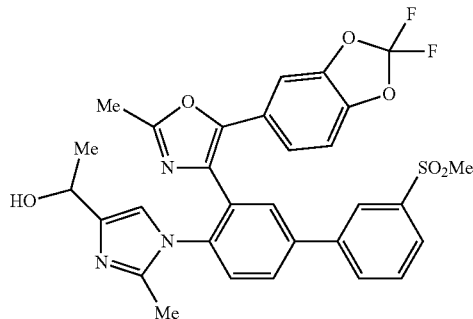 [SMILES: Cc1nc(-c2cc(-c3cccc(S(C)(=O)=O)c3)ccc2-n2cc(C(C)O)nc2C)c(-c2ccc3c(c2)OC(F)(F)O3)o1]

Example 372a

Preparation of 1-(4-bromo-2-(5-(2,2-difluorobenzo[d][1,3]dioxol-5-yl)-2-methyloxazol-4-yl)phenyl)-2-methyl-1H-imidazole-4-carbaldehyde

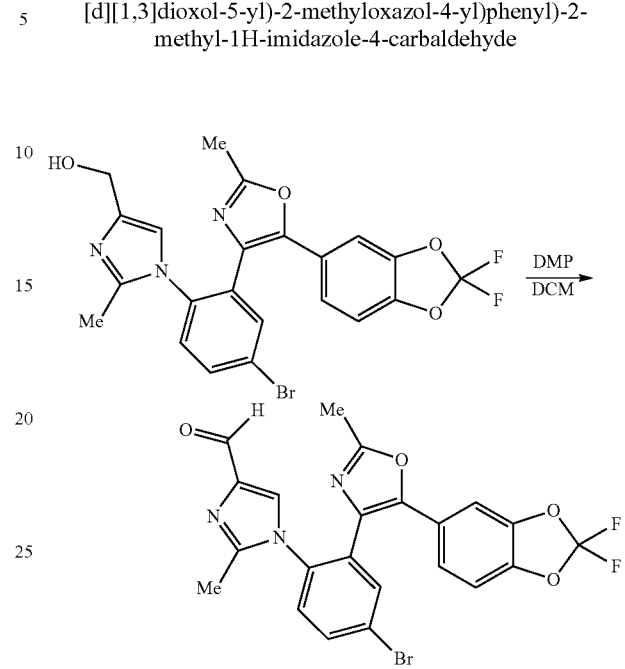

To a solution of Example 369c (0.23 g, 0.46 mmol) in DCM (10 mL) at 0° C. was added Dess-Martin Periodinane (0.39 g, 0.91 mmol). The reaction solution was stirred for 2 hrs. The reaction mixture was filtered through a celite bed. The filtrate was diluted with water (35 mL), and extracted with DCM (20 mL×3). The combined organics were dried over $Na_2SO_4$, filtered and concentrated in vacuo to yield the to give the crude product, which was purified by column chromatography using 40% EtOAc in Hx to yield the title product (80 mg, 0.16 mmol, 35% yield). MS (ESI) 504.1 [M+H]+.

Example 372b

Preparation of 1-(1-(4-bromo-2-(5-(2,2-difluorobenzo[d][1,3]dioxol-5-yl)-2-methyloxazol-4-yl)phenyl)-2-methyl-1H-imidazol-4-yl)ethanol

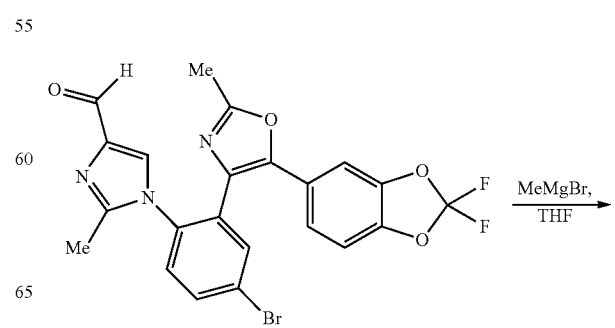

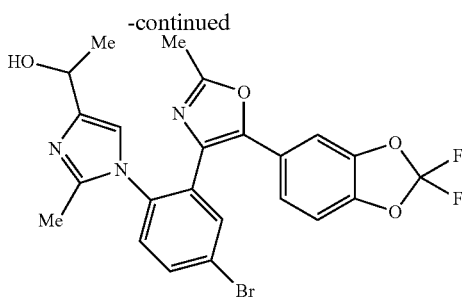

To a solution of Example 372a (60 mg, 0.12 mmol) in THF (5 mL) at 0° C. was added MeMgBr in THF (0.20 mL, 0.60 mmol) dropwise, and the reaction solution was stirred at rt overnight. The reaction solution was quenched with 20 mL of saturated aqueous NH$_4$Cl, and extracted with EtOAc (20 mL×3). The combined organics were washed with a brine solution (50 mL), and then dried over Na$_2$SO$_4$, filtered and concentrated in vacuo to give the crude product, which was purified by column chromatography using 70% EtOAc in Hx to yield the title product (50 mg, 0.096 mmol, 81% yield). MS (ESI) 520.2 [M+H]+.

Example 372 was prepared from Example 372b and 3-methylsulfonylphenylboronic acid using procedures similar to that described in Example 1f, and the chiral product was obtained by chiral prep HPLC, RT=7.22 [Chiral pak-IA (250×4.6 mm 5, 80% CO$_2$, 20% (0.5% DEA methonol), Flow rate (3.0 g/min)]. MS (ESI) 594.0 [M+H]+ $^1$H NMR (400 MHz, CDCl$_3$-d) δ ppm 8.17 (t, J=1.75 Hz, 1H), 8.00 (dt, J=7.75, 1.38 Hz, 1H), 7.85-7.90 (m, 2H), 7.80 (dd, J=8.25, 2.25 Hz, 1H), 7.69-7.74 (m, 1H), 7.45-7.54 (m, 1H), 7.11-7.18 (m, 2H), 6.93-7.02 (m, 1H), 6.45 (s, 1H), 4.65-4.74 (m, 1H), 3.12 (s, 3H), 2.46 (s, 3H), 2.05 (s, 3H), 1.36-1.42 (m, 3H), 1.23-1.28 (m, 1H).

The following compounds were prepared in a manner similar to that described in the procedures above:

| Ex # | Structure | Name and Characterization | Molecular Ion |
|---|---|---|---|
| 373 | 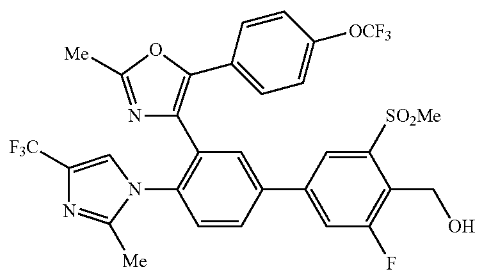 | [3-fluoro-5-(methylsulfonyl)-4'-[2-methyl-4-(trifluoromethyl)-1H-imidazol-1-yl]-3'-(2-methyl-5-{4-[(trifluoromethyl)oxy]phenyl}-1,3-oxazol-4-yl)biphenyl-4-yl]methanol | MS (ESI) 670.3 [M + H]+ |
| 374 | 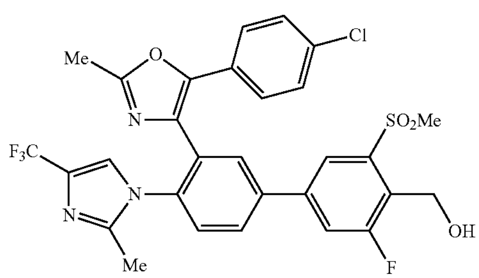 [SMILES: Cc1nc(-c2cc(-c3cc(F)c(CO)c(S(C)(=O)=O)c3)ccc2-n2cc(C(F)(F)F)nc2C)c(-c2ccc(Cl)cc2)o1] | {3'-[5-(4-chlorophenyl)-2-methyl-1,3-oxazol-4-yl]-3-fluoro-5-(methylsulfonyl)-4'-[2-methyl-4-(trifluoromethyl)-1H-imidazol-1-yl]biphenyl-4-yl}methanol | MS (ESI) 620.5 [M + H]+ |
| 375 | 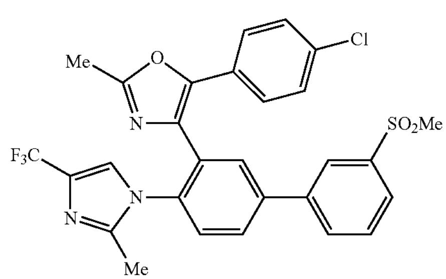 | 5-(4-chlorophenyl)-2-methyl-4-{3'-(methylsulfonyl)-4-[2-methyl-4-(trifluoromethyl)-1H-imidazol-1-yl]biphenyl-3-yl}-1,3-oxazole | MS (ESI) 672.3 [M + H]+ |

| Ex # | Structure | Name and Characterization | Molecular Ion |
|---|---|---|---|
| 376 | 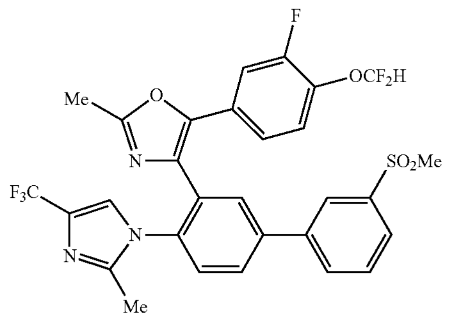 | 5-(4-(difluoromethoxy)-3-fluorophenyl)-2-methyl-4-(4-(2-methyl-4-(trifluoromethyl)-1H-imidazol-1-yl)-3'-(methylsulfonyl)biphenyl-3-yl)oxazole 1HNMR (400 MHz, METHANOL-d4) δ ppm 8.24 (t, J = 1.76 Hz, 1H), 8.13 (d, J = 2.01 Hz, 1H), 8.04-8.10 (m, 3H), 7.81 (t, J = 7.78 Hz, 1H), 7.72 (d, J = 8.28 Hz, 1H), 7.37 (d, J = 1.25 Hz, 1H), 7.18-7.33 (m, 3H), 6.70-7.10 (m, 1H), 3.22 (s, 3H), 2.49 (s, 3H), 2.10 (s, 3H). | MS (ESI) 622.0 [M + H]+ |
| 377 | 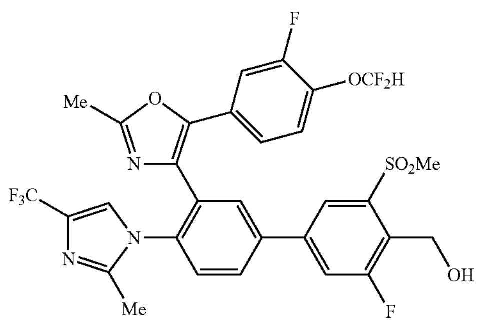 | (3'-(5-(4-difluoromethoxy)-3-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol 1H NMR (400 MHz, METHANOL-d4) δ ppm 8.16 (m, 2H), 8.06 (dd, J = 8.28, 2.26 Hz, 1H), 7.92 (dd, J = 10.42, 1.88 Hz, 1H), 7.73 (d, J = 8.28 Hz, 1 H), 7.37-7.40 (m, 1 H), 7.17-7.33 (m, 3 H), 6.70-7.10 (m, 1 H), 5.15 (d, J = 2.01 Hz, 2 H), 3.40 (s, 3 H), 2.49 (s, 3 H), 2.09 (s, 3 H) | MS (ESI) 670.0 [M + H]+ |
| 378 | 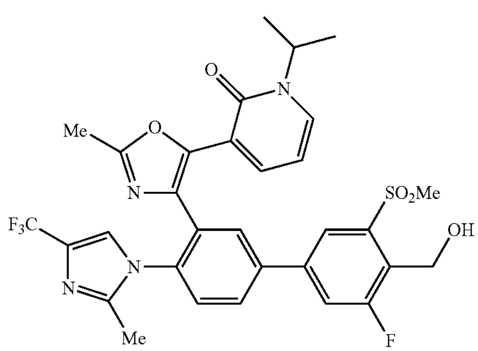 [SMILES: Cc1nc(-c2cc(-c3cc(F)c(CO)c(S(C)(=O)=O)c3)ccc2-n2cc(C(F)(F)F)nc2C)c(-c2cccn(C(C)C)c2=O)o1] | 3-(4-(3'-fluoro-4'-(hydroxymethyl)-4-(2-methyl-4-(trifluoromethyl)-1H-imidazol-1-yl)-5'-(methylsulfonyl)biphenyl-3-yl)-2-methyloxazol-5-yl)-1-isopropylpyridin-2(1H)-one | MS (ESI) 645.2 [M + H]+ |
| 379 | 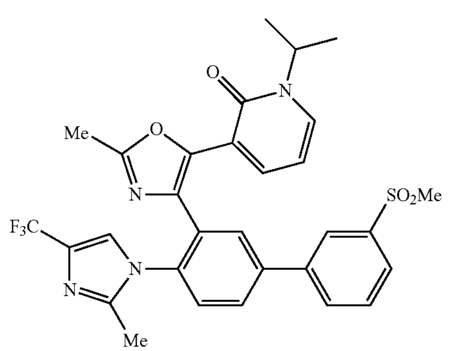 [SMILES: Cc1nc(-c2cc(-c3cccc(S(C)(=O)=O)c3)ccc2-n2cc(C(F)(F)F)nc2C)c(-c2cccn(C(C)C)c2=O)o1] | 1-isopropyl-3-(2-methyl-4-(4-(2-methyl-4-(trifluoromethyl)-1H-imidazol-1-yl)-3'-(methylsulfonyl)biphenyl-3-yl)oxazol-5-yl)pyridin-2(1H)-one | MS (ESI) 597.2 [M + H]+ |

-continued

| Ex # | Structure | Name and Characterization | Molecular Ion |
|---|---|---|---|
| 380 | 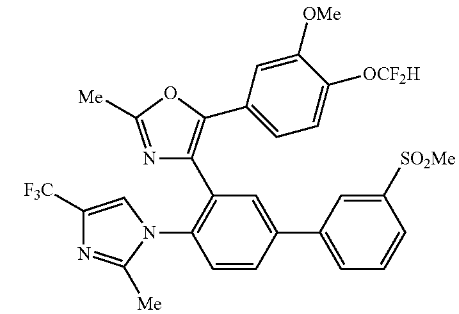 | 5-(4-(difluoromethoxy)-3-methoxyphenyl)-2-methyl-4-(4-(2-methyl-4-(trifluoromethyl)-1H-imidazol-1-yl)-3'-(methylsulfonyl)biphenyl-3-yl)oxazole | MS (ESI) 634.2 [M + H]+ |
| 381 | 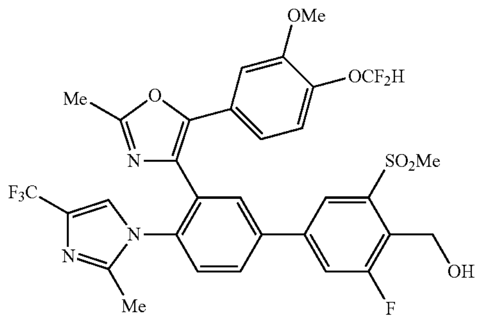 | (3'-(5-(4-(difluoromethoxy)-3-methoxyphenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 682.0 [M + H]+ |
| 382 | 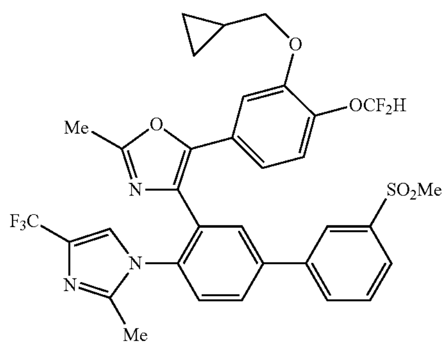 | 5-(3-(cyclopropylmethoxy)-4-(difluoromethoxy)phenyl)-2-methyl-4-(4-(2-methyl-4-(trifluoromethyl)-1H-imidazol-1-yl)-3'-(methylsulfonyl)biphenyl-3-yl)oxazole | MS (ESI) 674.0 [M + H]+ |
| 383 | 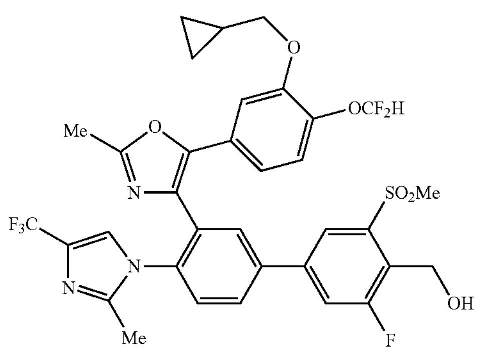 | (3'-(5-(3-cyclopropylmethoxy)-4-(difluoromethoxy)phenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 722.0 [M + H]+ |
| 384 | 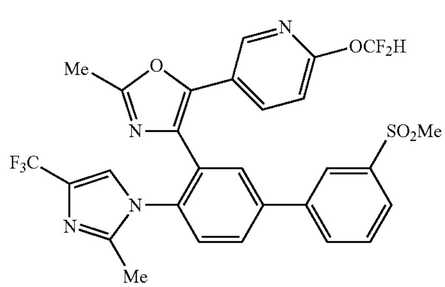 | 5-(6-(difluoromethoxy)pyridin-3-yl)-2-methyl-4-(4-(2-methyl-4-(trifluoromethyl)-1H-imidazol-1-yl)-3'-(methylsulfonyl)biphenyl-3-yl)oxazole 1H NMR (400 MHz, METHANOL-d4) δ ppm 8.21-8.23 (m, 2 H), 8.14 (d, J = Hz, 1H), 8.04-8.09 (m, 3 H), 7.73-7.87 (m, 2 H), 7.55 (t, J = 68 Hz, 1 H), 7.36-7.40 (m, 2 H), 6.99 (dd, J = 8.66, 0.63 Hz, 1 H), 3.22 (s, 3 H), 2.51 (s, 3 H), 2.10 (s, 3 H) | MS (ESI) 605.2 [M + H]+ |

-continued

| Ex # | Structure | Name and Characterization | Molecular Ion |
|---|---|---|---|
| 385 | 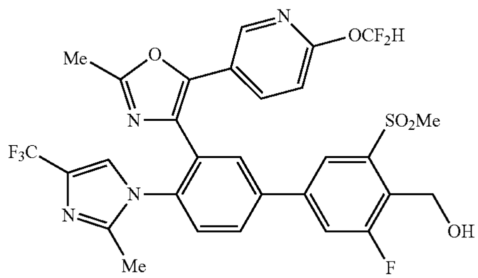 | (3'-(5-(6-(difluoromethoxy)pyridin-3-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol 1H NMR (400 MHz, METHANOL-d4) δ ppm 8.22 (s, 1 H) 8.13-8.16 (m, 2 H) 8.04-8.07 (m, 1 H) 7.91-7.94 (m, 1H) 7.84-7.87 (m, 1 H) 7.73-7.75 (m, 1 H) 7.55 (t, J = 68 Hz, 1 H) 7.36-7.41 (m, 1 H) 6.98 (dd, J = 8.53, 0.75 Hz, 1 H) 5.15 (s, 2 H) 3.40 (s, 3 H) 2.50 (s, 3 H) 2.10 (s, 3 H) | MS (ESI) 653.2 [M + H]+ |
| 386 | 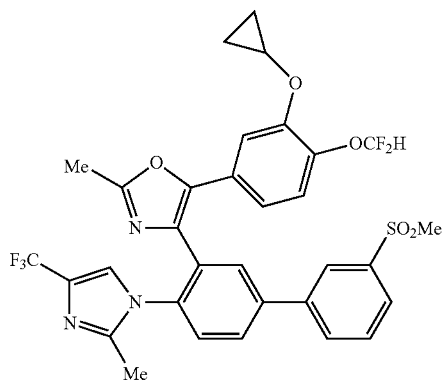 | 5-(3-cyclopropoxy-4-(difluoromethoxy)phenyl)-2-methyl-4-(4-(2-methyl-4-(trifluoromethyl)-1H-imidazol-1-yl)-3'-(methylsulfonyl)biphenyl-3-yl)oxazole | MS (ESI) 660.0 [M + H]+ |
| 387 | 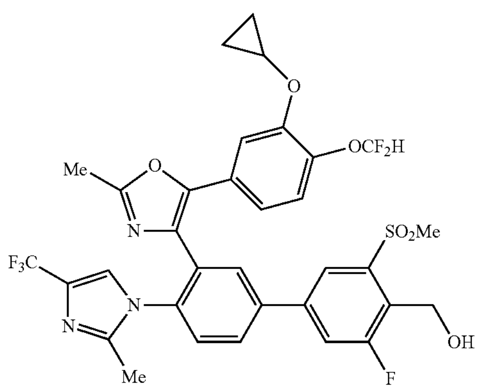 | (3'-(5-(3-cyclopropoxy-4-(difluoromethoxy)phenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol 1H NMR (400 MHz, METHANOL-d4) δ ppm 8.17 (dd, J = 9.91,1.88 Hz, 2 H) 8.06 (dd, J = 8.28, 2.26 Hz, 1 H) 7.92 (dd, J = 10.42, 1.88 Hz, 1 H) 7.71 (d, J = 8.28 Hz, 1 H) 7.32 (d, J = 1.25 Hz, 1 H) 7.05-7.13 (m, 2 H) 6.59-7.02 (m, 2 H) 5.15 (d, J = 1.76 Hz, 2 H) 3.79 (d, J = 7.03 Hz, 2 H) 3.38-3.43 (m, 3 H) 2.49 (s, 3 H) 2.06 (s, 3 H) 1.16-1.27 (m, 1 H) 0.55-0.64 (m, 2 H) 0.27-0.35 (m, 2 H) | MS (ESI) 708.0 [M + H]+ |
| 388 | 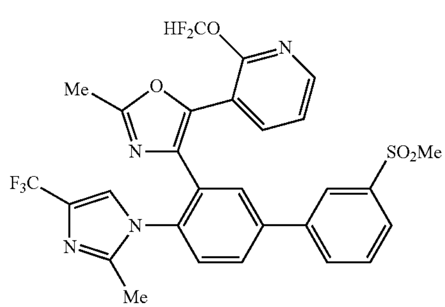 | 5-(2-(difluoromethoxy)pyridin-3-yl)-2-methyl-4-(4-(2-methyl-4-(trifluoromethyl)-1H-imidazol-1-yl)-3'-(methylsulfonyl)biphenyl-3-yl)oxazole | MS (ESI) 605.2 [M + H]+ |

-continued

| Ex # | Structure | Name and Characterization | Molecular Ion |
|---|---|---|---|
| 389 | 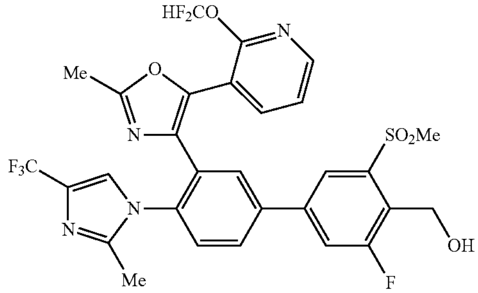 | (3'-(5-(2-(difluoromethoxy)pyridin-3-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 653.2 [M + H]+ |
| 390 | 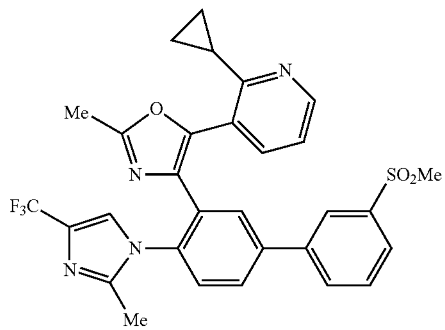 [SMILES: Cc1nc(-c2cc(-c3cccc(S(C)(=O)=O)c3)ccc2-n2cc(C(F)(F)F)nc2C)c(-c2cccnc2C2CC2)o1] | 5-(2-cyclopropylpyridin-3-yl)-2-methyl-4-(4-(2-methyl-4-(trifluoromethyl)-1H-imidazol-1-yl)-3'-(methylsulfonyl)biphenyl-3-yl)oxazole | MS (ESI) 579.2 [M + H]+ |
| 391 | 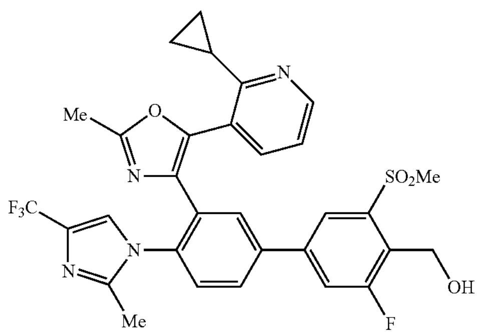 [SMILES: Cc1nc(-c2cc(-c3cc(F)c(CO)c(S(C)(=O)=O)c3)ccc2-n2cc(C(F)(F)F)nc2C)c(-c2cccnc2C2CC2)o1] | (3'-(5-(2-cyclopropylpyridin-3-yl)-2-methyloxazol-4-yl)-3-fluoro-4'-(2-methyl-4-(trifluoromethyl-1H-imidazol-1-yl)-5-(methylsulfonyl)biphenyl-4-yl)methanol | MS (ESI) 627.2 [M + H]+ |
| 392 | 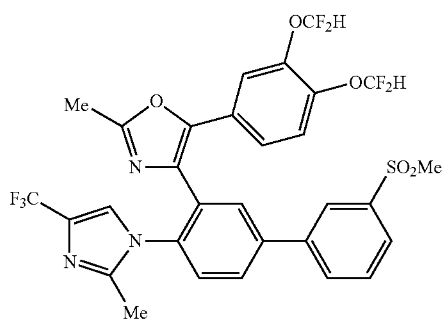 | 5-(3,4-bis(difluoromethoxy)ohenyl)-2-methyl-4-(4-(2-methyl-4-(trifluoromethyl)-1H-imidazol-1-yl)-3'-(methylsulfonyl)biphenyl-3-yl)oxazole | MS (ESI) 670.0 [M + H]+ |
| 393 | 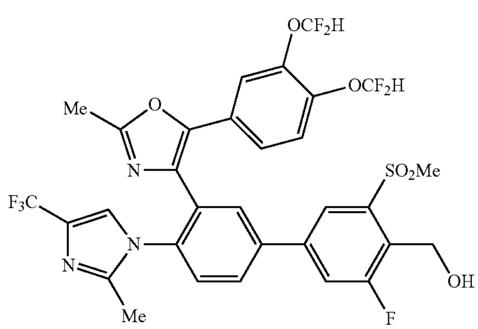 | (3'-(5-(3,4-bis(difluoromethoxy)phenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 718.0 [M + H]+ |

| Ex # | Structure | Name and Characterization | Molecular Ion |
|---|---|---|---|
| 394 | 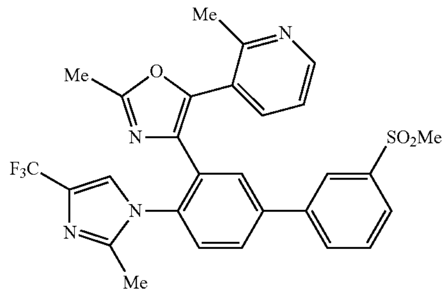 [SMILES: Cc1nc(-c2cc(-c3cccc(S(C)(=O)=O)c3)ccc2-n2cc(C(F)(F)F)nc2C)c(-c2cccnc2C)o1] | 2-methyl-4-(4-(2-methyl-4-(trifluoromethyl)-1H-imidazol-1-yl)-3'-(methylsulfonyl)biphenyl-3-yl)-5-(2-methylpyridin-3-yl)oxazole | MS (ESI) 553.2 [M + H]+ |
| 395 | 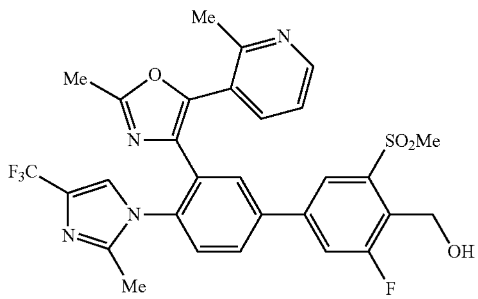 [SMILES: Cc1nc(-c2cc(-c3cc(F)c(CO)c(S(C)(=O)=O)c3)ccc2-n2cc(C(F)(F)F)nc2C)c(-c2cccnc2C)o1] | (3-fluoro-4'-(2-methyl-4-(trifluoromethyl)-1H-imidazol-1-yl)-3'-(2-methyl-5-(2-methylpyridin-3-yl)oxazol-4-yl)-5-(methylsulfonyl)biphenyl-4-yl)methanol | MS (ESI) 601.2 [M + H]+ |
| 396 | 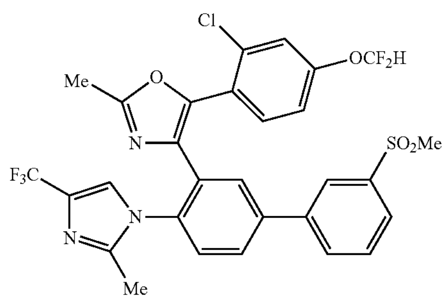 | 5-(2-chloro-4-(difluoromethoxy)phenyl)-2-methyl-4-(4-(2-methyl-4-(trifluoromethyl)-1H-imidazol-1-yl)-3'-(methylsulfonyl)biphenyl-3-yl)oxazole | MS (ESI) 638.0 [M + H]+ |
| 397 | 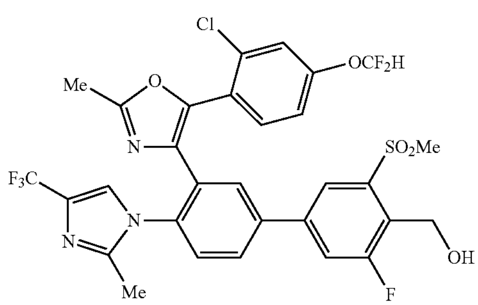 | (3'-(5-(2-chloro-4-(difluoromethoxy)phenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol 1H NMR (400 MHz, METHANOL-d4) δ ppm 8.03 (1 H, d, J = 1.26 Hz), 7.94-8.00 (1 H, m), 7.91 (1 H, s), 7.83 (1 H, dd, J = 10.29, 1.76 Hz), 7.64 (1 H, d, J = 8.28 Hz), 7.36-7.43 (2 H, m), 7.31 (1 H, d, J = 2.51 Hz), 6.78-1.21 (2 H, m), 5.14 (2 H, d, J = 1.76 Hz), 3.39 (3 H, s), 2.49 (3 H, s), 2.12 (3 H, s). | MS (ESI) 686.2 [M + H]+ |
| 398 | 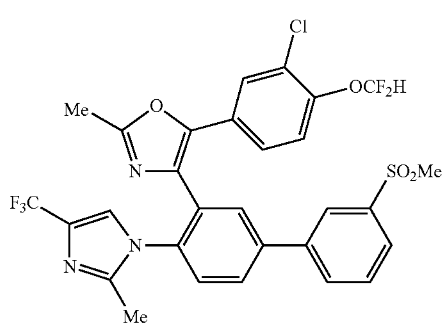 | 5-(3-chloro-4-(difluoromethoxy)phenyl)-2-methyl-4-(4-(2-methyl-4-(trifluoromethyl)-1H-imidazol-1-yl)-3'-(methylsulfonyl)biphenyl-3-yl)oxazole | MS (ESI) 639.8 [M + H]+ |

| Ex # | Structure | Name and Characterization | Molecular Ion |
|---|---|---|---|
| 399 | 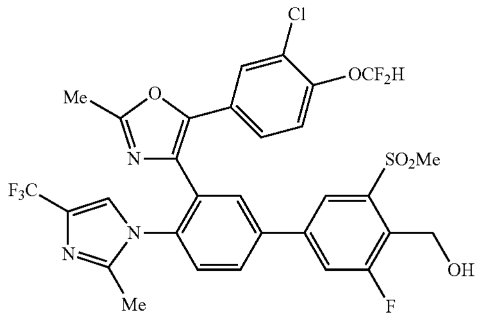 | (3'-(5-(3-chloro-4-(difluoromethoxy)phenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol 1H NMR (400 MHz, METHANOL-d4) δ ppm 8.15 (2 H, m), 8.06 (1 H, dd, J = 8.28, 2.26 Hz), 7.92 (1 H, dd, J = 10.29, 1.76 Hz), 7.73 (1 H, d, J = 8.28 Hz), 7.56 (1 H, d, J = 2.01 Hz), 7.34-7.43 (2 H, m), 7.23-7.30 (1 H, m), 6.72-7.14 (1 H, m), 5.14 (2 H, d, J = 1.76 Hz), 3.40 (3 H, s), 2.48 (3H, s), 2.10 (3 H, s). | MS (ESI) 687.1 [M + H]+ |
| 400 | 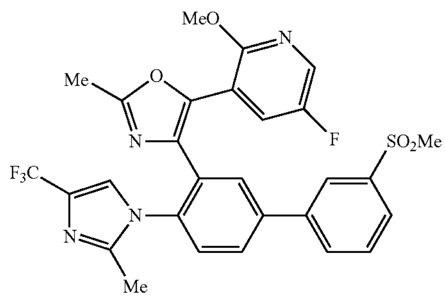 [SMILES: COc1ncc(F)cc1-c1oc(C)nc1-c1cc(-c2cccc(S(C)(=O)=O)c2)ccc1-n1cc(C(F)(F)F)nc1C] | 5-(5-fluoro-2-methoxypyridin-3-yl)-2-methyl-4-(4-2-methyl-4-(trifluoromethyl)-1H-imidazol-1-yl)-3'-(methylsulfonyl)biphenyl-3-yl)oxazole | MS (ESI) 587.2 [M + H]+ |
| 401 | 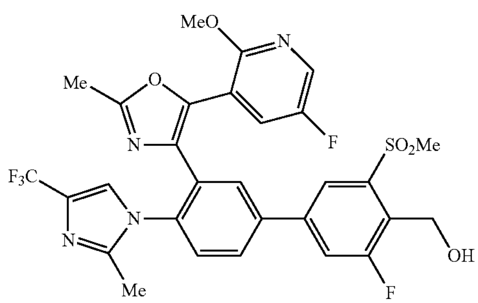 [SMILES: COc1ncc(F)cc1-c1oc(C)nc1-c1cc(-c2cc(F)c(CO)c(S(C)(=O)=O)c2)ccc1-n1cc(C(F)(F)F)nc1C] | (3-fluoro-3'-(5-(5-fluoro-2-methoxypyridin-3-yl)-2-methyloxazol-4-yl)-4'-(2-methyl-4-(trifluoromethyl)-1H-imidazol-1-yl)-5-(methylsulfonyl)biphenyl-4-yl)methanol | MS (ESI) 635.2 [M + H]+ |
| 402 | 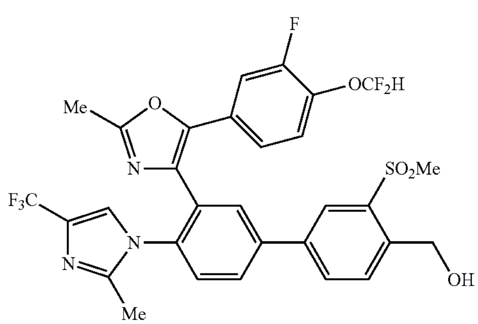 | (3'-(5-(4-(difluoromethoxy)-3-fluorophenyl)-2-methyloxazol-4-yl)-4'-(2-methyl-4-(trifluoromethyl)-1H-imidazol-1-yl)-3-(methylsulfonyl)biphenyl-4-yl)methanol 1H NMR (400 MHz, METHANOL-d4) δ ppm 8.27 (1 H, d, J = 2.01 Hz) 8.01-8.14 (3 H, m) 7.93 (1 H, d, J = 8.03 Hz) 7.72 (1 H, d, J = 8.28 Hz) 7.39 (1 H, d, J = 1.25 Hz) 7.14-7.35 (3 H, m) 6.69-7.12 (1 H, m) 5.11 (2 H, s) 3.29 (3 H, s) 2.48 (3 H, s) 2.10 (3 H, s) | MS (ESI) 652.0 [M + H]+ |
| 404 | 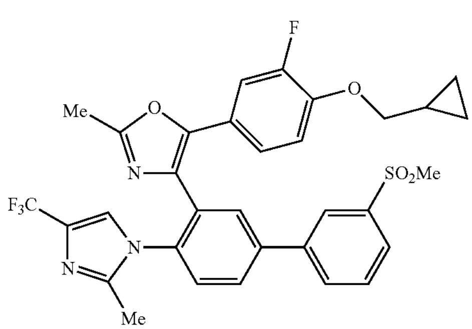 [SMILES: Cc1nc(-c2cc(-c3cccc(S(C)(=O)=O)c3)ccc2-n2cc(C(F)(F)F)nc2C)c(-c2ccc(OCC3CC3)c(F)c2)o1] | 5-(4-(cyclopropylmethoxy)-3-fluorophenyl)-2-methyl-4-(4-(2-methyl-4-(trifluoromethyl)-1H-imidazol-1-yl)-3'-(methylsulfonyl)biphenyl-3-yl)oxazole | MS (ESI) 626.2 [M + H]+ |

| Ex # | Structure | Name and Characterization | Molecular Ion |
|---|---|---|---|
| 405 | 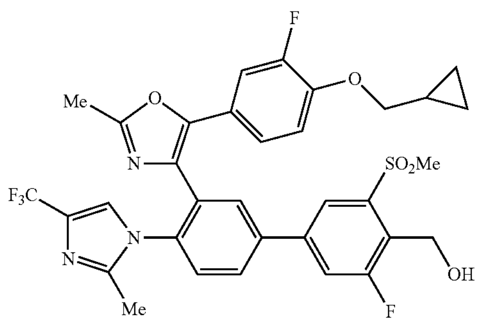 [SMILES: Cc1nc(-c2cc(-c3cc(F)c(CO)c(S(C)(=O)=O)c3)ccc2-n2cc(C(F)(F)F)nc2C)c(-c2ccc(OCC3CC3)c(F)c2)o1] | (3'-(5-(4-(cyclopropylmethoxy)-3-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 674.2 [M + H]+ |
| 406 | 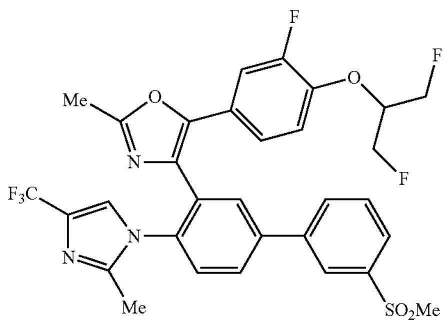 [SMILES: Cc1nc(-c2cc(-c3cccc(S(C)(=O)=O)c3)ccc2-n2cc(C(F)(F)F)nc2C)c(-c2ccc(OC(CF)CF)c(F)c2)o1] | 5-(4-(1,3-difluoropropan-2-yloxy)-3-fluorophenyl)-2-methyl-4-(4-(2-methyl-4-(trifluoromethyl)-1H-imidazol-1-yl)-3'-(methylsulfonyl)biphenyl-3-yl)oxazole | MS (ESI) 650.2 [M + H]+ |
| 407 | 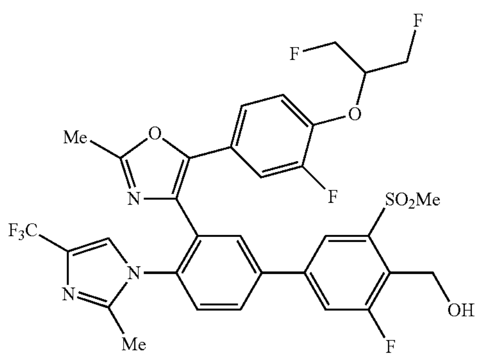 [SMILES: Cc1nc(-c2cc(-c3cc(F)c(CO)c(S(C)(=O)=O)c3)ccc2-n2cc(C(F)(F)F)nc2C)c(-c2ccc(OC(CF)CF)c(F)c2)o1] | (3'-(5-(4-(1,3-difluoropropan-2-yloxy)-3-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 698.2 [M + H]+ |
| 408 | 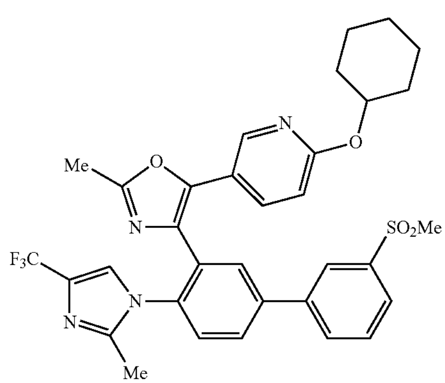 [SMILES: Cc1nc(-c2cc(-c3cccc(S(C)(=O)=O)c3)ccc2-n2cc(C(F)(F)F)nc2C)c(-c2ccc(OC3CCCCC3)nc2)o1] | 5-(6-(cyclohexyloxy)pyridin-3-yl)-2-methyl-4-(4-(2-methyl-4-(trifluoromethyl)-1H-imidazol-1-yl)-3'-(methylsulfonyl)biphenyl-3-yl)oxazole | MS (ESI) 637.2 [M + H]+ |

-continued

| Ex # | Structure | Name and Characterization | Molecular Ion |
|---|---|---|---|
| 409 | 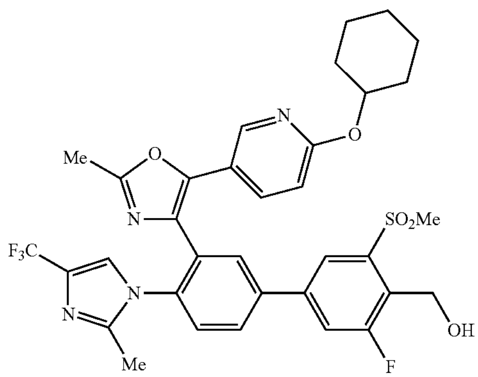 [SMILES: Cc1nc(-c2cc(-c3cc(F)c(CO)c(S(C)(=O)=O)c3)ccc2-n2cc(C(F)(F)F)nc2C)c(-c2ccc(OC3CCCCC3)nc2)o1] | (3'-(5-(6-(cyclohexyloxy)pyridin-3-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 685.2 [M + H]+ |
| 410 | 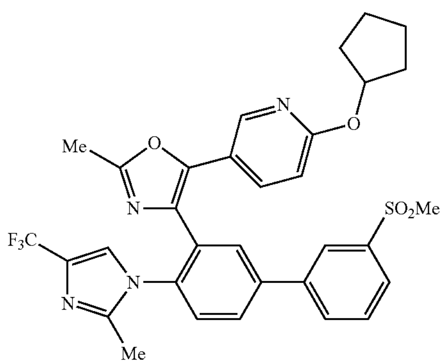 [SMILES: Cc1nc(-c2cc(-c3cccc(S(C)(=O)=O)c3)ccc2-n2cc(C(F)(F)F)nc2C)c(-c2ccc(OC3CCCC3)nc2)o1] | 5-(6-(cyclopentyloxy)pyridin-3-yl)-2-methyl-4-(4-(2-methyl-4-(trifluoromethyl)-1H-imidazol-1-yl)-3'-(methylsulfonyl)biphenyl-3-yl)oxazole | MS (ESI) 623.2 [M + H]+ |
| 411 | 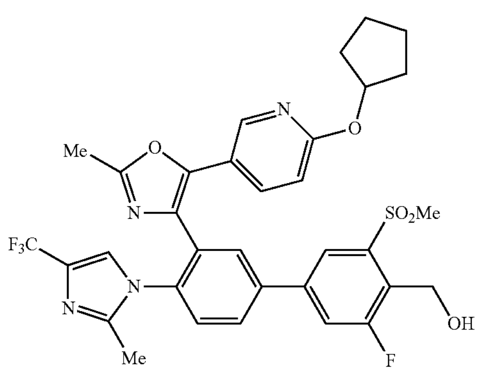 [SMILES: Cc1nc(-c2cc(-c3cc(F)c(CO)c(S(C)(=O)=O)c3)ccc2-n2cc(C(F)(F)F)nc2C)c(-c2ccc(OC3CCCC3)nc2)o1] | (3'-(5-(6-(cyclopentyloxy)pyridin-3-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 671.2 [M + H]+ |
| 412 | 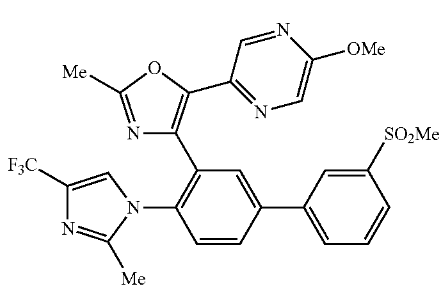 [SMILES: COc1cnc(-c2oc(C)nc2-c2cc(-c3cccc(S(C)(=O)=O)c3)ccc2-n2cc(C(F)(F)F)nc2C)cn1] | 5-(5-methoxypyrazin-2-yl)-2-methyl-4-(4-(2-methyl-4-(trifluoromethyl)-1H-imidazol-1-yl)-3'-(methylsulfonyl)biphenyl-3-yl)oxazole | MS (ESI) 570.2 [M + H]+ |

| Ex # | Structure | Name and Characterization | Molecular Ion |
|---|---|---|---|
| 413 | 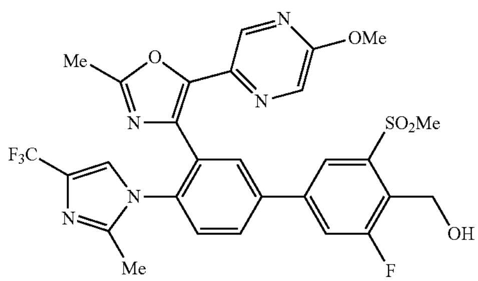 | (3-fluoro-3'-(5-(5-methoxypyrazin-2-yl)-2-methyloxazol-4-yl)-4'-(2-methyl-4-(trifluoromethyl)-1H-imidazol-1-yl)-5-(methylsulfonyl)biphenyl-4-yl)methanol | MS (ESI) 618.2 [M + H]+ |
| 414 | 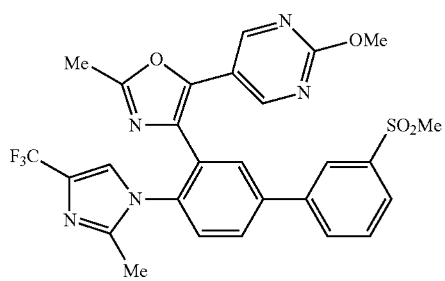 [SMILES: COc1ncc(-c2oc(C)nc2-c2cc(-c3cccc(S(C)(=O)=O)c3)ccc2-n2cc(C(F)(F)F)nc2C)cn1] | 5-(2-methoxypyrimidin-5-yl)-2-methyl-4-(4-(2-methyl-4-(trifluoromethyl)-1H-imidazol-1-yl)-3'-(methylsulfonyl)biphenyl-3-yl)oxazole | MS (ESI) 570.2 [M + H]+ |
| 415 | 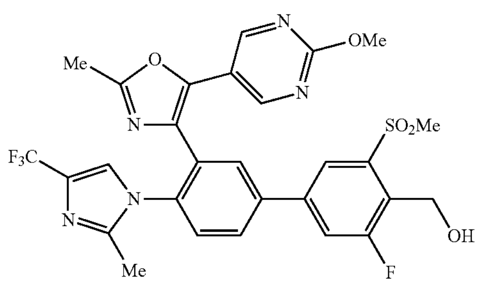 [SMILES: COc1ncc(-c2oc(C)nc2-c2cc(-c3cc(F)c(CO)c(S(C)(=O)=O)c3)ccc2-n2cc(C(F)(F)F)nc2C)cn1] | (3-fluoro-3'-(5-(2-methoxypyrimidin-5-yl)-2-methyloxazol-4-yl)-4'-(2-methyl-4-(trifluoromethyl)-1H-imidazol-1-yl)-5-(methylsulfonyl)biphenyl-4-yl)methanol | MS (ESI) 618.2 [M + H]+ |
| 416 | 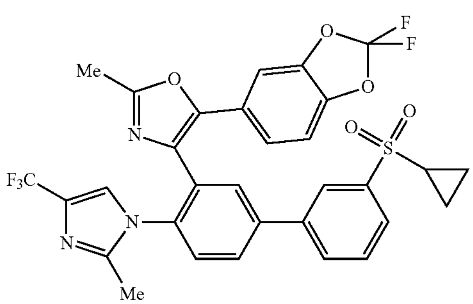 [SMILES: Cc1nc(-c2cc(-c3cccc(S(=O)(=O)C4CC4)c3)ccc2-n2cc(C(F)(F)F)nc2C)c(-c2ccc3c(c2)OC(F)(F)O3)o1] | 4-(3'-cyclopropylsulfonyl)-4-(2-methyl-4-(trifluoromethyl)-1H-imidazol-1-yl)-[1,1'-biphenyl]-3-yl)-5-(2,2-difluorobenzo[d][1,3]dioxol-5-yl)-2-methyloxazole 1H NMR (400 MHz, CHLOROFORM-d) δ ppm 8.12 (1 H, s) 7.90-8.01 (2 H, m) 7.84 (2 H, m) 7.66-7.75 (1 H, m) 7.49 (1 H, d, J = 8.28 Hz) 7.09-7.16 (2 H, m) 7.01 (1 H, d, J = 8.28 Hz) 6.92 (1 H, s) 2.48-2.56 (1 H, m) 2.47 (3 H, s) 2.11 (3 H, s) 1.35-1.44 (2 H, m) 1.02-1.14 (2 H, m) | MS (ESI) 644.2 [M + H]+ |
| 417 | 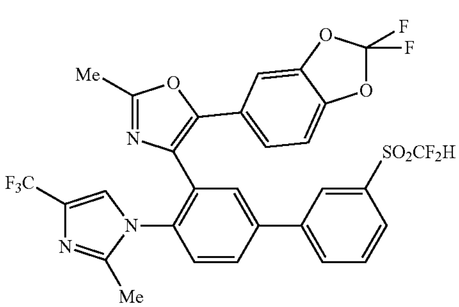 | 5-(2,2-difluorobenzo[d][1,3]dioxol-5-yl)-4-(3'-(difluoromethylsulfonyl)-4-(2-methyl-4-(trifluoromethyl)-1H-imidazol-1-yl)biphenyl-3-yl)-2-methyloxazole 1H NMR (400 MHz, CHLOROFORM-d) δ ppm 8.14 (1 H, s) 8.06 (1 H, d, J = 7.78 Hz) 7.99 (1 H, d, J = 8.03 Hz) 7.92 (1 H, d, J = 2.01 Hz) 7.75-7.85 (2 H, m) 7.51 (1H, d, J = 8.28 Hz) 7.10-7.16 (2 H, m) 6.98-7.05 (1 H, m) 6.94 (1 H, s) 6.05-6.42 (1H, m) 2.46 (3 H, s) 2.11 (3 H, s) | MS (ESI) 654.1 [M + H]+ |

-continued

| Ex # | Structure | Name and Characterization | Molecular Ion |
|---|---|---|---|
| 418 | 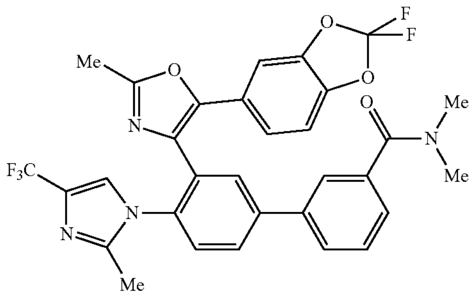 [SMILES: Cc1nc(-c2cc(-c3cccc(C(=O)N(C)C)c3)ccc2-n2cc(C(F)(F)F)nc2C)c(-c2ccc3c(c2)OC(F)(F)O3)o1] | 3'-(5-(2,2-difluorobenzo[d][1,3]dioxol-5-yl)-2-methyloxazol-4-yl)-N,N-dimethyl-4'-(2-methyl-4-(trifluoromethyl)-1H-imidazol-1-yl)biphenyl-3-carboxamide | MS (ESI) 611.2 [M + H]+ |
| 419 | 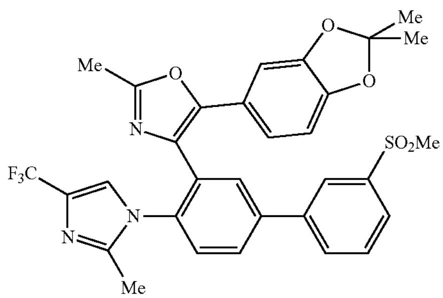 [SMILES: Cc1nc(-c2cc(-c3cccc(S(C)(=O)=O)c3)ccc2-n2cc(C(F)(F)F)nc2C)c(-c2ccc3c(c2)OC(C)(C)O3)o1] | 5-(2,2-dimethyl-2,3-dihydrobenzofuran-5-yl)-2-methyl-4-(4-(2-methyl-4-(trifluoromethyl)-1H-imidazol-1-yl)-3'-(methylsulfonyl)biphenyl-3-yl)oxazole | MS (ESI) 608.2 [M + H]+ |
| 420 | 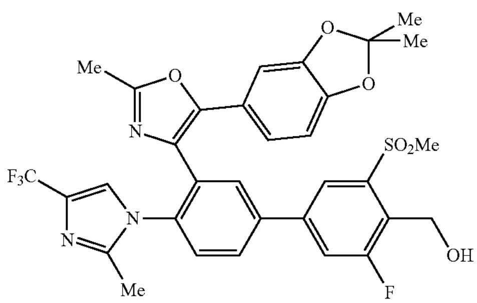 [SMILES: Cc1nc(-c2cc(-c3cc(F)c(CO)c(S(C)(=O)=O)c3)ccc2-n2cc(C(F)(F)F)nc2C)c(-c2ccc3c(c2)OC(C)(C)O3)o1] | (3'-(5-(2,2-dimethyl-2,3-dihydrobenzofuran-5-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 656.2 [M + H]+ |
| 421 | 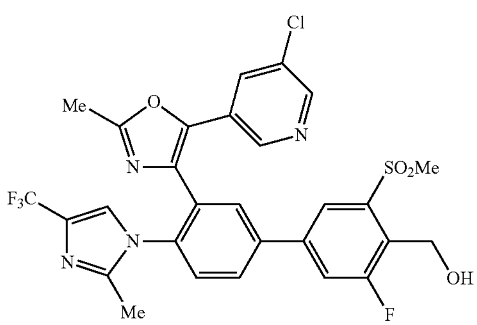 [SMILES: Cc1nc(-c2cc(-c3cc(F)c(CO)c(S(C)(=O)=O)c3)ccc2-n2cc(C(F)(F)F)nc2C)c(-c2cncc(Cl)c2)o1] | (3'-(5-(5-chloropyridin-3-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 621.2 [M + H]+ |
| 422 | 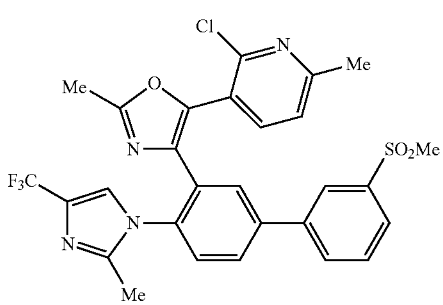 [SMILES: Cc1ccc(-c2oc(C)nc2-c2cc(-c3cccc(S(C)(=O)=O)c3)ccc2-n2cc(C(F)(F)F)nc2C)c(Cl)n1] | 5-(2-chloro-6-methylpyridin-3-yl)-2-methyl-4-(4-(2-methyl-4-(trifluoromethyl)-1H-imidazol-1-yl)-3'-(methylsulfonyl)biphenyl-3-yl)oxazole | MS (ESI) 587.2 [M + H]+ |

-continued

| Ex # | Structure | Name and Characterization | Molecular Ion |
|---|---|---|---|
| 423 | 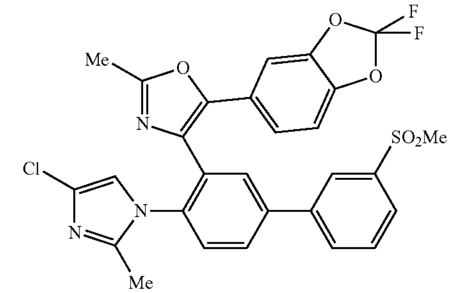 [SMILES: Cc1nc(-c2cc(-c3cccc(S(C)(=O)=O)c3)ccc2-n2cc(Cl)nc2C)c(-c2ccc3c(c2)OC(F)(F)O3)o1] | 4-(4-(4-chloro-2-methyl-1H-imidazol-1-yl)-3'-(methylsulfonyl)biphenyl-3-yl)-5-(2,2-difluorobenzo[d][1,3]dioxol-5-yl)-2-methyloxazole<br>$^1$H NMR (400 MHz, CHLOROFORM-d) δ ppm 8.16 (t, 1 H, J = 1.63 Hz), 8.01 (dt, 1 H, J = 7.78, 1.38 Hz), 7.84-7.91 (m, 2 H), 7.80 (dd, 1 H, J = 8.28, 2.26 Hz), 7.68-7.75 (m, 1 H), 7.45 (d, 1 H, J = 8.28 Hz), 7.10-7.18 (m, 2 H), 7.00 (d, 1 H, J = 8.28 Hz), 6.45 (s, 1 H), 3.11 (s, 3 H), 2.48 (s, 3 H), 2.03 (s, 3 H) | MS (ESI) 584.2 [M + H]$^+$ |
| 424 | 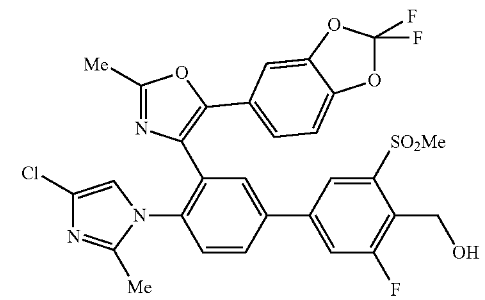 [SMILES: Cc1nc(-c2cc(-c3cc(F)c(CO)c(S(C)(=O)=O)c3)ccc2-n2cc(Cl)nc2C)c(-c2ccc3c(c2)OC(F)(F)O3)o1] | (4'-(4-chloro-2-methyl-1H-imidazol-1-yl)-3'-(5-(2,2-difluorobenzo[d][1,3]dioxol-5-yl)-2-methyloxazol-4-yl)-3-fluoro-5-(methylsulfonyl)biphenyl-4-yl)methanol | MS (ESI) 632.2 [M + H]$^+$ |
| 425 | 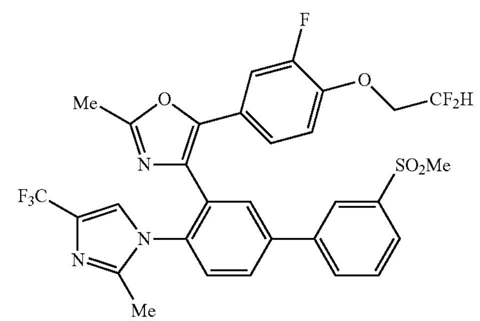 [SMILES: Cc1nc(-c2cc(-c3cccc(S(C)(=O)=O)c3)ccc2-n2cc(C(F)(F)F)nc2C)c(-c2ccc(OCC(F)F)c(F)c2)o1] | 5-(4-(2,2-difluoroethoxy)-3-fluorophenyl)-2-methyl-4-(4-(2-methyl-4-(trifluoromethyl)-1H-imidazol-1-yl)-3'-(methylsulfonyl)biphenyl-3-yl)oxazole | MS (ESI) 636.2 [M + H]$^+$ |
| 426 | 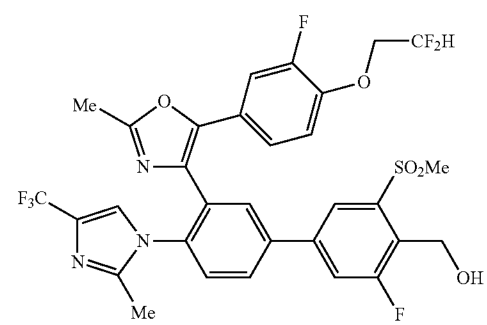 [SMILES: Cc1nc(-c2cc(-c3cc(F)c(CO)c(S(C)(=O)=O)c3)ccc2-n2cc(C(F)(F)F)nc2C)c(-c2ccc(OCC(F)F)c(F)c2)o1] | (3'-(5-(4-(2,2-difluoroethoxy)-3-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 684.2 [M + H]$^+$ |
| 427 | 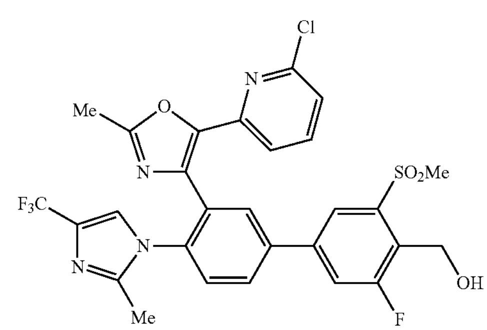 [SMILES: Cc1nc(-c2cc(-c3cc(F)c(CO)c(S(C)(=O)=O)c3)ccc2-n2cc(C(F)(F)F)nc2C)c(-c2cccc(Cl)n2)o1] | (3'-(5-(6-chloropyridin-2-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 621.2 [M + H]$^+$ |

-continued

| Ex # | Structure | Name and Characterization | Molecular Ion |
|---|---|---|---|
| 428 | 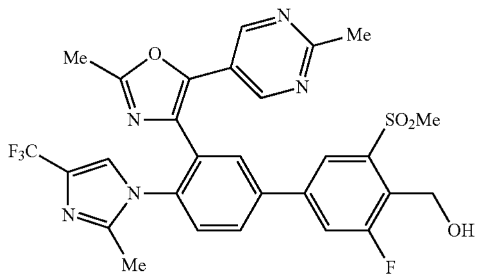 [SMILES: Cc1ncc(-c2oc(C)nc2-c2cc(-c3cc(F)c(CO)c(S(C)(=O)=O)c3)ccc2-n2cc(C(F)(F)F)nc2C)cn1] | (3-fluoro-4'-(2-methyl-4-(trifluoromethyl)-1H-imidazol-1-yl)-3'-(2-methyl-5-(2-methylpyrimidin-5-yl)oxazol-4-yl)-5-(methylsulfonyl)biphenyl-4-yl)methanol | MS (ESI) 602.2 [M + H]+ |
| 429 | 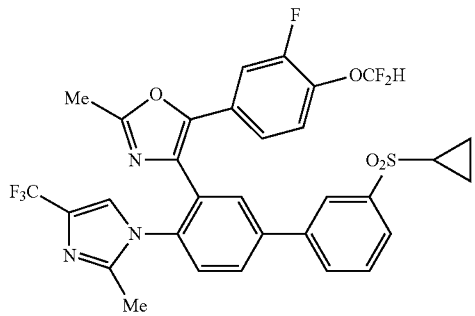 | 4-(3'-(cyclopropylsulfonyl)-4-(2-methyl-4-(trifluoromethyl)-1H-imidazol-1-yl)biphenyl-3-yl)-5-(4-(difluoromethoxy)-3-fluorophenyl)-2-methyloxazole 1H NMR (400 MHz, METHANOL-d4) δ ppm 8.15 (1 H, t, J = 1.63 Hz) 7.95-8.12 (4 H, m) 7.76-7.83 (1 H, m) 7.72 (1 H, d, J = 8.28 Hz) 7.39 (1 H, d, J = 1.25 Hz) 7.18-7.35 (3 H, m) 6.68-7.10 (1 H, m) 2.73-2.83 (1 H, m) 2.47 (3 H, s) 2.10 (3 H, s) 1.25-1.33 (2 H, m) 1.11 (2 H, m). | MS (ESI) 648.0 [M + H]+ |
| 430 | 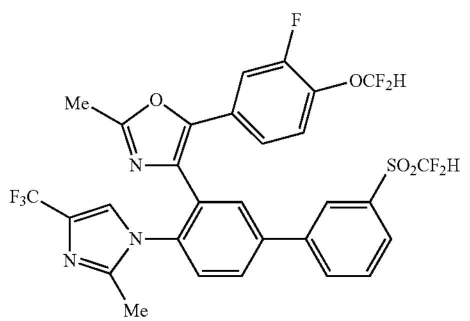 | 5-(4-(difluoromethoxy)-3-fluorophenyl)-4-(3'-(difluoromethylsulfonyl)-4-(2-methyl-4-(trifluoromethyl)-1H-imidazol-1-yl)biphenyl-3-yl)-2-methyloxazole | MS (ESI) 658.0 [M + H]+ |
| 431 | 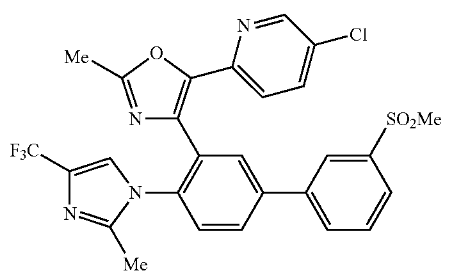 [SMILES: Cc1nc(-c2cc(-c3cccc(S(C)(=O)=O)c3)ccc2-n2cc(C(F)(F)F)nc2C)c(-c2ccc(Cl)cn2)o1] | 5-(5-chloropyridin-2-yl)-2-methyl-4-(4-(2-methyl-4-(trifluoromethyl)-1H-imidazol-1-yl)-3'-(methylsulfonyl)biphenyl-3-yl)oxazole | MS (ESI) 573.0 [M + H]+ |
| 432 | 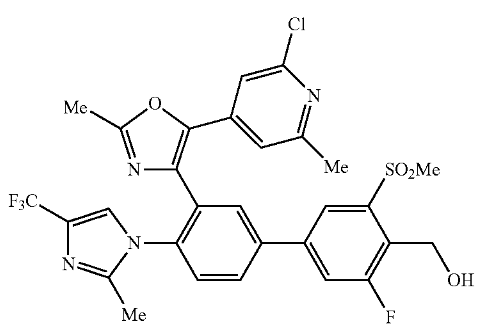 | (3'-(5-(2-chloro-6-methylpyridin-4-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 635.0 [M + H]+ |

-continued

| Ex # | Structure | Name and Characterization | Molecular Ion |
|---|---|---|---|
| 433 | 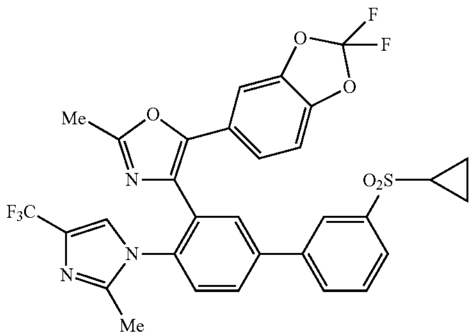 [SMILES: Cc1nc(-c2cc(-c3cccc(S(=O)(=O)C4CC4)c3)ccc2-n2cc(C(F)(F)F)nc2C)c(-c2ccc3c(c2)OC(F)(F)O3)o1] | 4-(3'-(cyclopropylsulfonyl)-4-(2-methyl-4-(trifluoromethyl)-1H-imidazol-1-yl)biphenyl-3-yl)-5-2,2-diflubenzo[d][1,3]dioxol-5-yl)-2-methyloxazole | MS (ESI) 644.2 [M + H]+ |
| 434 | 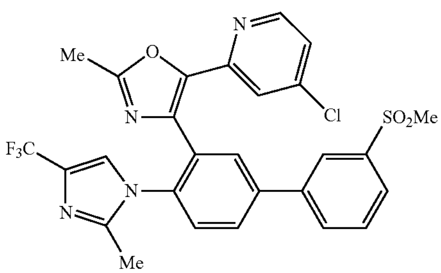 [SMILES: Cc1nc(-c2cc(-c3cccc(S(C)(=O)=O)c3)ccc2-n2cc(C(F)(F)F)nc2C)c(-c2cc(Cl)ccn2)o1] | 5-(4-chloropyridin-2-yl)-2-methyl-4-(4-(2-methyl-4-(trifluoromethyl)-1H-imidazol-1-yl)-3'-(methylsulfonyl)biphenyl-3-yl)oxazole | MS (ESI) 573.0 [M + H]+ |
| 435 | 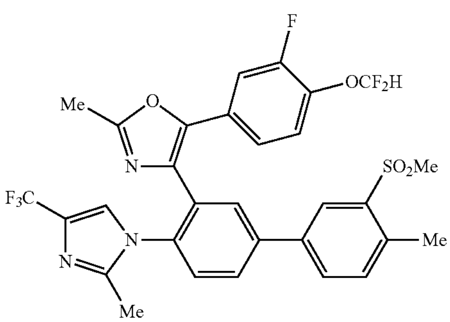 | 5-(4-(difluoromethoxy)-3-fluorophenyl)-2-methyl-4-(4'-methyl-4-(2-methyl-4-(trifluoromethyl)-1H-imidazol-1-yl)-3'-(methylsulfonyl)biphenyl-3-yl)oxazole | MS (ESI) 636.0 [M + H]+ |
| 436 | 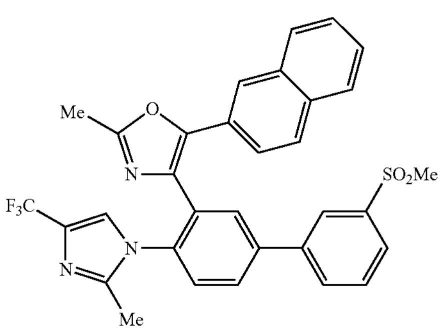 [SMILES: Cc1nc(-c2cc(-c3cccc(S(C)(=O)=O)c3)ccc2-n2cc(C(F)(F)F)nc2C)c(-c2ccc3ccccc3c2)o1] | 2-methyl-4-(4-(2-methyl-4-(trifluoromethyl)-1H-imidazol-1-yl)-3'-(methylsulfonyl)biphenyl-3-yl)-5-(naphthalen-2-yl)oxazole | MS (ESI) 588.2 [M + H]+ |
| 437 | 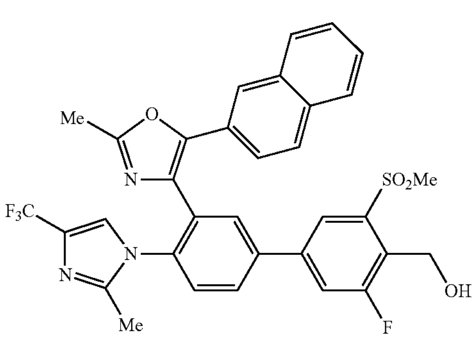 [SMILES: Cc1nc(-c2cc(-c3cc(F)c(CO)c(S(C)(=O)=O)c3)ccc2-n2cc(C(F)(F)F)nc2C)c(-c2ccc3ccccc3c2)o1] | (3-fluoro-4'-(2-methyl-4-(trifluoromethyl)-1H-imidazol-1-yl)-3'-(2-methyl-5-(naphthalen-2-yl)oxazol-4-yl)-5-(methylsulfonyl)biphenyl-4-yl)methanol | MS (ESI) 636.2 [M + H]+ |

-continued

| Ex # | Structure | Name and Characterization | Molecular Ion |
|---|---|---|---|
| 438 | 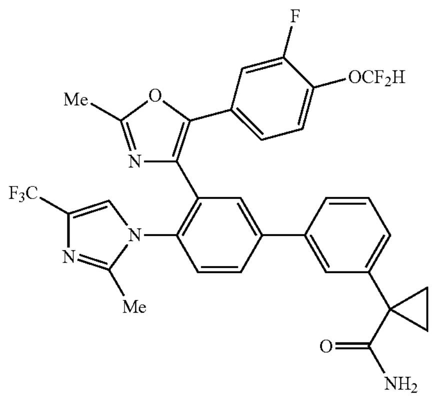 | 1-(3'-(5-(4-(difluoromethoxy)-3-fluorophenyl)-2-methyloxazol-4-yl)-4'-(2-methyl-4-(trifluoromethyl)-1H-imidazol-1-yl)biphenyl-3-yl)cyclopropanecarboxamide | MS (ESI) 627.2 [M + H]⁺ |
| 439 | 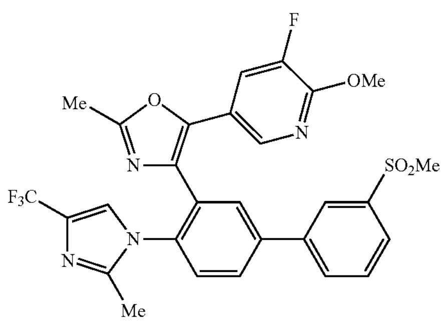 | 5-(5-fluoro-6-methoxypyridin-3-yl)-2-methyl-4-(4-(2-methyl-4-(trifluoromethyl)-1H-imidazol-1-yl)-3'-(methylsulfonyl)biphenyl-3-yl)oxazole<br>1H NMR (400 MHz, CHLOROFORM-d) δ ppm 8.14-8.21 (m, 1 H) 8.02 (d, J = 7.78 Hz, 1 H) 7.93 (s, 1 H) 7.79-7.90 (m, 3 H) 7.68-7.76 (m, 1 H) 7.44-7.54 (m, 2 H) 6.97 (d, J = 1.26 Hz, 1 H) 4.01 (s, 3 H) 3.12 (s, 3 H) 2.47 (s, 3 H) 2.10 (s, 3 H) | MS (ESI) 587.1 [M + H]⁺ |
| 440 | 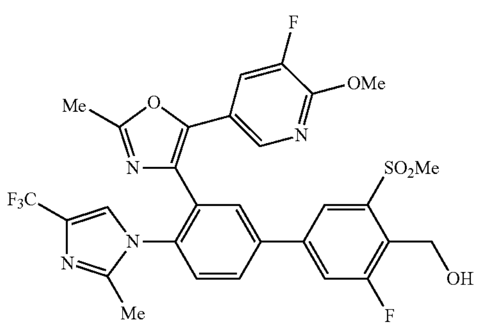 [SMILES: COc1ncc(-c2oc(C)nc2-c2cc(-c3cc(F)c(CO)c(S(C)(=O)=O)c3)ccc2-n2cc(C(F)(F)F)nc2C)cc1F] | (3-fluoro-3'-(5-(5-fluoro-6-methoxypyridin-3-yl)-2-methyloxazol-4-yl)-4'-(2-methyl-4-(trifluoromethyl)-1H-imidazol-1-yl)-5-(methylsulfonyl)biphenyl-4-yl)methanol<br>1H NMR (400 MHz, CHLOROFORM-d) δ ppm 8.12 (s, 1 H) 7.914 (d, J = 2.01 Hz, 1 H) 7.86 (d, J = 1.76 Hz, 1 H) 7.80 (dd, J = 8.16, 2.13 Hz, 1 H) 7.62 (d, J = 9.79 Hz, 1 H) 7.43-7.54 (m, 2 H) 6.97 (s, 1 H) 5.11 (s, 2 H) 4.01 (s, 3 H) 3.30 (s, 3 H) 2.46 (s, 3 H) 2.08 (s, 3 H) | MS (ESI) 635.1 [M + H]⁺ |
| 441 | 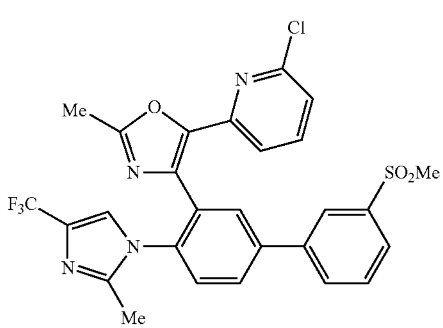 [SMILES: Cc1nc(-c2cc(-c3cccc(S(C)(=O)=O)c3)ccc2-n2cc(C(F)(F)F)nc2C)c(-c2cccc(Cl)n2)o1] | 5-(6-chloropyridin-2-yl)-2-methyl-4-(4-(2-methyl-4-(trifluoromethyl)-1H-imidazol-1-yl)-3'-(methylsulfonyl)biphenyl-3-yl)oxazole | MS (ESI) 573.0 [M + H]⁺ |

| Ex # | Structure | Name and Characterization | Molecular Ion |
|---|---|---|---|
| 442 | 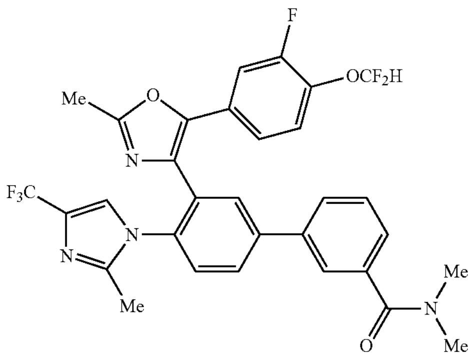 | 3'-(5-(4-(difluoromethoxy)-3-fluorophenyl)-2-methyloxazol-4-yl)-N,N-dimethyl-4'-(2-methyl-4-(trifluoromethyl)-1H-imidazol-1-yl)biphenyl-3-carboxamide | MS (ESI) 615.2 [M + H]+ |
| 443 | 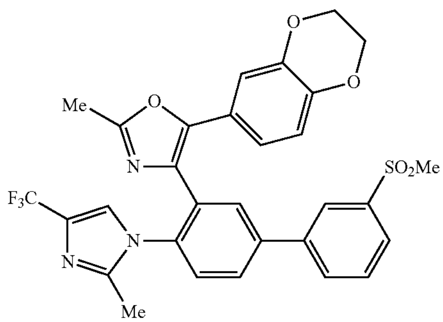 [SMILES: Cc1nc(-c2cc(-c3cccc(S(C)(=O)=O)c3)ccc2-n2cc(C(F)(F)F)nc2C)c(-c2ccc3c(c2)OCCO3)o1] | 5-(2,3-dihydrobenzo[b][1,4]dioxin-6-yl)-2-methyl-4-(4-(2-methyl-4-(trifluoromethyl)-1H-imidazol-1-yl)-3'-(methylsulfonyl)biphenyl-3-yl)oxazole | MS (ESI) 596.2 [M + H]+ |
| 444 | 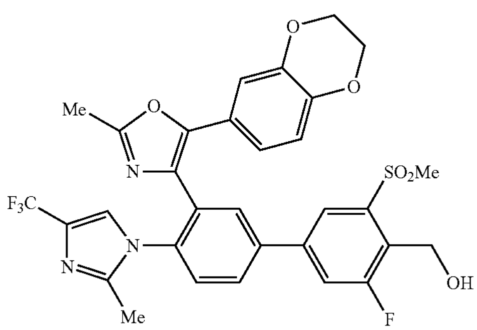 [SMILES: Cc1nc(-c2cc(-c3cc(F)c(CO)c(S(C)(=O)=O)c3)ccc2-n2cc(C(F)(F)F)nc2C)c(-c2ccc3c(c2)OCCO3)o1] | (3'-(5-(2,3-dihydrobenzo[b][1,4]dioxin-6-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 644.2 [M + H]+ |
| 445 | 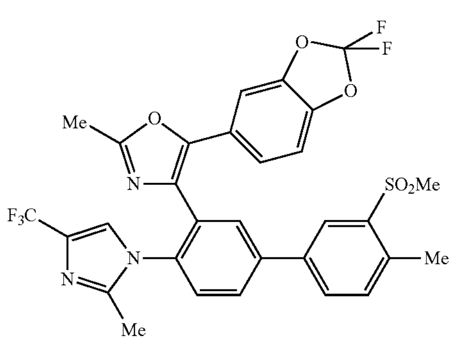 [SMILES: Cc1nc(-c2cc(-c3ccc(C)c(S(C)(=O)=O)c3)ccc2-n2cc(C(F)(F)F)nc2C)c(-c2ccc3c(c2)OC(F)(F)O3)o1] | 5-(2,2-difluorobenzo[d][1,3]dioxol-5-yl)-2-methyl-4-(4'-methyl-4-(2-methyl-4-(trifluoromethyl)-1H-imidazol-1-yl)-3'-(methylsulfonyl)biphenyl-3-yl)oxazole | MS (ESI) 632.0 [M + H]+ |

| Ex # | Structure | Name and Characterization | Molecular Ion |
|---|---|---|---|
| 446 | 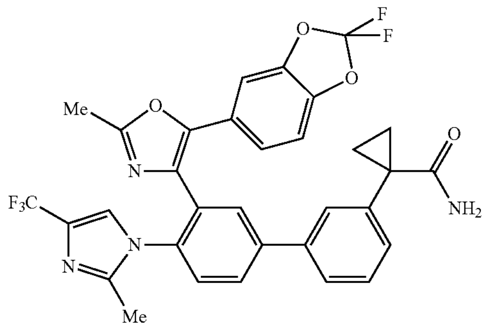 [SMILES: Cc1nc(-c2cc(-c3cccc(C4(C(N)=O)CC4)c3)ccc2-n2cc(C(F)(F)F)nc2C)c(-c2ccc3c(c2)OC(F)(F)O3)o1] | 1-(3'-(5-(2,2-difluorobenzo[d][1,3]dioxol-5-yl)-methyloxazol-4-yl)-4'-(2-methyl-4-(trifluoromethyl)-1H-imidazol-1-yl)biphenyl-3-yl)cyclopropanecarboxamide | MS (ESI) 623.2 [M + H]+ |
| 447 | 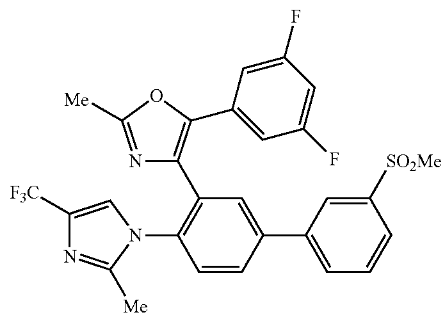 | 5-(3,5-difluorophenyl)-2-methyl-4-(4-(2-methyl-4-(trifluoromethyl)-1H-imidazol-1-yl)-3'-methylsulfonyl)biphenyl-3-yl)oxazole | MS (ESI) 574.2 [M + H]+ |
| 448 | 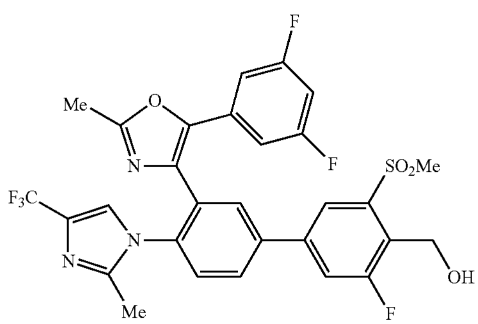 | (3'-(5-(3,5-difluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 622.2 [M + H]+ |
| 449 | 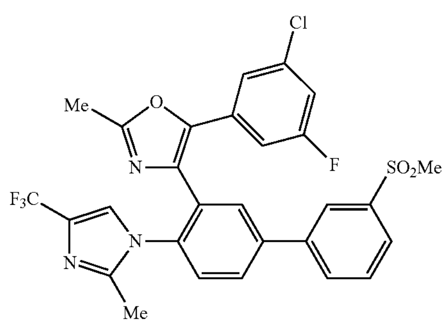 [SMILES: Cc1nc(-c2cc(-c3cccc(S(C)(=O)=O)c3)ccc2-n2cc(C(F)(F)F)nc2C)c(-c2cc(F)cc(Cl)c2)o1] | 5-(3-chloro-5-fluorophenyl)-2-methyl-4-(4-(2-methyl-4-(trifluoromethyl)-1H-imidazol-1-yl)-3'-(methylsulfonyl)biphenyl-3-yl)oxazole | MS (ESI) 590.0 [M + H]+ |
| 450 | 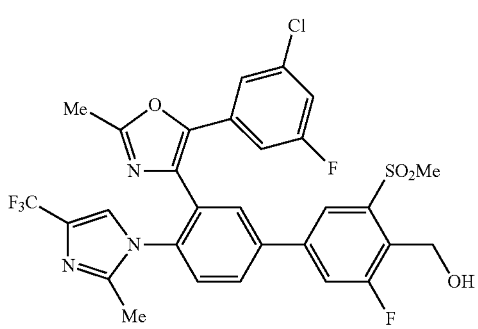 | (3'-(5-(3-chloro-5-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 638.0 [M + H]+ |

| Ex # | Structure | Name and Characterization | Molecular Ion |
|---|---|---|---|
| 451 | 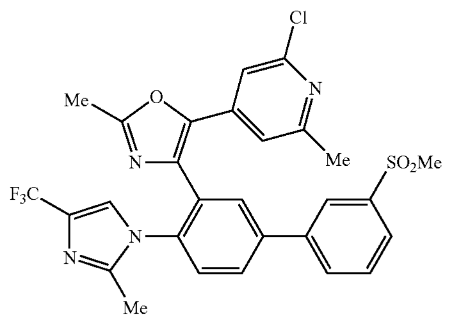 [SMILES: Cc1cc(-c2oc(C)nc2-c2cc(-c3cccc(S(C)(=O)=O)c3)ccc2-n2cc(C(F)(F)F)nc2C)cc(Cl)n1] | 5-(2-chloro-6-methylpyridin-4-yl)-2-methyl-4-(4-(2-methyl-4-(trifluoromethyl)-1H-imidazol-1-yl)-3'-(methylsulfonyl)biphenyl-3-yl)oxazole | MS (ESI) 587.0 [M + H]+ |
| 452 | 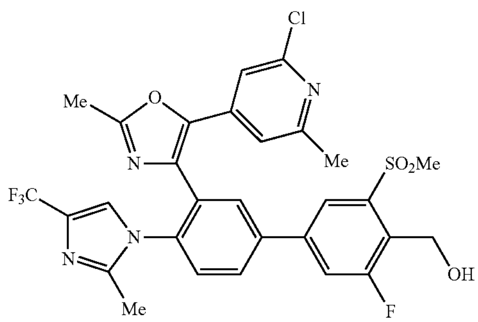 | (3'-(5-(2-chloro-6-methylpyridin-4-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 635.2 [M + H]+ |
| 453 | 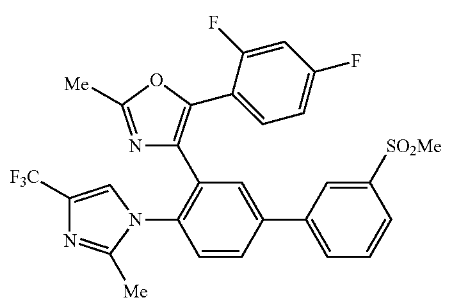 [SMILES: Cc1nc(-c2cc(-c3cccc(S(C)(=O)=O)c3)ccc2-n2cc(C(F)(F)F)nc2C)c(-c2ccc(F)cc2F)o1] | 5-(2,4-difluorophenyl)-2-methyl-4-(4-(2-methyl-4-(trifluoromethyl)-1H-imidazol-1-yl)-3'-(methylsulfonyl)biphenyl-3-yl)oxazole | MS (ESI) 574.1 [M + H]+ |
| 454 | 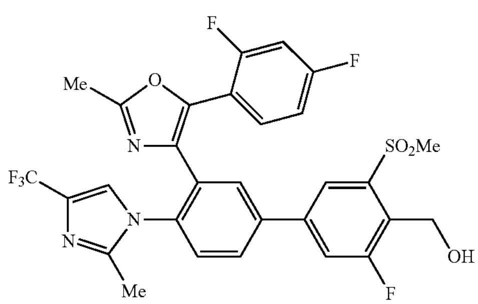 | (3'-(5-(2,4-difluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 622.2 [M + H]+ |
| 455 | 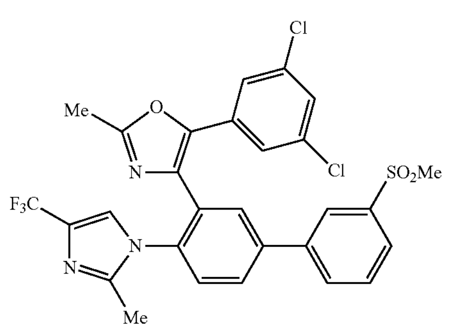 | 5-(3,5-dichlorophenyl)-2-methyl-4-(4-(2-methyl-4-(trifluoromethyl)-1H-imidazol-1-yl)-3'-(methylsulfonyl)biphenyl-3-yl)oxazole | MS (ESI) 606.0 [M + H]+ |

| Ex # | Structure | Name and Characterization | Molecular Ion |
|---|---|---|---|
| 456 | 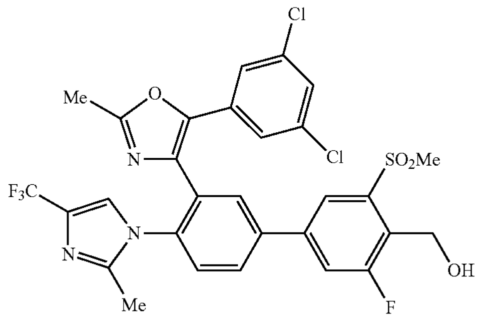 | (3'-(5-(3,5-dichlorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 654.0 [M + H]+ |
| 457 | 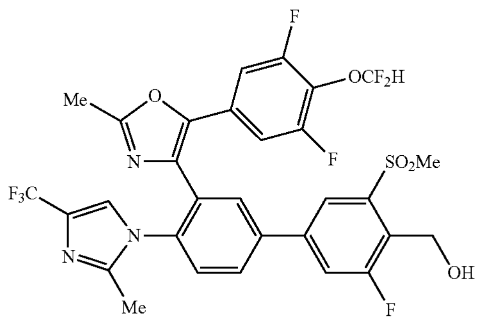 | (3'-(5-(4-(difluoromethoxy)-3,5-difluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol 1H NMR (400 MHz, CHLOROFORM-d) δ ppm 8.11 (d, J = 1.25 Hz, 1 H) 7.92 (d, J = 2.00 Hz, 1 H) 7.86 (dd, J = 8.25, 2.25 Hz, 1 H) 7.64 (dd, J = 9.76, 2.00 Hz, 1 H) 7.52-7.58 (m, 1 H) 7.02-7.11 (m, 2 H) 6.95-7.00 (m, 1 H) 6.39-6.81 (m, 1 H) 5.11 (d, J = 5.50 Hz, 2 H) 3.30 (s, 3 H) 2.86 (t, J = 6.75 Hz, 1 H) 2.45 (s, 3 H) 2.06 (s, 3 H) | MS (ESI) 688.0 [M + H]+ |
| 458 | 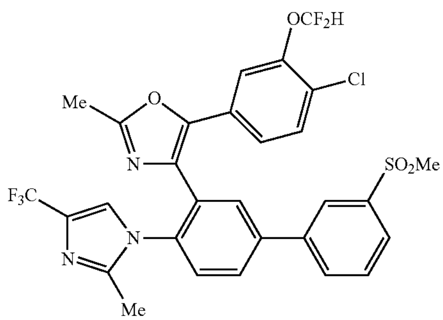 | 5-(4-chloro-3-(difluoromethoxy)phenyl)-2-methyl-4-(4-(2-methyl-4-(trifluoromethyl)-1H-imidazol-1-yl)-3'-(methylsulfonyl)biphenyl-3-yl)oxazole | MS (ESI) 638.0 [M + H]+ |
| 459 | 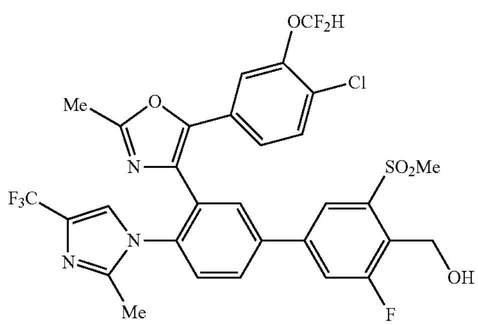 | (3'-(5-(4-chloro-3-(difluoromethoxy)phenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 686.0 [M + H]+ |
| 460 | 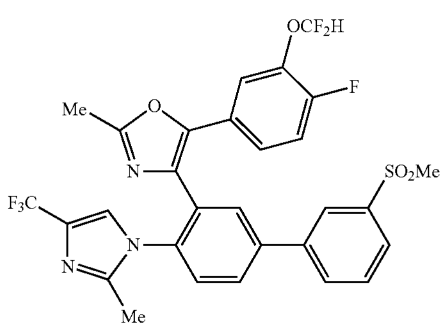 | 5-(3-(difluoromethoxy)-4-fluorophenyl)-2-methyl-4-(4-(2-methyl-4-(trifluoromethyl)-1H-imidazol-1-yl)-3'-(methylsulfonyl)biphenyl-3-yl)oxazole | MS (ESI) 622.2 [M + H]+ |

-continued

| Ex # | Structure | Name and Characterization | Molecular Ion |
|---|---|---|---|
| 461 | 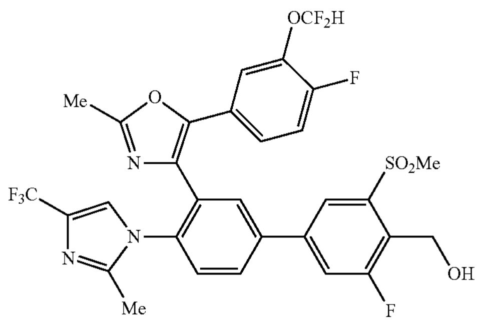 | (3'-(5-(3-(difluoromethoxy)-4-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 670.2 [M + H]+ |
| 462 | 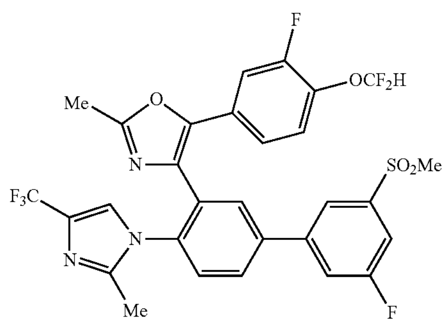 | 5-(4-difluoromethoxy)-3-fluorophenyl)-4-(3'-fluoro-4-(2-methyl-4-(trifluoromethyl)-1H-imidazol-1-yl)-5'-(methylsulfonyl)biphenyl-3-yl)-2-methyloxazole | MS (ESI) 640.0 [M + H]+ |
| 463 | 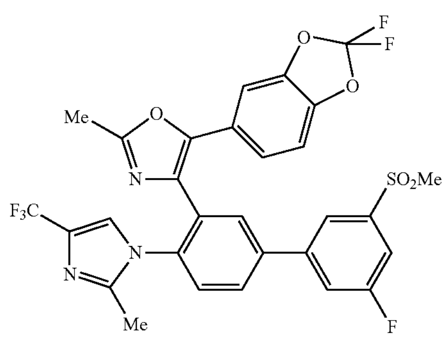 [SMILES: Cc1nc(-c2cc(-c3cc(F)cc(S(C)(=O)=O)c3)ccc2-n2cc(C(F)(F)F)nc2C)c(-c2ccc3c(c2)OC(F)(F)O3)o1] | 5-(2,2-difluorobenzo[d][1,3]dioxol-5-yl)-4-(3'-fluoro-4-(2-methyl-4-(trifluoromethyl)-1H-imidazol-1-yl)-5'-(methylsulfonyl)biphenyl-3-yl)-2-methyloxazole | MS (ESI) 636.0 [M + H]+ |
| 464 | 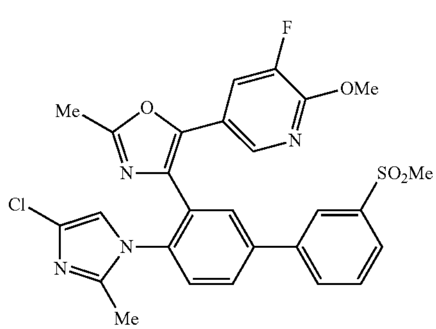 [SMILES: COc1ncc(-c2oc(C)nc2-c2cc(-c3cccc(S(C)(=O)=O)c3)ccc2-n2cc(Cl)nc2C)cc1F] | 4-(4-(4-chloro-2-methyl-1H-imidazol-1-yl)-3'-(methylsulfonyl)biphenyl-3-yl)-5-(5-fluoro-6-methoxypyridin-3-yl)-2-methyloxazole 1H NMR (400 MHz, CHLOROFORM-d) δ ppm 8.14-8.21 (m, 1 H), 8.02 (d, J = 7.78 Hz, 1 H), 7.93 (s, 1 H), 7.79-7.90 (m, 3 H), 7.68-7.76 (m, 1 H), 7.44-7.54 (m, 2 H), 6.97 (d, J = 1.26 Hz, 1 H), 4.01 (s, 3 H), 3.12 (s, 3 H), 2.47 (s, 3 H), 2.10 (s, 3 H) | MS (ESI) 553.2 [M + H]+ |

-continued

| Ex # | Structure | Name and Characterization | Molecular Ion |
|---|---|---|---|
| 465 | 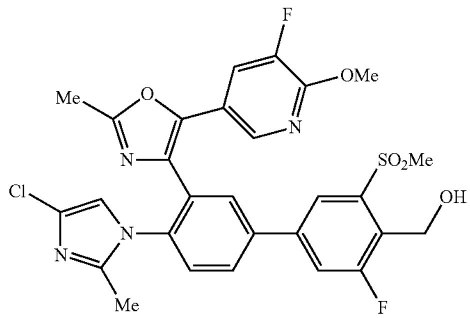 [SMILES: COc1ncc(-c2oc(C)nc2-c2cc(-c3cc(F)c(CO)c(S(C)(=O)=O)c3)ccc2-n2cc(Cl)nc2C)cc1F] | (4'-(4-chloro-2-methyl-1H-imidazol-1-yl)-3-fluoro-3'-(5-(5-fluoro-6-methoxypyridin-3-yl)-2-methyloxazol-4-yl)-5-(methylsulfonyl)biphenyl-4-yl)methanol | MS (ESI) 601.2 [M + H]+ |
| 466 | 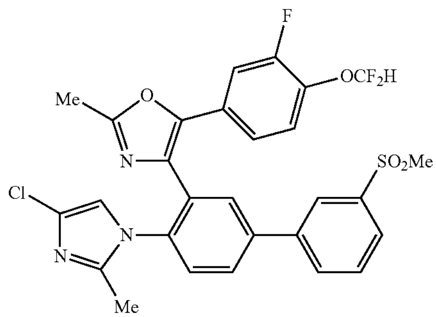 | 4-(4-(4-chloro-2-methyl-1H-imidazol-1-yl)-3'-(methylsulfonyl)biphenyl-3-yl)-5-(4-(difluoromethoxy)-3-fluorophenyl)-2-methyloxazole | MS (ESI) 588.2 [M + H]+ |
| 467 | 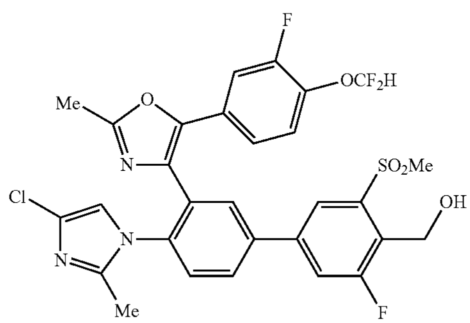 | (4'-(4-chloro-2-methyl-1H-imidazol-1-yl)-3'-(5-(4-(difluoromethoxy)-3-fluorophenyl)-2-methyloxazol-4-yl)-3-fluoro-5-(methylsulfonyl)biphenyl-4-yl)methanol | MS (ESI) 636.0 [M + H]+ |
| 468 | 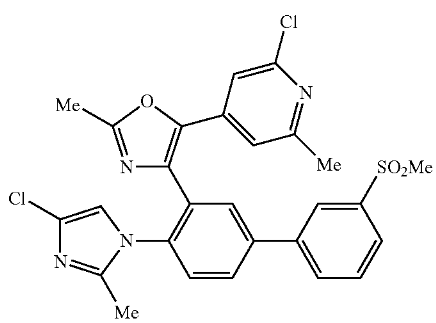 [SMILES: Cc1cc(-c2oc(C)nc2-c2cc(-c3cccc(S(C)(=O)=O)c3)ccc2-n2cc(Cl)nc2C)cc(Cl)n1] | 4-(4-(4-chloro-2-methyl-1H-imidazol-1-yl)-3'-(methylsulfonyl)biphenyl-3-yl)-5-(2-chloro-6-methylpyridin-4-yl)-2-methyloxazole | MS (ESI) 552.8 [M + H]+ |
| 469 | 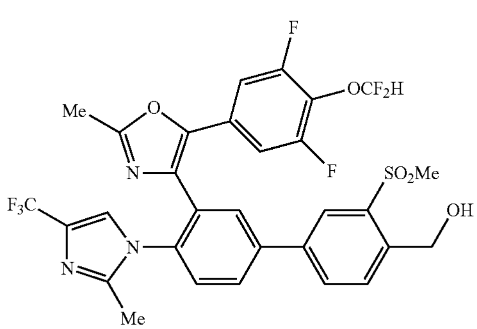 | (3'-(5-(4-(difluoromethoxy)-3,5-difluorophenyl)-2-methyloxazol-4-yl)-4'-(2-methyl-4-(trifluoromethyl)-1H-imidazol-1-yl)-3-(methylsulfonyl)biphenyl-4-yl)methanol | MS (ESI) 669.8 [M + H]+ |

-continued

| Ex # | Structure | Name and Characterization | Molecular Ion |
|---|---|---|---|
| 470 | 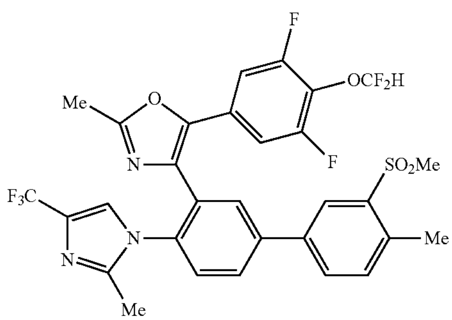 | 5-(4-(difluoromethoxy)-3,5-difluorophenyl)-2-methyl-4-(4'-methyl-4-(2-methyl-4-(trifluoromethyl)-1H-imidazol-1-yl)-3'-(methylsulfonyl)biphenyl-3-yl)oxazole 1H NMR (400 MHz, CHLOROFORM-d) δ ppm 8.27 (d, J = 2.01 Hz, 1 H) 7.81-7.96 (m, 2 H), 7.74 (dd, J = 7.78, 2.01 Hz, 1 H), 7.45-7.55 (m, 2 H), 7.05-7.14 (m, 2 H), 7.00 (d, J = 1.25 Hz, 1 H), 6.41-6.84 (m, 1 H), 3.14 (s, 3 H), 2.79 (s, 3 H), 2.44 (s, 3 H), 2.13 (s, 3 H) | MS (ESI) 553.8 [M + H]+ |
| 471 | 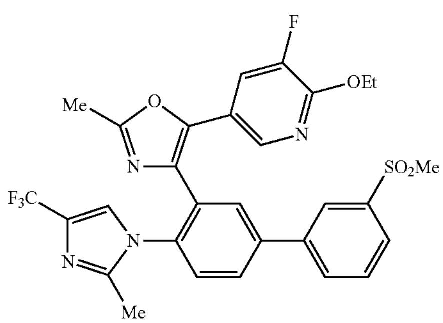 | 5-(6-ethoxy-5-fluoropyridin-3-yl)-2-methyl-4-(4-(2-methyl-4-(trifluoromethyl)-1H-imidazol-1-yl)-3'-(methylsulfonyl)biphenyl-3-yl)oxazole | MS (ESI) 601.2 [M + H]+ |
| 472 | 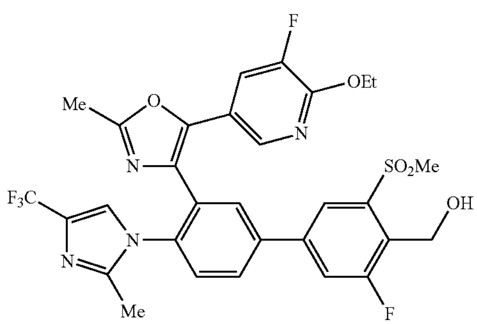 [SMILES: CCOc1ncc(-c2oc(C)nc2-c2cc(-c3cc(F)c(CO)c(S(C)(=O)=O)c3)ccc2-n2cc(C(F)(F)F)nc2C)cc1F] | (3'-(5-(6-ethoxy-5-fluoropyridin-3-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 649.4 [M + H]+ |
| 473 | 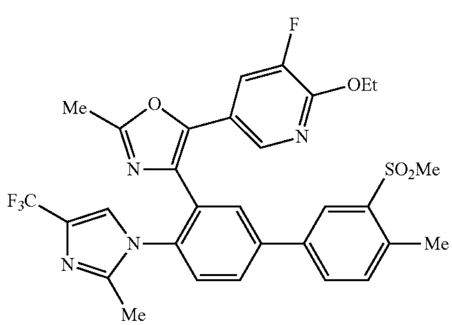 [SMILES: CCOc1ncc(-c2oc(C)nc2-c2cc(-c3ccc(C)c(S(C)(=O)=O)c3)ccc2-n2cc(C(F)(F)F)nc2C)cc1F] | 5-(6-ethoxy-5-fluoropyridn-3-yl)-2-methyl-4-(4'-methyl-4-(2-methyl-4-(trifluoromethyl)-1H-imidazol-1-yl)-3'-(methylsulfonyl)biphenyl-3-yl)oxazole | MS (ESI) 615.4 [M + H]+ |
| 474 | 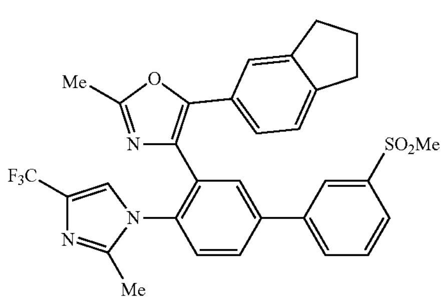 [SMILES: Cc1nc(-c2cc(-c3cccc(S(C)(=O)=O)c3)ccc2-n2cc(C(F)(F)F)nc2C)c(-c2ccc3c(c2)CCC3)o1] | 5-(2,3-dihydro-1H-inden-5-yl)-2-methyl-4-(4-(2-methyl-4-(trifluoromethyl)-1H-imidazol-1-yl)-3'-(methylsulfonyl)biphenyl-3-yl)oxazole | MS (ESI) 578.2 [M + H]+ |

| Ex # | Structure | Name and Characterization | Molecular Ion |
|---|---|---|---|
| 475 | 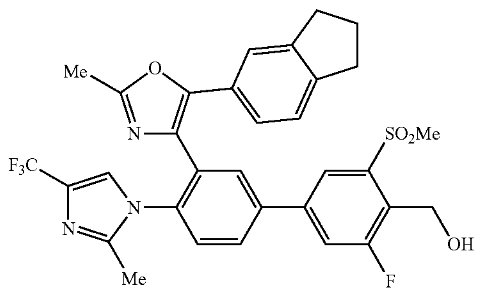 [SMILES: Cc1nc(-c2cc(-c3cc(F)c(CO)c(S(C)(=O)=O)c3)ccc2-n2cc(C(F)(F)F)nc2C)c(-c2ccc3c(c2)CCC3)o1] | (3'-(5-(2,3-dihydro-1H-inden-5-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 626.2 [M + H]+ |
| 476 | 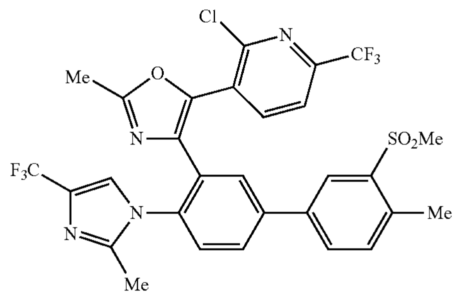 [SMILES: Cc1nc(-c2cc(-c3ccc(C)c(S(C)(=O)=O)c3)ccc2-n2cc(C(F)(F)F)nc2C)c(-c2ccc(C(F)(F)F)nc2Cl)o1] | 5-(2-chloro-6-(trifluoromethyl)pyridin-3-yl)-2-methyl-4-(4'-methyl-4-(2-methyl-4-(trifluoromethyl)-1H-imidazol-1-yl)-3'-(methylsulfonyl)biphenyl-3-yl)oxazole | MS (ESI) 655.0 [M + H]+ |
| 477 | 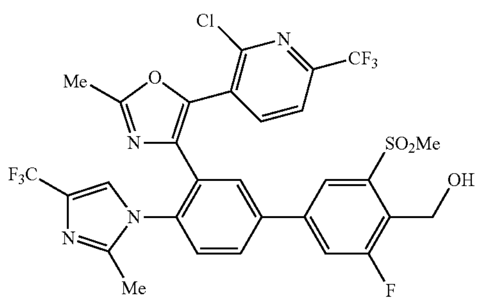 [SMILES: Cc1nc(-c2cc(-c3cc(F)c(CO)c(S(C)(=O)=O)c3)ccc2-n2cc(C(F)(F)F)nc2C)c(-c2ccc(C(F)(F)F)nc2Cl)o1] | (3'-(5-(2-chloro-6-(trifluoromethyl)pyridin-3-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 689.0 [M + H]+ |
| 478 | 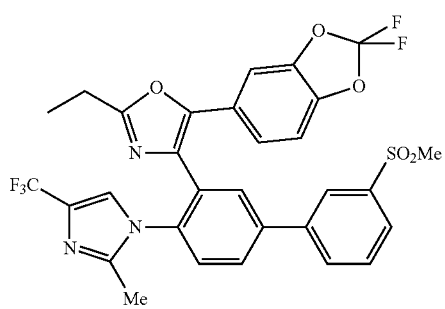 [SMILES: CCc1nc(-c2cc(-c3cccc(S(C)(=O)=O)c3)ccc2-n2cc(C(F)(F)F)nc2C)c(-c2ccc3c(c2)OC(F)(F)O3)o1] | 5-(2,2-difluorobenzo[d][1,3]dioxol-5-yl)-2-ethyl-4-(4-(2-methyl-4-(trifluoromethyl)-1H-imidazol-1-yl)-3'-(methylsulfonyl)biphenyl-3-yl)oxazole | MS (ESI) 632.2 [M + H]+ |
| 479 | 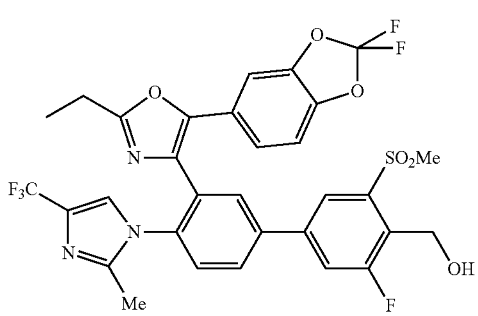 [SMILES: CCc1nc(-c2cc(-c3cc(F)c(CO)c(S(C)(=O)=O)c3)ccc2-n2cc(C(F)(F)F)nc2C)c(-c2ccc3c(c2)OC(F)(F)O3)o1] | (3'-(5-(2,2-difluorobenzo[d][1,3]dioxol-5-yl)-2-ethyloxazol-4-yl)-3-fluoro-4'-(2-methyl-4-(trifluoromethyl)-1H-imidazol-1-yl)-5-(methylsulfonyl)biphenyl-4-yl)methanol 1H NMR (400 MHz, CHLOROFORM-d) δ ppm 8.08 (s, 1 H) 7.88 (d, J = 2.00 Hz, 1 H) 7.80 (dd, J = 8.13, 2.38 Hz, 1 H) 7.60 (dd, J = 9.76, 1.75 Hz, 1 H) 7.47-7.54 (m, 1 H) 7.12-7.19 (m, 2 H) 6.98-7.04 (m, 1 H) 6.94 (d, J = 1.25 Hz, 1 H) 5.10 (d, J = 5.00 Hz, 2 H) 3.28 (s, 3 H) 2.87 (t, J = 6.75 Hz, 1 H) 2.76 (q, J = 7.50 Hz, 2 H) 2.09 (s, 3 H) 1.25 (t, J = 7.60 Hz, 3 H) | MS (ESI) 680.2 [M + H]+ |

| Ex # | Structure | Name and Characterization | Molecular Ion |
|---|---|---|---|
| 480 | 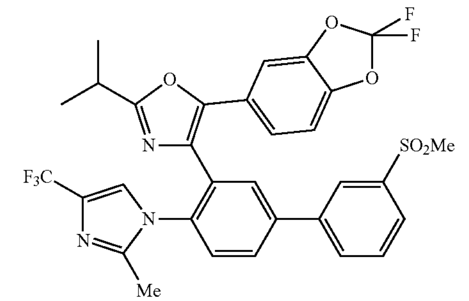 [SMILES: Cc1nc(C(F)(F)F)cn1-c1ccc(-c2cccc(S(C)(=O)=O)c2)cc1-c1nc(C(C)C)oc1-c1ccc2c(c1)OC(F)(F)O2] | 5-(2,2-difluorobenzo[d][1,3]dioxol-5-yl)-2-isopropyl-4-(4-(2-methyl-4-(trifluoromethyl)-1H-imidazol-1-yl)-3'-(methylsulfonyl)biphenyl-3-yl)oxazole 1H NMR (400 MHz, CDCl$_3$-d) δ ppm 8.13 (s, 1 H) 8.01 (d, J = 7.75 Hz, 1 H) 7.88 (d, J = 2.00 Hz, 1 H) 7.78-7.85 (m, 2 H) 7.68-7.75 (m, 1 H) 7.50 (d, J = 8.25 Hz, 1 H) 7.18-7.24 (m, 2 H) 6.96-7.05 (m, 2 H) 3.10 (s, 3 H) 3.00-3.07 (m, 1H) 2.14 (s, 3 H) 1.29 (d, J = 7.00 Hz, 6 H) | MS (ESI) 646.2 [M + H]+ |
| 481 | 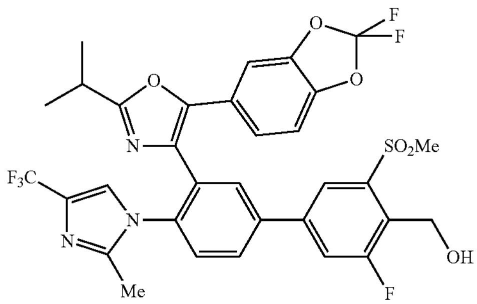 [SMILES: Cc1nc(C(F)(F)F)cn1-c1ccc(-c2cc(F)c(CO)c(S(C)(=O)=O)c2)cc1-c1nc(C(C)C)oc1-c1ccc2c(c1)OC(F)(F)O2] | (3'-(5-(2,2-difluorobenzo[d][1,3]dioxol-5-yl)-2-isopropyloxazol-4-yl)-3-fluoro-4'-(2-methyl-4-(trifluoromethyl)-1H-imidazol-1-yl)-5-(methylsulfonyl)biphenyl-4-yl)methanol 1H NMR (400 MHz, CDCl$_3$-d) δ ppm 8.05 (s, 1 H) 7.85 (d, J = 2.25 Hz, 1 H) 7.79 (dd, J = 8.25, 2.25 Hz, 1 H) 7.57 (dd, J = 10.01, 1.75 Hz, 1 H) 7.51 (d, J = 8.00 Hz, 1 H) 7.17-7.23 (m, 2 H) 6.94-7.05 (m, 2 H) 5.10 (s, 2 H) 3.28 (s, 3 H) 3.04 (dt, J = 14.01, 7.00 Hz, 1 H) 2.12 (s, 3 H) 1.29 (d, J = 7.00 Hz, 6 H) | MS (ESI) 694.2 [M + H]+ |
| 482 | 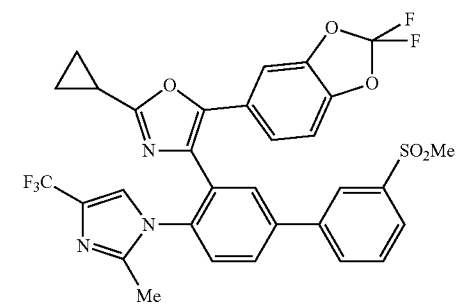 [SMILES: Cc1nc(C(F)(F)F)cn1-c1ccc(-c2cccc(S(C)(=O)=O)c2)cc1-c1nc(C2CC2)oc1-c1ccc2c(c1)OC(F)(F)O2] | 2-cyclopropyl-5-(2,2-difluorobenzo[d][1,3]dioxol-5-yl)-4-(4-(2-methyl-4-(trifluoromethyl)-1H-imidazol-1-yl)-3'-(methylsulfonyl)biphenyl-3-yl)oxazole 1H NMR (400 MHz, CDCl$_3$-d) δ ppm 8.09-8.15 (m, 1 H) 8.00 (d, J = 8.00 Hz, 1 H) 7.76-7.89 (m, 3 H) 7.66-7.75 (m, 1 H) 7.47 (d, J = 8.25 Hz, 1 H) 7.13-7.22 (m, 2 H) 6.91-7.05 (m, 2 H) 3.10 (s, 3 H) 2.10 (s, 3 H) 1.94-2.06 (m, 1 H) 1.02-1.11 (m, 2 H) 0.92-1.02 (m, 2 H) | MS (ESI) 644.2 [M + H]+ |
| 483 | 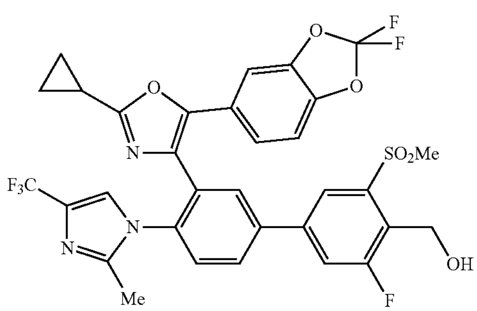 [SMILES: Cc1nc(C(F)(F)F)cn1-c1ccc(-c2cc(F)c(CO)c(S(C)(=O)=O)c2)cc1-c1nc(C2CC2)oc1-c1ccc2c(c1)OC(F)(F)O2] | (3'2-cyclopropyl-5-(2,2-difluorobenzo[d][1,3]dioxol-5-yl)oxazol-4-yl)-3-fluoro-4'-(2-methyl-(trifluoromethyl)-1H-imidazol-1-yl)-5-(methylsulfonyl)biphenyl-4-yl)methanol 1H NMR(400 MHz, CDCl3-d) δ ppm 8.05 (s, 1 H) 7.84 (d, J = 2.00 Hz, 1 H) 7.77 (dd, J = 8.25, 2.25 Hz, 1 H) 7.57 (dd, J = 9.76, 1.50 Hz, 1 H) 7.48 (d, J = 8.25 Hz, 1 H) 7.13-7.20 (m, 2 H) 6.92-7.05 (m, 2 H) 5.09 (d, J = 1.25 Hz, 2 H) 3.28 (s, 3 H) 2.11 (s, 3 H) 2.02 (t, J = 4.88 Hz, 1 H) 1.03-1.11 (m, 2 H) 0.93-1.02 (m, 2 H) | MS (ESI) 692.2 [M + H]+ |
| 484 | 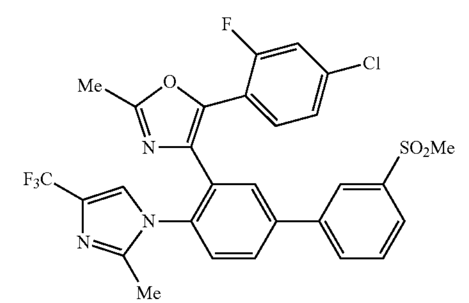 | 5-(4-chloro-2-fluorophenyl)-2-methyl-4-(4-(2-methyl-4-(trifluoromethyl)-1H-imidazol-1-yl)-3'-(methylsulfonyl)biphenyl-3-yl)oxazole | MS (ESI) 590.0 [M + H]+ |

-continued

| Ex # | Structure | Name and Characterization | Molecular Ion |
|---|---|---|---|
| 485 | 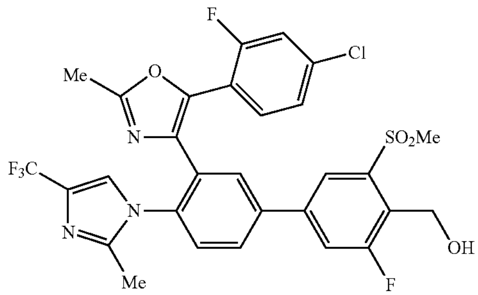 | (3'-(5-(4-chloro-2-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol<br>1H NMR (400 MHz, CDCl$_3$-d) δ ppm 8.06 (1 H, d, J = 1.00 Hz) 7.72-7.77 (2 H, m) 7.57 (1 H, dd, J = 9.76, 1.75 Hz) 7.43-7.52 (2 H, m) 7.21 (1 H, dd, J = 8.50, 2.00 Hz) 7.06 (1 H, dd, J = 10.26, 2.00 Hz) 7.01 (1 H, d, J = 1.25 Hz) 5.09 (2 H, d, J = 1.50 Hz) 3.29 (3 H, s) 2.47 (3 H, s) 2.10 (3 H, s) | MS (ESI) 638.0 [M + H]+ |
| 486 | 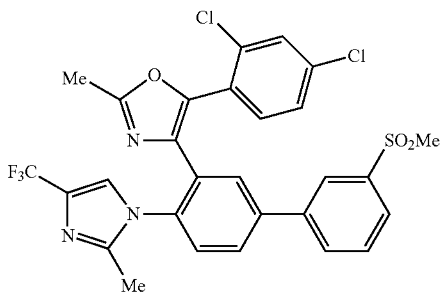 [SMILES: Cc1nc(-c2cc(-c3cccc(S(C)(=O)=O)c3)ccc2-n2cc(C(F)(F)F)nc2C)c(-c2ccc(Cl)cc2Cl)o1] | 5-(2,4-dichlorophenyl)-2-methyl-4-(4-(2-methyl-4-(trifluoromethyl)-1H-imidazol-1-yl)-3'-(methylsulfonyl)biphenyl-3-yl)oxazole | MS (ESI) 606.0 [M + H]+ |
| 487 | 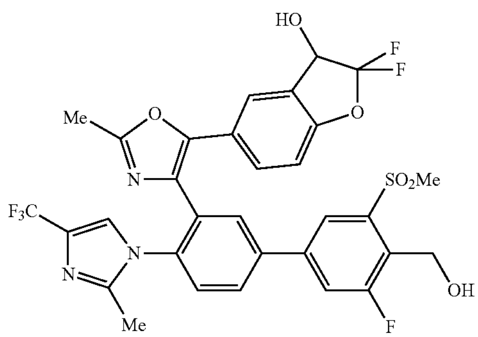 [SMILES: Cc1nc(-c2cc(-c3cc(F)c(CO)c(S(C)(=O)=O)c3)ccc2-n2cc(C(F)(F)F)nc2C)c(-c2ccc3c(c2)C(O)C(F)(F)O3)o1] | 2,2-difluoro-5-(4-(3'-fluoro-4'-(hydroxymethyl)-4-(2-methyl-4-(trifluoromethyl)-1H-imidazol-1-yl)-5'-(methylsulfonyl)biphenyl-3-yl)-2-methyloxazol-5-yl)-2,3-dihydrobenzofuran-3-ol | MS (ESI) 680.0 [M + H]+ |
| 488 | 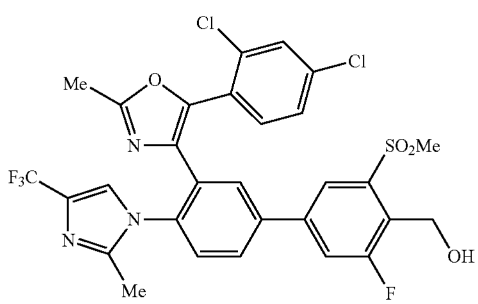 | (3'-(5-(2,4-dichlorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol 1H NMR (400 MHz, CDCl$_3$-d) δ ppm 8.05 (1H, d, J = 1.00 Hz) 7.70-7.75 (2 H, m) 7.53 (1 H, dd, J = 9.76, 1.75 Hz) 7.37-7.42 (2 H, m) 7.29 (2 H, m) 6.93 (1 H, d, J = 1.25 Hz) 5.10 (2 H, d, J = 1.50 Hz) 3.29 (3 H, s) 2.50 (3 H, s) 2.09 (3 H, s) | MS (ESI) 654.0 [M + H]+ |
| 489 | 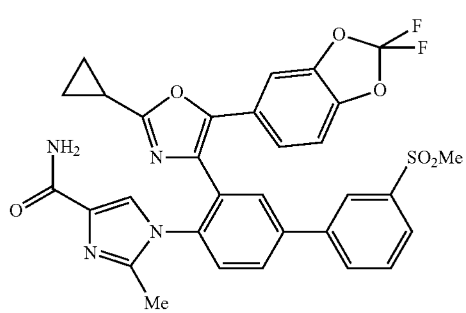 [SMILES: Cc1nc(C(N)=O)cn1-c1ccc(-c2cccc(S(C)(=O)=O)c2)cc1-c1nc(C2CC2)oc1-c1ccc2c(c1)OC(F)(F)O2] | 1-(3-(2-cyclopropyl-5-(2,2-difluorobenzo[d][1,3]dioxol-5-yl)oxazol-4-yl)-3'-(methylsulfonyl)biphenyl-4-yl)-2-methyl-1H-imidazole-4-carboxamide | MS (ESI) 619.2 [M + H]+ |

-continued

| Ex # | Structure | Name and Characterization | Molecular Ion |
|---|---|---|---|
| 490 | 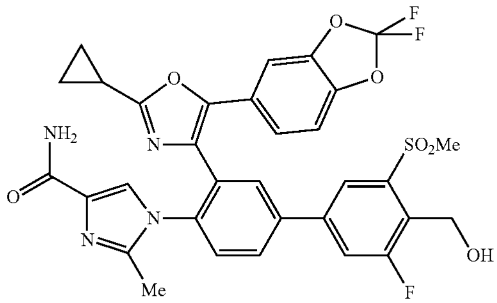 [SMILES: Cc1nc(C(N)=O)cn1-c1ccc(-c2cc(F)c(CO)c(S(C)(=O)=O)c2)cc1-c1nc(C2CC2)oc1-c1ccc2c(c1)OC(F)(F)O2] | 1-(3-(2-cyclopropyl-5-(2,2-difluorobenzo[d][1,3]dioxol-5-yl)oxazol-4-yl)-3'-fluoro-4'-(hydroxymethyl)-5'-(methylsulfonyl)biphenyl-4-yl)-2-methyl-1H-imidazole-4-carboxamide | MS (ESI) 667.2 [M + H]+ |
| 491 | 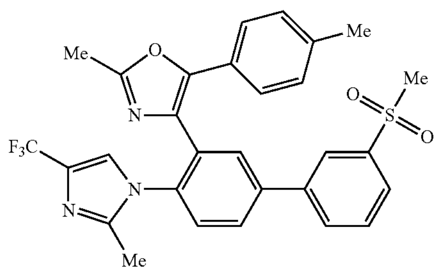 [SMILES: Cc1ccc(-c2oc(C)nc2-c2cc(-c3cccc(S(C)(=O)=O)c3)ccc2-n2cc(C(F)(F)F)nc2C)cc1] | 2-methyl-4-(4-(2-methyl-4-(trifluoromethyl)-1H-imidazol-1-yl)-3'-(methylsulfonyl)-[1,1'-biphenyl]-3-yl)-5-(p-tolyl)oxazole | MS (ESI) 552.3 [M + H]+ |
| 492 | 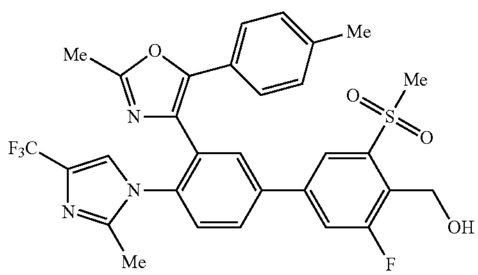 [SMILES: Cc1ccc(-c2oc(C)nc2-c2cc(-c3cc(F)c(CO)c(S(C)(=O)=O)c3)ccc2-n2cc(C(F)(F)F)nc2C)cc1] | (3-fluoro-4'-(2-methyl-4-(trifluoromethyl)-1H-imidazol-1-yl)-3'-(2-methyl-5-p-tolyloxazol-4-yl)-5-(methylsulfonyl)biphenyl-4-yl)methanol | MS (ESI) 600.3 [M + H]+ |
| 493 | 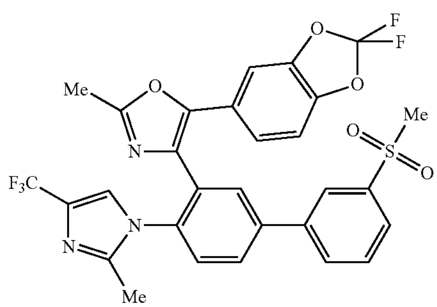 [SMILES: Cc1nc(-c2cc(-c3cccc(S(C)(=O)=O)c3)ccc2-n2cc(C(F)(F)F)nc2C)c(-c2ccc3c(c2)OC(F)(F)O3)o1] | 5-(2,2-difluorobenzo[d][1,3]dioxol-5-yl)-2-methyl-4-(4-(2-methyl-4-(trifluoromethyl)-1H-imidazol-1-yl)-3'-(methylsulfonyl)biphenyl-3-yl)oxazole 1H NMR (500 MHz, CDCl$_3$-d) δ ppm 2.07 (s, 3 H) 2.47 (s, 3 H) 3.13 (s, 3 H) 6.90 (s, 1 H) 7.01 (d, J = 8.25 Hz, 1 H) 7.11-7.15 (m, 2 H) 7.49 (d, J = 8.25 Hz, 1 H) 7.74 (t, J = 7.97 Hz, 1 H) 7.83 (d, J = 8.25 Hz, 1 H) 7.88 (d, J = 7.70 Hz, 1 H) 7.93 (s, 1 H) 8.03 (d, J = 7.15 Hz, 1 H) 8.18 (s, 1 H) | MS (ESI) 618.2 [M + H]+ |
| 494 | 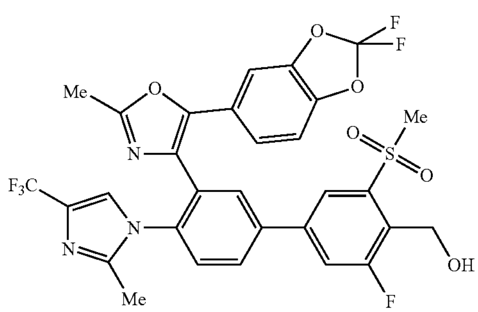 [SMILES: Cc1nc(-c2cc(-c3cc(F)c(CO)c(S(C)(=O)=O)c3)ccc2-n2cc(C(F)(F)F)nc2C)c(-c2ccc3c(c2)OC(F)(F)O3)o1] | (3'-(5-(2,2-difluorobenzo[d][1,3]dioxol-5-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 666.2 [M + H]+ |

| Ex # | Structure | Name and Characterization | Molecular Ion |
|---|---|---|---|
| 495 | 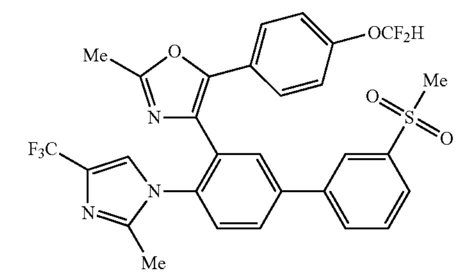 | 5-(4-(difluoromethoxy)phenyl)-2-methyl-4-(2-methyl-4-(trifluoromethyl)-1H-imidazol-1-yl)-3'-(methylsulfonyl)biphenyl-3-yl)oxazole | MS (ESI) 603.93 [M + H]+ |
| 496 | 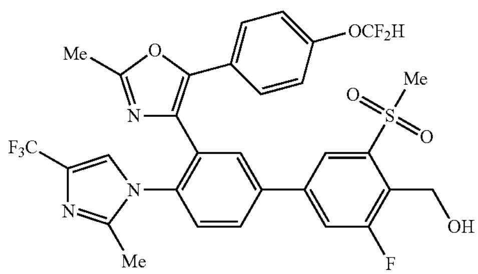 | (3'-(5-(4-(difluoromethoxy)phenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 651.94 [M + H]+ |
| 497 | 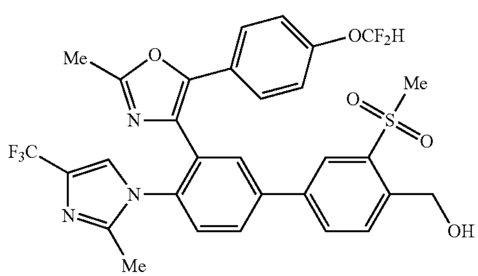 | (3'-(5-(4-(difluoromethoxy)phenyl)-2-methyloxazol-4-yl)-4'-(2-methyl-4-(trifluoromethyl)-1H-imidazol-1-yl)-3-(methylsulfonyl)biphenyl-4-yl)methanol | MS (ESI) 633.94 [M + H]+ |
| 498 | 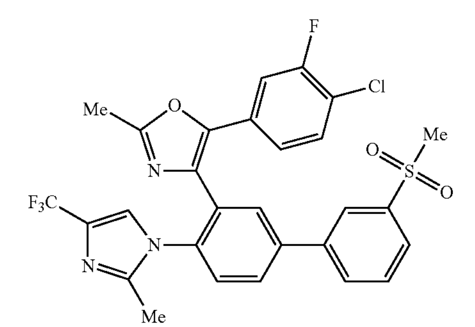 [SMILES: Cc1nc(-c2cc(-c3cccc(S(C)(=O)=O)c3)ccc2-n2cc(C(F)(F)F)nc2C)c(-c2ccc(Cl)c(F)c2)o1] | 5-(4-chloro-3-fluorophenyl)-2-methyl-4-(4-(2-methyl-4-(trifluoromethyl)-1H-imidazol-1-yl)-3'-(methylsulfonyl)biphenyl-3-yl)oxazole | MS (ESI) 589.89 [M + H]+ |
| 499 | 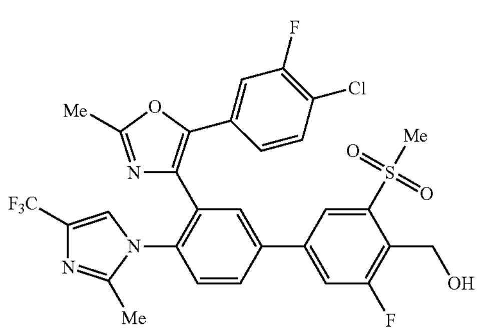 [SMILES: Cc1nc(-c2cc(-c3cc(F)c(CO)c(S(C)(=O)=O)c3)ccc2-n2cc(C(F)(F)F)nc2C)c(-c2ccc(Cl)c(F)c2)o1] | (3'-(5-(4-chloro-3-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 637.91 [M + H]+ |

| Ex # | Structure | Name and Characterization | Molecular Ion |
|---|---|---|---|
| 500 | 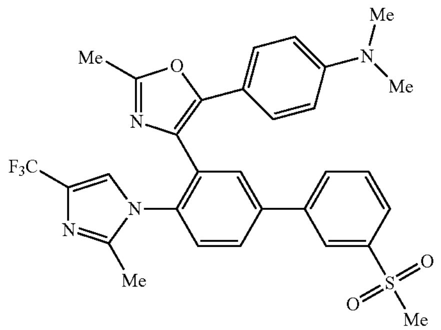 [SMILES: Cc1nc(-c2cc(-c3cccc(S(C)(=O)=O)c3)ccc2-n2cc(C(F)(F)F)nc2C)c(-c2ccc(N(C)C)cc2)o1] | N,N-dimethyl-4-(2-methyl-4-(4-(2-methyl-4-(trifluoromethyl)-1H-imidazol-1-yl)-3'-(methylsulfonyl)biphenyl-3-yl)oxazol-5-yl)aniline | MS (ESI) 580.96 [M + H]+ |
| 501 | 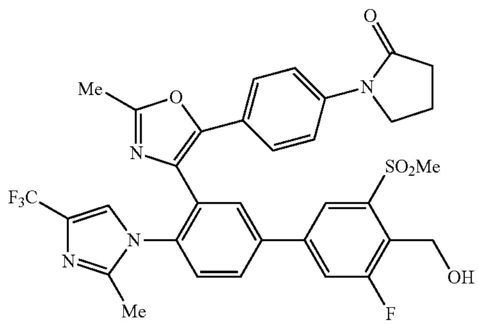 [SMILES: Cc1nc(-c2cc(-c3cc(F)c(CO)c(S(C)(=O)=O)c3)ccc2-n2cc(C(F)(F)F)nc2C)c(-c2ccc(N3CCCC3=O)cc2)o1] | 1-(4-(4-(3'-fluoro-4'-(hydroxymethyl-4-(2-methyl-4-(trifluoromethyl)-1H-imidazol-1-yl)-5'-(methylsulfonyl)biphenyl-3-yl)-2-methyloxazol-5-yl)phenyl)pyrrolidin-2-one | MS (ESI) 669.01 [M + H]+ |
| 502 | 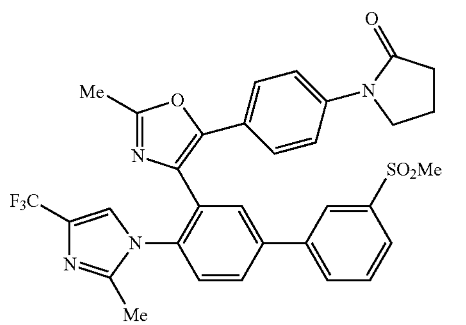 [SMILES: Cc1nc(-c2cc(-c3cccc(S(C)(=O)=O)c3)ccc2-n2cc(C(F)(F)F)nc2C)c(-c2ccc(N3CCCC3=O)cc2)o1] | 1-(4-(2-methyl-4-(4-(2-methyl-4-(trifluoromethyl)-1H-imidazol-1-yl)-3'-(methylsulfonyl)biphenyl-3-yl)oxazol-5-yl)phenyl)pyrrolidin-2-one | MS (ESI) 620.97 [M + H]+ |
| 503 | 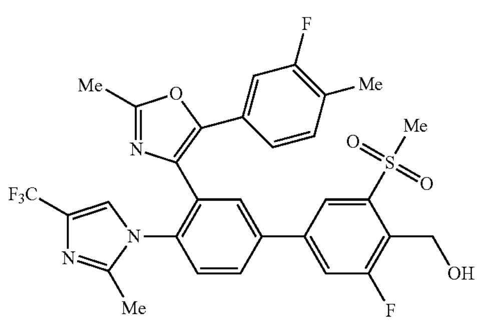 [SMILES: Cc1nc(-c2cc(-c3cc(F)c(CO)c(S(C)(=O)=O)c3)ccc2-n2cc(C(F)(F)F)nc2C)c(-c2ccc(C)c(F)c2)o1] | (3-fluoro-3'-(5-(3-fluoro-4-methylphenyl)-2-methyloxazol-4-yl)-4'-(2-methyl-4-(trifluoromethyl)-1H-imidazol-1-yl)-5-(methylsulfonyl)biphenyl-4-yl)methanol | MS (ESI) 617.95 [M + H]+ |
| 504 | 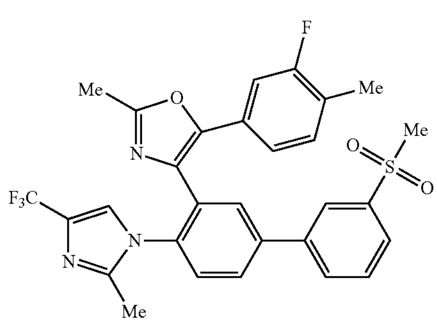 [SMILES: Cc1nc(-c2cc(-c3cccc(S(C)(=O)=O)c3)ccc2-n2cc(C(F)(F)F)nc2C)c(-c2ccc(C)c(F)c2)o1] | 5-(3-fluoro-4-methylphenyl)-2-methyl-4-(4-(2-methyl-4-(trifluoromethyl)-1H-imidazol-1-yl)-3'-(methylsulfonyl)biphenyl-3-yl)oxazole | MS (ESI) 569.96 [M + H]+ |

| Ex # | Structure | Name and Characterization | Molecular Ion |
|------|-----------|---------------------------|---------------|
| 505 | 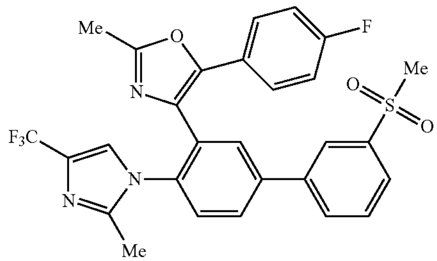 [SMILES: Cc1nc(-c2cc(-c3cccc(S(C)(=O)=O)c3)ccc2-n2cc(C(F)(F)F)nc2C)c(-c2ccc(F)cc2)o1] | 5-(4-fluorophenyl)-2-methyl-4-(4-(2-methyl-4-(trifluoromethyl)-1H-imidazol-1-yl)-3'-(methylsulfonyl)biphenyl-3-yl)oxazole | MS (ESI) 555.92 [M + H]+ |
| 506 | 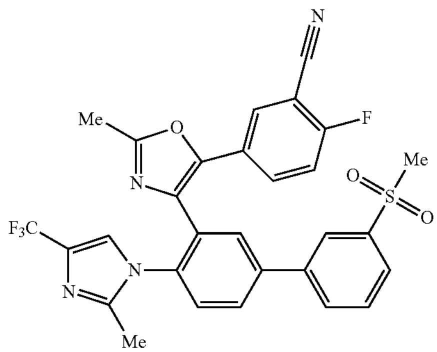 [SMILES: Cc1nc(-c2cc(-c3cccc(S(C)(=O)=O)c3)ccc2-n2cc(C(F)(F)F)nc2C)c(-c2ccc(F)c(C#N)c2)o1] | 2-fluoro-5-(2-methyl-4-(4-(2-methyl-4-(trifluoromethyl)-1H-imidazol-1-yl)-3'-(methylsulfonyl)biphenyl-3-yl)oxazol-5-yl)benzonitrile | MS (ESI) 581.0 [M + H]+ |
| 507 | 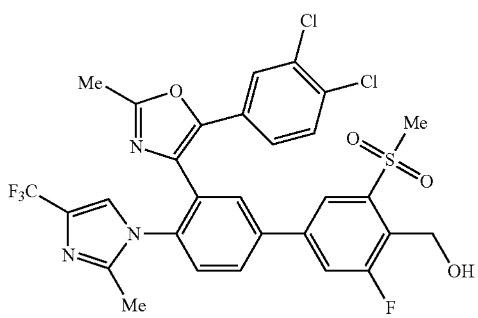 [SMILES: Cc1nc(-c2cc(-c3cc(F)c(CO)c(S(C)(=O)=O)c3)ccc2-n2cc(C(F)(F)F)nc2C)c(-c2ccc(Cl)c(Cl)c2)o1] | (3'-(5-(3,4-dichlorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 654.0 [M + H]+ |
| 508 | 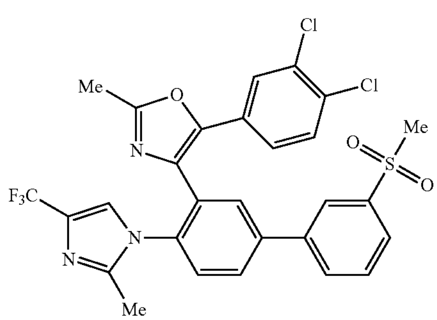 | 5-(3,4-dichlorophenyl)-2-methyl-4-(4-(2-methyl-4-(trifluoromethyl)-1H-imidazol-1-yl)-3'-(methylsulfonyl)biphenyl-3-yl)oxazole | MS (ESI) 606.0 [M + H]+ |
| 509 | 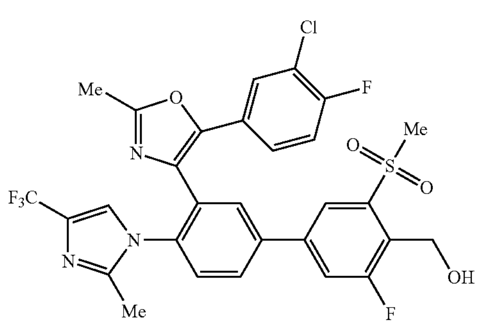 | (3'-(5-(3-chloro-4-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol | MS (ESI) 638.0 [M + H]+ |

| Ex # | Structure | Name and Characterization | Molecular Ion |
|---|---|---|---|
| 510 | 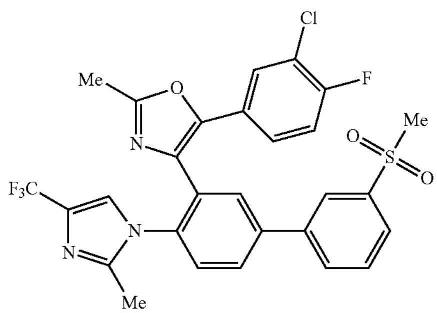 | 5-(3-chloro-4-fluorophenyl)-2-methyl-4-(4-(2-methyl-4-(trifluoromethyl)-1H-imidazol-1-yl)-3'-(methylsulfonyl)biphenyl-3-yl)oxazole | MS (ESI) 590.0 [M + H]+ |
| 511 | 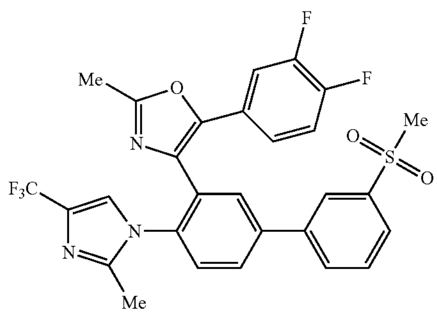 [SMILES: Cc1nc(-c2cc(-c3cccc(S(C)(=O)=O)c3)ccc2-n2cc(C(F)(F)F)nc2C)c(-c2ccc(F)c(F)c2)o1] | 5-(3,4-difluorophenyl)-2-methyl-4-(4-(2-methyl-4-(trifluoromethyl)-1H-imidazol-1-yl)-3'-(methylsulfonyl)biphenyl-3-yl)oxazole | MS (ESI) 573.84 [M + H]+ |
| 512 | 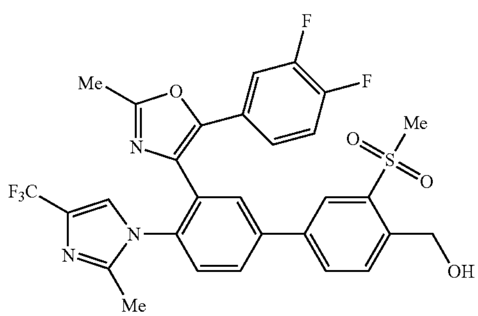 [SMILES: Cc1nc(-c2cc(-c3ccc(CO)c(S(C)(=O)=O)c3)ccc2-n2cc(C(F)(F)F)nc2C)c(-c2ccc(F)c(F)c2)o1] | (3'-(5-(3,4-difluorophenyl)-2-methyloxazol-4-yl)-4'-(2-methyl-4-(trifluoromethyl)-1H-imidazol-1-yl)-3-(methylsulfonyl)biphenyl-4-yl)methanol | MS (ESI) 604.02 [M + H]+ |
| 513 | 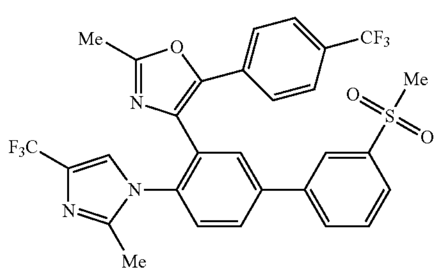 [SMILES: Cc1nc(-c2cc(-c3cccc(S(C)(=O)=O)c3)ccc2-n2cc(C(F)(F)F)nc2C)c(-c2ccc(C(F)(F)F)cc2)o1] | 2-methyl-4-(4-(2-methyl-4-(trifluoromethyl)-1H-imidazol-1-yl)-3'-(methylsulfonyl)biphenyl-3-yl)-5-(4-(trifluoromethyl)phenyl)oxazole | MS (ESI) 606.04 [M + H]+ |
| 514 | 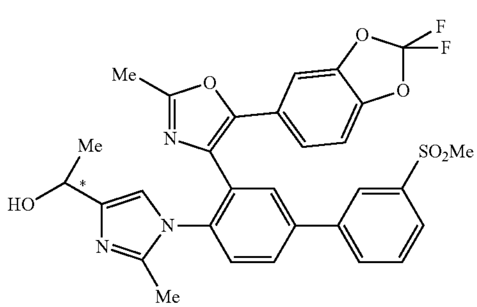 [SMILES: Cc1nc(-c2cc(-c3cccc(S(C)(=O)=O)c3)ccc2-n2cc(C(C)O)nc2C)c(-c2ccc3c(c2)OC(F)(F)O3)o1] | 1-(1-(3-(5-(2,2-difluorobenzo[d][1,3]dioxol-5-yl)-2-methyloxazol-4-yl)-3'-(methylsulfonyl)-[1,1'-biphenyl]-4-yl)-2-methyl-1H-imidazol-4-yl)ethanol RT = 7.69 [column: Chiralpak-IA, (4.6 × 250 mm, 5 micron); mobile phase A: 0.5% diethyl amine, Mobile phase B: EtOH, Flow: 3.0 mL]. | MS (ESI) 594.0 [M + H]+ |

| Ex # | Structure | Name and Characterization | Molecular Ion |
|---|---|---|---|
| 515 | 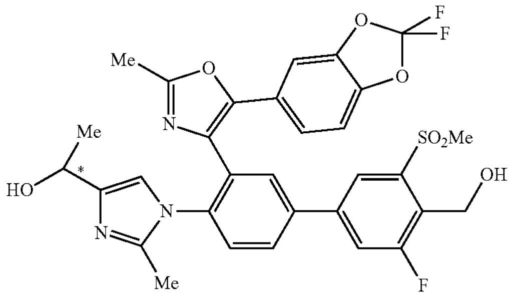 [SMILES: Cc1nc(-c2cc(-c3cc(F)c(CO)c(S(C)(=O)=O)c3)ccc2-n2cc(C(C)O)nc2C)c(-c2ccc3c(c2)OC(F)(F)O3)o1] | 1-(1-(3-(5-(2,2-difluorobenzo[d][1,3]dioxol-5-yl)-2-methyloxazol-4-yl)-3'-fluoro-4'-(hydroxymethyl)-5'-(methylsulfonyl)-[1,1'-biphenyl]-4-yl)-2-methyl-1H-imidazol-4-yl)ethanol Ret. time on chiral column RT = 7.17 [column: Chiralpak-IA, (4.6 × 250 mm, 5 micron); mobile phase A: 0.5% diethyl amine, Mobile phase B: EtOH, Flow: 3.0 mL]. | MS (ESI) 642.3 [M + H]+ |
| 516 | 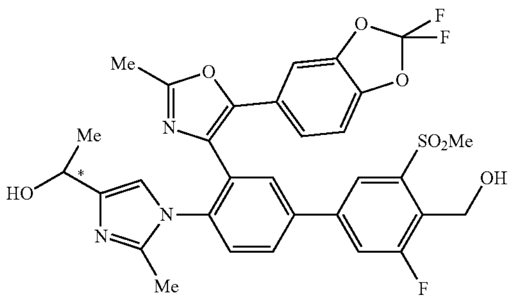 [SMILES: Cc1nc(-c2cc(-c3cc(F)c(CO)c(S(C)(=O)=O)c3)ccc2-n2cc(C(C)O)nc2C)c(-c2ccc3c(c2)OC(F)(F)O3)o1] | 1-(1-(3-(5-(2,2-difluorobenzo[d][1,3]dioxol-5-yl)-2-methyloxazol-4-yl)-3'-fluoro-4'-(hydroxymethyl)-5'-(methylsulfonyl)-[1,1'-biphenyl]-4-yl)-2-methyl-1H-imidazol-4-yl)ethanol Ret. time on column RT = 7.63 [column: Chiralpak-IA, (4.6 × 250 mm, 5 micron); mobile phase A: 0.5% diethyl amine, Mobile phase B: EtOH, Flow: 3.0 mL]. | MS (ESI) 642.3 [M + H]+ |
| 517 | 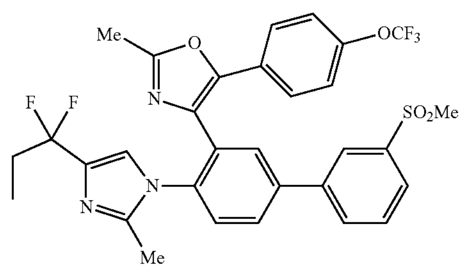 [SMILES: CCC(F)(F)c1cn(-c2ccc(-c3cccc(S(C)(=O)=O)c3)cc2-c2nc(C)oc2-c2ccc(OC(F)(F)F)cc2)c(C)n1] | 4-(4-(4-(1,1-difluoropropyl)-2-methyl-1H-imidazol-1-yl)-3'-(methylsulfonyl)-[1,1'-biphenyl]-3-yl)-2-methyl-5-(4-(trifluoromethoxy)phenyl)oxazole | MS (ESI) 632.2 [M + H]+ |
| 518 | 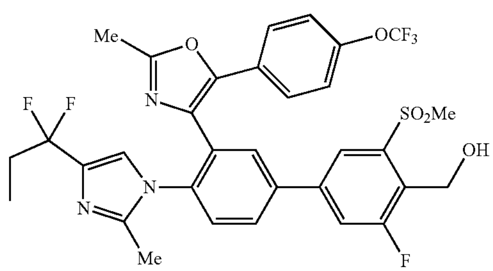 [SMILES: CCC(F)(F)c1cn(-c2ccc(-c3cc(F)c(CO)c(S(C)(=O)=O)c3)cc2-c2nc(C)oc2-c2ccc(OC(F)(F)F)cc2)c(C)n1] | (4'-(4-(1,1-difluoropropyl)-2-methyl-1H-imidazol-1-yl)-3-fluoro-3'-(2-methyl-5-(4-(trifluoromethoxy)phenyl)oxazol-4-yl)-5-(methylsulfonyl)-[1,1'-biphenyl]-4-yl)methanol | MS (ESI) 680.2 [M + H]+ |
| 519 | 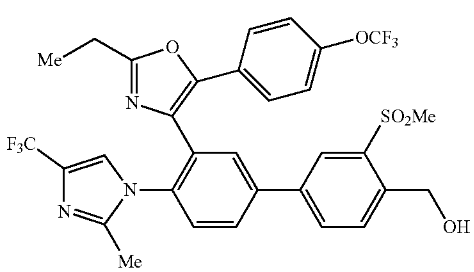 [SMILES: CCc1nc(-c2cc(-c3ccc(CO)c(S(C)(=O)=O)c3)ccc2-n2cc(C(F)(F)F)nc2C)c(-c2ccc(OC(F)(F)F)cc2)o1] | (3'-(2-ethyl-5-(4-(trifluoromethoxy)phenyl)oxazol-4-yl)-4'-(2-methyl-4-(trifluoromethyl)-1H-imidazol-1-yl)-3-(methylsulfonyl)-[1,1'-biphenyl]-4-yl)methanol | MS (ESI) 666.3 [M + H]+ |

-continued

| Ex # | Structure | Name and Characterization | Molecular Ion |
|---|---|---|---|
| 520 | 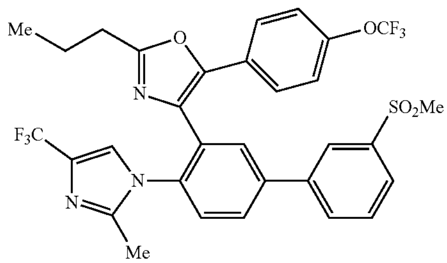 | 4-(4-(2-methyl-4-(trifluoromethyl)-1H-imidazol-1-yl)-3'-(methylsulfonyl)-[1,1'-biphenyl]-3-yl)-2-propyl-5-(4-(trifluoromethoxy)phenyl)oxazole | MS (ESI) 650.3 [M + H]+ |
| 521 | 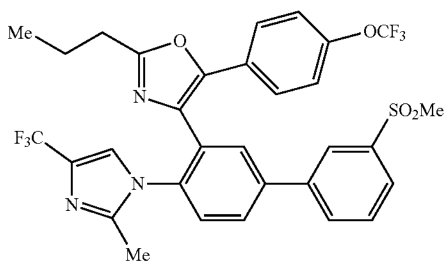 | (3'-(2-isopropyl-5-(4-(trifluoromethoxy)phenyl)oxazol-4-yl)-4'-(2-methyl-4-(trifluoromethyl)-1H-imidazol-1-yl)-3-(methylsulfonyl)-[1,1'-biphenyl]-4-yl)methanol | MS (ESI) 680.3 [M + H]+ |
| 522 | 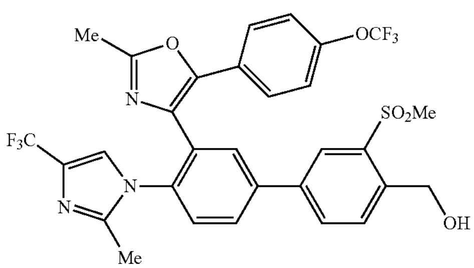 [SMILES: Cc1nc(-c2cc(-c3ccc(CO)c(S(C)(=O)=O)c3)ccc2-n2cc(C(F)(F)F)nc2C)c(-c2ccc(OC(F)(F)F)cc2)o1] | (4'-(2-methyl-4-(trifluoromethyl)-1H-imidazol-1-yl)-3'-(2-methyl-5-(4-(trifluoromethoxy)phenyl)oxazol-4-yl)-3-(methylsulfonyl)-[1,1'-biphenyl]4-yl)methanol | MS (ESI) 652.2 [M + H]+ |
| 523 | 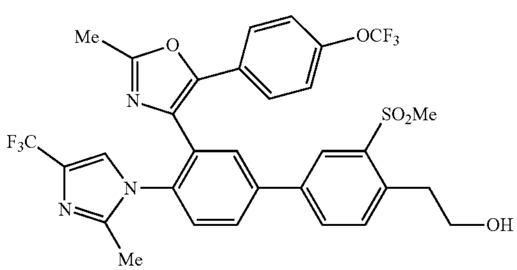 [SMILES: Cc1nc(-c2cc(-c3ccc(CCO)c(S(C)(=O)=O)c3)ccc2-n2cc(C(F)(F)F)nc2C)c(-c2ccc(OC(F)(F)F)cc2)o1] | 2-(4'-(2-methyl-4-(trifluoromethyl)-1H-imidazol-1-yl)-3'-(2-methyl-5-(4-(trifluoromethoxy)phenyl)oxazol-4-yl)-3-(methylsulfonyl)-[1,1'-biphenyl]-4-yl)ethanol | MS (ESI) 666.2 [M + H]+ |
| 524 | 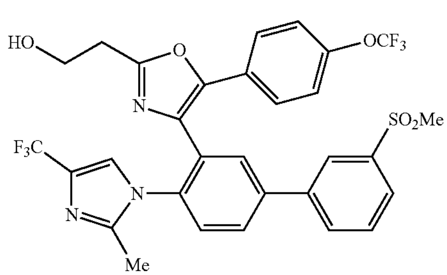 [SMILES: Cc1nc(C(F)(F)F)cn1-c1ccc(-c2cccc(S(C)(=O)=O)c2)cc1-c1nc(CCO)oc1-c1ccc(OC(F)(F)F)cc1] | 2-(4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazol-2-yl)ethanol | MS (ESI) 652.2 [M + H]+ |
| 525 | 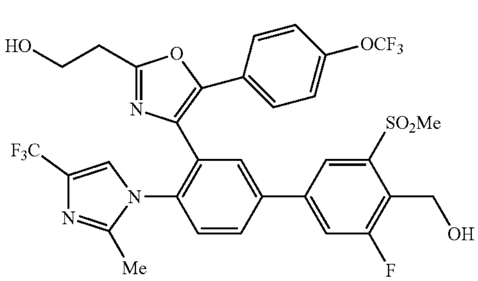 [SMILES: Cc1nc(C(F)(F)F)cn1-c1ccc(-c2cc(F)c(CO)c(S(C)(=O)=O)c2)cc1-c1nc(CCO)oc1-c1ccc(OC(F)(F)F)cc1] | 2-(4-(3'-fluoro-4'-(hydroxymethyl)-4-(2-methyl-4-(trifluoromethyl)-1H-imidazol-1-yl)-5'-(methylsulfonyl)-[1,1'-biphenyl]-3-yl)-5-(4-(trifluoromethoxy)phenyl)oxazol-2-yl)ethanol | MS (ESI) 700.2 [M + H]+ |

-continued

| Ex # | Structure | Name and Characterization | Molecular Ion |
|---|---|---|---|
| 526 | 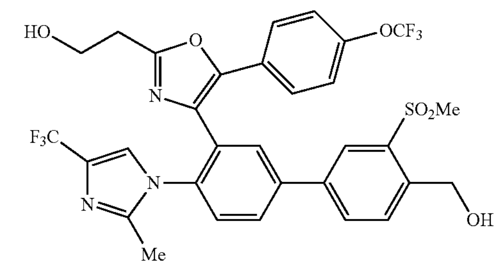 [SMILES: Cc1nc(C(F)(F)F)cn1-c1ccc(-c2ccc(CO)c(S(C)(=O)=O)c2)cc1-c1nc(CCO)oc1-c1ccc(OC(F)(F)F)cc1] | 2-(4-(4'-(hydroxymethyl)-4-(2-methyl-4-(trifluoromethyl)-1H-imidazol-1-yl)-3'-(methylsulfonyl)-[1,1'-biphenyl]-3-yl)-5-(4-trifluoromethoxy)phenyl)oxazol-2-yl)ethanol | MS (ESI) 682.2 [M + H]+ |
| 527 | 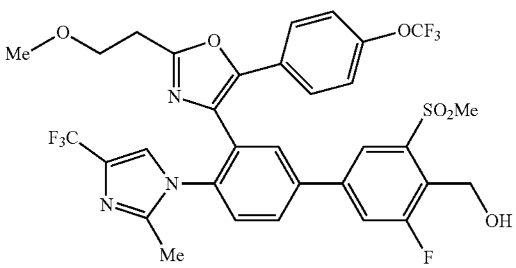 [SMILES: COCCc1nc(-c2cc(-c3cc(F)c(CO)c(S(C)(=O)=O)c3)ccc2-n2cc(C(F)(F)F)nc2C)c(-c2ccc(OC(F)(F)F)cc2)o1] | (3-fluoro-3'-(2-(2-methoxyethyl)-5-(4-(trifluoromethoxy)phenyl)oxazol-4-yl)-4'-(2-methyl-4-(trifluoromethyl)-1H-imidazol-1-yl)-5-(meththsulfonyl)-[1,1'-biphenyl]-4-yl)methanol | MS (ESI) 714.2 [M + H]+ |
| 528 | 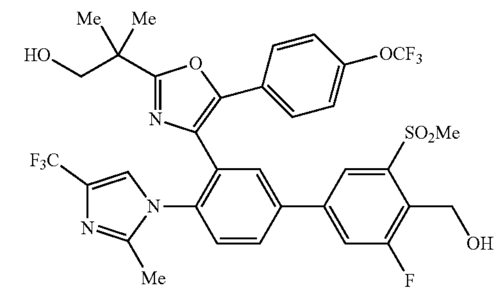 [SMILES: Cc1nc(C(F)(F)F)cn1-c1ccc(-c2cc(F)c(CO)c(S(C)(=O)=O)c2)cc1-c1nc(C(C)(C)CO)oc1-c1ccc(OC(F)(F)F)cc1] | 2-(4-(3'-fluoro-4'-(hydroxymethyl)-4-(2-methyl-4-(trifluoromethyl)-1H-imidazol-1-yl)-5'-(meththsulfonyl)-[1,1'-biphenyl]-3-yl)-5-(4-(trifluoromethoxy)phenyl)oxazol-2-yl)-2-methylpropan-1-ol | MS (ESI) 728.2 [M + H]+ |
| 529 | 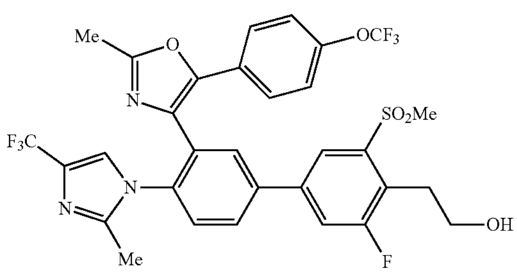 [SMILES: Cc1nc(-c2cc(-c3cc(F)c(CCO)c(S(C)(=O)=O)c3)ccc2-n2cc(C(F)(F)F)nc2C)c(-c2ccc(OC(F)(F)F)cc2)o1] | 2-(3-fluoro-4'-(2-methyl-4-(trifluoromethyl)-1H-imidazol-1-yl)-3'-(2-methyl-5-(4-(trifluoromethoxy)phenyl)oxazol-4-yl)-5-(methylsulfonyl)-[1,1'-biphenyl]-4-yl)ethanol | MS (ESI) 684.2 [M + H]+ |
| 530 | 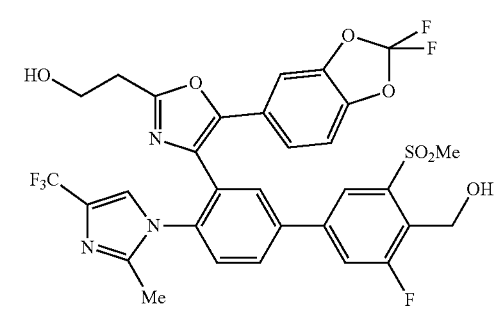 [SMILES: Cc1nc(C(F)(F)F)cn1-c1ccc(-c2cc(F)c(CO)c(S(C)(=O)=O)c2)cc1-c1nc(CCO)oc1-c1ccc2c(c1)OC(F)(F)O2] | 2-(5-(2,2-difluorobenzo[d][1,3]dioxol-5-yl)-4-(3'-fluoro-4'-(hydroxymethyl)-4-(2-methyl-4-(trifluoromethyl)-1H-imidazol-1-yl)-5'-(methylsulfonyl)-[1,1'-biphenyl]-3-yl)oxazol-2-yl)ethanol | MS (ESI) 696.2 [M + H]+ |

| Ex # | Structure | Name and Characterization | Molecular Ion |
|---|---|---|---|
| 531 | 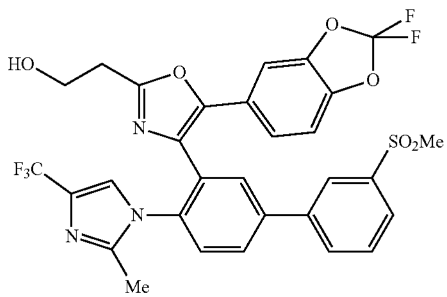 [SMILES: Cc1nc(C(F)(F)F)cn1-c1ccc(-c2cccc(S(C)(=O)=O)c2)cc1-c1nc(CCO)oc1-c1ccc2c(c1)OC(F)(F)O2] | 2-(5-(2,2-difluorobenzo[d][1,3]dioxol-5-4-(4-(2-methyl-4-(trifluoromethyl)-1H-imidazol-1-yl)-3'-(methylsulfonyl)-[1,1'-biphenyl]-3-yl)oxazol-2-yl)ethanol | MS (ESI) 648.2 [M + H]+ |
| 532 | 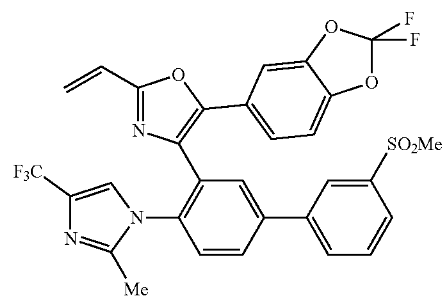 [SMILES: C=Cc1nc(-c2cc(-c3cccc(S(C)(=O)=O)c3)ccc2-n2cc(C(F)(F)F)nc2C)c(-c2ccc3c(c2)OC(F)(F)O3)o1] | 5-(2,2-difluorobenzo[d][1,3]dioxol-5-yl)-4-(4-(2-methyl-4-(trifluoromethyl)-1H-imidazol-1-yl)-3'-(methylsulfonyl)-[1,1'-biphenyl]-3-yl)-2-vinyloxazole | MS (ESI) 630.2 [M + H]+ |
| 533 | 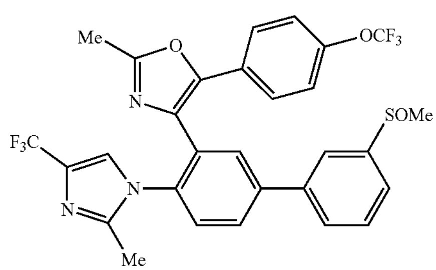 | 2-methyl-4-(4-(2-methyl-4-(trifluoromethyl)-1H-imidazol-1-yl)-3'-(methylsulfinyl)-[1,1'-biphenyl]-3-yl)-5-(4-(trifluoromethoxy)phenyl)oxazole | MS (ESI) 606.2 [M + H]+ |
| 534 | 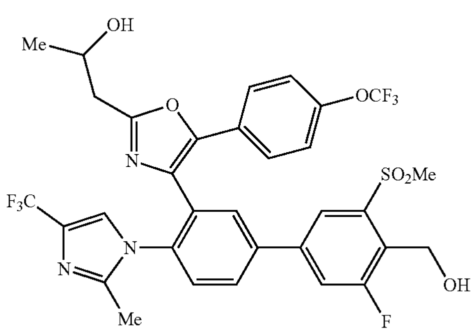 [SMILES: Cc1nc(C(F)(F)F)cn1-c1ccc(-c2cc(F)c(CO)c(S(C)(=O)=O)c2)cc1-c1nc(CC(C)O)oc1-c1ccc(OC(F)(F)F)cc1] | 1-(4-(3'-fluoro-4'-(hydroxymethyl)-4-(2-methyl-4-(trifluoromethyl)-1H-imidazol-1-yl)-5'-(methylsulfonyl)-[1,1'-biphenyl]-3-yl)-5-(4-(trifluoromethoxy)phenyl)oxazol-2-yl)propan-2-ol | MS (ESI) 714.2 [M + H]+ |
| 535 | 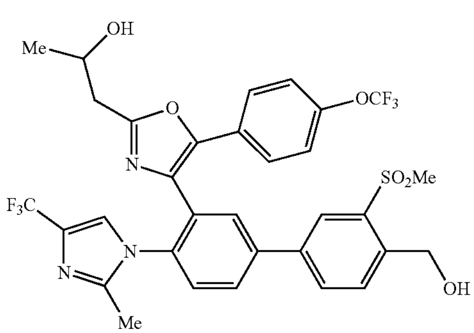 [SMILES: Cc1nc(C(F)(F)F)cn1-c1ccc(-c2ccc(CO)c(S(C)(=O)=O)c2)cc1-c1nc(CC(C)O)oc1-c1ccc(OC(F)(F)F)cc1] | 1-(4-(4'-(hydroxymethyl)-4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazol-2-yl)propan-2-ol | MS (ESI) 696.3 [M + H]+ |

| Ex # | Structure | Name and Characterization | Molecular Ion |
|---|---|---|---|
| 536 | 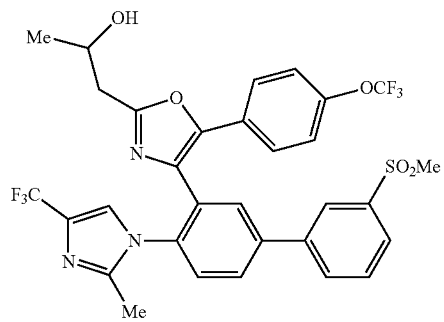 | 1-(4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazol-2-yl)propan-2-ol | MS (ESI) 666.1 [M + H]$^+$ |
| 537 | 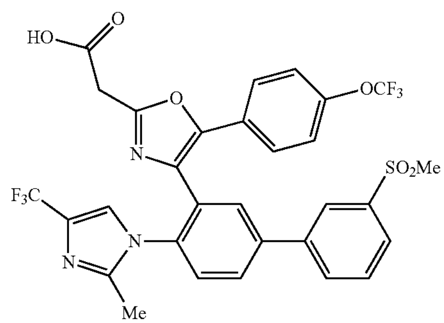 [SMILES: Cc1nc(C(F)(F)F)cn1-c1ccc(-c2cccc(S(C)(=O)=O)c2)cc1-c1nc(CC(=O)O)oc1-c1ccc(OC(F)(F)F)cc1] | 2-(4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazol-2-yl)acetic acid | MS (ESI) 666.0 [M + H]$^+$ |
| 538 | 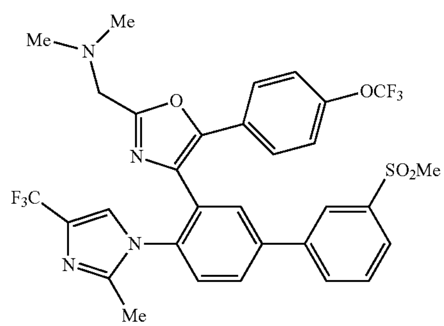 [SMILES: Cc1nc(C(F)(F)F)cn1-c1ccc(-c2cccc(S(C)(=O)=O)c2)cc1-c1nc(CN(C)C)oc1-c1ccc(OC(F)(F)F)cc1] | N,N-dimethyl-1-(4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazol-2-yl)methanamine | MS (ESI) 665.1 [M + H]$^+$ |
| 539 | 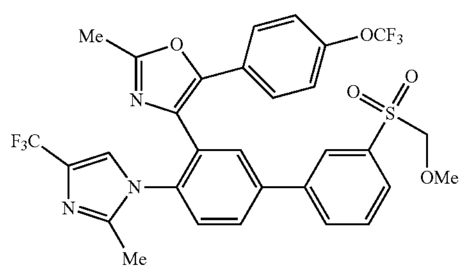 [SMILES: COCS(=O)(=O)c1cccc(-c2ccc(-n3cc(C(F)(F)F)nc3C)c(-c3nc(C)oc3-c3ccc(OC(F)(F)F)cc3)c2)c1] | 4-(3'-((methoxymethyl)sulfonyl)-4-(2-methyl-4-(trifluoromethyl)-1H-imidazol-1-yl)-[1,1'-biphenyl]-3-yl)-2-methyl-5-(4-(trifluoromethoxy)phenyl)oxazole | MS (ESI) 652.0 [M + H]$^+$ |
| 540 | 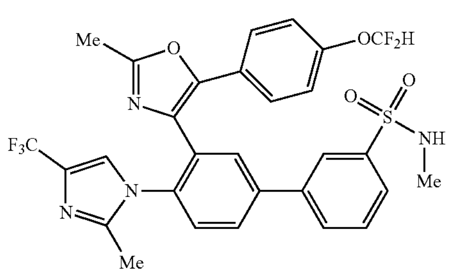 | 3'-(5-(4-(difluoromethoxy)phenyl)-2-methyloxazol-4-yl)-N-methyl-4'-(2-methyl-4-(trifluoromethyl)-1H-imidazol-1-yl)-[1,1'-biphenyl]-3-sulfonamide | MS (ESI) 619.0 [M + H]$^+$ |

-continued

| Ex # | Structure | Name and Characterization | Molecular Ion |
|---|---|---|---|
| 541 | 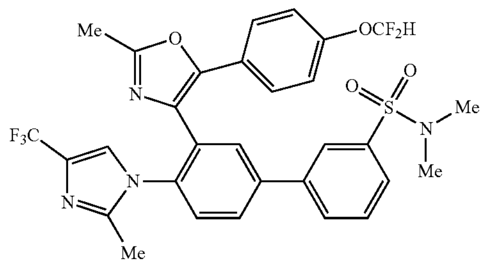 | 3'-(5-(4-(difluoromethoxy)phenyl)-2-methyloxazol-4-yl)-dimethyl-4'-(2-methyl-4-(trifluoromethyl)-1H-imidazol-1-yl)-[1,1'-biphenyl]-3-sulfonamide | MS (ESI) 633.0 [M + H]+ |
| 542 | 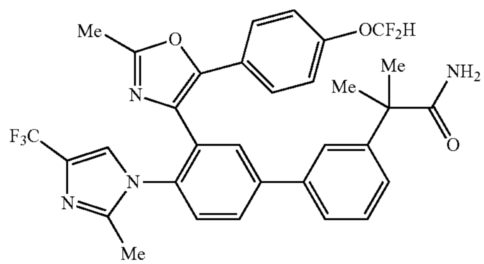 | 2-(3'-(5-(4-(difluoromethoxy)phenyl)-2-methyloxazol-4-yl)-4'-(2-methyl-4-(trifluoromethyl)-1H-imidazol-1-yl)-[1,1'-biphenyl]-3-yl)-2-methylpropanamide | MS (ESI) 611.1 [M + H]+ |
| 543 | 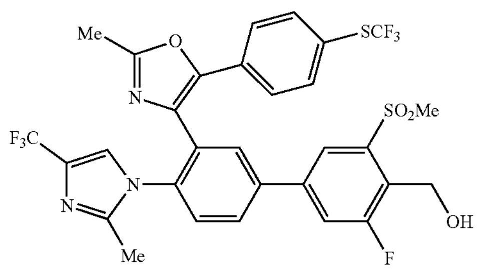 | (3-fluoro-4'-(2-methyl-4-(trifluoromethyl)-1H-imidazol-1-yl)-3'-(2-methyl-5-(4-(trifluoromethyl)thio)phenyl)oxazol-4-yl)-5-(methylsulfonyl)-[1,1'-biphenyl]-4-yl)methanol | MS (ESI) 686.0 [M + H]+ |
| 544 | 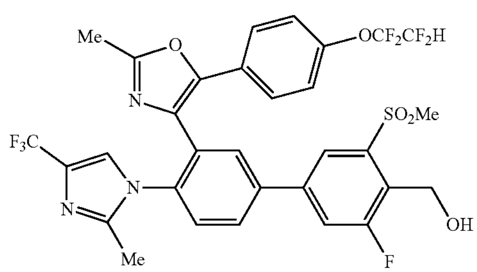 | (3-fluoro-4'-(2-methyl-4-(trifluoromethyl)-1H-imidazol-1-yl)-3'-(2-methyl-5-(4-(1,1,2,2-tetrafluoroethoxy)phenyl)oxazol-4-yl)-5-(methylsulfonyl)-[1,1'-biphenyl]-4-yl)methanol | MS (ESI) 702.1 [M + H]+ |
| 545 | 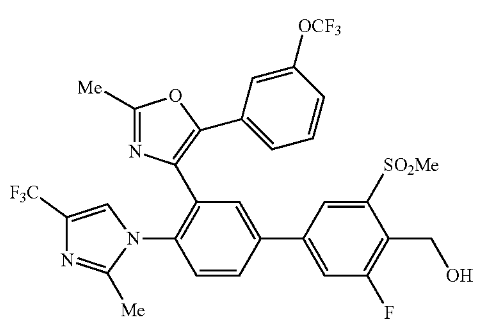 [SMILES: Cc1nc(-c2cc(-c3cc(F)c(CO)c(S(C)(=O)=O)c3)ccc2-n2cc(C(F)(F)F)nc2C)c(-c2cccc(OC(F)(F)F)c2)o1] | (3-fluoro-4'-(2-methyl-4-(trifluoromethyl)-1H-imidazol-1-yl)-3'-(2-methyl-5-(3-(trifluoromethoxy)phenyl)oxazol-4-yl)-5-(methylsulfonyl)-[1,1'-biphenyl]-4-yl)methanol | MS (ESI) 670..2 [M + H]+ |

| Ex # | Structure | Name and Characterization | Molecular Ion |
|---|---|---|---|
| 546 | 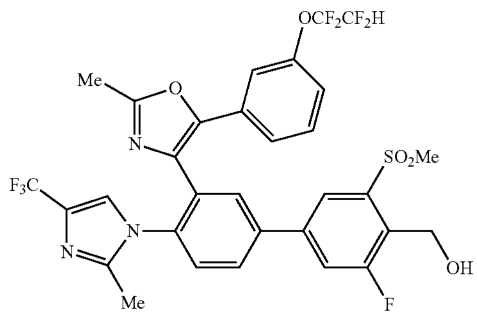 | (3-fluoro-4'-(2-methyl-4-(trifluoromethyl)-1H-imidazol-1-yl)-3'-(2-methyl-5-(3-(1,1,2,2-tetrafluoroethoxy)phenyl)oxazol-4-yl)-5-(methylsulfonyl)-[1,1'-biphenyl]-4-yl)methanol | MS (ESI) 702.0 [M + H]+ |
| 547 | 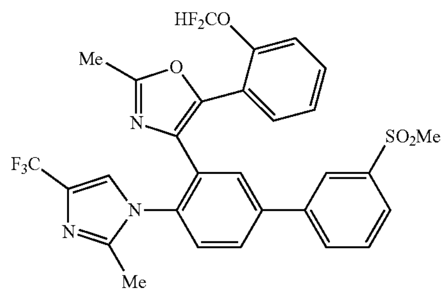 | 5-(2-(difluoromethoxy)phenyl)-2-methyl-4-(4-(2-methyl-4-(trifluoromethyl)-1H-imidazol-1-yl)-3'-(methylsulfonyl)-[1,1'-biphenyl]-3-yl)oxazole | MS (ESI) 604.1 [M + H]+ |
| 548 | 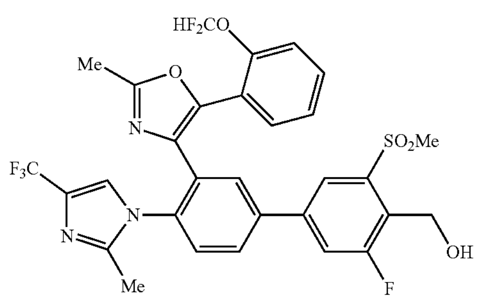 | (3'-(5-(2-(difluoromethoxy)phenyl)-2-methyloxazol-4-yl)-3-fluoro-4'-(2-methyl-4-(trifluoromethyl)-1H-imidazol-1-yl)-5-(methylsulfonyl)-[1,1'-biphenyl]-4-yl)methanol | MS (ESI) 652.2 [M + H]+ |
| 549 | 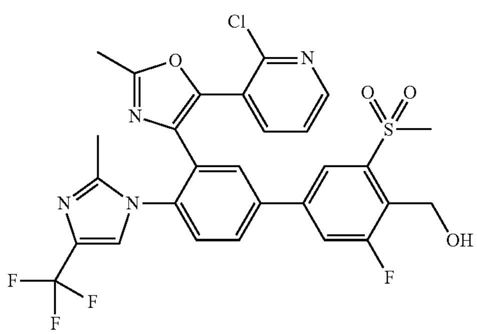 [SMILES: Cc1nc(-c2cc(-c3cc(F)c(CO)c(S(C)(=O)=O)c3)ccc2-n2cc(C(F)(F)F)nc2C)c(-c2cccnc2Cl)o1] | (3'-(5-(2-chloropyridin-3-yl)-2-methyloxazol-4-yl)-3-fluoro-4'-(2-methyl-4-(trifluoromethyl)-1H-imidazol-1-yl)-5-(methylsulfonyl)-[1,1'-biphenyl]-4-yl)methanol | MS (ESI) 621.1 [M + H]+ |
| 550 | 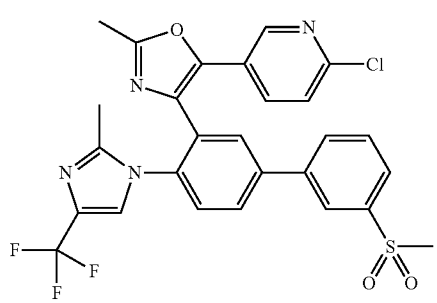 [SMILES: Cc1nc(-c2cc(-c3cccc(S(C)(=O)=O)c3)ccc2-n2cc(C(F)(F)F)nc2C)c(-c2ccc(Cl)nc2)o1] | 5-(6-chloropyridin-3-yl)-2-methyl-4-(4-(2-methyl-4-(trifluoromethyl)-1H-imidazol-1-yl)-3'-(methylsulfonyl)-[1,1'-biphenyl]-3-yl)oxazole | MS (ESI) 573.1 [M + H]+ |

| Ex # | Structure | Name and Characterization | Molecular Ion |
|---|---|---|---|
| 551 | 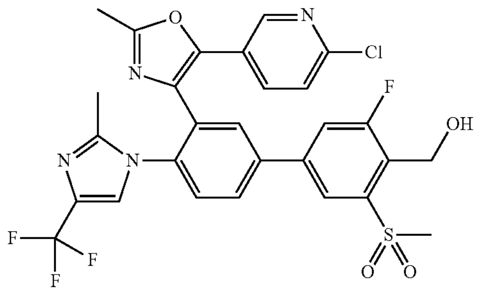 [SMILES: Cc1nc(-c2cc(-c3cc(F)c(CO)c(S(C)(=O)=O)c3)ccc2-n2cc(C(F)(F)F)nc2C)c(-c2ccc(Cl)nc2)o1] | (3'-(5-(6-chloropyridin-3-yl)-2-methyloxazol-4-yl)-3-fluoro-4'-(2-methyl-4-(trifluoromethyl)-1H-imidazol-1-yl)-5-(methylsulfonyl)-[1,1'-biphenyl]-4-yl)methanol | MS (ESI) 621.1 [M + H]+ |
| 552 | 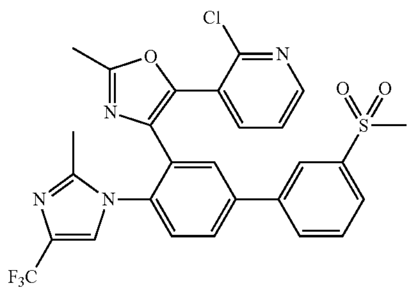 [SMILES: Cc1nc(-c2cc(-c3cccc(S(C)(=O)=O)c3)ccc2-n2cc(C(F)(F)F)nc2C)c(-c2cccnc2Cl)o1] | 5-(2-chloropyridin-3-yl)-2-methyl-4-(4-(2-methyl-4-(trifluoromethyl)-1H-imidazol-1-yl)-3'-(methylsulfonyl)-[1,1'-biphenyl]-3-yl)oxazole | |
| 553 | 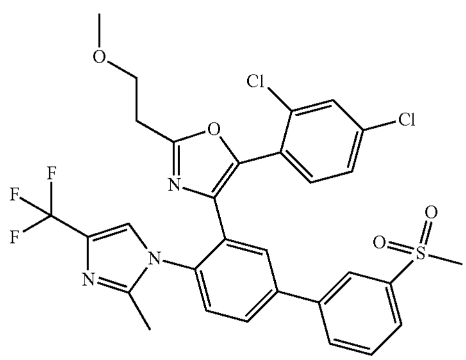 [SMILES: COCCc1nc(-c2cc(-c3cccc(S(C)(=O)=O)c3)ccc2-n2cc(C(F)(F)F)nc2C)c(-c2ccc(Cl)cc2Cl)o1] | 5-(2,4-dichlorophenyl)-2-(2-methoxyethyl)-4-(4-(2-methyl-4-(trifluoromethyl)-1H-imidazol-1-yl)-3'-(methylsulfonyl)-[1,1'-biphenyl]-3-yl)oxazole | |
| 554 | 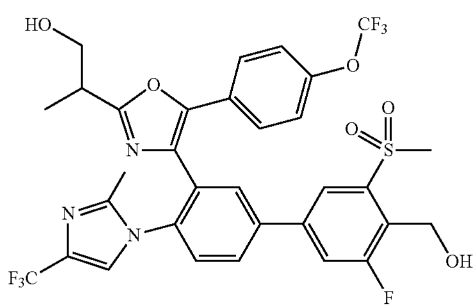 [SMILES: Cc1nc(C(F)(F)F)cn1-c1ccc(-c2cc(F)c(CO)c(S(C)(=O)=O)c2)cc1-c1nc(C(C)CO)oc1-c1ccc(OC(F)(F)F)cc1] | 2-(4-(3'-fluoro-4'-(hydroxymethyl)-4-(2-methyl-4-(trifluoromethyl)-1H-imidazol-1-yl)-5'-(methylsulfonyl)-[1,1'-biphenyl]-3-yl)-5-(4-(trifluoromethoxy)phenyl)oxazol-2-yl)propan-1-ol | |
| 555 | 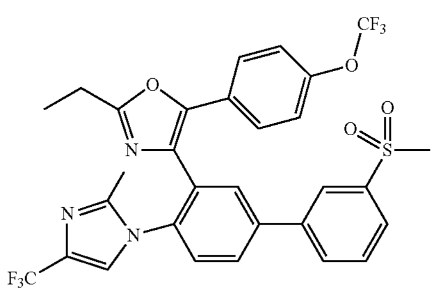 [SMILES: CCc1nc(-c2cc(-c3cccc(S(C)(=O)=O)c3)ccc2-n2cc(C(F)(F)F)nc2C)c(-c2ccc(OC(F)(F)F)cc2)o1] | 2-ethyl-4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazole | |

| Ex # | Structure | Name and Characterization | Molecular Ion |
|---|---|---|---|
| 556 | 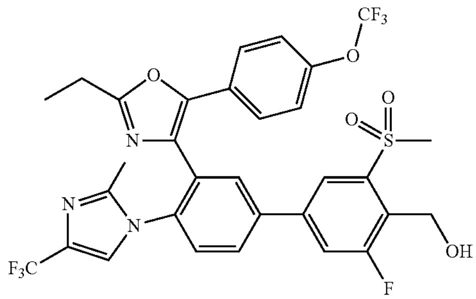 [SMILES: CCc1nc(-c2cc(-c3cc(F)c(CO)c(S(C)(=O)=O)c3)ccc2-n2cc(C(F)(F)F)nc2C)c(-c2ccc(OC(F)(F)F)cc2)o1] | (3'-(2-ethyl-5-(4-(trifluoromethoxy)phenyl)oxazol-4-yl)-3-fluoro-4'-(2-methyl-4-(trifluoromethyl)-1H-imidazol-1-yl)-5-(methylsulfonyl)-[1,1'-biphenyl]-4-yl)methanol | |
| 557 | 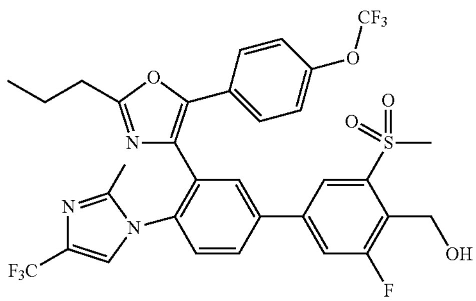 [SMILES: CCCc1nc(-c2cc(-c3cc(F)c(CO)c(S(C)(=O)=O)c3)ccc2-n2cc(C(F)(F)F)nc2C)c(-c2ccc(OC(F)(F)F)cc2)o1] | (3-fluoro-4'-(2-methyl-4-(trifluoromethyl)-1H-imidazol-1-yl)-5-(methylsulfonyl)-3'-(2-propyl-5-(4-(trifluoromethoxy)phenyl)oxazol-4-yl)-[1,1'-biphenyl]-4-yl)methanol | |
| 558 | 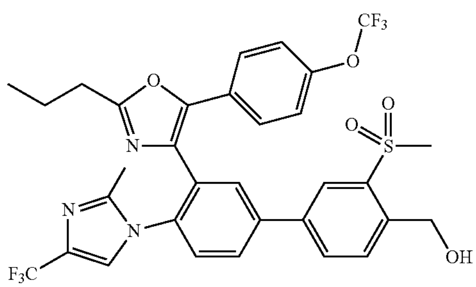 [SMILES: CCCc1nc(-c2cc(-c3ccc(CO)c(S(C)(=O)=O)c3)ccc2-n2cc(C(F)(F)F)nc2C)c(-c2ccc(OC(F)(F)F)cc2)o1] | (4'-(2-methyl-4-(trifluoromethyl)-1H-imidazol-1-yl)-3-(methylsulfonyl)-3'-(2-propyl-5-(4-(trifluoromethoxy)phenyl)oxazol-4-yl)-[1,1'-biphenyl]-4-yl)methanol | |
| 559 | 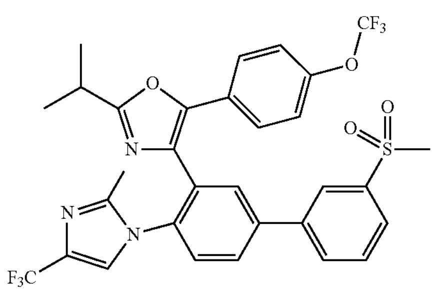 | 2-isopropyl-4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazole | |
| 560 | 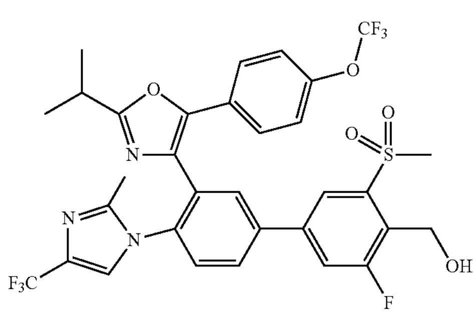 [SMILES: Cc1nc(C(F)(F)F)cn1-c1ccc(-c2cc(F)c(CO)c(S(C)(=O)=O)c2)cc1-c1nc(C(C)C)oc1-c1ccc(OC(F)(F)F)cc1] | (3-fluoro-3'-(2-isopropyl-5-(4-(trifluoromethoxy)phenyl)oxazol-4-yl)-4'-(2-methyl-4-(trifluoromethyl)-1H-imidazol-1-yl)-5-(methylsulfonyl)-[1,1'-biphenyl]-4-yl)methanol | |

| Ex # | Structure | Name and Characterization | Molecular Ion |
|---|---|---|---|
| 561 | 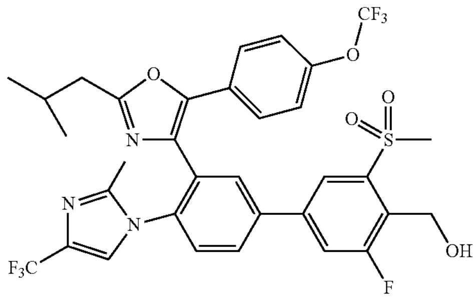 [SMILES: Cc1nc(C(F)(F)F)cn1-c1ccc(-c2cc(F)c(CO)c(S(C)(=O)=O)c2)cc1-c1nc(CC(C)C)oc1-c1ccc(OC(F)(F)F)cc1] | (3-fluoro-3'-(2-isobutyl-5-(4-(trifluoromethoxy)phenyl)oxazol-4-yl)-4'-(2-methyl-4-(trifluoromethyl)-1H-imidazol-1-yl)-5-(methylsulfonyl)-[1,1'-biphenyl]-4-yl)methanol | |
| 562 | 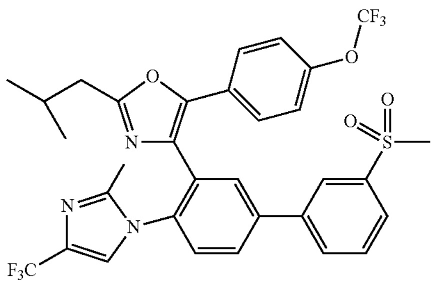 [SMILES: Cc1nc(C(F)(F)F)cn1-c1ccc(-c2cccc(S(C)(=O)=O)c2)cc1-c1nc(CC(C)C)oc1-c1ccc(OC(F)(F)F)cc1] | 2-isobutyl-4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazole | |
| 563 | 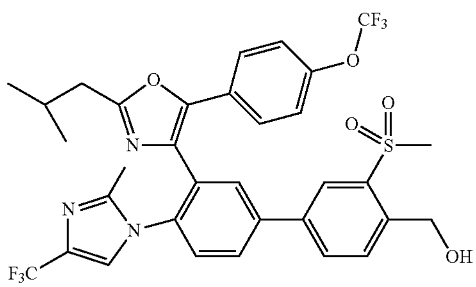 [SMILES: Cc1nc(C(F)(F)F)cn1-c1ccc(-c2ccc(CO)c(S(C)(=O)=O)c2)cc1-c1nc(CC(C)C)oc1-c1ccc(OC(F)(F)F)cc1] | (3'-(2-isobutyl-5-(4-(trifluoromethoxy)phenyl)oxazol-4-yl)-4'-(2-methyl-4-(trifluoromethyl)-1H-imidazol-1-yl)-3-(methylsulfonyl)-[1,1'-biphenyl]-4-yl)methanol | |
| 564 | 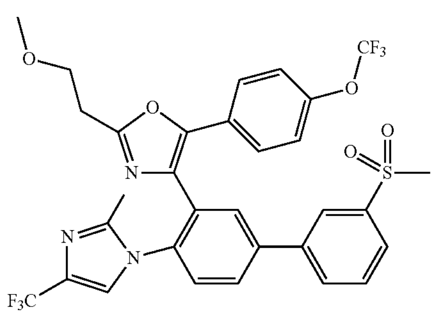 | 2-(2-methoxyethyl)-4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazole | |
| 565 | 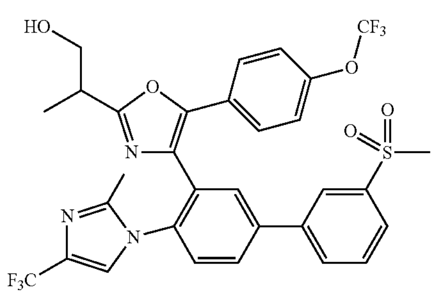 [SMILES: Cc1nc(C(F)(F)F)cn1-c1ccc(-c2cccc(S(C)(=O)=O)c2)cc1-c1nc(C(C)CO)oc1-c1ccc(OC(F)(F)F)cc1] | 2-(4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazol-2-yl)propan-1-ol | |

| Ex # | Structure | Name and Characterization | Molecular Ion |
|---|---|---|---|
| 566 | 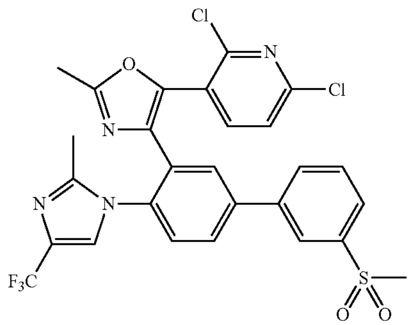 [SMILES: Cc1nc(-c2cc(-c3cccc(S(C)(=O)=O)c3)ccc2-n2cc(C(F)(F)F)nc2C)c(-c2ccc(Cl)nc2Cl)o1] | 5-(2,6-dichloropyridin-3-yl)-2-methyl-4-(4-(2-methyl-4-(trifluoromethyl)-1H-imidazol-1-yl)-3'-(methylsulfonyl)-[1,1'-biphenyl]-3-yl)oxazole | MS (ESI) 607.1 [M + H]+ |
| 567 | 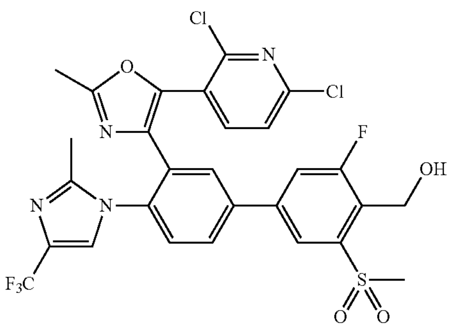 [SMILES: Cc1nc(-c2cc(-c3cc(F)c(CO)c(S(C)(=O)=O)c3)ccc2-n2cc(C(F)(F)F)nc2C)c(-c2ccc(Cl)nc2Cl)o1] | (3'-(5-(2,6-dichloropyridin-3-yl)-2-methyloxazol-4-yl)-3-fluoro-4'-(2-methyl-4-(trifluoromethyl)-1H-imidazol-1-yl)-5-(methylsulfonyl)-[1,1'-biphenyl]-4-yl)methanol | MS (ESI) 655.1 [M + H]+ |
| 568 | 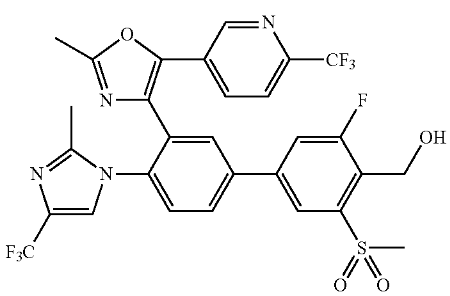 [SMILES: Cc1nc(-c2cc(-c3cc(F)c(CO)c(S(C)(=O)=O)c3)ccc2-n2cc(C(F)(F)F)nc2C)c(-c2ccc(C(F)(F)F)nc2)o1] | (3-fluoro-4'-(2-methyl-4-(trifluoromethyl)-1H-imidazol-1-yl)-3'-(2-methyl-5-(6-(trifluoromethyl)pyridin-3-yl)oxazol-4-yl)-5-(methylsulfonyl)-[1,1'-biphenyl]-4-yl)methanol | MS (ESI) 655.1 [M + H]+ |
| 569 | 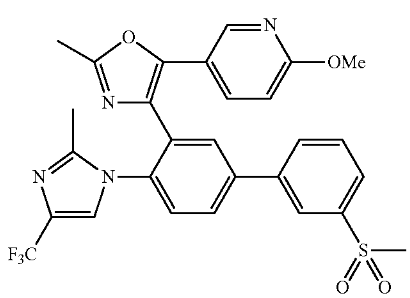 [SMILES: COc1ccc(-c2oc(C)nc2-c2cc(-c3cccc(S(C)(=O)=O)c3)ccc2-n2cc(C(F)(F)F)nc2C)cn1] | 5-(6-methoxypyridin-3-yl)-2-methyl-4-(4-(2-methyl-4-(trifluoromethyl)-1H-imidazol-1-yl)-3'-(methylsulfonyl)-[1,1'-biphenyl]-3-yl)oxazole | MS (ESI) 569.1 [M + H]+ |
| 570 | 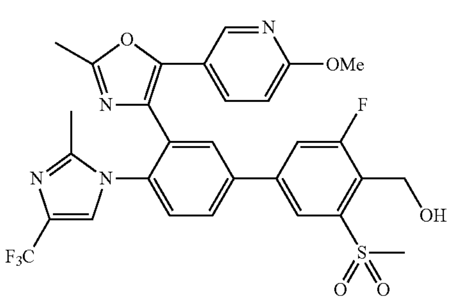 [SMILES: COc1ccc(-c2oc(C)nc2-c2cc(-c3cc(F)c(CO)c(S(C)(=O)=O)c3)ccc2-n2cc(C(F)(F)F)nc2C)cn1] | (3-fluoro-3'-(5-(6-methoxypyridin-3-yl)-2-methyloxazol-4-yl)-4'-(2-methyl-4-(trifluoromethyl)-1H-imidazol-1-yl)-5-(methylsulfonyl)-[1,1'-biphenyl]-4-yl)methanol | MS (ESI) 617.1 [M + H]+ |

-continued

| Ex # | Structure | Name and Characterization | Molecular Ion |
|---|---|---|---|
| 571 | 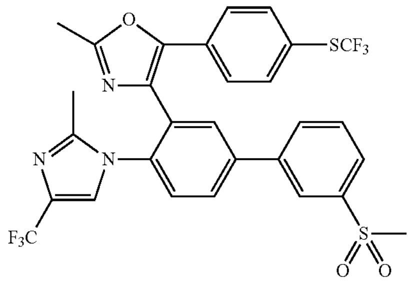 | 2-methyl-4-(4-(2-methyl-4-(trifluoromethyl)-1H-imidazol-1-yl)-3'-(methylsulfonyl)-[1,1'-biphenyl]-3-yl)-5-(4-((trifluoromethyl)thio)phenyl)oxazole | |
| 572 | 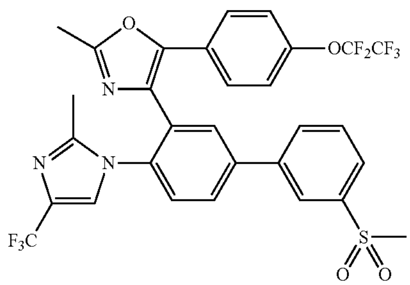 | 2-methyl-4-(4-(2-methyl-4-(trifluoromethyl)-1H-imidazol-1-yl)-3'-(methylsulfonyl)-[1,1'-biphenyl]-3-yl)-5-(4-(perfluoroethoxy)phenyl)oxazole | |
| 573 | 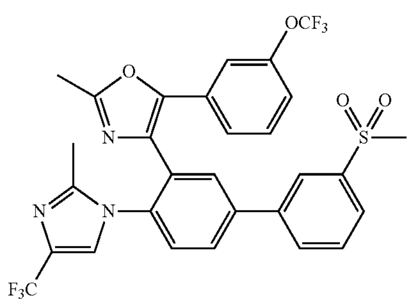 | 2-methyl-4-(4-(2-methyl-4-(trifluoromethyl)-1H-imidazol-1-yl)-3'-(methylsulfonyl)-[1,1'-biphenyl]-3-yl)-5-(3-(trifluoromethoxy)phenyl)oxazole | |
| 574 | 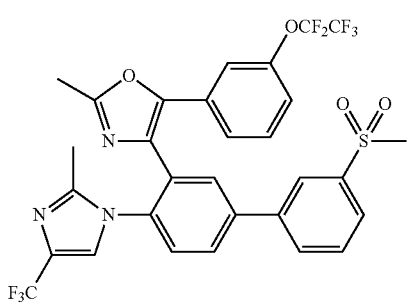 | 2-methyl-4-(4-(2-methyl-4-(trifluoromethyl)-1H-imidazol-1-yl)-3'-(methylsulfonyl)-[1,1'-biphenyl]-3-yl)-5-(3-(perfluoroethoxy)phenyl)oxazole | |

Scheme 8

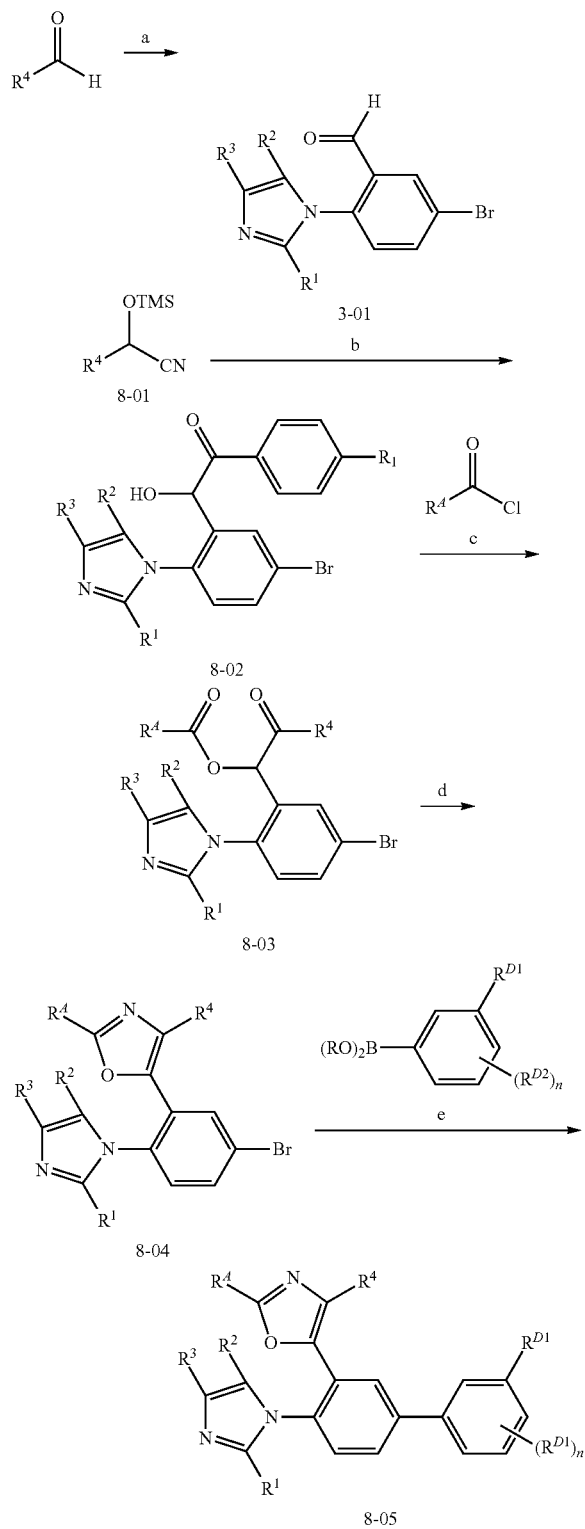

(a) TMSCN, ZnI₂, DCM; (b) LHMDS, THF, -78° C. -rt; (c) DMAP, DCM/py; (d) NH₄OAc, AcOH, reflux; (e) K₂CO₃, PdCl₂(dppf), DME/H₂O, 80° C.

In general, compounds represented by structure (8-05) are prepared by first reacting an appropriately substituted aldehyde with trimethylsilyl cyanide in the presence of catalytic zinc iodide to afford the TMS-cyanohydrin (8-01). The intermediate 8-01 is then deprotonated with lithium bis(trimethylsilyl)amide and reacted with imidazolobenzaldehyde (3-01) to provide the α-hydroxy ketone (8-02). Reaction with an appropriate acyl chloride in the presence of catalytic 4-(dimethylamino)pyridine provides the acylated material (8-03). Cyclization is accomplished with ammonium acetate in acetic acid to afford the oxazole 8-04, and the final compounds (8-05) are then obtained by subjecting 8-04 to a palladium-mediated coupling reaction with the aryl boronic acid or ester derivatives.

Example 600

{3'-(2-ethyl-4-{4-[(trifluoromethyl)oxy]phenyl}-1,3-oxazol-5-yl)-3-fluoro-5-(methylsulfonyl)-4'-[2-methyl-4-(trifluoromethyl)-1H-imidazol-1-yl]biphenyl-4-yl}methanol

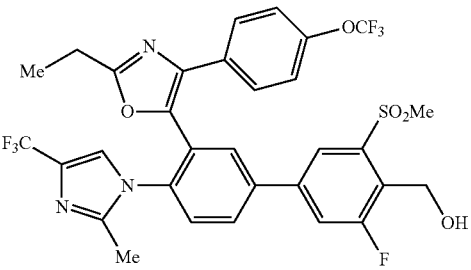 [SMILES: CCc1nc(-c2ccc(OC(F)(F)F)cc2)c(-c2cc(-c3cc(F)c(CO)c(S(C)(=O)=O)c3)ccc2-n2cc(C(F)(F)F)nc2C)o1]

Example 600a

Preparation of 2-(4-(trifluoromethoxy)phenyl)-2-(trimethylsilyloxy)acetonitrile

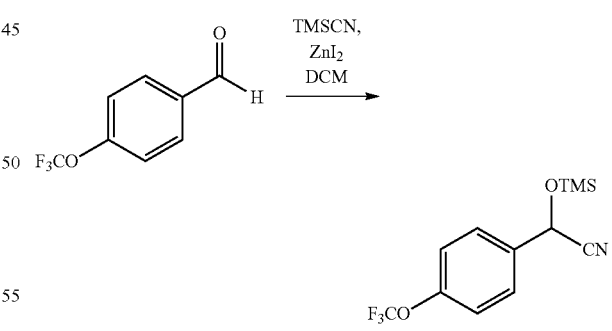

A 40 mL vial was charged with 4-(trifluoromethoxy)benzaldehyde (1.13 g, 5.92 mmol) and dissolved in DCM (20 mL). Trimethylsilyl cyanide (0.830 mL, 6.22 mmol) was added. The reaction mixture was cooled to 0° C., and then zinc iodide (95.0 mg, 296 mol) was added portionwise. The reaction mixture was allowed to warm to rt and was stirred for 17 h. The mixture was diluted with EtOAc, washed with brine (3×), dried over MgSO₄, and concentrated in vacuo to yield the title compound (1.50 g, 5.18 mmol).

Example 600b

Preparation of 2-(5-bromo-2-(2-methyl-4-(trifluoromethyl)-1H-imidazol-1-yl)phenyl)-2-hydroxy-1-(4-(trifluoromethoxy)phenyl)ethanone

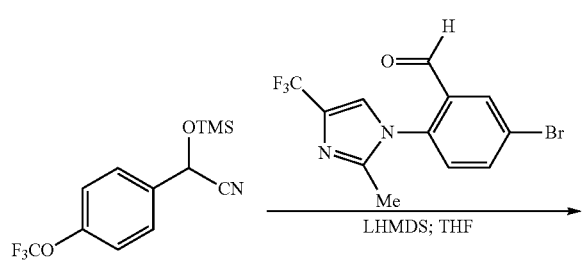

A 100 mL round-bottomed flask was purged with argon and charged with Example 600a (1.50 g, 5.18 mmol) and THF (15.0 mL), and cooled to −78° C. Lithium bis(trimethylsilyl)amide (4.86 mL, 4.86 mmol) was then added slowly, and the reaction mixture was allowed to stir at −78° C. for 45 min. 5-Bromo-2-(2-methyl-4-(trifluoromethyl)-1H-imidazol-1-yl)benzaldehyde (1.81 g, 5.44 mmol) was dissolved in THF (10.0 mL) and added dropwise to the reaction mixture. The mixture was subsequently allowed to warm to rt. After 19 h of stirring at rt, HCl (1 M, 20.0 mL) was added, and the mixture was allowed to stir for an additional 3 h. The mixture was then extracted with EtOAc, washed with H$_2$O and brine, dried over MgSO$_4$, and concentrated in vacuo. The resulting residue was then purified by flash column chromatography to yield the title compound (0.390 g, 0.750 mmol).

Example 600c

Preparation of 1-(5-bromo-2-(2-methyl-4-(trifluoromethyl)-1H-imidazol-1-yl)phenyl)-2-oxo-2-(4-(trifluoromethoxy)phenyl)ethyl propionate

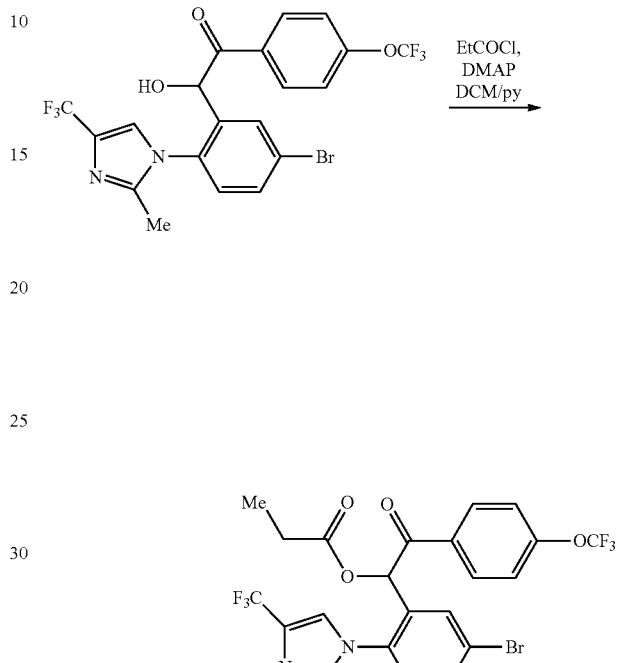

A 40 mL vial was charged with Example 600b (0.14 g, 0.26 mmol), DCM (5.0 mL), propionyl chloride (0.070 mL, 0.79 mmol), 4-(dimethylamino)pyridine (5.0 mg), and pyridine (1.0 mL). After stirring for 23 h, the reaction mixture was poured into saturated aqueous NaHCO$_3$, extracted with EtOAc, and then washed with H$_2$O, 1 M HCl, and brine. The organics were dried over MgSO$_4$, concentrated in vacuo to yield the crude title product (0.25 g, 0.43 mmol).

Example 600 was prepared from Example 600c using ammonium acetate to afford the cyclization to the oxazole as described in Example 367d, and a palladium coupling procedure similar to that described in Example 1f. MS (ES) 684.5 [M+H]$^+$. $^1$H NMR (400 MHz, CDCl$_3$) δ 8.10 (s, 1H), 7.88 (s, 1H), 7.80 (s, 1H), 7.58-7.50 (m, 2H), 7.47 (d, J=8.6 Hz, 2H), 7.19 (d, J=8.3 Hz, 2H), 6.95 (s, 1H), 5.10 (s, 2H), 3.29 (s, 3H), 2.77 (q, J=7.7 Hz, 2H), 2.14 (s, 3H), 1.30 (t, J=7.6 Hz, 3H).

The following compounds were prepared in a manner similar to that described in the experimental procedure above:

| Ex # | Stucture | Name | Molecular Ion |
|---|---|---|---|
| 601 | 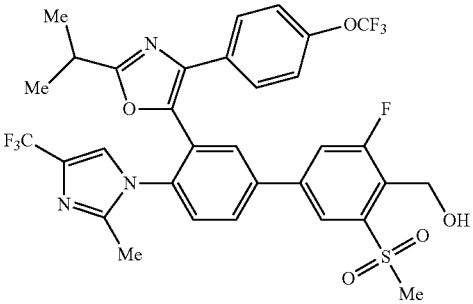 [SMILES: Cc1nc(C(F)(F)F)cn1-c1ccc(-c2cc(F)c(CO)c(S(C)(=O)=O)c2)cc1-c1oc(C(C)C)nc1-c1ccc(OC(F)(F)F)cc1] | {3-fluoro-3'-[2-(1-methylethyl)-4-{4-[(trifluoromethyl)oxy]phenyl}-1,3-oxazol-5-yl]-5-(methylsulfonyl)-4'-[2-methyl-4-(trifluoromethyl)-1H-imidazol-1-yl]biphenyl-4-yl}methanol; | MS (ESI) 698.5 [M + H]+. |
| 602 | 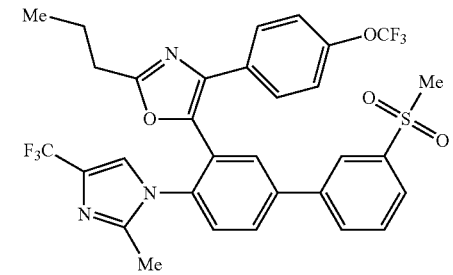 [SMILES: CCCc1nc(-c2ccc(OC(F)(F)F)cc2)c(-c2cc(-c3cccc(S(C)(=O)=O)c3)ccc2-n2cc(C(F)(F)F)nc2C)o1] | 5-{3'-(methylsulfonyl)-4-[2-methyl-4-(trifluoromethyl)-1H-imidazol-1-yl]biphenyl-3-yl}-2-propyl-{4-[(trifluoromethyl)oxy]phenyl}-1,3-oxazole | MS (ESI) 650.1 [M + H]+ |
| 603 | 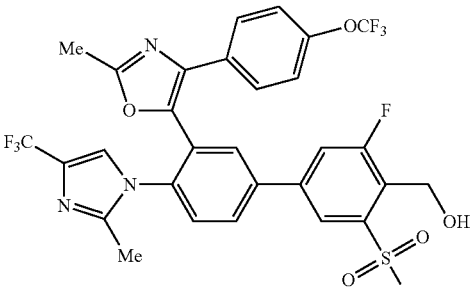 | (3-fluoro-3'-(2-methyl-4-(4-(trifluoromethoxy)phenyl)oxazol-5-yl)-4'-(2-methyl-4-(trifluoromethyl)-1H-imidazol-1-yl)-5-(methylsulfonyl)-[1,1'-biphenyl]-4-yl)methanol | MS (ESI) 670.3 [M + H]+ |
| 604 | 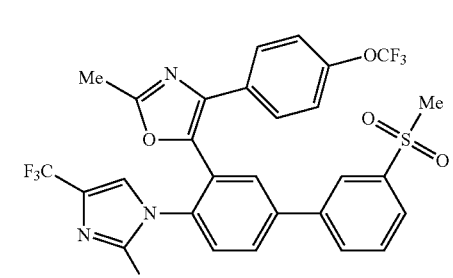 | 2-methyl-5-(4-(2-methyl-4-(trifluoromethyl)-1H-imidazol-1-yl)-3'-(methylsulfonyl)-[1,1'-biphenyl]-3-yl)-4-(4-(trifluoromethoxy)phenyl)oxazole | MS (ESI) 622.2 [M + H]+ |
| 605 | 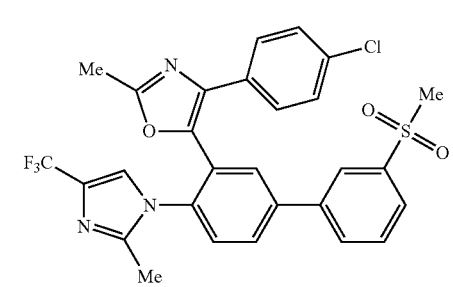 [SMILES: Cc1nc(-c2ccc(Cl)cc2)c(-c2cc(-c3cccc(S(C)(=O)=O)c3)ccc2-n2cc(C(F)(F)F)nc2C)o1] | 4-(4-chlorophenyl)-2-methyl-5-(4-(2-methyl-4-(trifluoromethyl)-1H-imidazol-1-yl)-3'-(methylsulfonyl)-[1,1'-biphenyl]-3-yl)oxazole | MS (ESI) 572.2 [M + H]+ |

| Ex # | Structure | Name | Molecular Ion |
|---|---|---|---|
| 606 | | (3'-(4-(4-chlorophenyl)-2-methyloxazol-5-yl)-3-fluoro-4'-(2-methyl-4-(trifluoromethyl)-1H-imidazol-1-yl)-5-(methylsulfonyl)-[1,1'-biphenyl]-4-yl)methanol | MS (ESI) 620.2 [M + H]+ |
| 607 | | (3'-(2-methyl-4-(4-(trifluoromethoxy)phenyl)oxazol-5-yl)-4'-(2-methyl-4-(trifluoromethyl)-1H-imidazol-1-yl)-3-(methylsulfonyl)-[1,1'-biphenyl]-4-yl)methanol | MS (ESI) 652.3 [M + H]+ |
| 608 | | 4-(2,4-dichlorophenyl)-2-methyl-5-(4-(2-methyl-4-(trifluoromethyl)-1H-imidazol-1-yl)-3'-(methylsulfonyl)-[1,1'-biphenyl]-3-yl)oxazole | MS (ESI) 606.0 [M + H]+ |
| 609 | | (3'-(4-(2,4-dichlorophenyl)-2-methyloxazol-5-yl)-3-fluoro-4'-(2-methyl-4-(trifluoromethyl)-1H-imidazol-1-yl)-5-(methylsulfonyl)-[1,1'-biphenyl]-4-yl)methanol | MS (ESI) 654.2 [M + H]+ |
| 610 | | 2-(5-(4-(2-methyl-4-(trifluoromethyl)-1H-imidazol-1-yl)-3'-(methylsulfonyl)-[1,1'-biphenyl]-3-yl)-4-(4-(trifluoromethoxy)phenyl)oxazol-2-yl)acetic acid | MS (ESI) 666.0 [M + H]+ |

| Ex # | Stucture | Name | Molecular Ion |
|---|---|---|---|
| 611 | | 2-(5-(4-(2-methyl-4-(trifluoromethyl)-1H-imidazol-1-yl)-3'-(methylsulfonyl)-[1,1'-biphenyl]-3-yl)-4-(4-(trifluoromethoxy)phenyl)oxazol-2-yl)ethanol | MS (ESI) 652.2 [M + H]+ |
| 612 | | 2-(5-(3'-fluoro-4'-(hydroxymethyl)-4-(2-methyl-4-(trifluoromethyl)-1H-imidazol-1-yl)-5'-(methylsulfonyl)-[1,1'-biphenyl]-3-yl)-4-(4-(trifluoromethoxy)phenyl)oxazol-2-yl)ethanol | MS (ESI) 700.2 [M + H]+ |
| 613 | | 2-(5-(4'-(hydroxymethyl)-4-(2-methyl-4-(trifluoromethyl)-1H-imidazol-1-yl)-3'-(methylsulfonyl)-[1,1'-biphenyl]-3-yl)-4-(4-(trifluoromethoxy)phenyl)oxazol-2-yl)ethanol | MS (ESI) 682.2 [M + H]+ |
| 614 | | (3'-(4-(2,4-dichlorophenyl)-2-methyloxazol-5-yl)-4'-(2-methyl-4-(trifluoromethyl)-1H-imidazol-1-yl)-3-(methylsulfonyl)-[1,1'-biphenyl]-4-yl)methanol | MS (ESI) 636.3 [M + H]+ |
| 615 | | 4-(2,2-difluorobenzo[d][1,3]dioxol-5-yl)-2-methyl-5-(4-(2-methyl-4-(trifluoromethyl)-1H-imidazol-1-yl)-3'-(methylsulfonyl)-[1,1'-biphenyl]-3-yl)oxazol | MS (ESI) 618.0 [M + H]+ |

| Ex # | Stucture | Name | Molecular Ion |
|---|---|---|---|
| 616 | | (3'-(4-(2,2-difluorobenzo[d][1,3]dioxol-5-yl)-2-methyloxazol-5-yl)-4'-(2-methyl-4-(trifluoromethyl)-1H-imidazol-1-yl)-3-(methylsulfonyl)-[1,1'-biphenyl]-4-yl)methanol | MS (ESI) 648.1 [M + H]$^+$ |
| 617 | | (3'-(4-(2,2-difluorobenzo[d][1,3]dioxol-5-yl)-2-methyloxazol-5-yl)-3-fluoro-4'-(2-methyl-4-(trifluoromethyl)-1H-imidazol-1-yl)-5-(methylsulfonyl)-[1,1'-biphenyl]-4-yl)methanol | MS (ESI) 666.0 [M + H]$^+$ |
| 618 | | 2-(4-(4-chlorophenyl)-5-(4-(2-methyl-4-(trifluoromethyl)-1H-imidazol-1-yl)-3'-(methylsulfonyl)-[1,1'-biphenyl]-3-yl)oxazol-2-yl)ethanol | MS (ESI) 602.2 [M + H]$^+$ |
| 619 | | 4-(4-(difluoromethoxy)phenyl)-2-methyl-5-(4-(2-methyl-4-(trifluoromethyl)-1H-imidazol-1-yl)-3'-(methylsulfonyl)-[1,1'-biphenyl]-3-yl)oxazole | MS (ESI) 604.2 [M + H]$^+$ |
| 620 | | 5-(4-(2-methyl-4-(trifluoromethyl)-1H-imidazol-1-yl)-3'-(methylsulfonyl)-[1,1'-biphenyl]-3-yl)-2-(2-(pyrrolidin-1-yl)ethyl)-4-(4-(trifluoromethoxy)phenyl)oxazole | MS (ESI) 705.2 [M + H]$^+$ |

-continued

| Ex # | Stucture | Name | Molecular Ion |
|---|---|---|---|
| 621 | | 2-(4-(2,2-difluorobenzo[d][1,3]dioxol-5-yl)-5-(3'-fluoro-4'-(hydroxymethyl)-4-(2-methyl-4-(trifluoromethyl)-1H-imidazol-1-yl)-5'-(methylsulfonyl)-[1,1'-biphenyl]-3-yl)oxazol-2-yl)ethanol | MS (ESI) 696.2 [M + H]+ |
| 622 | | 2-(4-(2,2-difluorobenzo[d][1,3]dioxol-5-yl)-5-(4-(2-methyl-4-(trifluoromethyl)-1H-imidazol-1-yl)-3'-(methylsulfonyl)-[1,1'-biphenyl]-3-yl)oxazol-2-yl)ethanol | MS (ESI) 648.1 [M + H]+ |
| 623 | | (3-chloro-3'-(4-(2,2-difluorobenzo[d][1,3]dioxol-5-yl)-2-methyloxazol-5-yl)-4'-(2-methyl-4-(trifluoromethyl)-1H-imidazol-1-yl)-5-(methylsulfonyl)-[1,1'-biphenyl]-4-yl)methanol | MS (ESI) 682.0 [M + H]+ |
| 624 | | (3'-(4-(4-(difluoromethoxy)phenyl)-2-methyloxazol-5-yl)-3-fluoro-4'-(2-methyl-4-(trifluoromethyl)-1H-imidazol-1-yl)-5-(methylsulfonyl)-[1,1'-biphenyl]-4-yl)methanol | MS (ESI) 652.1 [M + H]+ |

-continued

| Ex # | Stucture | Name | Molecular Ion |
|---|---|---|---|
| 625 | | (3'-(4-(4-(difluoromethoxy)phenyl)-2-methyloxazol-5-yl)-4'-(2-methyl-4-(trifluoromethyl)-1H-imidazol-1-yl)-3-(methylsulfonyl)-[1,1'-biphenyl]-4-yl)methanol | MS (ESI) 634.1 [M + H]$^+$ |
| 626 | | 2-(2-methyl-5-(4-(2-methyl-4-(trifluoromethyl)-1H-imidazol-1-yl)-3'-(methylsulfonyl)-[1,1'-biphenyl]-3-yl)oxazol-4-yl)-5-(trifluoromethoxy)phenol | MS (ESI) 638.3 [M + H]$^+$ |
| 627 | | 2-methyl-5-(4-(2-methyl-4-(trifluoromethyl)-1H-imidazol-1-yl)-3'-(methylsulfinyl)-[1,1'-biphenyl]-3-yl)-4-(4-(trifluoromethoxy)phenyl)oxazole | MS (ESI) 606.1 [M + H]$^+$ |
| 628 | | N,N-dimethyl-2-(5-(4-(2-methyl-4-(trifluoromethyl)-1H-imidazol-1-yl)-3'-(methylsulfonyl)-[1,1'-biphenyl]-3-yl)-4-(4-(trifluoromethoxy)phenyl)oxazol-2-yl)ethanamine | MS (ESI) 679.4 [M + H]$^+$ |
| 629 | | 2-methyl-5-(4-(2-methyl-4-(trifluoromethyl)-1H-imidazol-1-yl)-3'-(methylsulfonyl)-[1,1'-biphenyl]-3-yl)-4-(2-(trifluoromethyl)phenyl)oxazole | MS (ESI) 606.3 [M + H]$^+$ |

-continued

| Ex # | Structure | Name | Molecular Ion |
|---|---|---|---|
| 630 | | (3-fluoro-3'-(2-methyl-4-(2-(trifluoromethyl)phenyl)oxazol-5-yl)-4'-(2-methyl-4-(trifluoromethyl)-1H-imidazol-1-yl)-5-(methylsulfonyl)-[1,1'-biphenyl]-4-yl)methanol | MS (ESI) 654.3 [M + H]$^+$ |
| 631 | | 2-methyl-5-(4-(2-methyl-4-(trifluoromethyl)-1H-imidazol-1-yl)-3'-(methylsulfonyl)-[1,1'-biphenyl]-3-yl)-4-(2-(trifluoromethoxy)phenyl)oxazole | MS (ESI) 622.3 [M + H]$^+$ |
| 632 | | (3-fluoro-3'-(2-methyl-4-(2-(trifluoromethoxy)phenyl)oxazol-5-yl)-4'-(2-methyl-4-(trifluoromethyl)-1H-imidazol-1-yl)-5-(methylsulfonyl)-[1,1'-biphenyl]-4-yl)methanol | MS (ESI) 670.3 [M + H]$^+$ |
| 633 | | (3'-(4-(4-chlorobenzyl)oxazol-5-yl)-3-fluoro-4'-(2-methyl-4-(trifluoromethyl)-1H-imidazol-1-yl)-5-(methylsulfonyl)-[1,1'-biphenyl]-4-yl)methanol | MS (ESI) 620.2 [M + H]$^+$ |

| Ex # | Stucture | Name | Molecular Ion |
|---|---|---|---|
| 634 | | 4-(4-chlorobenzyl)-5-(4-(2-methyl-4-(trifluoromethyl)-1H-imidazol-1-yl)-3'-(methylsulfonyl)-[1,1'-biphenyl]-3-yl)oxazole | MS (ESI) 572.3 [M + H]+ |
| 635 | | (3'-(4-(4-chlorobenzyl)oxazol-5-yl)-4'-(2-methyl-4-(trifluoromethyl)-1H-imidazol-1-yl)-3-(methylsulfonyl)-[1,1'-biphenyl]-4-yl)methanol | |
| 636 | | 5-(4-(2-methyl-4-(trifluoromethyl)-1H-imidazol-1-yl)-3'-(methylsulfonyl)-[1,1'-biphenyl]-3-yl)-4-(4-(trifluoromethoxy)benzyl)oxazole | |
| 637 | | 4-(2-methoxy-4-(trifluoromethoxy)phenyl)-2-methyl-5-(4-(2-methyl-4-(trifluoromethyl)-1H-imidazol-1-yl)-3'-(methylsulfonyl)-[1,1'-biphenyl]-3-yl)oxazole | |

Scheme 9

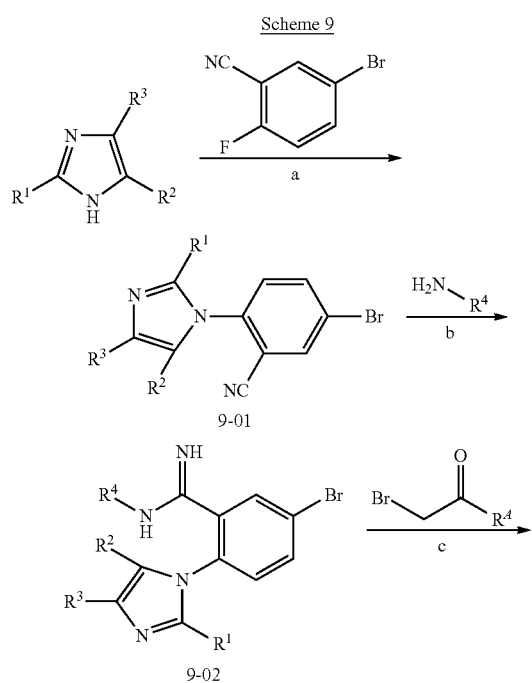

(a) K₂CO₃, DMF; (b) AlMe₃, xylenes; (c) i. K₂CO₃, THF, toluene; ii. TFA, EtOH; (d) PdCl₂(dppf), K₂CO₃, DME, H₂O In general, the imidazole compounds of formula 9-04 can be synthesized following the methodology shown in Scheme 9. The imidazole reacts with 5-bromo-2-fluorobenzonitrile in the presence of K₂CO₃ in DMF to give the aryl imidazole (9-01). The nitrile (9-01) is converted to the amidine (9-02) by reaction with a functionalized amine and trimethyl aluminum. The amidine (9-02) is transformed to the imidazole (9-03) by reaction with an appropriately functionalized α-bromoketone. Suzuki coupling between the aryl bromide (9-03) with an aryl boronic acid or ester produces the final imidazole product 9-04.

Example 638

(3'-(1-(2,2-difluorobenzo[d][1,3]dioxol-5-yl)-4-(trifluoromethyl)-1H-imidazol-2-yl)-3-fluoro-4'-(2-methyl-4-(trifluoromethyl)-1H-imidazol-1-yl)-5-(methylsulfonyl)biphenyl-4-yl)methanol

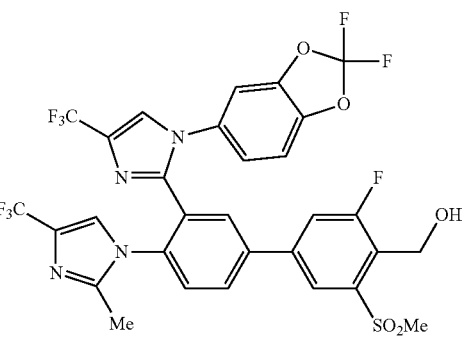

Example 638a

Preparation of 5-bromo-2-(2-methyl-4-(trifluoromethyl)-1H-imidazol-1-yl)benzonitrile

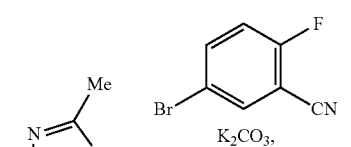

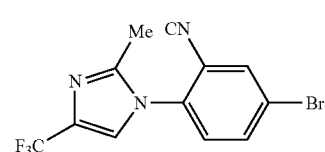

In a 100 mL round bottom flask, 2-methyl-4-(trifluoromethyl)-1H-imidazole (8.0 g, 53 mmol), 5-bromo-2-fluorobenzonitrile (11 g, 53 mmol) and K₂CO₃ (22 g, 160 mmol) were brought up in solution with DMF (80 mL) to give a yellow suspension. The reaction mixture was stirred overnight at 100° C. The DMF was removed from the mixture in vacuo, and the residue was diluted with EtOAc (350 mL). The organic solution was washed with saturated NH₄Cl, followed by H₂O, and then brine. The organic solution was dried over Na₂SO₄, filtered and concentrated to give the crude product. The crude material was purified by chromatography thru a SiO₂ column using a mobile phase gradient of 5% to 15% EtOAc in petroleum ethers to afford the title compound as a white solid (17 g, 52 mmol, 97% yield). ¹H NMR (400 MHz, CHLOROFORM-d) δ ppm 8.00 (d, 1H, J=2 Hz), 7.92 (m, 1H), 7.34 (m, 2H), 2.36 (s, 3H).

Example 638b

Preparation of 5-bromo-N-(2,2-difluorobenzo[d][1,3]dioxol-5-yl)-2-(2-methyl-4-(trifluoromethyl)-1H-imidazol-1-yl)benzimidamide

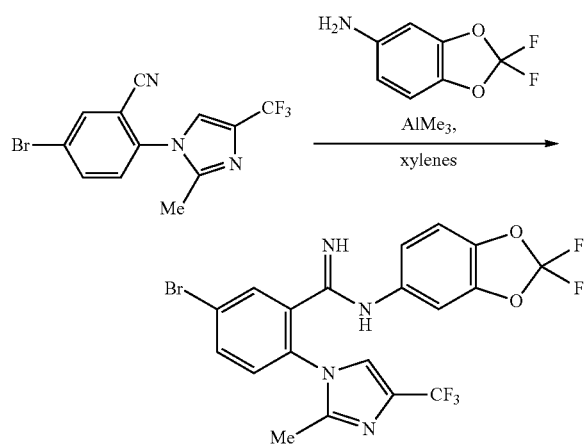

In a 100 mL round bottom flask, 5-bromo-2-(2-methyl-4-(trifluoromethyl)-1H-imidazol-1-yl)benzonitrile (1.8 g, 5.6 mmol) and 2,2-difluorobenzo[d][1,3]dioxol-5-amine (0.80 g, 4.6 mmol) were brought up in xylene (20 mL) to give a yellow solution. The reaction mixture was heated to 70° C. for 20 min before trimethylaluminum (3.2 mL, 6.5 mmol) was added dropwise. The reaction mixture was heated to 100° C. overnight. Excess xylene was removed from the reaction mixture in vacuo, and the mixture was diluted with 40% MeOH in chloroform (150 mL). The solution was made into as slurry with silica gel [200-400 mm] and then filtered through a celite bed and washed with a 40% MeOH in chloroform solution (50 mL). The filtrates were concentrated in vacuo to give the crude product. The crude material was purified by chromatography thru a SiO₂ column using a mobile phase gradient of 5% to 15% EtOAc in Hx to afford the title compound as a thick yellow oil (550 mg, 1.1 mmol, 24% yield). MS (ESI) 503.0 [M+H]+.

Example 638c

Preparation of 1-(4-bromo-2-(1-(2,2-difluorobenzo[d][1,3]dioxol-5-yl)-4-(trifluoromethyl)-1H-imidazol-2-yl)phenyl)-2-methyl-4-(trifluoromethyl)-1H-imidazole

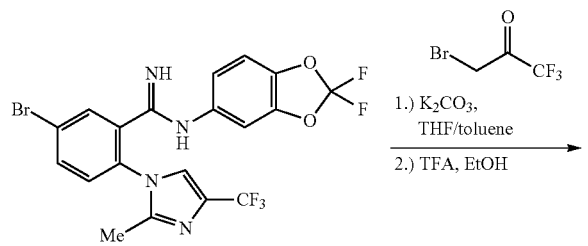

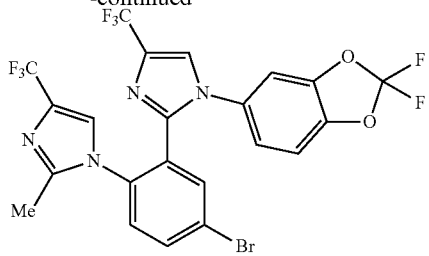

In a 50 mL round bottom flask, Example 638b (200 mg, 0.40 mmol) and K₂CO₃ (170 mg, 1.2 mmol) were brought up in THF (5 mL) and toluene (5 mL). The reaction mixture was heated to 60° C. for 20 min before 3-bromo-1,1,1-trifluoropropan-2-one (99 mg, 0.52 mmol) in THF (2 mL) was added dropwise. The reaction mixture was heated to 100° C. for 24 hrs. The reaction mixture was cooled to rt and diluted with cold water (50 mL). The aqueous solution was extracted with EtOAc (50 mL×3) and the combined organic layers were washed with brine (25 mL). The organic solution was dried over Na₂SO₄, filtered and concentrated to obtain the intermediate as a yellow oil (MS (ESI) 615.0 [M+H]+). The intermediate (250 mg, 0.40 mmol) was brought up in EtOH (3 mL) and TFA (3.0 mL, 39 mmol). The reaction mixture was heated to 75° C. overnight and then the excess TFA was removed in vacuo. The reaction mixture was diluted with EtOAc (100 mL) and washed with saturated NaHCO₃, followed by H₂O, and brine. The organic solution was dried over Na₂SO₄, filtered and concentrated to obtain the crude product. The crude material was purified by chromatography thru a SiO₂ column using a mobile phase gradient of 5% to 15% EtOAc in Hx to afford the title compound as a thick yellow oil (200 mg, 0.34 mmol, 82% yield). MS (ESI) 596.0 [M+H]+.

Example 638 was prepared from Example 638c using procedures similar to that described in Example 1f. MS (ESI) 718.8 [M+H]+. $^1$H NMR (400 MHz, MeOH-d₄) δ ppm 8.21 (s, 1H), 8.19 (d, 1H, J=2.01 Hz), 8.08 (dd, 1H, J=8.41, 2.13 Hz), 8.03 (d, 1H, J=1.00 Hz), 7.95 (dd, 1H, J=10.54, 1.76 Hz), 7.62 (d, 1H, J=8.28 Hz), 7.24 (d, 1H, J=8.53 Hz), 7.03 (m, 2H), 6.88 (dd, 1H, J=8.53, 2.26 Hz), 5.15 (s, 2H) 3.41 (s, 3H), 1.93 (s, 3H).

Example 639

(3'-(4-cyclopropyl-1-(2,2-difluorobenzo[d][1,3]dioxol-5-yl)-1H-imidazol-2-yl)-3-fluoro-4'-(2-methyl-4-(trifluoromethyl)-1H-imidazol-1-yl)-5-(methylsulfonyl)biphenyl-4-yl)methanol

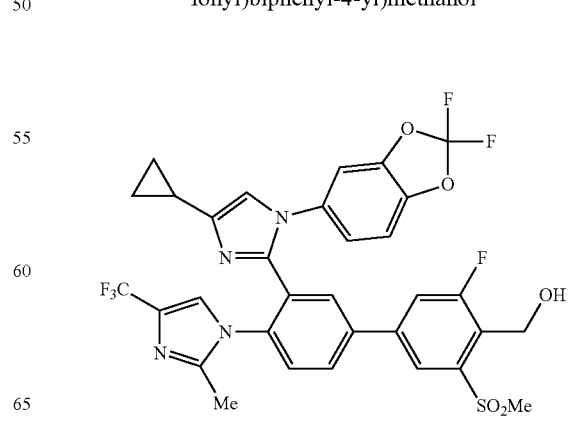

Example 639 was prepared from Example 638b and 2-bromo-1-cyclopropylethanone using procedures similar to that described in Example 638 and Example 1f. MS (ESI) 691.2 [M+H]+. ¹H NMR (400 MHz, CDCl₃-d) δ ppm 8.18 (s, 1H), 8.12 (s, 1H), 7.71-7.80 (m, 2H), 7.27-7.30 (m, 1H) 6.94-6.98 (m, 1H), 6.79 (s, 1H), 6.45-6.54 (m, 3H), 5.09-5.14 (m, 2H), 3.31 (s, 3H), 1.87-1.95 (m, 1H), 1.82 (s, 3H), 0.90-0.97 (m, 2H), 0.77-0.84 (m, 2H).

The following compounds were prepared in a manner similar to that described in the previous experimental procedures above:

| Ex # | Structure | Name | Molecular Ion |
|---|---|---|---|
| 640 | | 1-(2,2-difluorobenzo[d][1,3]dioxol-5-yl)-2-(4-(2-methyl-4-(trifluoromethyl)-1H-imidazol-1-yl)-3'-(methylsulfonyl)biphenyl-3-yl)-4-(trifluoromethyl)-1H-imidazole | MS (ESI) 670.8 [M + H]+. |
| 641 | | 1-(2,2-difluorobenzo[d][1,3]dioxol-5-yl)-2-(3'-fluoro-4-(2-methyl-4-(trifluoromethyl)-1H-imidazol-1-yl)-5'-(methylsulfonyl)biphenyl-3-yl)-4-(trifluoromethyl)-1H-imidazole | MS (ESI) 688.8 [M + H]+. |
| 642 | | 2-chloro-5-(2-(4-(2-methyl-4-(trifluoromethyl)-1H-imidazol-1-yl)-3'-(methylsulfonyl)biphenyl-3-yl)-4-(trifluoromethyl)-1H-imidazol-1-yl)pyridine | MS (ESI) 625.8 [M + H]+. |
| 643 | | 4-cyclopropyl-1-(2,2-difluorobenzo[d][1,3]dioxol-5-yl)-2-(4-(2-methyl-4-(trifluoromethyl)-1H-imidazol-1-yl)-3'-(methylsulfonyl)biphenyl-3-yl)-1H-imidazole | MS (ESI) 643.2 [M + H]+. |

| Ex # | Stucture | Name | Molecular Ion |
|---|---|---|---|
| 644 | | 1-(4-chlorophenyl)-2-(4-(2-methyl-4-(trifluoromethyl)-1H-imidazol-1-yl)-3'-(methylsulfonyl)biphenyl-3-yl)-4-(trifluoromethyl)-1H-imidazole | MS (ESI) 625.0 [M + H]+. |
| 645 | | (3'-(1-(4-chlorophenyl)-4-(trifluotomethyl)-1H-imidazol-2-yl)-3-fluoro-4'-(2-methyl-4-(trifluoromethyl)-1H-imidazol-1-yl)-5-(methylsulfonyl)biphenyl-4-yl)methanol | MS (ESI) 673.0 [M + H]+. |
| 646 | | 1-(4-chlorophenyl)-4-cyclopropyl-2-(4-(2-methyl-4-(trifluoromethyl)-1H-imidazol-1-yl)-3'-(methylsulfonyl)-[1,1'-biphenyl]-3-yl)-1H-imidazole | MS (ESI) 597.2 [M + H]+. |
| 647 | | (3'-(1-(4-chlorophenyl)-4-cyclopropyl-1H-imidazol-2-yl)-3-fluoro-4'-(2-methyl-4-(trifluoromethyl)-1H-imidazol-1-yl)-5-(methylsulfonyl)-[1,1'-biphenyl]-4-yl)methanol | MS (ESI) 645.2 [M + H]+. |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:
1. A compound of formula

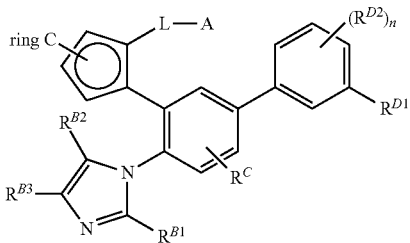

or a pharmaceutically acceptable salt thereof, wherein
L is a bond, —[C(R$^1$)$_2$]$_m$—, -cyclopropyl-, or —CO—;
m is 1 or 2;
n is 0, 1, 2, 3, or 4;
R$^1$ is independently selected from H, C$_{1-3}$alkyl, C$_{1-3}$haloalkyl, —OH, or halo;
A is phenyl, cyclohexyl, a 5 or 6 membered heterocyclyl, or a 5 or 6 membered heteroaryl, wherein the phenyl is optionally fused to a 5 or 6 membered heterocyclyl or 5 or 6 membered heteroaryl,
wherein A is optionally substituted with 1, 2, or 3 R$^A$ groups, wherein
each R$^A$ is independently R$^{A1}$, —C$_1$-C$_6$alkyl-R$^{A1}$, C$_1$-C$_6$alkyl, C1-C$_6$haloalkyl, C$_2$-C$_6$alkenyl, C$_2$-C$_6$alkynyl, C$_3$-C$_8$cycloalkyl, or heterocyclyl wherein the cycloalkyl and heterocyclyl are each optionally substituted with 1, 2, 3, or 4 groups that are independently R$^{A1}$, C$_1$-C$_6$alkyl, or —C$_1$-C$_6$alkyl-R$^{A1}$, wherein
each R$^{A1}$ is independently halogen, cyano, nitro, —OR, —NR$_2$, —SR, —C(O)R, or —C(O)OR;
alternatively, 2R$^A$ on adjacent carbons can join to form a —O—CH$_2$—O—, —O—CH$_2$—CH$_2$—, —O—CH$_2$—CH$_2$—O—, —CH$_2$—CH$_2$—CH$_2$—, or —O—CF$_2$—O—;
ring C is a 5 membered heterocyclic ring selected from triazolyl, imidazolyl, pyrrazolyl, oxazolyl; wherein when ring C is pyrrazolyl, imidazolyl, or oxazolyl, then ring C is optionally substituted with C$_{1-4}$alkyl, C$_{2-3}$alkenyl, C$_{1-3}$haloalkyl, C$_{3-6}$cycloalkyl, —CF$_3$, —C$_{1-4}$alkyl-OH, —C$_{1-4}$alkyl-O—C$_{1-3}$alkyl, —C$_{1-3}$alkyl-NR$_2$; —C$_{1-3}$alkyl-CO$_2$H, —C$_{1-3}$alkyl-NHSO$_2$—C$_{1-3}$alkyl, —NH—C$_{1-3}$alkyl-OR, —C$_{1-3}$alkyl-pyrrolidinyl;
R$^{B1}$ is hydrogen, C$_{1-3}$alkyl, halo, or C$_{1-3}$haloalkyl;
R$^{B2}$ is hydrogen or halo;
R$^{B3}$ is hydrogen, C$_{1-3}$alkyl, halo, —CN, C$_{1-3}$haloalkyl, —C(O)—C$_{1-3}$alkyl, —CO—NH$_2$, —CO—N(R)$_2$, or —C$_{1-3}$alkyl-OH,
each R$^{D1}$ and R$^{D2}$ are independently R$^{D3}$, C$_1$-C$_6$alkyl, —C$_1$-C$_6$alkyl-R$^{D3}$, C$_1$-C$_6$haloalkyl, C$_2$-C$_6$alkenyl, C$_2$-C$_6$alkynyl, C$_3$-C$_8$cycloalkyl, or heterocyclyl, wherein the cycloalkyl or heterocyclyl are each optionally substituted with 1, 2, 3, or 4 groups that are independently R$^{D3}$, C$_1$-C$_6$alkyl, C$_3$-C$_6$cycloalkyl, or —C$_1$-C$_6$alkyl-R$^{D3}$, wherein
each R$^{D3}$ is independently halogen, cyano, —OR, —NR$_2$, —SR, —C(O)R, —C(O)OR, —C(O)NR$_2$, —S(O)R, —S(O)$_2$R, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)$_2$R, —N(R)S(O)$_2$OR, —N(R)S(O)$_2$NR$_2$, or —S(O)$_2$N(R)C(O)NR$_2$; and
R$^C$ is hydrogen, halogen, C$_1$-C$_6$alkyl, cyano, or nitro;
each R group is independently hydrogen, C$_1$-C$_6$alkyl, —C$_1$-C$_6$alkyl-R$^2$, C$_1$-C$_6$haloalkyl, —C$_1$-C$_6$haloalkyl-R$^2$, C$_2$-C$_6$alkenyl, C$_2$-C$_6$alkynyl, or C$_3$-C$_8$cycloalkyl, wherein each R$^2$ is independently cyano, —OR$^3$, —N(R$^3$)$_2$, —N(R$^3$)S(O)$_2$R$^3$, —N(R$^3$)S(O)$_2$OR$^3$, or —N(R$^3$)S(O)$_2$N(R$^3$)$_2$, wherein each R$^3$ is independently hydrogen, C$_1$-C$_6$alkyl, or C$_1$-C$_6$haloalkyl.

2. A compound of the formula I,

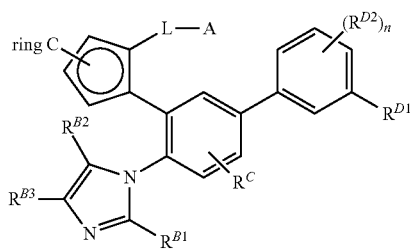

or pharmaceutically acceptable salt thereof, wherein
L is a bond, —[C(R$^1$)$_2$]$_m$—, -cyclopropyl-, or —CO—;
m is 1 or 2;
R$^1$ is independently selected from H, C$_{1-3}$alkyl, —OH, or halo;
A is phenyl, cyclohexyl, naphthalenyl, benzofuranyl, 2,3-dihydro-1H-indenyl, 1H-indolyl, pyridyl, pyrazinyl, pyrimidinyl, dihydrobenzofuranyl, pyridin-2(1H)-one, imidazo[1,2-a]pyridinyl, or piperidinyl, wherein A is optionally substituted with 1, 2, or 3 R$^A$ groups; wherein
each R$^A$ is independently halo, —CN, C$_1$-C$_6$alkyl, C$_1$-C$_6$haloalkyl, —O—R, —NR$_2$, —O—C$_{1-6}$alkyl, —O—C$_{1-6}$alkyl-C$_{3-6}$cycloalkyl, —S—R, —CO—R, —C(O)O—R, —C$_{1-6}$alkyl-CO—NR$_2$, pyrrolidinone, or pyrrolidinyl;
alternatively, 2R$^A$ on adjacent carbons can join to form a —O—CH$_2$—O—, —O—CH$_2$—CH$_2$—, —O—CH$_2$—CH$_2$—O—, or —O—CF$_2$—O—;
ring C is a 5 membered heterocyclic ring selected from triazolyl, imidazolyl, pyrrazolyl, and oxazolyl; wherein when ring C is pyrrazolyl, imidazolyl, or oxazolyl, then ring C is optionally substituted with C$_{1-4}$alkyl, C$_{2-3}$alkenyl, C$_{1-3}$haloalkyl, C$_{3-6}$cycloalkyl, —CF$_3$—, —C$_{1-4}$alkyl-OH, —C$_{1-4}$alkyl-O—C$_{1-3}$alkyl, —C$_{1-3}$alkyl-NR$_2$; —C$_{1-3}$alkyl-CO$_2$H, —C$_{1-3}$alkyl-NHSO$_2$—C$_{1-3}$alkyl, —NH—C$_{1-3}$alkyl-OR, or —C$_{1-3}$alkyl-pyrrolidinyl;
R$^{B1}$ is hydrogen, C$_{1-3}$alkyl, halo, or C$_{1-3}$haloalkyl;
R$^{B2}$ is hydrogen or halo;
R$^{B3}$ is hydrogen, C$_{1-3}$alkyl, halo, —CN, C$_{1-4}$haloalkyl, cyclopropyl, —CO—NH$_2$, —CO—NR$_2$, or —C$_{1-3}$alkyl-OH,
R$^C$ is hydrogen, halogen, or cyano;
n is 0, 1, 2, 3, or 4; and $R^{D1}$ is —SO$_2$—C$_{1-6}$alkyl, —SO$_2$—C$_{1-6}$haloalkyl, —SO$_2$—C$_{3-6}$cycloalkyl, —SO$_2$—C$_{1-6}$ alkyl-OH, —SO$_2$—C$_{1-6}$alkyl-O—C$_{1-6}$alkyl, —C(Me)$_2$-COOH, —C(Me)$_2$-CONR$_2$, -cyclopropyl-CONR$_2$, —SO$_2$NR$_2$, —SO$_2$NR—C$_{1-6}$alkyl-OH, —SO$_2$-pyrrolidinyl, or —CONR$_2$ $R^{D2}$ is independently —C$_{1-6}$haloalkyl-C$_{1-6}$alkyl-OH, halo, —C$_{1-6}$ alkyl-O—C$_{1-6}$ alkyl, C$_{1-6}$alkyl-NHSO$_2$—C$_{1-6}$alkyl, C$_{1-6}$ haloalkyl, or —O—C$_{1-6}$alkyl-O—C$_{1-6}$ haloalkyl, each R group is independently hydrogen, C$_1$-C$_6$alkyl, —C$_1$-C$_6$alkyl-R$^2$, C$_1$-C$_6$haloalkyl, —C$_1$-C$_6$haloalkyl-R$^2$, C$_2$-C$_6$alkenyl, C$_2$-C$_6$alkynyl, C$_3$-C$_8$cycloalkyl; each R$^2$ is independently —OR$^3$, wherein each R$^3$ is independently hydrogen, C$_1$-C$_6$alkyl, or C$_1$-C$_6$haloalkyl.

3. The compound of claim 1, or a pharmaceutically acceptable salt thereof, wherein
$R^{B1}$ is H, alkyl, or haloalkyl;
$R^{B2}$ is H, alkyl, or halo; and
$R^C$ is hydrogen or halo.

4. The compound of claim 1, or a pharmaceutically acceptable salt thereof, wherein
L is a bond; and
A is phenyl, pyridyl or pyrimidinyl.

5. The compound of claim 1, or a pharmaceutically acceptable salt thereof, wherein
ring C is a 5 membered heterocyclic ring selected from triazolyl, imidazolyl, pyrrazolyl, and oxazolyl; wherein when ring C is pyrrazolyl, imidazolyl, or oxazolyl, then ring C is optionally substituted with C$_{1-4}$ alkyl, C$_{2-3}$ alkenyl, C$_{1-3}$ haloalkyl, C$_{3-6}$cycloalkyl, —CF$_3$, —C$_{1-4}$ alkyl-OH, —C$_{1-4}$alkyl-O—C$_{1-3}$alkyl, —C$_{1-3}$alkyl-NR$^2$; —C$_{1-3}$alkyl-CO$_2$H, —C$_{1-3}$alkyl-NHSO$_2$—C$_{1-3}$ alkyl, —NH—C$_{1-3}$ alkyl-OR, or —C$_{1-3}$ alkyl-pyrrolidinyl.

6. The compound of claim 1, or a pharmaceutically acceptable salt thereof, wherein
$R^{D1}$ is —SO$_2$-alkyl, SO$_2$NR$_2$, —C(Me)$_2$-CONH$_2$, or

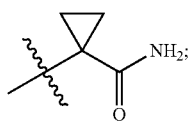 [SMILES: *C1(C(N)=O)CC1]

and
$R^{D2}$ is —C$_{1-6}$ alkyl-OH or halo.

7. The compound of claim 1, or a pharmaceutically acceptable salt thereof, wherein
ring C is a 5 membered heterocyclic ring selected from triazolyl, imidazolyl, pyrrazolyl, oxazolyl; wherein when ring C is pyrrazolyl, imidazolyl, or oxazolyl, then ring C is optionally substituted with C$_{1-4}$ alkyl, —CF$_3$, cyclopropyl, —C$_{1-3}$alkyl-N(CH$_3$)$_2$; —C$_{1-4}$alkyl-OH, or —C$_{1-4}$alkyl-O—C$_{1-3}$alkyl.

8. The compound of claim 1, or a pharmaceutically acceptable salt thereof, wherein
ring C is a 5 membered heterocyclic ring selected from triazolyl, imidazolyl, pyrrazolyl, oxazolyl; wherein when ring C is pyrrazolyl, imidazolyl, or oxazolyl, then ring C is optionally substituted with —CH$_3$, —CF$_3$, or cyclopropyl.

9. The compound of claim 1, or a pharmaceutically acceptable salt thereof, wherein
$R^{D1}$ is —SO$_2$—CH$_3$, or —SO$_2$NR$_2$.

10. The compound of claim 1, or a pharmaceutically acceptable salt thereof, wherein
$R^{D1}$ is —SO$_2$—CH$_3$.

11. The compound of claim 1, or a pharmaceutically acceptable salt thereof, wherein the compound of formula (I) is

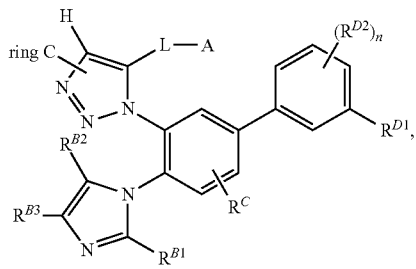

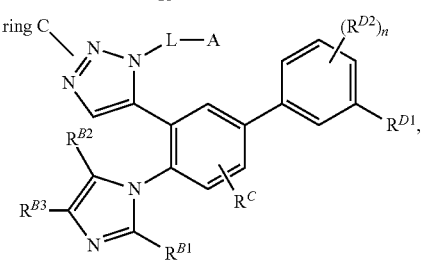

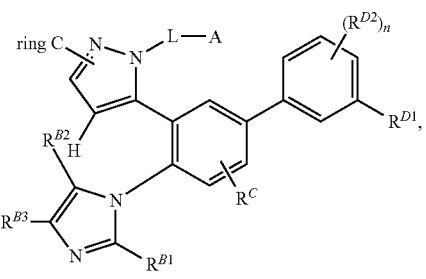

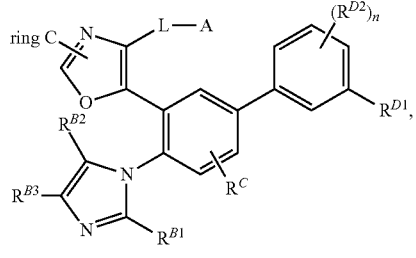

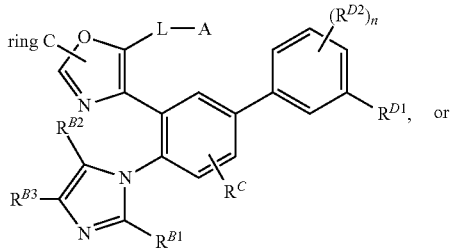

-continued

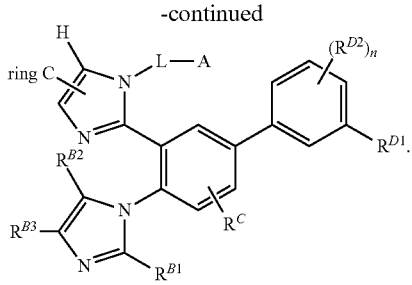

12. The compound of claim 1, or a pharmaceutically acceptable salt thereof, wherein the compound of formula (I) is

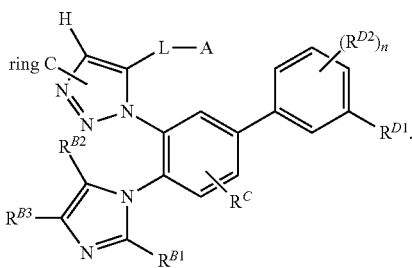

13. The compound of claim 1, or a pharmaceutically acceptable salt thereof, wherein the compound of formula (I) is

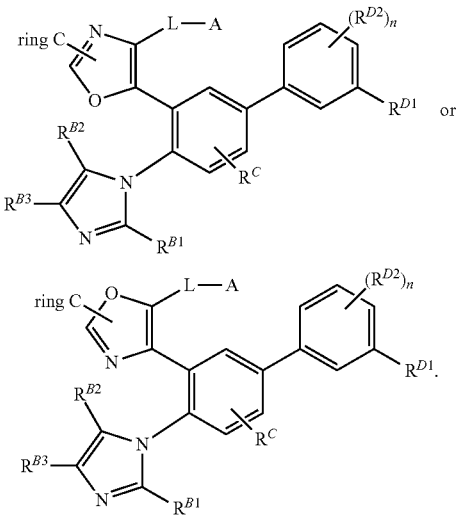

14. A compound selected from Examples 1 to 647 listed below, or a pharmaceutically acceptable salt thereof

| Ex # | Structure | Name |
|---|---|---|
| 1 | 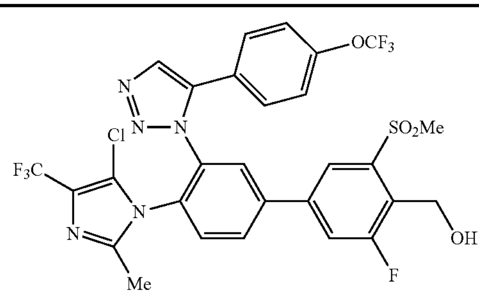 | {4'-[5-chloro-2-methyl-4-(trifluoromethyl)-1H-imidazol-1-yl]-3-fluoro-5-(methylsulfonyl)-3'-(5-{4-[(trifluoromethyl)oxy]phenyl}-1H-1,2,3-triazol-1-yl)biphenyl-4-yl}methanol |
| 2 | 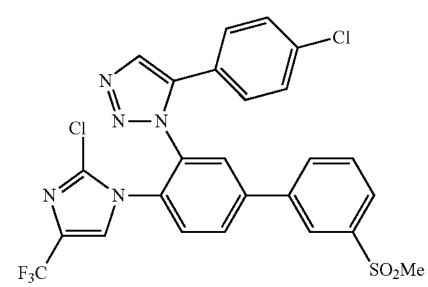 | Preparation of 5-(4-chlorophenyl)-1-{4-[2-chloro-4-(trifluoromethyl)-1H-imidazol-1-yl]-3'-(methylsulfonyl)biphenyl-3-yl}-1H-1,2,3-triazole |
| 3 | 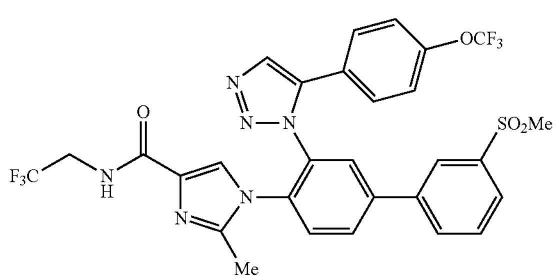 [SMILES: Cc1nc(C(=O)NCC(F)(F)F)cn1-c1ccc(-c2cccc(S(C)(=O)=O)c2)cc1-n1nncc1-c1ccc(OC(F)(F)F)cc1] | 2-methyl-1-[3'-(methylsulfonyl)-3-(5-{4-[(trifluoromethyl)oxy]phenyl}-1H-1,2,3-triazol-1-yl)biphenyl-4-yl]-N-(2,2,2-trifluoroethyl)-1H-imidazole-4-carboxamide |

-continued

| Ex # | Structure | Name |
|---|---|---|
| 4 | 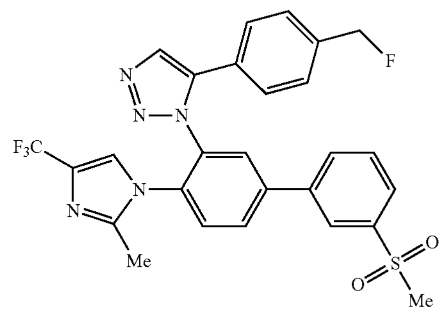 [SMILES: Cc1nc(C(F)(F)F)cn1-c1ccc(-c2cccc(S(C)(=O)=O)c2)cc1-n1nncc1-c1ccc(CF)cc1] | 5-[4-(fluoromethyl)phenyl]-1-{3'-(methylsulfonyl)-4-[2-methyl-4-(trifluoromethyl)-1H-imidazol-1-yl]biphenyl-3-yl}-1H-1,2,3-triazole |
| 5 | 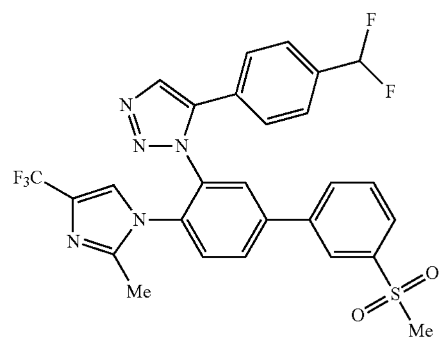 [SMILES: Cc1nc(C(F)(F)F)cn1-c1ccc(-c2cccc(S(C)(=O)=O)c2)cc1-n1nncc1-c1ccc(C(F)F)cc1] | 5-[4-(difluoromethyl)phenyl]-1-{3'-(methylsulfonyl)-4-[2-methyl-4-(trifluoromethyl)-1H-imidazol-1-yl]biphenyl-3-yl}-1H-1,2,3-triazole |
| 6 | 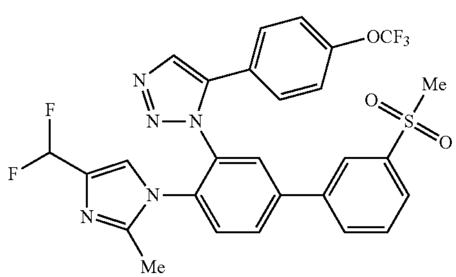 [SMILES: Cc1nc(C(F)F)cn1-c1ccc(-c2cccc(S(C)(=O)=O)c2)cc1-n1nncc1-c1ccc(OC(F)(F)F)cc1] | 1-(4-(4-(difluoromethyl)-2-methyl-1H-imidazol-1-yl)-3'-(methylsulfonyl)-[1,1'-biphenyl]-3-yl)-5-(4-(trifluoromethoxy)phenyl)-1H-1,2,3-triazole |
| 7 | 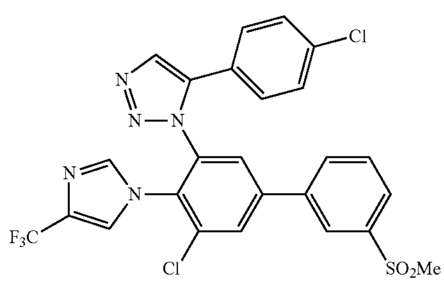 [SMILES: CS(=O)(=O)c1cccc(-c2cc(Cl)c(-n3cnc(C(F)(F)F)c3)c(-n3nncc3-c3ccc(Cl)cc3)c2)c1] | 1-(5-chloro-3'-(methylsulfonyl)-4-(4-(trifluoromethyl)-1H-imidazol-1-yl)biphenyl-3-yl)-5-(4-chlorophenyl)-1H-1,2,3-triazole |
| 8 | 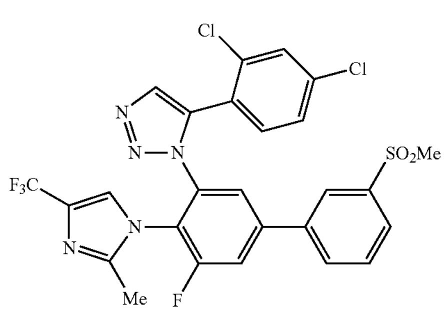 [SMILES: Cc1nc(C(F)(F)F)cn1-c1c(F)cc(-c2cccc(S(C)(=O)=O)c2)cc1-n1nncc1-c1ccc(Cl)cc1Cl] | 5-(2,4-dichlorophenyl)-1-{5-fluoro-3'-(methylsulfonyl)-4-[2-methyl-4-(trifluoromethyl)-1H-imidazol-1-yl]biphenyl-3-yl}-1H-1,2,3-triazole |

| Ex # | Structure | Name |
|---|---|---|
| 9 | 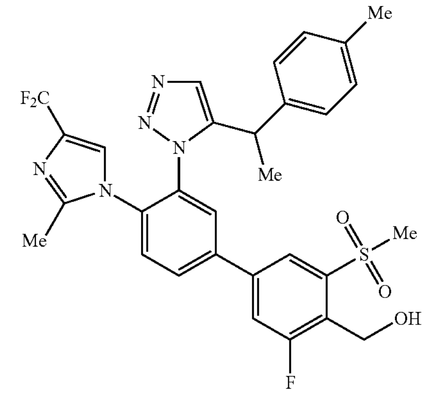 | (3-fluoro-3'-{5-[1-(4-methylphenyl)ethyl]-1H-1,2,3-triazol-1-yl}-5-(methylsulfonyl)-4'-[2-methyl-4-(trifluoromethyl)-1H-imidazol-1-yl]biphenyl-4-yl)methanol |
| 10 | 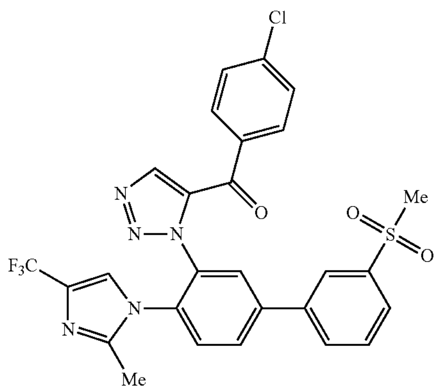 [SMILES: Cc1nc(C(F)(F)F)cn1-c1ccc(-c2cccc(S(C)(=O)=O)c2)cc1-n1nncc1C(=O)c1ccc(Cl)cc1] | (4-chlorophenyl)(1-{3'-(methylsulfonyl)-4-[2-methyl-4-(trifluoromethyl)-1H-imidazol-1-yl]biphenyl-3-yl}-1H-1,2,3-triazol-5-yl)methanone |
| 11 | 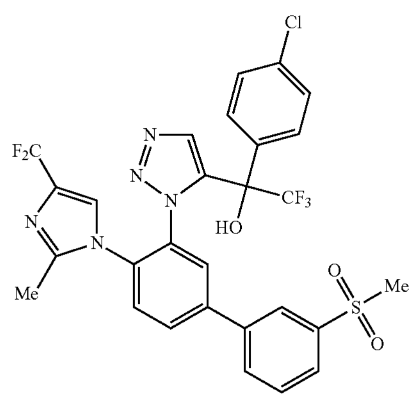 | 1-(4-chlorophenyl)-2,2,2-trifluoro-1-(1-{3'-(methylsulfonyl)-4-[2-methyl-4-(trifluoromethyl)-1H-imidazol-1-yl]biphenyl-3-yl}-1H-1,2,3-triazol-5-yl)ethanol |
| 12 | 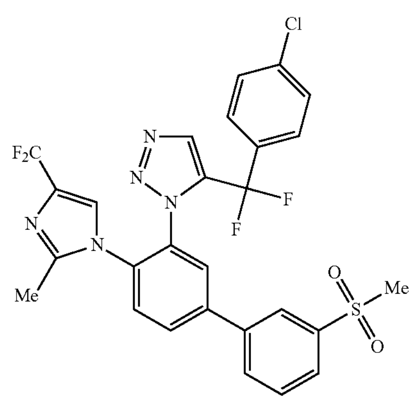 | 5-[(4-chlorophenyl)(difluoro)methyl]-1-{3'-(methylsulfonyl)-4-[2-methyl-4-(trifluoromethyl)-1H-imidazol-1-yl]biphenyl-3-yl}-1H-1,2,3-triazole |

-continued

| Ex # | Structure | Name |
|---|---|---|
| 13 | 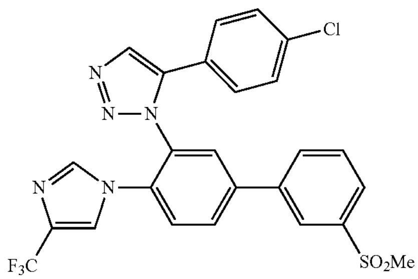 [SMILES: CS(=O)(=O)c1cccc(-c2ccc(-n3cnc(C(F)(F)F)c3)c(-n3nncc3-c3ccc(Cl)cc3)c2)c1] | 5-(4-chlorophenyl)-1-{3'-(methylsulfonyl)-4-[4-(trifluoromethyl)-1H-imidazol-1-yl]biphenyl-3-yl}-1H-1,2,3-triazole |
| 18 | 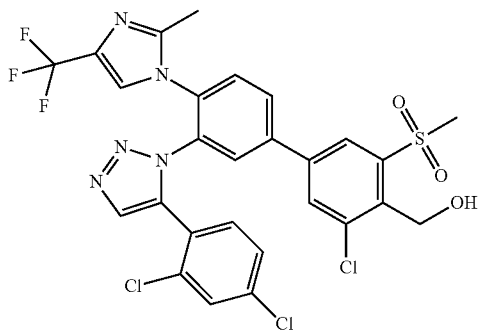 [SMILES: Cc1nc(C(F)(F)F)cn1-c1ccc(-c2cc(Cl)c(CO)c(S(C)(=O)=O)c2)cc1-n1nncc1-c1ccc(Cl)cc1Cl] | {3-chloro-3'-[5-(2,4-dichlorophenyl)-1H-1,2,3-triazol-1-yl]-5-(methylsulfonyl)-4'-[2-methyl-4-(trifluoromethyl)-1H-imidazol-1-yl]biphenyl-4-yl}methanol |
| 19 | 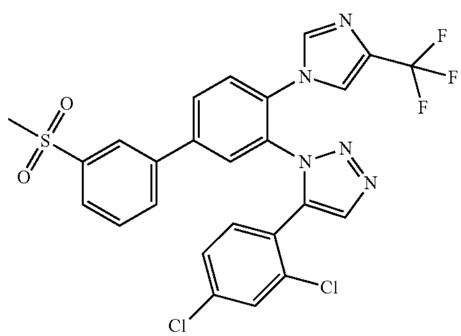 [SMILES: CS(=O)(=O)c1cccc(-c2ccc(-n3cnc(C(F)(F)F)c3)c(-n3nncc3-c3ccc(Cl)cc3Cl)c2)c1] | 5-(2,4-dichlorophenyl)-1-{3'-(methylsulfonyl)-4-[4-(trifluoromethyl)-1H-imidazol-1-yl]biphenyl-3-yl}-1H-1,2,3-triazole |
| 20 | 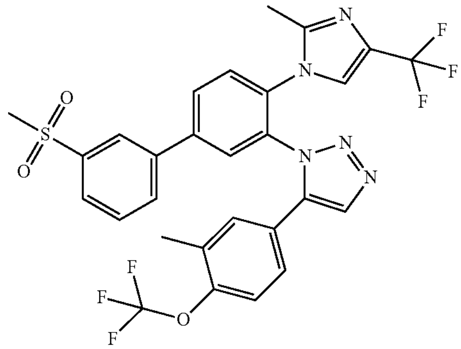 [SMILES: Cc1cc(-c2cnnn2-c2cc(-c3cccc(S(C)(=O)=O)c3)ccc2-n2cc(C(F)(F)F)nc2C)ccc1OC(F)(F)F] | 1-{3'-(methylsulfonyl)-4-[2-methyl-4-(trifluoromethyl)-1H-imidazol-1-yl]biphenyl-3-yl}-5-{3-methyl-4-[(trifluoromethyl)oxy]phenyl}-1H-1,2,3-triazole |

| Ex # | Structure | Name |
|---|---|---|
| 21 | 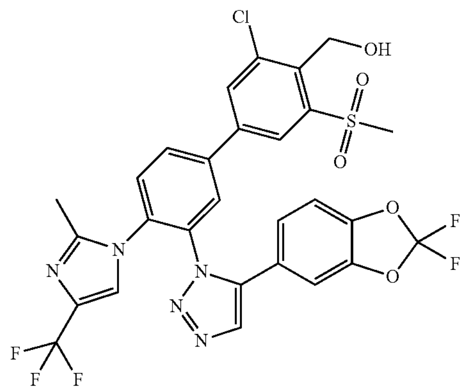 | {3-chloro-3'-[5-(2,2-difluoro-1,3-benzodioxol-5-yl)-1H-1,2,3-triazol-1-yl]-5-(methylsulfonyl)-4'-[2-methyl-4-(trifluoromethyl)-1H-imidazol-1-yl]biphenyl-4-yl}methanol |
| 22 | 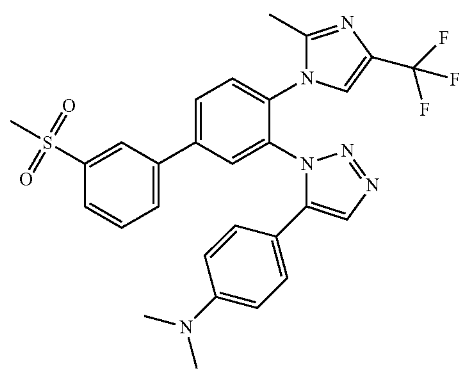 [SMILES: Cc1nc(C(F)(F)F)cn1-c1ccc(-c2cccc(S(C)(=O)=O)c2)cc1-n1nncc1-c1ccc(N(C)C)cc1] | N,N-dimethyl-4-(1-{3'-(methylsulfonyl)-4-[2-methyl-4-(trifluoromethyl)-1H-imidazol-1-yl]biphenyl-3-yl}-1H-1,2,3-triazol-5-yl)aniline |
| 23 | 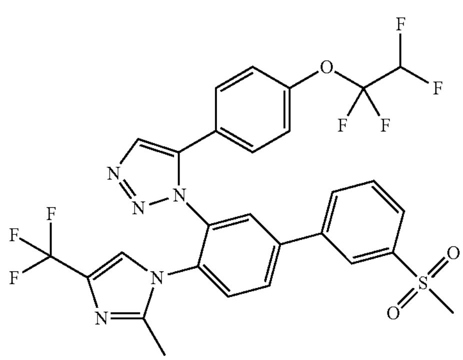 [SMILES: Cc1nc(C(F)(F)F)cn1-c1ccc(-c2cccc(S(C)(=O)=O)c2)cc1-n1nncc1-c1ccc(OC(F)(F)C(F)F)cc1] | 1-{3'-(methylsulfonyl)-4-[2-methyl-4-(trifluoromethyl)-1H-imidazol-1-yl]biphenyl-3-yl}-5-{4-[(1,1,2,2-tetrafluoroethyl)oxy]phenyl}-1H-1,2,3-triazole |
| 24 | 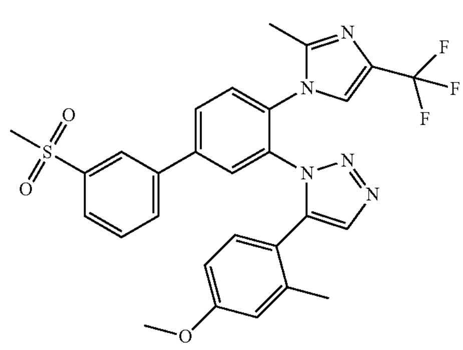 [SMILES: COc1ccc(-c2cnnn2-c2cc(-c3cccc(S(C)(=O)=O)c3)ccc2-n2cc(C(F)(F)F)nc2C)c(C)c1] | 5-[2-methyl-4-(methyloxy)phenyl]-1-{3'-(methylsulfonyl)-4-[2-methyl-4-(trifluoromethyl)-1H-imidazol-1-yl]biphenyl-3-yl}-1H-1,2,3-triazole |

| Ex # | Structure | Name |
|---|---|---|
| 25 | 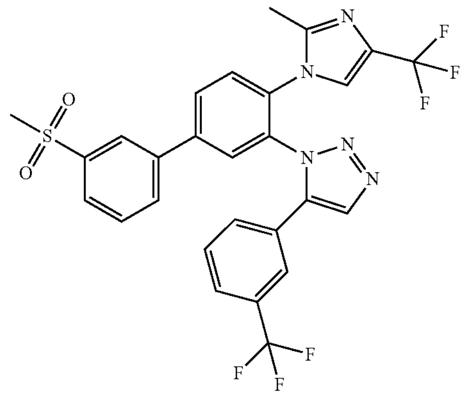 [SMILES: Cc1nc(C(F)(F)F)cn1-c1ccc(-c2cccc(S(C)(=O)=O)c2)cc1-n1nncc1-c1cccc(C(F)(F)F)c1] | 1-{3'-(methylsulfonyl)-4-[2-methyl-4-trifluoromethyl)-1H-imidazol-1-yl]biphenyl-3-yl}-5-[3-(trifluoromethyl)phenyl]-1H-1,2,3-triazole |
| 26 | 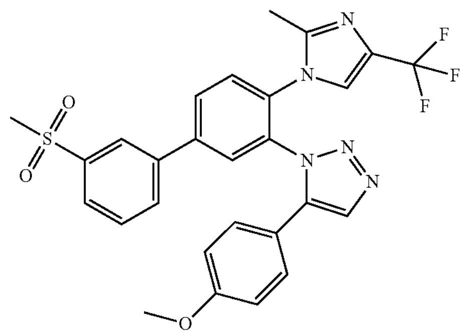 [SMILES: COc1ccc(-c2cnnn2-c2cc(-c3cccc(S(C)(=O)=O)c3)ccc2-n2cc(C(F)(F)F)nc2C)cc1] | 5-[4-(methyloxy)phenyl]-1-{3'-(methylsulfonyl)-4-[2-methyl-4-(trifluoromethyl)-1H-imidazol-1-yl]biphenyl-3-yl}-1H-1,2,3-triazole |
| 27 | 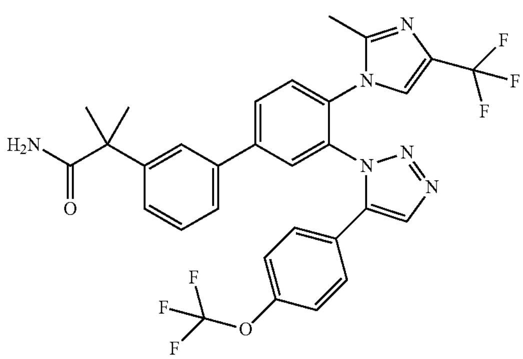 [SMILES: Cc1nc(C(F)(F)F)cn1-c1ccc(-c2cccc(C(C)(C)C(N)=O)c2)cc1-n1nncc1-c1ccc(OC(F)(F)F)cc1] | 2-methyl-2-{4'-[2-methyl-4-(trifluoromethyl)-1H-imidazol-1-yl]-3'-(5-{4-[(trifluoromethyl)oxy]phenyl}-1H-1,2,3-triazol-1-yl)biphenyl-3-yl}propanamide |
| 28 | 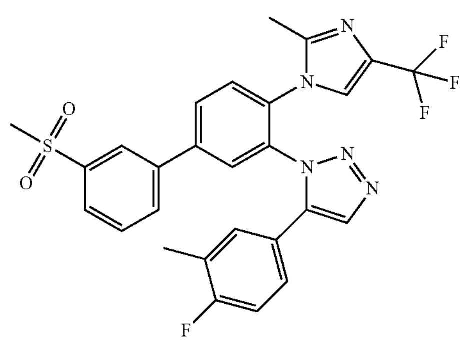 [SMILES: Cc1cc(-c2cnnn2-c2cc(-c3cccc(S(C)(=O)=O)c3)ccc2-n2cc(C(F)(F)F)nc2C)ccc1F] | 5-(4-fluoro-3-methylphenyl)-1-{3'-(methylsulfonyl)-4-[2-methyl-4-(trifluoromethyl)-1H-imidazol-1-yl]biphenyl-3-yl}-1H-1,2,3-triazole |

| Ex # | Structure | Name |
|---|---|---|
| 29 | 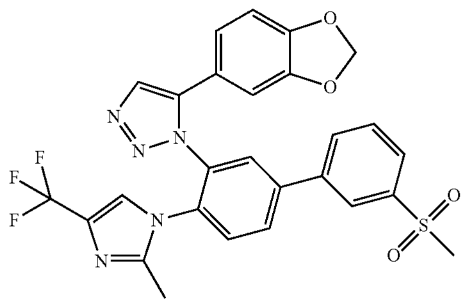 [SMILES: Cc1nc(C(F)(F)F)cn1-c1ccc(-c2cccc(S(C)(=O)=O)c2)cc1-n1nncc1-c1ccc2c(c1)OCO2] | 5-(1,3-benzodioxol-5-yl)-1-{3'-(methylsulfonyl)-4-[2-methyl-4-(trifluoromethyl)-1H-imidazol-1-yl]biphenyl-3-yl}-1H-1,2,3-triazole |
| 30 | 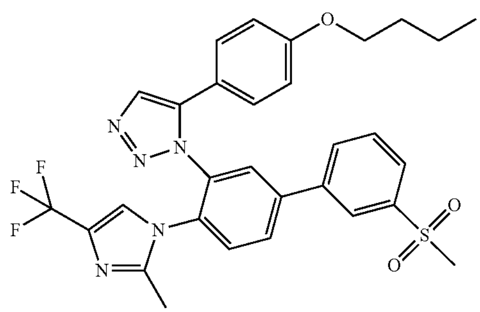 [SMILES: CCCCOc1ccc(-c2cnnn2-c2cc(-c3cccc(S(C)(=O)=O)c3)ccc2-n2cc(C(F)(F)F)nc2C)cc1] | 5-[4-(butyloxy)phenyl]-1-{3'-(methylsulfonyl)-4-[2-methyl-4-(trifluoromethyl)-1H-imidazol-1-yl]biphenyl-3-yl}-1H-1,2,3-triazole |
| 31 | 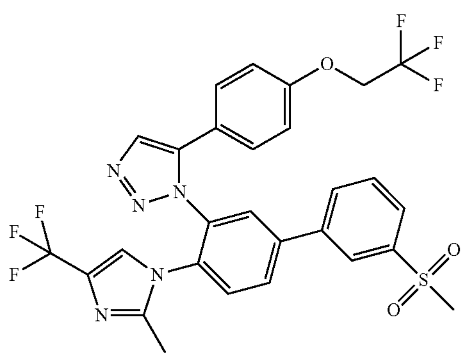 [SMILES: Cc1nc(C(F)(F)F)cn1-c1ccc(-c2cccc(S(C)(=O)=O)c2)cc1-n1nncc1-c1ccc(OCC(F)(F)F)cc1] | 1-{3'-(methylsulfonyl)-4-[2-methyl-4-(trifluoromethyl)-1H-imidazol-1-yl]biphenyl-3-yl}-5-{4-[(2,2,2-trifluoroethyl)oxy]phenyl}-1H-1,2,3-triazole |
| 32 | 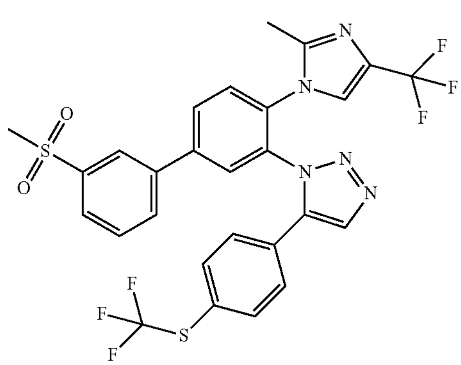 [SMILES: Cc1nc(C(F)(F)F)cn1-c1ccc(-c2cccc(S(C)(=O)=O)c2)cc1-n1nncc1-c1ccc(SC(F)(F)F)cc1] | 1-{3'-(methylsulfonyl)-4-[2-methyl-4-(trifluoromethyl)-1H-imidazol-1-yl]biphenyl-3-yl}-5-{4-[(trifluoromethyl)thio]phenyl}-1H-1,2,3-triazole |

-continued

| Ex # | Structure | Name |
|---|---|---|
| 33 | 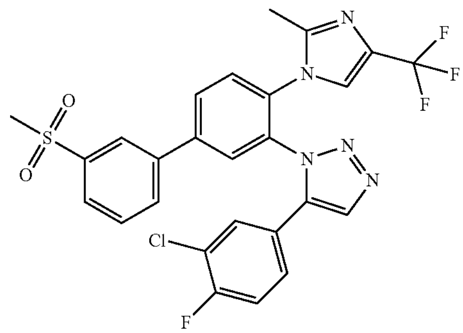 [SMILES: Cc1nc(C(F)(F)F)cn1-c1ccc(-c2cccc(S(C)(=O)=O)c2)cc1-n1nncc1-c1ccc(F)c(Cl)c1] | 5-(3-chloro-4-fluorophenyl)-1-{3'-(methylsulfonyl)-4-[2-methyl-4-(trifluoromethyl)-1H-imidazol-1-yl]biphenyl-3-yl}-1H-1,2,3-triazole |
| 34 | 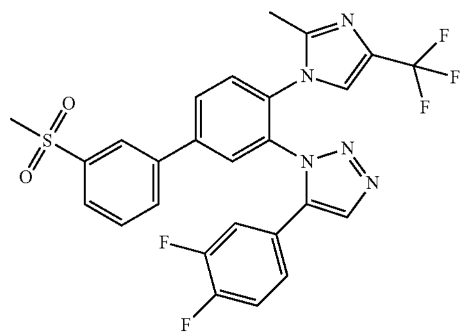 [SMILES: Cc1nc(C(F)(F)F)cn1-c1ccc(-c2cccc(S(C)(=O)=O)c2)cc1-n1nncc1-c1ccc(F)c(F)c1] | 5-(3,4-difluorophenyl)-1-{3'-(methylsulfonyl)-4-[2-methyl-4-(trifluoromethyl)-1H-imidazol-1-yl]biphenyl-3-yl}-1H-1,2,3-triazole |
| 35 | 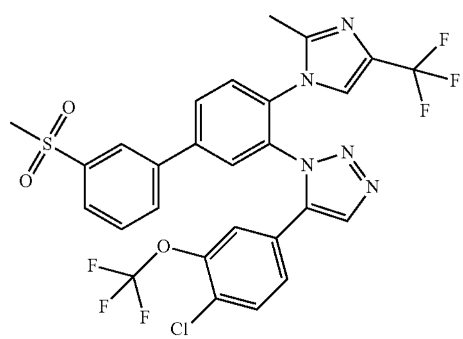 [SMILES: Cc1nc(C(F)(F)F)cn1-c1ccc(-c2cccc(S(C)(=O)=O)c2)cc1-n1nncc1-c1ccc(Cl)c(OC(F)(F)F)c1] | 5-{4-chloro-3-[(trifluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole |
| 36 | 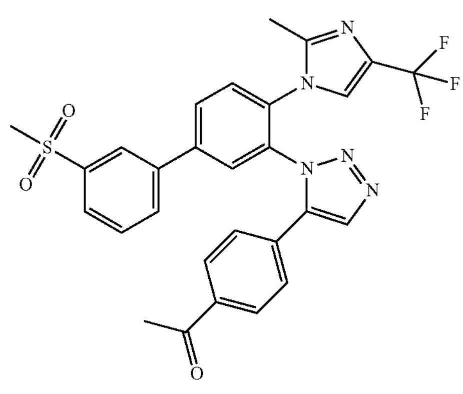 [SMILES: CC(=O)c1ccc(-c2cnnn2-c2cc(-c3cccc(S(C)(=O)=O)c3)ccc2-n2cc(C(F)(F)F)nc2C)cc1] | 1-[4-(1-{3'-(methylsulfonyl)-4-[2-methyl-4-(trifluoromethyl)-1H-imidazol-1-yl]biphenyl-3-yl}-1H-1,2,3-triazol-5-yl)phenyl]ethanone |

| Ex # | Structure | Name |
|---|---|---|
| 37 | 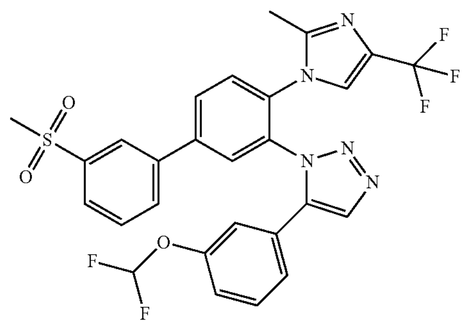 [SMILES: Cc1nc(C(F)(F)F)cn1-c1ccc(-c2cccc(S(C)(=O)=O)c2)cc1-n1nncc1-c1cccc(OC(F)F)c1] | 5-{3-[(difluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole |
| 39 | 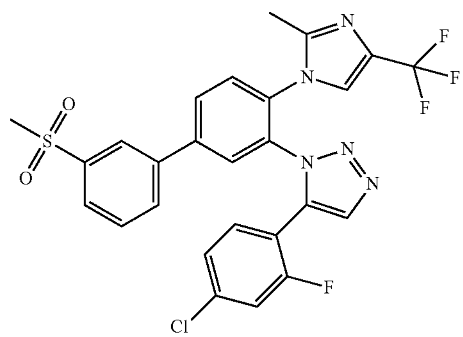 [SMILES: Cc1nc(C(F)(F)F)cn1-c1ccc(-c2cccc(S(C)(=O)=O)c2)cc1-n1nncc1-c1ccc(Cl)cc1F] | 5-(4-chloro-2-fluorophenyl)-1-{3'-(methylsulfonyl)-4-[2-methyl-4-(trifluoromethyl)-1H-imidazol-1-yl]biphenyl-3-yl}-1H-1,2,3-triazole |
| 40 | 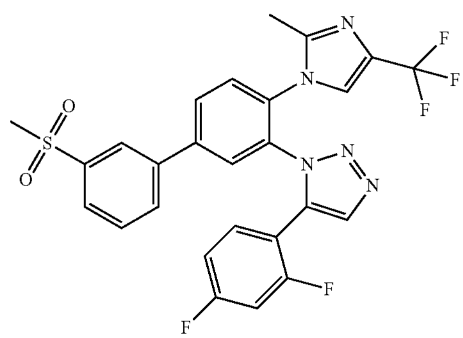 [SMILES: Cc1nc(C(F)(F)F)cn1-c1ccc(-c2cccc(S(C)(=O)=O)c2)cc1-n1nncc1-c1ccc(F)cc1F] | 5-(2,4-difluorophenyl)-1-{3'-(methylsulfonyl)-4-[2-methyl-4-(trifluoromethyl)-1H-imidazol-1-yl]biphenyl-3-yl}-1H-1,2,3-triazole |
| 41 | 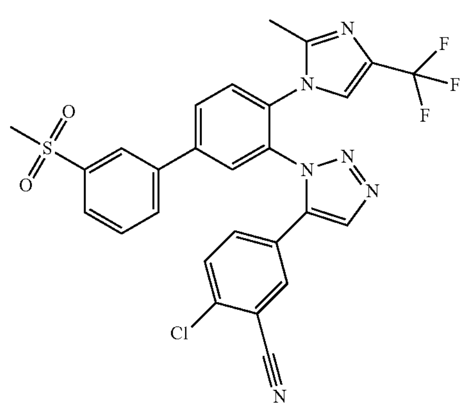 [SMILES: Cc1nc(C(F)(F)F)cn1-c1ccc(-c2cccc(S(C)(=O)=O)c2)cc1-n1nncc1-c1ccc(Cl)c(C#N)c1] | 2-chloro-5-(1-{3'-(methylsulfonyl)-4-[2-methyl-4-(trifluoromethyl)-1H-imidazol-1-yl]biphenyl-3-yl}-1H-1,2,3-triazol-5-yl)benzonitrile |

| Ex # | Structure | Name |
|---|---|---|
| 42 | 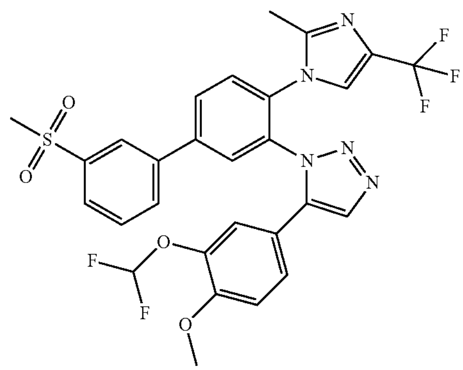 [SMILES: COc1ccc(-c2cnnn2-c2cc(-c3cccc(S(C)(=O)=O)c3)ccc2-n2cc(C(F)(F)F)nc2C)cc1OC(F)F] | 5-{3-[(difluoromethyl)oxy]-4-(methyloxy)phenyl}-1-{3'-(methylsulfonyl)-4-[2-methyl-4-(trifluoromethyl)-1H-imidazol-1-yl]biphenyl-3-yl}-1H-1,2,3-triazole |
| 43 | 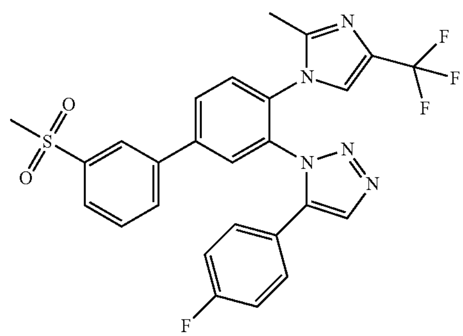 [SMILES: Cc1nc(C(F)(F)F)cn1-c1ccc(-c2cccc(S(C)(=O)=O)c2)cc1-n1nncc1-c1ccc(F)cc1] | 5-(4-fluorophenyl)-1-{3'-(methylsulfonyl)-4-[2-methyl-4-(trifluoromethyl)-1H-imidazol-1-yl]biphenyl-3-yl}-1H-1,2,3-triazole |
| 44 | 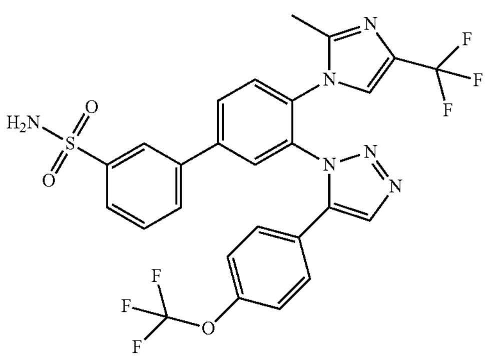 [SMILES: Cc1nc(C(F)(F)F)cn1-c1ccc(-c2cccc(S(N)(=O)=O)c2)cc1-n1nncc1-c1ccc(OC(F)(F)F)cc1] | 4'-[2-methyl-4-(trifluoromethyl)-1H-imidazol-1-yl]-3'-(5-{4-[(trifluoromethyl)oxy]phenyl}-1H-1,2,3-triazol-1-yl)biphenyl-3-sulfonamide |
| 45 | 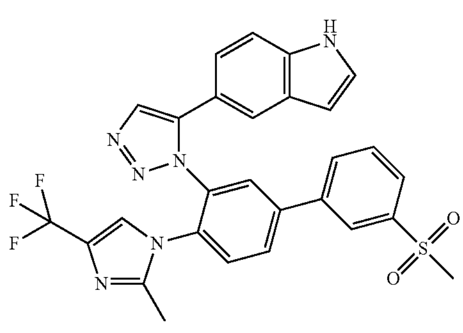 [SMILES: Cc1nc(C(F)(F)F)cn1-c1ccc(-c2cccc(S(C)(=O)=O)c2)cc1-n1nncc1-c1ccc2[nH]ccc2c1] | 5-(1-{3'-(methylsulfonyl)-4-[2-methyl-4-(trifluoromethyl)-1H-imidazol-1-yl]biphenyl-3-yl}-1H-1,2,3-triazol-5-yl)-1H-indole |

| Ex # | Structure | Name |
|---|---|---|
| 46 | 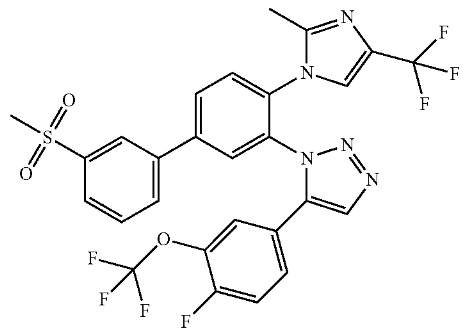 [SMILES: Cc1nc(C(F)(F)F)cn1-c1ccc(-c2cccc(S(C)(=O)=O)c2)cc1-n1nncc1-c1ccc(F)c(OC(F)(F)F)c1] | 5-{4-fluoro-3-[(trifluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole |
| 47 | 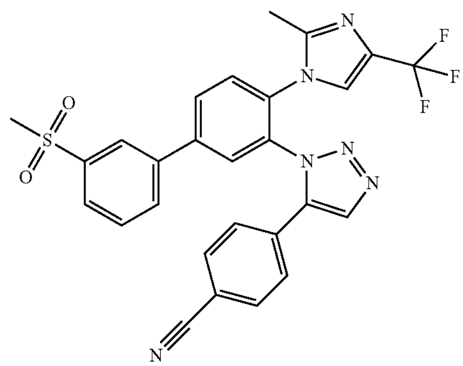 [SMILES: Cc1nc(C(F)(F)F)cn1-c1ccc(-c2cccc(S(C)(=O)=O)c2)cc1-n1nncc1-c1ccc(C#N)cc1] | 4-(1-{3'-(methylsulfonyl)-4-[2-methyl-4-(trifluoromethyl)-1H-imidazol-1-yl]biphenyl-3-yl}-1H-1,2,3-triazol-5-yl)benzonitrile |
| 48 | 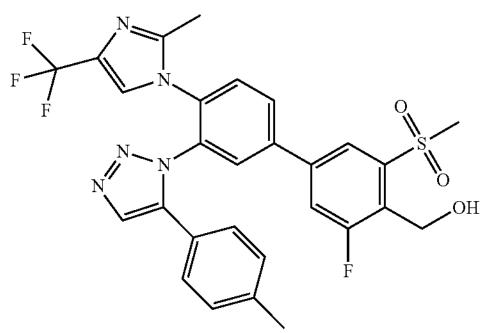 [SMILES: Cc1ccc(-c2cnnn2-c2cc(-c3cc(F)c(CO)c(S(C)(=O)=O)c3)ccc2-n2cc(C(F)(F)F)nc2C)cc1] | {3-fluoro-3'-[5-(4-methylphenyl)-1H-1,2,3-triazol-1-yl]-5-(methylsulfonyl)-4'-[2-methyl-4-(trifluoromethyl)-1H-imidazol-1-yl]biphenyl-4-yl}methanol |
| 49 | 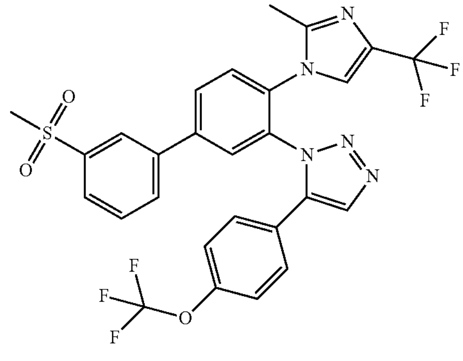 | 1-{3'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole |

| Ex # | Structure | Name |
|---|---|---|
| 50 | 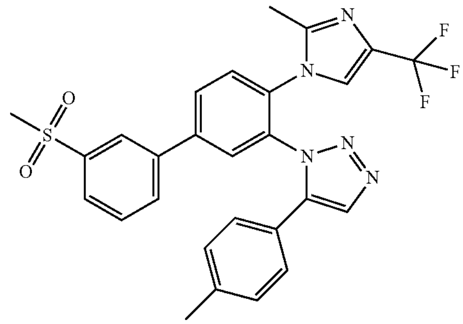 [SMILES: Cc1ccc(-c2cnnn2-c2cc(-c3cccc(S(C)(=O)=O)c3)ccc2-n2cc(C(F)(F)F)nc2C)cc1] | 5-(4-methylphenyl)-1-{3'-(methylsulfonyl)-4-[2-methyl-4-(trifluoromethyl)-1H-imidazol-1-yl]biphenyl-3-yl}-1H-1,2,3-triazole |
| 51 | 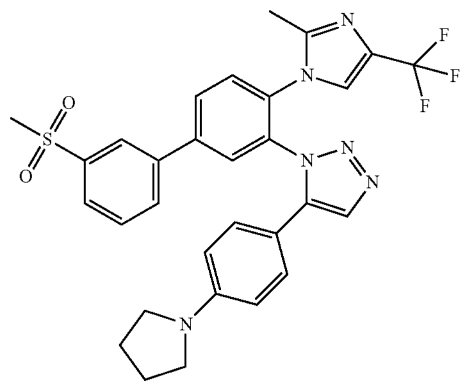 [SMILES: Cc1nc(C(F)(F)F)cn1-c1ccc(-c2cccc(S(C)(=O)=O)c2)cc1-n1nncc1-c1ccc(N2CCCC2)cc1] | 1-{3'-(methylsulfonyl)-4-[2-methyl-4-(trifluoromethyl)-1H-imidazol-1-yl]biphenyl-3-yl}-5-(4-pyrrolidin-1-ylphenyl)-1H-1,2,3-triazole |
| 52 | 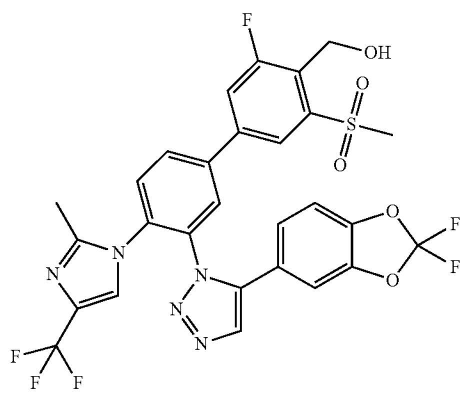 [SMILES: Cc1nc(C(F)(F)F)cn1-c1ccc(-c2cc(F)c(CO)c(S(C)(=O)=O)c2)cc1-n1nncc1-c1ccc2c(c1)OC(F)(F)O2] | {3'-[5-(2,2-difluoro-1,3-benzodioxol-5-yl)-1H-1,2,3-triazol-1-yl]-3-fluoro-5-(methylsulfonyl)-4'-[2-methyl-4-(trifluoromethyl)-1H-imidazol-1-yl]biphenyl-4-yl}methanol |
| 53 | 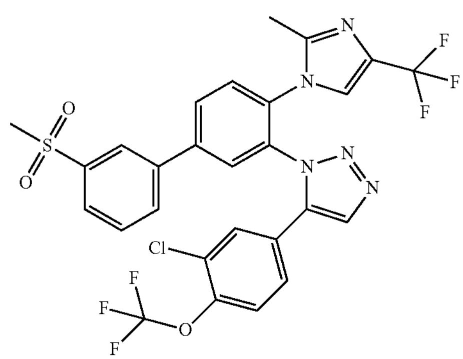 [SMILES: Cc1nc(C(F)(F)F)cn1-c1ccc(-c2cccc(S(C)(=O)=O)c2)cc1-n1nncc1-c1ccc(OC(F)(F)F)c(F)c1] | 5-{3-chloro-4-[(trifluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole |

| Ex # | Structure | Name |
|---|---|---|
| 54 | 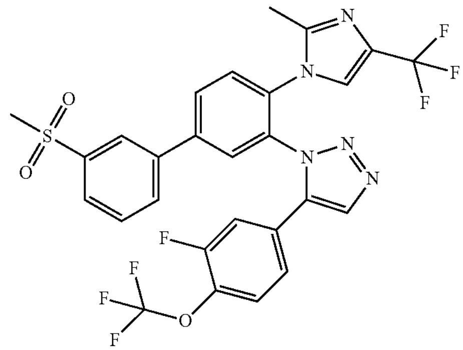 | 5-{3-fluoro-4-[(trifluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole |
| 55 | 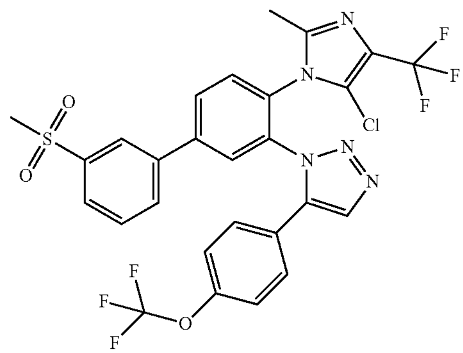 [SMILES: Cc1nc(C(F)(F)F)c(Cl)n1-c1ccc(-c2cccc(S(C)(=O)=O)c2)cc1-n1nncc1-c1ccc(OC(F)(F)F)cc1] | 1-{4-[5-chloro-2-methyl-4-(trifluoromethyl)-1H-imidazol-1-yl]-3'-(methylsulfonyl)biphenyl-3-yl}-5-{4-[(trifluoromethyl)oxy]phenyl}-1H-1,2,3-triazole |
| 56 | 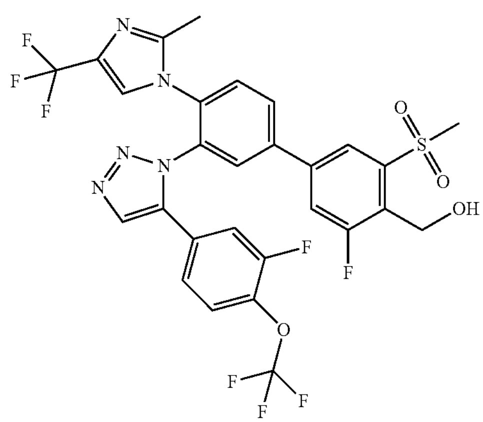 [SMILES: Cc1nc(C(F)(F)F)cn1-c1ccc(-c2cc(F)c(CO)c(S(C)(=O)=O)c2)cc1-n1nncc1-c1ccc(OC(F)(F)F)c(F)c1] | {3-fluoro-3'-(5-{3-fluoro-4-[(trifluoromethyl)oxy]phenyl}-1H-1,2,3-triazol-1-yl)-5-(methylsulfonyl)-4'-[2-methyl-4-(trifluoromethyl)-1H-imidazol-1-yl]biphenyl-4-yl}methanol |
| 57 | 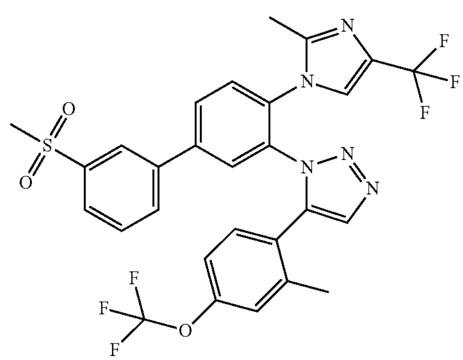 [SMILES: Cc1cc(OC(F)(F)F)ccc1-c1cnnn1-c1cc(-c2cccc(S(C)(=O)=O)c2)ccc1-n1cc(C(F)(F)F)nc1C] | 1-{3'-(methylsulfonyl)-4-[2-methyl-4-(trifluoromethyl)-1H-imidazol-1-yl]biphenyl-3-yl}-5-{2-methyl-4-(trifluoromethyl)oxy]phenyl}-1H-1,2,3-triazole |

| Ex # | Structure | Name |
|---|---|---|
| 58 | 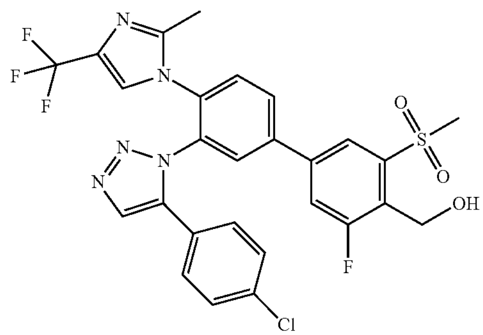 [SMILES: Cc1nc(C(F)(F)F)cn1-c1ccc(-c2cc(F)c(CO)c(S(C)(=O)=O)c2)cc1-n1nncc1-c1ccc(Cl)cc1] | {3'-[5-(4-chlorophenyl)-1H-1,2,3-triazol-1-yl]-3-fluoro-5-(methylsulfonyl)-4'-[2-methyl-4-(trifluoromethyl)-1H-imidazol-1-yl]biphenyl-4-yl}methanol |
| 59 | 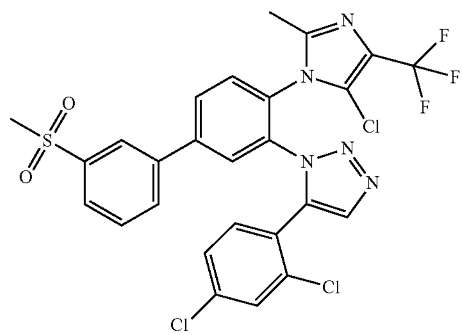 [SMILES: Cc1nc(C(F)(F)F)c(Cl)n1-c1ccc(-c2cccc(S(C)(=O)=O)c2)cc1-n1nncc1-c1ccc(Cl)cc1Cl] | 1-{4-[5-chloro-2-methyl-4-(trifluoromethyl)-1H-imidazol-1-yl]-3'-(methylsulfonyl)biphenyl-3-yl}-5-(2,4-dichlorophenyl)-1H-1,2,3-triazole |
| 60 | 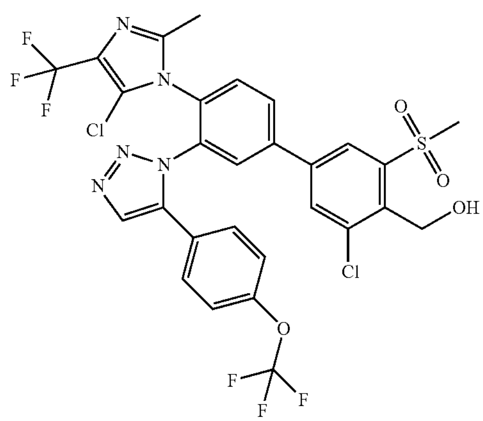 [SMILES: Cc1nc(C(F)(F)F)c(Cl)n1-c1ccc(-c2cc(Cl)c(CO)c(S(C)(=O)=O)c2)cc1-n1nncc1-c1ccc(OC(F)(F)F)cc1] | {3-chloro-4'-[5-chloro-2-methyl-4-(trifluoromethyl)-1H-imidazol-1-yl]-5-(methylsulfonyl)-3'-(5-{4-[(trifluoromethyl)oxy]phenyl}-1H-1,2,3-triazol-1-yl)biphenyl-4-yl}methanol |
| 61 | 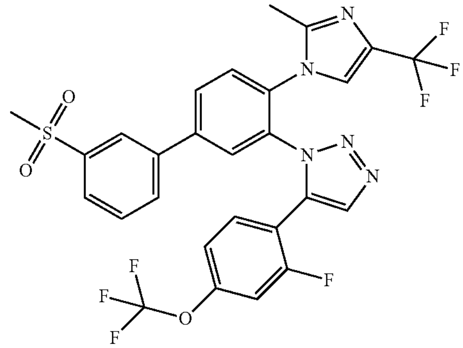 | 5-{2-fluoro-4-[(trifluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole |

| Ex # | Structure | Name |
|---|---|---|
| 62 | 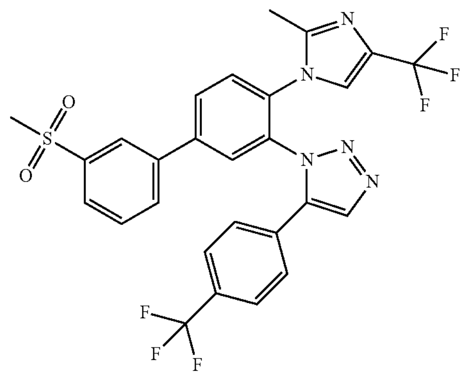 [SMILES: Cc1nc(C(F)(F)F)cn1-c1ccc(-c2cccc(S(C)(=O)=O)c2)cc1-n1nncc1-c1ccc(C(F)(F)F)cc1] | 1-{3'-(methylsulfonyl)-4-[2-methyl-4-(trifluoromethyl)-1H-imidazol-1-yl]biphenyl-3-yl}-5-[4-(trifluoromethyl)phenyl]-1H-1,2,3-triazole |
| 63 | 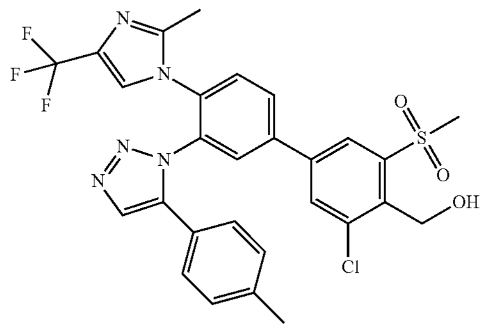 | {3-chloro-3'-[5-(4-methylphenyl)-1H-1,2,3-triazol-1-yl]-5-(methylsulfonyl)-4'-[2-methyl-4-(trifluoromethyl)-1H-imidazol-1-yl]biphenyl-4-yl}methanol |
| 64 | 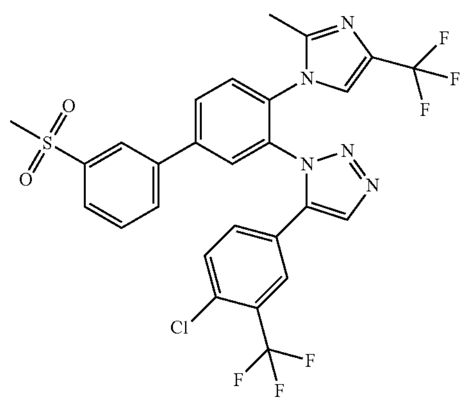 [SMILES: Cc1nc(C(F)(F)F)cn1-c1ccc(-c2cccc(S(C)(=O)=O)c2)cc1-n1nncc1-c1ccc(Cl)c(C(F)(F)F)c1] | 5-[4-chloro-3-(trifluoromethyl)phenyl]-1-{3'-(methylsulfonyl)-4-[2-methyl-4-(trifluoromethyl)-1H-imidazol-1-yl]biphenyl-3-yl}-1H-1,2,3-triazole |
| 65 | 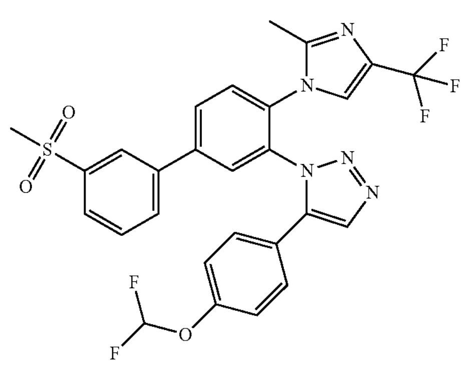 [SMILES: Cc1nc(C(F)(F)F)cn1-c1ccc(-c2cccc(S(C)(=O)=O)c2)cc1-n1nncc1-c1ccc(OC(F)F)cc1] | 5-{4-[(difluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole |

| Ex # | Structure | Name |
|---|---|---|
| 66 | 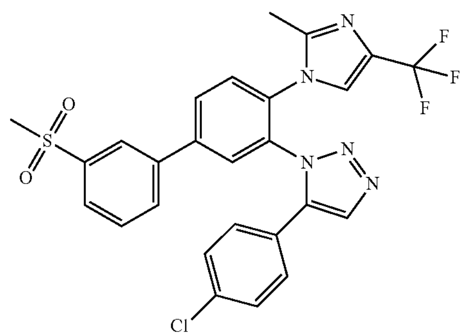 [SMILES: Cc1nc(C(F)(F)F)cn1-c1ccc(-c2cccc(S(C)(=O)=O)c2)cc1-n1nncc1-c1ccc(Cl)cc1] | 5-(4-chlorophenyl)-1-{3'-(methylsulfonyl)-4-[2-methyl-4-(trifluoromethyl)-1H-imidazol-1-yl]biphenyl-3-yl}-1H-1,2,3-triazole |
| 67 | 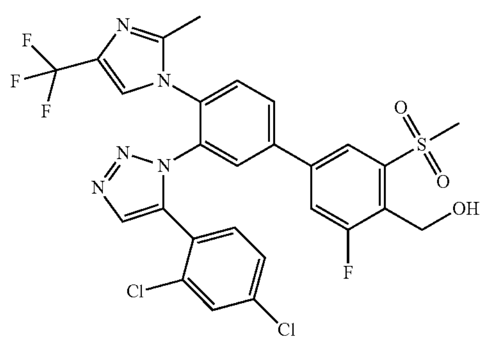 [SMILES: Cc1nc(C(F)(F)F)cn1-c1ccc(-c2cc(F)c(CO)c(S(C)(=O)=O)c2)cc1-n1nncc1-c1ccc(Cl)cc1Cl] | {3'-[5-(2,4-dichlorophenyl)-1H-1,2,3-triazol-1-yl]-3-fluoro-5-(methylsulfonyl)-4'-[2-methyl-4-(trifluoromethyl)-1H-imidazol-1-yl]biphenyl-4-yl}methanol |
| 68 | 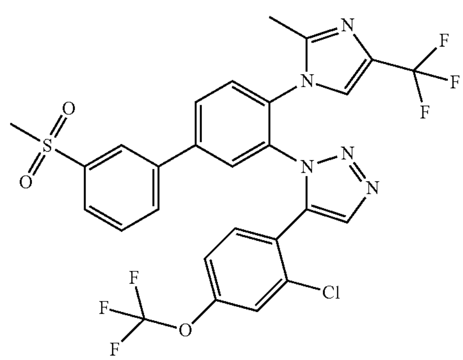 | 5-{2-chloro-4-[(trifluoromethyl)oxy]phenyl}-1-{3'-(methylsulfonyl)-4-[2-methyl-4-(trifluoromethyl)-1H-imidazol-1-yl]biphenyl-3-yl}-1H-1,2,3-triazole |
| 69 | 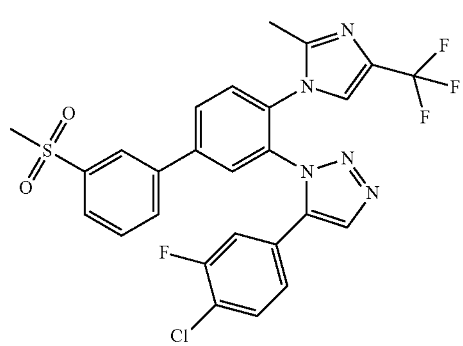 [SMILES: Cc1nc(C(F)(F)F)cn1-c1ccc(-c2cccc(S(C)(=O)=O)c2)cc1-n1nncc1-c1ccc(Cl)c(F)c1] | 5-(4-chloro-3-fluorophenyl)-1-{3'-(methylsulfonyl)-4-[2-methyl-4-(trifluoromethyl)-1H-imidazol-1-yl]biphenyl-3-yl}-1H-1,2,3-triazole |

| Ex # | Structure | Name |
|---|---|---|
| 70 | 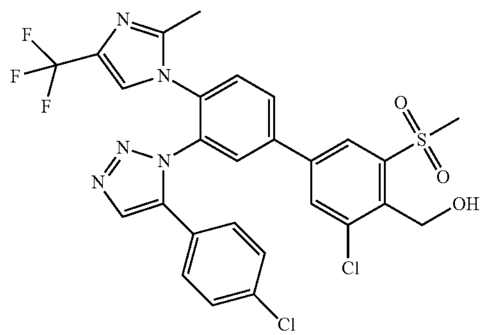 | {3-chloro-3'-[5-(4-chlorophenyl)-1H-1,2,3-triazol-1-yl]-5-(methylsulfonyl)-4'-[2-methyl-4-(trifluoromethyl)-1H-imidazol-1-yl]biphenyl-4-yl}methanol |
| 71 | 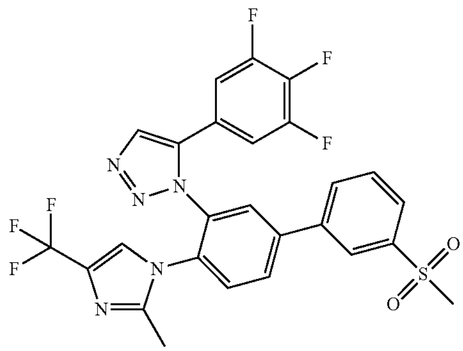 [SMILES: Cc1nc(C(F)(F)F)cn1-c1ccc(-c2cccc(S(C)(=O)=O)c2)cc1-n1nncc1-c1cc(F)c(F)c(F)c1] | 1-{3'-(methylsulfonyl)-4-[2-methyl-4-(trifluoromethyl)-1H-imidazol-1-yl]biphenyl-3-yl}-5-(3,4,5-trifluorophenyl)-1H-1,2,3-triazole |
| 72 | 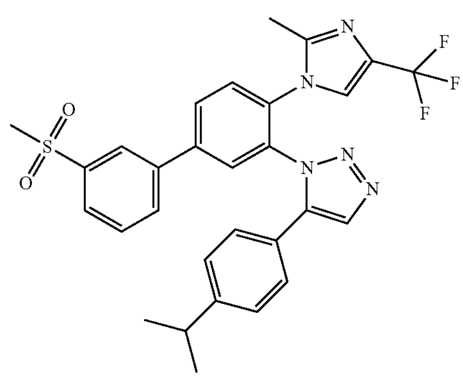 [SMILES: Cc1nc(C(F)(F)F)cn1-c1ccc(-c2cccc(S(C)(=O)=O)c2)cc1-n1nncc1-c1ccc(C(C)C)cc1] | 5-[4-(1-methylethyl)phenyl]-1-{3'-(methylsulfonyl)-4-[2-methyl-4-(trifluoromethyl)-1H-imidazol-1-yl]biphenyl-3-yl}-1H-1,2,3-triazole |
| 73 | 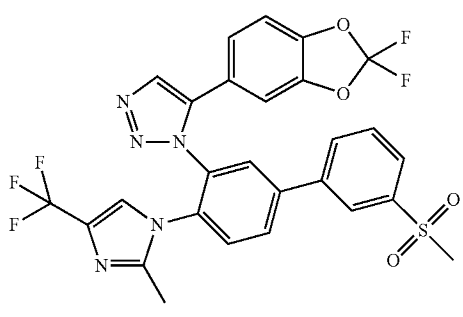 [SMILES: Cc1nc(C(F)(F)F)cn1-c1ccc(-c2cccc(S(C)(=O)=O)c2)cc1-n1nncc1-c1ccc2c(c1)OC(F)(F)O2] | 5-(2,2-difluoro-1,3-benzodioxol-5-yl)-1-{3'-(methylsulfonyl)-4-[2-methyl-4-(trifluoromethyl)-1H-imidazol-1-yl]biphenyl-3-yl}-1H-1,2,3-triazole |

| Ex # | Structure | Name |
|---|---|---|
| 74 | 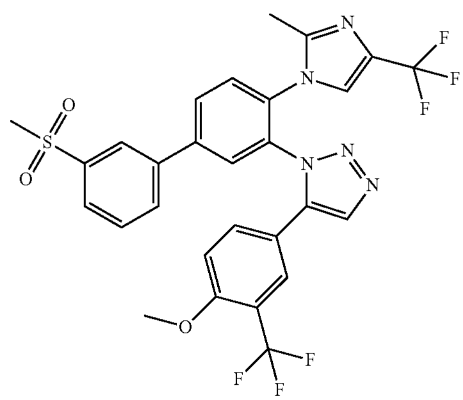 [SMILES: COc1ccc(-c2cnnn2-c2cc(-c3cccc(S(C)(=O)=O)c3)ccc2-n2cc(C(F)(F)F)nc2C)cc1C(F)(F)F] | 5-[4-(methyloxy)-3-(trifluoromethyl)phenyl]-1-{3'-(methylsulfonyl)-4-[2-methyl-4-(trifluoromethyl)-1H-imidazol-1-yl]biphenyl-3-yl}-1H-1,2,3-triazole |
| 75 | 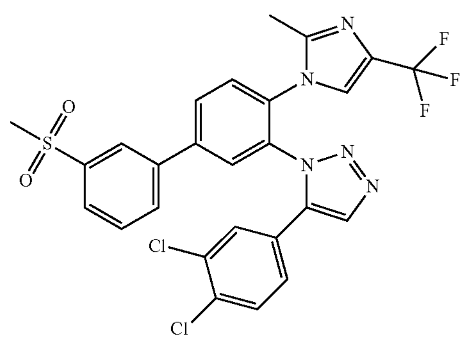 [SMILES: Cc1nc(C(F)(F)F)cn1-c1ccc(-c2cccc(S(C)(=O)=O)c2)cc1-n1nncc1-c1ccc(Cl)c(Cl)c1] | 5-(3,4-dichlorophenyl)-1-{3'-(methylsulfonyl)-4-[2-methyl-4-(trifluoromethyl)-1H-imidazol-1-yl]biphenyl-3-yl}-1H-1,2,3-triazole |
| 76 | 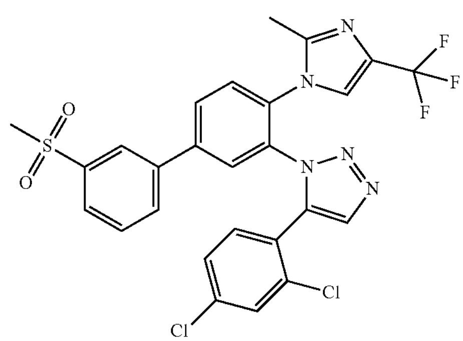 [SMILES: Cc1nc(C(F)(F)F)cn1-c1ccc(-c2cccc(S(C)(=O)=O)c2)cc1-n1nncc1-c1ccc(Cl)cc1Cl] | 5-(2,4-dichlorophenyl)-1-{3'-(methylsulfonyl)-4-[2-methyl-4-(trifluoromethyl)-1H-imidazol-1-yl]biphenyl-3-yl}-1H-1,2,3-triazole |
| 77 | 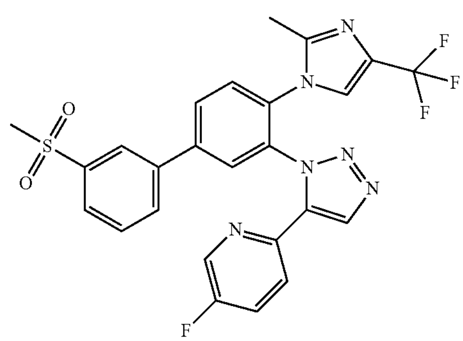 [SMILES: Cc1nc(C(F)(F)F)cn1-c1ccc(-c2cccc(S(C)(=O)=O)c2)cc1-n1nncc1-c1ccc(F)cn1] | 5-fluoro-2-(1-{3'-(methylsulfonyl)-4-[2-methyl-4-(trifluoromethyl)-1H-imidazol-1-yl]biphenyl-3-yl}-1H-1,2,3-triazol-5-yl)pyridine |

| Ex # | Structure | Name |
|---|---|---|
| 78 | 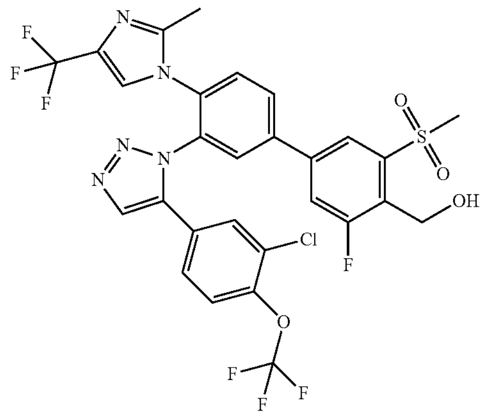 [SMILES: Cc1nc(C(F)(F)F)cn1-c1ccc(-c2cc(F)c(CO)c(S(C)(=O)=O)c2)cc1-n1nncc1-c1ccc(OC(F)(F)F)c(Cl)c1] | {3'-(5-{3-chloro-4-(trifluoromethyl)oxy]phenyl}-1H-1,2,3-triazol-1-yl)-3-fluoro-5-(methylsulfonyl)-4'-[2-methyl-4-(trifluoromethyl)-1H-imidazol-1-yl]biphenyl-4-yl}methanol |
| 79 | 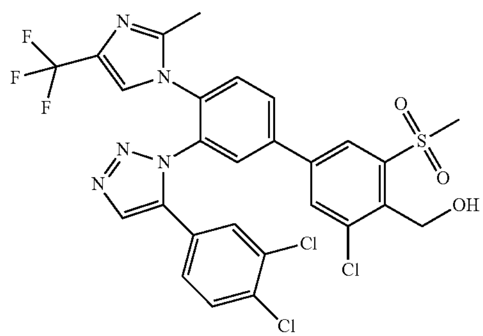 | {3-chloro-3'-[5-(3,4-dichlorophenyl)-1H-1,2,3-triazol-1-yl]-5-(methylsulfonyl)-4'-[2-methyl-4-(trifluoromethyl)-1H-imidazol-1-yl]biphenyl-4-yl}methanol |
| 80 | 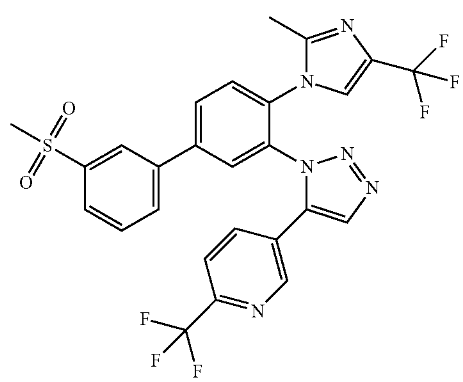 [SMILES: Cc1nc(C(F)(F)F)cn1-c1ccc(-c2cccc(S(C)(=O)=O)c2)cc1-n1nncc1-c1ccc(C(F)(F)F)nc1] | 5-(1-{3'-(methylsulfonyl)-4-[2-methyl-4-(trifluoromethyl)-1H-imidazol-1-yl]biphenyl-3-yl}-1H-1,2,3-triazol-5-yl)-2-(trifluoromethyl)pyridine |
| 81 | 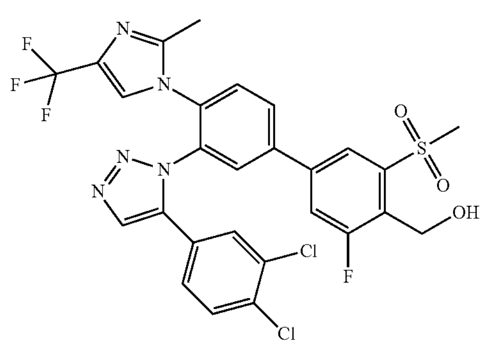 [SMILES: Cc1nc(C(F)(F)F)cn1-c1ccc(-c2cc(F)c(CO)c(S(C)(=O)=O)c2)cc1-n1nncc1-c1ccc(Cl)c(Cl)c1] | {3'-[5-(3,4-dichlorophenyl)-1H-1,2,3-triazol-1-yl]-3-fluoro-5-(methylsulfonyl)-4'-[2-methyl-4-(trifluoromethyl)-1H-imidazol-1-yl]biphenyl-4-yl}methanol |

| Ex # | Structure | Name |
|---|---|---|
| 82 | 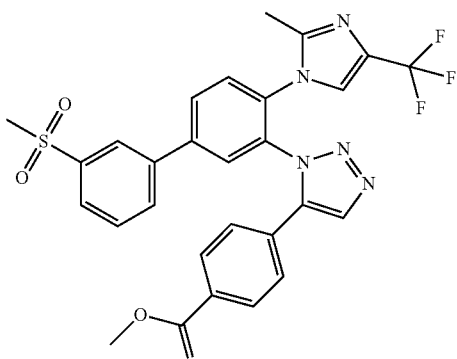 | methyl 4-(1-{3'-(methylsulfonyl)-4-[2-methyl-4-(trifluoromethyl)-1H-imidazol-1-yl]biphenyl-3-yl}-1H-1,2,3-triazol-5-yl)benzoate |
| 83 | 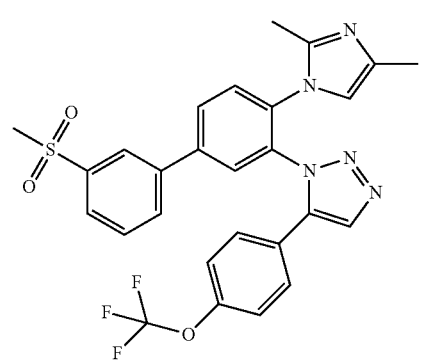 | 1-[4-(2,4-dimethyl-1H-imidazol-1-yl)-3'-(methylsulfonyl)biphenyl-3-yl]-5-{4-[(trifluoromethyl)oxy]phenyl}-1H-1,2,3-triazole |
| 84 | 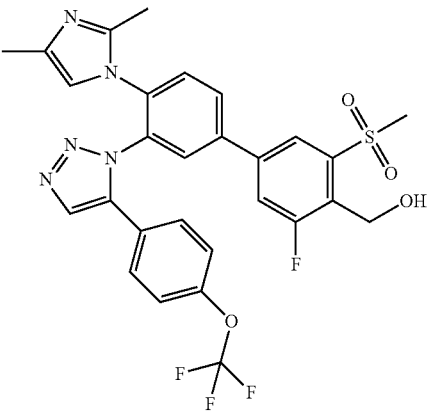 | [4'-(2,4-dimethyl-1H-imidazol-1-yl)-3-fluoro-5-(methylsulfonyl)-3'-(5-{4-[(trifluoromethyl)oxy]phenyl}-1H-1,2,3-triazol-1-yl)biphenyl-4-yl]methanol |
| 85 | 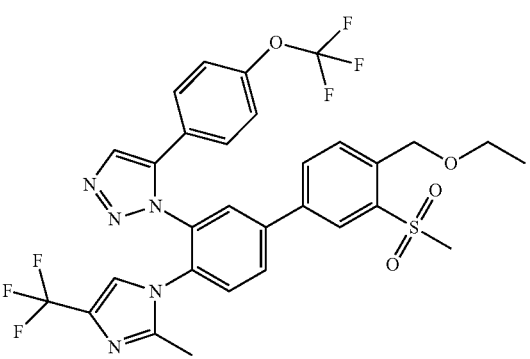 [SMILES: CCOCc1ccc(-c2ccc(-n3cc(C(F)(F)F)nc3C)c(-n3nncc3-c3ccc(OC(F)(F)F)cc3)c2)cc1S(C)(=O)=O] | 1-{4'-[(ethyloxy)methyl]-3'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole |

| Ex # | Structure | Name |
|---|---|---|
| 86 | 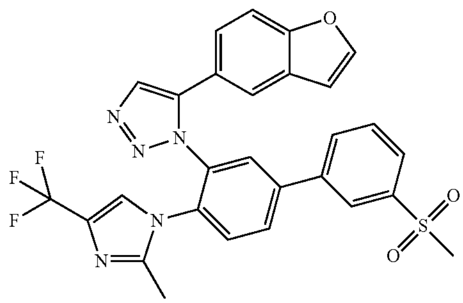 [SMILES: Cc1nc(C(F)(F)F)cn1-c1ccc(-c2cccc(S(C)(=O)=O)c2)cc1-n1nncc1-c1ccc2occc2c1] | 5-(1-benzofuran-5-yl)-1-{3'-(methylsulfonyl)-4-[2-methyl-4-(trifluoromethyl)-1H-imidazol-1-yl]biphenyl-3-yl}-1H-1,2,3-triazole |
| 87 | 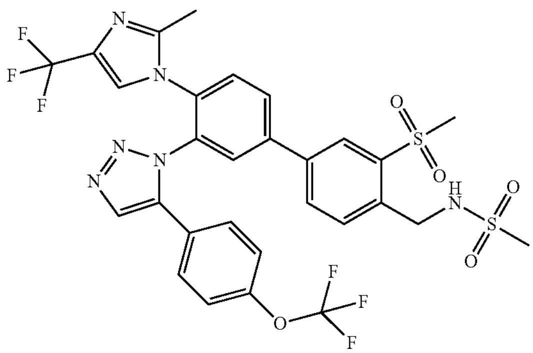 [SMILES: Cc1nc(C(F)(F)F)cn1-c1ccc(-c2ccc(CNS(C)(=O)=O)c(S(C)(=O)=O)c2)cc1-n1nncc1-c1ccc(OC(F)(F)F)cc1] | N-{[3-(methylsulfonyl)-4'-[2-methyl-4-(trifluoromethyl)-1H-imidazol-1-yl]-3'-(5-{4-[(trifluoromethyl)oxy]pheny}-1H-1,2,3-triazol-1-yl)biphenyl-4-yl]methyl}methanesulfonamide |
| 88 | 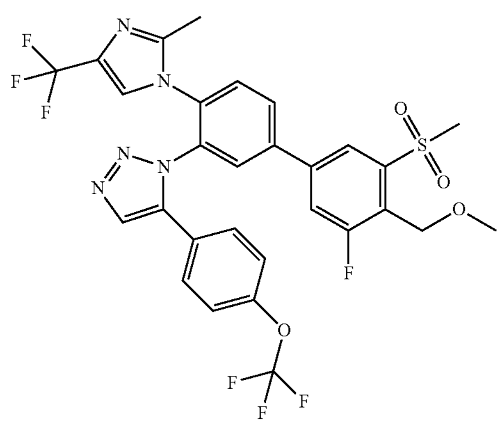 [SMILES: COCc1c(F)cc(-c2ccc(-n3cc(C(F)(F)F)nc3C)c(-n3nncc3-c3ccc(OC(F)(F)F)cc3)c2)cc1S(C)(=O)=O] | 1-{3'-fluoro-4'-[(methyloxy)methyl]-5'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole |
| 89 | 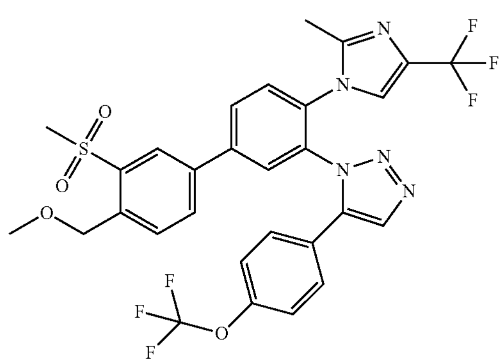 [SMILES: COCc1ccc(-c2ccc(-n3cc(C(F)(F)F)nc3C)c(-n3nncc3-c3ccc(OC(F)(F)F)cc3)c2)cc1S(C)(=O)=O] | 1-{4'-[(methyloxy)methyl]-3'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole |

| Ex # | Structure | Name |
|---|---|---|
| 90 | 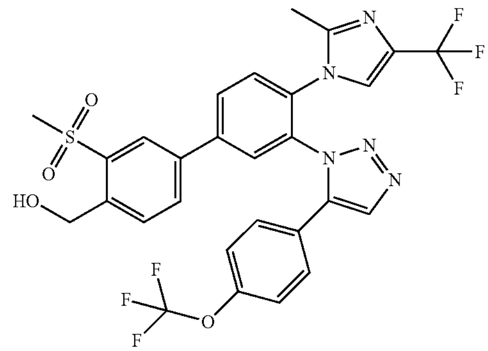 [SMILES: Cc1nc(C(F)(F)F)cn1-c1ccc(-c2ccc(CO)c(S(C)(=O)=O)c2)cc1-n1nncc1-c1ccc(OC(F)(F)F)cc1] | [3-(methylsulfonyl)-4'-[2-methyl-4-(trifluoromethyl)-1H-imidazol-1-yl]-3'-(5-{4-[(trifluoromethyl)oxy]phenyl}-1H-1,2,3-triazol-1-yl)biphenyl-4-yl]methanol |
| 91 | 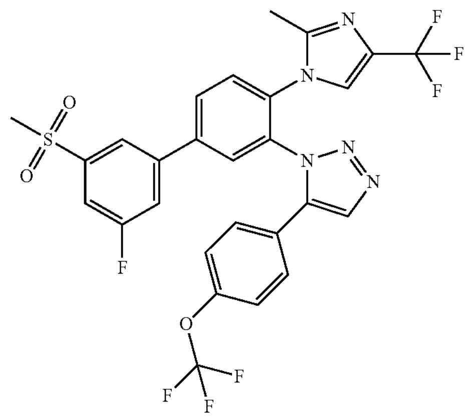 [SMILES: Cc1nc(C(F)(F)F)cn1-c1ccc(-c2cc(F)cc(S(C)(=O)=O)c2)cc1-n1nncc1-c1ccc(OC(F)(F)F)cc1] | 1-{3'-fluoro-5'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole |
| 92 | 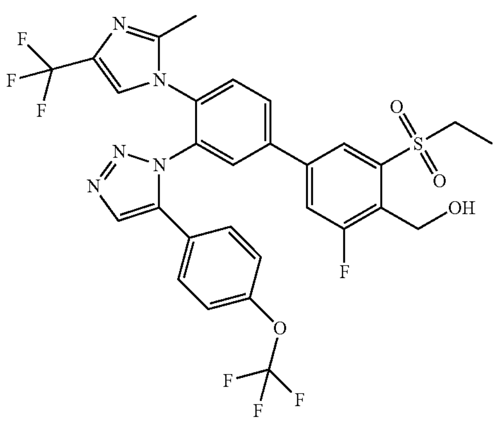 [SMILES: CCS(=O)(=O)c1cc(-c2ccc(-n3cc(C(F)(F)F)nc3C)c(-n3nncc3-c3ccc(OC(F)(F)F)cc3)c2)cc(F)c1CO] | [3-(ethylsulfonyl)-5-fluoro-4'-[2-methyl-4-(trifluoromethyl)-1H-imidazol-1-yl]-3'-(5-{4-[(trifluoromethyl)oxy]phenyl}-1H-1,2,3-triazol-1-yl)biphenyl-4-yl]methanol |
| 93 | 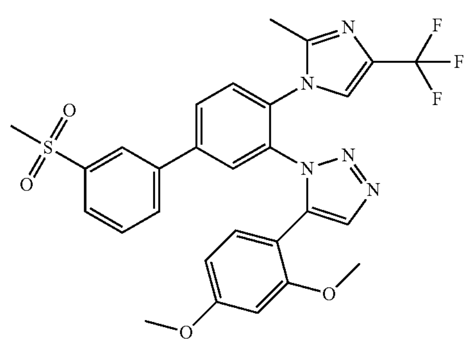 [SMILES: COc1ccc(-c2cnnn2-c2cc(-c3cccc(S(C)(=O)=O)c3)ccc2-n2cc(C(F)(F)F)nc2C)c(OC)c1] | 5-[2,4-bis(methyloxy)phenyl]-1-{3'-(methylsulfonyl)-4-[2-methyl-4-(trifluoromethyl)-1H-imidazol-1-yl]biphenyl-3-yl}-1H-1,2,3-triazole |

| Ex # | Structure | Name |
|---|---|---|
| 94 | 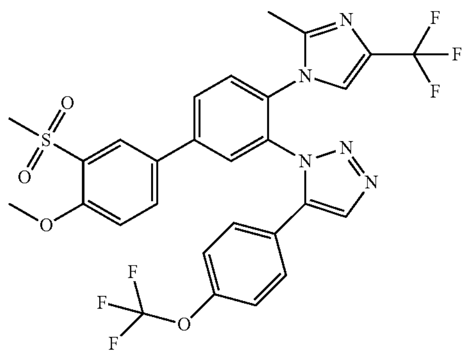 [SMILES: COc1ccc(-c2ccc(-n3cc(C(F)(F)F)nc3C)c(-n3nncc3-c3ccc(OC(F)(F)F)cc3)c2)cc1S(C)(=O)=O] | 1-{4'-(methyloxy)-3'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole |
| 95 | 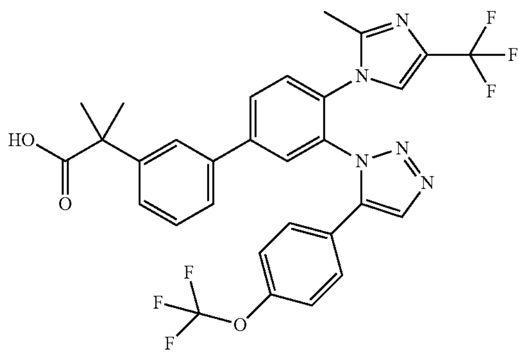 [SMILES: Cc1nc(C(F)(F)F)cn1-c1ccc(-c2cccc(C(C)(C)C(=O)O)c2)cc1-n1nncc1-c1ccc(OC(F)(F)F)cc1] | 2-methyl-2-{4'-[2-methyl-4-(trifluoromethyl)-1H-imidazol-1-yl]-3'-(5-{4-[(trifluoromethyl)oxy]phenyl}-1H-1,2,3-triazol-1-yl)biphenyl-3-yl}propanoic acid |
| 98 | 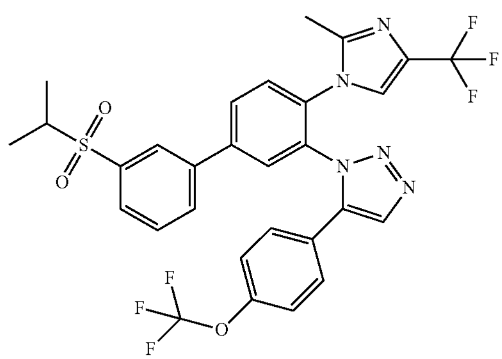 [SMILES: Cc1nc(C(F)(F)F)cn1-c1ccc(-c2cccc(S(=O)(=O)C(C)C)c2)cc1-n1nncc1-c1ccc(OC(F)(F)F)cc1] | 1-{3'-[(1-methylethyl)sulfonyl]-4-[2-methyl-4-(trifluoromethyl)-1H-imidazol-1-yl]biphenyl-3-yl}-5-{4-[(trifluoromethyl)oxy]phenyl}-1H-1,2,3-triazole |
| 99 | 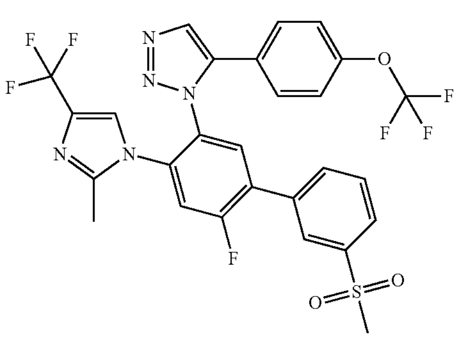 [SMILES: Cc1nc(C(F)(F)F)cn1-c1cc(F)c(-c2cccc(S(C)(=O)=O)c2)cc1-n1nncc1-c1ccc(OC(F)(F)F)cc1] | 1-{6-fluoro-3'-(methylsulfonyl)-4-[2-methyl-4-(trifluoromethyl)-1H-imidazol-1-yl]biphenyl-3-yl}-5-{4-(trifluoromethyl)oxy]phenyl}-1H-1,2,3-triazole |

-continued

| Ex # | Structure | Name |
|---|---|---|
| 100 | 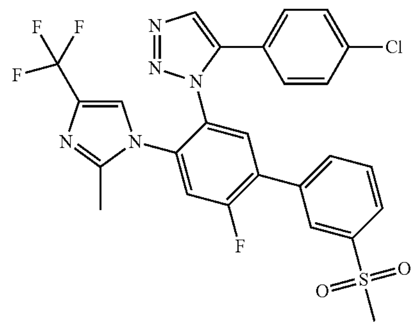 [SMILES: Cc1nc(C(F)(F)F)cn1-c1cc(F)c(-c2cccc(S(C)(=O)=O)c2)cc1-n1nncc1-c1ccc(Cl)cc1] | 5-(4-chlorophenyl)-1-{6-fluoro-3'-(methylsulfonyl)-4-[2-methyl-4-(trifluoromethyl)-1H-imidazol-1-yl]biphenyl-3-yl}-1H-1,2,3-triazole |
| 101 | 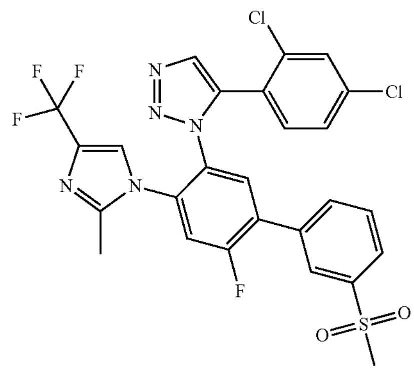 [SMILES: Cc1nc(C(F)(F)F)cn1-c1cc(F)c(-c2cccc(S(C)(=O)=O)c2)cc1-n1nncc1-c1ccc(Cl)cc1Cl] | 5-(2,4-dichlorophenyl)-1-{6-fluoro-3'-(methylsulfonyl)-4-[2-methyl-4-(trifluoromethyl)-1H-imidazol-1-yl]biphenyl-3-yl}-1H-1,2,3-triazole |
| 102 | 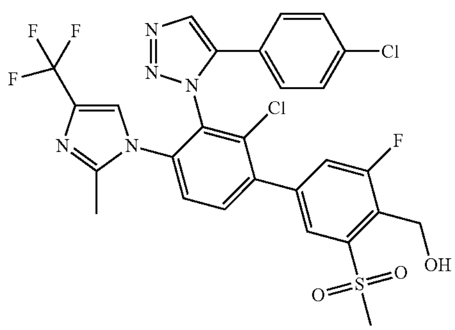 [SMILES: Cc1nc(C(F)(F)F)cn1-c1ccc(-c2cc(F)c(CO)c(S(C)(=O)=O)c2)c(Cl)c1-n1nncc1-c1ccc(Cl)cc1] | {2'-chloro-3'-[5-(4-chlorophenyl)-1H-1,2,3-triazol-1-yl]-3-fluoro-5-(methylsulfonyl)-4'-[2-methyl-4-(trifluoromethyl)-1H-imidazol-1-yl]biphenyl-4-yl}methanol |
| 103 | 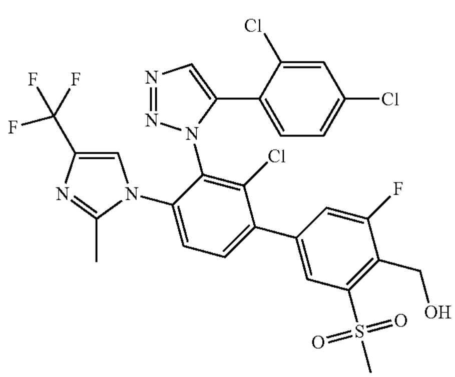 [SMILES: Cc1nc(C(F)(F)F)cn1-c1ccc(-c2cc(F)c(CO)c(S(C)(=O)=O)c2)c(Cl)c1-n1nncc1-c1ccc(Cl)cc1Cl] | {2'-chloro-3'-[5-(2,4-dichlorophenyl)-1H-1,2,3-triazol-1-yl]-3-fluoro-5-(methylsulfonyl)-4'-[2-methyl-4-(trifluoromethyl)-1H-imidazol-1-yl]biphenyl-4-yl}methanol |

| Ex # | Structure | Name |
|---|---|---|
| 105 | 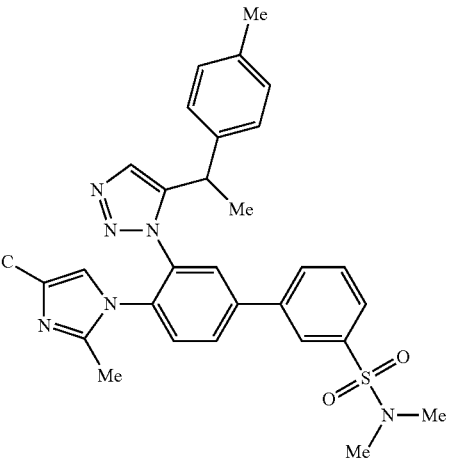 | N,N-dimethyl-3'-{5-[1-(4-methylphenyl)ethyl]-1H-1,2,3-triazol-1-yl}-4'-[2-methyl-4-(trifluoromethyl)-1H-imidazol-1-yl]biphenyl-3-sulfonamide |
| 106 | 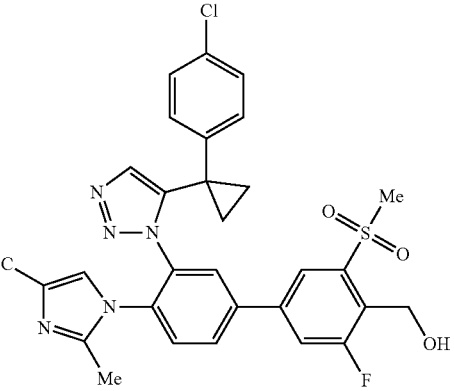 | (3'-{5-[1-(4-chlorophenyl)cyclopropyl]-1H-1,2,3-triazol-1-yl}-3-fluoro-5-(methylsulfonyl)-4'-[2-methyl-4-(trifluoromethyl)-1H-imidazol-1-yl]biphenyl-4-yl)methanol; |
| 107 | 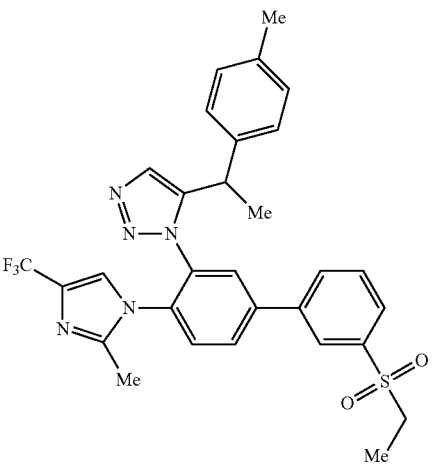 [SMILES: CCS(=O)(=O)c1cccc(-c2ccc(-n3cc(C(F)(F)F)nc3C)c(-n3nncc3C(C)c3ccc(C)cc3)c2)c1] | 1-{3'-(ethylsulfonyl)-4-[2-methyl-4-(trifluoromethyl)-1H-imidazol-1-yl]biphenyl-3-yl}-5-[1-(4-methylphenyl)ethyl]-1H-1,2,3-triazole |

-continued

| Ex # | Structure | Name |
|---|---|---|
| 108 | 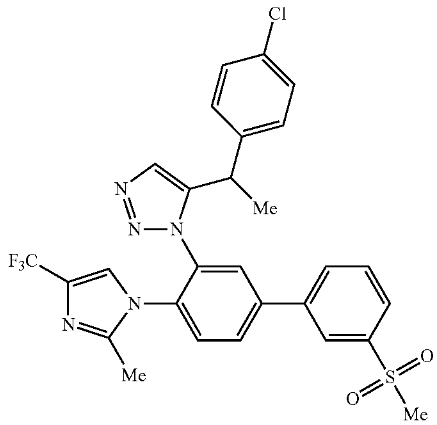 [SMILES: Cc1nc(C(F)(F)F)cn1-c1ccc(-c2cccc(S(C)(=O)=O)c2)cc1-n1nncc1C(C)c1ccc(Cl)cc1] | 5-[1-(4-chlorophenyl)ethyl]-1-{3'-(methylsulfonyl)-4-[2-methyl-4-(trifluoromethyl)-1H-imidazol-1-yl]biphenyl-3-yl}-1H-1,2,3-triazole |
| 109 | 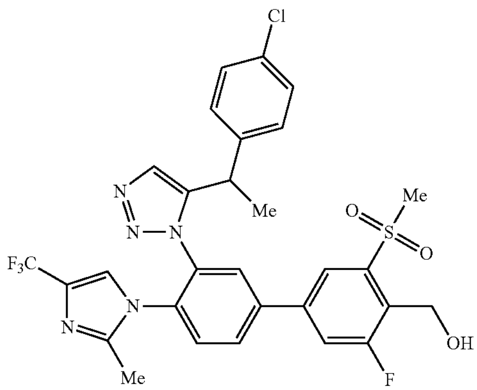 [SMILES: Cc1nc(C(F)(F)F)cn1-c1ccc(-c2cc(F)c(CO)c(S(C)(=O)=O)c2)cc1-n1nncc1C(C)c1ccc(Cl)cc1] | (3'-{5-[1-(4-chlorophenyl)ethyl]-1H-1,2,3-triazol-1-yl}-3-fluoro-5-(methylsulfonyl)-4'-[2-methyl-4-(trifluoromethyl)-1H-imidazol-1-yl]biphenyl-4-yl)methanol |
| 110 | 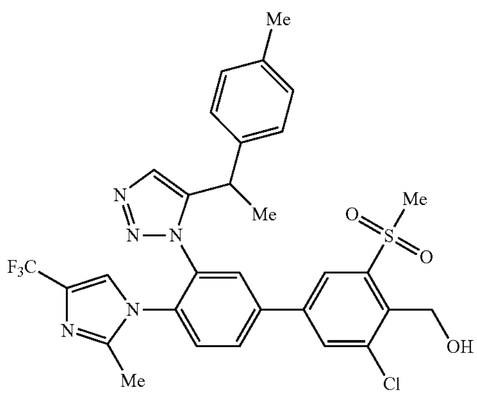 [SMILES: Cc1ccc(C(C)c2cnnn2-c2cc(-c3cc(Cl)c(CO)c(S(C)(=O)=O)c3)ccc2-n2cc(C(F)(F)F)nc2C)cc1] | (3-chloro-3'-{5-[1-(4-methylphenyl)ethyl]-1H-1,2,3-triazol-1-yl}-5-(methylsulfonyl)-4'-[2-methyl-4-(trifluoromethyl)-1H-imidazol-1-yl]biphenyl-4-yl)methanol |
| 111 | 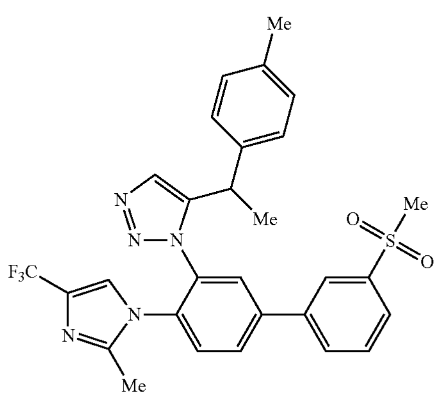 [SMILES: Cc1ccc(C(C)c2cnnn2-c2cc(-c3cccc(S(C)(=O)=O)c3)ccc2-n2cc(C(F)(F)F)nc2C)cc1] | 5-[1-(4-methylphenyl)ethyl]-1-{3'-methylsulfonyl)-4-[2-methyl-4-(trifluoromethyl)-1H-imidazol-1-yl]biphenyl-3-yl}-1H-1,2,3-triazole |

-continued

| Ex # | Structure | Name |
|---|---|---|
| 112 | 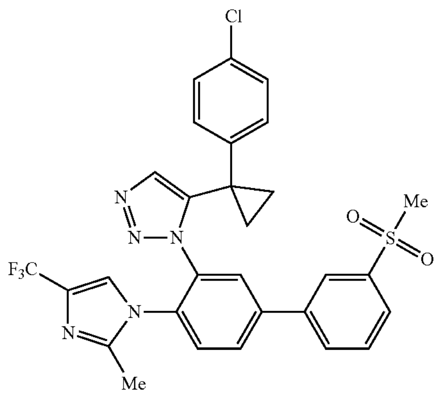 [SMILES: Cc1nc(C(F)(F)F)cn1-c1ccc(-c2cccc(S(C)(=O)=O)c2)cc1-n1nncc1C1(c2ccc(Cl)cc2)CC1] | 5-[1-(4-chlorophenyl)cyclopropyl]-1-{3'-(methylsulfonyl)-4-[2-methyl-4-(trifluoromethyl)-1H-imidazol-1-yl]biphenyl-3-yl}-1H-1,2,3-triazole |
| 113 | 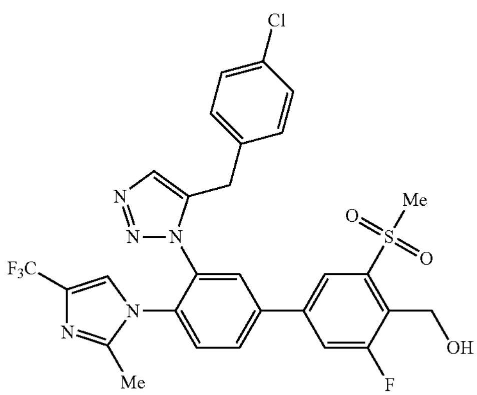 [SMILES: Cc1nc(C(F)(F)F)cn1-c1ccc(-c2cc(F)c(CO)c(S(C)(=O)=O)c2)cc1-n1nncc1Cc1ccc(Cl)cc1] | (3'-{5-[(4-chlorophenyl)methyl]-1H-1,2,3-triazol-1-yl}-3-fluoro-5-(methylsulfonyl)-4'-[2-methyl-4-(trifluoromethyl)-1H-imidazol-1-yl]biphenyl-4-yl)methanol |
| 114 | 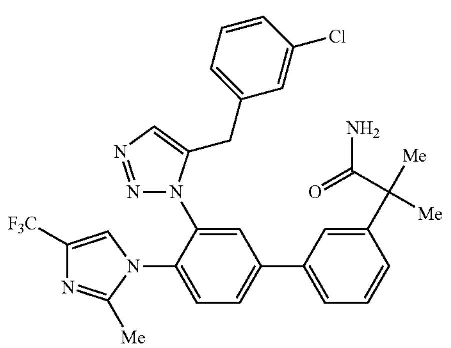 [SMILES: Cc1nc(C(F)(F)F)cn1-c1ccc(-c2cccc(C(C)(C)C(N)=O)c2)cc1-n1nncc1Cc1cccc(Cl)c1] | 2-(3'-{5-[(3-chlorophenyl)methyl]-1H-1,2,3-triazol-1-yl}-4'-[2-methyl-4-(trifluoromethyl)-1H-imidazol-1-yl]biphenyl-3-yl)-2-methylpropanamide |
| 115 | 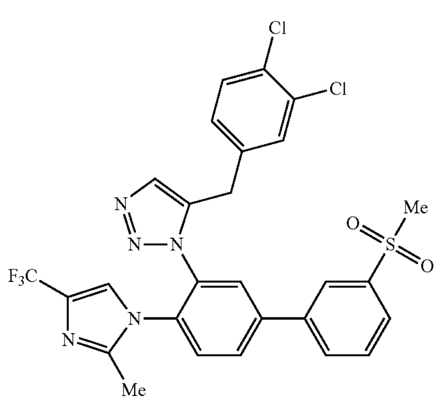 [SMILES: Cc1nc(C(F)(F)F)cn1-c1ccc(-c2cccc(S(C)(=O)=O)c2)cc1-n1nncc1Cc1ccc(Cl)c(Cl)c1] | 5-[(3,4-dichlorophenyl)methyl]-1-{3'-(methylsulfonyl)-4-[2-methyl-4-(trifluoromethyl)-1H-imidazol-1-yl]biphenyl-3-yl}-1H-1,2,3-triazole |

| Ex # | Structure | Name |
|---|---|---|
| 116 | 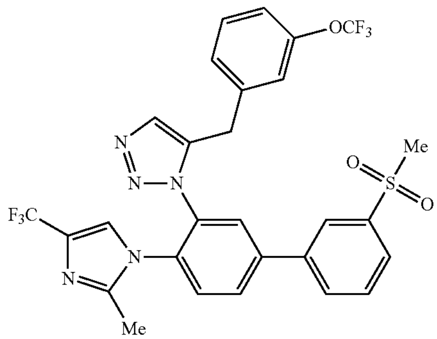 [SMILES: Cc1nc(C(F)(F)F)cn1-c1ccc(-c2cccc(S(C)(=O)=O)c2)cc1-n1nncc1Cc1cccc(OC(F)(F)F)c1] | 1-{3'-(methylsulfonyl)-4-[2-methyl-4-(trifluoromethyl)-1H-imidazol-1-yl]biphenyl-3-yl}-5-({3-[(trifluoromethyl)oxy]phenyl}methyl)-1H-1,2,3-triazole |
| 117 | 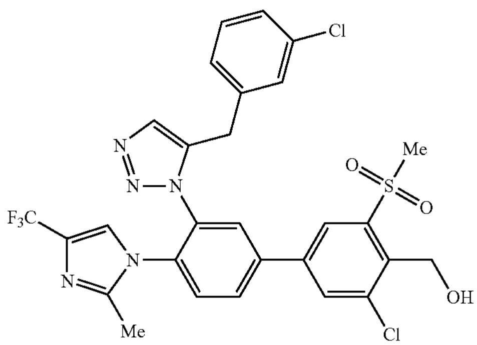 [SMILES: Cc1nc(C(F)(F)F)cn1-c1ccc(-c2cc(Cl)c(CO)c(S(C)(=O)=O)c2)cc1-n1nncc1Cc1cccc(Cl)c1] | (3-chloro-3'-{5-[(3-chlorophenyl)methyl]-1H-1,2,3-triazol-1-yl}-5-(methylsulfonyl)-4'-[2-methyl-4-(trifluoromethyl)-1H-imidazol-1-yl]biphenyl-4-yl)methanol |
| 118 | 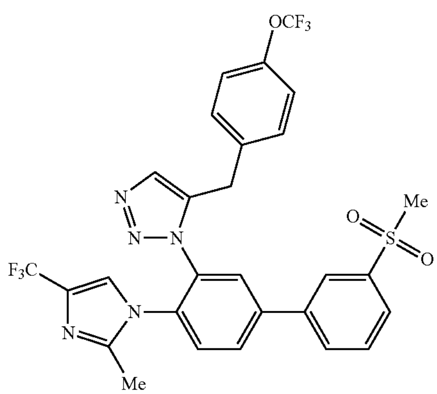 [SMILES: Cc1nc(C(F)(F)F)cn1-c1ccc(-c2cccc(S(C)(=O)=O)c2)cc1-n1nncc1Cc1ccc(OC(F)(F)F)cc1] | 1-{3'-(methylsulfonyl)-4-[2-methyl-4-(trifluoromethyl)-1H-imidazol-1-yl]biphenyl-3-yl}-5-({4-[(trifluoromethyl)oxy]phenyl}methyl)-1H-1,2,3-triazole |
| 119 | 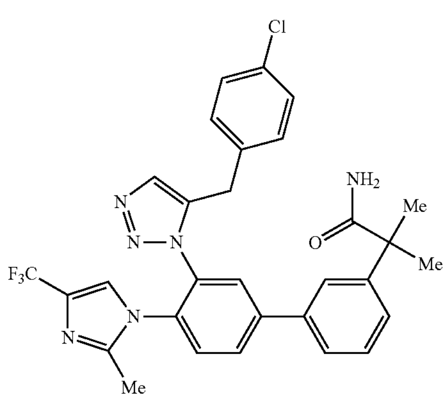 [SMILES: Cc1nc(C(F)(F)F)cn1-c1ccc(-c2cccc(C(C)(C)C(N)=O)c2)cc1-n1nncc1Cc1ccc(Cl)cc1] | 2-(3'-{5-[(4-chlorophenyl)methyl]-1H-1,2,3-triazol-1-yl}-4'-[2-methyl-4-(trifluoromethyl)-1H-imidazol-1-yl]biphenyl-3-yl)-2-methylpropanamide |

-continued

| Ex # | Structure | Name |
|---|---|---|
| 120 | 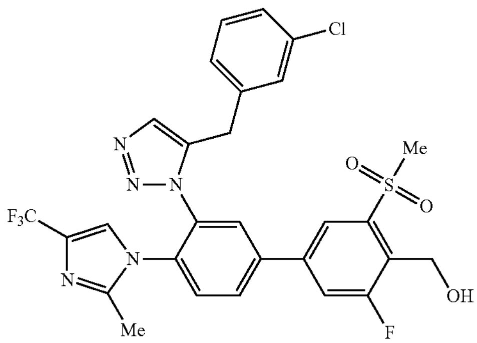 [SMILES: Cc1nc(C(F)(F)F)cn1-c1ccc(-c2cc(F)c(CO)c(S(C)(=O)=O)c2)cc1-n1nncc1Cc1cccc(Cl)c1] | (3'-{5-[(3-chlorophenyl)methyl]-1H-1,2,3-triazol-1-yl}-3-fluoro-5-(methylsulfonyl)-4'-[2-methyl-4-(trifluoromethyl)-1H-imidazol-1-yl]biphenyl-4-yl)methanol |
| 121 | 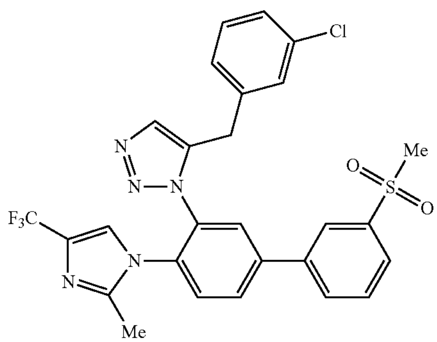 [SMILES: Cc1nc(C(F)(F)F)cn1-c1ccc(-c2cccc(S(C)(=O)=O)c2)cc1-n1nncc1Cc1cccc(Cl)c1] | 5-[(3-chlorophenyl)methyl]-1-{3'-(methylsulfonyl)-4-[2-methyl-4-(trifluoromethyl)-1H-imidazol-1-yl]biphenyl-3-yl}-1H-1,2,3-triazole |
| 122 | 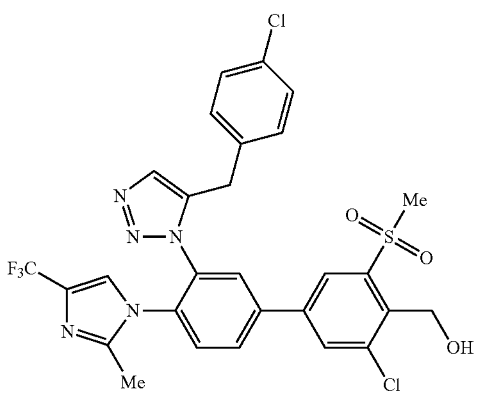 [SMILES: Cc1nc(C(F)(F)F)cn1-c1ccc(-c2cc(Cl)c(CO)c(S(C)(=O)=O)c2)cc1-n1nncc1Cc1ccc(Cl)cc1] | (3-chloro-3'-{5-[(4-chlorophenyl)methyl]-1H-1,2,3-triazol-1-yl}-5-(methylsulfonyl)-4'-[2-methyl-4-(trifluoromethyl)-1H-imidazol-1-yl]biphenyl-4-yl)methanol |
| 123 | 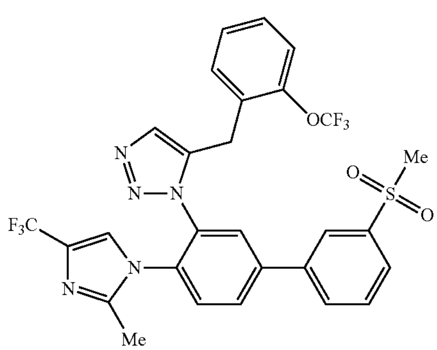 | 1-{3'-(methylsulfonyl)-4-[2-methyl-4-(trifluoromethyl)-1H-imidazol-1-yl]biphenyl-3-yl}-5-({2-[(trifluoromethyl)oxy]phenyl}methyl)-1H-1,2,3-triazole |

| Ex # | Structure | Name |
|---|---|---|
| 124 | 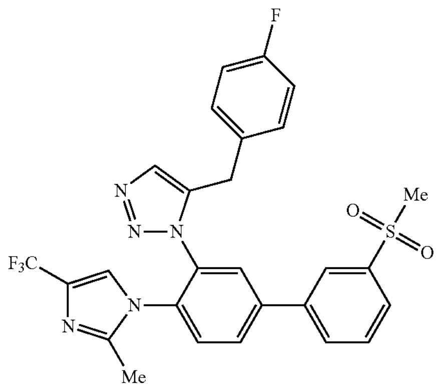 | 5-[(4-fluorophenyl)methyl]-1-{3'-(methylsulfonyl)-4-[2-methyl-4-(trifluoromethyl)-1H-imidazol-1-yl]biphenyl-3-yl}-1H-1,2,3-triazole |
| 125 | 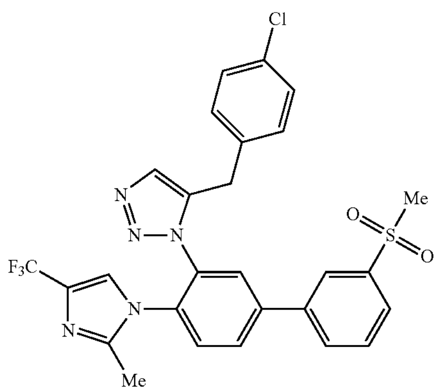 [SMILES: Cc1nc(C(F)(F)F)cn1-c1ccc(-c2cccc(S(C)(=O)=O)c2)cc1-n1nncc1Cc1ccc(F)cc1] | 5-[(4-chlorophenyl)methyl]-1-{3'-(methylsulfonyl)-4-[2-methyl-4-(trifluoromethyl)-1H-imidazol-1-yl]biphenyl-3-yl}-1H-1,2,3-triazole |
| 126 | 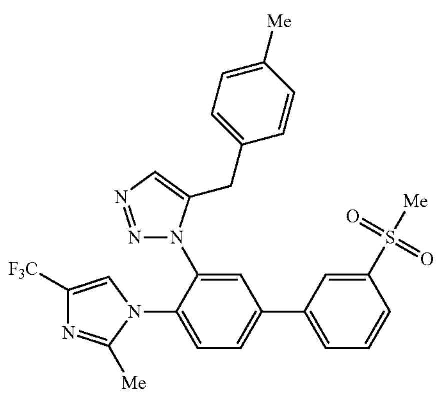 [SMILES: Cc1ccc(Cc2cnnn2-c2cc(-c3cccc(S(C)(=O)=O)c3)ccc2-n2cc(C(F)(F)F)nc2C)cc1] | 5-[(4-methylphenyl)methyl]-1-{3'-(methylsulfonyl)-4-[2-methyl-4-(trifluoromethyl)-1H-imidazol-1-yl]biphenyl-3-yl}-1H-1,2,3-triazole |
| 127 | 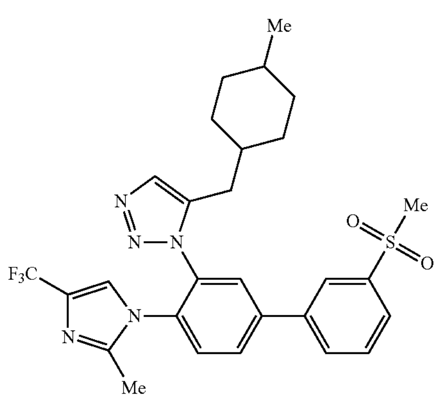 [SMILES: Cc1nc(C(F)(F)F)cn1-c1ccc(-c2cccc(S(C)(=O)=O)c2)cc1-n1nncc1CC1CCC(C)CC1] | 5-[(4-methylcyclohexyl)methyl]-1-{3'-(methylsulfonyl)-4-[2-methyl-4-(trifluoromethyl)-1H-imidazol-1-yl]biphenyl-3-yl}-1H-1,2,3-triazole |

| Ex # | Structure | Name |
|---|---|---|
| 129 | 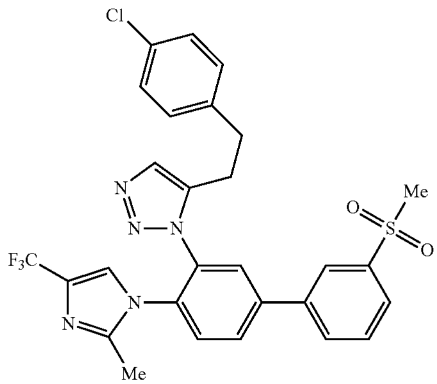 [SMILES: Cc1nc(C(F)(F)F)cn1-c1ccc(-c2cccc(S(C)(=O)=O)c2)cc1-n1nncc1CCc1ccc(Cl)cc1] | 5-[2-(4-chlorophenyl)ethyl]-1-{3'-(methylsulfonyl)-4-[2-methyl-4-(trifluoromethyl)-1H-imidazol-1-yl]biphenyl-3-yl}-1H-1,2,3-triazole |
| 130 | 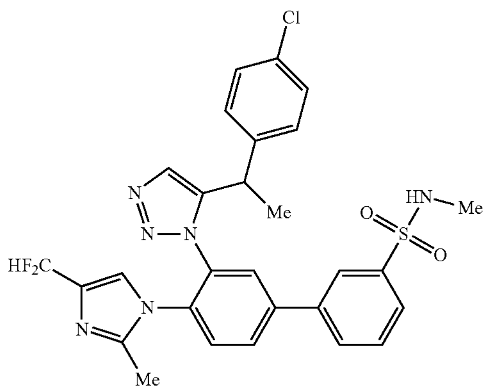 | 3'-{5-[1-(4-chlorophenyl)ethyl]-1H-1,2,3-triazol-1-yl}-4'-[4-(difluoromethyl)-2-methyl-1H-imidazol-1-yl]-N-methylbiphenyl-3-sulfonamide |
| 131 | 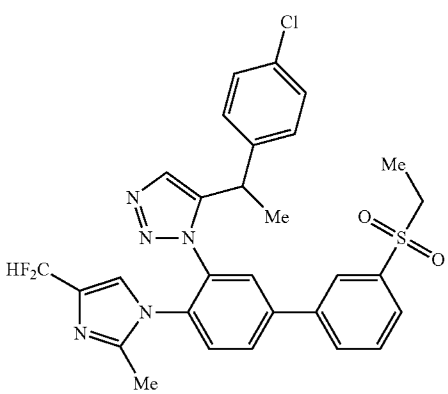 | 5-[1-(4-chlorophenyl)ethyl]-1-{4-[4-(difluoromethyl)-2-methyl-1H-imidazol-1-yl]-3'-(ethylsulfonyl)biphenyl-3-yl}-1H-1,2,3-triazole |
| 132 | 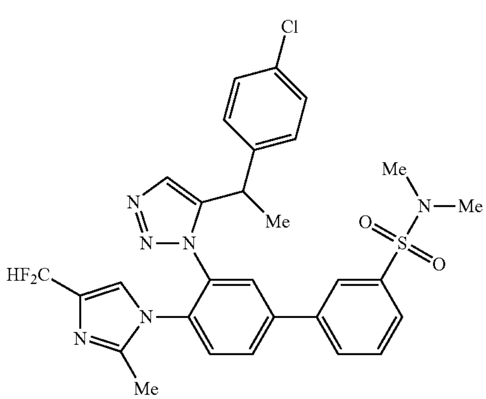 | 3'-{5-[1-(4-chlorophenyl)ethyl]-1H-1,2,3-triazol-1-yl}-4'-[4-(difluoromethyl)-2-methyl-1H-imidazol-1-yl]-N,N-dimethylbiphenyl-3-sulfonamide |

| Ex # | Structure | Name |
|---|---|---|
| 133 | 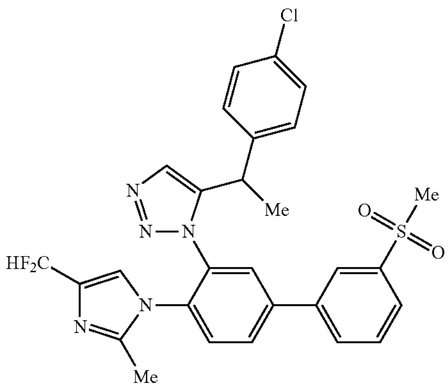 | 5-[1-(4-chlorophenyl)ethyl]-1-{4-[4-(difluoromethyl)-2-methyl-1H-imidazol-1-yl]-3'-(methylsulfonyl)biphenyl-3-yl}-1H-1,2,3-triazole |
| 134 | 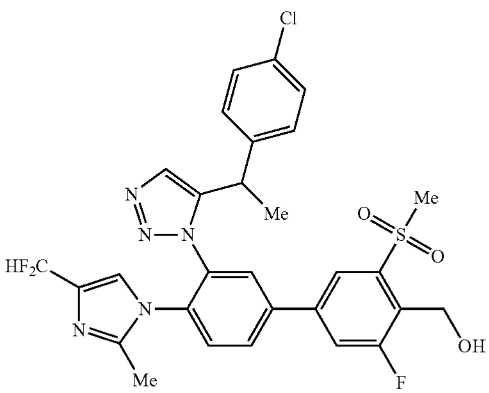 | [3'-{5-[1-(4-chlorophenyl)ethyl]-1H-1,2,3-triazol-1-yl}-4'-[4-(difluoromethyl)-2-methyl-1H-imidazol-1-yl]-3-fluoro-5-(methylsulfonyl)biphenyl-4-yl]methanol |
| 135 | 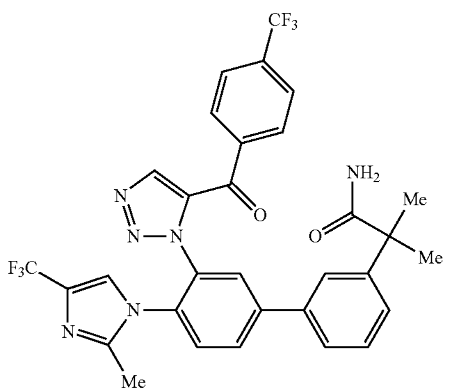 [SMILES: Cc1nc(C(F)(F)F)cn1-c1ccc(-c2cccc(C(C)(C)C(N)=O)c2)cc1-n1nncc1C(=O)c1ccc(C(F)(F)F)cc1] | 2-methyl-2-{4'-[2-methyl-4-(trifluoromethyl)-1H-imidazol-1-yl]-3'-(5-{[4-(trifluoromethyl)phenyl]carbonyl}-1H-1,2,3-triazol-1-yl)biphenyl-3-yl}propanamide |
| 136 | 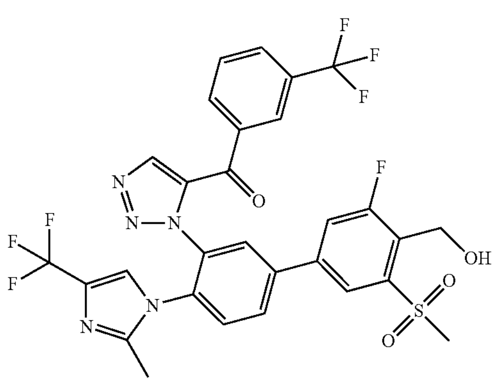 [SMILES: Cc1nc(C(F)(F)F)cn1-c1ccc(-c2cc(F)c(CO)c(S(C)(=O)=O)c2)cc1-n1nncc1C(=O)c1cccc(C(F)(F)F)c1] | (1-{3'-fluoro-4'-(hydroxymethyl)-5'-(methylsulfonyl)-4-[2-methyl-4-(trifluoromethyl)-1H-imidazol-1-yl]biphenyl-3-yl}-1H-1,2,3-triazol-5-yl)[3-(trifluoromethyl)phenyl]methanone |

| Ex # | Structure | Name |
|---|---|---|
| 137 | 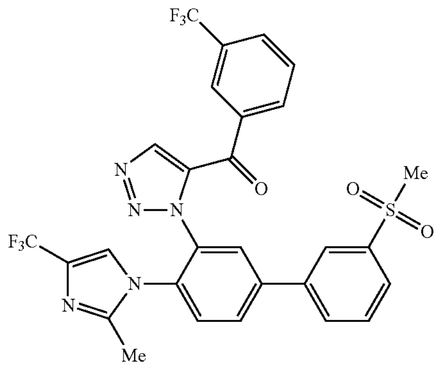 [SMILES: Cc1nc(C(F)(F)F)cn1-c1ccc(-c2cccc(S(C)(=O)=O)c2)cc1-n1nncc1C(=O)c1cccc(C(F)(F)F)c1] | (1-{3'-(methylsulfonyl)-4-[2-methyl-4-(trifluoromethyl)-1H-imidazol-1-yl]biphenyl-3-yl}-1H-1,2,3-triazol-5-yl)[3-(trifluoromethyl)phenyl]methanone |
| 138 | 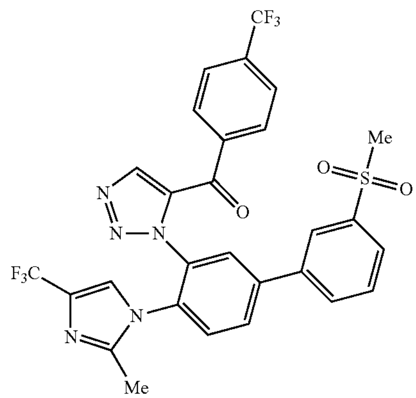 [SMILES: Cc1nc(C(F)(F)F)cn1-c1ccc(-c2cccc(S(C)(=O)=O)c2)cc1-n1nncc1C(=O)c1ccc(C(F)(F)F)cc1] | (1-{3'-(methylsulfonyl)-4-[2-methyl-4-(trifluoromethyl)-1H-imidazol-1-yl]biphenyl-3-yl}-1H-1,2,3-triazol-5-yl)[4-(trifluoromethyl)phenyl]methanone |
| 139 | 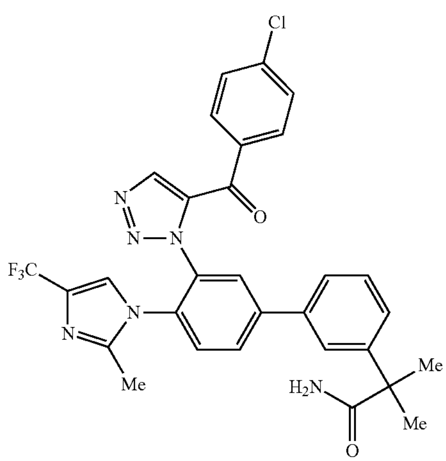 [SMILES: Cc1nc(C(F)(F)F)cn1-c1ccc(-c2cccc(C(C)(C)C(N)=O)c2)cc1-n1nncc1C(=O)c1ccc(Cl)cc1] | 2-(3'-{5-[(4-chlorophenyl)carbonyl]-1H-1,2,3-triazol-1-yl}-4'-[2-methyl-4-(trifluoromethyl)-1H-imidazol-1-yl]biphenyl-3-yl)-2-methylpropanamide |
| 140 | 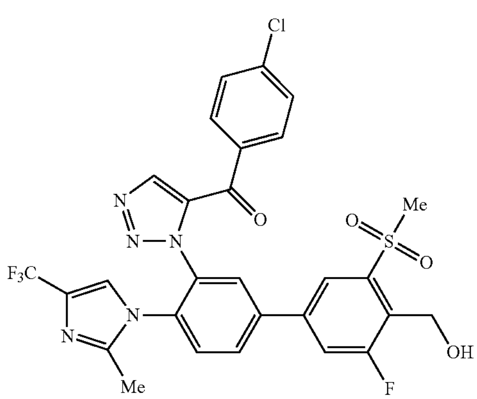 [SMILES: Cc1nc(C(F)(F)F)cn1-c1ccc(-c2cc(F)c(CO)c(S(C)(=O)=O)c2)cc1-n1nncc1C(=O)c1ccc(Cl)cc1] | (4-chlorophenyl)(1-{3'-fluoro-4'-(hydroxymethyl)-5'-(methylsulfonyl)-4-[2-methyl-4-(trifluoromethyl)-1H-imidazol-1-yl]biphenyl-3-yl}-1H-1,2,3-triazol-5-yl)methanone |

| Ex # | Structure | Name |
|---|---|---|
| 141 | 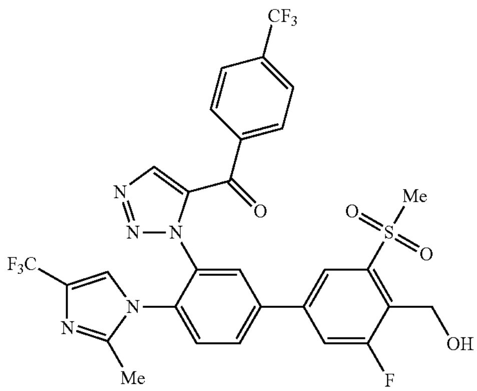 [SMILES: Cc1nc(C(F)(F)F)cn1-c1ccc(-c2cc(F)c(CO)c(S(C)(=O)=O)c2)cc1-n1nncc1C(=O)c1ccc(C(F)(F)F)cc1] | (1-{3'-fluoro-4'-(hydroxymethyl)-5'-(methylsulfonyl)-4-[2-methyl-4-(trifluoromethyl)-1H-imidazol-1-yl]biphenyl-3-yl}-1H-1,2,3-triazol-5-yl)[4-(trifluoromethyl)phenyl]methanone |
| 142 | 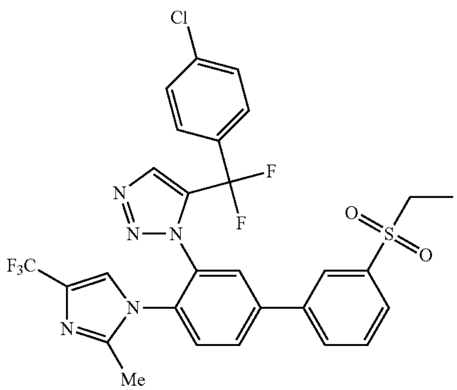 [SMILES: CCS(=O)(=O)c1cccc(-c2ccc(-n3cc(C(F)(F)F)nc3C)c(-n3nncc3C(F)(F)c3ccc(Cl)cc3)c2)c1] | 5-[(4-chlorophenyl)(difluoro)methyl]-1-{3'-(ethylsulfonyl)-4-[2-methyl-4-(trifluoromethyl)-1H-imidazol-1-yl]biphenyl-3-yl}-1H-1,2,3-triazole |
| 143 | 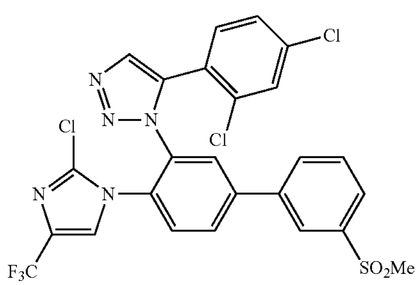 [SMILES: CS(=O)(=O)c1cccc(-c2ccc(-n3cc(C(F)(F)F)nc3Cl)c(-n3nncc3-c3ccc(Cl)cc3Cl)c2)c1] | 1-{4-[2-chloro-4-(trifluoromethyl)-1H-imidazol-1-yl]-3'-(methylsulfonyl)biphenyl-3-yl}-5-(2,4-dichlorophenyl)-1H-1,2,3-triazole |
| 144 | 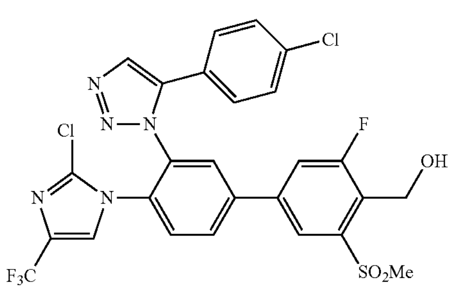 [SMILES: CS(=O)(=O)c1cc(-c2ccc(-n3cc(C(F)(F)F)nc3Cl)c(-n3nncc3-c3ccc(Cl)cc3)c2)cc(F)c1CO] | {3'-[5-(4-chlorophenyl)-1H-1,2,3-triazol-1-yl]-4'-[2-chloro-4-(trifluoromethyl)-1H-imidazol-1-yl]-3-fluoro-5-(methylsulfonyl)biphenyl-4-yl}methanol |

| Ex # | Structure | Name |
|---|---|---|
| 145 | 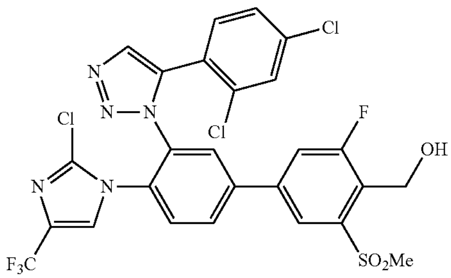 [SMILES: CS(=O)(=O)c1cc(-c2ccc(-n3cc(C(F)(F)F)nc3Cl)c(-n3nncc3-c3ccc(Cl)cc3Cl)c2)cc(F)c1CO] | {4'-[2-chloro-4-(trifluoromethyl)-1H-imidazol-1-yl]-3'-[5-(2,4-dichlorophenyl)-1H-1,2,3-triazol-1-yl]-3-fluoro-5-methylsulfonyl)biphenyl-4-yl}methanol |
| 146 | 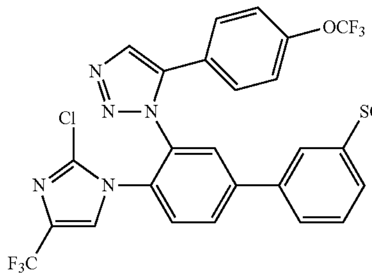 | 1-{4-[2-chloro-4-(trifluoromethyl)-1H-imidazol-1-yl]-3'-(methylsulfonyl)biphenyl-3-yl}-5-{4-[(trifluoromethyl)oxy]phenyl}-1H-1,2,3-triazole |
| 147 | 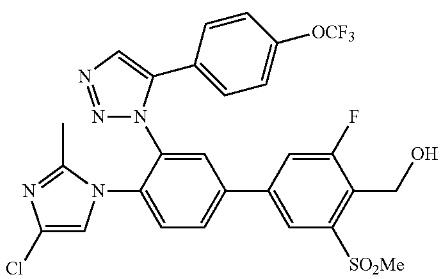 [SMILES: Cc1nc(Cl)cn1-c1ccc(-c2cc(F)c(CO)c(S(C)(=O)=O)c2)cc1-n1nncc1-c1ccc(Cl)cc1] | [4'-(4-chloro-2-methyl-1H-imidazol-1-yl)-3-fluoro-5-(methylsulfonyl)-3'-(5-{4-[(trifluoromethyl)oxy]phenyl}-1H-1,2,3-triazol-1-yl)biphenyl-4-yl]methanol |
| 148 | 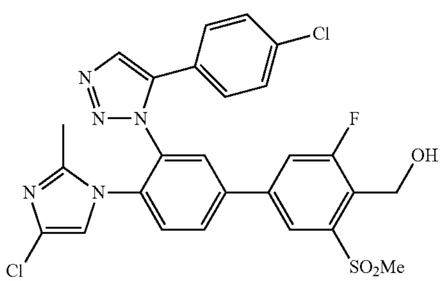 | [4'-(4-chloro-2-methyl-1H-imidazol-1-yl)-3'-[5-(4-chlorophenyl)-1H-1,2,3-triazol-1-yl]-3-fluoro-5-(methylsulfonyl)biphenyl-4-yl]methanol |
| 149 | 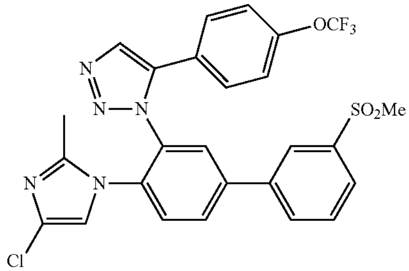 [SMILES: Cc1nc(Cl)cn1-c1ccc(-c2cccc(S(C)(=O)=O)c2)cc1-n1nncc1-c1ccc(OC(F)(F)F)cc1] | 1-[4-(4-chloro-2-methyl-1H-imidazol-1-yl)-3'-(methylsulfonyl)biphenyl-3-yl]-5-{4-[(trifluoromethyl)oxy]phenyl}-1H-1,2,3-triazole |

-continued

| Ex # | Structure | Name |
|---|---|---|
| 150 | 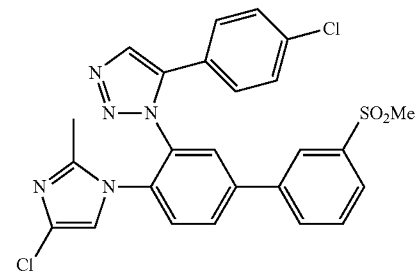 [SMILES: Cc1nc(Cl)cn1-c1ccc(-c2cccc(S(C)(=O)=O)c2)cc1-n1nncc1-c1ccc(Cl)cc1] | 1-[4-(4-chloro-2-methyl-1H-imidazol-1-yl)-3'-(methylsulfonyl)biphenyl-3-yl]-5-(4-chlorophenyl)-1H-1,2,3-triazole |
| 151 | 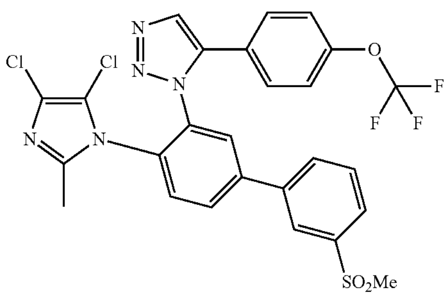 [SMILES: Cc1nc(Cl)c(Cl)n1-c1ccc(-c2cccc(S(C)(=O)=O)c2)cc1-n1nncc1-c1ccc(OC(F)(F)F)cc1] | 1-[4-(4,5-dichloro-2-methyl-1H-imidazol-1-yl)-3'-(methylsulfonyl)biphenyl-3-yl]-5-{4-[(trifluoromethyl)oxy]phenyl}-1H-1,2,3-triazole |
| 152 | 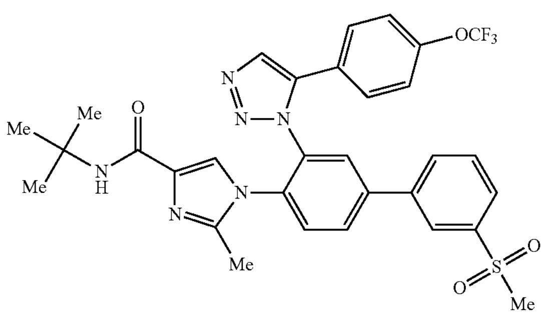 [SMILES: Cc1nc(C(=O)NC(C)(C)C)cn1-c1ccc(-c2cccc(S(C)(=O)=O)c2)cc1-n1nncc1-c1ccc(OC(F)(F)F)cc1] | N-(1,1-dimethylethyl)-2-methyl-1-[3'-methylsulfonyl)-3-(5-{4-[(trifluoromethyl)oxy]phenyl}-1H-1,2,3-triazol-1-yl)biphenyl-4-yl]-1H-imidazole-4-carboxamide |
| 154 | 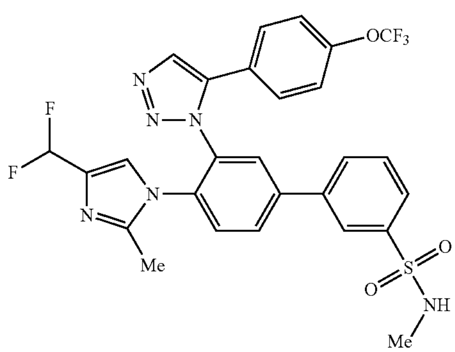 [SMILES: CNS(=O)(=O)c1cccc(-c2ccc(-n3cc(C(F)F)nc3C)c(-n3nncc3-c3ccc(OC(F)(F)F)cc3)c2)c1] | 4'-[4-(difluoromethyl)-2-methyl-1H-imidazol-1-yl]-N-methyl-3'-(5-{4-[(trifluoromethyl)oxy]phenyl}-1H-1,2,3-triazol-1-yl)biphenyl-3-sulfonamide |
| 155 | 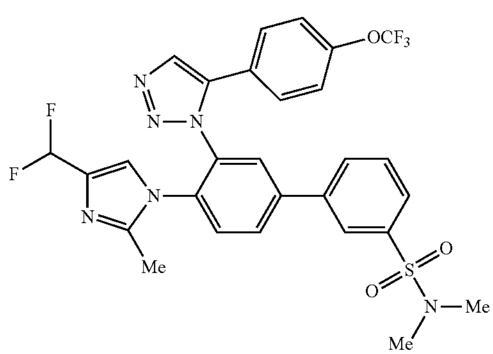 [SMILES: Cc1nc(C(F)F)cn1-c1ccc(-c2cccc(S(=O)(=O)N(C)C)c2)cc1-n1nncc1-c1ccc(OC(F)(F)F)cc1] | 4'-[4-(difluoromethyl)-2-methyl-1H-imidazol-1-yl]-N,N-dimethyl-3'-(5-{4-[(trifluoromethyl)oxy]phenyl}-1H-1,2,3-triazol-1-yl)biphenyl-3-sulfonamide |

| Ex # | Structure | Name |
|---|---|---|
| 156 | 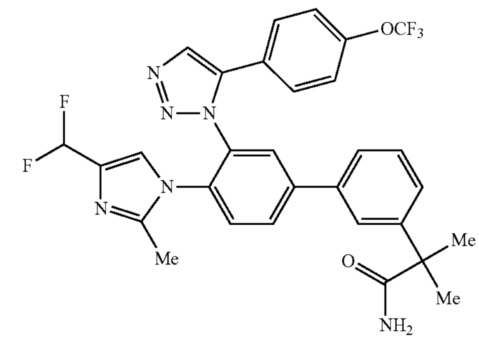 [SMILES: Cc1nc(C(F)F)cn1-c1ccc(-c2cccc(C(C)(C)C(N)=O)c2)cc1-n1nncc1-c1ccc(OC(F)(F)F)cc1] | 2-{4'-[4-(difluoromethyl)-2-methyl-1H-imidazol-1-yl]-3'-(5-{4-[(trifluoromethyl)oxy]phenyl}-1H-1,2,3-triazol-1-yl)biphenyl-3-yl}-2-methylpropanamide |
| 157 | 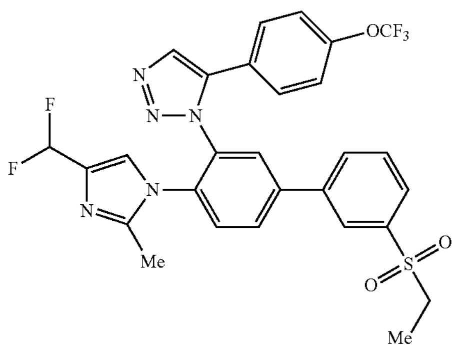 [SMILES: CCS(=O)(=O)c1cccc(-c2ccc(-n3cc(C(F)F)nc3C)c(-n3nncc3-c3ccc(OC(F)(F)F)cc3)c2)c1] | 1-{4-[4-(difluoromethyl)-2-methyl-1H-imidazol-1-yl]-3'-(ethylsulfonyl)biphenyl-3-yl}-5-{4-[(trifluoromethyl)oxy]phenyl}-1H-1,2,3-triazole |
| 158 | 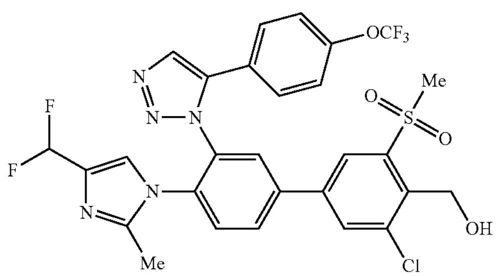 [SMILES: Cc1nc(C(F)F)cn1-c1ccc(-c2cc(Cl)c(CO)c(S(C)(=O)=O)c2)cc1-n1nncc1-c1ccc(OC(F)(F)F)cc1] | {3-chloro-4'-[4-(difluoromethyl)-2-methyl-1H-imidazol-1-yl]-5-(methylsulfonyl)-3'-(5-{4-[(trifluoromethyl)oxy]phenyl}-1H-1,2,3-triazol-1-yl)biphenyl-4-yl}methanol |
| 159 | 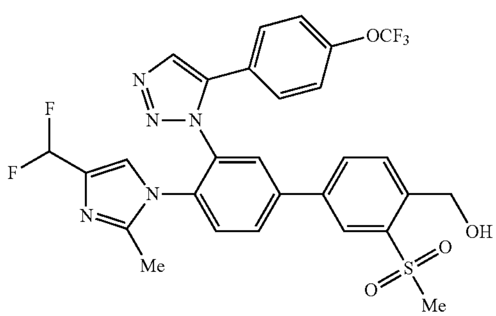 [SMILES: Cc1nc(C(F)F)cn1-c1ccc(-c2ccc(CO)c(S(C)(=O)=O)c2)cc1-n1nncc1-c1ccc(OC(F)(F)F)cc1] | {4'-[4-(difluoromethyl)-2-methyl-1H-imidazol-1-yl]-3-(methylsulfonyl)-3'-(5-{4-[(trifluoromethyl)oxy]phenyl}-1H-1,2,3-triazol-1-yl)biphenyl-4-yl}methanol |
| 162 | 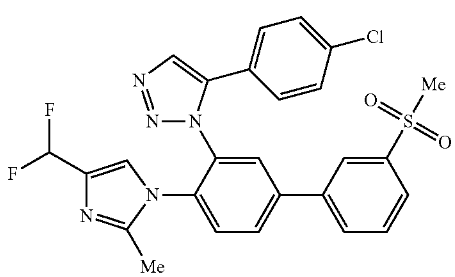 [SMILES: Cc1nc(C(F)F)cn1-c1ccc(-c2cccc(S(C)(=O)=O)c2)cc1-n1nncc1-c1ccc(Cl)cc1] | 5-(4-chlorophenyl)-1-{4-[4-(difluoromethyl)-2-methyl-1H-imidazol-1-yl]-3'-(methylsulfonyl)biphenyl-3-yl}-1H-1,2,3-triazole |

| Ex # | Structure | Name |
|---|---|---|
| 163 | 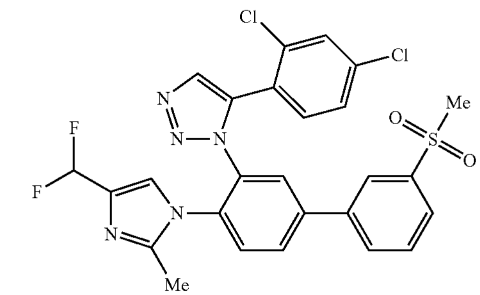 [SMILES: Cc1nc(C(F)F)cn1-c1ccc(-c2cccc(S(C)(=O)=O)c2)cc1-n1nncc1-c1ccc(Cl)cc1Cl] | 5-(2,4-dichlorophenyl)-1-{4-[4-(difluoromethyl)-2-methyl-1H-imidazol-1-yl]-3'-methylsulfonyl)biphenyl-3-yl}-1H-1,2,3-triazole |
| 164 | 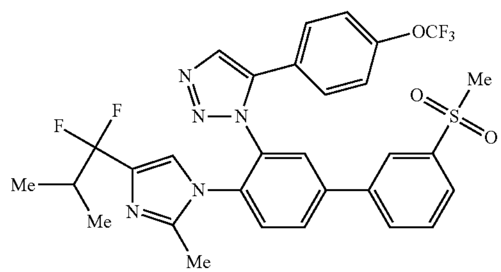 [SMILES: Cc1nc(C(F)(F)C(C)C)cn1-c1ccc(-c2cccc(S(C)(=O)=O)c2)cc1-n1nncc1-c1ccc(OC(F)(F)F)cc1] | 1-{4-[4-(1,1-difluoro-2-methylpropyl)-2-methyl-1H-imidazol-1-yl]-3'-(methylsulfonyl)biphenyl-3-yl}-5-{4-[(trifluoromethyl)oxy]phenyl}-1H-1,2,3-triazole |
| 165 | 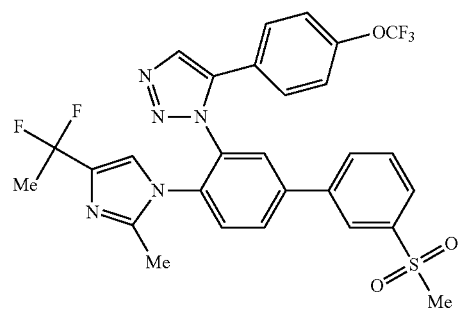 [SMILES: Cc1nc(C(C)(F)F)cn1-c1ccc(-c2cccc(S(C)(=O)=O)c2)cc1-n1nncc1-c1ccc(OC(F)(F)F)cc1] | 1-{4-[4-(1,1-difluoroethyl)-2-methyl-1H-imidazol-1-yl]-3'-(methylsulfonyl)biphenyl-3-yl}-5-{4-[(trifluoromethyl)oxy]phenyl}-1H-1,2,3-triazole |
| 166 | 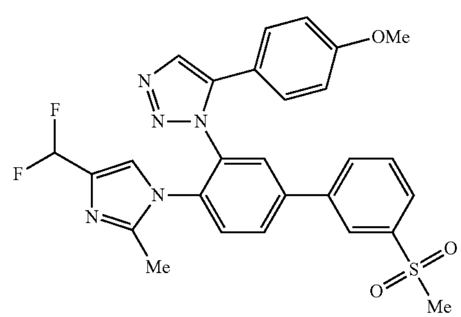 [SMILES: COc1ccc(-c2cnnn2-c2cc(-c3cccc(S(C)(=O)=O)c3)ccc2-n2cc(C(F)F)nc2C)cc1] | 1-{4-[4-(difluoromethyl)-2-methyl-1H-imidazol-1-yl]-3'-(methylsulfonyl)biphenyl-3-yl}-5-[4-(methyloxy)phenyl]-1H-1,2,3-triazole |
| 167 | 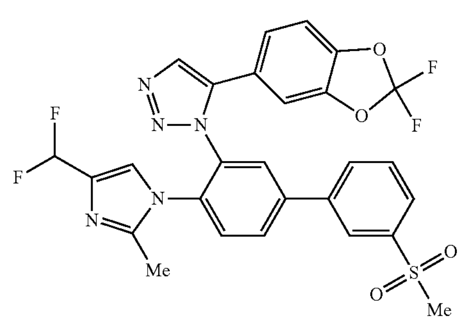 [SMILES: Cc1nc(C(F)F)cn1-c1ccc(-c2cccc(S(C)(=O)=O)c2)cc1-n1nncc1-c1ccc2c(c1)OC(F)(F)O2] | 5-(2,2-difluoro-1,3-benzodioxol-5-yl)-1-{4-[4-(difluoromethyl)-2-methyl-1H-imidazol-1-yl]-3'-(methylsulfonyl)biphenyl-3-yl}-1H-1,2,3-triazole |

| Ex # | Structure | Name |
|---|---|---|
| 168 | 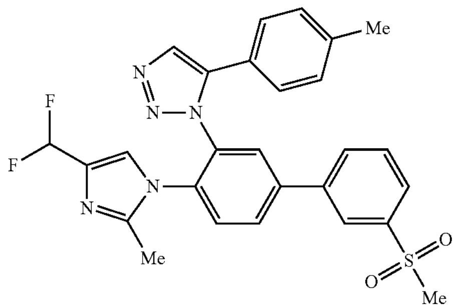 [SMILES: Cc1ccc(-c2cnnn2-c2cc(-c3cccc(S(C)(=O)=O)c3)ccc2-n2cc(C(F)F)nc2C)cc1] | 1-{4-[4-(difluoromethyl)-2-methyl-1H-imidazol-1-yl]-3'-(methylsulfonyl)biphenyl-3-yl}-5-(4-methylphenyl)-1H-1,2,3-triazole |
| 169 | 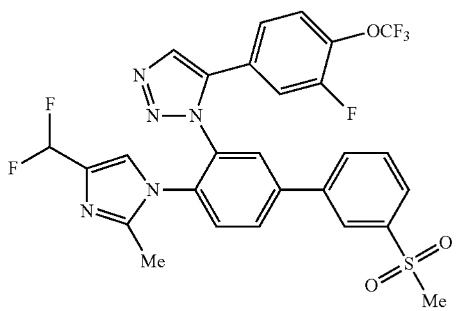 [SMILES: Cc1nc(C(F)F)cn1-c1ccc(-c2cccc(S(C)(=O)=O)c2)cc1-n1nncc1-c1ccc(OC(F)(F)F)c(F)c1] | 1-{4-[4-(difluoromethyl)-2-methyl-1H-imidazol-1-yl]-3'-(methylsulfonyl)biphenyl-3-yl}-5-{3-fluoro-4-[(trifluoromethyl)oxy]phenyl}-1H-1,2,3-triazole |
| 170 | 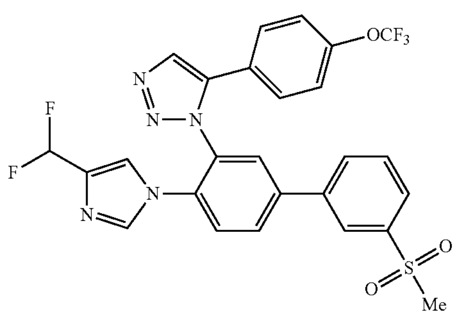 [SMILES: CS(=O)(=O)c1cccc(-c2ccc(-n3cnc(C(F)F)c3)c(-n3nncc3-c3ccc(OC(F)(F)F)cc3)c2)c1] | 1-{4-[4-(difluoromethyl)-1H-imidazol-1-yl]-3'-(methylsulfonyl)biphenyl-3-yl}-5-{4-[(trifluoromethyl)oxy]phenyl}-1H-1,2,3-triazole |
| 171 | 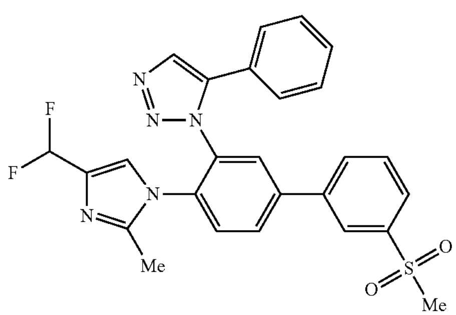 [SMILES: Cc1nc(C(F)F)cn1-c1ccc(-c2cccc(S(C)(=O)=O)c2)cc1-n1nncc1-c1ccccc1] | 1-{4-[4-(difluoromethyl)-2-methyl-1H-imidazol-1-yl]-3'-(methylsulfonyl)biphenyl-3-yl}-5-phenyl-1H-1,2,3-triazole |
| 172 | 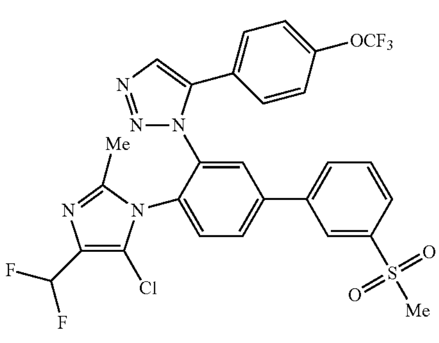 [SMILES: Cc1nc(C(F)F)c(Cl)n1-c1ccc(-c2cccc(S(C)(=O)=O)c2)cc1-n1nncc1-c1ccc(OC(F)(F)F)cc1] | 1-{4-[5-chloro-4-(difluoromethyl)-2-methyl-1H-imidazol-1-yl]-3'-(methylsulfonyl)biphenyl-3-yl}-5-{4-[(trifluoromethyl)oxy]phenyl}-1H-1,2,3-triazole |

-continued

| Ex # | Structure | Name |
|---|---|---|
| 173 | 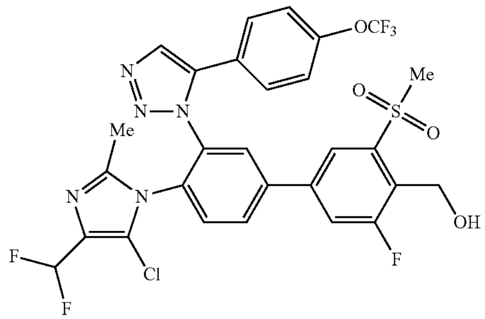 [SMILES: Cc1nc(C(F)F)c(Cl)n1-c1ccc(-c2cc(F)c(CO)c(S(C)(=O)=O)c2)cc1-n1nncc1-c1ccc(OC(F)(F)F)cc1] | {4'-[5-chloro-4-(difluoromethyl)-2-methyl-1H-imidazol-1-yl]-3-fluoro-5-(methylsulfonyl)-3'-(5-{4-[(trifluoromethyl)oxy]phenyl}-1H-1,2,3-triazol-1-yl)biphenyl-4-yl}methanol |
| 174 | 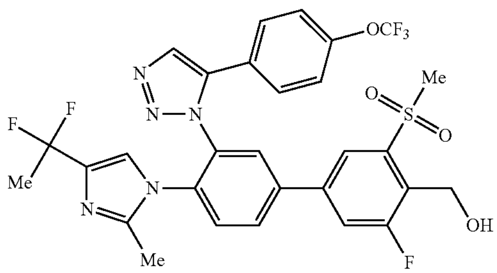 [SMILES: Cc1nc(C(C)(F)F)cn1-c1ccc(-c2cc(F)c(CO)c(S(C)(=O)=O)c2)cc1-n1nncc1-c1ccc(OC(F)(F)F)cc1] | {4'-[4-(1,1-difluoroethyl)-2-methyl-1H-imidazol-1-yl]-3-fluoro-5-(methylsulfonyl)-3'-(5-{4-[(trifluoromethyl)oxy]phenyl}-1H-1,2,3-triazol-1-yl)biphenyl-4-yl}methanol |
| 175 | 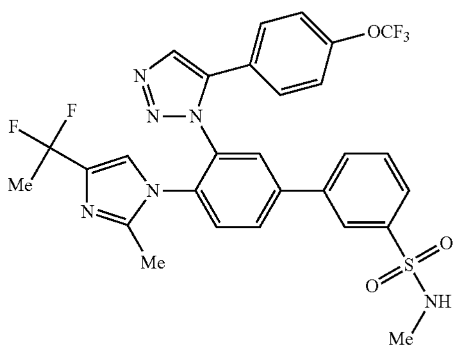 [SMILES: CNS(=O)(=O)c1cccc(-c2ccc(-n3cc(C(C)(F)F)nc3C)c(-n3nncc3-c3ccc(OC(F)(F)F)cc3)c2)c1] | 4'-[4-(1,1-difluoroethyl)-2-methyl-1H-imidazol-1-yl]-N-methyl-3'-(5-{4-[(trifluoromethyl)oxy]phenyl}-1H-1,2,3-triazol-1-yl)biphenyl-3-sulfonamide |
| 176 | 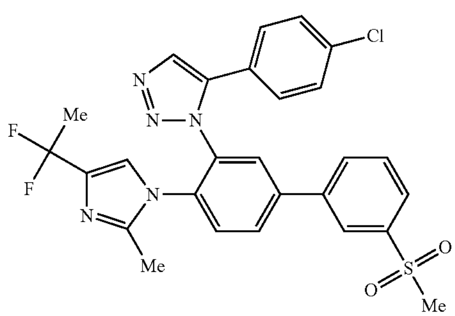 [SMILES: Cc1nc(C(C)(F)F)cn1-c1ccc(-c2cccc(S(C)(=O)=O)c2)cc1-n1nncc1-c1ccc(Cl)cc1] | 5-(4-chlorophenyl)-1-{4-[4-(1,1-difluoroethyl)-2-methyl-1H-imidazol-1-yl]-3'-(methylsulfonyl)biphenyl-3-yl}-1H-1,2,3-triazole |
| 177 | 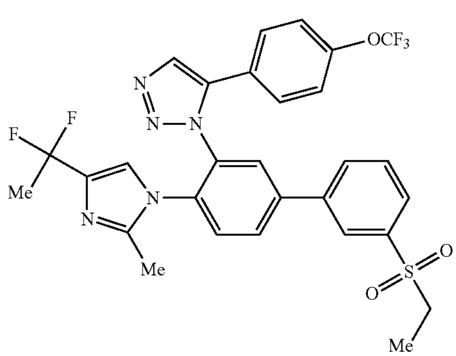 [SMILES: CCS(=O)(=O)c1cccc(-c2ccc(-n3cc(C(C)(F)F)nc3C)c(-n3nncc3-c3ccc(OC(F)(F)F)cc3)c2)c1] | 1-{4-[4-(1,1-difluoroethyl)-2-methyl-1H-imidazol-1-yl]-3'-(ethylsulfonyl)biphenyl-3-yl}-5-{4-[(trifluoromethyl)oxy]phenyl}-1H-1,2,3-triazole |

| Ex # | Structure | Name |
|---|---|---|
| 178 | 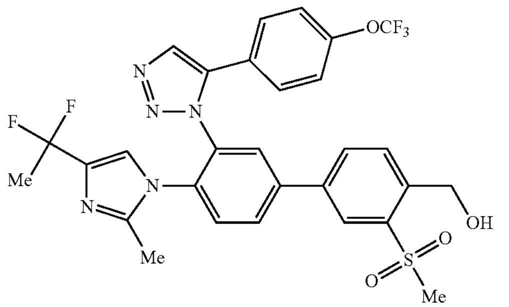 [SMILES: Cc1nc(C(C)(F)F)cn1-c1ccc(-c2ccc(CO)c(S(C)(=O)=O)c2)cc1-n1nncc1-c1ccc(OC(F)(F)F)cc1] | {4'-[4-(1,1-difluoroethyl)-2-methyl-1H-imidazol-1-yl]-3-(methylsulfonyl)-3'-(5-{4-[(trifluoromethyl)oxy]phenyl}-1H-1,2,3-triazol-1-yl)biphenyl-4-yl}methanol |
| 179 | 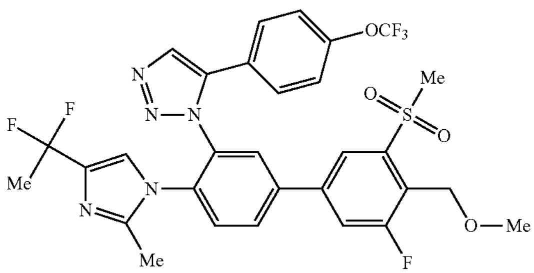 [SMILES: COCc1c(F)cc(-c2ccc(-n3cc(C(C)(F)F)nc3C)c(-n3nncc3-c3ccc(OC(F)(F)F)cc3)c2)cc1S(C)(=O)=O] | 1-{4-[4-(1,1-difluoroethyl)-2-methyl-1H-imidazol-1-yl]-3'-fluoro-4'-[(methyloxy)methyl]-5'-(methylsulfonyl)biphenyl-3-yl}-5-{4-[(trifluoromethyl)oxy]phenyl}-1H-1,2,3-triazole |
| 180 | 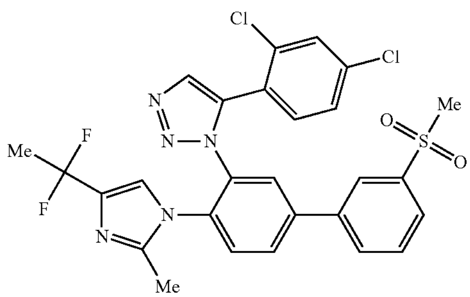 [SMILES: Cc1nc(C(C)(F)F)cn1-c1ccc(-c2cccc(S(C)(=O)=O)c2)cc1-n1nncc1-c1ccc(Cl)cc1Cl] | 5-(2,4-dichlorophenyl)-1-{4-[4-(1,1-difluoroethyl)-2-methyl-1H-imidazol-1-yl]-3'-(methylsulfonyl)biphenyl-3-yl}-1H-1,2,3-triazole |
| 181 | 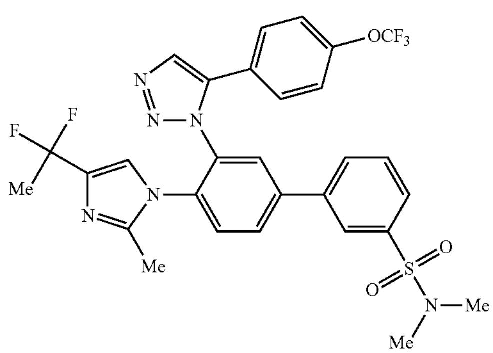 [SMILES: Cc1nc(C(C)(F)F)cn1-c1ccc(-c2cccc(S(=O)(=O)N(C)C)c2)cc1-n1nncc1-c1ccc(OC(F)(F)F)cc1] | 4'-[4-(1,1-difluoroethyl)-2-methyl-1H-imidazol-1-yl]-N,N-dimethyl-3'-(5-{4-[(trifluoromethyl)oxy]phenyl}-1H-1,2,3-triazol-1-yl)biphenyl-3-sulfonamide |
| 182 | 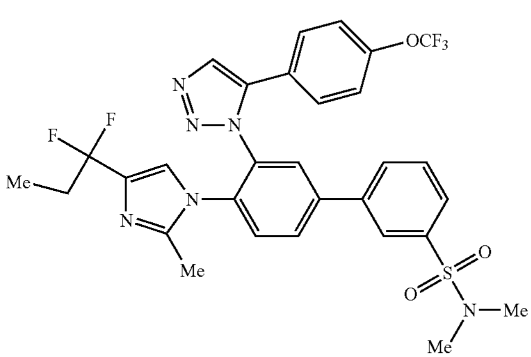 [SMILES: CCC(F)(F)c1cn(-c2ccc(-c3cccc(S(=O)(=O)N(C)C)c3)cc2-n2nncc2-c2ccc(OC(F)(F)F)cc2)c(C)n1] | 4'-[4-(1,1-difluoropropyl)-2-methyl-1H-imidazol-1-yl]-N,N-dimethyl-3'-(5-{4-[(trifluoromethyl)oxy]phenyl}-1H-1,2,3-triazol-1-yl)biphenyl-3-sulfonamide |

| Ex # | Structure | Name |
|---|---|---|
| 183 | 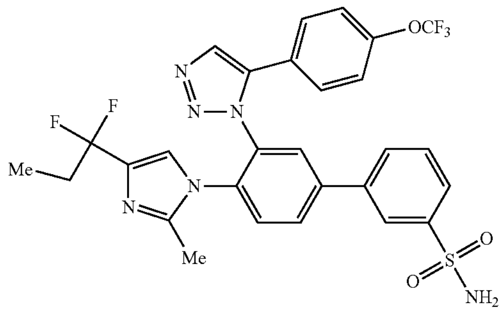 [SMILES: CCC(F)(F)c1cn(-c2ccc(-c3cccc(S(N)(=O)=O)c3)cc2-n2nncc2-c2ccc(OC(F)(F)F)cc2)c(C)n1] | 4'-[4-(1,1-difluoropropyl)-2-methyl-1H-imidazol-1-yl]-3'-(5-{4-[(trifluoromethyl)oxy]phenyl}-1H-1,2,3-triazol-1-yl)biphenyl-3-sulfonamide |
| 184 | 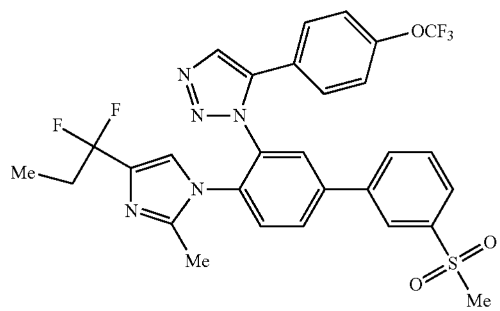 [SMILES: CCC(F)(F)c1cn(-c2ccc(-c3cccc(S(C)(=O)=O)c3)cc2-n2nncc2-c2ccc(OC(F)(F)F)cc2)c(C)n1] | 1-{4-[4-(1,1-difluoropropyl)-2-methyl-1H-imidazol-1-yl]-3'-(methylsulfonyl)biphenyl-3-yl}-5-{4-[(trifluoromethyl)oxy]phenyl}-1H-1,2,3-triazole |
| 185 | 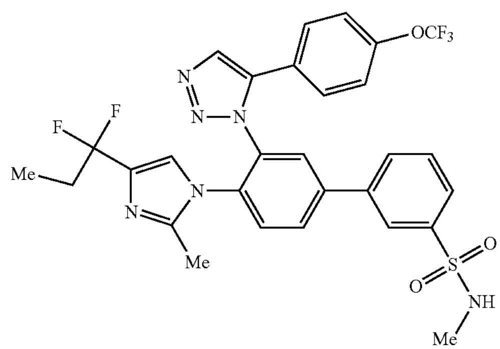 [SMILES: CCC(F)(F)c1cn(-c2ccc(-c3cccc(S(=O)(=O)NC)c3)cc2-n2nncc2-c2ccc(OC(F)(F)F)cc2)c(C)n1] | 4'-[4-(1,1-difluoropropyl)-2-methyl-1H-imidazol-1-yl]-N-methyl-3'-(5-{4-[(trifluoromethyl)oxy]phenyl}-1H-1,2,3-triazol-1-yl)biphenyl-3-sulfonamide |
| 186 | 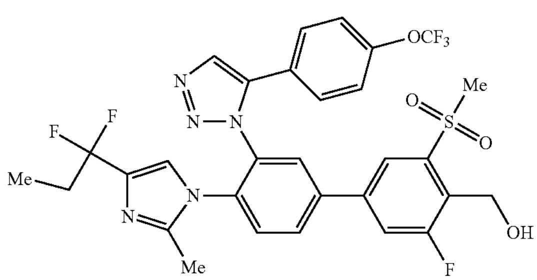 [SMILES: CCC(F)(F)c1cn(-c2ccc(-c3cc(F)c(CO)c(S(C)(=O)=O)c3)cc2-n2nncc2-c2ccc(OC(F)(F)F)cc2)c(C)n1] | {4'-[4-(1,1-difluoropropyl)-2-methyl-1H-imidazol-1-yl]-3-fluoro-5-(methylsulfonyl)-3'-(5-{4-[(trifluoromethyl)oxy]phenyl}-1H-1,2,3-triazol-1-yl)biphenyl-4-yl}methanol |
| 187 | 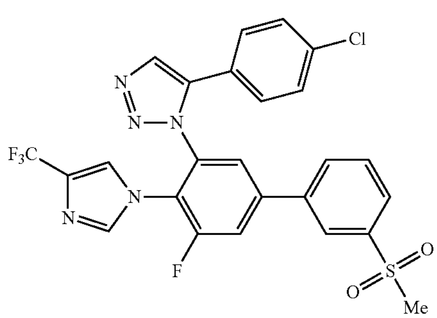 [SMILES: CS(=O)(=O)c1cccc(-c2cc(F)c(-n3cnc(C(F)(F)F)c3)c(-n3nncc3-c3ccc(Cl)cc3)c2)c1] | 5-(4-chlorophenyl)-1-{5-fluoro-3'-(methylsulfonyl)-4-[4-(trifluoromethyl)-1H-imidazol-1-yl]biphenyl-3-yl}-1H-1,2,3-triazole |

-continued

| Ex # | Structure | Name |
|---|---|---|
| 188 | 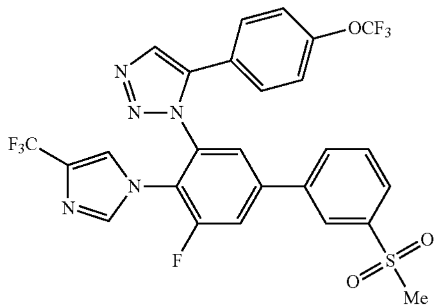 [SMILES: CS(=O)(=O)c1cccc(-c2cc(F)c(-n3cnc(C(F)(F)F)c3)c(-n3nncc3-c3ccc(OC(F)(F)F)cc3)c2)c1] | 1-{5-fluoro-3'-(methylsulfonyl)-4-[4-(trifluoromethyl)-1H-imidazol-1-yl]biphenyl-3-yl}-5-{4-[(trifluoromethyl)oxy]phenyl}-1H-1,2,3-triazole |
| 189 | 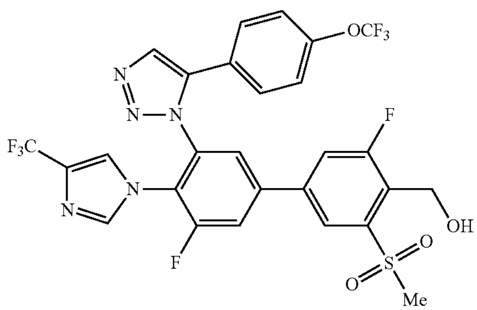 | [3,3'-difluoro-5-(methylsulfonyl)-4'-[4-(trifluoromethyl)-1H-imidazol-1-yl]-5'-(5-{4-[(trifluoromethyl)oxy]phenyl}-1H-1,2,3-triazol-1-yl)biphenyl-4-yl]methanol |
| 190 | 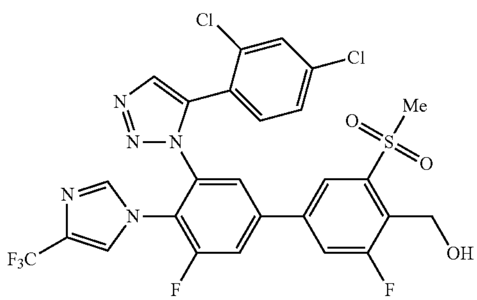 [SMILES: CS(=O)(=O)c1cc(-c2cc(F)c(-n3cnc(C(F)(F)F)c3)c(-n3nncc3-c3ccc(Cl)cc3Cl)c2)cc(F)c1CO] | {3'-[5-(2,4-dichlorophenyl)-1H-1,2,3-triazol-1-yl]-3,5'-difluoro-5-(methylsulfonyl)-4'-[4-(trifluoromethyl)-1H-imidazol-1-yl]biphenyl-4-yl}methanol |
| 191 | 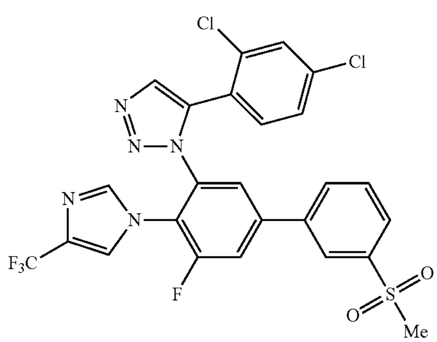 [SMILES: CS(=O)(=O)c1cccc(-c2cc(F)c(-n3cnc(C(F)(F)F)c3)c(-n3nncc3-c3ccc(Cl)cc3Cl)c2)c1] | 5-(2,4-dichlorophenyl)-1-{5-fluoro-3'-(methylsulfonyl)-4-[4-(trifluoromethyl)-1H-imidazol-1-yl]biphenyl-3-yl}-1H-1,2,3-triazole |
| 192 | 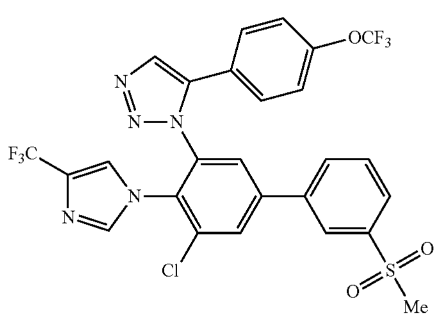 [SMILES: CS(=O)(=O)c1cccc(-c2cc(Cl)c(-n3cnc(C(F)(F)F)c3)c(-n3nncc3-c3ccc(OC(F)(F)F)cc3)c2)c1] | 1-{5-chloro-3'-(methylsulfonyl)-4-[4-(trifluoromethyl)-1H-imidazol-1-yl]biphenyl-3-yl}-5-{4-[(trifluoromethyl)oxy]phenyl}-1H-1,2,3-triazole |

-continued

| Ex # | Structure | Name |
|---|---|---|
| 193 | 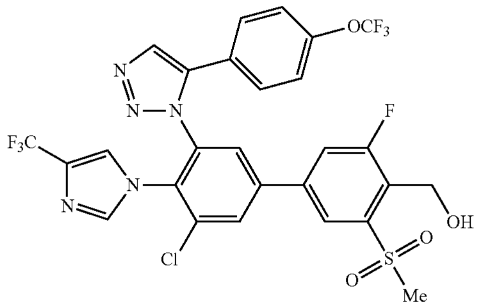 [SMILES: CS(=O)(=O)c1cc(-c2cc(Cl)c(-n3cnc(C(F)(F)F)c3)c(-n3nncc3-c3ccc(OC(F)(F)F)cc3)c2)cc(F)c1CO] | [3'-chloro-3-fluoro-5-(methylsulfonyl)-4'-[4-(trifluoromethyl)-1H-imidazol-1-yl]-5'-(5-{4-[(trifluoromethyl)oxy]phenyl}-1H-1,2,3-triazol-1-yl)biphenyl-4-yl]methanol |
| 195 | 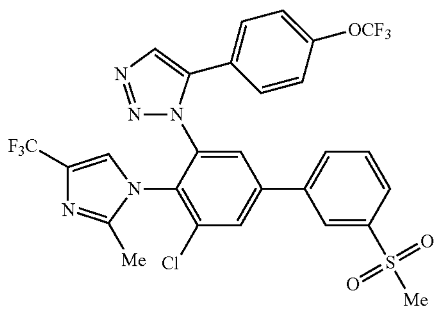 [SMILES: Cc1nc(C(F)(F)F)cn1-c1c(Cl)cc(-c2cccc(S(C)(=O)=O)c2)cc1-n1nncc1-c1ccc(OC(F)(F)F)cc1] | 1-{5-chloro-3'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole |
| 196 | 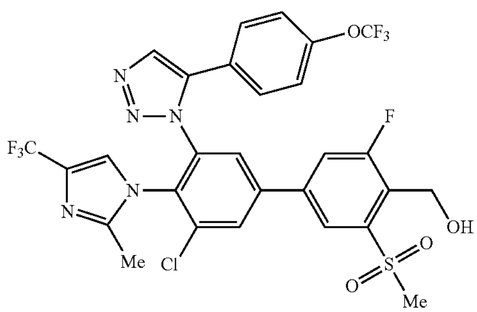 | [3'-chloro-3-fluoro-5-(methylsulfonyl)-4'-[2-methyl-4-(trifluoromethyl)-1H-imidazol-1-yl]-5'-(5-{4-[(trifluoromethyl)oxy]phenyl}-1H-1,2,3-triazol-1-yl)biphenyl-4-yl]methanol |
| 197 | 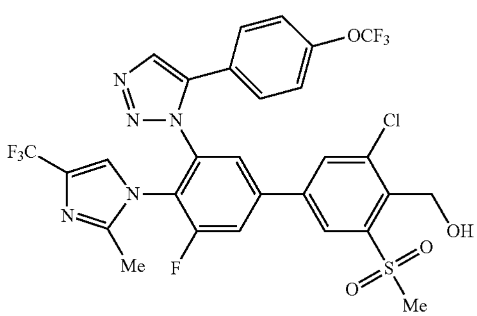 [SMILES: Cc1nc(C(F)(F)F)cn1-c1c(F)cc(-c2cc(Cl)c(CO)c(S(C)(=O)=O)c2)cc1-n1nncc1-c1ccc(OC(F)(F)F)cc1] | [3-chloro-3'-fluoro-5-(methylsulfonyl)-4'-[2-methyl-4-(trifluoromethyl)-1H-imidazol-1-yl]-5'-(5-{4-[(trifluoromethyl)oxy]phenyl}-1H-1,2,3-triazol-1-yl)biphenyl-4-yl]methanol |
| 198 | 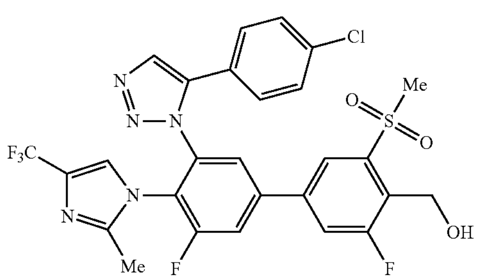 [SMILES: Cc1nc(C(F)(F)F)cn1-c1c(F)cc(-c2cc(F)c(CO)c(S(C)(=O)=O)c2)cc1-n1nncc1-c1ccc(Cl)cc1] | {3'-[5-(4-chlorophenyl)-1H-1,2,3-triazol-1-yl]-3,5'-difluoro-5-(methylsulfonyl)-4'-[2-methyl-4-(trifluoromethyl)-1H-imidazol-1-yl]biphenyl-4-yl}methanol |

| Ex # | Structure | Name |
|---|---|---|
| 199 | 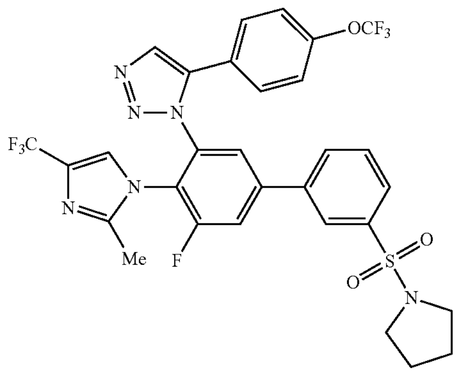 [SMILES: Cc1nc(C(F)(F)F)cn1-c1c(F)cc(-c2cccc(S(=O)(=O)N3CCCC3)c2)cc1-n1nncc1-c1ccc(OC(F)(F)F)cc1] | 1-{5-fluoro-4-[2-methyl-4-(trifluoromethyl)-1H-imidazol-1-yl]-3'-(pyrrolidin-1-ylsulfonyl)biphenyl-3-yl}-5-{4-[(trifluoromethyl)oxy]phenyl}-1H-1,2,3-triazole |
| 200 | 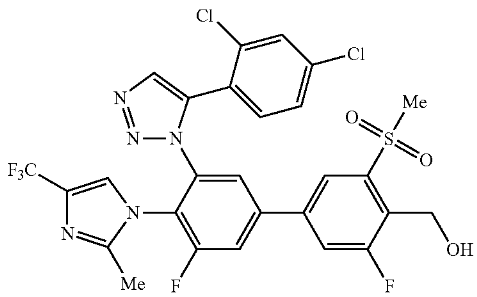 [SMILES: Cc1nc(C(F)(F)F)cn1-c1c(F)cc(-c2cc(F)c(CO)c(S(C)(=O)=O)c2)cc1-n1nncc1-c1ccc(Cl)cc1Cl] | {3'-[5-(2,4-dichlorophenyl)-1H-1,2,3-triazol-1-yl]-3,5'-difluoro-5-(methylsulfonyl)-4'-[2-methyl-4-(trifluoromethyl)-1H-imidazol-1-yl]biphenyl-4-yl}methanol |
| 201 | 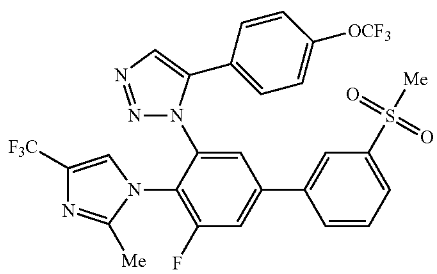 [SMILES: Cc1nc(C(F)(F)F)cn1-c1c(F)cc(-c2cccc(S(C)(=O)=O)c2)cc1-n1nncc1-c1ccc(OC(F)(F)F)cc1] | 1-{5-fluoro-3'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole |
| 202 | 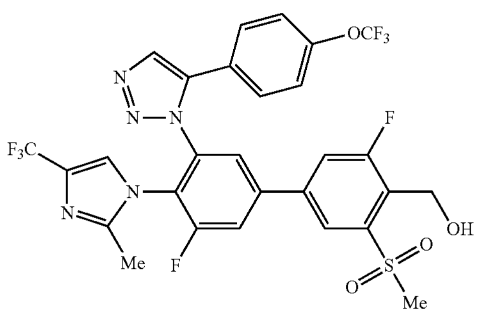 [SMILES: Cc1nc(C(F)(F)F)cn1-c1c(F)cc(-c2cc(F)c(CO)c(S(C)(=O)=O)c2)cc1-n1nncc1-c1ccc(OC(F)(F)F)cc1] | [3,3'-difluoro-5-(methylsulfonyl)-4'-[2-methyl-4-(trifluoromethyl)-1H-imidazol-1-yl]-5'-(5-{4-[(trifluoromethyl)oxy]phenyl}-1H-1,2,3-triazol-1-yl)biphenyl-4-yl]methanol |
| 203 | 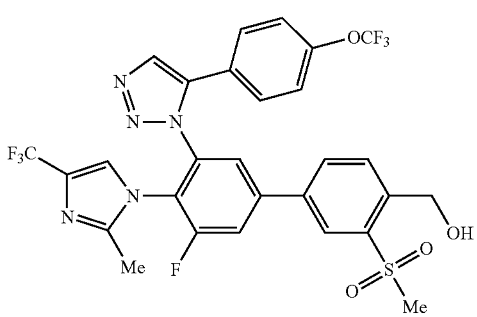 [SMILES: Cc1nc(C(F)(F)F)cn1-c1c(F)cc(-c2ccc(CO)c(S(C)(=O)=O)c2)cc1-n1nncc1-c1ccc(OC(F)(F)F)cc1] | [3'-fluoro-3-(methylsulfonyl)-4'-[2-methyl-4-(trifluoromethyl)-1H-imidazol-1-yl]-5'-(5-{4-[(trifluoromethyl)oxy]phenyl}-1H-1,2,3-triazol-1-yl)biphenyl-4-yl]methanol |

| Ex # | Structure | Name |
|---|---|---|
| 204 | 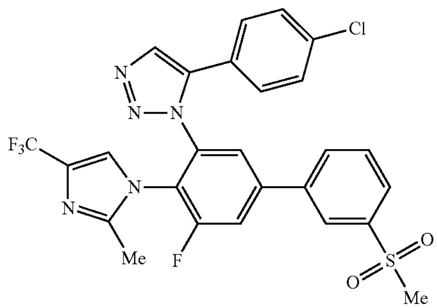 [SMILES: Cc1nc(C(F)(F)F)cn1-c1c(F)cc(-c2cccc(S(C)(=O)=O)c2)cc1-n1nncc1-c1ccc(Cl)cc1] | 5-(4-chlorophenyl)-1-{5-fluoro-3'-(methylsulfonyl)-4-[2-methyl-4-(trifluoromethyl)-1H-imidazol-1-yl]biphenyl-3-yl}-1H-1,2,3-triazole |
| 205 | 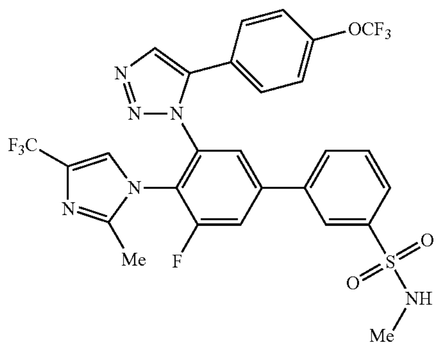 [SMILES: CNS(=O)(=O)c1cccc(-c2cc(F)c(-n3cc(C(F)(F)F)nc3C)c(-n3nncc3-c3ccc(OC(F)(F)F)cc3)c2)c1] | 3'-fluoro-N-methyl-4'-[2-methyl-4-(trifluoromethyl)-1H-imidazol-1-yl]-5'-(5-{4-[(trifluoromethyl)oxy]phenyl}-1H-1,2,3-triazol-1-yl)biphenyl-3-sulfonamide |
| 206 | 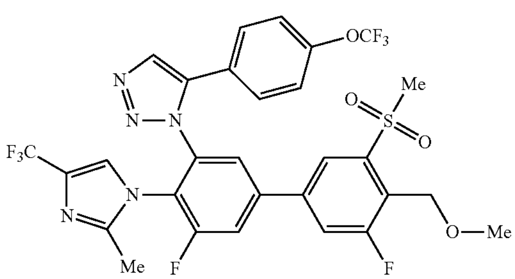 [SMILES: COCc1c(F)cc(-c2cc(F)c(-n3cc(C(F)(F)F)nc3C)c(-n3nncc3-c3ccc(OC(F)(F)F)cc3)c2)cc1S(C)(=O)=O] | 1-{3',5-difluoro-4'-[(methyloxy)methyl]-5'-(methylsulfonyl)-4-[2-methyl-4-(trifluoromethyl)-1H-imidazol-1-yl]biphenyl-3-yl}-5-{4-[(trifluoromethyl)oxy]phenyl}-1H-1,2,3-triazole |
| 207 | 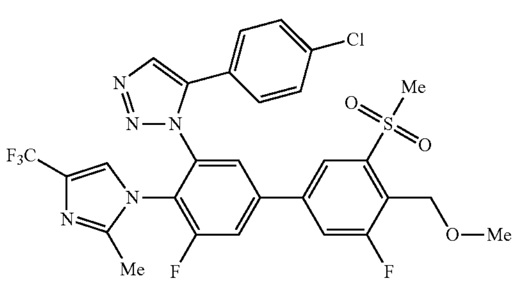 [SMILES: COCc1c(F)cc(-c2cc(F)c(-n3cc(C(F)(F)F)nc3C)c(-n3nncc3-c3ccc(Cl)cc3)c2)cc1S(C)(=O)=O] | 5-(4-chlorophenyl)-1-{3',5-difluoro-4'-[(methyloxy)methyl]-5'-(methylsulfonyl)-4-[2-methyl-4-(trifluoromethyl)-1H-imidazol-1-yl]biphenyl-3-yl}-1H-1,2,3-triazole |

-continued

| Ex # | Structure | Name |
|---|---|---|
| 208 | 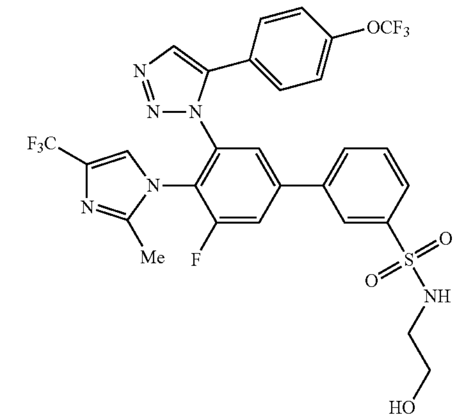 [SMILES: Cc1nc(C(F)(F)F)cn1-c1c(F)cc(-c2cccc(S(=O)(=O)NCCO)c2)cc1-n1nncc1-c1ccc(OC(F)(F)F)cc1] | 3'-fluoro-N-(2-hydroxyethyl)-4'-[2-methyl-4-(trifluoromethyl)-1H-imidazol-1-yl]-5'-(5-{4-[(trifluoromethyl)oxy]phenyl}-1H-1,2,3-triazol-1-yl)biphenyl-3-sulfonamide |
| 209 | 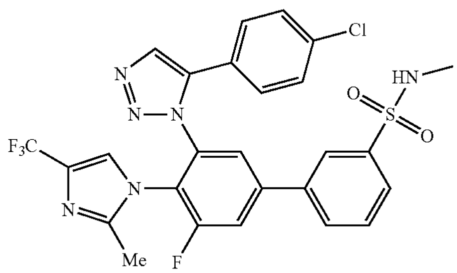 [SMILES: CNS(=O)(=O)c1cccc(-c2cc(F)c(-n3cc(C(F)(F)F)nc3C)c(-n3nncc3-c3ccc(Cl)cc3)c2)c1] | 3'-[5-(4-chlorophenyl)-1H-1,2,3-triazol-1-yl]-5'-fluoro-N-methyl-4'-[2-methyl-4-(trifluoromethyl)-1H-imidazol-1-yl]biphenyl-3-sulfonamide |
| 210 | 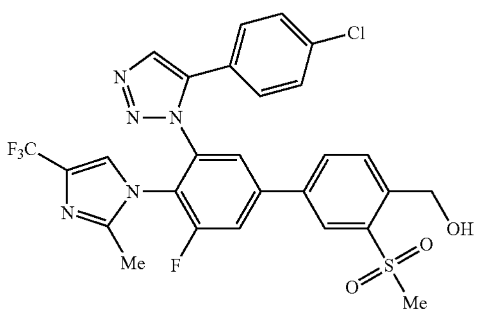 [SMILES: Cc1nc(C(F)(F)F)cn1-c1c(F)cc(-c2ccc(CO)c(S(C)(=O)=O)c2)cc1-n1nncc1-c1ccc(Cl)cc1] | {3'-[5-(4-chlorophenyl)-1H-1,2,3-triazol-1-yl]-5'-fluoro-3-(methylsulfonyl)-4'-[2-methyl-4-(trifluoromethyl)-1H-imidazol-1-yl]biphenyl-4-yl}methanol |
| 211 | 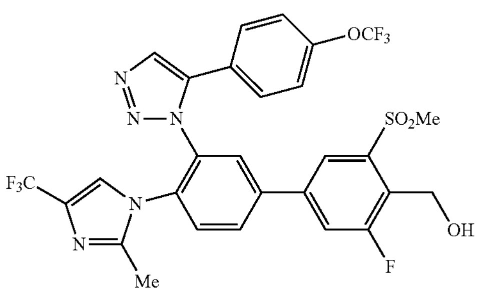 | (3-fluoro-4'-(2-methyl-4-(trifluoromethyl)-1H-imidazol-1-yl)-5-(methylsulfonyl)-3'-(5-(4-(trifluoromethoxy)phenyl)-1H-1,2,3-triazol-1-yl)-[1,1'-biphenyl]-4-yl)methanol |
| 212 | 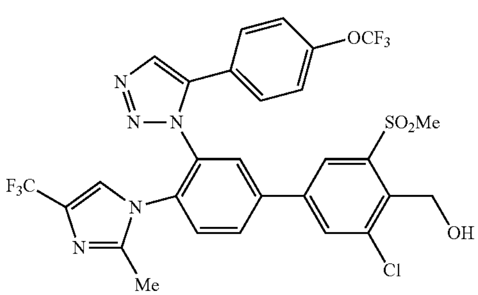 [SMILES: Cc1nc(C(F)(F)F)cn1-c1ccc(-c2cc(F)c(CO)c(S(C)(=O)=O)c2)cc1-n1nncc1-c1ccc(OC(F)(F)F)cc1] | (3-chloro-4'-(2-methyl-4-(trifluoromethyl)-1H-imidazol-1-yl)-5-(methylsulfonyl)-3'-(5-(4-(trifluoromethoxy)phenyl)-1H-1,2,3-triazol-1-yl)-[1,1'-biphenyl]-4-yl)methanol |

| Ex # | Structure | Name |
|---|---|---|
| 213 | 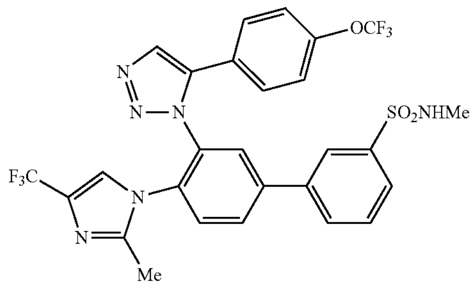 | N-methyl-4'-(2-methyl-4-(trifluoromethyl)-1H-imidazol-1-yl)-3'-(5-(4-(trifluoromethoxy)phenyl)-1H-1,2,3-triazol-1-yl)-[1,1'-biphenyl]-3-sulfonamide |
| 214 | 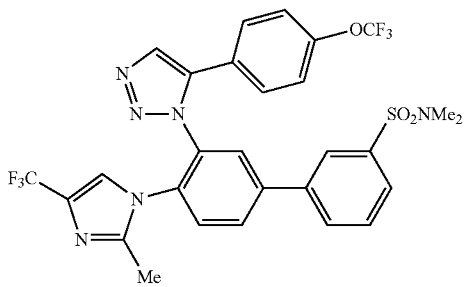 | N,N-dimethyl-4'-(2-methyl-4-(trifluoromethyl)-1H-imidazol-1-yl)-3'-(5-(4-(trifluoromethoxy)phenyl)-1H-1,2,3-triazol-1-yl)-[1,1'-biphenyl]-3-sulfonamide |
| 215 | 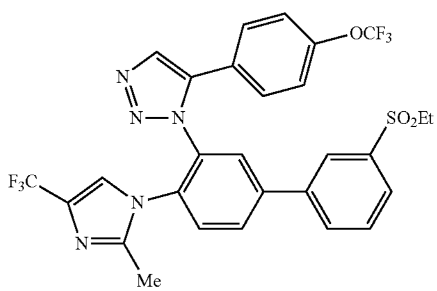 | 1-(3'-(ethylsulfonyl)-4-(2-methyl-4-(trifluoromethyl)-1H-imidazol-1-yl)-[1,1'-biphenyl]-3-yl)-5-(4-(trifluoromethoxy)phenyl)-1H-1,2,3-triazole |
| 216 | 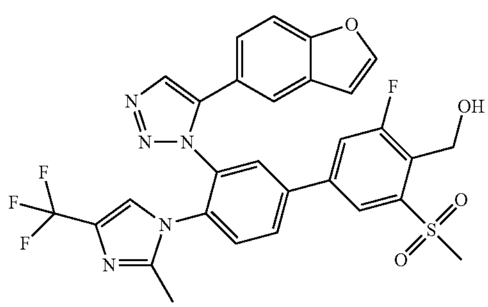 [SMILES: Cc1nc(C(F)(F)F)cn1-c1ccc(-c2cc(F)c(CO)c(S(C)(=O)=O)c2)cc1-n1nncc1-c1ccc2occc2c1] | (3'-(5-(benzofuran-5-yl)-1H-1,2,3-triazol-1-yl)-3-fluoro-4'-(2-methyl-4-(trifluoromethyl)-1H-imidazol-1-yl)-5-(methylsulfonyl)-[1,1'-biphenyl]-4-yl)methanol |
| 219 | 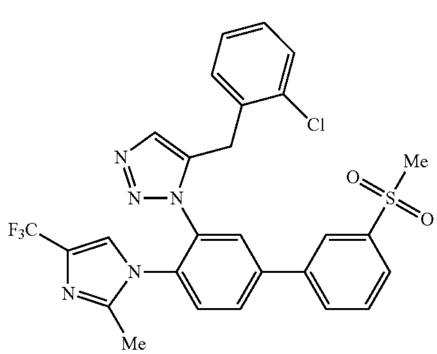 [SMILES: Cc1nc(C(F)(F)F)cn1-c1ccc(-c2cccc(S(C)(=O)=O)c2)cc1-n1nncc1Cc1ccccc1Cl] | 5-(2-chlorobenzyl)-1-(4-(2-methyl-4-(trifluoromethyl)-1H-imidazol-1-yl)-3'-(methylsulfonyl)-[1,1'-biphenyl]-3-yl)-1H-1,2,3-triazole |

-continued

| Ex # | Structure | Name |
|------|-----------|------|
| 220 | 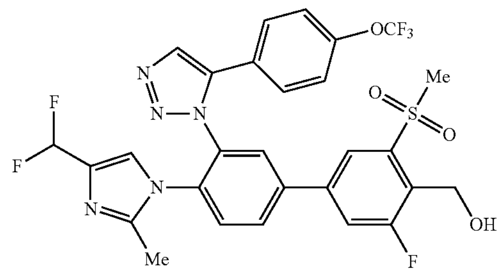 | (4'-(4-(difluoromethyl)-2-methyl-1H-imidazol-1-yl)-3-fluoro-5-(methylsulfonyl)-3'-(5-(4-(trifluoromethoxy)phenyl)-1H-1,2,3-triazol-1-yl)-[1,1'-biphenyl]-4-yl)methanol |
| 221 | 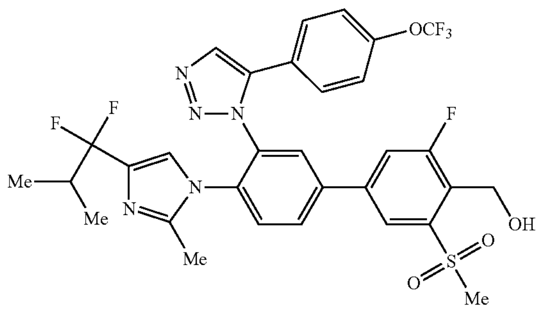 [SMILES: Cc1nc(C(F)(F)C(C)C)cn1-c1ccc(-c2cc(F)c(CO)c(S(C)(=O)=O)c2)cc1-n1nncc1-c1ccc(OC(F)(F)F)cc1] | (4'-(4-(1,1-difluoro-2-methylpropyl)-2-methyl-1H-imidazol-1-yl)-3-fluoro-5-(methylsulfonyl)-3'-(5-(4-(trifluoromethoxy)phenyl)-1H-1,2,3-triazol-1-yl)-[1,1'-biphenyl]-4-yl)methanol |
| 222 | 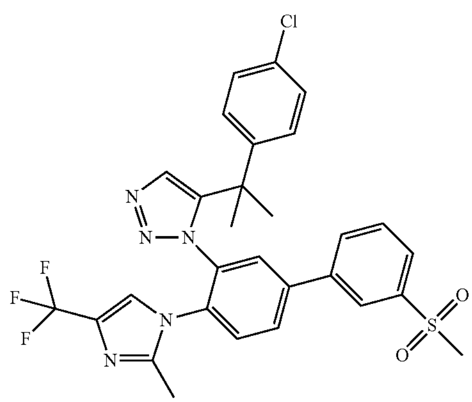 | 5-(2-(4-chlorophenyl)propan-2-yl)-1-(4-(2-methyl-4-(trifluoromethyl)-1H-imidazol-1-yl)-3'-(methylsulfonyl)-[1,1'-biphenyl]-3-yl)-1H-1,2,3-triazole |
| 223 | 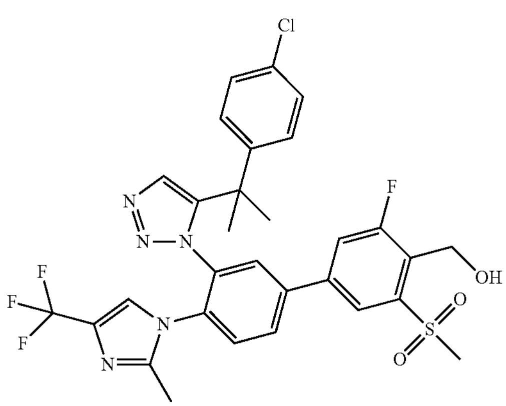 [SMILES: Cc1nc(C(F)(F)F)cn1-c1ccc(-c2cc(F)c(CO)c(S(C)(=O)=O)c2)cc1-n1nncc1C(C)(C)c1ccc(Cl)cc1] | (3'-(5-(2-(4-chlorophenyl)propan-2-yl)-1H-1,2,3-triazol-1-yl)-3-fluoro-4'-(2-methyl-4-(trifluoromethyl)-1H-imidazol-1-yl)-5-(methylsulfonyl)-[1,1'-biphenyl]-4-yl)methanol |

| Ex # | Structure | Name |
|---|---|---|
| 224 | 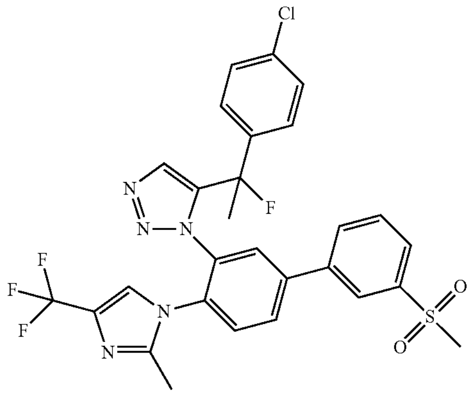 [SMILES: Cc1nc(C(F)(F)F)cn1-c1ccc(-c2cccc(S(C)(=O)=O)c2)cc1-n1nncc1C(C)(F)c1ccc(Cl)cc1] | 5-(1-(4-chlorophenyl)-1-fluoroethyl)-1-(4-(2-methyl-4-(trifluoromethyl)-1H-imidazol-1-yl)-3'-(methylsulfonyl)-[1,1'-biphenyl]-3-yl)-1H-1,2,3-triazole |
| 225 | 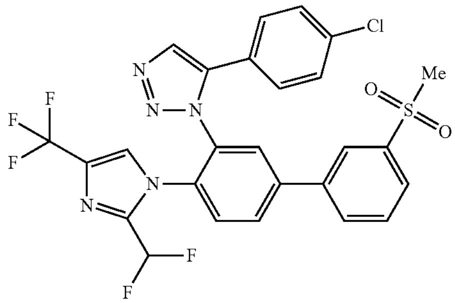 [SMILES: CS(=O)(=O)c1cccc(-c2ccc(-n3cc(C(F)(F)F)nc3C(F)F)c(-n3nncc3-c3ccc(Cl)cc3)c2)c1] | 5-(4-chlorophenyl)-1-(4-(2-(difluoromethyl)-4-(trifluoromethyl)-1H-imidazol-1-yl)-3'-(methylsulfonyl)-[1,1'-biphenyl]-3-yl)-1H-1,2,3-triazole |
| 226 | 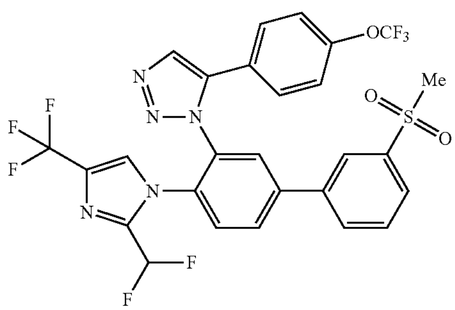 [SMILES: CS(=O)(=O)c1cccc(-c2ccc(-n3cc(C(F)(F)F)nc3C(F)F)c(-n3nncc3-c3ccc(OC(F)(F)F)cc3)c2)c1] | 1-(4-(2-(difluoromethyl)-4-(trifluoromethyl)-1H-imidazol-1-yl)-3'-(methylsulfonyl)-[1,1'-biphenyl]-3-yl)-5-(4-(trifluoromethoxy)phenyl)-1H-1,2,3-triazole |
| 227 | 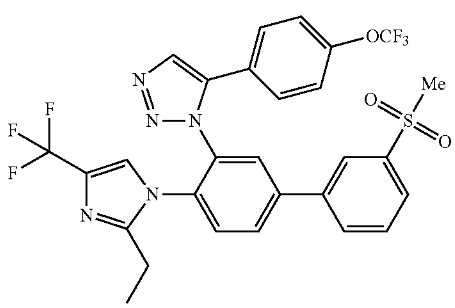 [SMILES: CCc1nc(C(F)(F)F)cn1-c1ccc(-c2cccc(S(C)(=O)=O)c2)cc1-n1nncc1-c1ccc(OC(F)(F)F)cc1] | 1-(4-(2-ethyl-4-(trifluoromethyl)-1H-imidazol-1-yl)-3'-(methylsulfonyl)-[1,1'-biphenyl]-3-yl)-5-(4-(trifluoromethoxy)phenyl)-1H-1,2,3-triazole |
| 228 | 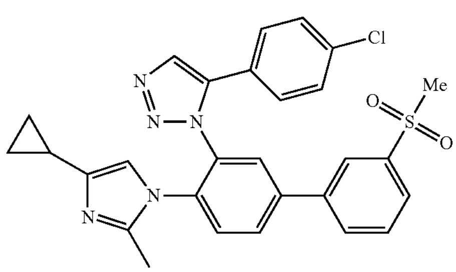 [SMILES: Cc1nc(C2CC2)cn1-c1ccc(-c2cccc(S(C)(=O)=O)c2)cc1-n1nncc1-c1ccc(Cl)cc1] | 5-(4-chlorophenyl)-1-(4-(4-cyclopropyl-2-methyl-1H-imidazol-1-yl)-3'-(methylsulfonyl)-[1,1'-biphenyl]-3-yl)-1H-1,2,3-triazole |

| Ex # | Structure | Name |
|---|---|---|
| 229 | 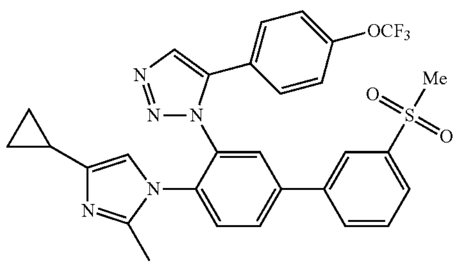 [SMILES: Cc1nc(C2CC2)cn1-c1ccc(-c2cccc(S(C)(=O)=O)c2)cc1-n1nncc1-c1ccc(OC(F)(F)F)cc1] | 1-(4-(4-cyclopropyl-2-methyl-1H-imidazol-1-yl)-3'-(methylsulfonyl)-[1,1'-biphenyl]-3-yl)-5-(4-(trifluoromethoxy)phenyl)-1H-1,2,3-triazole |
| 230 | 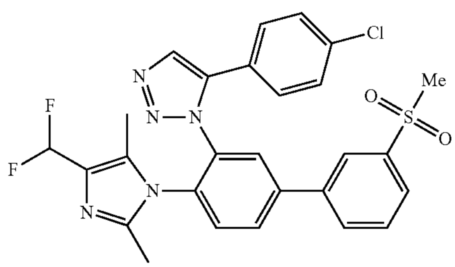 [SMILES: Cc1nc(C(F)F)c(C)n1-c1ccc(-c2cccc(S(C)(=O)=O)c2)cc1-n1nncc1-c1ccc(Cl)cc1] | 5-(4-chlorophenyl)-1-(4-(4-(difluoromethyl)-2,5-dimethyl-1H-imidazol-1-yl)-3'-(methylsulfonyl)-[1,1'-biphenyl]-3-yl)-1H-1,2,3-triazole |
| 231 | 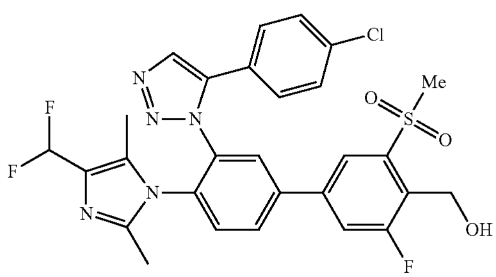 [SMILES: Cc1nc(C(F)F)c(C)n1-c1ccc(-c2cc(F)c(CO)c(S(C)(=O)=O)c2)cc1-n1nncc1-c1ccc(Cl)cc1] | (3'-(5-(4-chlorophenyl)-1H-1,2,3-triazol-1-yl)-4'-(4-(difluoromethyl)-2,5-dimethyl-1H-imidazol-1-yl)-3-fluoro-5-(methylsulfonyl)-[1,1'-biphenyl]-4-yl)methanol |
| 232 | 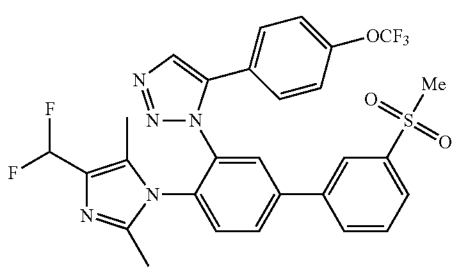 [SMILES: Cc1nc(C(F)F)c(C)n1-c1ccc(-c2cccc(S(C)(=O)=O)c2)cc1-n1nncc1-c1ccc(OC(F)(F)F)cc1] | 1-(4-(4-(difluoromethyl)-2,5-dimethyl-1H-imidazol-1-yl)-3'-(methylsulfonyl)-[1,1'-biphenyl]-3-yl)-5-(4-(trifluoromethoxy)phenyl)-1H-1,2,3-triazole |
| 233 | 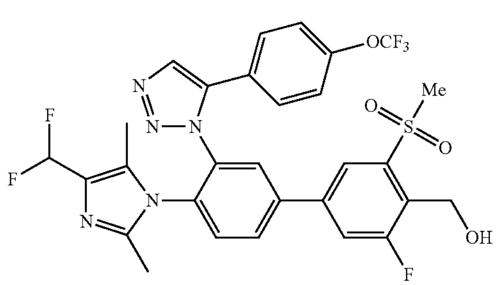 | (4'-(4-(difluoromethyl)-2,5-dimethyl-1H-imidazol-1-yl)-3-fluoro-5-methylsulfonyl)-3'-(5-(4-(trifluoromethoxy)phenyl)-1H-1,2,3-triazol-1-yl)-[1,1'-biphenyl]-4-yl)methanol |

| Ex # | Structure | Name |
|---|---|---|
| 234 | 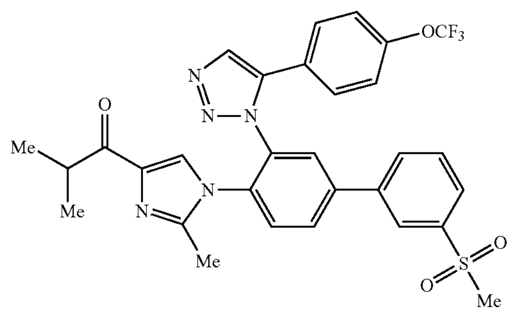 [SMILES: Cc1nc(C(=O)C(C)C)cn1-c1ccc(-c2cccc(S(C)(=O)=O)c2)cc1-n1nncc1-c1ccc(OC(F)(F)F)cc1] | 2-methyl-1-(2-methyl-1-(3'-(methylsulfonyl)-3-(5-(4-(trifluoromethoxy)phenyl)-1H-1,2,3-triazol-1-yl)-[1,1'-biphenyl]-4-yl)-1H-imidazol-4-yl)propan-1-one |
| 235 | 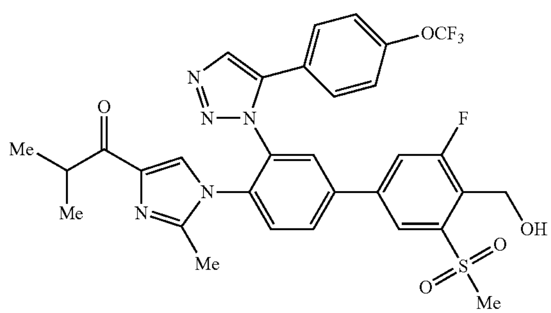 [SMILES: Cc1nc(C(=O)C(C)C)cn1-c1ccc(-c2cc(F)c(CO)c(S(C)(=O)=O)c2)cc1-n1nncc1-c1ccc(OC(F)(F)F)cc1] | 1-(1-(3'-fluoro-4'-(hydroxymethyl)-5'-(methylsulfonyl)-3-(5-(4-(trifluoromethoxy)phenyl)-1H-1,2,3-triazol-1-yl)-[1,1'-biphenyl]-4-yl)-2-methyl-1H-imidazol-4-yl)-2-methylpropan-1-one |
| 236 | 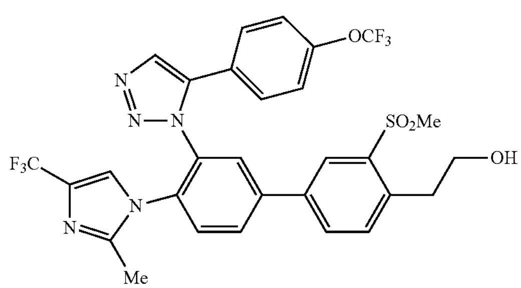 [SMILES: Cc1nc(C(F)(F)F)cn1-c1ccc(-c2ccc(CCO)c(S(C)(=O)=O)c2)cc1-n1nncc1-c1ccc(OC(F)(F)F)cc1] | 2-(4'-(2-methyl-4-(trifluoromethyl)-1H-imidazol-1-yl)-3-(methylsulfonyl)-3'-(5-(4-(trifluoromethoxy)phenyl)-1H-1,2,3-triazol-1-yl)-[1,1'-biphenyl]-4-yl)ethanol |
| 237 | 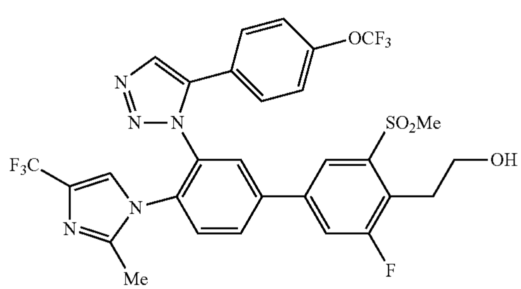 [SMILES: Cc1nc(C(F)(F)F)cn1-c1ccc(-c2cc(F)c(CCO)c(S(C)(=O)=O)c2)cc1-n1nncc1-c1ccc(OC(F)(F)F)cc1] | 2-(3-fluoro-4'-(2-methyl-4-(trifluoromethyl)-1H-imidazol-1-yl)-5-(methylsulfonyl)-3'-(5-(4-(trifluoromethoxy)phenyl)-1H-1,2,3-triazol-1-yl)-[1,1'-biphenyl]-4-yl)ethanol |
| 238 | 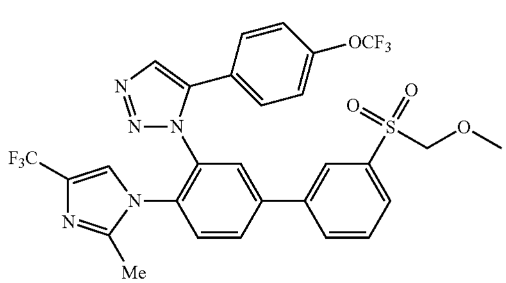 [SMILES: COCS(=O)(=O)c1cccc(-c2ccc(-n3cc(C(F)(F)F)nc3C)c(-n3nncc3-c3ccc(OC(F)(F)F)cc3)c2)c1] | 1-(3'-((methoxymethyl)sulfonyl)-4-(2-methyl-4-(trifluoromethyl)-1H-imidazol-1-yl)-[1,1'-biphenyl]-3-yl)-5-(4-(trifluoromethoxy)phenyl)-1H-1,2,3-triazole |

-continued

| Ex # | Structure | Name |
|---|---|---|
| 241 | 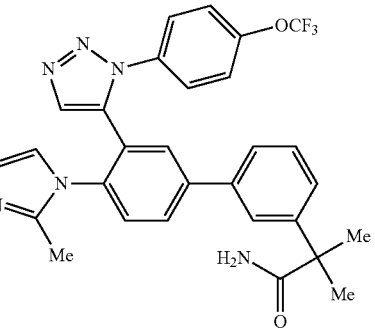 | 2-methyl-2-{4'-[2-methyl-4-(trifluoromethyl)-1H-imidazol-1-yl]-3'-(1-{4-[(trifluoromethyl)oxy]phenyl}-1H-1,2,3-triazol-5-yl)biphenyl-3-yl}propanamide |
| 242 | 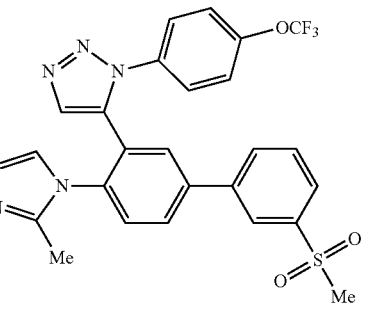 | 5-{3'-(methylsulfonyl)-4-[2-methyl-4-(trifluoromethyl)-1H-imidazol-1-yl]biphenyl-3-yl}-1-{4-[(trifluoromethyl)oxy]phenyl}-1H-1,2,3-triazole |
| 243 | 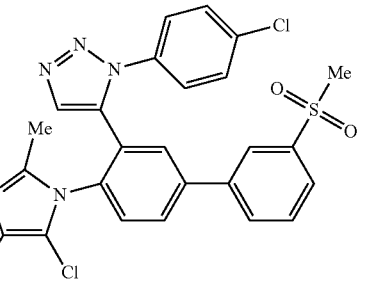 | 5-{4-[5-chloro-2-methyl-4-(trifluoromethyl)-1H-imidazol-1-yl]-3'-(methylsulfonyl)biphenyl-3-yl}-1-(4-chlorophenyl)-1H-1,2,3-triazole |
| 244 | 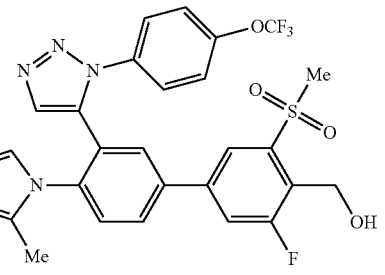 | [3-fluoro-5-(methylsulfonyl)-4'-[2-methyl-4-(trifluoromethyl)-1H-imidazol-1-yl]-3'-(1-{4-[(trifluoromethyl)oxy]phenyl}-1H-1,2,3-triazol-5-yl)biphenyl-4-yl]methanol |
| 245 | 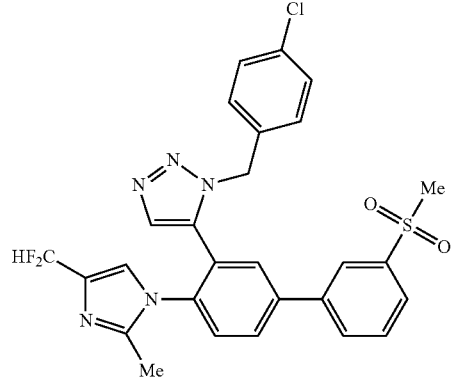 | 1-(4-chlorobenzyl)-5-(4-(4-(difluoromethyl)-2-methyl-1H-imidazol-1-yl)-3'-(methylsulfonyl)-[1,1'-biphenyl]-3-yl)-1H-1,2,3-triazole |

| Ex # | Structure | Name |
|---|---|---|
| 246 | 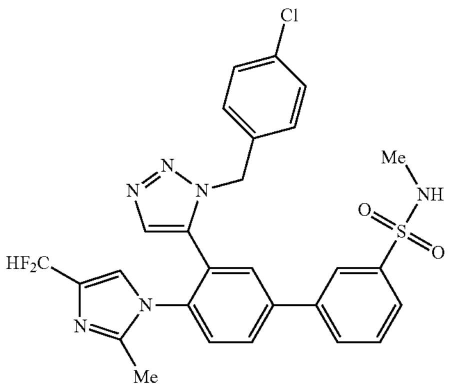 | 3'-(1-(4-chlorobenzyl)-1H-1,2,3-triazol-5-yl)-4'-(4-(difluoromethyl)-2-methyl-1H-imidazol-1-yl)-N-methyl-[1,1'-biphenyl]-3-sulfonamide |
| 247 | 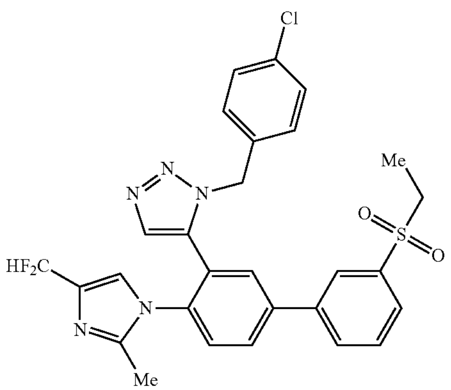 | 1-(4-chlorobenzyl)-5-(4-(4-(difluoromethyl)-2-methyl-1H-imidazol-1-yl)-3'-(ethylsulfonyl)-[1,1'-biphenyl]-3-yl)-1H-1,2,3-triazole |
| 248 | 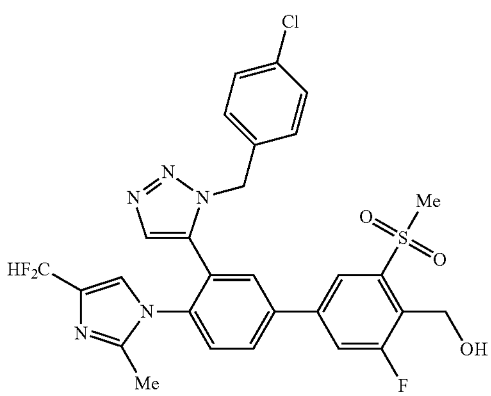 | (3'-(1-(4-chlorobenzyl)-1H-1,2,3-triazol-5-yl)-4'-(4-(difluoromethyl)-2-methyl-1H-imidazol-1-yl)-3-fluoro-5-(methylsulfonyl)-[1,1'-biphenyl]-4-yl)methanol |
| 286 | 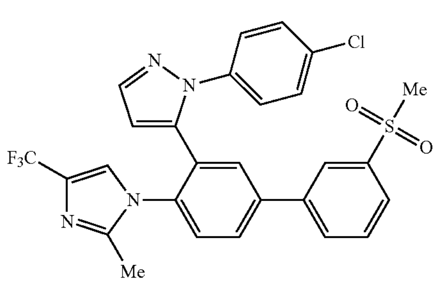 [SMILES: Cc1nc(C(F)(F)F)cn1-c1ccc(-c2cccc(S(C)(=O)=O)c2)cc1-c1ccnn1-c1ccc(Cl)cc1] | 1-(4-chlorophenyl)-5-{3'-(methylsulfonyl)-4-[2-methyl-4-(trifluoromethyl)-1H-imidazol-1-yl]biphenyl-3-yl}-1H-pyrazole |

-continued

| Ex # | Structure | Name |
|---|---|---|
| 287 | 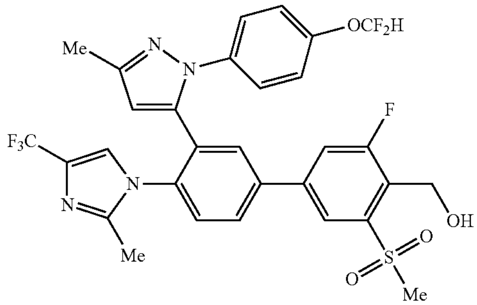 | (3'-(1-(4-(difluoromethoxy)phenyl)-3-methyl-1H-pyrazol-5-yl)-3-fluoro-4'-(2-methyl-4-(trifluoromethyl)-1H-imidazol-1-yl)-5-(methylsulfonyl)biphenyl-4-yl)methanol |
| 288 | 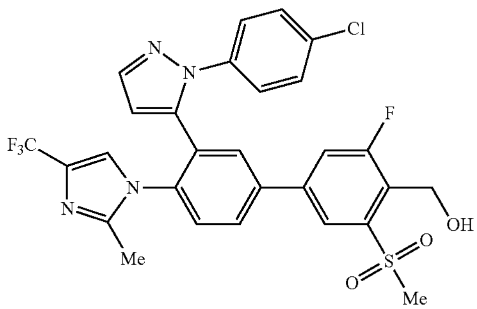 [SMILES: Cc1nc(C(F)(F)F)cn1-c1ccc(-c2cc(F)c(CO)c(S(C)(=O)=O)c2)cc1-c1ccnn1-c1ccc(Cl)cc1] | {3'-[1-(4-chlorophenyl)-1H-pyrazol-5-yl]-3-fluoro-5-(methylsulfonyl)-4'-[2-methyl-4-(trifluoromethyl)-1H-imidazol-1-yl]biphenyl-4-yl}methanol |
| 289 | 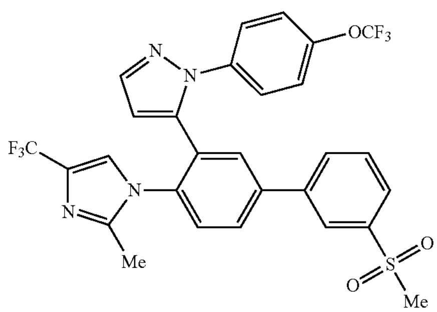 [SMILES: Cc1nc(C(F)(F)F)cn1-c1ccc(-c2cccc(S(C)(=O)=O)c2)cc1-c1ccnn1-c1ccc(OC(F)(F)F)cc1] | 5-{3'-(methylsulfonyl)-4-[2-methyl-4-(trifluoromethyl)-1H-imidazol-1-yl]biphenyl-3-yl}-1-{4-[(trifluoromethyl)oxy]phenyl}-1H-pyrazole |
| 290 | 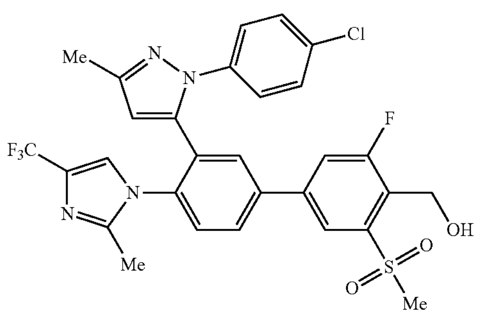 [SMILES: Cc1cc(-c2cc(-c3cc(F)c(CO)c(S(C)(=O)=O)c3)ccc2-n2cc(C(F)(F)F)nc2C)n(-c2ccc(Cl)cc2)n1] | {3'-[1-(4-chlorophenyl)-3-methyl-1H-pyrazol-5-yl}-3-fluoro-5-(methylsulfonyl)-4'-[2-methyl-4-(trifluoromethyl)-1H-imidazol-1-yl]biphenyl-4-yl}methanol |
| 291 | 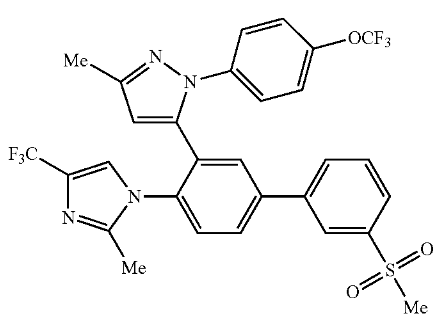 [SMILES: Cc1cc(-c2cc(-c3cccc(S(C)(=O)=O)c3)ccc2-n2cc(C(F)(F)F)nc2C)n(-c2ccc(OC(F)(F)F)cc2)n1] | 3-methyl-5-{3'-(methylsulfonyl)-4-[2-methyl-4-(trifluoromethyl)-1H-imidazol-1-yl]biphenyl-3-yl}-1-{4-[(trifluoromethyl)oxy]phenyl}-1H-pyrazole |

| Ex # | Structure | Name |
|---|---|---|
| 292 | 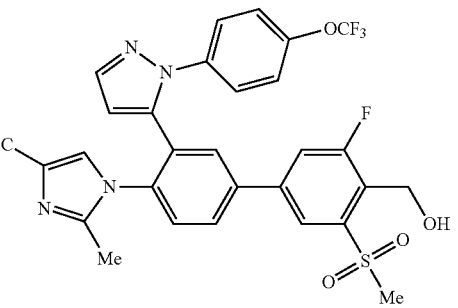 | [3-fluoro-5-(methylsulfonyl)-4'-[2-methyl-4-(trifluoromethyl)-1H-imidazol-1-yl]-3'-(1-{4-[(trifluoromethyl)oxy]phenyl}-1H-pyrazol-5-yl)biphenyl-4-yl]methanol |
| 293 | 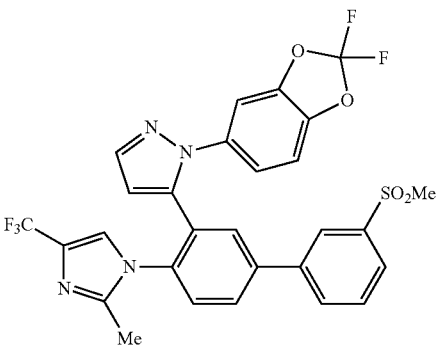 [SMILES: Cc1nc(C(F)(F)F)cn1-c1ccc(-c2cccc(S(C)(=O)=O)c2)cc1-c1ccnn1-c1ccc2c(c1)OC(F)(F)O2] | 1-(2,2-difluorobenzo[d][1,3]dioxol-5-yl)-5-(4-(2-methyl-4-(trifluoromethyl)-1H-imidazol-1-yl)-3'-(methylsulfonyl)biphenyl-3-yl)-1H-pyrazole |
| 294 | 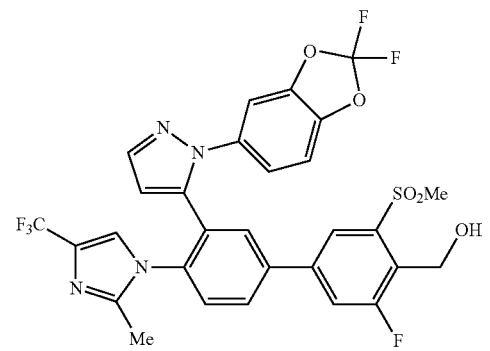 [SMILES: Cc1nc(C(F)(F)F)cn1-c1ccc(-c2cc(F)c(CO)c(S(C)(=O)=O)c2)cc1-c1ccnn1-c1ccc2c(c1)OC(F)(F)O2] | (3'-(1-(2,2-difluorobenzo[d][1,3]dioxol-5-yl)-1H-pyrazol-5-yl)-3-fluoro-4'-(2-methyl-4-(trifluoromethyl)-1H-imidazol-1-yl)-5-(methylsulfonyl)biphenyl-4-yl)methanol |
| 295 | 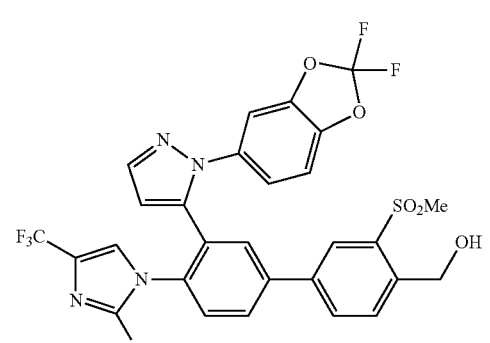 | (3'-(1-(2,2-difluorobenzo[d][1,3]dioxol-5-yl)-1H-pyrazol-5-yl)-4'-(2-methyl-4-(trifluoromethyl)-1H-imidazol-1-yl)-3-(methylsulfonyl)biphenyl-4-yl)methanol |

| Ex # | Structure | Name |
|---|---|---|
| 296 | 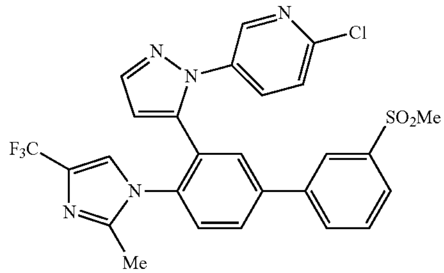 [SMILES: Cc1nc(C(F)(F)F)cn1-c1ccc(-c2cccc(S(C)(=O)=O)c2)cc1-c1ccnn1-c1ccc(Cl)nc1] | 2-chloro-5-(5-(4-(2-methyl-4-(trifluoromethyl)-1H-imidazol-1-yl)-3'-(methylsulfonyl)biphenyl-3-yl)-1H-pyrazol-1-yl)pyridine |
| 297 | 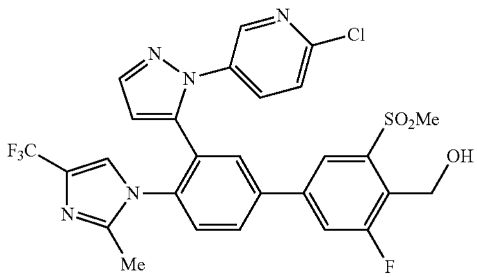 [SMILES: Cc1nc(C(F)(F)F)cn1-c1ccc(-c2cc(F)c(CO)c(S(C)(=O)=O)c2)cc1-c1ccnn1-c1ccc(Cl)nc1] | (3'-(1-(6-chloropyridin-3-yl)-1H-pyrazol-5-yl)-3-fluoro-4'-(2-methyl-4-(trifluoromethyl)-1H-imidazol-1-yl)-5-(methylsulfonyl)biphenyl-4-yl)methanol |
| 298 | 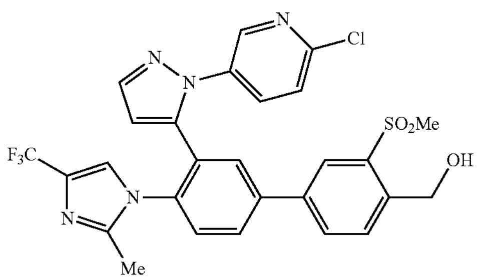 [SMILES: Cc1nc(C(F)(F)F)cn1-c1ccc(-c2ccc(CO)c(S(C)(=O)=O)c2)cc1-c1ccnn1-c1ccc(Cl)nc1] | (3'-(1-(6-chloropyridin-3-yl)-1H-pyrazol-5-yl)-4'-(2-methyl-4-(trifluoromethyl)-1H-imidazol-1-yl)-3-(methylsulfonyl)biphenyl-4-yl)methanol |
| 299 | 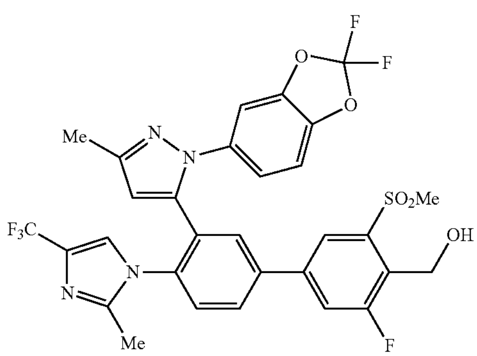 [SMILES: Cc1cc(-c2cc(-c3cc(F)c(CO)c(S(C)(=O)=O)c3)ccc2-n2cc(C(F)(F)F)nc2C)n(-c2ccc3c(c2)OC(F)(F)O3)n1] | (3'-(1-(2,2-difluorobenzo[d][1,3]dioxol-5-yl)-3-methyl-1H-pyrazol-5-yl)-3-fluoro-4'-(2-methyl-4-(trifluoromethyl)-1H-imidazol-1-yl)-5-(methylsulfonyl)biphenyl-4-yl)methanol |
| 300 | 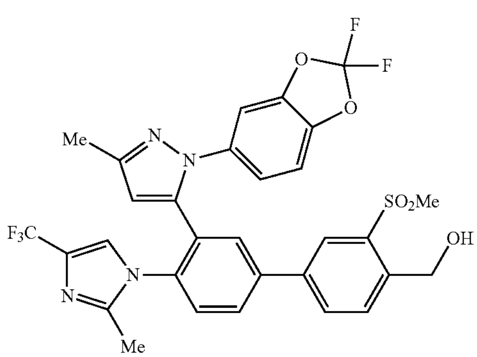 [SMILES: Cc1cc(-c2cc(-c3ccc(CO)c(S(C)(=O)=O)c3)ccc2-n2cc(C(F)(F)F)nc2C)n(-c2ccc3c(c2)OC(F)(F)O3)n1] | (3'-(1-(2,2-difluorobenzo[d][1,3]dioxol-5-yl)-3-methyl-1H-pyrazol-5-yl)-4'-(2-methyl-4-(trifluoromethyl)-1H-imidazol-1-yl)-3-(methylsulfonyl)biphenyl-4-yl)methanol |

-continued

| Ex # | Structure | Name |
|---|---|---|
| 301 | 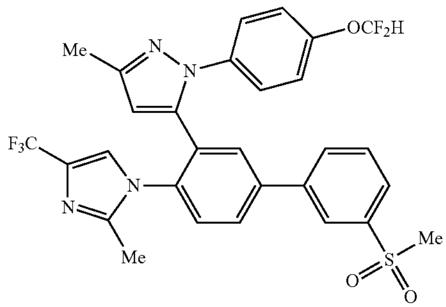 | 1-(4-(difluoromethoxy)phenyl)-3-methyl-5-(4-(2-methyl-4-(trifluoromethyl)-1H-imidazol-1-yl)-3'-(methylsulfonyl)biphenyl-3-yl)-1H-pyrazole |
| 302 | 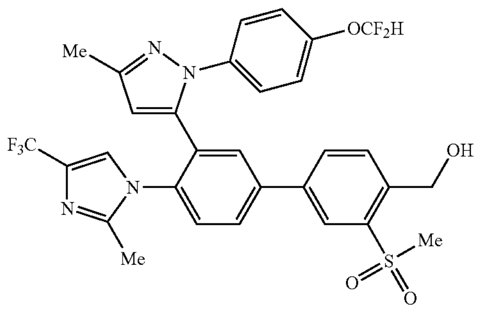 | (3'-(1-(4-(difluoromethoxy)phenyl)-3-methyl-1H-pyrazol-5-yl)-4'-(2-methyl-4-(trifluoromethyl)-1H-imidazol-1-yl)-3-(methylsulfonyl)-[1,1'-biphenyl]-4-yl)methanol |
| 303 | 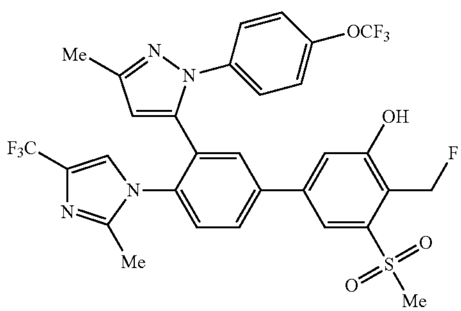 [SMILES: Cc1cc(-c2cc(-c3cc(O)c(CF)c(S(C)(=O)=O)c3)ccc2-n2cc(C(F)(F)F)nc2C)n(-c2ccc(OC(F)(F)F)cc2)n1] | 4-(fluoromethyl)-3'-(3-methyl-1-(4-(trifluoromethoxy)phenyl)-1H-pyrazol-5-yl)-4'-(2-methyl-4-(trifluoromethyl)-1H-imidazol-1-yl)-5-(methylsulfonyl)-[1,1'-biphenyl]-3-ol |
| 304 | 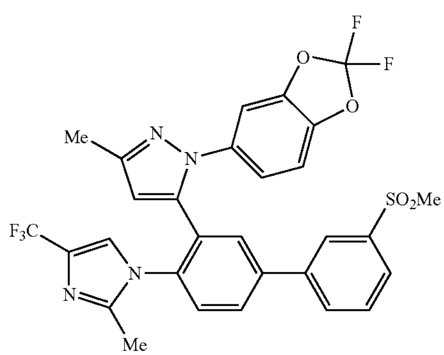 [SMILES: Cc1cc(-c2cc(-c3cccc(S(C)(=O)=O)c3)ccc2-n2cc(C(F)(F)F)nc2C)n(-c2ccc3c(c2)OC(F)(F)O3)n1] | 1-(2,2-difluorobenzo[d][1,3]dioxol-5-yl)-3-methyl-5-(4-(2-methyl-4-(trifluoromethyl)-1H-imidazol-1-yl)-3'-(methylsulfonyl)-[1,1'-biphenyl]-3-yl)-1H-pyrazole |
| 354 | 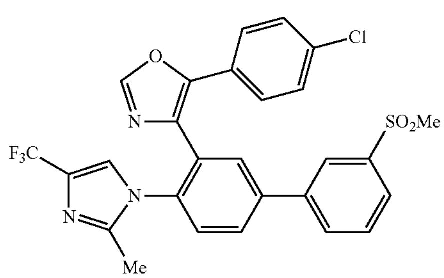 [SMILES: Cc1nc(C(F)(F)F)cn1-c1ccc(-c2cccc(S(C)(=O)=O)c2)cc1-c1ncoc1-c1ccc(Cl)cc1] | 5-(4-chlorophenyl)-4-{3'-(methylsulfonyl)-4-[2-methyl-4-(trifluoromethyl)-1H-imidazol-1-yl]biphenyl-3-yl}-1,3-oxazole |

| Ex # | Structure | Name |
|---|---|---|
| 355 | 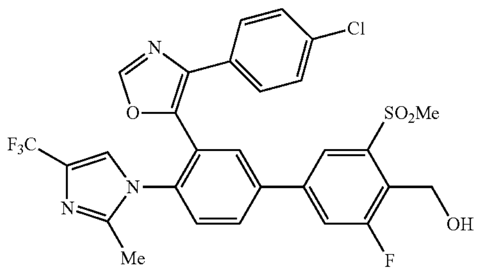 [SMILES: Cc1nc(C(F)(F)F)cn1-c1ccc(-c2cc(F)c(CO)c(S(C)(=O)=O)c2)cc1-c1ocnc1-c1ccc(Cl)cc1] | {3'-[4-(4-chlorophenyl)-1,3-oxazol-5-yl]-3-fluoro-5-(methylsulfonyl)-4'-[2-methyl-4-(trifluoromethyl)-1H-imidazol-1-yl]biphenyl-4-yl}methanol |
| 356 | 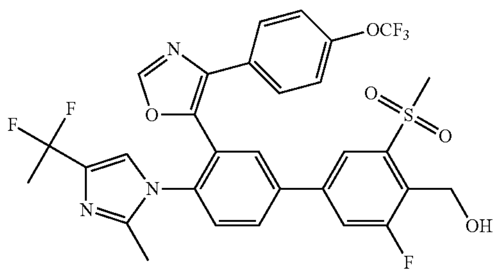 [SMILES: Cc1nc(C(C)(F)F)cn1-c1ccc(-c2cc(F)c(CO)c(S(C)(=O)=O)c2)cc1-c1ocnc1-c1ccc(OC(F)(F)F)cc1] | (4'-(4-(1,1-difluoroethyl)-2-methyl-1H-imidazol-1-yl)-3-fluoro-5-(methylsulfonyl)-3'-(4-(4-(trifluoromethoxy)phenyl)oxazol-5-yl)biphenyl-4-yl)methanol |
| 357 | 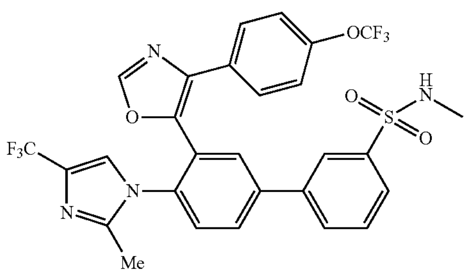 [SMILES: CNS(=O)(=O)c1cccc(-c2ccc(-n3cc(C(F)(F)F)nc3C)c(-c3ocnc3-c3ccc(OC(F)(F)F)cc3)c2)c1] | N-methyl-4'-[2-[2-4-(trifluoromethyl)-1H-imidazol-1-yl]-3'-(4-{4-[(trifluoromethyl)oxy]phenyl}-1,3-oxazol-5-yl)biphenyl-3-sulfonamide |
| 358 | 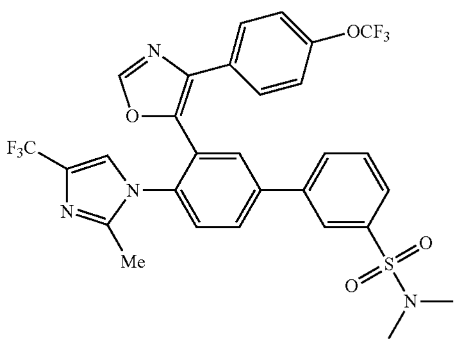 [SMILES: Cc1nc(C(F)(F)F)cn1-c1ccc(-c2cccc(S(=O)(=O)N(C)C)c2)cc1-c1ocnc1-c1ccc(OC(F)(F)F)cc1] | N,N-dimethyl-4'-[2-methyl-4-(trifluoromethyl)-1H-imidazol-1-yl]-3'-(4-{4-[(trifluoromethyl)oxy]phenyl}-1,3-oxazol-5-yl)biphenyl-3-sulfonamide |
| 359 | 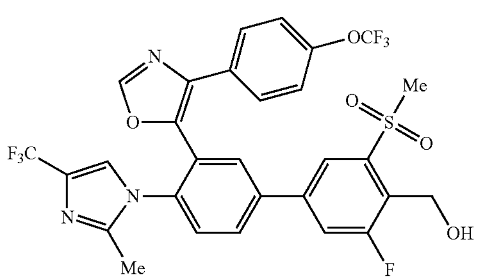 [SMILES: Cc1nc(C(F)(F)F)cn1-c1ccc(-c2cc(F)c(CO)c(S(C)(=O)=O)c2)cc1-c1ocnc1-c1ccc(OC(F)(F)F)cc1] | [3-fluoro-5-(methylsulfonyl)-4'-[2-methyl-4-(trifluoromethyl)-1H-imidazol-1-yl]-3'-(4-{4-[(trifluoromethyl)oxy]phenyl}-1,3-oxazol-5-yl)biphenyl-4-yl]methanol |

| Ex # | Structure | Name |
|---|---|---|
| 360 | 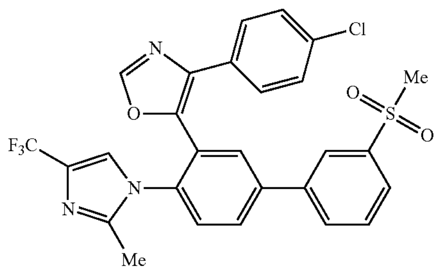 [SMILES: Cc1nc(C(F)(F)F)cn1-c1ccc(-c2cccc(S(C)(=O)=O)c2)cc1-c1ocnc1-c1ccc(Cl)cc1] | 4-(4-chlorophenyl)-5-{3'-(methylsulfonyl)-4-[2-methyl-4-(trifluoromethyl)-1H-imidazol-1-yl]biphenyl-3-yl}-1,3-oxazole |
| 361 | 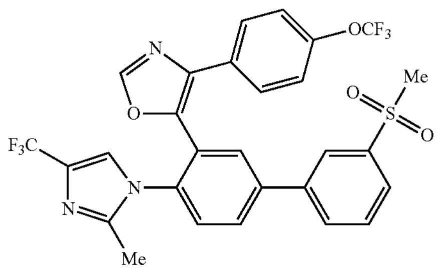 | 5-{3'-(methylsulfonyl)-4-[2-methyl-4-(trifluoromethyl)-1H-imidazol-1-yl]biphenyl-3-yl}-4-{4-[(trifluoromethyl)oxy]phenyl}-1,3-oxazole |
| 362 | 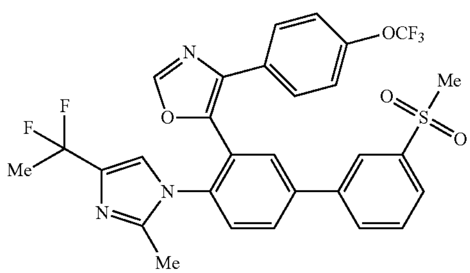 [SMILES: Cc1nc(C(C)(F)F)cn1-c1ccc(-c2cccc(S(C)(=O)=O)c2)cc1-c1ocnc1-c1ccc(OC(F)(F)F)cc1] | 5-{4-[4-(1,1-difluoroethyl)-2-methyl-1H-imidazol-1-yl]-3'-(methylsulfonyl)biphenyl-3-yl}-4-{4-[(trifluoromethyl)oxy]phenyl}-1,3-oxazole |
| 363 | 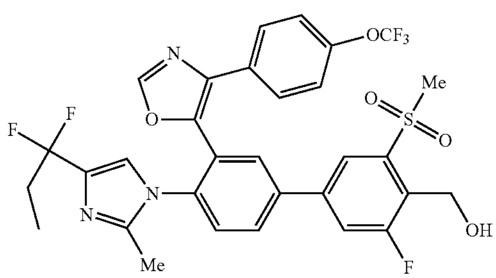 [SMILES: CCC(F)(F)c1cn(-c2ccc(-c3cc(F)c(CO)c(S(C)(=O)=O)c3)cc2-c2ocnc2-c2ccc(OC(F)(F)F)cc2)c(C)n1] | {4'-[4-(1,1-difluoropropyl)-2-methyl-1H-imidazol-1-yl]-3-fluoro-5-(methylsulfonyl)-3'-(4-{4-[(trifluoromethyl)oxy]phenyl}-1,3-oxazol-5-yl)biphenyl-4-yl}methanol |
| 364 | 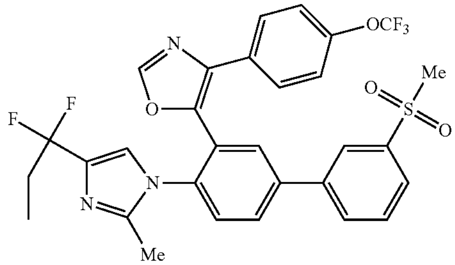 [SMILES: CCC(F)(F)c1cn(-c2ccc(-c3cccc(S(C)(=O)=O)c3)cc2-c2ocnc2-c2ccc(OC(F)(F)F)cc2)c(C)n1] | 5-{4-[4-(1,1-difluoropropyl)-2-methyl-1H-imidazol-1-yl]-3'-(methylsulfonyl)biphenyl-3-yl}-4-{4-[(trifluoromethyl)oxy]phenyl}-1,3-oxazole |

-continued

| Ex # | Structure | Name |
|---|---|---|
| 365 | 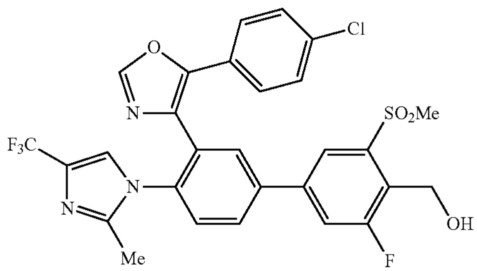 [SMILES: Cc1nc(C(F)(F)F)cn1-c1ccc(-c2cc(F)c(CO)c(S(C)(=O)=O)c2)cc1-c1ncoc1-c1ccc(Cl)cc1] | {3'-[5-(4-chlorophenyl)-1,3-oxazol-4-yl]-3-fluoro-5-(methylsulfonyl)-4'-[2-methyl-4-(trifluoromethyl)-1H-imidazol-1-yl]biphenyl-4-yl}methanol |
| 366 | 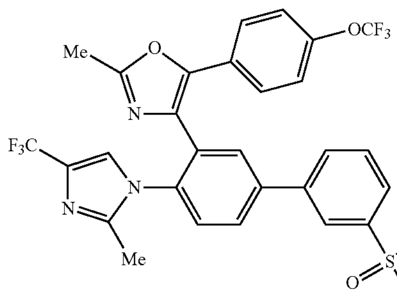 | 2-methyl-4-{3'-(methylsulfonyl)-4-[2-methyl-4-(trifluoromethyl)-1H-imidazol-1-yl]biphenyl-3-yl}-5-{4-[(trifluoromethyl)oxy]phenyl}-1,3-oxazole |
| 367 | 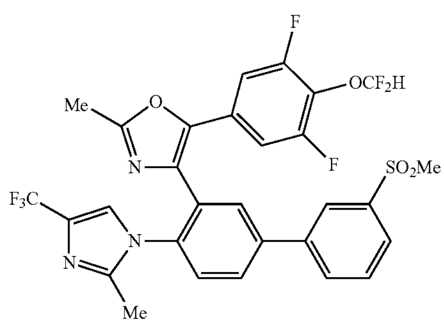 | 5-(4-(difluoromethoxy)-3,5-difluorophenyl)-2-methyl-4-(4-(2-methyl-4-(trifluoromethyl)-1H-imidazol-1-yl)-3'-(methylsulfonyl)-[1,1'-biphenyl]-3-yl)oxazole |
| 368 | 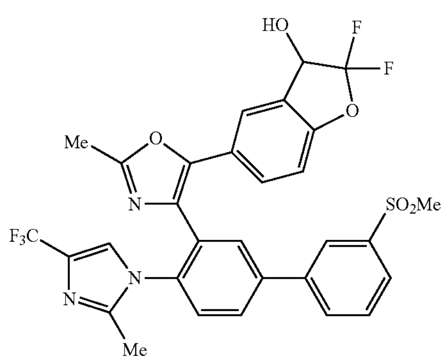 [SMILES: Cc1nc(-c2cc(-c3cccc(S(C)(=O)=O)c3)ccc2-n2cc(C(F)(F)F)nc2C)c(-c2ccc3c(c2)C(O)C(F)(F)O3)o1] | 2,2-difluoro-5-(2-methyl-4-(4-2-methyl-4-(trifluoromethyl)-1H-imidazol-1-yl)-3'-methylsulfonyl)biphenyl-3-yl)oxazol-5-yl)-2,3-dihydrobenzofuran-3-ol |
| 369 | 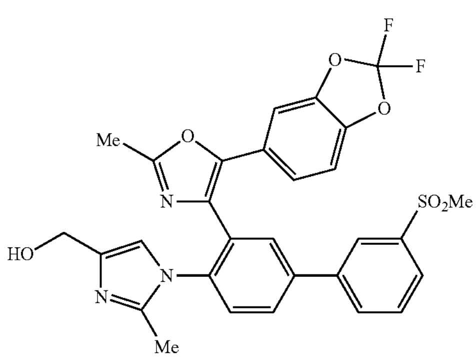 [SMILES: Cc1nc(-c2cc(-c3cccc(S(C)(=O)=O)c3)ccc2-n2cc(CO)nc2C)c(-c2ccc3c(c2)OC(F)(F)O3)o1] | (1-(3-(5-(2,2-difluorobenzo[d][1,3]dioxol-5-yl)-2-methyloxazol-4-yl)-3'-(methylsulfonyl)biphenyl-4-yl)-2-methyl-1H-imidazol-4-yl)methanol |

| Ex # | Structure | Name |
|------|-----------|------|
| 370 | 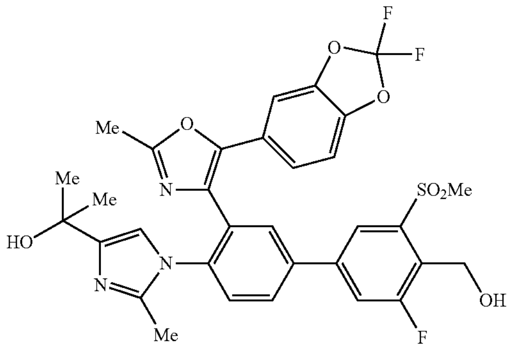 [SMILES: Cc1nc(-c2cc(-c3cc(F)c(CO)c(S(C)(=O)=O)c3)ccc2-n2cc(C(C)(C)O)nc2C)c(-c2ccc3c(c2)OC(F)(F)O3)o1] | 2-(1-(3-(5-(2,2-difluorobenzo[d][1,3]dioxol-5-yl)-2-methyloxazol-4-yl)-3'-fluoro-4'-(hydroxymethyl)-5'-(methylsulfonyl)biphenyl-4-yl)-2-methyl-1H-imidazol-4-yl)propan-2-ol |
| 371 | 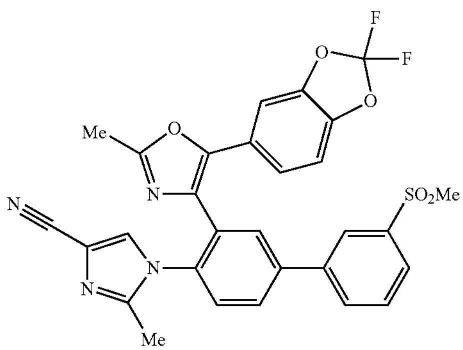 [SMILES: Cc1nc(-c2cc(-c3cccc(S(C)(=O)=O)c3)ccc2-n2cc(C#N)nc2C)c(-c2ccc3c(c2)OC(F)(F)O3)o1] | 1-(3-(5-(2,2-difluorobenzo[d][1,3]dioxol-5-yl)-2-methyloxazol-4-yl)-3'-(methylsulfonyl)biphenyl-4-yl)-2-methyl-1H-imidazole-4-carbonitrile |
| 372 | 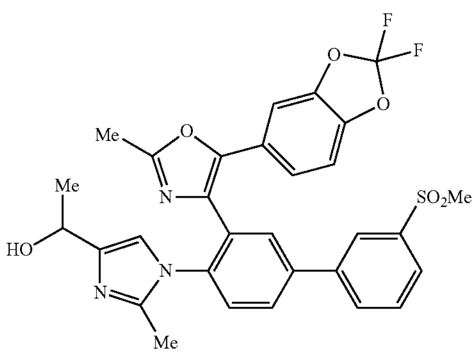 [SMILES: Cc1nc(-c2cc(-c3cccc(S(C)(=O)=O)c3)ccc2-n2cc(C(C)O)nc2C)c(-c2ccc3c(c2)OC(F)(F)O3)o1] | 1-(1-(3-(5-(2,2-difluorobenzo[d][1,3]dioxol-5-yl)-2-methyloxazol-4-yl)-3'-(methylsulfonyl)-[1,1'-biphenyl]-4-yl)-2-methyl-1H-imidazol-4-yl)ethanol |
| 373 | 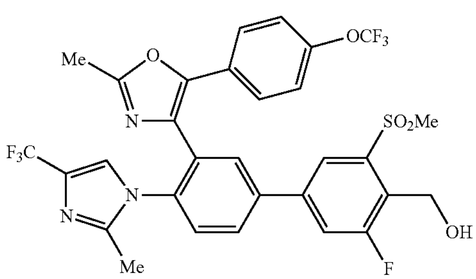 [SMILES: Cc1nc(-c2cc(-c3cc(F)c(CO)c(S(C)(=O)=O)c3)ccc2-n2cc(C(F)(F)F)nc2C)c(-c2ccc(OC(F)(F)F)cc2)o1] | [3-fluoro-5-(methylsulfonyl)-4'-[2-methyl-4-(trifluoromethyl)-1H-imidazol-1-yl]-3'-(2-methyl-5-{4-[(trifluoromethyl)oxy]phenyl}-1,3-oxazol-4-yl)biphenyl-4-yl]methanol |

| Ex # | Structure | Name |
|---|---|---|
| 374 | 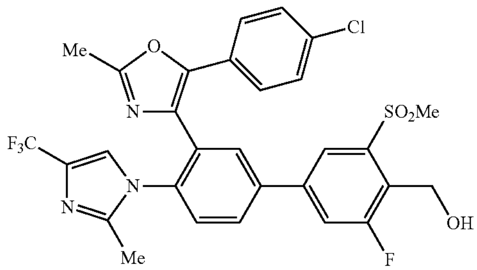 [SMILES: Cc1nc(-c2cc(-c3cc(F)c(CO)c(S(C)(=O)=O)c3)ccc2-n2cc(C(F)(F)F)nc2C)c(-c2ccc(Cl)cc2)o1] | {3'-[5-(4-chlorophenyl)-2-methyl-1,3-oxazol-4-yl]-3-fluoro-5-(methylsulfonyl)-4'-[2-methyl-4-(trifluoromethyl)-1H-imidazol-1-yl]biphenyl-4-yl}methanol |
| 375 | 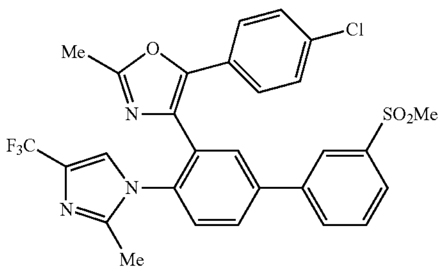 [SMILES: Cc1nc(-c2cc(-c3cccc(S(C)(=O)=O)c3)ccc2-n2cc(C(F)(F)F)nc2C)c(-c2ccc(Cl)cc2)o1] | 5-(4-chlorophenyl)-2-methyl-4-{3'-(methylsulfonyl)-4-[2-methyl-4-(trifluoromethyl)-1H-imidazol-1-yl]biphenyl-3-yl}-1,3-oxazole |
| 376 | 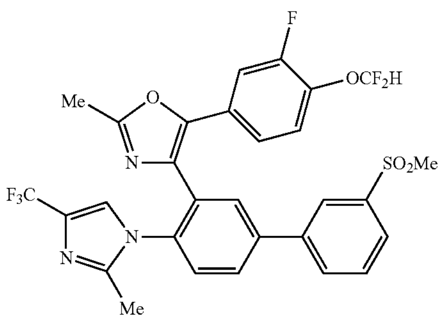 | 5-(4-(difluoromethoxy)-3-fluorophenyl)-2-methyl-4-(4-(2-methyl-4-(trifluoromethyl)-1H-imidazol-1-yl)-3'-(methylsulfonyl)biphenyl-3-yl)oxazole |
| 377 | 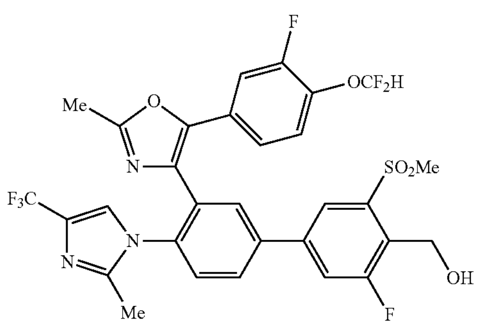 | (3'-(5-(4-(difluoromethoxy)-3-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 378 | 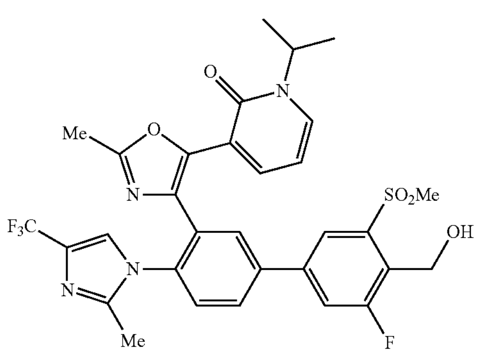 [SMILES: Cc1nc(-c2cc(-c3cc(F)c(CO)c(S(C)(=O)=O)c3)ccc2-n2cc(C(F)(F)F)nc2C)c(-c2cccn(C(C)C)c2=O)o1] | 3-(4-(3'-fluoro-4'-(hydroxymethyl)-4-(2-methyl-4-(trifluoromethyl)-1H-imidazol-1-yl)-5'-(methylsulfonyl)biphenyl-3-yl)-2-methyloxazol-5-yl)-1-isopropylpyridin-2(1H)-one |

-continued

| Ex # | Structure | Name |
|---|---|---|
| 379 | 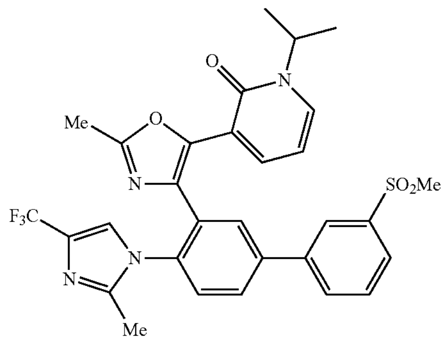 [SMILES: Cc1nc(-c2cc(-c3cccc(S(C)(=O)=O)c3)ccc2-n2cc(C(F)(F)F)nc2C)c(-c2cccn(C(C)C)c2=O)o1] | 1-isopropyl-3-(2-methyl-4-(4-(2-methyl-4-(trifluoromethyl)-1H-imidazol-1-yl)-3'-(methylsulfonyl)biphenyl-3-yl)oxazol-5-yl)pyridin-2(1H)-one |
| 380 | 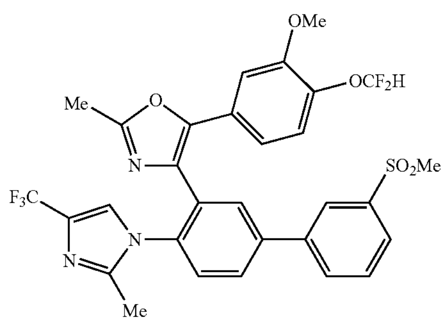 | 5-(4-(difluoromethoxy)-3-methoxyphenyl)-2-methyl-4-(4-(2-methyl-4-(trifluoromethyl)-1H-imidazol-1-yl)-3'-(methylsulfonyl)biphenyl-3-yl)oxazole |
| 381 | 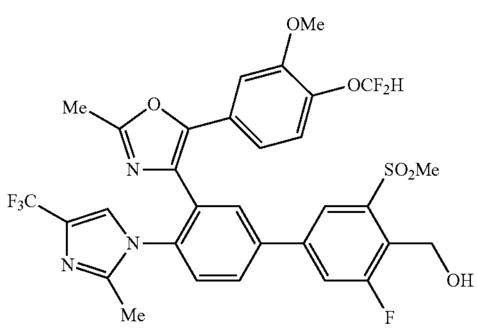 | (3'-(5-(4-(difluoromethoxy)-3-methoxyphenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 382 | 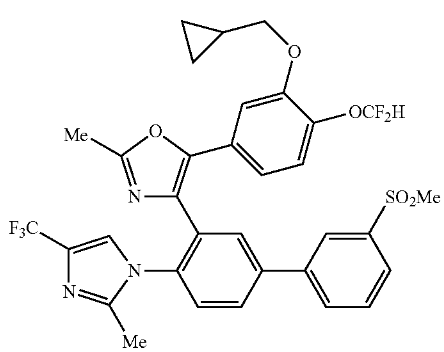 | 5-(3-(cyclopropylmethoxy)-4-(difluoromethoxy)phenyl)-2-methyl-4-(4-(2-methyl-4-(trifluoromethyl)-1H-imidazol-1-yl)-3'-(methylsulfonyl)biphenyl-3-yl)oxazole |

| Ex # | Structure | Name |
|---|---|---|
| 383 | 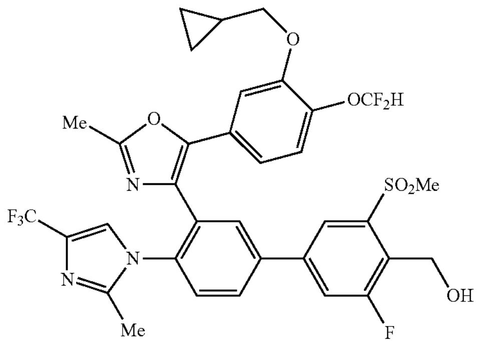 | (3'-(5-(3-(cyclopropylmethoxy)-4-(difluoromethoxy)phenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 384 | 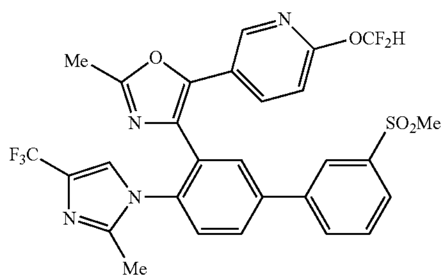 | 5-(6-(difluoromethoxy)pyridin-3-yl)-2-methyl-4-(4-(2-methyl-4-(trifluoromethyl)-1H-imidazol-1-yl)-3'-(methylsulfonyl)biphenyl-3-yl)oxazole |
| 385 | 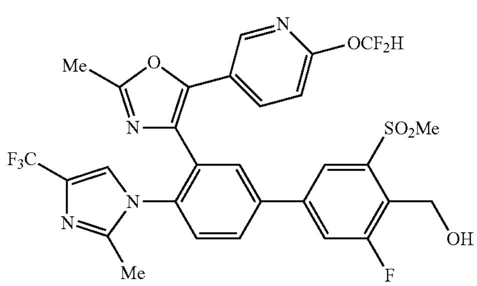 | (3'-(5-(6-(difluoromethoxy)pyridin-3-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 386 | 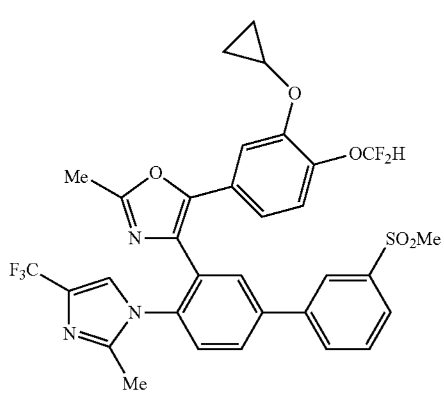 | 5-(3-cyclopropoxy-4-(difluoromethoxy)phenyl)-2-methyl-4-(4-(2-methyl-4-(trifluoromethyl)-1H-imidazol-1-yl)-3'-(methylsulfonyl)biphenyl-3-yl)oxazole |

| Ex # | Structure | Name |
|------|-----------|------|
| 387 | 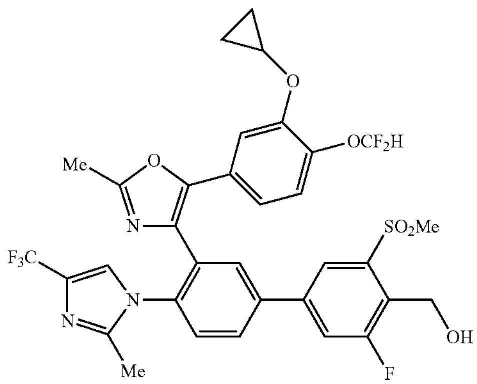 | (3'-(5-(3-cyclopropoxy-4-(difluoromethoxy)phenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 388 | 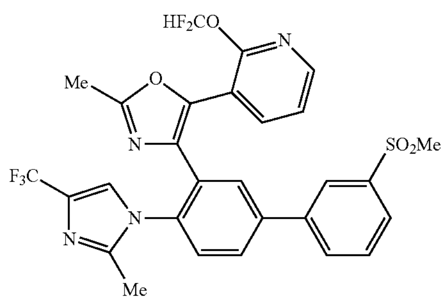 | 5-(2-(difluoromethoxy)pyridin-3-yl)-2-methyl-4-(4-(2-methyl-4-(trifluoromethyl)-1H-imidazol-1-yl)-3'-(methylsulfonyl)biphenyl-3-yl)oxazole |
| 389 | 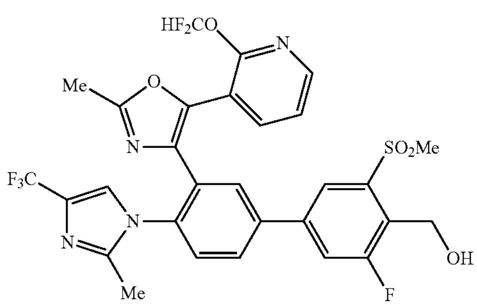 | (3'-(5-(2-(difluoromethoxy)pyridin-3-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 390 | 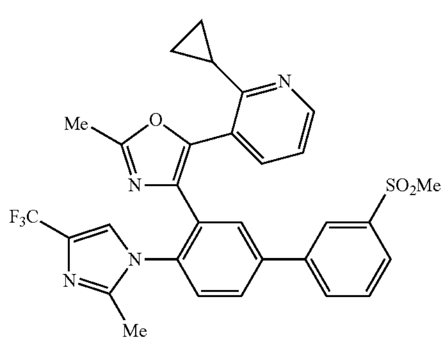 [SMILES: Cc1nc(-c2cc(-c3cccc(S(C)(=O)=O)c3)ccc2-n2cc(C(F)(F)F)nc2C)c(-c2cccnc2C2CC2)o1] | 5-(2-cyclopropylpyridin-3-yl)-2-methyl-4-(4-(2-methyl-4-(trifluoromethyl)-1H-imidazol-1-yl)-3'-(methylsulfonyl)biphenyl-3-yl)oxazole |

-continued

| Ex # | Structure | Name |
|---|---|---|
| 391 | 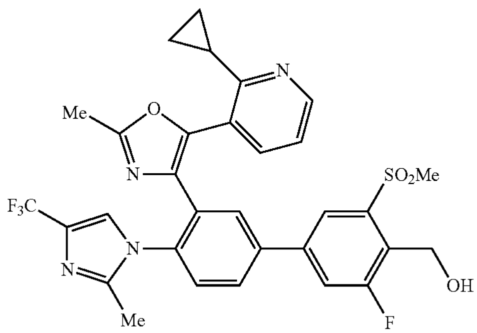 [SMILES: Cc1nc(-c2cc(-c3cc(F)c(CO)c(S(C)(=O)=O)c3)ccc2-n2cc(C(F)(F)F)nc2C)c(-c2cccnc2C2CC2)o1] | (3'-(5-(2-cyclopropylpyridin-3-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 392 | 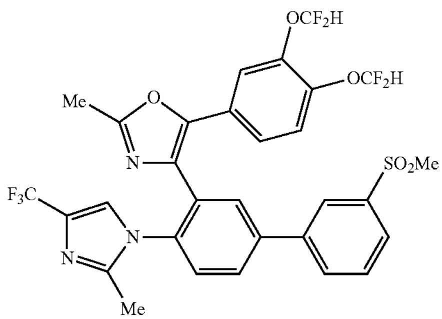 | 5-(3,4-bis(difluoromethoxy)phenyl)-2-methyl-4-(4-(2-methyl-4-(trifluoromethyl)-1H-imidazol-1-yl)-3'-(methylsulfonyl)biphenyl-3-yl)oxazole |
| 393 | 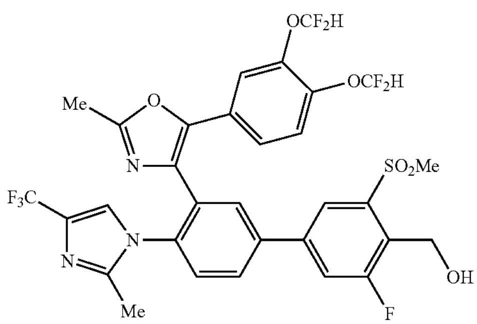 | (3'-(5-(3,4-bis(difluoromethoxy)phenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 394 | 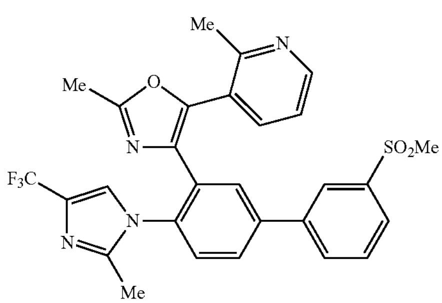 [SMILES: Cc1nc(-c2cc(-c3cccc(S(C)(=O)=O)c3)ccc2-n2cc(C(F)(F)F)nc2C)c(-c2cccnc2C)o1] | 2-methyl-4-(4-(2-methyl-4-(trifluoromethyl)-1H-imidazol-1-yl)-3'-(methylsulfonyl)biphenyl-3-yl)-5-(2-methylpyridin-3-yl)oxazole |
| 395 | 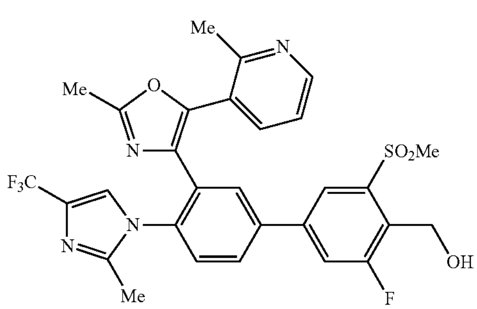 [SMILES: Cc1nc(-c2cc(-c3cc(F)c(CO)c(S(C)(=O)=O)c3)ccc2-n2cc(C(F)(F)F)nc2C)c(-c2cccnc2C)o1] | (3-fluoro-4'-(2-methyl-4-(trifluoromethyl)-1H-imidazol-1-yl)-3'-(2-methyl-5-(2-methylpyridin-3-yl)oxazol-4-yl)-5-(methylsulfonyl)biphenyl-4-yl)methanol |

-continued

| Ex # | Structure | Name |
|---|---|---|
| 396 | 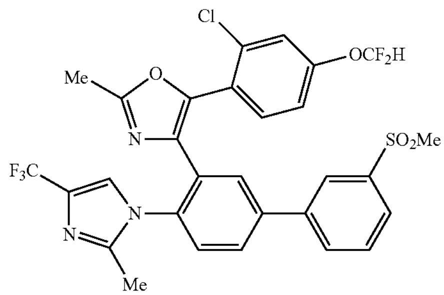 | 5-(2-chloro-4-(difluoromethoxy)phenyl)-2-methyl-4-(4-(2-methyl-4-(trifluoromethyl)-1H-imidazol-1-yl)-3'-(methylsulfonyl)biphenyl-3-yl)oxazole |
| 397 | 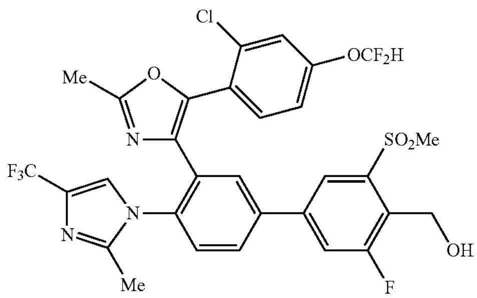 | (3'-(5-(2-chloro-4-(difluoromethoxy)phenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 398 | 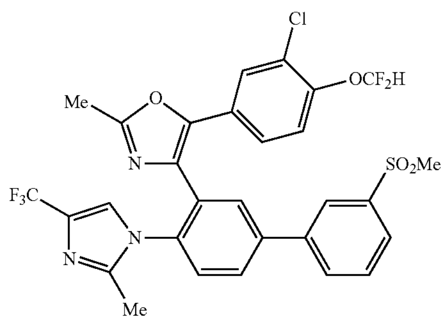 | 5-(3-chloro-4-(difluoromethoxy)phenyl)-2-methyl-4-(4-(2-methyl-4-(trifluoromethyl)-1H-imidazol-1-yl)-3'-(methylsulfonyl)biphenyl-3-yl)oxazole |
| 399 | 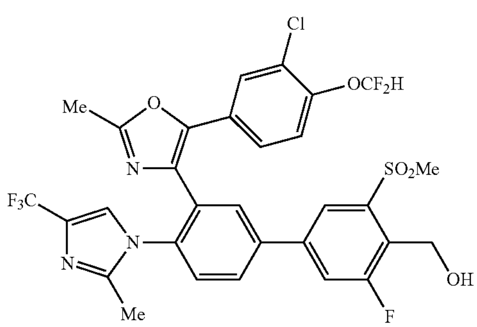 | (3'-(5-(3-chloro-4-(difluoromethoxy)phenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 400 | 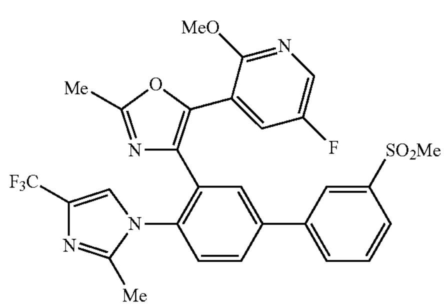 [SMILES: COc1ncc(F)cc1-c1oc(C)nc1-c1cc(-c2cccc(S(C)(=O)=O)c2)ccc1-n1cc(C(F)(F)F)nc1C] | 5-(5-fluoro-2-methoxypyridin-3-yl)-2-methyl-4-(4-(2-methyl-4-(trifluoromethyl)-1H-imidazol-1-yl)-3'-(methylsulfonyl)biphenyl-3-yl)oxazole |

-continued

| Ex # | Structure | Name |
|---|---|---|
| 401 | 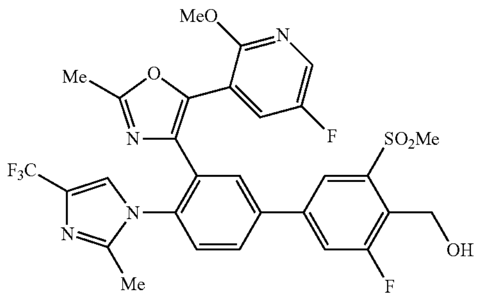 [SMILES: COc1ncc(F)cc1-c1oc(C)nc1-c1cc(-c2cc(F)c(CO)c(S(C)(=O)=O)c2)ccc1-n1cc(C(F)(F)F)nc1C] | (3-fluoro-3'-(5-(5-fluoro-2-methoxypyridin-3-yl)-2-methyloxazol-4-yl)-4'-(2-methyl-4-(trifluoromethyl)-1H-imidazol-1-yl)-5-(methylsulfonyl)biphenyl-4-yl)methanol |
| 402 | 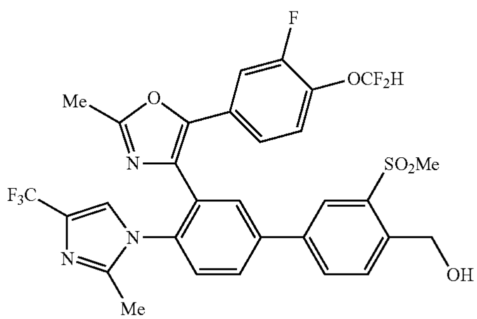 | (3'-(5-(4-(difluoromethoxy)-3-fluorophenyl)-2-methyloxazol-4-yl)-4'-(2-methyl-4-(trifluoromethyl)-1H-imidazol-1-yl)-3-(methylsulfonyl)biphenyl-4-yl)methanol |
| 404 | 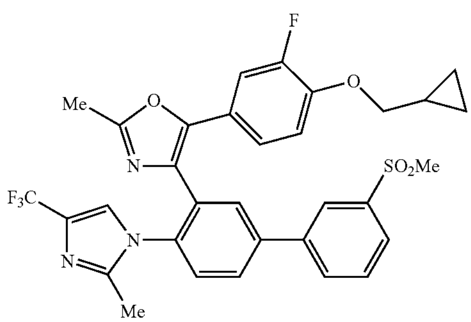 [SMILES: Cc1nc(-c2cc(-c3cccc(S(C)(=O)=O)c3)ccc2-n2cc(C(F)(F)F)nc2C)c(-c2ccc(OCC3CC3)c(F)c2)o1] | 5-(4-(cyclopropylmethoxy)-3-fluorophenyl)-2-methyl-4-(4-(2-methyl-4-(trifluoromethyl)-1H-imidazol-1-yl)-3'-(methylsulfonyl)biphenyl-3-yl)oxazole |
| 405 | 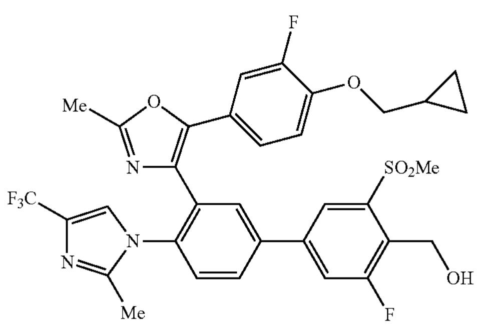 [SMILES: Cc1nc(-c2cc(-c3cc(F)c(CO)c(S(C)(=O)=O)c3)ccc2-n2cc(C(F)(F)F)nc2C)c(-c2ccc(OCC3CC3)c(F)c2)o1] | (3'-(5-(4-(cyclopropylmethoxy)-3-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 406 | 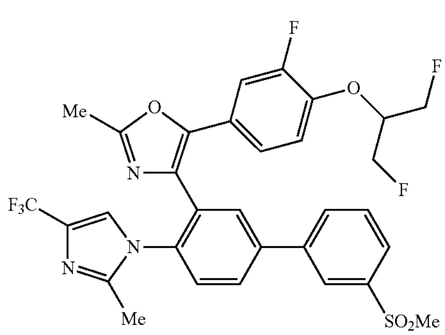 [SMILES: Cc1nc(-c2cc(-c3cccc(S(C)(=O)=O)c3)ccc2-n2cc(C(F)(F)F)nc2C)c(-c2ccc(OC(CF)CF)c(F)c2)o1] | 5-(4-(1,3-difluoropropan-2-yloxy)-3-fluorophenyl)-2-methyl-4-(4-(2-methyl-4-(trifluoromethyl)-1H-imidazol-1-yl)-3'-(methylsulfonyl)biphenyl-3-yl)oxazole |

| Ex # | Structure | Name |
|---|---|---|
| 407 | 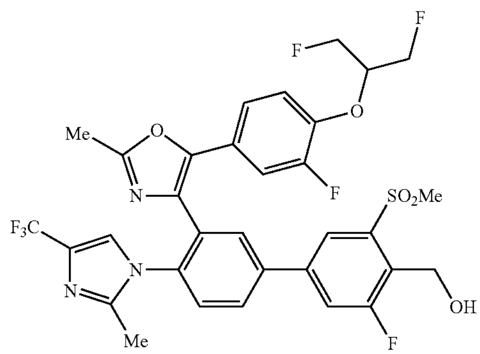 [SMILES: Cc1nc(-c2cc(-c3cc(F)c(CO)c(S(C)(=O)=O)c3)ccc2-n2cc(C(F)(F)F)nc2C)c(-c2ccc(OC(CF)CF)c(F)c2)o1] | (3'-(5-(4-(1,3-difluoropropan-2-yloxy)-3-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 408 | 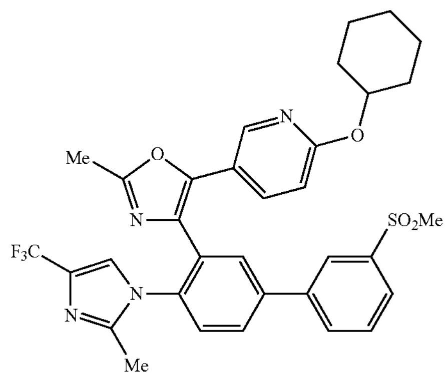 [SMILES: Cc1nc(-c2cc(-c3cccc(S(C)(=O)=O)c3)ccc2-n2cc(C(F)(F)F)nc2C)c(-c2ccc(OC3CCCCC3)nc2)o1] | 5-(6-(cyclohexyloxy)pyridin-3-yl)-2-methyl-4-(2-methyl-4-(trifluoromethyl)-1H-imidazol-1-yl)-3'-(methylsulfonyl)biphenyl-3-yl)oxazole |
| 409 | 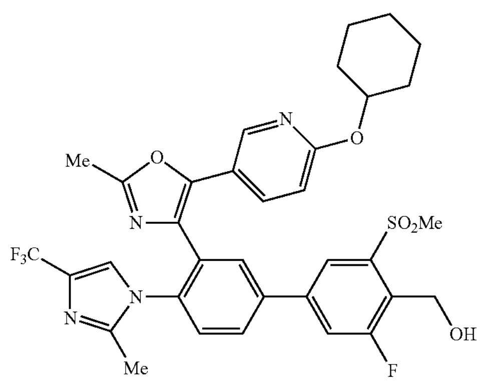 [SMILES: Cc1nc(-c2cc(-c3cc(F)c(CO)c(S(C)(=O)=O)c3)ccc2-n2cc(C(F)(F)F)nc2C)c(-c2ccc(OC3CCCCC3)nc2)o1] | (3'-(5-(6-(cyclohexyloxy)pyridin-3-yl)-2-methyloxazol-4-yl)-3-fluoro-4'-(2-methyl-4-(trifluoromethyl)-1H-imidazol-1-yl)-5-methylsulfonyl)biphenyl-4-yl)methanol |
| 410 | 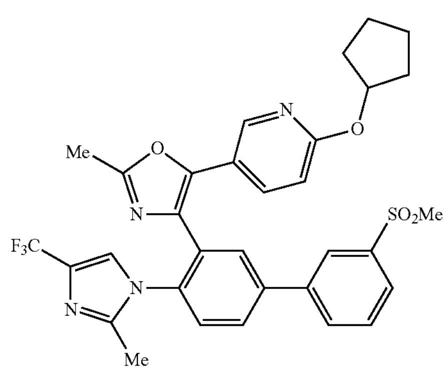 [SMILES: Cc1nc(-c2cc(-c3cccc(S(C)(=O)=O)c3)ccc2-n2cc(C(F)(F)F)nc2C)c(-c2ccc(OC3CCCC3)nc2)o1] | 5-(6-(cyclopentyloxy)pyridin-3-yl)-2-methyl-4-(4-(2-methyl-4-(trifluoromethyl)-1H-imidazol-1-yl)-3'-(methylsulfonyl)biphenyl-3-yl)oxazole |

-continued

| Ex # | Structure | Name |
|---|---|---|
| 411 | 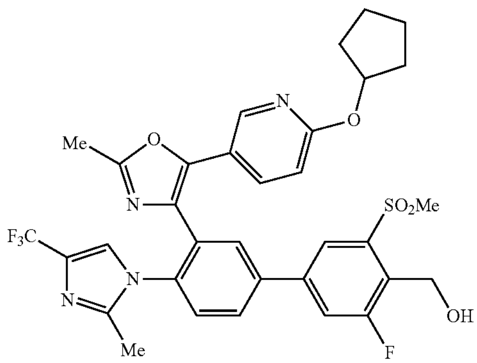 [SMILES: Cc1nc(-c2cc(-c3cc(F)c(CO)c(S(C)(=O)=O)c3)ccc2-n2cc(C(F)(F)F)nc2C)c(-c2ccc(OC3CCCC3)nc2)o1] | (3'-(5-(6-(cyclopentyloxy)pyridin-3-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 412 | 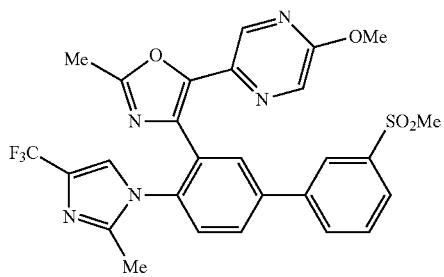 [SMILES: COc1cnc(-c2oc(C)nc2-c2cc(-c3cccc(S(C)(=O)=O)c3)ccc2-n2cc(C(F)(F)F)nc2C)cn1] | 5-(5-methoxypyrazin-2-yl)-2-methyl-4-(4-(2-methyl-4-(trifluoromethyl)-1H-imidazol-1-yl)-3'-(methylsulfonyl)biphenyl-3-yl)oxazole |
| 413 | 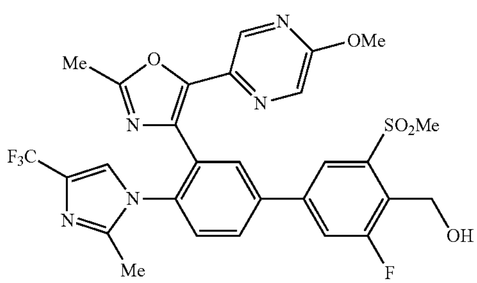 [SMILES: COc1cnc(-c2oc(C)nc2-c2cc(-c3cc(F)c(CO)c(S(C)(=O)=O)c3)ccc2-n2cc(C(F)(F)F)nc2C)cn1] | (3-fluoro-3'-(5-(5-methoxypyrazin-2-yl)-2-methyloxazol-4-yl)-4'-(2-methyl-4-(trifluoromethyl)-1H-imidazol-1-yl)-5-(methylsulfonyl)biphenyl-4-yl)methanol |
| 414 | 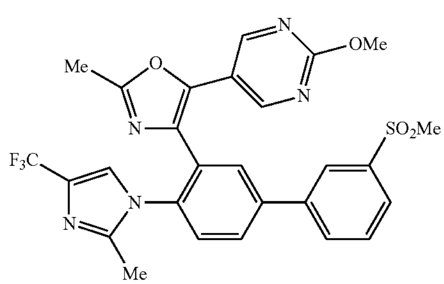 [SMILES: COc1ncc(-c2oc(C)nc2-c2cc(-c3cccc(S(C)(=O)=O)c3)ccc2-n2cc(C(F)(F)F)nc2C)cn1] | 5-(2-methoxypyrimidin-5-yl)-2-methyl-4-(4-(2-methyl-4-(trifluoromethyl)-1H-imidazol-1-yl)-3'-(methylsulfonyl)biphenyl-3-yl)oxazole |
| 415 | 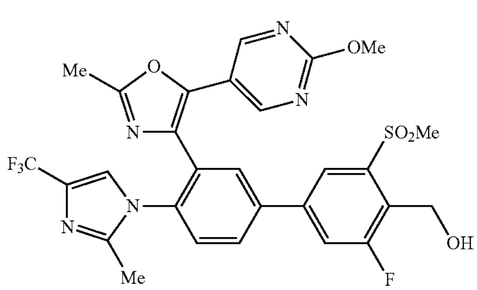 [SMILES: COc1ncc(-c2oc(C)nc2-c2cc(-c3cc(F)c(CO)c(S(C)(=O)=O)c3)ccc2-n2cc(C(F)(F)F)nc2C)cn1] | (3-fluoro-3'-(5-(2-methoxypyrimidin-5-yl)-2-methyloxazol-4-yl)-4'-(2-methyl-4-(trifluoromethyl)-1H-imidazol-1-yl)-5-(methylsulfonyl)biphenyl-4-yl)methanol |

| Ex # | Structure | Name |
| --- | --- | --- |
| 416 | 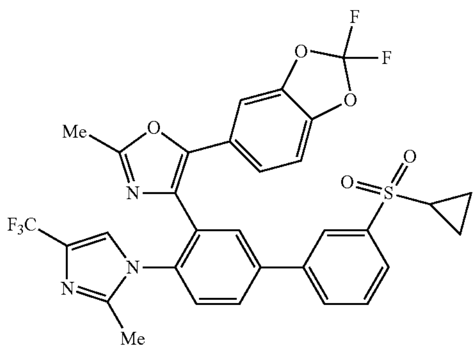 [SMILES: Cc1nc(-c2cc(-c3cccc(S(=O)(=O)C4CC4)c3)ccc2-n2cc(C(F)(F)F)nc2C)c(-c2ccc3c(c2)OC(F)(F)O3)o1] | 4-(3'-(cyclopropylsulfonyl)-4-(2-methyl-4-(trifluoromethyl)-1H-imidazol-1-yl)-[1,1'-biphenyl]-3-yl)-5-(2,2-difluorobenzo[d][1,3]dioxol-5-yl)-2-methyloxazole |
| 417 | 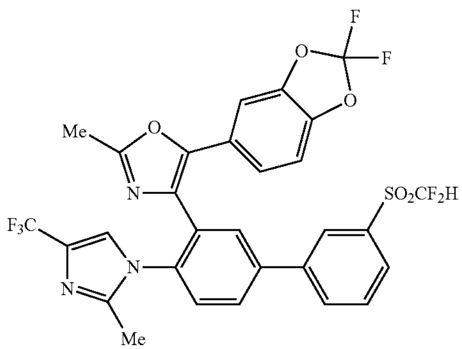 | 5-(2,2-difluorobenzo[d][1,3]dioxol-5-yl)-4-(3'-(difluoromethylsulfonyl)-4-(2-methyl-4-(trifluoromethyl)-1H-imidazol-1-yl)biphenyl-3-yl)-2-methyloxazole |
| 418 | 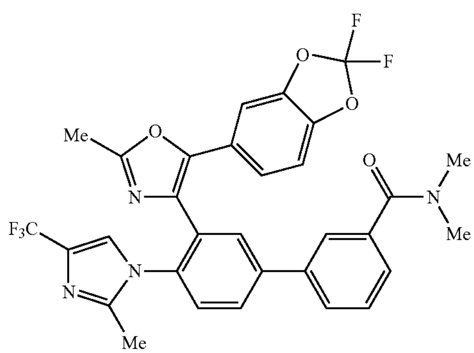 [SMILES: Cc1nc(-c2cc(-c3cccc(C(=O)N(C)C)c3)ccc2-n2cc(C(F)(F)F)nc2C)c(-c2ccc3c(c2)OC(F)(F)O3)o1] | 3'-(5-(2,2-difluorobenzo[d][1,3]dioxol-5-yl)-2-methyloxazol-4-yl)-N,N-dimethyl-4'-(2-methyl-4-(trifluoromethyl)-1H-imidazol-1-yl)biphenyl-3-carboxamide |
| 419 | 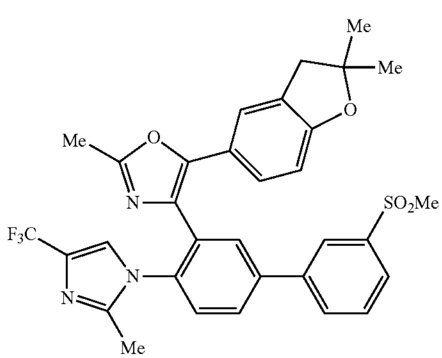 [SMILES: Cc1nc(-c2cc(-c3cccc(S(C)(=O)=O)c3)ccc2-n2cc(C(F)(F)F)nc2C)c(-c2ccc3c(c2)CC(C)(C)O3)o1] | 5-(2,2-dimethyl-2,3-dihydrobenzofuran-5-yl)-2-methyl-4-(4-(2-methyl-4-(trifluoromethyl)-1H-imidazol-1-yl)-3'-(methylsulfonyl)biphenyl-3-yl)oxazole |

| Ex # | Structure | Name |
|---|---|---|
| 420 | 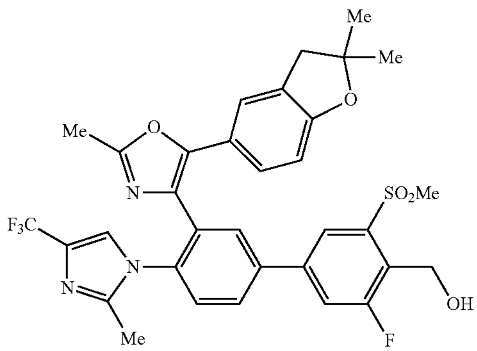 [SMILES: Cc1nc(-c2cc(-c3cc(F)c(CO)c(S(C)(=O)=O)c3)ccc2-n2cc(C(F)(F)F)nc2C)c(-c2ccc3c(c2)CC(C)(C)O3)o1] | 3'-(5-(2,2-dimethyl-2,3-dihydrobenzofuran-5-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 421 | 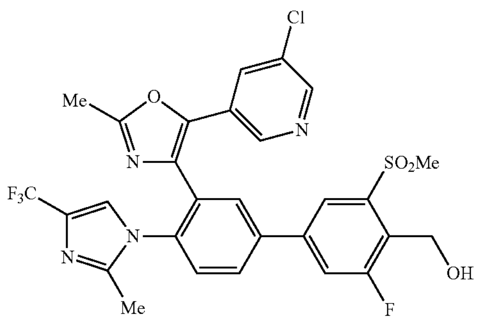 [SMILES: Cc1nc(-c2cc(-c3cc(F)c(CO)c(S(C)(=O)=O)c3)ccc2-n2cc(C(F)(F)F)nc2C)c(-c2cncc(Cl)c2)o1] | (3'-(5-(5-chloropyridin-3-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 422 | 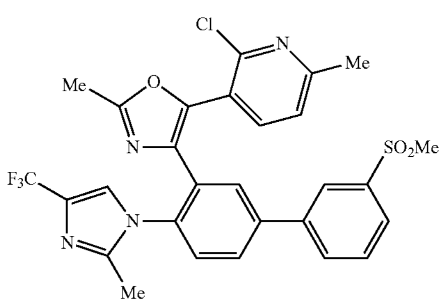 [SMILES: Cc1ccc(-c2oc(C)nc2-c2cc(-c3cccc(S(C)(=O)=O)c3)ccc2-n2cc(C(F)(F)F)nc2C)c(Cl)n1] | 5-(2-chloro-6-methylpyridin-3-yl)-2-methyl-4-(4-(2-methyl-4-(trifluoromethyl)-1H-imidazol-1-yl)-3'-(methylsulfonyl)biphenyl-3-yl)oxazole |
| 423 | 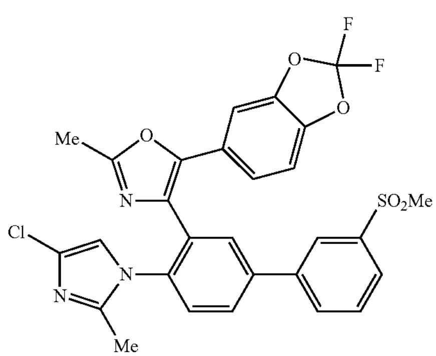 [SMILES: Cc1nc(-c2cc(-c3cccc(S(C)(=O)=O)c3)ccc2-n2cc(Cl)nc2C)c(-c2ccc3c(c2)OC(F)(F)O3)o1] | 4-(4-(4-chloro-2-methyl-1H-imidazol-1-yl)-3'-(methylsulfonyl)biphenyl-3-yl)-5-(2,2-difluorobenzo[d][1,3]dioxol-5-yl)-2-methyloxazole |

| Ex # | Structure | Name |
|---|---|---|
| 424 | 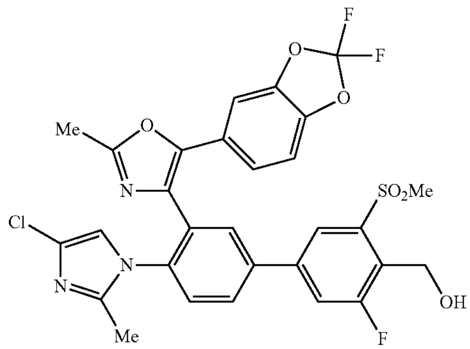 [SMILES: Cc1nc(-c2cc(-c3cc(F)c(CO)c(S(C)(=O)=O)c3)ccc2-n2cc(Cl)nc2C)c(-c2ccc3c(c2)OC(F)(F)O3)o1] | (4'-(4-chloro-2-methyl-1H-imidazol-1-yl)-3'-(5-(2,2-difluorobenzo[d][1,3]dioxol-5-yl)-2-methyloxazol-4-yl)-3-fluoro-5-(methylsulfonyl)biphenyl-4-yl)methanol |
| 425 | 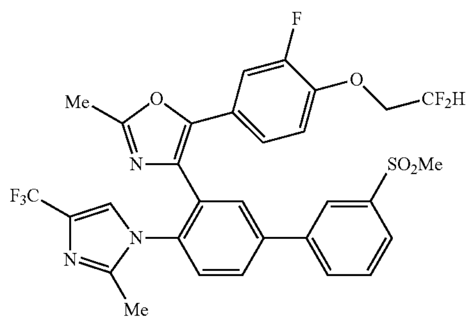 [SMILES: Cc1nc(-c2cc(-c3cccc(S(C)(=O)=O)c3)ccc2-n2cc(C(F)(F)F)nc2C)c(-c2ccc(OCC(F)F)c(F)c2)o1] | 5-(4-(2,2-difluoroethoxy)-3-fluorophenyl)-2-methyl-4-(4-(2-methyl-4-(trifluoromethyl)-1H-imidazol-1-yl)-3'-(methylsulfonyl)biphenyl-3-yl)oxazole |
| 426 | 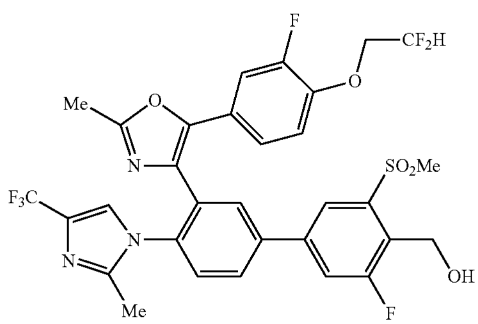 [SMILES: Cc1nc(-c2cc(-c3cc(F)c(CO)c(S(C)(=O)=O)c3)ccc2-n2cc(C(F)(F)F)nc2C)c(-c2ccc(OCC(F)F)c(F)c2)o1] | (3'-(5-(4-(2,2-difluoroethoxy)-3-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 427 | 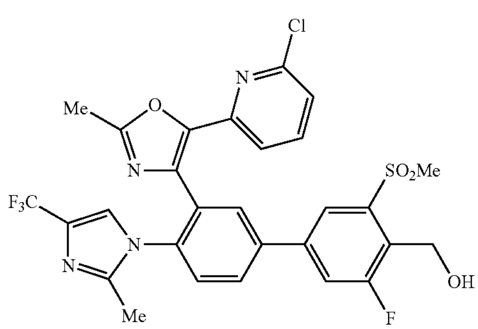 [SMILES: Cc1nc(-c2cc(-c3cc(F)c(CO)c(S(C)(=O)=O)c3)ccc2-n2cc(C(F)(F)F)nc2C)c(-c2cccc(Cl)n2)o1] | (3'-(5-(6-chloropyridin-2-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 428 | 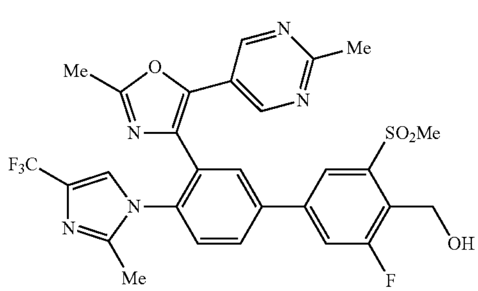 [SMILES: Cc1ncc(-c2oc(C)nc2-c2cc(-c3cc(F)c(CO)c(S(C)(=O)=O)c3)ccc2-n2cc(C(F)(F)F)nc2C)cn1] | (3-fluoro-4'-(2-methyl-4-(trifluoromethyl)-1H-imidazol-1-yl)-3'-(2-methyl-5-(2-methylpyrimidin-5-yl)oxazol-4-yl)-5-(methylsulfonyl)biphenyl-4-yl)methanol |

| Ex # | Structure | Name |
|---|---|---|
| 429 | 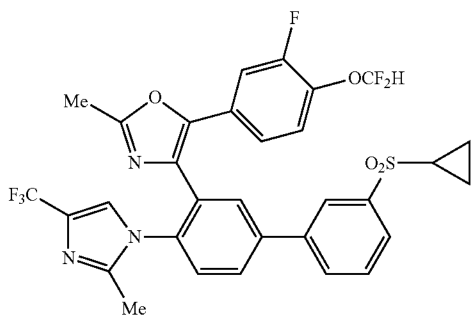 | 4-(3'-(cyclopropylsulfonyl)-4-(2-methyl-4-(trifluoromethyl)-1H-imidazol-1-yl)biphenyl-3-yl)-5-(4-(difluoromethoxy)-3-fluorophenyl)-2-methyloxazole |
| 430 | 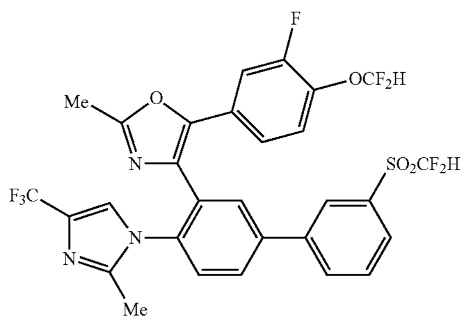 | 5-(4-(difluoromethoxy)-3-fluorophenyl)-4-(3'-(difluoromethylsulfonyl)-4-(2-methyl-4-(trifluoromethyl)-1H-imidazol-1-yl)biphenyl-3-yl)-2-methyloxazole |
| 431 | 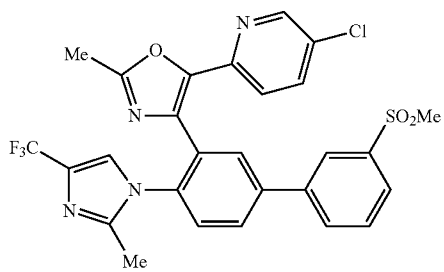 [SMILES: Cc1nc(-c2cc(-c3cccc(S(C)(=O)=O)c3)ccc2-n2cc(C(F)(F)F)nc2C)c(-c2ccc(Cl)cn2)o1] | 5-(5-chloropyridin-2-yl)-2-methyl-4-(4-(2-methyl-4-(trifluoromethyl)-1H-imidazol-1-yl)-3'-(methylsulfonyl)biphenyl-3-yl)oxazole |
| 432 | 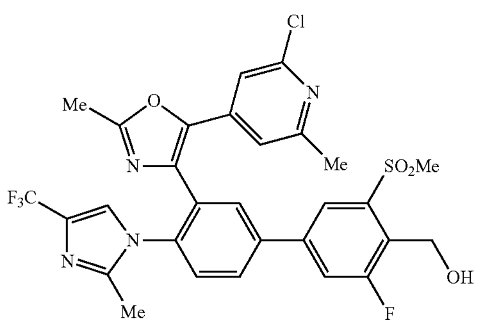 | (3'-(5-(2-chloro-6-methylpyridin-4-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 433 | 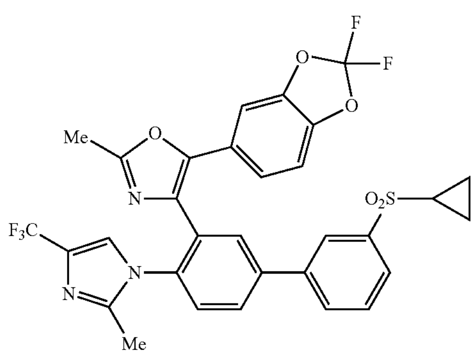 [SMILES: Cc1nc(-c2cc(-c3cccc(S(=O)(=O)C4CC4)c3)ccc2-n2cc(C(F)(F)F)nc2C)c(-c2ccc3c(c2)OC(F)(F)O3)o1] | 4-(3'-(cyclopropylsulfonyl)-4-(2-methyl-4-(trifluoromethyl)-1H-imidazol-1-yl)biphenyl-3-yl)-5-(2,2-difluorobenzo[d][1,3]dioxol-5-yl)-2-methyloxazole |

-continued

| Ex # | Structure | Name |
|---|---|---|
| 434 | 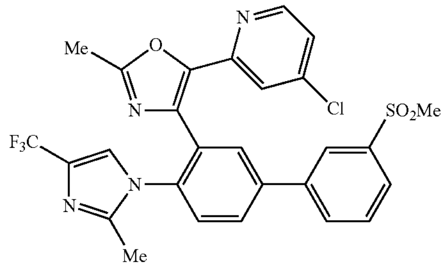 [SMILES: Cc1nc(-c2cc(-c3cccc(S(C)(=O)=O)c3)ccc2-n2cc(C(F)(F)F)nc2C)c(-c2cc(Cl)ccn2)o1] | 5-(4-chloropyridin-2-yl)-2-methyl-4-(4-(2-methyl-4-(trifluoromethyl)-1H-imidazol-1-yl)-3'-(methylsulfonyl)biphenyl-3-yl)oxazole |
| 435 | 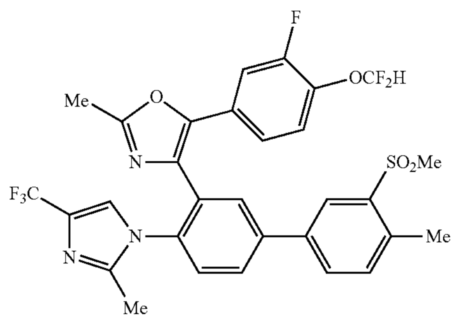 | 5-(4-(difluoromethoxy)-3-fluorophenyl)-2-methyl-4-(4'-methyl-4-(2-methyl-4-(trifluoromethyl)-1H-imidazol-1-yl)-3'-(methylsulfonyl)biphenyl-3-yl)oxazole |
| 436 | 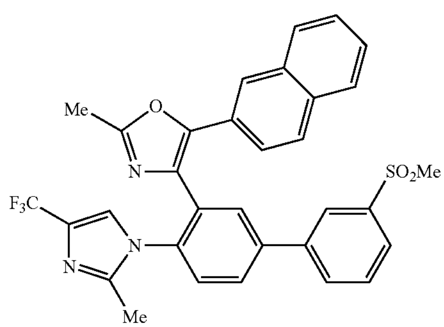 [SMILES: Cc1nc(-c2cc(-c3cccc(S(C)(=O)=O)c3)ccc2-n2cc(C(F)(F)F)nc2C)c(-c2ccc3ccccc3c2)o1] | 2-methyl-4-(4-(2-methyl-4-(trifluoromethyl)-1H-imidazol-1-yl)-3'-(methylsulfonyl)biphenyl-3-yl)-5-(naphthalen-2-yl)oxazole |
| 437 | 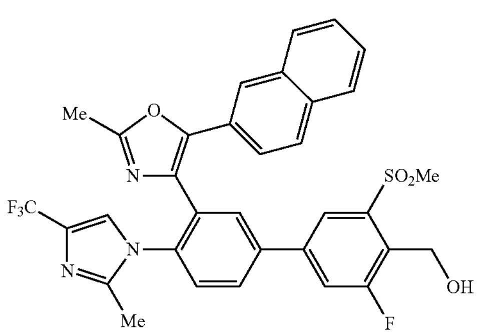 [SMILES: Cc1nc(-c2cc(-c3cc(F)c(CO)c(S(C)(=O)=O)c3)ccc2-n2cc(C(F)(F)F)nc2C)c(-c2ccc3ccccc3c2)o1] | (3-fluoro-4'-(2-methyl-4-(trifluoromethyl)-1H-imidazol-1-yl)-3'-(2-methyl-5-(naphthalen-2-yl)oxazol-4-yl)-5-(methylsulfonyl)biphenyl-4-yl)methanol |

-continued

| Ex # | Structure | Name |
|---|---|---|
| 438 | 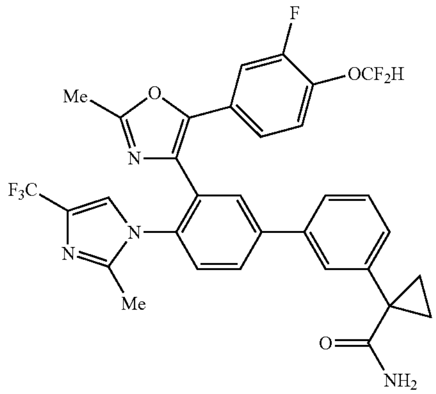 | 1-(3'-(5-(4-(difluoromethoxy)-3-fluorophenyl)-2-methyloxazol-4-yl)-4'-(2-methyl-4-(trifluoromethyl)-1H-imidazol-1-yl)biphenyl-3-yl)cyclopropanecarboxamide |
| 439 | 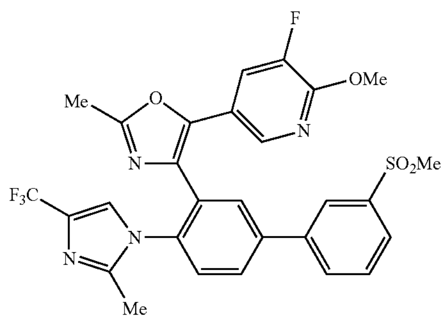 | 5-(5-fluoro-6-methoxypyridin-3-yl)-2-methyl-4-(4-(2-methyl-4-(trifluoromethyl)-1H-imidazol-1-yl)-3'-(methylsulfonyl)biphenyl-3-yl)oxazole |
| 440 | 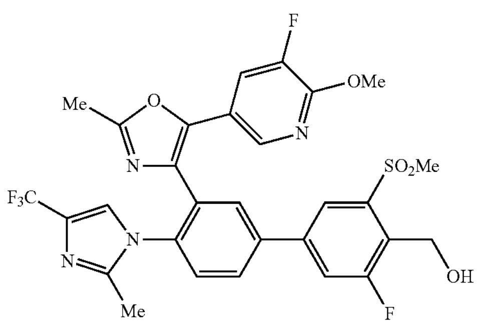 [SMILES: COc1ncc(-c2oc(C)nc2-c2cc(-c3cc(F)c(CO)c(S(C)(=O)=O)c3)ccc2-n2cc(C(F)(F)F)nc2C)cc1F] | (3-fluoro-3'-(5-(5-fluoro-6-methoxypyridin-3-yl)-2-methyloxazol-4-yl)-4'-(2-methyl-4-(trifluoromethyl)-1H-imidazol-1-yl)-5-(methylsulfonyl)biphenyl-4-yl)methanol |
| 441 | 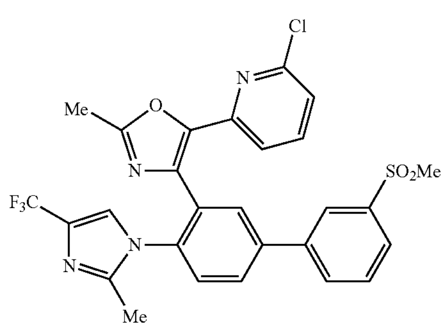 [SMILES: Cc1nc(-c2cc(-c3cccc(S(C)(=O)=O)c3)ccc2-n2cc(C(F)(F)F)nc2C)c(-c2cccc(Cl)n2)o1] | 5-(6-chloropyridin-2-yl)-2-methyl-4-(4-(2-methyl-4-(trifluoromethyl)-1H-imidazol-1-yl)-3'-(methylsulfonyl)biphenyl-3-yl)oxazole |

| Ex # | Structure | Name |
|---|---|---|
| 442 | 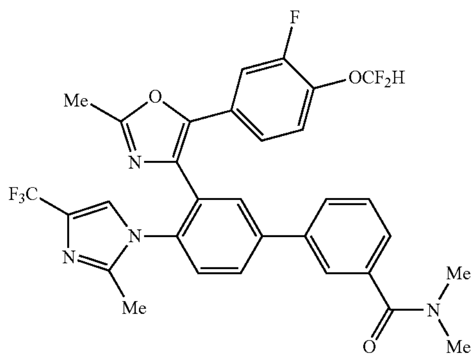 | 3'-(5-(4-(difluoromethoxy)-3-fluorophenyl)-2-methyloxazol-4-yl)-N,N-dimethyl-4'-(2-methyl-4-(trifluoromethyl)-1H-imidazol-1-yl)biphenyl-3-carboxamide |
| 443 | 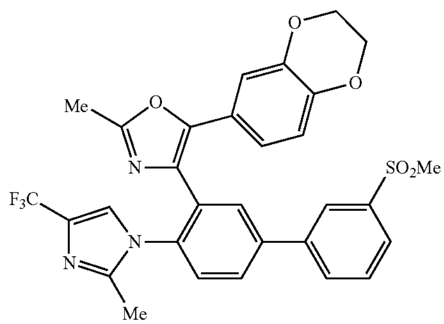 [SMILES: Cc1nc(-c2cc(-c3cccc(S(C)(=O)=O)c3)ccc2-n2cc(C(F)(F)F)nc2C)c(-c2ccc3c(c2)OCCO3)o1] | 5-(2,3-dihydrobenzo[b][1,4]dioxin-6-yl)-2-methyl-4-(4-(2-methyl-4-(trifluoromethyl)-1H-imidazol-1-yl)-3'-(methylsulfonyl)biphenyl-3-yl)oxazole |
| 444 | 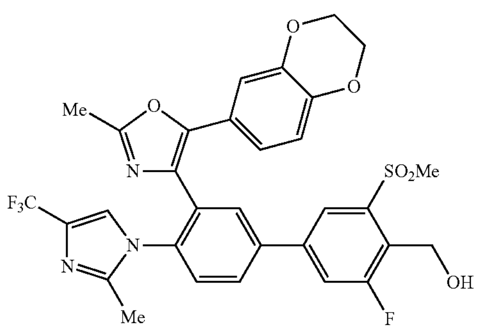 [SMILES: Cc1nc(-c2cc(-c3cc(F)c(CO)c(S(C)(=O)=O)c3)ccc2-n2cc(C(F)(F)F)nc2C)c(-c2ccc3c(c2)OCCO3)o1] | 3'-(5-(2,3-dihydrobenzo[b][1,4]dioxin-6-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 445 | 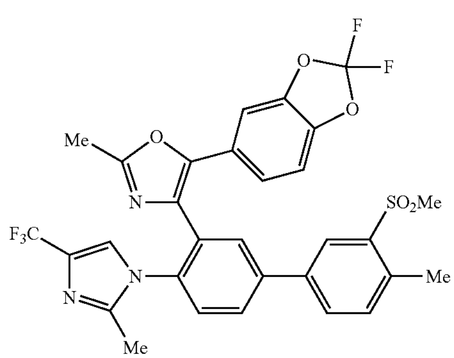 [SMILES: Cc1nc(-c2cc(-c3ccc(C)c(S(C)(=O)=O)c3)ccc2-n2cc(C(F)(F)F)nc2C)c(-c2ccc3c(c2)OC(F)(F)O3)o1] | 5-(2,2-difluorobenzo[d][1,3]dioxol-5-yl)-2-methyl-4-(4'-methyl-4-(2-methyl-4-(trifluoromethyl)-1H-imidazol-1-yl)-3'-(methylsulfonyl)biphenyl-3-yl)oxazole |

| Ex # | Structure | Name |
|---|---|---|
| 446 | 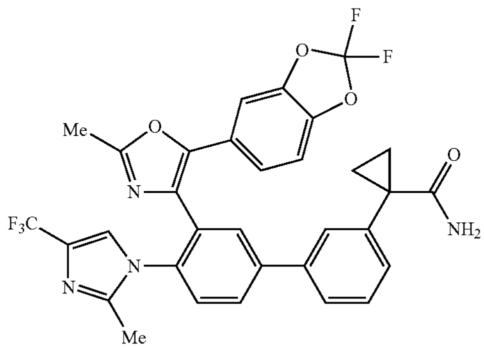 [SMILES: Cc1nc(-c2cc(-c3cccc(C4(C(N)=O)CC4)c3)ccc2-n2cc(C(F)(F)F)nc2C)c(-c2ccc3c(c2)OC(F)(F)O3)o1] | 1-(3'-(5-(2,2-difluorobenzo[d][1,3]dioxol-5-yl)-2-methyloxazol-4-yl)-4'-(2-methyl-4-(trifluoromethyl)-1H-imidazol-1-yl)biphenyl-3-yl)cyclopropanecarboxamide |
| 447 | 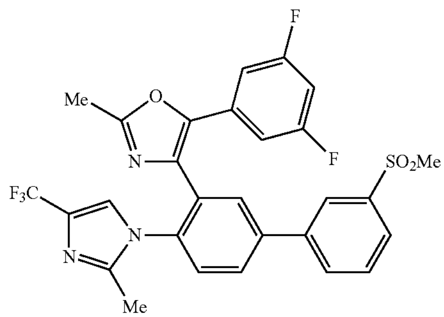 | 5-(3,5-difluorophenyl)-2-methyl-4-(4-(2-methyl-4-(trifluoromethyl)-1H-imidazol-1-yl)-3'-(methylsulfonyl)biphenyl-3-yl)oxazole |
| 448 | 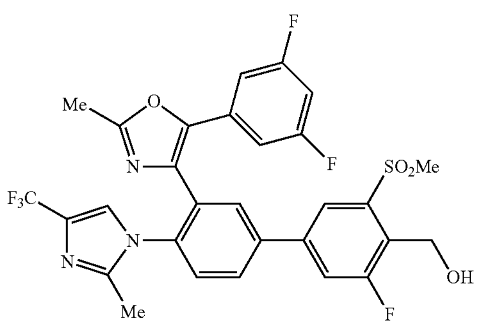 [SMILES: Cc1nc(-c2cc(-c3cc(F)c(CO)c(S(C)(=O)=O)c3)ccc2-n2cc(C(F)(F)F)nc2C)c(-c2cc(F)cc(F)c2)o1] | (3'-(5-(3,5-difluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 449 | 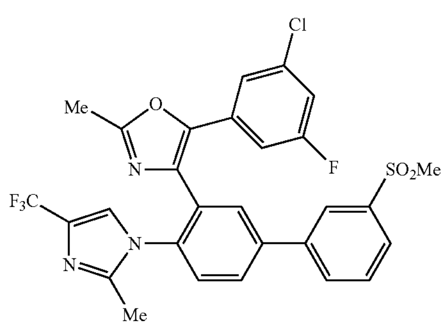 [SMILES: Cc1nc(-c2cc(-c3cccc(S(C)(=O)=O)c3)ccc2-n2cc(C(F)(F)F)nc2C)c(-c2cc(F)cc(Cl)c2)o1] | 5-(3-chloro-5-fluorophenyl)-2-methyl-4-(4-(2-methyl-4-(trifluoromethyl)-1H-imidazol-1-yl)-3'-(methylsulfonyl)biphenyl-3-yl)oxazole |

-continued

| Ex # | Structure | Name |
|---|---|---|
| 450 | 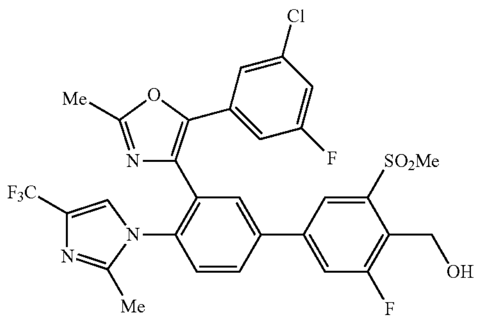 | (3'-(5-(3-chloro-5-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 451 | 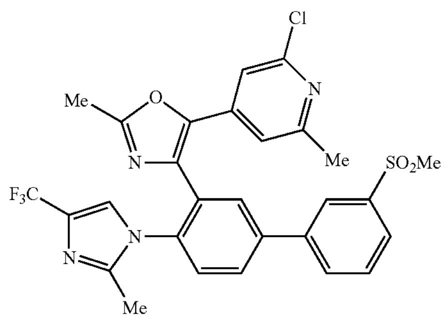 | 5-(2-chloro-6-methylpyridin-4-yl)-2-methyl-4-(4-(2-methyl-4-(trifluoromethyl)-1H-imidazol-1-yl)-3'-(methylsulfonyl)biphenyl-3-yl)oxazole |
| 452 | 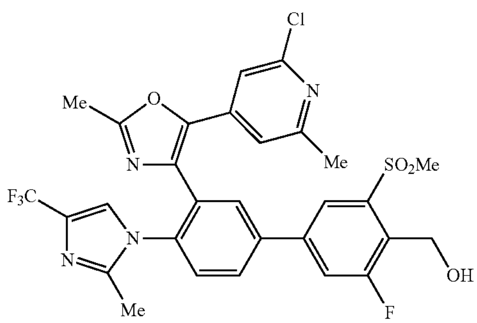 | (3'-(5-(2-chloro-6-methylpyridin-4-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 453 | 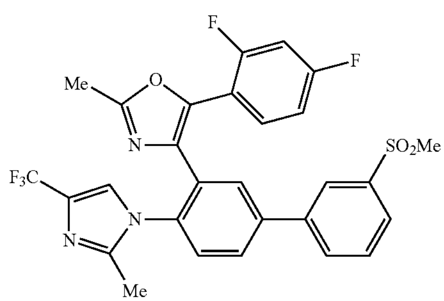 [SMILES: Cc1nc(-c2cc(-c3cccc(S(C)(=O)=O)c3)ccc2-n2cc(C(F)(F)F)nc2C)c(-c2ccc(F)cc2F)o1] | 5-(2,4-difluorophenyl)-2-methyl-4-(4-(2-methyl-4-(trifluoromethyl)-1H-imidazol-1-yl)-3'-(methylsulfonyl)biphenyl-3-yl)oxazole |
| 454 | 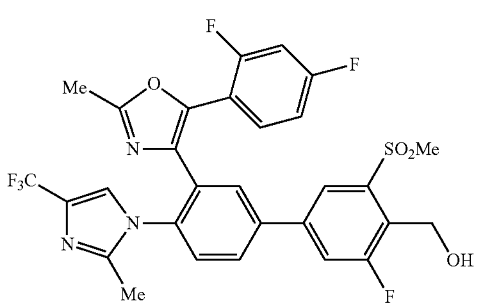 [SMILES: Cc1nc(-c2cc(-c3cc(F)c(CO)c(S(C)(=O)=O)c3)ccc2-n2cc(C(F)(F)F)nc2C)c(-c2ccc(F)cc2F)o1] | (3'-(5-(2,4-difluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |

-continued

| Ex # | Structure | Name |
|---|---|---|
| 455 | 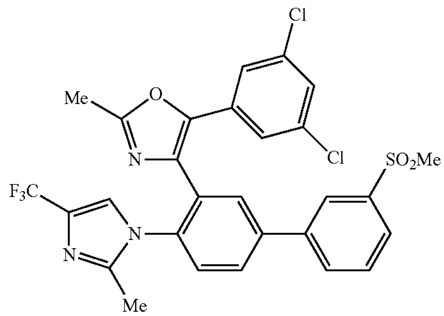 [SMILES: Cc1nc(-c2cc(-c3cccc(S(C)(=O)=O)c3)ccc2-n2cc(C(F)(F)F)nc2C)c(-c2cc(Cl)cc(Cl)c2)o1] | 5-(3,5-dichlorophenyl)-2-methyl-4-(4-(2-methyl-4-(trifluoromethyl)-1H-imidazol-1-yl)-3'-(methylsulfonyl)biphenyl-3-yl)oxazole |
| 456 | 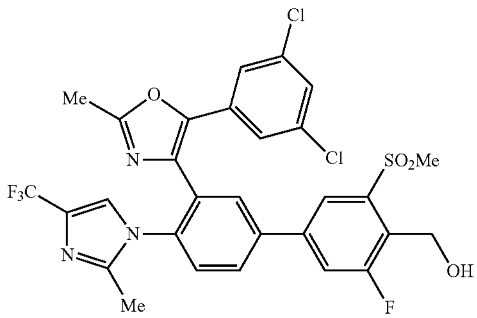 | (3'-(5-(3,5-dichlorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 457 | 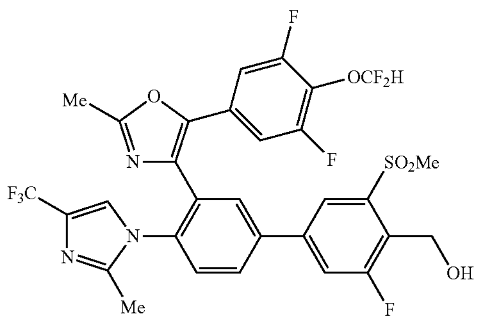 | (3'-(5-(4-(difluoromethoxy)-3,5-difluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 458 | 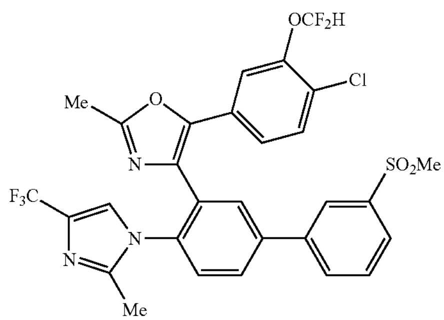 | 5-(4-chloro-3-(difluoromethoxy)phenyl)-2-methyl-4-(4-(2-methyl-4-(trifluoromethyl)-1H-imidazol-1-yl)-3'-(methylsulfonyl)biphenyl-3-yl)oxazole |
| 459 | 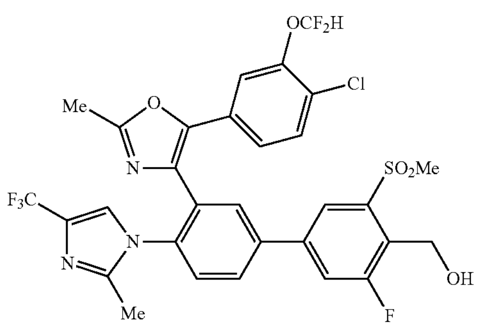 | (3'-(5-(4-chloro-3-(difluoromethoxy)phenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |

| Ex # | Structure | Name |
|------|-----------|------|
| 460 | 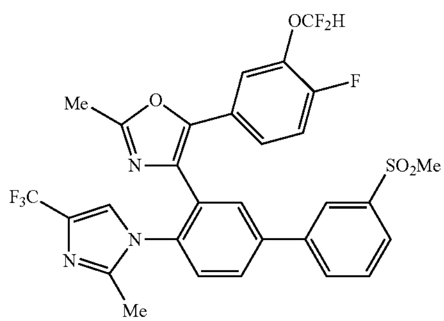 | 5-(3-(difluoromethoxy)-4-fluorophenyl)-2-methyl-4-(4-(2-methyl-4-(trifluoromethyl)-1H-imidazol-1-yl)-3'-(methylsulfonyl)biphenyl-3-yl)oxazole |
| 461 | 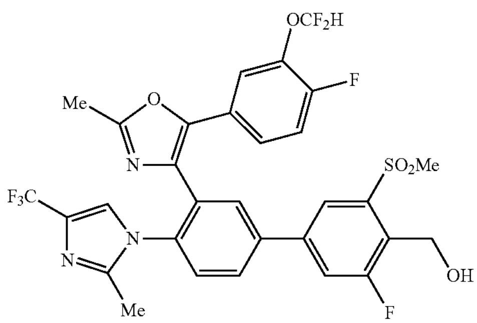 | (3'-(5-(3-(difluoromethoxy)-4-fluorophenyl)-2-methyloxazol-4-yl)-3-fluoro-4'-(2-methyl-4-(trifluoromethyl)-1H-imidazol-1-yl)-5-methylsulfonyl)biphenyl-4-yl)methanol |
| 462 | 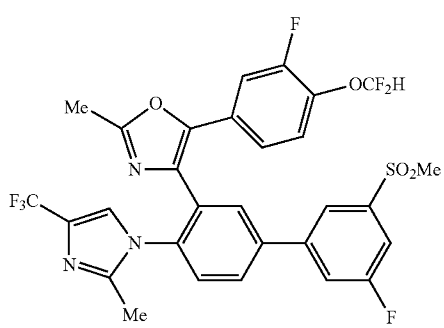 | 5-(4-(difluoromethoxy)-3-fluorophenyl)-4-(3'-fluoro-4-(2-methyl-4-(trifluoromethyl)-1H-imidazol-1-yl)-5'-methylsulfonyl)biphenyl-3-yl)-2-methyloxazole |
| 463 | 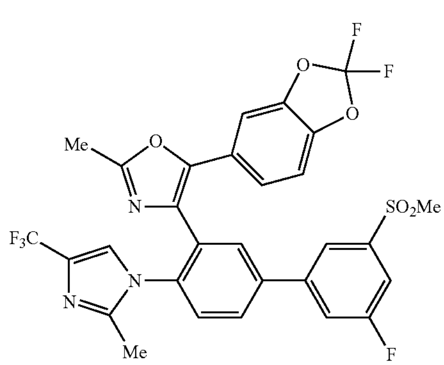 [SMILES: Cc1nc(-c2cc(-c3cc(F)cc(S(C)(=O)=O)c3)ccc2-n2cc(C(F)(F)F)nc2C)c(-c2ccc3c(c2)OC(F)(F)O3)o1] | 5-(2,2-difluorobenzo[d][1,3]dioxol-5-yl)-4-(3'-fluoro-4-(2-methyl-4-(trifluoromethyl)-1H-imidazol-1-yl)-5'-(methylsulfonyl)biphenyl-3-yl)-2-methyloxazole |

-continued

| Ex # | Structure | Name |
|------|-----------|------|
| 464 | 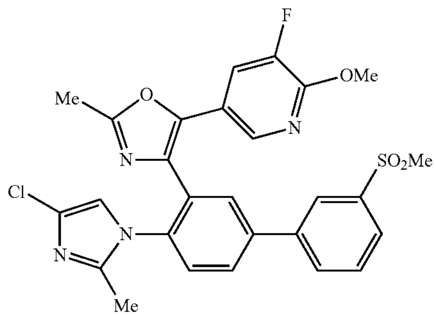 [SMILES: COc1ncc(-c2oc(C)nc2-c2cc(-c3cccc(S(C)(=O)=O)c3)ccc2-n2cc(Cl)nc2C)cc1F] | 4-(4-(4-chloro-2-methyl-1H-imidazol-1-yl)-3'-(methylsulfonyl)biphenyl-3-yl)-5-(5-fluoro-6-methoxypyridin-3-yl)-2-methyloxazole |
| 465 | 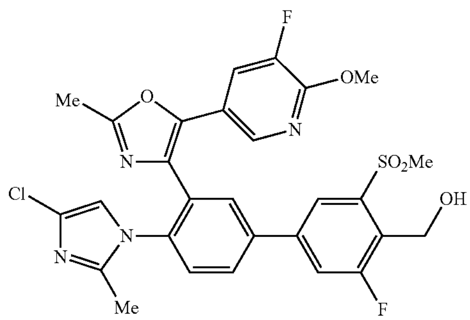 [SMILES: COc1ncc(-c2oc(C)nc2-c2cc(-c3cc(F)c(CO)c(S(C)(=O)=O)c3)ccc2-n2cc(Cl)nc2C)cc1F] | (4'-(4-chloro-2-methyl-1H-imidazol-1-yl)-3-fluoro-3'-(5-(5-fluoro-6-methoxypyridin-3-yl)-2-methyloxazol-4-yl)-5-(methylsulfonyl)biphenyl-4-yl)methanol |
| 466 | 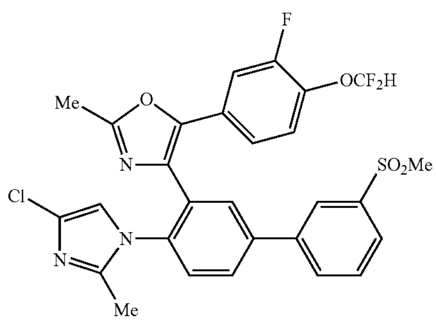 | 4-(4-(4-chloro-2-methyl-1H-imidazol-1-yl)-3'-(methylsulfonyl)biphenyl-3-yl)-5-(4-(difluoromethoxy)-3-fluorophenyl)-2-methyloxazole |
| 467 | 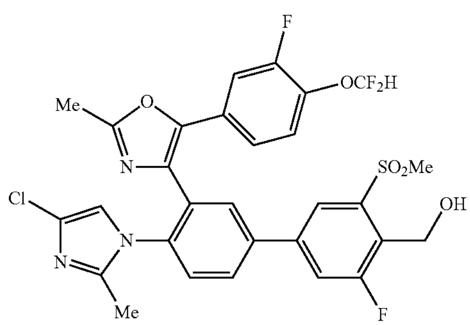 | (4'-(4-chloro-2-methyl-1H-imidazol-1-yl)-3'-(5-(4-(difluoromethoxy)-3-fluorophenyl)-2-methyloxazol-4-yl)-3-fluoro-5-(methylsulfonyl)biphenyl-4-yl)methanol |
| 468 | 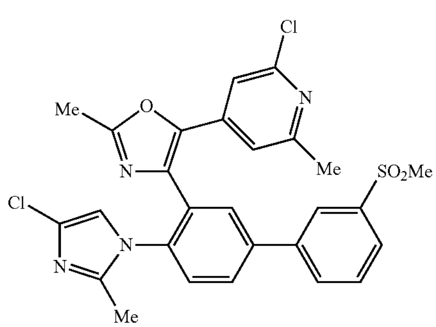 [SMILES: Cc1cc(-c2oc(C)nc2-c2cc(-c3cccc(S(C)(=O)=O)c3)ccc2-n2cc(Cl)nc2C)cc(Cl)n1] | 4-(4-(4-chloro-2-methyl-1H-imidazol-1-yl)-3'-(methylsulfonyl)biphenyl-3-yl)-5-(2-chloro-6-methylpyridin-4-yl)-2-methyloxazole |

| Ex # | Structure | Name |
|---|---|---|
| 469 | 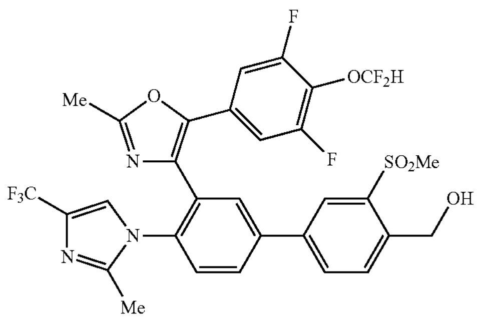 | (3'-(5-(4-(difluoromethoxy)-3,5-difluorophenyl)-2-methyloxazol-4-yl)-4'-(2-methyl-4-(trifluoromethyl)-1H-imidazol-1-yl)-3-(methylsulfonyl)biphenyl-4-yl)methanol |
| 470 | 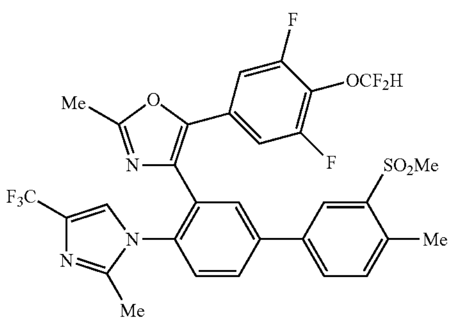 | 5-(4-(difluoromethoxy)-3,5-difluorophenyl)-2-methyl-4-(4'-methyl-4-(2-methyl-4-(trifluoromethyl)-1H-imidazol-1-yl)-3'-(methylsulfonyl)biphenyl-3-yl)oxazole |
| 471 | 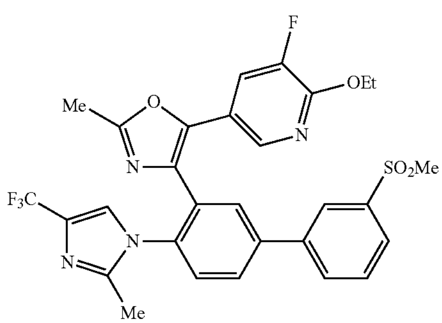 [SMILES: CCOc1ncc(-c2oc(C)nc2-c2cc(-c3cccc(S(C)(=O)=O)c3)ccc2-n2cc(C(F)(F)F)nc2C)cc1F] | 5-(6-ethoxy-5-fluoropyridin-3-yl)-2-methyl-4-(4-(2-methyl-4-(trifluoromethyl)-1H-imidazol-1-yl)-3'-(methylsulfonyl)biphenyl-3-yl)oxazole |
| 472 | 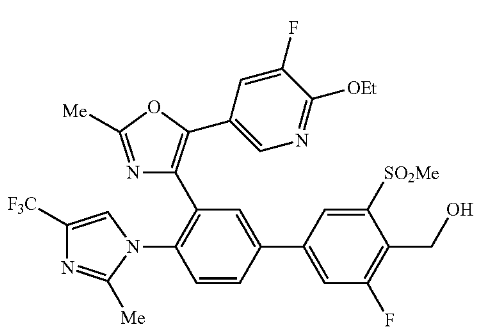 [SMILES: CCOc1ncc(-c2oc(C)nc2-c2cc(-c3cc(F)c(CO)c(S(C)(=O)=O)c3)ccc2-n2cc(C(F)(F)F)nc2C)cc1F] | (3'-(5-(6-ethoxy-5-fluoropyridin-3-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol |

| Ex # | Structure | Name |
|---|---|---|
| 473 | 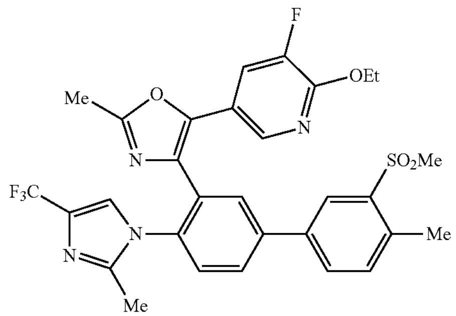 [SMILES: CCOc1ncc(-c2oc(C)nc2-c2cc(-c3ccc(C)c(S(C)(=O)=O)c3)ccc2-n2cc(C(F)(F)F)nc2C)cc1F] | 5-(6-ethoxy-5-fluoropyridin-3-yl)-2-methyl-4-(4'-methyl-4-(2-methyl-4-(trifluoromethyl)-1H-imidazol-1-yl)-3'-(methylsulfonyl)biphenyl-3-yl)oxazole |
| 474 | 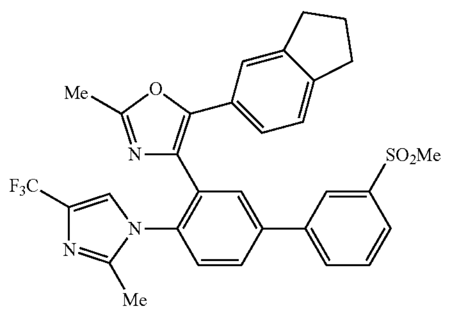 [SMILES: Cc1nc(-c2cc(-c3cccc(S(C)(=O)=O)c3)ccc2-n2cc(C(F)(F)F)nc2C)c(-c2ccc3c(c2)CCC3)o1] | 5-(2,3-dihydro-1H-inden-5-yl)-2-methyl-4-(4-(2-methyl-4-(trifluoromethyl)-1H-imidazol-1-yl)-3'-(methylsulfonyl)biphenyl-3-yl)oxazole |
| 475 | 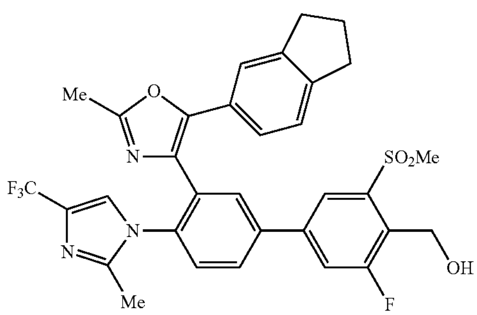 [SMILES: Cc1nc(-c2cc(-c3cc(F)c(CO)c(S(C)(=O)=O)c3)ccc2-n2cc(C(F)(F)F)nc2C)c(-c2ccc3c(c2)CCC3)o1] | (3'-(5-(2,3-dihydro-1H-inden-5-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 476 | 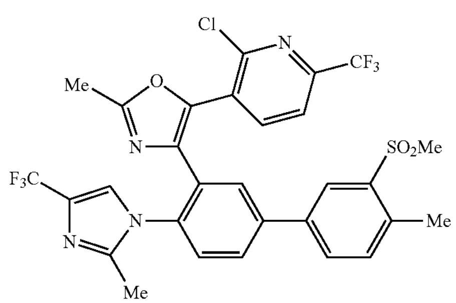 [SMILES: Cc1nc(-c2cc(-c3ccc(C)c(S(C)(=O)=O)c3)ccc2-n2cc(C(F)(F)F)nc2C)c(-c2ccc(C(F)(F)F)nc2Cl)o1] | 5-(2-chloro-6-(trifluoromethyl)pyridin-3-yl)-2-methyl-4-(4'-methyl-4-(2-methyl-4-(trifluoromethyl)-1H-imidazol-1-yl)-3'-(methylsulfonyl)biphenyl-3-yl)oxazole |
| 477 | 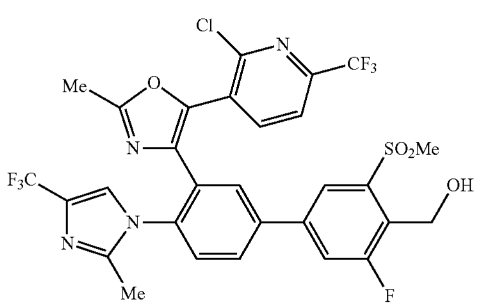 [SMILES: Cc1nc(-c2cc(-c3cc(F)c(CO)c(S(C)(=O)=O)c3)ccc2-n2cc(C(F)(F)F)nc2C)c(-c2ccc(C(F)(F)F)nc2Cl)o1] | (3'-(5-(2-chloro-6-(trifluoromethyl)pyridin-3-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol |

| Ex # | Structure | Name |
|---|---|---|
| 478 | 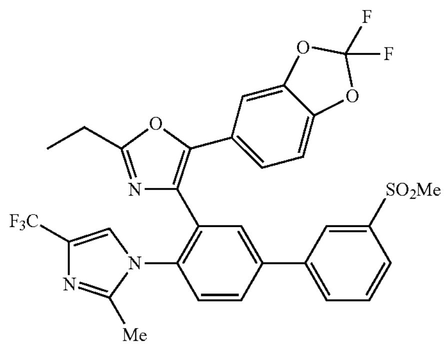 [SMILES: CCc1nc(-c2cc(-c3cccc(S(C)(=O)=O)c3)ccc2-n2cc(C(F)(F)F)nc2C)c(-c2ccc3c(c2)OC(F)(F)O3)o1] | 5-(2,2-difluorobenzo[d][1,3]dioxol-5-yl)-2-ethyl-4-(4-(2-methyl-4-(trifluoromethyl)-1H-imidazol-1-yl)-3'-(methylsulfonyl)biphenyl-3-yl)oxazole |
| 479 | 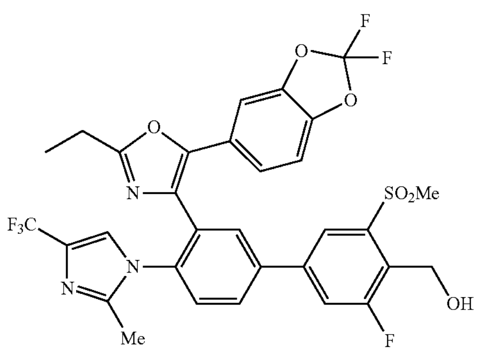 [SMILES: CCc1nc(-c2cc(-c3cc(F)c(CO)c(S(C)(=O)=O)c3)ccc2-n2cc(C(F)(F)F)nc2C)c(-c2ccc3c(c2)OC(F)(F)O3)o1] | (3'-(5-(2,2-difluorobenzo[d][1,3]dioxol-5-yl)-2-ethyloxazol-4-yl)-3-fluoro-4'-(2-methyl-4-(trifluoromethyl)-1H-imidazol-1-yl)-5-(methylsulfonyl)biphenyl-4-yl)methanol |
| 480 | 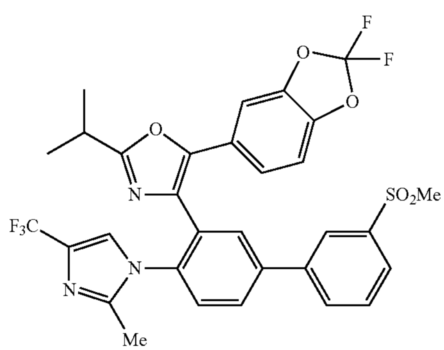 [SMILES: Cc1nc(C(F)(F)F)cn1-c1ccc(-c2cccc(S(C)(=O)=O)c2)cc1-c1nc(C(C)C)oc1-c1ccc2c(c1)OC(F)(F)O2] | 5-(2,2-difluorobenzo[d][1,3]dioxol-5-yl)-2-isopropyl-4-(4-(2-methyl-4-(trifluoromethyl)-1H-imidazol-1-yl)-3'-(methylsulfonyl)biphenyl-3-yl)oxazole |
| 481 | 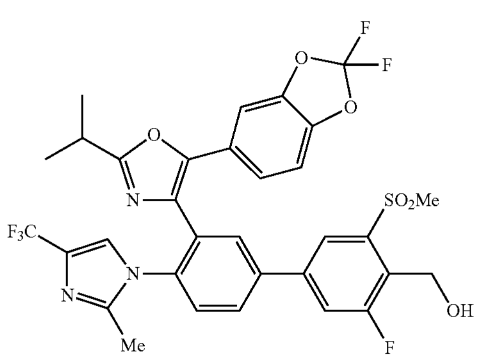 [SMILES: Cc1nc(C(F)(F)F)cn1-c1ccc(-c2cc(F)c(CO)c(S(C)(=O)=O)c2)cc1-c1nc(C(C)C)oc1-c1ccc2c(c1)OC(F)(F)O2] | (3'-(5-(2,2-difluorobenzo[d][1,3]dioxol-5-yl)-2-isopropyloxazol-4-yl)-3-fluoro-4'-(2-methyl-4-(trifluoromethyl)-1H-imidazol-1-yl)-5-(methylsulfonyl)biphenyl-4-yl)methanol |

-continued

| Ex # | Structure | Name |
|---|---|---|
| 482 | 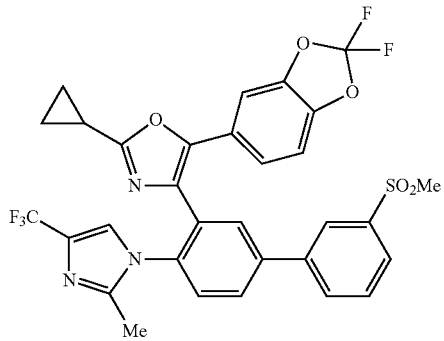 [SMILES: Cc1nc(C(F)(F)F)cn1-c1ccc(-c2cccc(S(C)(=O)=O)c2)cc1-c1nc(C2CC2)oc1-c1ccc2c(c1)OC(F)(F)O2] | 2-cyclopropyl-5-(2,2-difluorobenzo[d][1,3]dioxol-5-yl)-4-(4-(2-methyl-4-(trifluoromethyl)-1H-imidazol-1-yl)-3'-(methylsulfonyl)biphenyl-3-yl)oxazole |
| 483 | 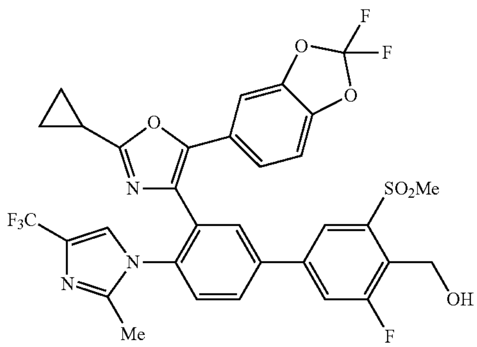 [SMILES: Cc1nc(C(F)(F)F)cn1-c1ccc(-c2cc(F)c(CO)c(S(C)(=O)=O)c2)cc1-c1nc(C2CC2)oc1-c1ccc2c(c1)OC(F)(F)O2] | (3'-(2-cyclopropyl-5-(2,2-difluorobenzo[d][1,3]dioxol-5-yl)oxazol-4-yl)-3-fluoro-4'-(2-methyl-4-(trifluoromethyl)-1H-imidazol-1-yl)-5-(methylsulfonyl)biphenyl-4-yl)methanol |
| 484 | 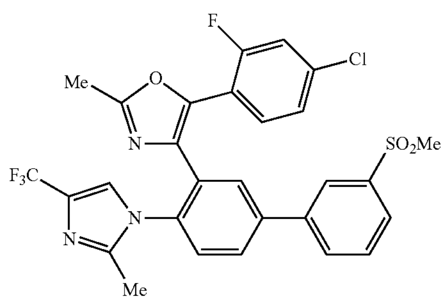 | 5-(4-chloro-2-fluorophenyl)-2-methyl-4-(4-(2-methyl-4-(trifluoromethyl)-1H-imidazol-1-yl)-3'-(methylsulfonyl)biphenyl-3-yl)oxazole |
| 485 | 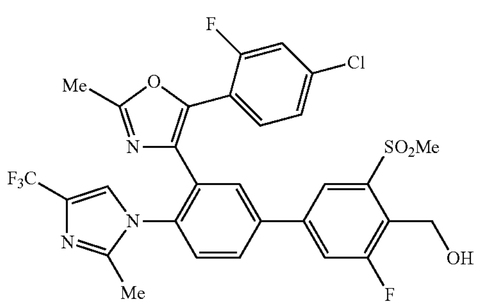 [SMILES: Cc1nc(-c2cc(-c3cc(F)c(CO)c(S(C)(=O)=O)c3)ccc2-n2cc(C(F)(F)F)nc2C)c(-c2ccc(Cl)cc2F)o1] | (3'-(5-(4-chloro-2-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 486 | 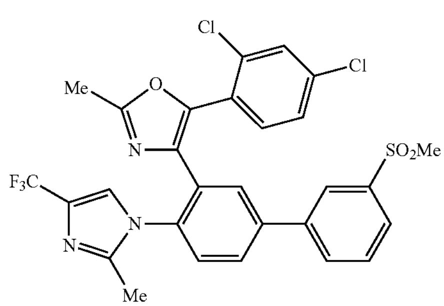 [SMILES: Cc1nc(-c2cc(-c3cccc(S(C)(=O)=O)c3)ccc2-n2cc(C(F)(F)F)nc2C)c(-c2ccc(Cl)cc2Cl)o1] | 5-(2,4-dichlorophenyl)-2-methyl-4-(4-(2-methyl-4-(trifluoromethyl)-1H-imidazol-1-yl)-3'-(methylsulfonyl)biphenyl-3-yl)oxazole |

-continued

| Ex # | Structure | Name |
|---|---|---|
| 487 | 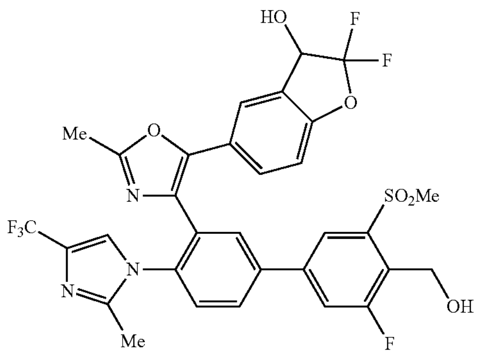 [SMILES: Cc1nc(-c2cc(-c3cc(F)c(CO)c(S(C)(=O)=O)c3)ccc2-n2cc(C(F)(F)F)nc2C)c(-c2ccc3c(c2)C(O)C(F)(F)O3)o1] | 2,2-difluoro-5-(4-(3'-fluoro-4'-(hydroxymethyl)-4-(2-methyl-4-(trifluoromethyl)-1H-imidazol-1-yl)-5'-(methylsulfonyl)biphenyl-3-yl)-2-methyloxazol-5-yl)-2,3-dihydrobenzofuran-3-ol |
| 488 | 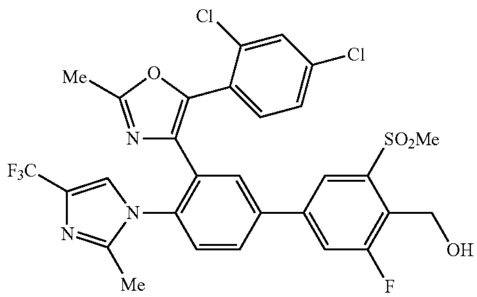 [SMILES: Cc1nc(-c2cc(-c3cc(F)c(CO)c(S(C)(=O)=O)c3)ccc2-n2cc(C(F)(F)F)nc2C)c(-c2ccc(Cl)cc2Cl)o1] | (3'-(5-(2,4-dichlorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 489 | 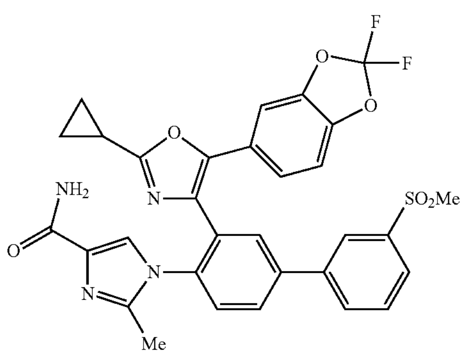 [SMILES: Cc1nc(C(N)=O)cn1-c1ccc(-c2cccc(S(C)(=O)=O)c2)cc1-c1nc(C2CC2)oc1-c1ccc2c(c1)OC(F)(F)O2] | 1-(3-(2-cyclopropyl-5-(2,2-difluorobenzo[d][1,3]dioxol-5-yl)oxazol-4-yl)-3'-(methylsulfonyl)biphenyl-4-yl)-2-methyl-1H-imidazole-4-carboxamide |
| 490 | 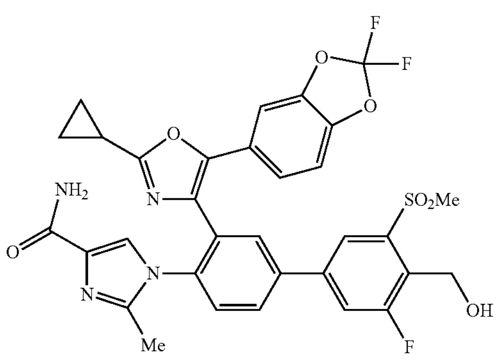 [SMILES: Cc1nc(C(N)=O)cn1-c1ccc(-c2cc(F)c(CO)c(S(C)(=O)=O)c2)cc1-c1nc(C2CC2)oc1-c1ccc2c(c1)OC(F)(F)O2] | 1-(3-(2-cyclopropyl-5-(2,2-difluorobenzo[d][1,3]dioxol-5-yl)oxazol-4-yl)-3'-fluoro-4'-(hydroxymethyl)-5'-methylsulfonyl)biphenyl-4-yl)-2-methyl-1H-imidazole-4-carboxamide |

-continued

| Ex # | Structure | Name |
|---|---|---|
| 491 | 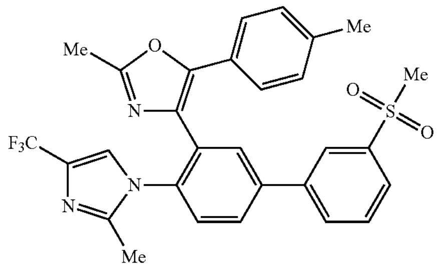 [SMILES: Cc1ccc(-c2oc(C)nc2-c2cc(-c3cccc(S(C)(=O)=O)c3)ccc2-n2cc(C(F)(F)F)nc2C)cc1] | 2-methyl-4-(4-(2-methyl-4-(trifluoromethyl)-1H-imidazol-1-yl)-3'-(methylsulfonyl)-[1,1'-biphenyl]-3-yl)-5-(p-tolyl)oxazole |
| 492 | 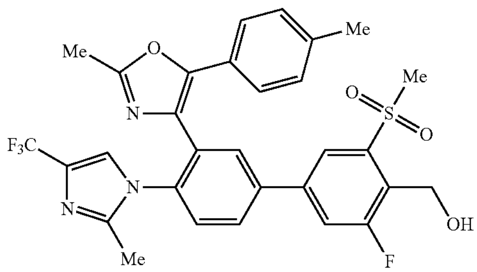 [SMILES: Cc1ccc(-c2oc(C)nc2-c2cc(-c3cc(F)c(CO)c(S(C)(=O)=O)c3)ccc2-n2cc(C(F)(F)F)nc2C)cc1] | (3-fluoro-4'-(2-methyl-4-(trifluoromethyl)-1H-imidazol-1-yl)-3'-(2-methyl-5-p-tolyloxazol-4-yl)-5-(methylsulfonyl)biphenyl-4-yl)methanol |
| 493 | 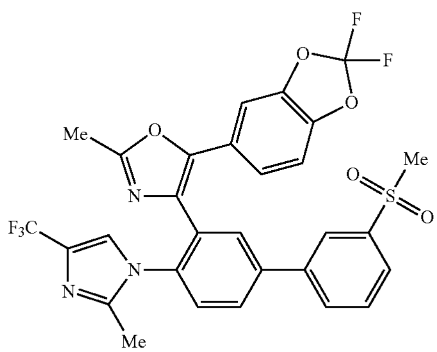 [SMILES: Cc1nc(-c2cc(-c3cccc(S(C)(=O)=O)c3)ccc2-n2cc(C(F)(F)F)nc2C)c(-c2ccc3c(c2)OC(F)(F)O3)o1] | 5-(2,2-difluorobenzo[d][1,3]dioxol-5-yl)-2-methyl-4-(4-(2-methyl-4-(trifluoromethyl)-1H-imidazol-1-yl)-3'-(methylsulfonyl)biphenyl-3-yl)oxazole |
| 494 | 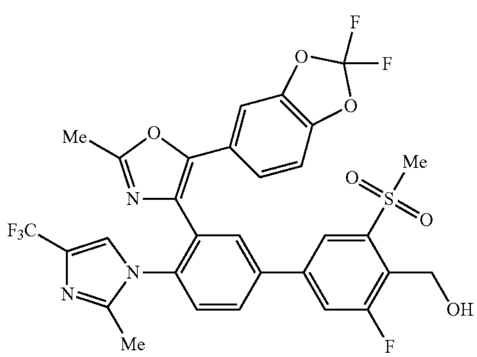 [SMILES: Cc1nc(-c2cc(-c3cc(F)c(CO)c(S(C)(=O)=O)c3)ccc2-n2cc(C(F)(F)F)nc2C)c(-c2ccc3c(c2)OC(F)(F)O3)o1] | (3'-(5-(2,2-difluorobenzo[d][1,3]dioxol-5-yl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 495 | 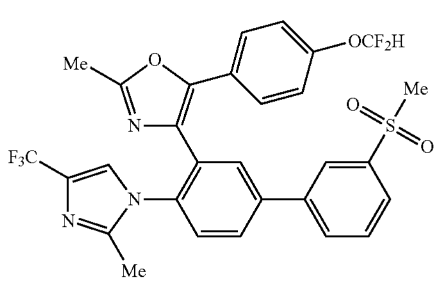 | 5-(4-(difluoromethoxy)phenyl)-2-methyl-4-(4-(2-methyl-4-(trifluoromethyl)-1H-imidazol-1-yl)-3'-(methylsulfonyl)biphenyl-3-yl)oxazole |

-continued

| Ex # | Structure | Name |
|---|---|---|
| 496 | 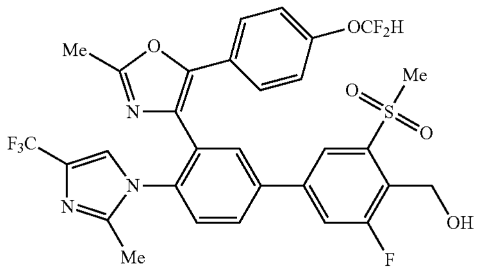 | (3'-(5-(4-(difluoromethoxy)phenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 497 | 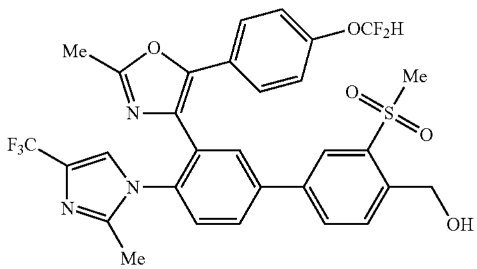 | (3'-(5-(4-(difluoromethoxy)phenyl)-2-methyloxazol-4-yl)-4'-(2-methyl-4-(trifluoromethyl)-1H-imidazol-1-yl)-3-(methylsulfonyl)biphenyl-4-yl)methanol |
| 498 | 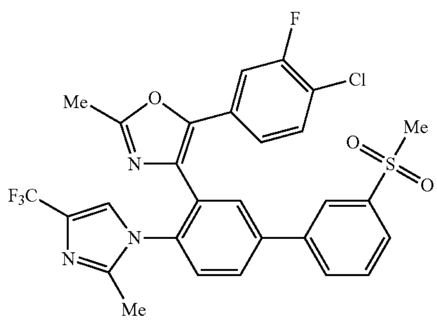 | 5-(4-chloro-3-fluorophenyl)-2-methyl-4-(4-(2-methyl-4-(trifluoromethyl)-1H-imidazol-1-yl)-3'-(methylsulfonyl)biphenyl-3-yl)oxazole |
| 499 | 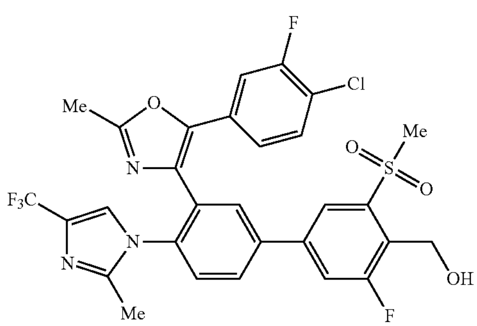 [SMILES: Cc1nc(-c2cc(-c3cc(F)c(CO)c(S(C)(=O)=O)c3)ccc2-n2cc(C(F)(F)F)nc2C)c(-c2ccc(Cl)c(F)c2)o1] | (3'-(5-(4-chloro-3-fluorophenyl)-2-methyloxazol-4-yl)-3-fluoro-4'-(2-methyl-4-(trifluoromethyl)-1H-imidazol-1-yl)-5-methylsulfonyl)biphenyl-4-yl)methanol |
| 500 | 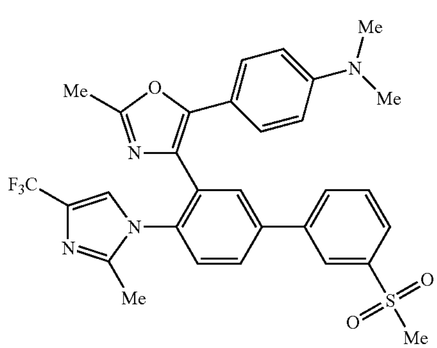 [SMILES: Cc1nc(-c2cc(-c3cccc(S(C)(=O)=O)c3)ccc2-n2cc(C(F)(F)F)nc2C)c(-c2ccc(N(C)C)cc2)o1] | N,N-dimethyl-4-(2-methyl-4-(4-(2-methyl-4-(trifluoromethyl)-1H-imidazol-1-yl)-3'-(methylsulfonyl)biphenyl-3-yl)oxazol-5-yl)aniline |

-continued

| Ex # | Structure | Name |
|---|---|---|
| 501 | 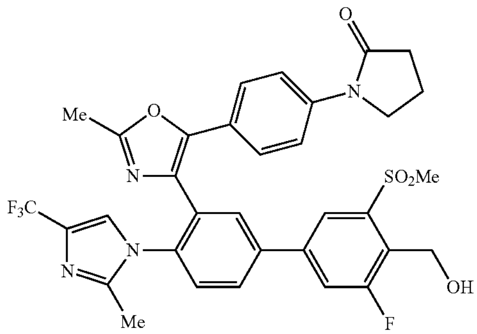 [SMILES: Cc1nc(-c2cc(-c3cc(F)c(CO)c(S(C)(=O)=O)c3)ccc2-n2cc(C(F)(F)F)nc2C)c(-c2ccc(N3CCCC3=O)cc2)o1] | 1-(4-(4-(3'-fluoro-4'-(hydroxmethyl)-4-(2-methyl-4-(trifluoromethyl)-1H-imidazol-1-yl)-5'-(methylsulfonyl)biphenyl-3-yl)-2-methyloxazol-5-yl)phenyl)pyrrolidin-2-one |
| 502 | 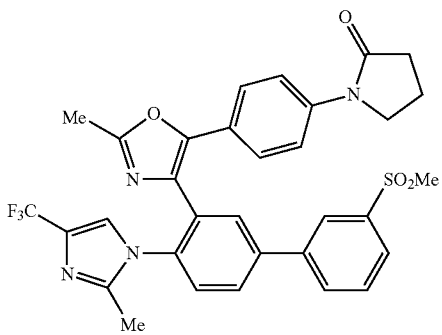 [SMILES: Cc1nc(-c2cc(-c3cccc(S(C)(=O)=O)c3)ccc2-n2cc(C(F)(F)F)nc2C)c(-c2ccc(N3CCCC3=O)cc2)o1] | 1-(4-(2-methyl-4-(4-(2-methyl-4-(trifluoromethyl)-1H-imidazol-1-yl)-3'-(methylsulfonyl)biphenyl-3-yl)oxazol-5-yl)phenyl)pyrrolidin-2-one |
| 503 | 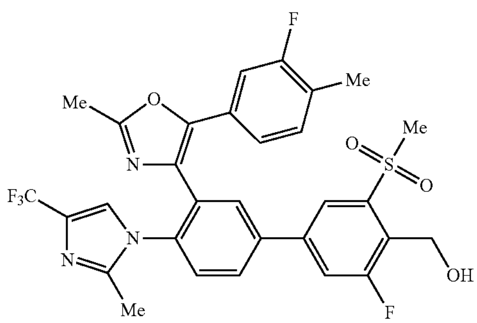 | (3-fluoro-3'-(5-(3-fluoro-4-methylphenyl)-2-methyloxazol-4-yl)-4'-(2-methyl-4-(trifluoromethyl)-1H-imidazol-1-yl)-5-(methylsulfonyl)biphenyl-4-yl)methanol |
| 504 | 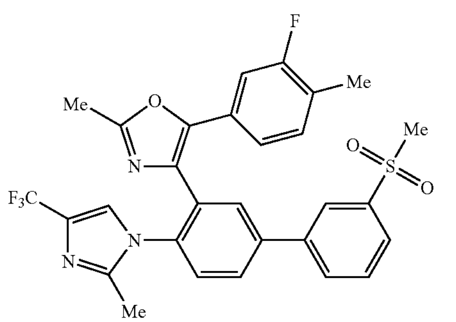 [SMILES: Cc1nc(-c2cc(-c3cccc(S(C)(=O)=O)c3)ccc2-n2cc(C(F)(F)F)nc2C)c(-c2ccc(C)c(F)c2)o1] | 5-(3-fluoro-4-methylphenyl)-2-methyl-4-(4-(2-methyl-4-(trifluoromethyl)-1H-imidazol-1-yl)-3'-(methylsulfonyl)biphenyl-3-yl)oxazole |
| 505 | 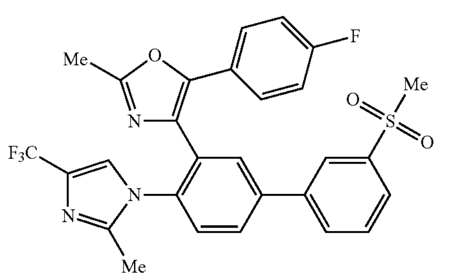 [SMILES: Cc1nc(-c2cc(-c3cccc(S(C)(=O)=O)c3)ccc2-n2cc(C(F)(F)F)nc2C)c(-c2ccc(F)cc2)o1] | 5-(4-fluorophenyl)-2-methyl-4-(4-(2-methyl-4-(trifluoromethyl)-1H-imidazol-1-yl)-3'-(methylsulfonyl)biphenyl-3-yl)oxazole |

| Ex # | Structure | Name |
|---|---|---|
| 506 | 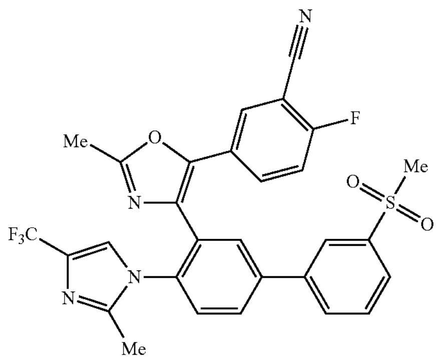 [SMILES: Cc1nc(-c2cc(-c3cccc(S(C)(=O)=O)c3)ccc2-n2cc(C(F)(F)F)nc2C)c(-c2ccc(F)c(C#N)c2)o1] | 2-fluoro-5-(2-methyl-4-(4-(2-methyl-4-(trifluoromethyl)-1H-imidazol-1-yl)-3'-(methylsulfonyl)biphenyl-3-yl)oxazol-5-yl)benzonitrile |
| 507 | 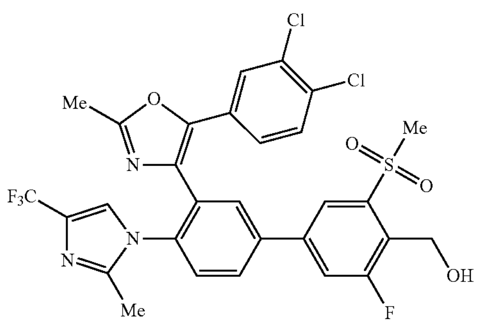 [SMILES: Cc1nc(-c2cc(-c3cc(F)c(CO)c(S(C)(=O)=O)c3)ccc2-n2cc(C(F)(F)F)nc2C)c(-c2ccc(Cl)c(Cl)c2)o1] | (3'-(5-(3,4-dichlorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |
| 508 | 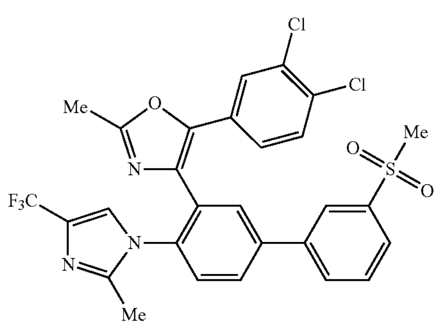 [SMILES: Cc1nc(-c2cc(-c3cccc(S(C)(=O)=O)c3)ccc2-n2cc(C(F)(F)F)nc2C)c(-c2ccc(Cl)c(Cl)c2)o1] | 5-(3,4-dichlorophenyl)-2-methyl-4-(4-(2-methyl-4-(trifluoromethyl)-1H-imidazol-1-yl)-3'-(methylsulfonyl)biphenyl-3-yl)oxazole |
| 509 | 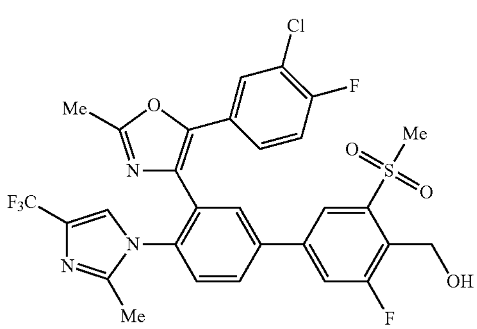 | (3'-(5-(3-chloro-4-fluorophenyl)-2-methyloxazol-4-yl)-3-fluoro-4'-(2-methyl-4-(trifluoromethyl)-1H-imidazol-1-yl)-5-(methylsulfonyl)biphenyl-4-yl)methanol |

-continued

| Ex # | Structure | Name |
|---|---|---|
| 510 | 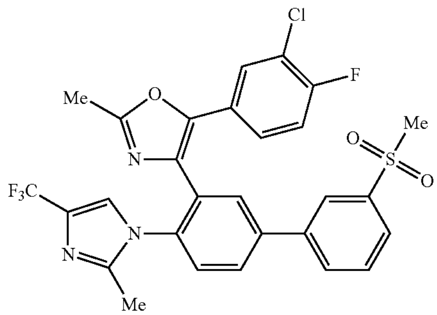 [SMILES: Cc1nc(-c2cc(-c3cccc(S(C)(=O)=O)c3)ccc2-n2cc(C(F)(F)F)nc2C)c(-c2ccc(F)c(Cl)c2)o1] | 5-(3-chloro-4-fluorophenyl)-2-methyl-4-(4-(2-methyl-4-(trifluoromethyl)-1H-imidazol-1-yl)-3'-(methylsulfonyl)biphenyl-3-yl)oxazole |
| 511 | 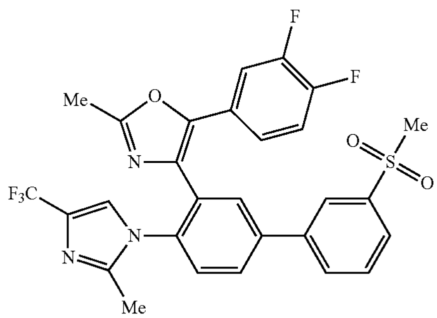 | 5-(3,4-difluorophenyl)-2-methyl-4-(4-(2-methyl-4-(trifluoromethyl)-1H-imidazol-1-yl)-3'-(methylsulfonyl)biphenyl-3-yl)oxazole |
| 512 | 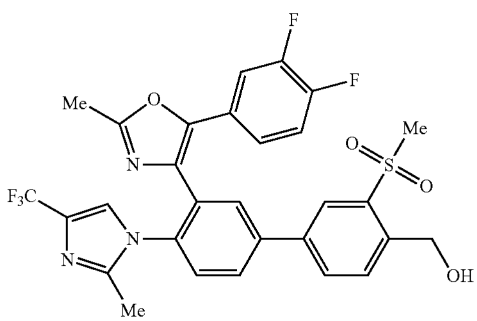 [SMILES: Cc1nc(-c2cc(-c3ccc(CO)c(S(C)(=O)=O)c3)ccc2-n2cc(C(F)(F)F)nc2C)c(-c2ccc(F)c(F)c2)o1] | (3'-(5-(3,4-difluorophenyl)-2-methyloxazol-4-yl)-4'-(2-methyl-4-(trifluoromethyl)-1H-imidazol-1-yl)-3-(methylsulfonyl)biphenyl-4-yl)methanol |
| 513 | 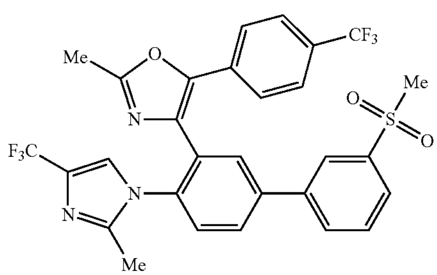 [SMILES: Cc1nc(-c2cc(-c3cccc(S(C)(=O)=O)c3)ccc2-n2cc(C(F)(F)F)nc2C)c(-c2ccc(C(F)(F)F)cc2)o1] | 2-methyl-4-(4-(2-methyl-4-(trifluoromethyl)-1H-imidazol-1-yl)-3'-(methylsulfonyl)biphenyl-3-yl)-5-(4-(trifluoromethyl)phenyl)oxazole |
| 514 | 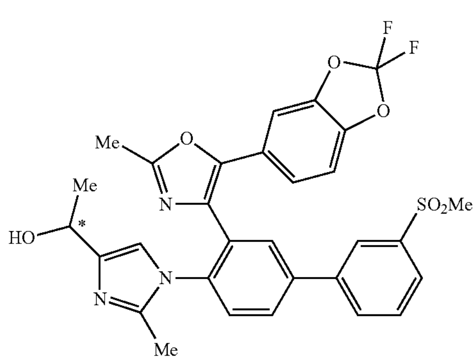 [SMILES: Cc1nc(-c2cc(-c3cccc(S(C)(=O)=O)c3)ccc2-n2cc(C(C)O)nc2C)c(-c2ccc3c(c2)OC(F)(F)O3)o1] | 1-(1-(3-(5-(2,2-difluorobenzo[d][1,3]dioxol-5-yl)-2-methyloxazol-4-yl)-3'-(methylsulfonyl)-[1,1'-biphenyl]-4-yl)-2-methyl-1H-imidazol-4-yl)ethanol One enantiomer |

| Ex # | Structure | Name |
|---|---|---|
| 515 | 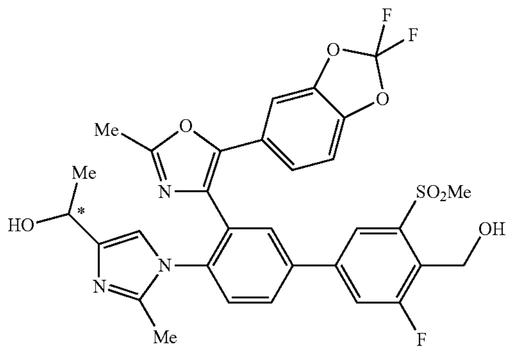 [SMILES: Cc1nc(-c2cc(-c3cc(F)c(CO)c(S(C)(=O)=O)c3)ccc2-n2cc(C(C)O)nc2C)c(-c2ccc3c(c2)OC(F)(F)O3)o1] | 1-(1-(3-(5-(2,2-difluorobenzo[d][1,3]dioxol-5-yl)-2-methyloxazol-4-yl)-3'-fluoro-4'-(hydroxymethyl)-5'-(methylsulfonyl)-[1,1'-biphenyl]-4-yl)-2-methyl-1H-imidazol-4-yl)ethanol, one enantiomer |
| 516 | 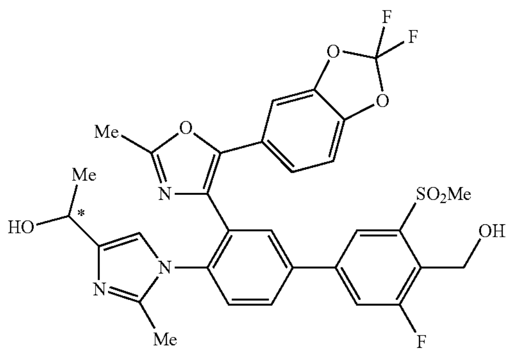 [SMILES: Cc1nc(-c2cc(-c3cc(F)c(CO)c(S(C)(=O)=O)c3)ccc2-n2cc(C(C)O)nc2C)c(-c2ccc3c(c2)OC(F)(F)O3)o1] | 1-(1-(3-(5-(2,2-difluorobenzo[d][1,3]dioxol-5-yl)-2-methyloxazol-4-yl)-3'-fluoro-4'-(hydroxymethyl)-5'-(methylsulfonyl)-[1,1'-biphenyl]-4-yl)-2-methyl-1H-imidazol-4-yl)ethanol, another enantiomer |
| 517 | 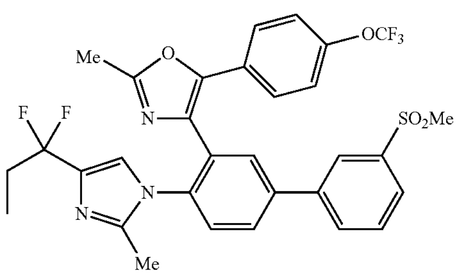 [SMILES: CCC(F)(F)c1cn(-c2ccc(-c3cccc(S(C)(=O)=O)c3)cc2-c2nc(C)oc2-c2ccc(OC(F)(F)F)cc2)c(C)n1] | 4-(4-(4-(1,1-difluoropropyl)-2-methyl-1H-imidazol-1-yl)-3'-(methylsulfonyl)-[1,1'-biphenyl]-3-yl)-2-methyl-5-(4-(trifluoromethoxy)phenyl)oxazole |
| 518 | 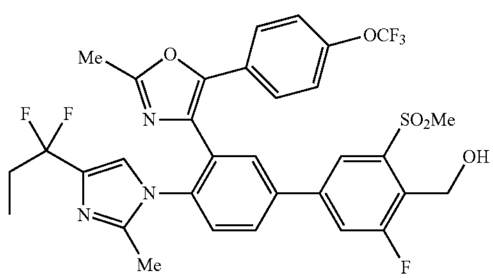 [SMILES: CCC(F)(F)c1cn(-c2ccc(-c3cc(F)c(CO)c(S(C)(=O)=O)c3)cc2-c2nc(C)oc2-c2ccc(OC(F)(F)F)cc2)c(C)n1] | (4'-(4-(1,1-difluoropropyl)-2-methyl-1H-imidazol-1-yl)-3-fluoro-3'-(2-methyl-5-(4-(trifluoromethoxy)phenyl)oxazol-4-yl)-5-(methylsulfonyl)-[1,1'-biphenyl]-4-yl)methanol |
| 519 | 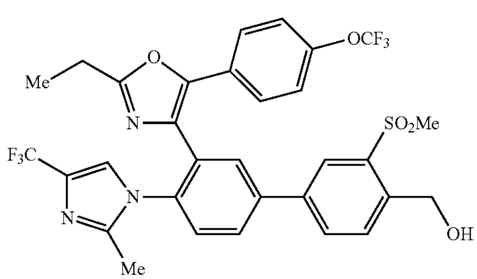 [SMILES: CCc1nc(-c2cc(-c3ccc(CO)c(S(C)(=O)=O)c3)ccc2-n2cc(C(F)(F)F)nc2C)c(-c2ccc(OC(F)(F)F)cc2)o1] | (3'-(2-ethyl-5-(4-(trifluoromethoxy)phenyl)oxazol-4-yl)-4'-(2-methyl-4-(trifluoromethyl)-1H-imidazol-1-yl)-3-(methylsulfonyl)-[1,1'-biphenyl]-4-yl)methanol |

| Ex # | Structure | Name |
|---|---|---|
| 520 | 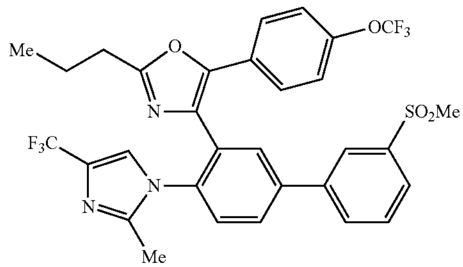 | 4-(4-(2-methyl-4-(trifluoromethyl)-1H-imidazol-1-yl)-3'-(methylsulfonyl)-[1,1'-biphenyl]-3-yl)-2-propyl-5-(4-(trifluoromethoxy)phenyl)oxazole |
| 521 | 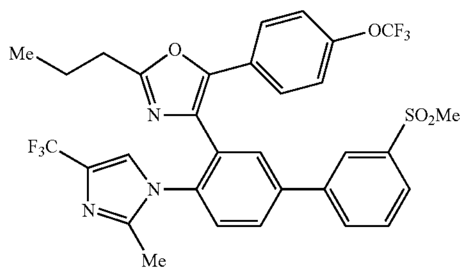 [SMILES: CCCc1nc(-c2cc(-c3cccc(S(C)(=O)=O)c3)ccc2-n2cc(C(F)(F)F)nc2C)c(-c2ccc(OC(F)(F)F)cc2)o1] | (3'-(2-isopropyl-5-(4-(trifluoromethoxy)phenyl)oxazol-4-yl)-4'-(2-methyl-4-(trifluoromethyl)-1H-imidazol-1-yl)-3-(methylsulfonyl)-[1,1'-biphenyl]-4-yl)methanol |
| 522 | 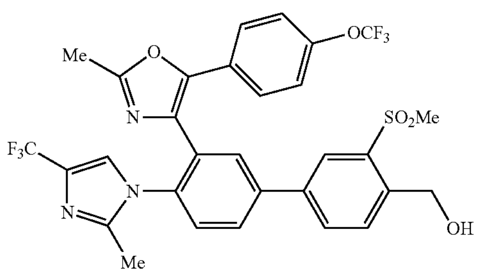 [SMILES: Cc1nc(-c2cc(-c3ccc(CO)c(S(C)(=O)=O)c3)ccc2-n2cc(C(F)(F)F)nc2C)c(-c2ccc(OC(F)(F)F)cc2)o1] | (4'-(2-methyl-4-(trifluoromethyl)-1H-imidazol-1-yl)-3'-(2-methyl-5-(4-(trifluoromethoxy)phenyl)oxazol-4-yl)-3-(methylsulfonyl)-[1,1'-biphenyl]-4-yl)methanol |
| 523 | 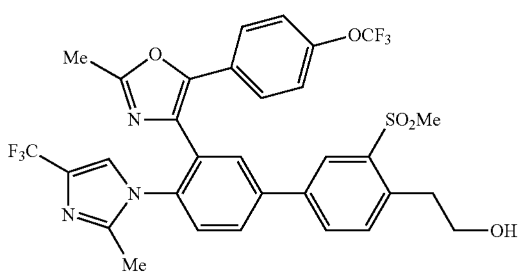 [SMILES: Cc1nc(-c2cc(-c3ccc(CCO)c(S(C)(=O)=O)c3)ccc2-n2cc(C(F)(F)F)nc2C)c(-c2ccc(OC(F)(F)F)cc2)o1] | 2-(4'-(2-methyl-4-(trifluoromethyl)-1H-imidazol-1-yl)-3'-(2-methyl-5-(4-(trifluoromethoxy)phenyl)oxazol-4-yl)-3-(methylsulfonyl)-[1,1'-biphenyl]-4-yl)ethanol |
| 524 | 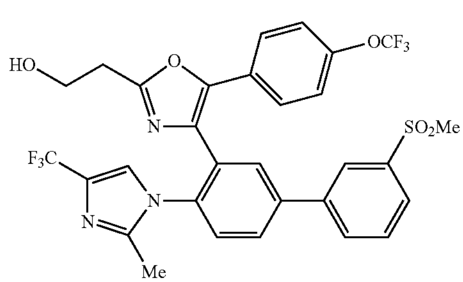 [SMILES: Cc1nc(C(F)(F)F)cn1-c1ccc(-c2cccc(S(C)(=O)=O)c2)cc1-c1nc(CCO)oc1-c1ccc(OC(F)(F)F)cc1] | 2-(4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazol-2-yl)ethanol |

-continued

| Ex # | Structure | Name |
|---|---|---|
| 525 | 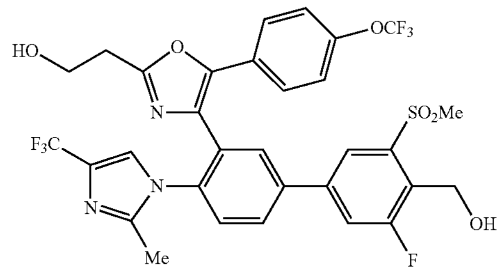 [SMILES: Cc1nc(C(F)(F)F)cn1-c1ccc(-c2cc(F)c(CO)c(S(C)(=O)=O)c2)cc1-c1nc(CCO)oc1-c1ccc(OC(F)(F)F)cc1] | 2-(4-(3'-fluoro-4'-(hydroxymethyl)-4-(2-methyl-4-(trifluoromethyl)-1H-imidazol-1-yl)-5'-(methylsulfonyl)-[1,1'-biphenyl]-3-yl)-5-(4-(trifluoromethoxy)phenyl)oxazol-2-yl)ethanol |
| 526 | 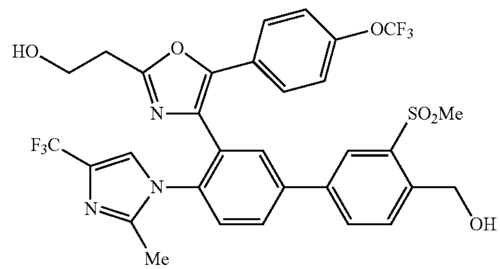 [SMILES: Cc1nc(C(F)(F)F)cn1-c1ccc(-c2ccc(CO)c(S(C)(=O)=O)c2)cc1-c1nc(CCO)oc1-c1ccc(OC(F)(F)F)cc1] | 2-(4-(4'-(hydroxymethyl)-4-(2-methyl-4-(trifluoromethyl)-1H-imidazol-1-yl)-3'-(methylsulfonyl)-[1,1'-biphenyl]-3-yl)-5-(4-trifluoromethoxy)phenyl)oxazol-2-yl)ethanol |
| 527 | 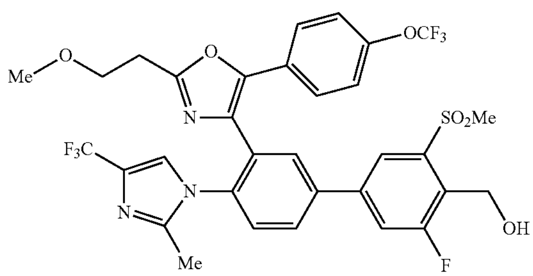 [SMILES: COCCc1nc(-c2cc(-c3cc(F)c(CO)c(S(C)(=O)=O)c3)ccc2-n2cc(C(F)(F)F)nc2C)c(-c2ccc(OC(F)(F)F)cc2)o1] | (3-fluoro-3'-(2-(2-methoxyethyl)-5-(4-(trifluoromethoxy)phenyl)oxazol-4-yl)-4'-(2-methyl-4-(trifluoromethyl)-1H-imidazol-1-yl)-5-(methylsulfonyl)-[1,1'-biphenyl]-4-yl)methanol |
| 528 | 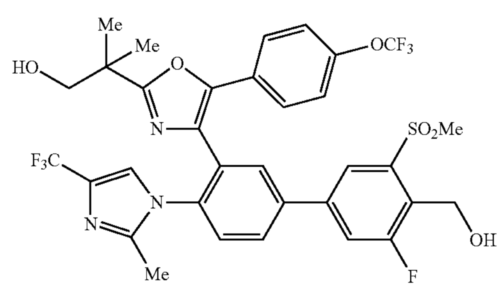 [SMILES: Cc1nc(C(F)(F)F)cn1-c1ccc(-c2cc(F)c(CO)c(S(C)(=O)=O)c2)cc1-c1nc(C(C)(C)CO)oc1-c1ccc(OC(F)(F)F)cc1] | 2-(4-(3'-fluoro-4'-(hydroxymethyl)-4-(2-methyl-4-(trifluoromethyl)-1H-imidazol-1-yl)-5'-(methylsulfonyl)-[1,1'-biphenyl]-3-yl)-5-(4-(trifluoromethoxy)phenyl)oxazol-2-yl)-2-methylpropan-1-ol |
| 529 | 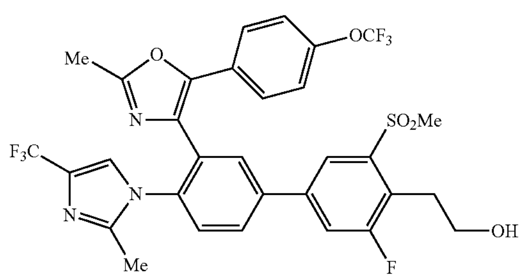 [SMILES: Cc1nc(-c2cc(-c3cc(F)c(CCO)c(S(C)(=O)=O)c3)ccc2-n2cc(C(F)(F)F)nc2C)c(-c2ccc(OC(F)(F)F)cc2)o1] | 2-(3-fluoro-4'-(2-methyl-4-(trifluoromethyl)-1H-imidazol-1-yl)-3'-(2-methyl-5-(4-(trifluoromethoxy)phenyl)oxazol-4-yl)-5-(methylsulfonyl)-[1,1'-biphenyl]-4-yl)ethanol |

| Ex # | Structure | Name |
|---|---|---|
| 530 | 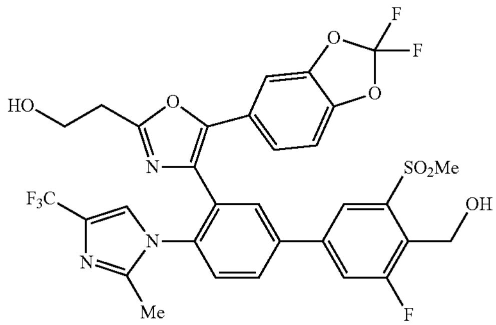 [SMILES: Cc1nc(C(F)(F)F)cn1-c1ccc(-c2cc(F)c(CO)c(S(C)(=O)=O)c2)cc1-c1nc(CCO)oc1-c1ccc2c(c1)OC(F)(F)O2] | 2-(5-(2,2-difluorobenzo[d][1,3]dioxol-5-yl)-4-(3'-fluoro-4'-(hydroxymethyl)-4-(2-methyl-4-(trifluoromethyl)-1H-imidazol-1-yl)-5'-(methylsulfonyl)-[1,1'-biphenyl]-3-yl)oxazol-2-yl)ethanol |
| 531 | 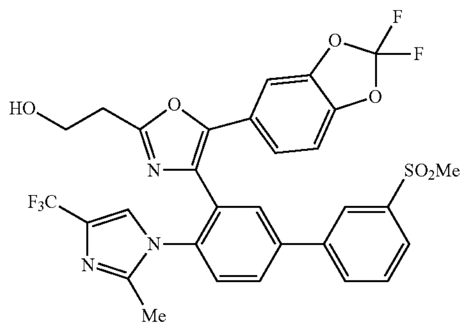 [SMILES: Cc1nc(C(F)(F)F)cn1-c1ccc(-c2cccc(S(C)(=O)=O)c2)cc1-c1nc(CCO)oc1-c1ccc2c(c1)OC(F)(F)O2] | 2-(5-(2,2-difluorobenzo[d][1,3]dioxol-5-yl)-4-(4-(2-methyl-4-(trifluoromethyl)-1H-imidazol-1-yl)-3'-(methylsulfonyl)-[1,1'-biphenyl]-3-yl)oxazol-2-yl)ethanol |
| 532 | 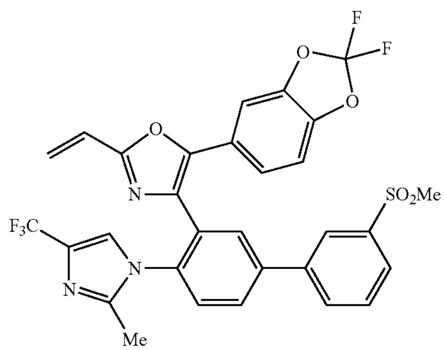 [SMILES: C=Cc1nc(-c2cc(-c3cccc(S(C)(=O)=O)c3)ccc2-n2cc(C(F)(F)F)nc2C)c(-c2ccc3c(c2)OC(F)(F)O3)o1] | 5-(2,2-difluorobenzo[d][1,3]dioxol-5-yl)-4-(4-(2-methyl-4-(trifluoromethyl)-1H-imidazol-1-yl)-3'-(methylsulfonyl)-[1,1'-biphenyl]-3-yl)-2-vinyloxazole |
| 533 | 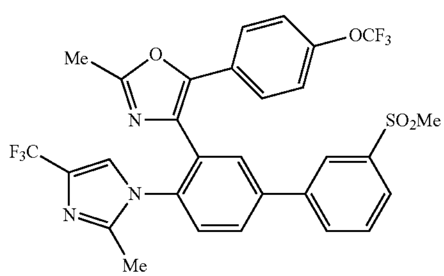 [SMILES: Cc1nc(-c2cc(-c3cccc(S(C)(=O)=O)c3)ccc2-n2cc(C(F)(F)F)nc2C)c(-c2ccc(OC(F)(F)F)cc2)o1] | 2-methyl-4-(4-(2-methyl-4-(trifluoromethyl)-1H-imidazol-1-yl)-3'-(methylsulfinyl)-[1,1'-biphenyl]-3-yl)-5-(4-(trifluoromethoxy)phenyl)oxazole |
| 534 | 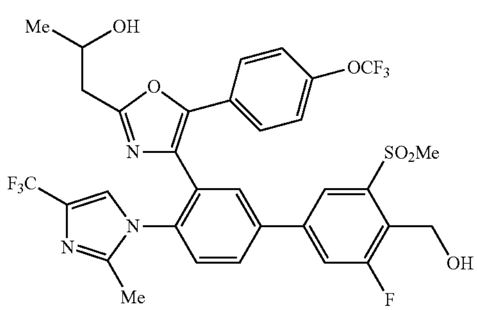 [SMILES: Cc1nc(C(F)(F)F)cn1-c1ccc(-c2cc(F)c(CO)c(S(C)(=O)=O)c2)cc1-c1nc(CC(C)O)oc1-c1ccc(OC(F)(F)F)cc1] | 1-(4-(3'-fluoro-4'-(hydroxymethyl)-4-(2-methyl-4-(trifluoromethyl)-1H-imidazol-1-yl)-5'-(methylsulfonyl)-[1,1'-biphenyl]-3-yl)-5-(4-(trifluoromethoxy)phenyl)oxazol-2-yl)propan-2-ol |

-continued

| Ex # | Structure | Name |
|---|---|---|
| 535 | 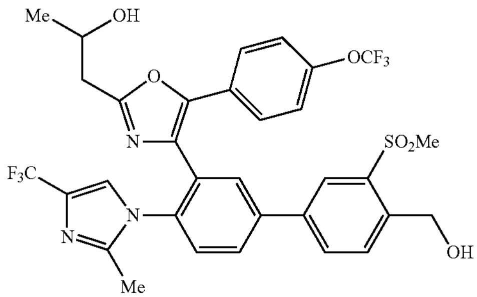 [SMILES: Cc1nc(C(F)(F)F)cn1-c1ccc(-c2ccc(CO)c(S(C)(=O)=O)c2)cc1-c1nc(CC(C)O)oc1-c1ccc(OC(F)(F)F)cc1] | 1-(4-(4'-(hydroxymethyl)-4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazol-2-yl)propan-2-ol |
| 536 | 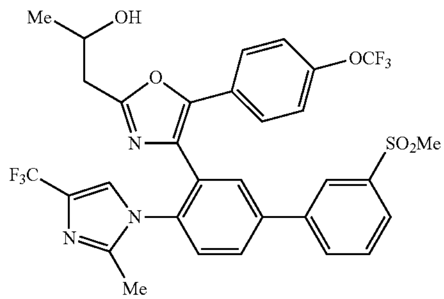 [SMILES: Cc1nc(C(F)(F)F)cn1-c1ccc(-c2cccc(S(C)(=O)=O)c2)cc1-c1nc(CC(C)O)oc1-c1ccc(OC(F)(F)F)cc1] | 1-(4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazol-2-yl)propan-2-ol |
| 537 | 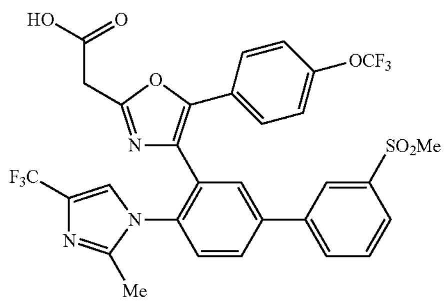 [SMILES: Cc1nc(C(F)(F)F)cn1-c1ccc(-c2cccc(S(C)(=O)=O)c2)cc1-c1nc(CC(=O)O)oc1-c1ccc(OC(F)(F)F)cc1] | 2-(4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazol-2-yl)acetic acid |
| 538 | 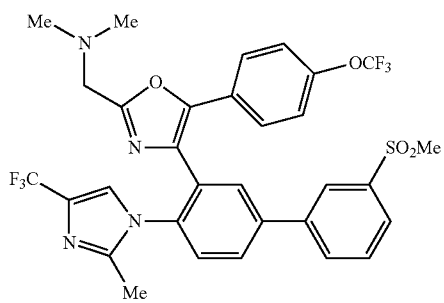 [SMILES: Cc1nc(C(F)(F)F)cn1-c1ccc(-c2cccc(S(C)(=O)=O)c2)cc1-c1nc(CN(C)C)oc1-c1ccc(OC(F)(F)F)cc1] | N,N-dimethyl-1-(4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazol-2-yl)methanamine |
| 539 | 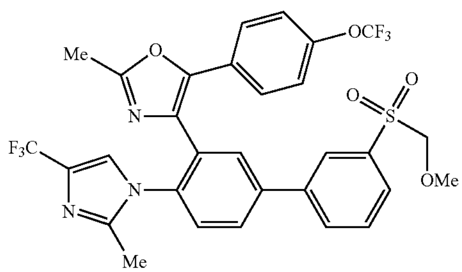 [SMILES: COCS(=O)(=O)c1cccc(-c2ccc(-n3cc(C(F)(F)F)nc3C)c(-c3nc(C)oc3-c3ccc(OC(F)(F)F)cc3)c2)c1] | 4-(3'-((methoxymethyl)sulfonyl)-4-(2-methyl-4-(trifluoromethyl)-1H-imidazol-1-yl)-[1,1'-biphenyl]-3-yl)-2-methyl-5-(4-(trifluoromethoxy)phenyl)oxazole |

-continued

| Ex # | Structure | Name |
|---|---|---|
| 540 | 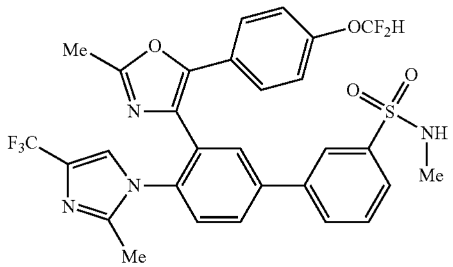 | 3'-(5-(4-(difluoromethoxy)phenyl)-2-methyloxazol-4-yl)-N-methyl-4'-(2-methyl-4-(trifluoromethyl)-1H-imidazol-1-yl)-[1,1'-biphenyl]-3-sulfonamide |
| 541 | 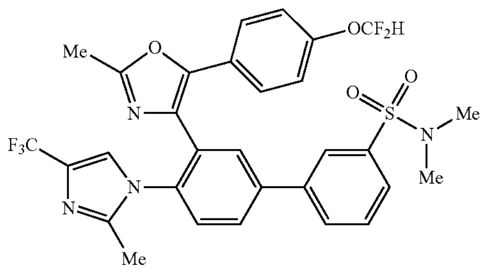 | 3'-(5-(4-(difluoromethoxy)phenyl)-2-methyloxazol-4-yl)-N,N-dimethyl-4'-(2-methyl-4-(trifluoromethyl)-1H-imidazol-1-yl)-[1,1'-biphenyl]-3-sulfonamide |
| 542 | 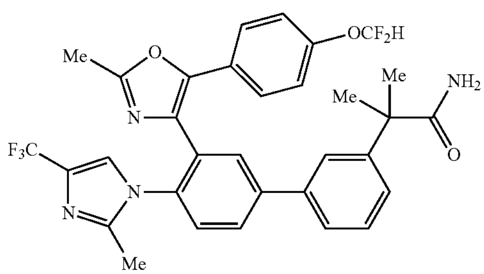 | 2-(3'-(5-(4-(difluoromethoxy)phenyl)-2-methyloxazol-4-yl)-4'-(2-methyl-4-(trifluoromethyl)-1H-imidazol-1-yl)-[1,1'-biphenyl]-3-yl)-2-methylpropanamide |
| 543 | 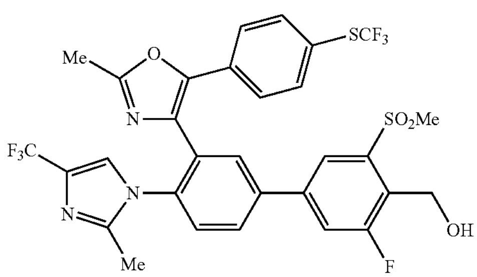 | (3-fluoro-4'-(2-methyl-4-(trifluoromethyl)-1H-imidazol-1-yl)-3'-(2-methyl-5-(4-((trifluoromethyl)thio)phenyl)oxazol-4-yl)-5-(methylsulfonyl)-[1,1'-biphenyl]-4-yl)methanol |
| 544 | 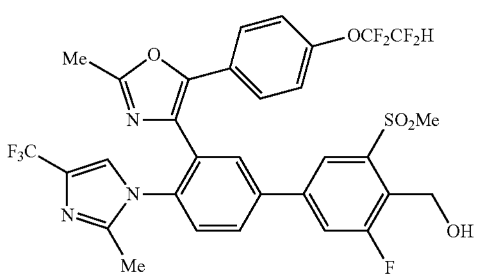 | (3-fluoro-4'-(2-methyl-4-(trifluoromethyl)-1H-imidazol-1-yl)-3'-(2-methyl-5-(4-(1,1,2,2-tetrafluoroethoxy)phenyl)oxazol-4-yl)-5-(methylsulfonyl)-[1,1'-biphenyl]-4-yl)methanol |

-continued

| Ex # | Structure | Name |
|---|---|---|
| 545 | 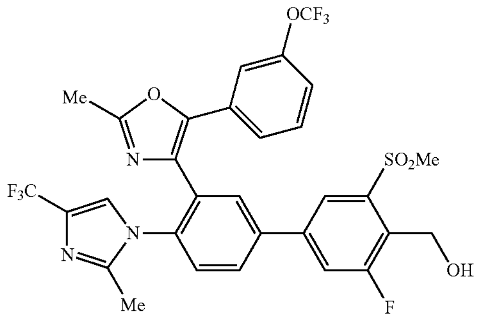 | (3-fluoro-4'-(2-methyl-4-(trifluoromethyl)-1H-imidazol-1-yl)-3'-(2-methyl-5-(3-(trifluoromethoxy)phenyl)oxazol-4-yl)-5-(methylsulfonyl)-[1,1'-biphenyl]-4-yl)methanol |
| 546 | 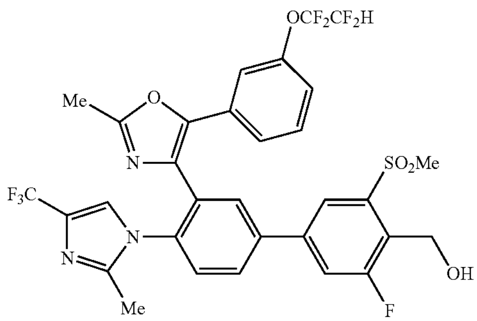 | (3-fluoro-4'-(2-methyl-4-(trifluoromethyl)-1H-imidazol-1-yl)-3'-(2-methyl-5-(3-(1,1,2,2-tetrafluoroethoxy)phenyl)oxazol-4-yl)-5-(methylsulfonyl)-[1,1'-biphenyl]-4-yl)methanol |
| 547 | 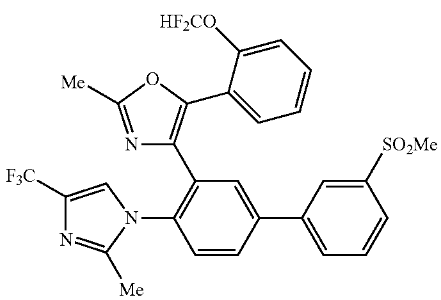 | 5-(2-(difluoromethoxy)phenyl)-2-methyl-4-(4-(2-methyl-4-(trifluoromethyl)-1H-imidazol-1-yl)-3'-(methylsulfonyl)-[1,1'-biphenyl]-3-yl)oxazole |
| 548 | 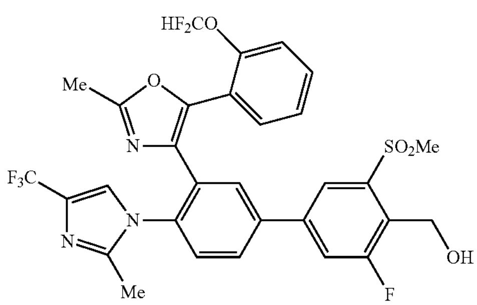 | (3'-(5-(2-(difluoromethoxy)phenyl)-2-methyloxazol-4-yl)-3-fluoro-4'-(2-methyl-4-(trifluoromethyl)-1H-imidazol-1-yl)-5-(methylsulfonyl)-[1,1'-biphenyl]-4-yl)methanol |
| 549 | 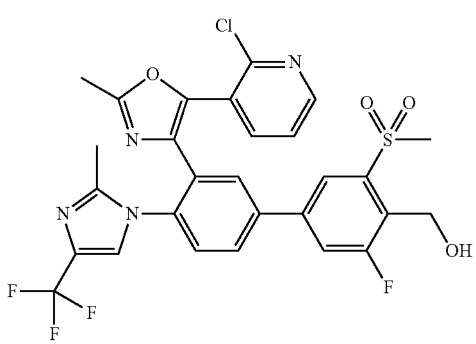 [SMILES: Cc1nc(-c2cc(-c3cc(F)c(CO)c(S(C)(=O)=O)c3)ccc2-n2cc(C(F)(F)F)nc2C)c(-c2cccnc2Cl)o1] | (3'-(5-(2-chloropyridin-3-yl)-2-methyloxazol-4-yl)-3-fluoro-4'-(2-methyl-4-(trifluoromethyl)-1H-imidazol-1-yl)-5-(methylsulfonyl)-[1,1'-biphenyl]-4-yl)methanol |

-continued

| Ex # | Structure | Name |
|---|---|---|
| 550 | 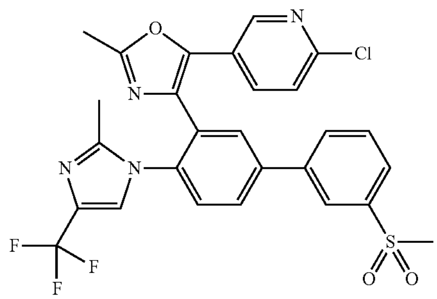 [SMILES: Cc1nc(-c2cc(-c3cccc(S(C)(=O)=O)c3)ccc2-n2cc(C(F)(F)F)nc2C)c(-c2ccc(Cl)nc2)o1] | 5-(6-chloropyridin-3-yl)-2-methyl-4-(4-(2-methyl-4-(trifluoromethyl)-1H-imidazol-1-yl)-3'-(methylsulfonyl)-[1,1'-biphenyl]-3-yl)oxazole |
| 551 | 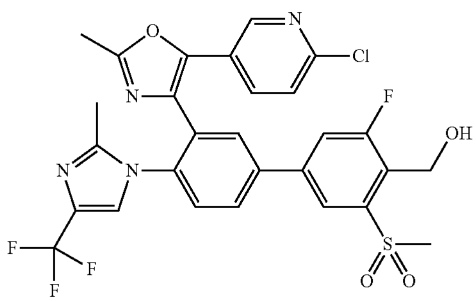 [SMILES: Cc1nc(-c2cc(-c3cc(F)c(CO)c(S(C)(=O)=O)c3)ccc2-n2cc(C(F)(F)F)nc2C)c(-c2ccc(Cl)nc2)o1] | (3'-(5-(6-chloropyridin-3-yl)-2-methyloxazol-4-yl)-3-fluoro-4'-(2-methyl-4-(trifluoromethyl)-1H-imidazol-1-yl)-5-(methylsulfonyl)-[1,1'-biphenyl]-4-yl)methanol |
| 552 | 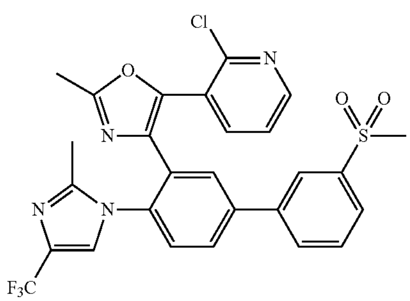 [SMILES: Cc1nc(-c2cc(-c3cccc(S(C)(=O)=O)c3)ccc2-n2cc(C(F)(F)F)nc2C)c(-c2cccnc2Cl)o1] | 5-(2-chloropyridin-3-yl)-2-methyl-4-(4-(2-methyl-4-(trifluoromethyl)-1H-imidazol-1-yl)-3'-(methylsulfonyl)-[1,1'-biphenyl]-3-yl)oxazole |
| 553 | 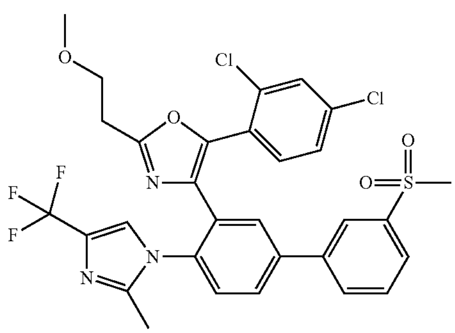 [SMILES: COCCc1nc(-c2cc(-c3cccc(S(C)(=O)=O)c3)ccc2-n2cc(C(F)(F)F)nc2C)c(-c2ccc(Cl)cc2Cl)o1] | 5-(2,4-dichlorophenyl)-2-(2-methoxyethyl)-4-(4-(2-methyl-4-(trifluoromethyl)-1H-imidazol-1-yl)-3'-(methylsulfonyl)-[1,1'-biphenyl]-3-yl)oxazole |
| 554 | 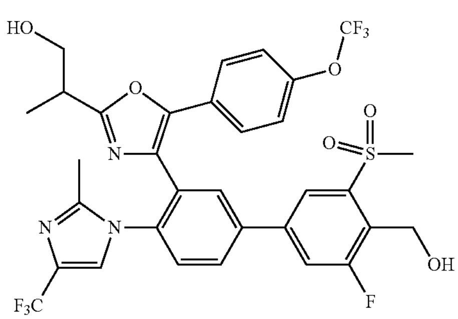 [SMILES: Cc1nc(C(F)(F)F)cn1-c1ccc(-c2cc(F)c(CO)c(S(C)(=O)=O)c2)cc1-c1nc(C(C)CO)oc1-c1ccc(OC(F)(F)F)cc1] | 2-(4-(3'-fluoro-4'-(hydroxymethyl)-4-(2-methyl-4-(trifluoromethyl)-1H-imidazol-1-yl)-5'-(methylsulfonyl)-[1,1'-biphenyl]-3-yl)-5-(4-(trifluoromethoxy)phenyl)oxazol-2-yl)propan-1-ol |

-continued

| Ex # | Structure | Name |
|---|---|---|
| 555 | 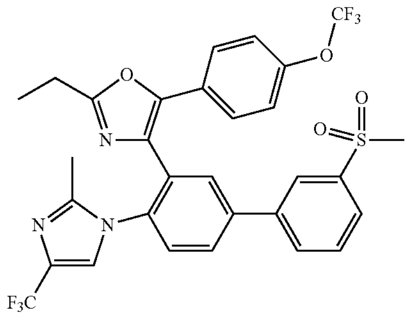 [SMILES: CCc1nc(-c2cc(-c3cccc(S(C)(=O)=O)c3)ccc2-n2cc(C(F)(F)F)nc2C)c(-c2ccc(OC(F)(F)F)cc2)o1] | 2-ethyl-4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazole |
| 556 | 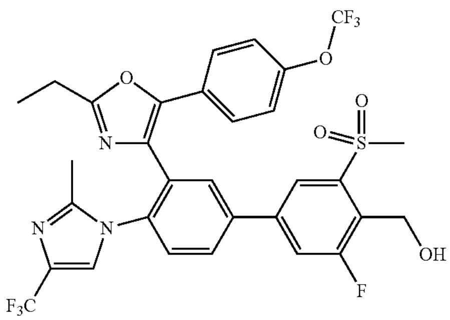 [SMILES: CCc1nc(-c2cc(-c3cc(F)c(CO)c(S(C)(=O)=O)c3)ccc2-n2cc(C(F)(F)F)nc2C)c(-c2ccc(OC(F)(F)F)cc2)o1] | (3'-(2-ethyl-5-(4-(trifluoromethoxy)phenyl)oxazol-4-yl)-3-fluoro-4'-(2-methyl-4-(trifluoromethyl)-1H-imidazol-1-yl)-5-(methylsulfonyl)-[1,1'-biphenyl]-4-yl)methanol |
| 557 | 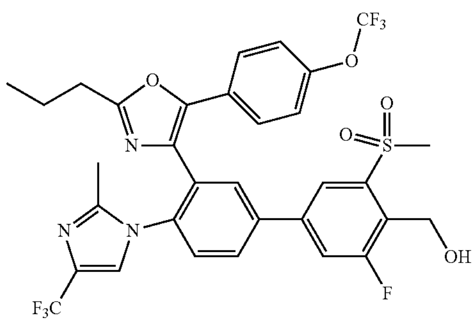 [SMILES: CCCc1nc(-c2cc(-c3cc(F)c(CO)c(S(C)(=O)=O)c3)ccc2-n2cc(C(F)(F)F)nc2C)c(-c2ccc(OC(F)(F)F)cc2)o1] | (3-fluoro-4'-(2-methyl-4-(trifluoromethyl)-1H-imidazol-1-yl)-5-(methylsulfonyl)-3'-(2-propyl-5-(4-(trifluoromethoxy)phenyl)oxazol-4-yl)-[1,1'-biphenyl]-4-yl)methanol |
| 558 | 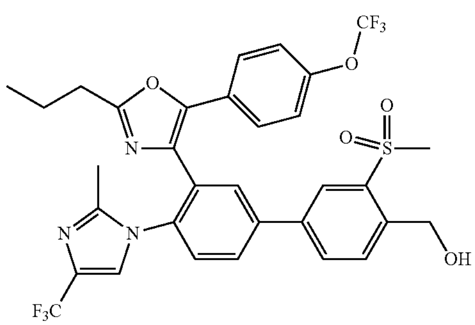 [SMILES: CCCc1nc(-c2cc(-c3ccc(CO)c(S(C)(=O)=O)c3)ccc2-n2cc(C(F)(F)F)nc2C)c(-c2ccc(OC(F)(F)F)cc2)o1] | (4'-(2-methyl-4-(trifluoromethyl)-1H-imidazol-1-yl)-3-(methylsulfonyl)-3'-(2-propyl-5-(4-(trifluoromethoxy)phenyl)oxazol-4-yl)-[1,1'-biphenyl]-4-yl)methanol |
| 559 | 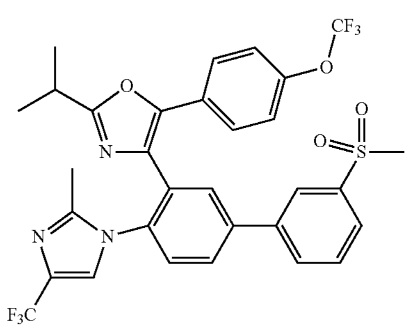 [SMILES: Cc1nc(C(F)(F)F)cn1-c1ccc(-c2cccc(S(C)(=O)=O)c2)cc1-c1nc(C(C)C)oc1-c1ccc(OC(F)(F)F)cc1] | 2-isopropyl-4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazole |

| Ex # | Structure | Name |
|---|---|---|
| 560 | 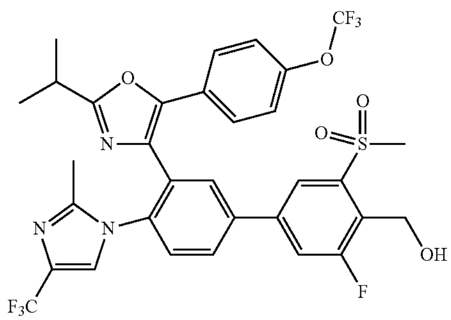 [SMILES: Cc1nc(C(F)(F)F)cn1-c1ccc(-c2cc(F)c(CO)c(S(C)(=O)=O)c2)cc1-c1nc(C(C)C)oc1-c1ccc(OC(F)(F)F)cc1] | (3-fluoro-3'-(2-isopropyl-5-(4-(trifluoromethoxy)phenyl)oxazol-4-yl)-4'-(2-methyl-4-(trifluoromethyl)-1H-imidazol-1-yl)-5-(methylsulfonyl)-[1,1'-biphenyl]-4-yl)methanol |
| 561 | 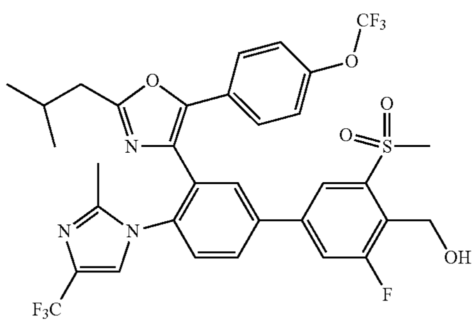 [SMILES: Cc1nc(C(F)(F)F)cn1-c1ccc(-c2cc(F)c(CO)c(S(C)(=O)=O)c2)cc1-c1nc(CC(C)C)oc1-c1ccc(OC(F)(F)F)cc1] | (3-fluoro-3'-(2-isobutyl-5-(4-(trifluoromethoxy)phenyl)oxazol-4-yl)-4'-(2-methyl-4-(trifluoromethyl)-1H-imidazol-1-yl)-5-(methylsulfonyl)-[1,1'-biphenyl]-4-yl)methanol |
| 562 | 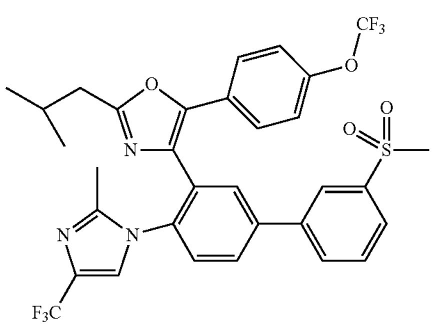 [SMILES: Cc1nc(C(F)(F)F)cn1-c1ccc(-c2cccc(S(C)(=O)=O)c2)cc1-c1nc(CC(C)C)oc1-c1ccc(OC(F)(F)F)cc1] | 2-isobutyl-4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazole |
| 563 | 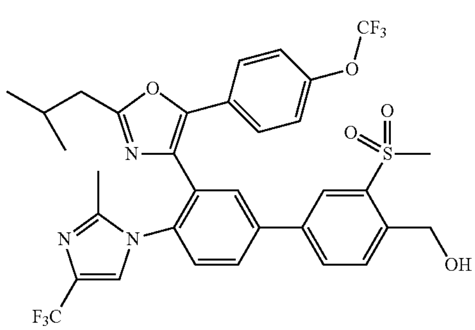 [SMILES: Cc1nc(C(F)(F)F)cn1-c1ccc(-c2ccc(CO)c(S(C)(=O)=O)c2)cc1-c1nc(CC(C)C)oc1-c1ccc(OC(F)(F)F)cc1] | (3'-(2-isobutyl-5-(4-(trifluoromethoxy)phenyl)oxazol-4-yl)-4'-(2-methyl-4-(trifluoromethyl)-1H-imidazol-1-yl)-3-(methylsulfonyl)-[1,1'-biphenyl]-4-yl)methanol |

| Ex # | Structure | Name |
|---|---|---|
| 564 | 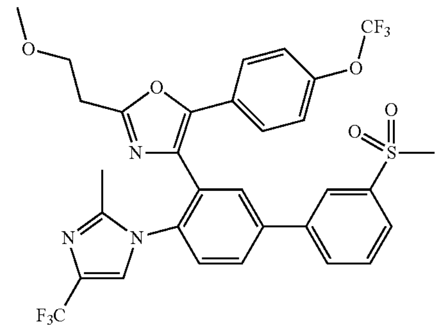 | 2-(2-methoxyethyl)-4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazole |
| 565 | 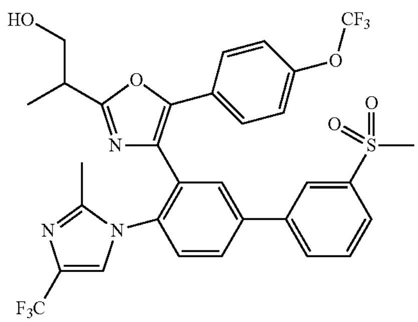 [SMILES: Cc1nc(C(F)(F)F)cn1-c1ccc(-c2cccc(S(C)(=O)=O)c2)cc1-c1nc(C(C)CO)oc1-c1ccc(OC(F)(F)F)cc1] | 2-(4-(4-(2-methyl-4-(trifluoromethyl)-1H-imidazol-1-yl)-3'-(methylsulfonyl)-[1,1'-biphenyl]-3-yl)-5-(4-(trifluoromethoxy)phenyl)oxazol-2-yl)propan-1-ol |
| 566 | 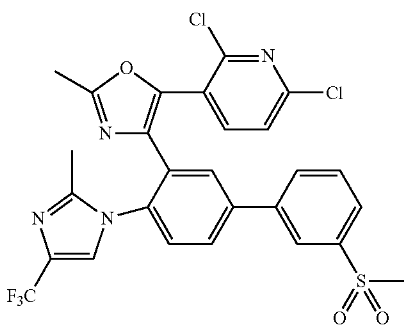 [SMILES: Cc1nc(-c2cc(-c3cccc(S(C)(=O)=O)c3)ccc2-n2cc(C(F)(F)F)nc2C)c(-c2ccc(Cl)nc2Cl)o1] | 5-(2,6-dichloropyridin-3-yl)-2-methyl-4-(2-methyl-4-(trifluoromethyl)-1H-imidazol-1-yl)-3'-(methylsulfonyl)-[1,1'-biphenyl]-3-yl)oxazole |
| 567 | 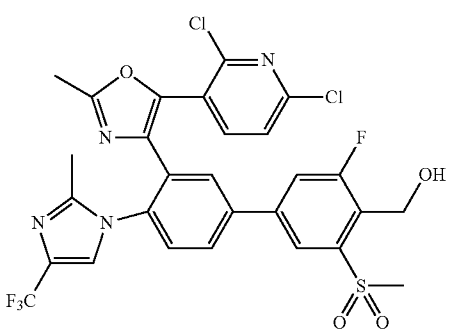 [SMILES: Cc1nc(-c2cc(-c3cc(F)c(CO)c(S(C)(=O)=O)c3)ccc2-n2cc(C(F)(F)F)nc2C)c(-c2ccc(Cl)nc2Cl)o1] | (3'-(5-(2,6-dichloropyridin-3-yl)-2-methyloxazol-4-yl)-3-fluoro-4'-(2-methyl-4-(trifluoromethyl)-1H-imidazol-1-yl)-5-(methylsulfonyl)-[1,1'-biphenyl]-4-yl)methanol |
| 568 | 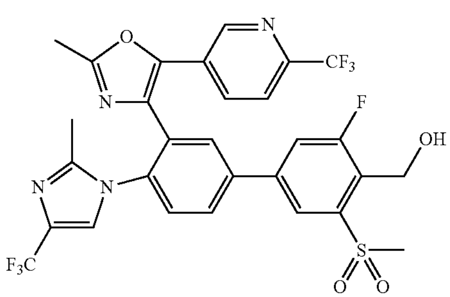 [SMILES: Cc1nc(-c2cc(-c3cc(F)c(CO)c(S(C)(=O)=O)c3)ccc2-n2cc(C(F)(F)F)nc2C)c(-c2ccc(C(F)(F)F)nc2)o1] | (3-fluoro-4'-(2-methyl-4-(trifluoromethyl)-1H-imidazol-1-yl)-3'-(2-methyl-5-(6-(trifluoromethyl)pyridin-3-yl)oxazol-4-yl)-5-(methylsulfonyl)-[1,1'-biphenyl]-4-yl)methanol |

| Ex # | Structure | Name |
|---|---|---|
| 569 | 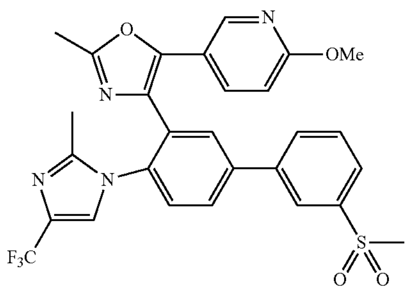 [SMILES: COc1ccc(-c2oc(C)nc2-c2cc(-c3cccc(S(C)(=O)=O)c3)ccc2-n2cc(C(F)(F)F)nc2C)cn1] | 5-(6-methoxypyridin-3-yl)-2-methyl-4-(4-(2-methyl-4-(trifluoromethyl)-1H-imidazol-1-yl)-3'-(methylsulfonyl)-[1,1'-biphenyl]-3-yl)oxazole |
| 570 | 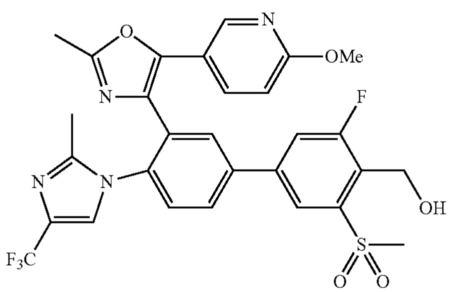 [SMILES: COc1ccc(-c2oc(C)nc2-c2cc(-c3cc(F)c(CO)c(S(C)(=O)=O)c3)ccc2-n2cc(C(F)(F)F)nc2C)cn1] | (3-fluoro-3'-(5-(6-methoxypyridin-3-yl)-2-methyloxazol-4-yl)-4'-(2-methyl-4-(trifluoromethyl)-1H-imidazol-1-yl)-5-(methylsulfonyl)-[1,1'-biphenyl]-4-yl)methanol |
| 571 | 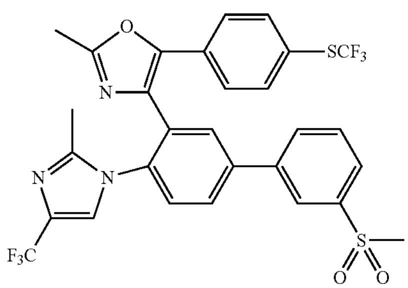 | 2-methyl-4-(4-(2-methyl-4-(trifluoromethyl)-1H-imidazol-1-yl)-3'-(methylsulfonyl)-[1,1'-biphenyl]-3-yl)-5-(4-((trifluoromethyl)thio)phenyl)oxazole |
| 572 | 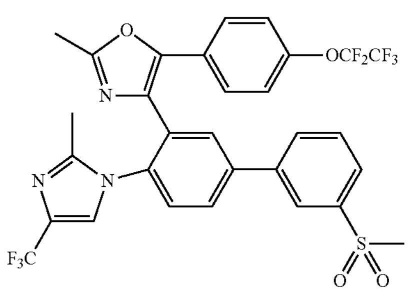 | 2-methyl-4-(4-(2-methyl-4-(trifluoromethyl)-1H-imidazol-1-yl)-3'-(methylsulfonyl)-[1,1'-biphenyl]-3-yl)-5-(4-(perfluoroethoxy)phenyl)oxazole |
| 573 | 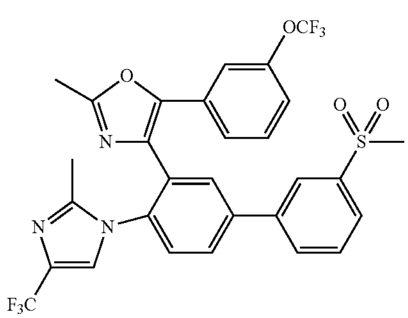 [SMILES: Cc1nc(-c2cc(-c3cccc(S(C)(=O)=O)c3)ccc2-n2cc(C(F)(F)F)nc2C)c(-c2cccc(OC(F)(F)F)c2)o1] | 2-methyl-4-(4-(2-methyl-4-(trifluoromethyl)-1H-imidazol-1-yl)-3'-(methylsulfonyl)-[1,1'-biphenyl]-3-yl)-5-(3-(trifluoromethoxy)phenyl)oxazole |

| Ex # | Structure | Name |
|---|---|---|
| 574 | 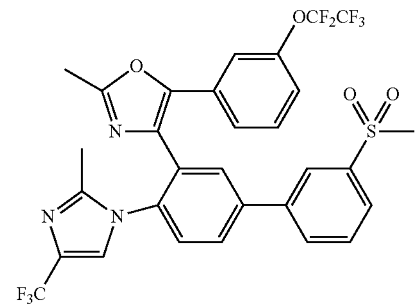 | 2-methyl-4-(4-(2-methyl-4-(trifluoromethyl)-1H-imidazol-1-yl)-3'-(methylsulfonyl)-[1,1'-biphenyl]-3-yl)-5-(3-(perfluoroethoxy)phenyl)oxazole |
| 600 | 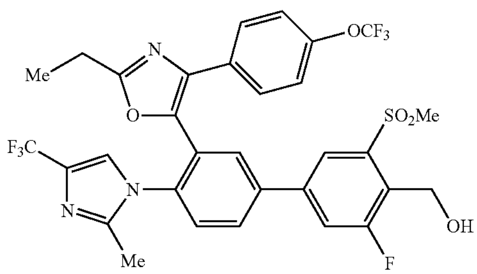 [SMILES: CCc1nc(-c2ccc(OC(F)(F)F)cc2)c(-c2cc(-c3cc(F)c(CO)c(S(C)(=O)=O)c3)ccc2-n2cc(C(F)(F)F)nc2C)o1] | {3'-(2-ethyl-4-{4-[(trifluoromethyl)oxy]phenyl}-1,3-oxazol-5-yl)-3-fluoro-5-(methylsulfonyl)-4'-[2-methyl-4-(trifluoromethyl)-1H-imidazol-1-yl]biphenyl-4-yl}methanol |
| 601 | 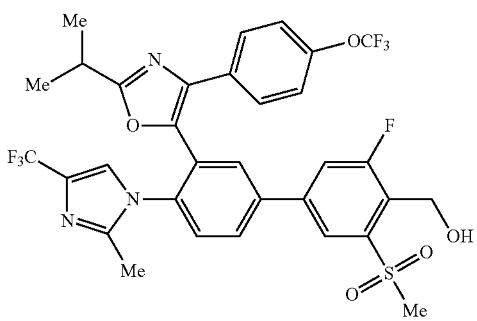 [SMILES: Cc1nc(C(F)(F)F)cn1-c1ccc(-c2cc(F)c(CO)c(S(C)(=O)=O)c2)cc1-c1oc(C(C)C)nc1-c1ccc(OC(F)(F)F)cc1] | {3-fluoro-3'-[2-(1-methylethyl)-4-{4-[(trifluoromethyl)oxy]phenyl}-1,3-oxazol-5-yl]-5-(methylsulfonyl)-4'-[2-methyl-4-(trifluoromethyl)-1H-imidazol-1-yl]biphenyl-4-yl}methanol; |
| 602 | 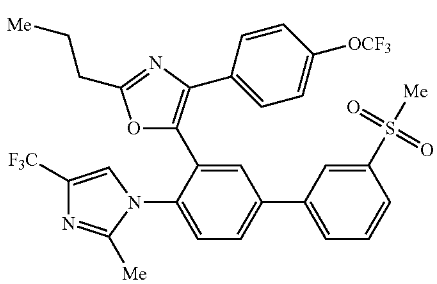 [SMILES: CCCc1nc(-c2ccc(OC(F)(F)F)cc2)c(-c2cc(-c3cccc(S(C)(=O)=O)c3)ccc2-n2cc(C(F)(F)F)nc2C)o1] | 5-{3'-(methylsulfonyl)-4-[2-methyl-4-(trifluoromethyl)-1H-imidazol-1-yl]biphenyl-3-yl}-2-propyl-4-{4-[(trifluoromethyl)oxy]phenyl}-1,3-oxazole |
| 603 | 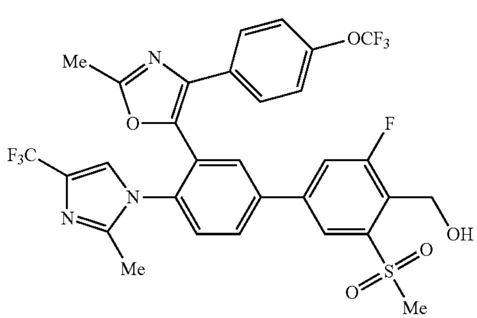 [SMILES: Cc1nc(-c2ccc(OC(F)(F)F)cc2)c(-c2cc(-c3cc(F)c(CO)c(S(C)(=O)=O)c3)ccc2-n2cc(C(F)(F)F)nc2C)o1] | (3-fluoro-3'-(2-methyl-4-(4-(trifluoromethoxy)phenyl)oxazol-5-yl)-4'-(2-methyl-4-(trifluoromethyl)-1H-imidazol-1-yl)-5-(methylsulfonyl)-[1,1'-biphenyl]-4-yl)methanol |

-continued

| Ex # | Structure | Name |
|---|---|---|
| 604 | 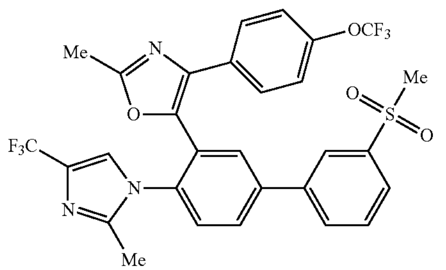 | 2-methyl-5-(4-(2-methyl-4-(trifluoromethyl)-1H-imidazol-1-yl)-3'-(methylsulfonyl)-[1,1'-biphenyl]-3-(trifluoromethoxy)phenyl)oxazole BMS-930815/EXEL-04613389 |
| 605 | 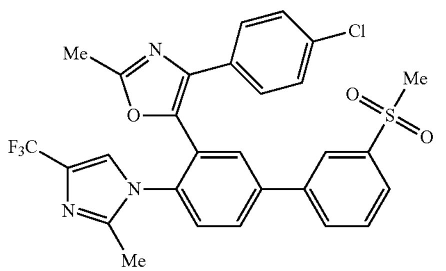 [SMILES: Cc1nc(-c2ccc(Cl)cc2)c(-c2cc(-c3cccc(S(C)(=O)=O)c3)ccc2-n2cc(C(F)(F)F)nc2C)o1] | 4-(4-chlorophenyl)-2-methyl-5-(4-(2-methyl-4-(trifluoromethyl)-1H-imidazol-1-yl)-3'-(methylsulfonyl)-[1,1'-biphenyl]-3-yl)oxazole |
| 606 | 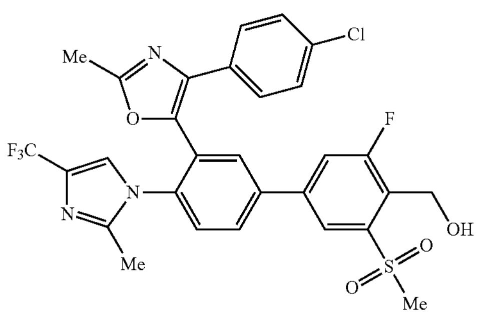 [SMILES: Cc1nc(-c2ccc(Cl)cc2)c(-c2cc(-c3cc(F)c(CO)c(S(C)(=O)=O)c3)ccc2-n2cc(C(F)(F)F)nc2C)o1] | (3'-(4-(4-chlorophenyl)-2-methyloxazol-5-yl)-3-fluoro-4'-(2-methyl-4-(trifluoromethyl)-1H-imidazol-1-yl)-5-(methylsulfonyl)-[1,1'-biphenyl]-4-yl)methanol |
| 607 | 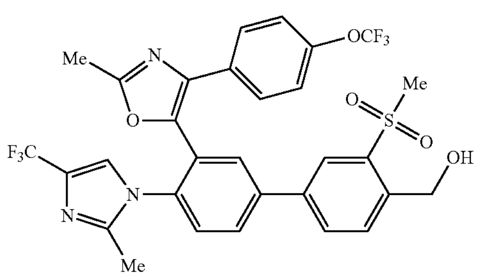 [SMILES: Cc1nc(-c2ccc(OC(F)(F)F)cc2)c(-c2cc(-c3ccc(CO)c(S(C)(=O)=O)c3)ccc2-n2cc(C(F)(F)F)nc2C)o1] | (3'-(2-methyl-4-(4-(trifluoromethoxy)phenyl)oxazol-5-yl)-4'-(2-methyl-4-(trifluoromethyl)-1H-imidazol-1-yl)-3-(methylsulfonyl)-[1,1'-biphenyl]-4-yl)methanol |
| 608 | 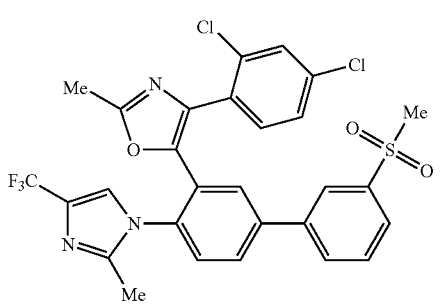 [SMILES: Cc1nc(-c2ccc(Cl)cc2Cl)c(-c2cc(-c3cccc(S(C)(=O)=O)c3)ccc2-n2cc(C(F)(F)F)nc2C)o1] | 4-(2,4-dichlorophenyl)-2-methyl-5-(4-(2-methyl-4-(trifluoromethyl)-1H-imidazol-1-yl)-3'-(methylsulfonyl)-[1,1'-biphenyl]-3-yl)oxazole |

| Ex # | Structure | Name |
|---|---|---|
| 609 | 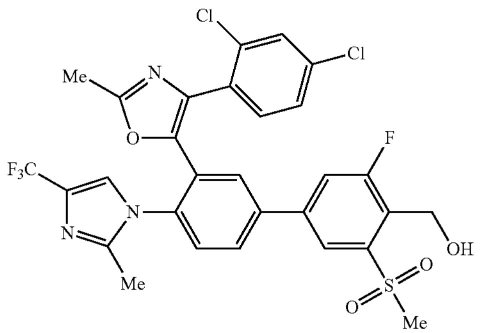 [SMILES: Cc1nc(-c2ccc(Cl)cc2Cl)c(-c2cc(-c3cc(F)c(CO)c(S(C)(=O)=O)c3)ccc2-n2cc(C(F)(F)F)nc2C)o1] | (3'-(4-(2,4-dichlorophenyl)-2-methyloxazol-5-yl)-3-fluoro-4'-(2-methyl-4-(trifluoromethyl)-1H-imidazol-1-yl)-5-(methylsulfonyl)-[1,1'-biphenyl]-4-yl)methanol |
| 610 | 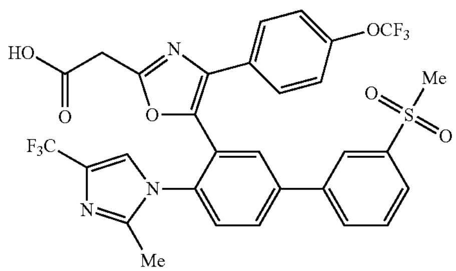 [SMILES: Cc1nc(C(F)(F)F)cn1-c1ccc(-c2cccc(S(C)(=O)=O)c2)cc1-c1oc(CC(=O)O)nc1-c1ccc(OC(F)(F)F)cc1] | 2-(5-(4-(2-methyl-4-(trifluoromethyl)-1H-imidazol-1-yl)-3'-(methylsulfonyl)-[1,1'-biphenyl]-3-yl)-4-(4-(trifluoromethoxy)phenyl)oxazol-2-yl)acetic acid |
| 611 | 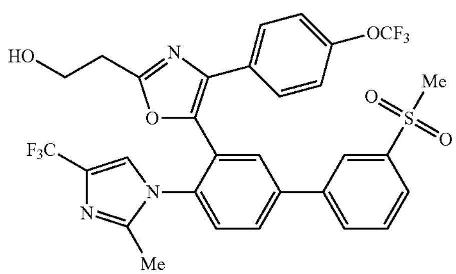 | 2-(5-(4-(2-methyl-4-(trifluoromethyl)-1H-imidazol-1-yl)-3'-(methylsulfonyl)-[1,1'-biphenyl]-3-yl)-4-(4-(trifluoromethoxy)phenyl)oxazol-2-yl)ethanol |
| 612 | 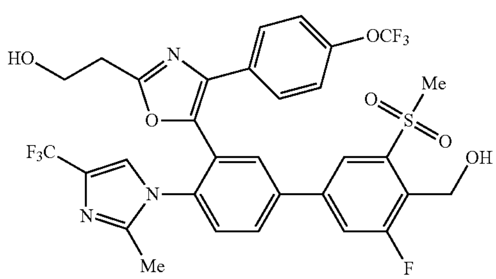 [SMILES: Cc1nc(C(F)(F)F)cn1-c1ccc(-c2cc(F)c(CO)c(S(C)(=O)=O)c2)cc1-c1oc(CCO)nc1-c1ccc(OC(F)(F)F)cc1] | 2-(5-(3'-fluoro-4'-(hydroxymethyl)-4-(2-methyl-4-(trifluoromethyl)-1H-imidazol-1-yl)-5'-(methylsulfonyl)-[1,1'-biphenyl]-3-yl)-4-(4-(trifluoromethoxy)phenyl)oxazol-2-yl)ethanol |
| 613 | 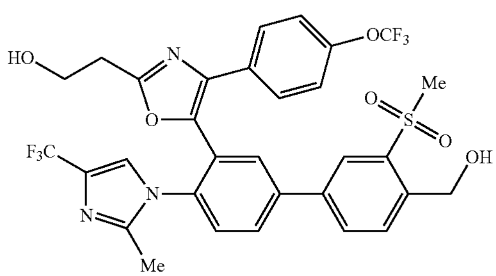 [SMILES: Cc1nc(C(F)(F)F)cn1-c1ccc(-c2ccc(CO)c(S(C)(=O)=O)c2)cc1-c1oc(CCO)nc1-c1ccc(OC(F)(F)F)cc1] | 2-(5-(4'-(hydroxymethyl)-4-(2-methyl-4-(trifluoromethyl)-1H-imidazol-1-yl)-3'-(methylsulfonyl)-[1,1'-biphenyl]-3-yl)-4-(4-(trifluoromethoxy)phenyl)oxazol-2-yl)ethanol |

| Ex # | Structure | Name |
|---|---|---|
| 614 | 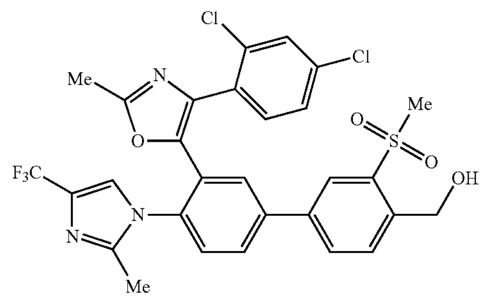 [SMILES: Cc1nc(-c2ccc(Cl)cc2Cl)c(-c2cc(-c3ccc(CO)c(S(C)(=O)=O)c3)ccc2-n2cc(C(F)(F)F)nc2C)o1] | (3'-(4-(2,4-dichlorophenyl)-2-methyloxazol-5-yl)-4'-(2-methyl-4-(trifluoromethyl)-1H-imidazol-1-yl)-3-(methylsulfonyl)-[1,1'-biphenyl]-4-yl)methanol |
| 615 | 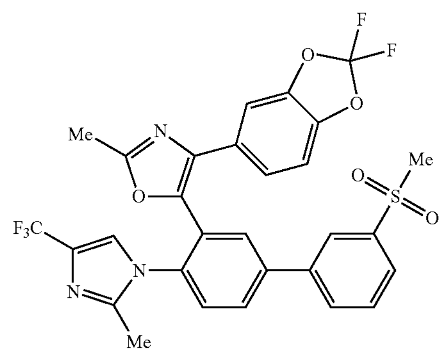 [SMILES: Cc1nc(-c2ccc3c(c2)OC(F)(F)O3)c(-c2cc(-c3cccc(S(C)(=O)=O)c3)ccc2-n2cc(C(F)(F)F)nc2C)o1] | 4-(2,2-difluorobenzo[d][1,3]dioxol-5-yl)-2-methyl-5-(4-(2-methyl-4-(trifluoromethyl)-1H-imidazol-1-yl)-3'-(methylsulfonyl)-[1,1'-biphenyl]-3-yl)oxazole |
| 616 | 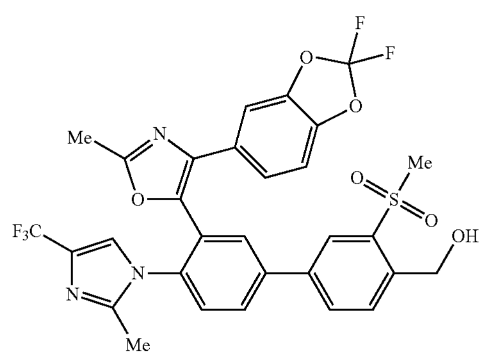 [SMILES: Cc1nc(-c2ccc3c(c2)OC(F)(F)O3)c(-c2cc(-c3ccc(CO)c(S(C)(=O)=O)c3)ccc2-n2cc(C(F)(F)F)nc2C)o1] | (3'-(4-(2,2-difluorobenzo[d][1,3]dioxol-5-yl)-2-methyloxazol-5-yl)-4'-(2-methyl-4-(trifluoromethyl)-1H-imidazol-1-yl)-3-(methylsulfonyl)-[1,1'-biphenyl]-4-yl)methanol |
| 617 | 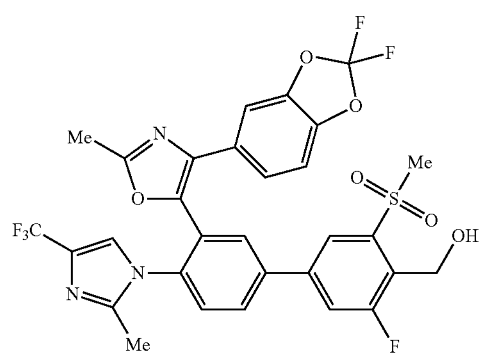 [SMILES: Cc1nc(-c2ccc3c(c2)OC(F)(F)O3)c(-c2cc(-c3cc(F)c(CO)c(S(C)(=O)=O)c3)ccc2-n2cc(C(F)(F)F)nc2C)o1] | (3'-(4-(2,2-difluorobenzo[d][1,3]dioxol-5-yl)-2-methyloxazol-5-yl)-3-fluoro-4'-(2-methyl-4-(trifluoromethyl)-1H-imidazol-1-yl)-5-(methylsulfonyl)-[1,1'-biphenyl]-4-yl)methanol |

-continued

| Ex # | Structure | Name |
|---|---|---|
| 618 | 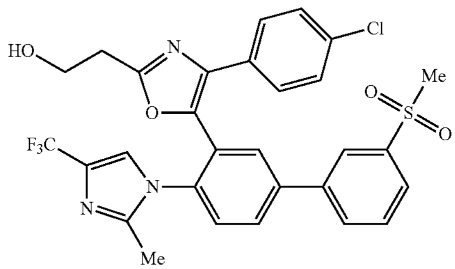 [SMILES: Cc1nc(C(F)(F)F)cn1-c1ccc(-c2cccc(S(C)(=O)=O)c2)cc1-c1oc(CCO)nc1-c1ccc(Cl)cc1] | 2-(4-(4-chlorophenyl)-5-(4-(2-methyl-4-(trifluoromethyl)-1H-imidazol-1-yl)-3'-(methylsulfonyl)-[1,1'-biphenyl]-3-yl)oxazol-2-yl)ethanol |
| 619 | 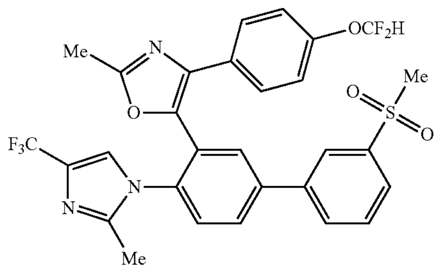 | 4-(4-(difluoromethoxy)phenyl)-2-methyl-5-(4-(2-methyl-4-(trifluoromethyl)-1H-imidazol-1-yl)-3'-(methylsulfonyl)-[1,1'-biphenyl]-3-yl)oxazole |
| 620 | 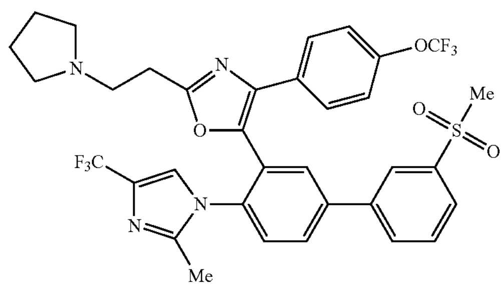 [SMILES: Cc1nc(C(F)(F)F)cn1-c1ccc(-c2cccc(S(C)(=O)=O)c2)cc1-c1oc(CCN2CCCC2)nc1-c1ccc(OC(F)(F)F)cc1] | 5-(4-(2-methyl-4-(trifluoromethyl)-1H-imidazol-1-yl)-3'-(methylsulfonyl)-[1,1'-biphenyl]-3-yl)-2-(2-(pyrrolidin-1-yl)ethyl)-4-(4-(trifluoromethoxy)phenyl)oxazole |
| 621 | 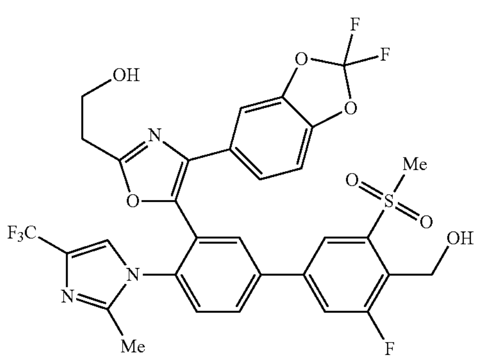 [SMILES: Cc1nc(C(F)(F)F)cn1-c1ccc(-c2cc(F)c(CO)c(S(C)(=O)=O)c2)cc1-c1oc(CCO)nc1-c1ccc2c(c1)OC(F)(F)O2] | 2-(4-(2,2-difluorobenzo[d][1,3]dioxol-5-yl)-5-(3'-fluoro-4'-(hydroxymethyl)-4-(2-methyl-4-(trifluoromethyl)-1H-imidazol-1-yl)-5'-(methylsulfonyl)-[1,1'-biphenyl]-3-yl)oxazol-2-yl)ethanol |
| 622 | 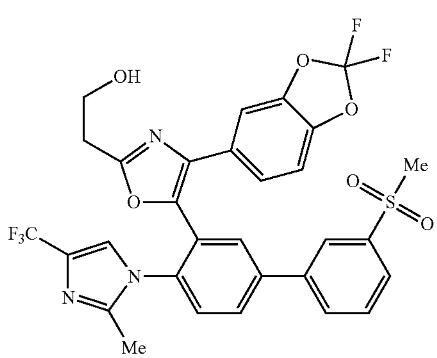 [SMILES: Cc1nc(C(F)(F)F)cn1-c1ccc(-c2cccc(S(C)(=O)=O)c2)cc1-c1oc(CCO)nc1-c1ccc2c(c1)OC(F)(F)O2] | 2-(4-(2,2-difluorobenzo[d][1,3]dioxol-5-yl)-5-(4-(2-methyl-4-(trifluoromethyl)-1H-imidazol-1-yl)-3'-(methylsulfonyl)-[1,1'-biphenyl]-3-yl)oxazol-2-yl)ethanol |

| Ex # | Structure | Name |
|---|---|---|
| 623 | 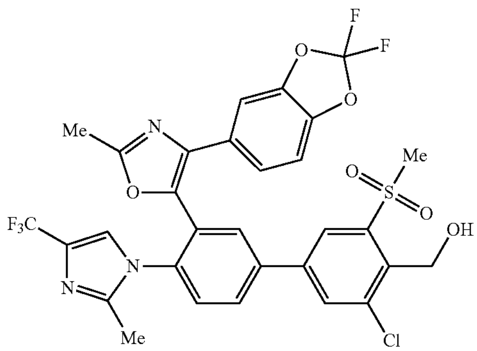 | (3-chloro-3'-(4-(2,2-difluorobenzo[d][1,3]dioxol-5-yl)-2-methyloxazol-5-yl)-4'-(2-methyl-4-(trifluoromethyl)-1H-imidazol-1-yl)-5-(methylsulfonyl)-[1,1'-biphenyl]-4-yl)methanol |
| 624 | 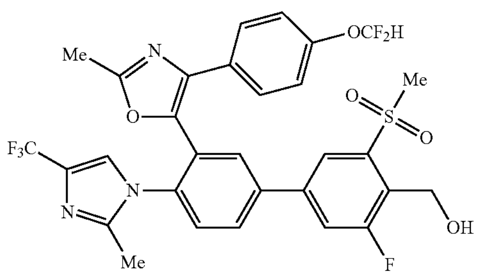 | (3'-(4-(4-(difluoromethoxy)phenyl)-2-methyloxazol-5-yl)-3-fluoro-4'-(2-methyl-4-(trifluoromethyl)-1H-imidazol-1-yl)-5-(methylsulfonyl)-[1,1'-biphenyl]-4-yl)methanol |
| 625 | 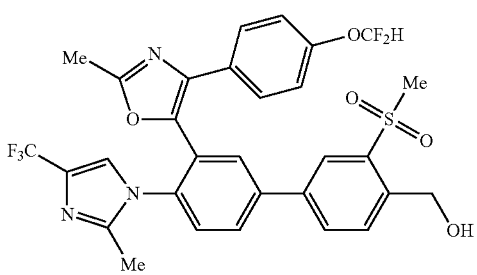 | (3'-(4-(4-(difluoromethoxy)phenyl)-2-methyloxazol-5-yl)-4'-(2-methyl-4-(trifluoromethyl)-1H-imidazol-1-yl)-3-(methylsulfonyl)-[1,1'-biphenyl]-4-yl)methanol |
| 626 | 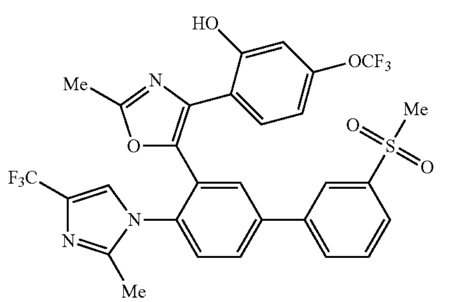 | 2-(2-methyl-5-(4-(2-methyl-4-(trifluoromethyl)-1H-imidazol-1-yl)-3'-(methylsulfonyl)-[1,1'-biphenyl]-3-yl)oxazol-4-yl)-5-(trifluoromethoxy)phenol |
| 627 | 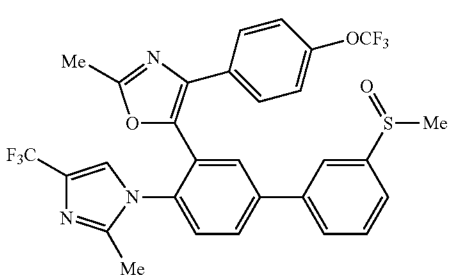 [SMILES: Cc1nc(-c2ccc(OC(F)(F)F)cc2)c(-c2cc(-c3cccc(S(C)=O)c3)ccc2-n2cc(C(F)(F)F)nc2C)o1] | 2-methyl-5-(4-(2-methyl-4-(trifluoromethyl)-1H-imidazol-1-yl)-3'-(methylsulfinyl)-[1,1'-biphenyl]-3-yl)-4-(4-(trifluoromethoxy)phenyl)oxazole |

| Ex # | Structure | Name |
|---|---|---|
| 628 | 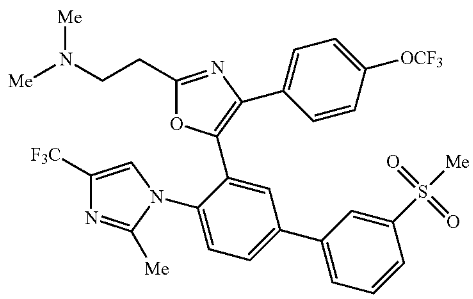 [SMILES: Cc1nc(C(F)(F)F)cn1-c1ccc(-c2cccc(S(C)(=O)=O)c2)cc1-c1oc(CCN(C)C)nc1-c1ccc(OC(F)(F)F)cc1] | N,N-dimethyl-2-(5-(4-(2-methyl-4-(trifluoromethyl)-1H-imidazol-1-yl)-3'-(methylsulfonyl)-[1,1'-biphenyl]-3-yl)-4-(4-(trifluoromethoxy)phenyl)oxazol-2-yl)ethanamine |
| 629 | 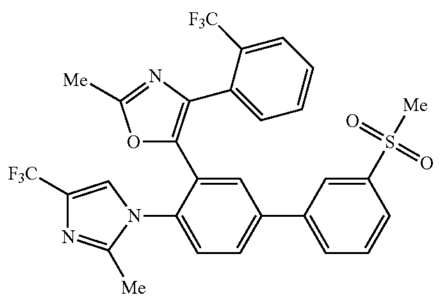 [SMILES: Cc1nc(-c2ccccc2C(F)(F)F)c(-c2cc(-c3cccc(S(C)(=O)=O)c3)ccc2-n2cc(C(F)(F)F)nc2C)o1] | 2-methyl-5-(4-(2-methyl-4-(trifluoromethyl)-1H-imidazol-1-yl)-3'-(methylsulfonyl)-[1,1'-biphenyl]-3-yl)-4-(2-(trifluoromethyl)phenyl)oxazole |
| 630 | 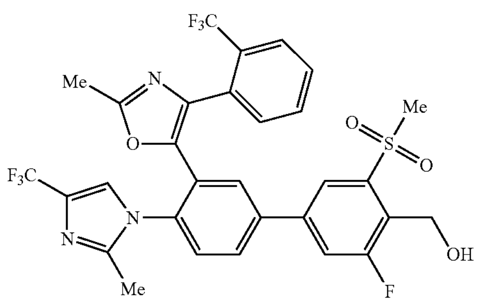 [SMILES: Cc1nc(-c2ccccc2C(F)(F)F)c(-c2cc(-c3cc(F)c(CO)c(S(C)(=O)=O)c3)ccc2-n2cc(C(F)(F)F)nc2C)o1] | (3-fluoro-3'-(2-methyl-4-(2-(trifluoromethyl)phenyl)oxazol-5-yl)-4'-(2-methyl-4-(trifluoromethyl)-1H-imidazol-1-yl)-5-(methylsulfonyl)-[1,1'-biphenyl]-4-yl)methanol |
| 631 | 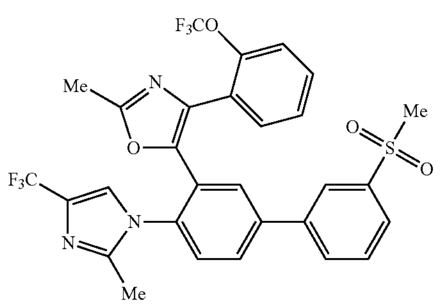 [SMILES: Cc1nc(-c2ccccc2OC(F)(F)F)c(-c2cc(-c3cccc(S(C)(=O)=O)c3)ccc2-n2cc(C(F)(F)F)nc2C)o1] | 2-methyl-5-(4-(2-methyl-4-(trifluoromethyl)-1H-imidazol-1-yl)-3'-(methylsulfonyl)-[1,1'-biphenyl]-3-yl)-4-(2-(trifluoromethoxy)phenyl)oxazole |
| 632 | 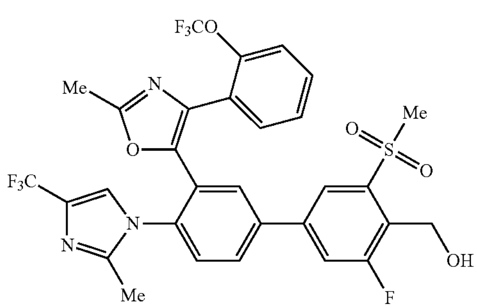 [SMILES: Cc1nc(-c2ccccc2OC(F)(F)F)c(-c2cc(-c3cc(F)c(CO)c(S(C)(=O)=O)c3)ccc2-n2cc(C(F)(F)F)nc2C)o1] | (3-fluoro-3'-(2-methyl-4-(2-(trifluoromethoxy)phenyl)oxazol-5-yl)-4'-(2-methyl-4-(trifluoromethyl)-1H-imidazol-1-yl)-5-(methylsulfonyl)-[1,1'-biphenyl]-4-yl)methanol |

-continued

| Ex # | Structure | Name |
|---|---|---|
| 633 | 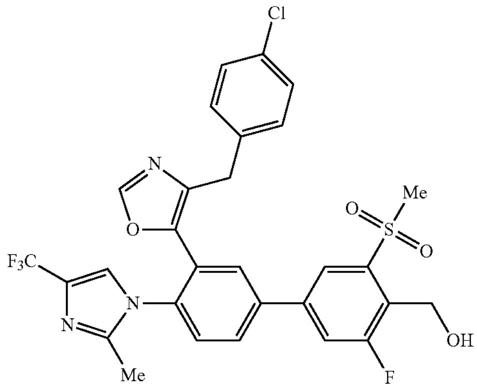 [SMILES: Cc1nc(C(F)(F)F)cn1-c1ccc(-c2cc(F)c(CO)c(S(C)(=O)=O)c2)cc1-c1ocnc1Cc1ccc(Cl)cc1] | (3'-(4-(4-chlorobenzyl)oxazol-5-yl)-3-fluoro-4'-(2-methyl-4-(trifluoromethyl)-1H-imidazol-1-yl)-5-(methylsulfonyl)-[1,1'-biphenyl]-4-yl)methanol |
| 634 | 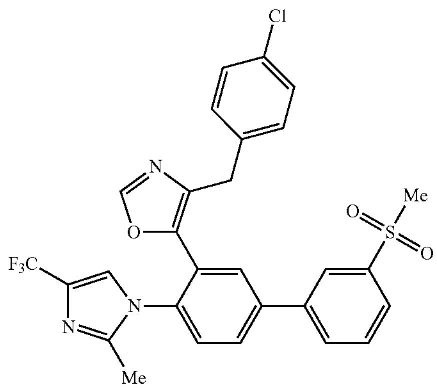 [SMILES: Cc1nc(C(F)(F)F)cn1-c1ccc(-c2cccc(S(C)(=O)=O)c2)cc1-c1ocnc1Cc1ccc(Cl)cc1] | 4-(4-chlorobenzyl)-5-(4-(2-methyl-4-(trifluoromethyl)-1H-imidazol-1-yl)-3'-(methylsulfonyl)-[1,1'-biphenyl]-3-yl)oxazole |
| 635 | 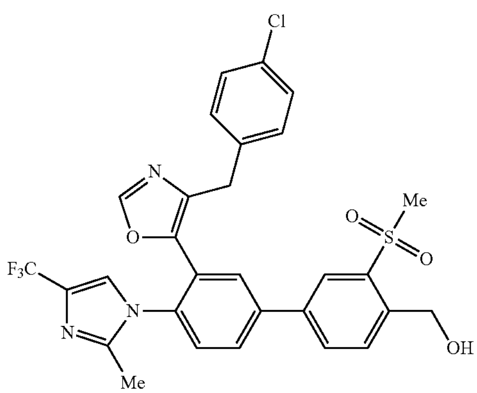 [SMILES: Cc1nc(C(F)(F)F)cn1-c1ccc(-c2ccc(CO)c(S(C)(=O)=O)c2)cc1-c1ocnc1Cc1ccc(Cl)cc1] | (3'-(4-(4-chlorobenzyl)oxazol-5-yl)-4'-(2-methyl-4-(trifluoromethyl)-1H-imidazol-1-yl)-3-(methylsulfonyl)-[1,1'-biphenyl]-4-yl)methanol |
| 636 | 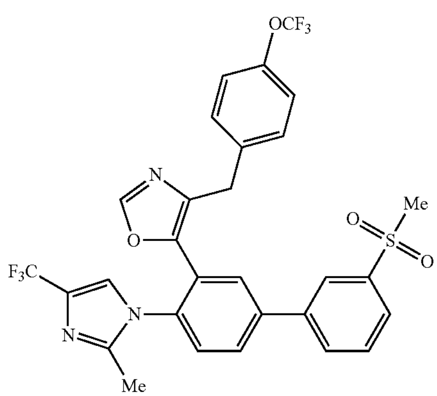 [SMILES: Cc1nc(C(F)(F)F)cn1-c1ccc(-c2cccc(S(C)(=O)=O)c2)cc1-c1ocnc1Cc1ccc(OC(F)(F)F)cc1] | 5-(4-(2-methyl-4-(trifluoromethyl)-1H-imidazol-1-yl)-3'-(methylsulfonyl)-[1,1'-biphenyl]-3-yl)-4-(4-(trifluoromethoxy)benzyl)oxazole |

| Ex # | Structure | Name |
|---|---|---|
| 637 | 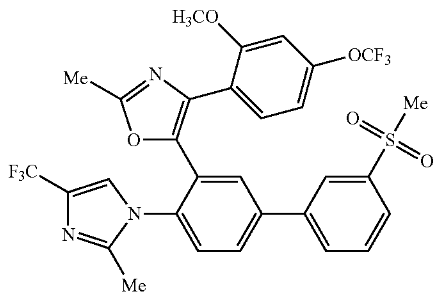 [SMILES: COc1cc(OC(F)(F)F)ccc1-c1nc(C)oc1-c1cc(-c2cccc(S(C)(=O)=O)c2)ccc1-n1cc(C(F)(F)F)nc1C] | 4-(2-methoxy-4-(trifluoromethoxy)phenyl)-2-methyl-5-(4-(2-methyl-4-(trifluoromethyl)-1H-imidazol-1-yl)-3'-(methylsulfonyl)-[1,1'-biphenyl]-3-yl)oxazole |
| 638 | 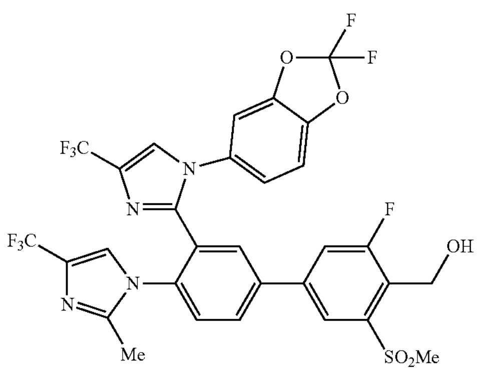 [SMILES: Cc1nc(C(F)(F)F)cn1-c1ccc(-c2cc(F)c(CO)c(S(C)(=O)=O)c2)cc1-c1nc(C(F)(F)F)cn1-c1ccc2c(c1)OC(F)(F)O2] | (3'-(1-(2,2-difluorobenzo[d][1,3]dioxol-5-yl)-4-(trifluoromethyl)-1H-imidazol-2-yl)-3-fluoro-4'-(2-methyl-4-(trifluoromethyl)-1H-imidazol-1-yl)-5-methylsulfonyl)biphenyl-4-yl)methanol |
| 639 | 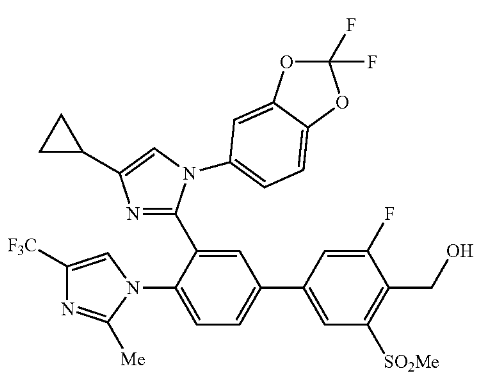 [SMILES: Cc1nc(C(F)(F)F)cn1-c1ccc(-c2cc(F)c(CO)c(S(C)(=O)=O)c2)cc1-c1nc(C2CC2)cn1-c1ccc2c(c1)OC(F)(F)O2] | (3'-(4-cyclopropyl-1-(2,2-difluorobenzo[d][1,3]dioxol-5-yl)-1H-imidazol-2-yl)-3-fluoro-4'-(2-methyl-4-(trifluoromethyl)-1H-imidazol-1-yl)-5-(methylsulfonyl)biphenyl-4-yl)methanol |
| 640 | 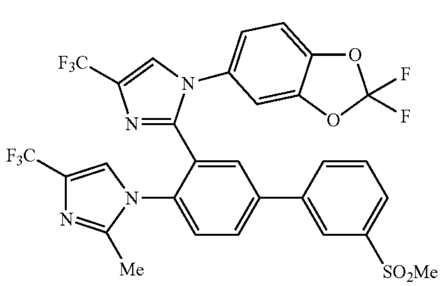 [SMILES: Cc1nc(C(F)(F)F)cn1-c1ccc(-c2cccc(S(C)(=O)=O)c2)cc1-c1nc(C(F)(F)F)cn1-c1ccc2c(c1)OC(F)(F)O2] | 1-(2,2-difluorobenzo[d][1,3]dioxol-5-yl)-2-(4-(2-methyl-4-(trifluoromethyl)-1H-imidazol-1-yl)-3'-(methylsulfonyl)biphenyl-3-yl)-4-(trifluoromethyl)-1H-imidazole |

-continued

| Ex # | Structure | Name |
|---|---|---|
| 641 | 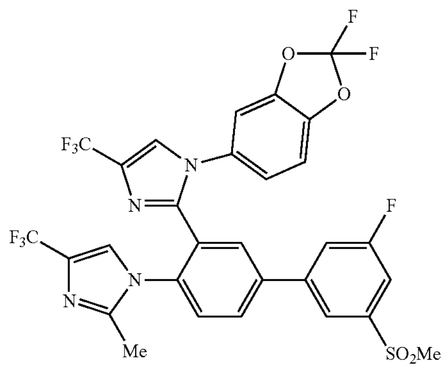 [SMILES: Cc1nc(C(F)(F)F)cn1-c1ccc(-c2cc(F)cc(S(C)(=O)=O)c2)cc1-c1nc(C(F)(F)F)cn1-c1ccc2c(c1)OC(F)(F)O2] | 1-(2,2-difluorobenzo[d][1,3]dioxol-5-yl)-2-(3'-fluoro-4-(2-methyl-4-(trifluoromethyl)-1H-imidazol-1-yl)-5'-(methylsulfonyl)biphenyl-3-yl)-4-(trifluoromethyl)-1H-imidazole |
| 642 | 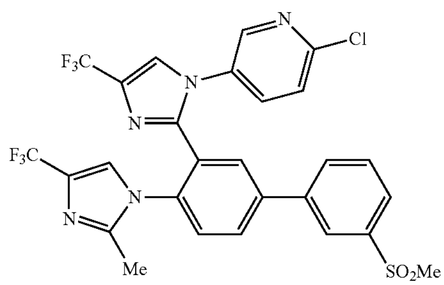 [SMILES: Cc1nc(C(F)(F)F)cn1-c1ccc(-c2cccc(S(C)(=O)=O)c2)cc1-c1nc(C(F)(F)F)cn1-c1ccc(Cl)nc1] | 2-chloro-5-(2-(4-(2-methyl-4-(trifluoromethyl)-1H-imidazol-1-yl)-3'-(methylsulfonyl)biphenyl-3-yl)-4-(trifluoromethyl)-1H-imidazol-1-yl)pyridine |
| 643 | 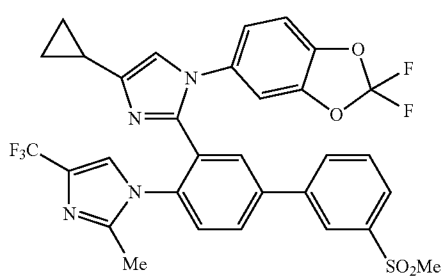 [SMILES: Cc1nc(C(F)(F)F)cn1-c1ccc(-c2cccc(S(C)(=O)=O)c2)cc1-c1nc(C2CC2)cn1-c1ccc2c(c1)OC(F)(F)O2] | 4-cyclopropyl-1-(2,2-difluorobenzo[d][1,3]dioxol-5-yl)-2-(4-(2-methyl-4-(trifluoromethyl)-1H-imidazol-1-yl)-3'-(methylsulfonyl)biphenyl-3-yl)-1H-imidazole |
| 644 | 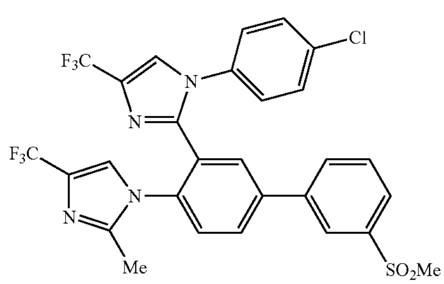 [SMILES: Cc1nc(C(F)(F)F)cn1-c1ccc(-c2cccc(S(C)(=O)=O)c2)cc1-c1nc(C(F)(F)F)cn1-c1ccc(Cl)cc1] | 1-(4-chlorophenyl)-2-(4-(2-methyl-4-(trifluoromethyl)-1H-imidazol-1-yl)-3'-(methylsulfonyl)biphenyl-3-yl)-4-(trifluoromethyl)-1H-imidazole |
| 645 | 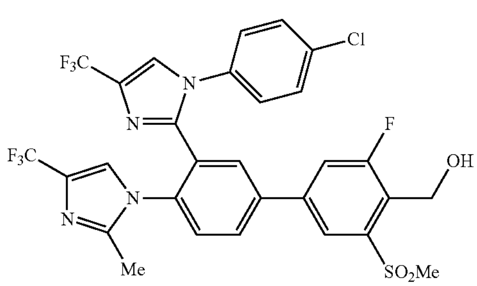 [SMILES: Cc1nc(C(F)(F)F)cn1-c1ccc(-c2cc(F)c(CO)c(S(C)(=O)=O)c2)cc1-c1nc(C(F)(F)F)cn1-c1ccc(Cl)cc1] | (3'-(1-(4-chlorophenyl)-4-(trifluoromethyl)-1H-imidazol-2-yl)-3-fluoro-4'-(2-methyl-4-(trifluoromethyl)-1H-imidazol-1-yl)-5-(methylsulfonyl)biphenyl-4-yl)methanol |

| Ex # | Structure | Name |
|---|---|---|
| 646 | 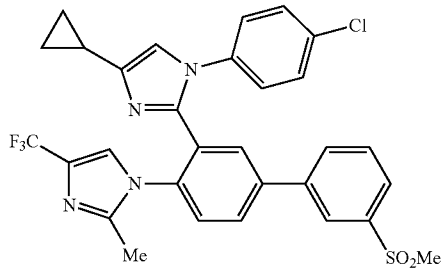 [SMILES: Cc1nc(C(F)(F)F)cn1-c1ccc(-c2cccc(S(C)(=O)=O)c2)cc1-c1nc(C2CC2)cn1-c1ccc(Cl)cc1] | 1-(4-chlorophenyl)-4-cyclopropyl-2-(4-(2-methyl-4-(trifluoromethyl)-1H-imidazol-1-yl)-3'-(methylsulfonyl)-[1,1'-biphenyl]-3-yl)-1H-imidazole |
| 647 | 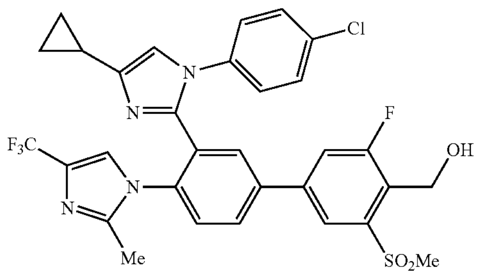 [SMILES: Cc1nc(C(F)(F)F)cn1-c1ccc(-c2cc(F)c(CO)c(S(C)(=O)=O)c2)cc1-c1nc(C2CC2)cn1-c1ccc(Cl)cc1] | (3'-(1-(4-chlorophenyl)-4-cyclopropyl-1H-imidazol-2-yl)-3-fluoro-4'-(2-methyl-4-(trifluoromethyl)-1H-imidazol-1-yl)-5-(methylsulfonyl)-[1,1'-biphenyl]-4-yl)methanol. |

15. A composition comprising a compound of claim 1, or a pharmaceutically acceptable salt thereof, and one or more pharmaceutically acceptable carriers.

16. A method of therapeutically treating a disease or disorder comprising administering to a subject in need thereof a therapeutically effective amount of a compound of claim 1, wherein the disease or disorder is atherosclerosis, insulin resistance, osteoarthritis, stroke, hyperglycemia, dyslipidemia, psoriasis, aged and UV skin wrinkling, diabetes, inflammation, immunological disorders, lipid disorders, obesity, conditions characterized by a perturbed epidermal barrier function, conditions of disturbed differentiation or excess proliferation of the epidermis or mucous membrane, or cardiovascular disorders.

17. The method of claim 16, wherein the disease or disorder is atherosclerosis, diabetes, or dyslipidemia.

18. The method of claim 17, wherein the disease or disorder is atherosclerosis.

19. The method of claim 17, wherein the disease or disorder is diabetes.

* * * * *